US010981911B2

(12) United States Patent
Bacani et al.

(10) Patent No.: US 10,981,911 B2
(45) Date of Patent: *Apr. 20, 2021

(54) IMIDAZOPYRROLOPYRIDINE AS INHIBITORS OF THE JAK FAMILY OF KINASES

(71) Applicant: Janssen Pharmaceutica NV, Beerse (BE)

(72) Inventors: Genesis M. Bacani, San Diego, CA (US); Wenying Chai, San Diego, CA (US); Tatiana Koudriakova, Poway, CA (US); Paul J. Krawczuk, Newtown, PA (US); Kevin D. Kreutter, Arlington, MA (US); Kristi Leonard, Lansdale, PA (US); Michele C. Rizzolio, San Diego, CA (US); Mark Seierstad, Escondido, CA (US); Russell C. Smith, San Diego, CA (US); Mark S. Tichenor, San Diego, CA (US); Jennifer D. Venable, Solana Beach, CA (US); Aihua Wang, Jamison, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/469,939

(22) PCT Filed: Dec. 15, 2017

(86) PCT No.: PCT/US2017/066754
§ 371 (c)(1),
(2) Date: Jun. 14, 2019

(87) PCT Pub. No.: WO2018/112382
PCT Pub. Date: Jun. 21, 2018

(65) Prior Publication Data
US 2019/0322665 A1    Oct. 24, 2019

Related U.S. Application Data

(60) Provisional application No. 62/596,636, filed on Dec. 8, 2017, provisional application No. 62/592,747, filed on Nov. 30, 2017, provisional application No. 62/435,639, filed on Dec. 16, 2016.

(51) Int. Cl.
C07D 471/14        (2006.01)
(52) U.S. Cl.
CPC .................. C07D 471/14 (2013.01)
(58) Field of Classification Search
USPC ........................................... 546/82
See application file for complete search history.

(56) References Cited

U.S. PATENT DOCUMENTS

| 6,080,747 | A  | 6/2000  | Uckun et al. |
| 8,426,411 | B2 | 4/2013  | Wishart et al. |
| 8,461,328 | B2 | 6/2013  | Babu et al. |
| 8,841,078 | B2 | 9/2014  | Silvennoinen et al. |
| 8,962,629 | B2 | 2/2015  | Wishart et al. |
| 10,294,226 | B2 | 5/2019  | Koudriakova et al. |
| 10,364,246 | B2 | 7/2019  | Koudriakova et al. |
| 10,487,083 | B2* | 11/2019 | Kreutter ............... C07D 471/14 |
| 2009/0312338 | A1 | 12/2009 | Wishart et al. |
| 2011/0190489 | A1* | 8/2011 | Wishart ............... C07D 471/14 544/115 |
| 2011/0311474 | A1 | 12/2011 | Wishart et al. |
| 2013/0216497 | A1* | 8/2013 | Wishart ............... C07D 471/14 424/85.2 |
| 2015/0210708 | A1* | 7/2015 | Wishart ............... C07D 487/14 544/346 |
| 2019/0177321 | A1 | 6/2019  | Koudriakova et al. |
| 2019/0177322 | A1 | 6/2019  | Kreutter et al. |
| 2020/0017498 | A1* | 1/2020 | Fernandes ........... C07D 471/14 |
| 2020/0165250 | A1 | 5/2020  | Fernandes et al. |
| 2020/0338051 | A1* | 10/2020 | Rizzolio ............... A61K 47/40 |

FOREIGN PATENT DOCUMENTS

| CL | 201201396 | 9/2012 |
| CL | 201901077 | 4/2019 |
| CL | 201901416 | 5/2019 |
| CL | 201901551 | 6/2019 |
| CL | 201901651 | 6/2019 |
| CL | 201901652 | 6/2019 |
| CL | 201901991 | 7/2019 |
| CL | 201903015 | 10/2019 |
| WO | WO2011/068881 A1 | 6/2011 |
| WO | WO2011068899 A1 | 6/2011 |
| WO | WO2011/086053 A1 | 7/2011 |
| WO | WO2013/007765 A1 | 1/2013 |
| WO | WO2015/144773 A1 | 10/2015 |

(Continued)

OTHER PUBLICATIONS

Leonard; J. Med. Chem. 2020, 63, 6, 2915-2929. (Year: 2020).*
U.S. Appl. No. 16/441,656, filed Jun. 14, 2019, Fernandes, Philippe, et al.
Alves De Medeiros, et al., JAK3 as an Emerging Target for Topical Treatment of Inflammatory Skin Diseases, PLoS One, 2016, pp. 1-16, 11(10): e0164080. doi:10.1371/journal.pone.0164080.
Amano, et al., JAK inhibitor JTE-052 regulates contact hypersensitivity by downmodulating T cell activation and differentiation, Journal of Dermatological Science, 2016, pp. 258-265, vol. 84.
Ambeu N'Ta C., et al., A practical multi-step synthesis of ethyl N-functionalized β-amino benzimidazole acrylate derivatives as promising cytotoxic agents, Molecular Diversity (2018) vol. 22, pp. 685-708.
Baumgart, et al., Inflammatory bowel disease: cause and immunobiology, Lancet, 2007, pp. 1627-1640, vol. 369.

(Continued)

Primary Examiner — Daniel R Carcanague

(57)  ABSTRACT

2-((1r,4r)-4-(imidazo[4,5-d]pyrrolo[2,3-b]pyridin-1(6H)-yl)cyclohexyl)acetonitrile compounds, pharmaceutical compositions containing them, methods of making them, and methods of using them including methods for treating disease states, disorders, and conditions mediated by JAK, such as inflammatory bowel disease.

2 Claims, 6 Drawing Sheets

Specification includes a Sequence Listing.

(56) References Cited

FOREIGN PATENT DOCUMENTS

| WO | WO2016/191524 A1 | 12/2016 |
|---|---|---|
| WO | WO2017/079639 A1 | 5/2017 |
| WO | WO2018077630 A1 | 5/2018 |
| WO | WO2018/112379 A1 | 6/2018 |
| WO | WO2018/112382 A1 | 6/2018 |
| WO | WO2018108671 A1 | 6/2018 |
| WO | WO2018109074 A1 | 6/2018 |
| WO | WO2018109607 A1 | 6/2018 |
| WO | WO2018111707 A1 | 6/2018 |
| WO | WO2018138303 A1 | 8/2018 |
| WO | WO2018195397 A2 | 10/2018 |
| WO | WO2019239387 A1 | 12/2019 |

OTHER PUBLICATIONS

Baumgart, et al., Inflammatory bowel disease: clinical aspects and established and evolving therapies, Lancet, 2007, pp. 1641-1657, vol. 369.

Baxter, et al., Acquired mutation of the tyrosine kinase JAK2 in human myeloproliferative disorders, Lancet, 2005, pp. 1054-1061, vol. 365.

Behbod, et al., Concomitant Inhibition of Janus Kinase 3 and Calcineurin-Dependent Signaling Pathways Synergistically Prolongs the Survival of Rat Heart Allografts, The Journal of Immunology, 2001, pp. 3724-3732, vol. 166.

Benveniste, et al., Involvement of the Janus Kinase/Signal Transducer and Activator of Transcription Signaling Pathway in Multiple Sclerosis and the Animal Model of Experimental Autoimmune Encephalomyelitis, Journal of Interferon & Cytokine Research, 2014, pp. 577-588, vol. 34, Issue 8.

Berge, et al., Pharmaceutical Salts, Journal of Pharmaceutical Sciences, 1977, pp. 1-19, vol. 66, No. 1.

Berthier, et al., Enhanced Expression of Janus Kinase—Signal Transducer and Activator of Transcription Pathway Members in Human Diabetic Nephropathy, Diabetes, 2009, pp. 469-477, vol. 58.

Bissonnette, et al., Topical tofacitinib for atopic dermatitis: a phase IIa randomized trial, British Journal of Dermatology, 2016, pp. 902-911, vol. 175.

Brosius, et al., JAK inhibition in the treatment of diabetic kidney disease, Diabetologia, 2016, pp. 1624-1627, vol. 59.

Bunnage, Mark E., Getting pharmaceutical R&D back on target, Nature Chemical Biology, 2011, pp. 335-339, vol. 7.

Busque, et al., Calcineurin-Inhibitor-Free Immunosuppression Based on the JAK Inhibitor CP-690,550: A Pilot Study in De Novo Kidney Allograft Recipients, American Journal of Transplantation, 2009, pp. 1936-1945, vol. 9.

Cargill, et al., A Large-Scale Genetic Association Study Confirms IL12B and Leads to the Identification of IL23R as Psoriasis-Risk Genes, The American Journal of Human Genetics, 2007, pp. 273-290, vol. 80.

Casanova, et al., Revisiting Crohn's disease as a primary immunodeficiency of macrophages, J. Exp. Med., 2009, pp. 1839-1843, vol. 206, No. 9.

Chan et al., Dose-dependent reduction in psoriasis severity as evidence of immunosuppressive activity of an oral Jak3 inhibitor in humans, Am. J. Transplant., 2006, S87, vol. 6.

Changelian, et al., Prevention of Organ Allograft Rejection by a Specific Janus Kinase 3 Inhibitor, Science, 2003, pp. 875-878, vol. 302.

Charmot, Dominique, Non-Systemic Drugs: A Critical Review, Current Pharmaceutical Design, 2012, pp. 1434-1445, vol. 18.

Clark, et al., Discovery and Development of Janus Kinase (JAK) Inhibitors for Inflammatory Diseases, Journal of Medicinal Chemistry, 2014, pp. 5023-5038, vol. 57.

Colligris, et al., Recent developments on dry eye disease treatment compounds, Saudi Journal of Ophthalmology, 2014, pp. 19-30, vol. 28.

Coskun, et al., Involvement of JAK/STAT signaling in the pathogenesis of inflammatory bowel disease, Pharmacological Research, 2013, pp. 1-8, vol. 76.

Danese, et al., JAK inhibition using tofacitinib for inflammatory bowel disease treatment: a hub for multiple inflammatory cytokines, Am J Physiol Gastrointest Liver Physiol, 2016, pp. G155-G162, vol. 310.

Duerr, et al., A Genome-Wide Association Study Identifies IL23R as an Inflammatory Bowel Disease Gene, Science, 2006, pp. 1461-1463, vol. 314.

Filipski, et al., Intestinal Targeting of Drugs: Rational Design Approaches and Challenges, Current Topics in Medicinal Chemistry, 2013, pp. 776-802, vol. 13.

Folster-Holst, et al., Topical hydrocortisone 17-butyrate 21-propionate in the treatment of inflammatory skin diseases: pharmacological data, clinical efficacy, safety and calculation of the therapeutic index, Pharmazie, 2016, pp. 115-121, vol. 71.

Fujimura, et al., Significance of Interleukin-6/STAT Pathway for the Gene Expression of REG Iα, a New Autoantigen in Sjögren's Syndrome Patients, in Salivary Duct Epithelial Cells, Clinic Rev Allerg Immunol, 2016, pp. 1-13, DOI 10.1007/s12016-016-8570-7.

Fukuyama, et al., Topically Administered Janus-Kinase Inhibitors Tofacitinib and Oclacitinib Display Impressive Antipruritic and Anti-Inflammatory Responses in a Model of Allergic Dermatitis, J Pharmacol Exp Ther, 2015, pp. 394-405, vol. 354.

Furumoto, et al., Tofacitinib Ameliorates Murine Lupus and Its Associated Vascular Dysfunction, Arthritis & Rheumatology, 2017, pp. 148-160, vol. 69 Issue 1.

Fyfe, Matthew C.T., Non-systemic Intestine-Targeted Drugs, Progress in Medicinal Chemistry, 2016, pp. 1-44, vol. 55.

Gaudana, et al., Ocular Drug Delivery, The AAPS Journal, 2010, pp. 348-360, vol. 12 Issue 3.

Ginzinger, Werner, et al., A SAR Study of Novel Antiproliferative Ruthenium and Osmium Complexes with Quinoxalinone Ligands in Human Cancer Cell Lines, J. Med. Chem. (2012) vol. 55, pp. 3398-3413.

Goropevsek, et al., The Role of STAT Signaling Pathways in the Pathogenesis of Systemic Lupus Erythematosus, Clinic Rev Allerg Immunol, May 23, 2016, pp. 1-18, DOI 10.1007/s12016-016-8550-y.

Gurzov, et al., The JAK/STAT pathway in obesity and diabetes, The FEBS Journal, 2016, pp. 3002-3015, vol. 283.

Hay, et al., Clinical development success rates for investigational drugs, Nature Biotechnology, 2014, pp. 40-51, vol. 32 Issue 1.

Helandr, et al., Surface area of the digestive tract—revisited, Scandinavian Journal of Gastroenterology, 2014, pp. 681-689, vol. 49.

Hirschmann, Ralph, et al., Nonpeptidal Peptidomimetics with a β-D-Glucose Scaffolding. A Partial Somatostatin Agonist Bearing a Close Structural Relationship to a Potent, Selective Substance P Antagonist, J. Am. Chem. Soc. (1992) vol. 114, pp. 9217-9218.

Honda, Masanori, et al., A Synthesis of (±)—Brefeldin A, Tetrahedron Letters (1981) vol. 22, No. 28, pp. 2679-2682.

International Search Report and Written Opinion dated Apr. 4, 2018, for International Application PCT/US2017/066754.

International Search Report and Written Opinion dated May 11, 2018, for International Application PCT/US2017/066744.

James, et al., A unique clonal JAK2 mutation leading to constitutive signalling causes polycythaemia vera, Nature, 2005, pp. 1144-1148, vol. 434.

Jursic, Branko S., et al., A Simple Preparation of Amides from Acids and Amines by Heating of their Mixture, Synthetic Communications, (1993), vol. 23, No. 19, pp. 2761-2770.

Kawasaki, et al., Possible role of the JAK/STAT pathways in the regulation of T cell-interferon related genes in systemic lupus erythematosus, Lupus, 2011, pp. 1231-1239, vol. 20.

Kocienski, Philip J., Chapter 6.3.1: N-Sulfonyl Derivatives of Indoles, Pyrroles, and Imidazoles, Protecting Groups; Georg Thieme Verlag Stuttgart: NY, (1994), pp. 209-211.

Kola, et al., Can the pharmaceutical industry reduce attrition rates?, Nature Reviews/Drug Discovery, 2004, pp. 711-715, vol. 3.

Kontzias et al., Jakinibs: A new class of kinase inhibitors in cancer and autoimmune disease, Current Opinion in Pharmacology, 2012, pp. 464-470, vol. 12.

(56) References Cited

OTHER PUBLICATIONS

Kopf et al., Averting inflammation by targeting the cytokine environment, Nature Reviews/Drug Discovery, 2010, pp. 703-718, vol. 9.

Kornbluth, et al., Ulcerative Colitis Practice Guidelines in Adults: American College of Gastroenterology, Practice Parameters Committee, The American Journal of Gastroenterology, 2010, pp. 501-523, vol. 105.

Kralovics, et al., A Gain-of-Function Mutation of JAK2 in Myeloproliferative Disorders, The New England Journal of Medicine, 2005, pp. 1779-1790, vol. 352 Issue 17.

Kremer, et al., A Randomized, Double-Blind, Placebo-Controlled Trial of 3 Dose Levels of CP690,550 Versus Placebo in the Treatment of Active Rheumatoid Arthritis, Arthritis Rheum. 54 (annual meeting abstract), 2006, L40.

Kremer, et al., The Safety and Efficacy of a JAK Inhibitor in Patients with Active Rheumatoid Arthritis, Arthritis & Rheumatism, 2009, pp. 1895-1905, vol. 60 Issue 7.

Kumar, Vasantha et al., Synthesis of Some Novel 1,2-Disubstituted Benzimidazole-5-Carboxylates Via One-Pot Method Using Sodium Dithionite and its Effect on N-Debenzylation, Synthetic Communications (2014) vol. 44, pp. 3414-3425.

Lalande, et al., Mycobacteria in Crohn's disease: how innate immune deficiency may result in chronic inflammation, Expert Review of Clinical Immunology, 2010, pp. 633-641, vol. 6 Issue 4.

Langholz, et al., Course of Ulcerative Colitis: Analysis of Changes in Disease Activity Over Years, Gastroenterology, 1994, pp. 3-11, vol. 107 Issue 01.

Leonardi, et al., Efficacy and safety of ustekinumab, a human interleukin-12/23 monoclonal antibody, in patients with psoriasis: 76-week results from a randomised, double-blind, placebo-controlled trial (Phoenix 1), Lancet, 2008, pp. 1665-1674, vol. 371.

Levine, et al., Activating Mutation in the Tyrosine Kinase JAK2 in Polycythemia Vera, Essential Thrombocythemia, and Myeloid Metaplasia with Myelofibrosis, Cancer Cell, 2005, pp. 387-397, vol. 7.

Li, et al., Effect of miR-19a and miR-21 on the JAK/STAT signaling pathway in the peripheral blood mononuclear cells of patients with systemic juvenile idiopathic arthritis, Experimental and Therapeutic Medicine, 2016, pp. 2531-2536, vol. 11.

Liu, et al., Therapeutic Efficacy of Suppressing the JAK/STAT Pathway in Multiple Models of Experimental Autoimmune Encephalomyelitis, The Journal of Immunology, 2014, pp. 59-72, vol. 192.

Liu, Zhenming et al., Identification of Small-Molecule Inhibitors against Human Leukocyte Antigen-Death Receptor 4 (HLA-DR4) Through a Comprehensive Strategy, J. Chem. Inf. Model. (2011) vol. 51, pp. 326-334.

Marks, et al., Crohn's Disease: an Immune Deficiency State, Clinic Rev Allerg Immunol, 2010, pp. 20-31, vol. 38.

Menet, et al., Triazolopyridines as Selective JAK1 Inhibitors: From Hit Identification to GLPG0634, Journal of Medicinal Chemistry, 2014, pp. 9323-9342, vol. 57.

Nangia, Ashwini, Pseudopolymorph: Retain This Widely Accepted Term, Crystal Growth & Design, 2006, pp. 2-4, vol. 6 Issue 1.

Neurath, Markus F., Cytokines in inflammatory bowel disease, Nature Reviews/Immunology, 2014, pp. 329-342, vol. 14.

NIDDK (National Institute of Diabetes, and Digestive and Kidney Diseases, National Institutes of Health, US Department of Health and Human Services, <http://spotidoc.com/doc/71780/crohns-disease---national-digestive-diseases-information>, accessed Nov. 29, 2016.

Nielsen, et al., Will novel oral formulations change the management of inflammatory bowel disease?, Expert Opinion on Investigational Drugs, 2016, pp. 709-718, vol. 25 Issue 6.

Nishimoto, et al., Study of active controlled monotherapy used for rheumatoid arthritis, an IL-6 inhibitor (Samurai): evidence of clinical and radiographic benefit from an x ray reader-blinded randomised controlled trial of tocilizumab, Ann Rheum Dis, 2007, pp. 1162-1167, vol. 66.

Norman, Peter, Selective JAK inhibitors in development for rheumatoid arthritis, Expert Opinion on Investigational Drugs, 2014, pp. 1067-1077, vol. 23 Issue 8.

Oda, Shinichi et al., Development of Safe One-Pot Synthesis of N-1- and C-2-Substituted Benzimidazole via Reductive Cyclization of o-Nitroarylamine Using Na2S2O4, Org. Process Res. Dev. (2012) vol. 16, pp. 96-101.

O'Shea, et al., JAKs and STATs in Immunity, Immunodeficiency, and Cancer, The New England Journal of Medicine, 2013, pp. 161-170, vol. 368.

O'Shea, et al., A New Modality for Immunosuppression: Targeting the JAK/STAT Pathway, Nature Reviews/Drug Discovery, 2004, pp. 555-564, vol. 3.

O'Shea, et al., Janus kinase inhibitors in autoimmune diseases, Ann Rheum Dis, 2013, pp. ii111-ii115, vol. 72.

Özil, Musa et al., A simple and efficient synthesis of benzimidazoles containing piperazine or morpholine skeleton at C-6 position as glucosidase inhibitors with antioxidant activity, Bioorganic Chemistry (2018) vol. 76, pp. 468-477.

Panes, et al., Efficacy and safety of oral tofacitinib for induction therapy in patients with moderate-to-severe Crohn's disease: results of a Phase 2b randomised placebo-controlled trial, J. Crohn's Colitis, 2016, S18-S19, vol. 10.

Papp, et al., Efficacy and safety of tofacitinib, an oral Janus kinase inhibitor, in the treatment of psoriasis: a Phase 2b randomized placebo-controlled dose-ranging study, British Journal of Dermatology, 2012, pp. 668-677, vol. 167.

Patil, et al., Pulmonary drug delivery strategies: A concise, systematic review, Lung India, 2012, pp. 44-49, vol. 29 Issue 1.

Pesu et al., Therapeutic targeting of Janus kinases, Immunological Reviews, 2008, pp. 132-142, vol. 223.

Qiao, et al., Pharmaceutical cocrystals: An overview, International Journal of Pharmaceutics, 2011, pp. 1-11, vol. 419.

Reinisch, et al., Adalimumab for induction of clinical remission in moderately to severely active ulcerative colitis: results of a randomised controlled trial, Gut, 2011, pp. 780-787, vol. 60.

Rylander, P.N., Chapter 8: Hydrogenation of Nitro Compounds, Hydrogenation Methods; Academic Press: NY, (1985) pp. 104-116.

Rylander, P.N., Choosing and Using Noble Metal Hydrogenation Catalysts, Aldrichimica Acta (1979), vol. 12, No. 3, pp. 53-57.

Sandborn, et al., A Phase 2 Study of Tofacitinib, an Oral Janus Kinase Inhibitor, in Patients With Crohn's Disease, Clinical Gastroenterology and Hepatology, 2014, pp. 1485-1493, vol. 12 Issue 9.

Sandborn, et al., Efficacy and safety of oral tofacitinib as induction therapy in patients with moderate-to-severe ulcerative colitis: results from 2 phase 3 randomised controlled trials, J. Crohn's Colitis, 2016, S15-S, vol. 10.

Sandborn, et al., Tofacitinib, an Oral Janus Kinase Inhibitor, in Active Ulcerative Colitis, N Engl J Med, 2012, pp. 616-624, vol. 367 Issue 7.

Segal, et al., Repeated subcutaneous injections of IL12/23 p40 neutralising antibody, ustekinumab, in patients with relapsing-remitting multiple sclerosis: a phase II, double-blind, placebo-controlled, randomised, dose-ranging study, Lancet Neurol, 2008, pp. 796-804, vol. 7.

Shan, et al., The role of cocrystals in pharmaceutical science, Drug Discovery Today, 2008, pp. 440-446, vol. 13 Nos. 9/10.

Stephenson et al., Physical Stability of Salts of Weak Bases in the Solid-State, Journal of Pharmaceutical Sciences, 2011, pp. 1607-1617, vol. 100 Issue 5.

Strober, et al., Proinflammatory Cytokines in the Pathogenesis of Inflammatory Bowel Diseases, Gastroenterology, 2011, pp. 1756-1767, vol. 140 Issue 6.

Thakuria, et al., Pharmaceutical cocrystals and poorly soluble drugs, International Journal of Pharmaceutics, 2013, pp. 101-125, vol. 453.

Thomas et al., The role of JAK/STAT signaling in the pathogenesis, prognosis and treatment of solid tumours, British Journal of Cancer, 2015, pp. 365-371, vol. 113.

Thompson, et al., Anti cytokine therapy in chronic inflammatory arthritis, Cytokine, 2016, pp. 92-99, vol. 86.

Torchilin, Vladimir P., Drug targeting, European Journal of Pharmaceutical Sciences, 2000, pp. S81-S91, vol. 11 Suppl. 2.

(56) References Cited

OTHER PUBLICATIONS

Travis et al., European evidence-based Consensus on the management of ulcerative colitis: Current management, Journal of Crohn's and Colitis, 2008, pp. 24-62, vol. 2.
Vale, Kara, Targeting the JAK-STAT pathway in the treatment of 'Th2-high' severe asthma, Future Med. Chem., 2016, pp. 405-419, vol. 8 Issue 4.
Vermeire, et al., Filgotinib (GLPG0634), an Oral JAK1 Selective Inhibitor, Induces Clinical Remission in Patients With Moderate-to-Severe Crohn's Disease: Results From the Phase 2 Fitzroy Study Interim Analysis, Gastroenterology, 2016, S-1267, vol. 150.
Waldner et al., Master regulator of intestinal disease: IL-6 in chronic inflammation and cancer development, Seminars in Immunology, 2014, pp. 75-79, vol. 26.
Waring, et al., An analysis of the attrition of drug candidates from four major pharmaceutical companies, Nature Reviews/Drug Discovery, 2015, pp. 475-486, vol. 14.
Wernig, et al., Efficacy of TG101348, a Selective JAK2 Inhibitor, in Treatment of a Murine Model of JAK2V617F- Induced Polycythemia Vera, Cancer Cell, 2008, pp. 311-320, vol. 13.
Wilding, et al., Targeting of Drugs and Vaccines to the Gut, Pharmac. Ther., 1994, pp. 97-124, vol. 62.
Williams et al., A randomized placebo-controlled study of INCB018424, a selective Janus kinase1&2 (JAK1&2) inhibitor in rheumatoid arthritis (RA), Arthritis Rheum., 2008, S431, vol. 58.
Wolk, et al., New targeting strategies in drug therapy of inflammatory bowel disease: mechanistic approaches and opportunities, Expert Opin. Drug Deliv., 2013, pp. 1275-1286, vol. 10 Issue 9.
Xing, et al., Alopecia areata is driven by cytotoxic T lymphocytes and is reversed by JAK inhibition, Nature Medicine, 2014, pp. 1043-1051, vol. 20 Issue 9.
Yamamoto-Furusho, et al., Crohn's disease: Innate immunodeficiency, World J Gastroenterol, 2006, pp. 6751-6755, vol. 12 Issue 42.
Yan, et al., Role of the JAK/STAT signaling pathway in regulation of innate immunity in neuroinflammatory diseases, Clin. Immunol., 2016, http://dx.doi.org/10.1016/j.clim.2016.09.014.
Zak, et al., Discovery and Optimization of C-2 Methyl Imidazopyrrolopyridines as Potent and Orally Bioavailable JAK1 Inhibitors with Selectivity over JAK2, J. Med. Chem, 2012, pp. 6176-6193, vol. 55.
Zak, Mark et al., Identification of C-2 Hydroxyethyl Imidazopyrrolopyridines as Potent JAK1 Inhibitors with Favorable Physicochemical Properties and High Selectivity over JAK2, J. Med. Chem. 2013, 56, 4764-4785.
Zakhs, E.R., et al., Synthesis and Photochromic Properties of 2-(3-Nitro-2-pyridylmethyl)benzazoles, Russian Journal of General Chemistry, (2001) vol. 71, No. 7, pp. 1076-1087. Translated from Zhurnal Obshchei Khimii, (2001) vol. 71, No. 7, pp. 1142-1153.
U.S. Appl. No. 16/581,081, Philippe Fernandes et al., filed Sep. 24, 2019.
International Search Report and Written Opinion dated Dec. 2, 2019, for International Application PCT/IB2019/055005.
Ma, Christopher et al., "Systematic review with meta-analysis: efficacy and safety of oral Janus kinase inhibitors for inflammatory bowel disease", Aliment Pharmacol Ther., (2019) vol. 50, pp. 5-23.

* cited by examiner

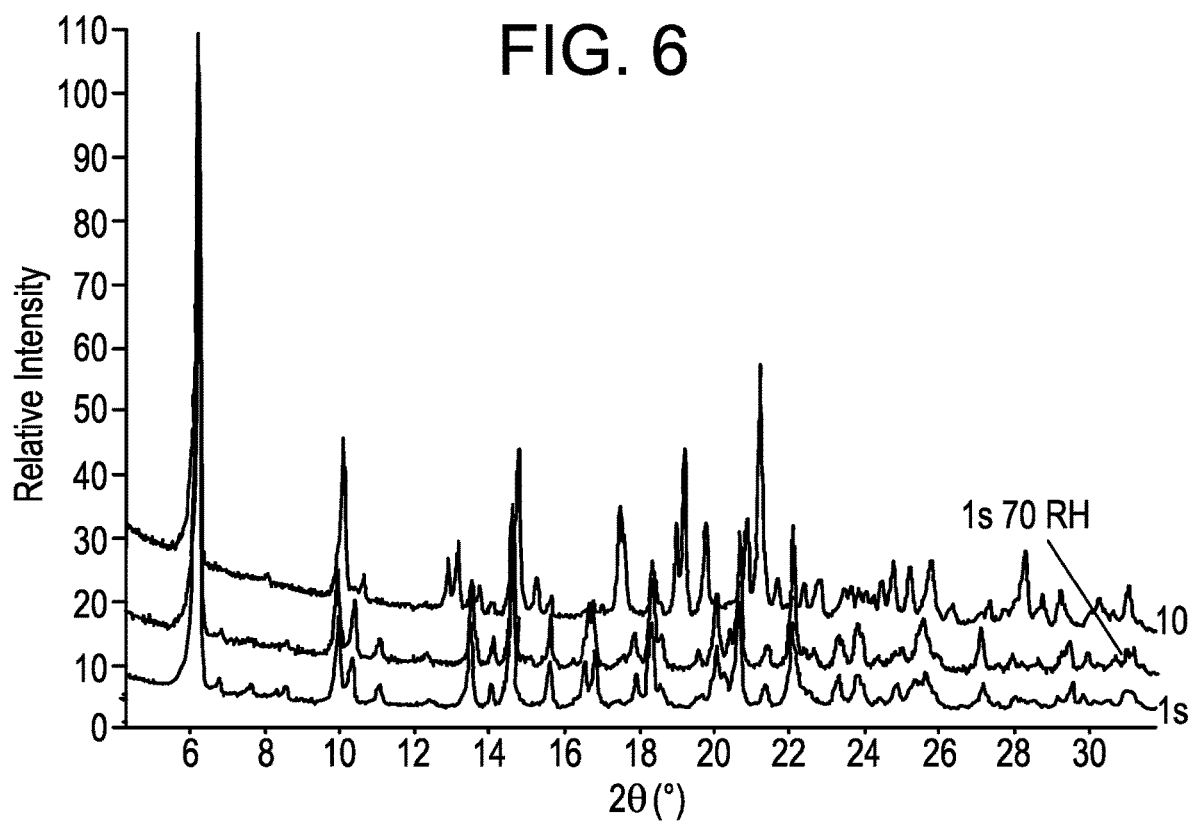

IMIDAZOPYRROLOPYRIDINE AS INHIBITORS OF THE JAK FAMILY OF KINASES

This application is a national stage of PCT Application No. PCT/US2017/066754, filed on Dec. 15, 2017, which claims the benefit of U.S. Provisional Application 62/596,636, filed on Dec. 8, 2017, U.S. Provisional Application 62/592,747, filed on Nov. 30, 2017, and U.S. Provisional Application 62/435,639, filed on Dec. 16, 2016.

SEQUENCE LISTING

The instant application contains a Sequence Listing which has been filed electronically in ASCII format and is hereby incorporated by reference in its entirety. Said ASCII copy, created on Mar. 5, 2018, is named PRD3441USPCT_SL.txt and is 1,336 bytes in size.

FIELD OF THE INVENTION

The present invention relates to certain imidazopyrrolopyridine compounds, pharmaceutical compositions containing them, methods of making them, and methods of using them as JAK inhibitors and for the treatment of disease states, disorders, and conditions mediated by JAK.

BACKGROUND

Internal factors, external factors or a combination of both factors can trigger or be associated with the development of abnormal immune responses in the body. Consequently, pathological states develop in which constituents, such as substances and tissues, that are normally present in the body are subject to such immune response. These states are generically referred to as immune system diseases. Because the body's immune system is involved and the damage affects body tissue, such diseases are also referred to as autoimmune diseases. Because such system and tissue are part of the same body, the terms "autoimmune disease" and "immune system disease" are used here interchangeably, regardless of what triggers the anomalous immune system response. Furthermore, the identity or the mechanism of the underlying immune problem is not always clear. See, for example, D. J. Marks, et al., Crohn's disease: An immune deficiency state, Clinical Reviews in Allergy and Immunology 38(1), 20-31 (2010); J. D. Lalande, et al, Mycobacteria in Crohn's disease: How innate immune deficiency may result in chronic inflammation, Expert Reviews of Clinical Immunology 6(4), 633-41 (2010); J. K. Yamamoto-Furusho, et al., Crohn's disease: Innate immunodeficiency, World Journal of Gastroenterology, 12(42), 6751-55 (2006). As used herein, the term "autoimmune disease" does not exclude conditions whose causes comprise external factors or agents, such as environmental or bacterial factors, and internal factors such as genetic susceptibility. Accordingly, a condition such as Crohn's disease (CD) is referred to herein as an autoimmune disease, regardless of whether it is triggered by the body itself or by external factors. See, e.g., J. L. Casanova, et al., Revisiting Crohn's disease as a primary immunodeficiency of macrophages, J. Exp. Med. 206(9), 1839-43 (2009).

Among the various adverse effects caused by autoimmune diseases, at least one of the following is typically observed: Damage to, and sometimes destruction of, tissues, and organ alteration that can impact organ growth and organ function. Examples of autoimmune diseases affect most major organs, endocrine and exocrine glands, the blood and muscles, and a plurality of systems, such as the digestive, vascular, connective and nervous systems. Immunosuppressive treatments are often adopted to treat autoimmune diseases.

Multiple theories are known to explain how autoimmune diseases arise, some focusing on endogenous factors and others also including exogenous factors. At the molecular level, the Janus kinase/signal transducer and activator of transcription (JAK/STAT) signaling pathway is considered to play an important role in transmitting information from extracellular chemical signals to the cell nucleus resulting in regulation of genes that are involved in cellular activities such as immunity. Cytokines are an example of an extracellular molecule that plays an important role in cell signaling. Leukocytes such as neutrophils are recruited by cytokines and chemokines to ultimately cause tissue damage in chronic inflammatory diseases.

The Janus kinase (JAK) family of proteins consists of 4 tyrosine kinases, JAK1, JAK2, JAK3 and Tyk2, which are central to the intracellular signaling of type I and type II cytokine receptors. The term JAK refers to either JAK1, JAK2, JAK3 or Tyk2, or any combination thereof. Each JAK selectively associates with receptor subunits which dimerize (or multimerize) to form functional receptors. According to J. D. Clark, et al., Discovery and Development of Janus Kinase (JAK) Inhibitors for Inflammatory Diseases, J. Med. Chem. 57(12), 5023-38 (2014), "the activation step occurs when a cytokine binds to its receptor, inducing a multimerization (dimerization or higher order complexes) of receptor subunits. This brings the JAKs associated with each subunit proximal to one another, triggering a series of phosphorylation events ultimately resulting in the phosphorylation and activation of signal transducers and activators of transcription (STAT) proteins. A phosphorylated STAT dimer then translocates to the nucleus of the cell where it binds to target genes modulating their expression." Once in the nucleus, STATs regulate gene transcription of numerous mediators in the inflammatory process via binding to specific recognition sites on DNA. See, for example, J. Med. Chem. 57(12), 5023-38 (2014), cited above. Considerable evidence exists demonstrating the importance for the JAK/STAT pathway in inflammatory, autoimmune diseases and cancer. See, for example, M. Coskun, et al., Involvement of JAK/STAT signaling in the pathogenesis of inflammatory bowel disease, Pharmacological Research 76, 1-8 (2013); and J. J. O'Shea, et al., JAKs and STATs in immunity, immunodeficiency, and cancer, The New England Journal of Medicine 368, 161-70 (2013).

Inflammatory bowel diseases, including Crohn's disease and ulcerative colitis (UC), are characterized by recurrent intestinal inflammation, disruption of the epithelial barrier and microbial dysbiosis. The excessive inflammatory response in the gastrointestinal tract is mediated by several pro-inflammatory cytokines including TNFα, IFN-γ, IL-1, IL-2, IL-4, IL-6, IL-12, IL-13, IL-15, IL-17, IL-21, and IL-23 that exert their effects on cells of the innate and adaptive immune system including T and B lymphocytes, epithelial cells, macrophages and dendritic cells (DC). See, for example, Pharmacological Research 76, 1-8 (2013), cited above; S. Danese, et al., JAK inhibition using tofacitinib for inflammatory bowel disease treatment: A hub for multiple inflammatory cytokines, American Journal of Physiology, Gastrointestinal and Liver Physiology 310, G155-62 (2016); and M. F. Neurath, Cytokines in inflammatory bowel disease, Nature Reviews Immunology 14, 329-42 (2014).

Prevention and/or control of such excessive inflammatory response is desirable. In light of the mechanism of such response as summarized above, JAK inhibition (see illustration in FIG. 1 in the form of an jagged arrow showing a pan-JAK inhibitor striking upon the JAK/STAT signaling pathway and inflammation) is envisaged to prevent or control excessive inflammatory response. JAK inhibitors that inhibit a plurality of such JAK proteins, are referred to here as pan-JAK inhibitors. Examples of therapeutic benefits of such prevention or control have been seen with tofacitinib, an orally bioavailable pan-JAK inhibitor approved in the United States for the treatment of rheumatoid arthritis and currently in clinical development for ulcerative colitis. In a Phase 2 clinical trial, 194 patients with moderate to severe ulcerative colitis were reportedly evaluated for clinical efficacy. See, e.g., W. J. Sandborn, et al., Tofacitinib, an oral Janus kinase inhibitor, in active ulcerative colitis, The New England Journal of Medicine 367, 616-24 (2012). Published information on this trial indicates that patients receiving twice a day (BID) doses of 0.5, 3, 10 and 15 mg achieved clinical response rates of 32, 48, 61 and 78%, respectively, compared to 42% observed in placebo. It was further reported that the secondary end point of clinical remission (Mayo score ≤2) was 13, 33, 48 and 41% compared to 10% observed in placebo. See, e.g., The New England Journal of Medicine 367, 616-24 (2012), cited above. In a Phase 3 UC clinical trial, 88 out of 476 patients reportedly achieved clinical remission following 8 weeks of treatment with tofacitinib (10 mg BID) compared to 10 out of 122 patients receiving placebo treatment. See W. J. Sandborn, et al. Efficacy and safety of oral tofacitinib as induction therapy in patients with moderate-to-severe ulcerative colitis: results from 2 phase 3 randomised controlled trials, J. Crohns Colitis 10, S15-S (2016). Reports on Crohn's disease indicate that tofacitinib was also in development for the treatment of CD; however, it was reportedly discontinued due to failure to achieve clinical efficacy in a 4 week/Phase 2 clinical trial for moderate to severe CD. See W. J. Sandborn, et al., A phase 2 study of tofacitinib, an oral Janus kinase inhibitor, in patients with Crohn's disease, Clinical gastroenterology and hepatology: The official clinical practice journal of the American Gastroenterological Association 12, 1485-93 e2 (2014). Based on consulted publicly available literature, it is currently unclear whether the tofacitinib failure in CD relates to clinical study design, mechanistic differences between UC and CD or dose-limiting systemic adverse events. See Pharmacological Research 76, 1-8 (2013), cited above; Clinical gastroenterology and hepatology: the official clinical practice journal of the American Gastroenterological Association 12, 1485-93 e2 (2014), cited above; and C. J. Menet, et al., Triazolopyridines as selective JAK1 inhibitors: from hit identification to GLPG0634, J. Med. Chem. 57, 9323-42 (2014). In light of the features of this JAK inhibitor, it is desirable to find additional JAK inhibitors for the prevention and/or control of excessive inflammatory response.

Systemic adverse events have been reported with respect to both Phase 2 and Phase 3 inflammatory bowel disease (IBD) clinical trials with tofacitinib. See The New England Journal of Medicine 367, 616-24 (2012), cited above; Clinical gastroenterology and hepatology: the official clinical practice journal of the American Gastroenterological Association 12, 1485-93 e2 (2014), cited above; and J. Panes, et al. Efficacy and safety of oral tofacitinib for induction therapy in patients with moderate-to-severe Crohn's disease: results of a Phase 2b randomised placebo-controlled trial, J. Crohns Colitis 10, S18-S19 (2016). These adverse events include decreased absolute neutrophil counts (ANC), elevated total cholesterol (low and high-density lipid), intestinal perforation, and infection. Such adverse events are consistent with those observed following tofacitinib treatment in rheumatoid arthritis (RA) patients (see, for example, J. M. Kremer, et al. The safety and efficacy of a JAK inhibitor in patients with active rheumatoid arthritis: Results of a double-blind, placebo-controlled phase IIa trial of three dosage levels of CP-690,550 versus placebo, Arthritis and Rheumatism 60, 1895-905 (2009)), some of which likely result from either JAK2 dependent inhibition of EPO, TPO and colony stimulating factors (csf-2 and GM-CSF (granulocyte macrophage-colony stimulating factor)) and/or JAK1 dependent inhibition of IL-6. See, Arthritis and Rheumatism 60, 1895-905 (2009), cited above; and O. H. Nielsen, et al., Will novel oral formulations change the management of inflammatory bowel disease? Expert opinion on investigational drugs 25, 709-18 (2016).

In reference to FIG. 1, an orally administered medication can in principle follow the gastro-intestinal tract from the mouth to the esophagus (1), to the stomach (2) through the duodenum (3) to the jejunum (4), then to the ileum (5), and then to the colon (6). The relative absorption areas for such various parts are approximately 60% for the jejunum (4), approximately 26% for the ileum (5), and approximately 13% for the colon (6). Absorption through these various gastro-intestinal regions can lead to the onset of systemic distribution that in turn could lead to undesirable side-effects. The gastro-intestinal tract has a very large surface area. See, for example, H. F. Helander, et al., Surface area of the digestive tract—revisited, Scandinavian Journal of Gastroenterology 49(6), 681-89 (2014); and K. J. Filipski, et al., Intestinal Targeting of Drugs: Rational Design Approaches and Challenges Current Topics in Medicinal Chemistry 13, 776-802 (2013). Such an extensive absorption surface area favors systemic distribution of substances that can go through the walls of the various parts of the intestinal tract and into the blood stream, and in turn have the potential to lead to unwanted side effects of a systemically distributed substance. Systemic distribution is represented by dashed line arrows in FIG. 1 as permeating through the colon walls for simplified illustrative purposes, but such distribution is not limited to the colon walls, for it also can take place through the walls of other parts of the gastrointestinal tract shown in FIG. 1, such as those of the small intestine. It is also understood that the dashed arrow lines in FIG. 1 represent systemic distribution beyond the gastrointestinal track as such systemic distribution is known to take place in reference to the gastrointestinal track physiology, and that such dashed line arrows simply refer in a schematic illustrative manner to such systemic distribution. See, for example, Current Topics in Medicinal Chemistry 13, 777-80 (2013), cited above, for a description of intestinal tissue, transport across the same, and metabolism.

One major reason for attrition in drug candidates is safety and tolerability. See, for example, I. Kola, et al., Can the pharmaceutical industry reduce attrition rates? Nature Reviews Drug discovery 3, 711-5 (2004); M. J. Waring, et al., An analysis of the attrition of drug candidates from four major pharmaceutical companies. Nature Reviews Drug Discovery 14, 475-86 (2015); M. Hay, et al., Clinical development success rates for investigational drugs, Nature Biotechnology 32, 40-51 (2014); and M. E. Bunnage, Getting pharmaceutical R&D back on target, Nature Chemical Biology 7, 335-9 (2011). Increasing local tissue concentrations of compound to the intended target tissue, while limiting exposure to other tissue, can reduce unwanted side effects. See, for example, V. P. Torchilin, Drug targeting. European Journal of Pharmaceutical Sciences: Official Journal of the European Federation for Pharmaceutical Sciences 11 Suppl 2, S81-91 (2000). This concept has widely been accepted for certain diseases and tissues, such as eye (see, for example, R. Gaudana, et al., Ocular drug delivery, The AAPS Journal 12, 348-60 (2010)), skin (see, for example, R. Folster-Holst, et al., Topical hydrocortisone 17-butyrate 21-propionate in the treatment of inflammatory skin diseases: pharmacological data, clinical efficacy, safety and calculation of the therapeutic index, Die Pharmazie 71, 115-21 (2016)), and lung (see, for example, J. S. Patil, et al., Pulmonary drug delivery strategies: A concise, systematic review, Lung India: official organ of Indian Chest Society 29, 44-9 (2012)). Similar to these tissue-targeting approaches, increasing intestinal drug concentrations while limiting unwanted drug levels in other tissue can increase safety margins. See, for example, I. R. Wilding, et al., Targeting of drugs and vaccines to the gut, Pharmacology & Therapeutics 62, 97-124 (1994); D. Charmot, Non-systemic drugs: a critical review, Current Pharmaceutical Design 18, 1434-45 (2012); and Current Topics in Medicinal Chemistry 13, at 780 (2013), cited above. Tissue-selective modulation of targets in the gastrointestinal tissue with compounds achieving limited systemic exposures can potentially improve the therapeutic index of such compounds for the treatment of diseases of the gastrointestinal tract including ulcerative colitis and Crohn's disease. See, for example, O. Wolk, et al., New targeting strategies in drug therapy of inflammatory bowel disease: mechanistic approaches and opportunities, Expert Opin. Drug Deliv. 10(9), 1275-86 (2013). The term "systemic effects" is used herein to refer to systemic exposure and the effects of any such systemic exposure, even though they are not always the same.

Because some known JAK inhibitors have adverse effects that are associated with their systemic effects, it is desirable to find new JAK inhibitors as active substances for the prevention and/or control of excessive inflammatory response and whose systemic effects are eliminated or reduced. It is furthermore desirable to find JAK inhibitors with local effects on gastro-intestinal tissues for the treatment of conditions such as, but not limited to IBD, with reduced systemic effects. Because of the role played by the various JAK proteins, it is furthermore desirable to find pan-JAK inhibitors.

Intestinal tissue targeting can in principle be pursued according to multiple strategies. See, for example, Current Topics in Medicinal Chemistry 13, at 780-95 (2013), cited above, referring to approaches that include physicochemical property approaches, transport-mediated approaches, prodrug approaches, and formulation and technology approaches. It is acknowledged, however, that a "number of challenges and pitfalls exist that are endemic to tissue targeting programs" and in particular to intestinally targeted compounds, as described in Current Topics in Medicinal Chemistry 13, at 795 (2013), cited above.

IBD conditions can extend to multiple parts of the gastrointestinal tract. Even though for simplified illustrative purposes only a colonic disease site (10) is shown in the descending colon in FIG. 1, inflammatory bowel disease may affect any part of the gastrointestinal tract as is the case with Crohn's disease, or in the rectum and colon, as with ulcerative colitis. See, for example, NIDDK (National Institute of Diabetes, and Digestive and Kidney Diseases, National Institutes of Health, US Department of Health and Human Services, <http://spotidoc.com/doc/71780/crohns-disease---national-digestive-diseases-information>, accessed Nov. 29, 2016. IBD disease sites can be, for example, (ileum-located), ileocolic (affecting portions of the ileum and colon), and colonic (located in the colon, as illustratively shown in the descending colon in FIG. 1). So, in certain disease scenarios, a drug delivery along the entire or a large portion of the intestinal tract may be desirable. In other disease scenarios, it may be desirable to increase local concentration at any given portion of the gastrointestinal tract. Still in other scenarios, a combination of these two forms of delivery at different sites in the intestinal tract could be desirable.

One of such scenarios would focus on the delivery of an active substance that has limited systemic effects due to limited absorption when passing through the gastrointestinal tract as exemplified by the solid line arrows in FIG. 1, while being available to act in extensive portions of the gastrointestinal (GI) tract, a feature that is referred to herein as "local GI effects". Because of reduced systemic effects, a wider range of dosages could be evaluated for such substance. It would be further desirable if such active substance had low permeability, so that only a small amount passes through the intestinal wall into the blood stream to limit undesirable adverse side effects when it reaches non-targeted areas.

In addition, JAK inhibitors are envisaged as treatment candidates for other diseases. They are envisaged for use in the treatment of ocular conditions including dry eye (Colligris, B., et al., Recent developments on dry eye disease treatment compounds, Saudi J. Ophthalmol. 28(1), 19-30 (2014)), myeloproliferative neoplasms, myeloproliferative diseases (E. J. Baxter, et al., Acquired mutation of the tyrosine kinase JAK2 in human myeloproliferative disorders, Lancet 365, 1054-1061 (2005); C. James, et al., A unique clonal JAK2 mutation leading to constitutive signalling causes polycythaemia vera, Nature 434, 1144-1148 (2005); R. Kralovics, et al., A gain-of-function mutation of JAK2 in myeloproliferative disorders, N. Engl. J. Med. 352, 1779-1790 (2005); R. L. Levine, et al., Activating mutation in the tyrosine kinase JAK2 in polycythemia vera, essential thrombocythemia, and myeloid metaplasia with myelofibrosis, Cancer Cell 7, 387-397 (2005); G. Wernig, et al., Efficacy of TG101348, a selective JAK2 inhibitor, in treatment of a murine model of JAK2V617F-induced polycythemia vera, Cancer Cell 13, 311-320 (2008)), myeloproliferative syndrome, acute myeloid leukemia, systemic inflammatory response syndrome, systemic onset juvenile rheumatoid arthritis, juvenile idiopathic arthritis (H. W. Li, et al., Effect of miR-19a and miR-21 on the JAK/STAT signaling pathway in the peripheral blood mononuclear cells of patients with systemic juvenile idiopathic arthritis, Exp. Ther. Med. 11(6), 2531-2536 (2016)), type III hypersensitivity reactions, type IV hypersensitivity, inflammation of the aorta, iridocyclitis/uveitis/optic neuritis, juvenile spinal muscular atrophy, diabetic retinopathy, diabetic kidney disease including diabetic nephropathy (F. C. Brosius, et al., JAK inhibition in the treatment of diabetic kidney disease, Diabetologia 59(8), 1624-7, (2016); C. C. Berthier, et al., Enhanced expression of Janus kinase-signal transducer and activator of transcription pathway members in human diabetic nephropathy, Diabetes 58(2), 469-77, (2009); E. N. Gurzov, et al., The JAK/STAT pathway in obesity and diabetes, FEBS J. 283(16), 3002-15 (2016)), microangiopathy, inflammation (M. Kopf, et al., Averting inflammation by targeting the cytokine environment, Nature Reviews Drug Discovery 9, 703-718 (2010); J. J. O'Shea, et al., A new modality for immunosuppression: targeting the JAK/STAT pathway, Nature Rev. Drug Discov. 3, 555-564 (2004)) chronic inflammation, inflammatory bowel disease including ulcerative colitis (UC) and Crohn's disease (R. H. Duerr, et al., A genome-wide association study identifies IL23R as an inflammatory bowel disease gene, Science 314, 1461-1463 (2006); M. Coskun, et al., Involvement of JAK/STAT signaling in the pathogenesis of inflammatory bowel disease, Pharmacol. Res. 76, 1-8 (2013); M. J. Waldner, et al., Master regulator of intestinal disease: IL-6 in chronic inflammation and cancer development, Semin. Immunol. 26(1), 75-9 (2014); S. Danese, et al., JAK inhibition using tofacitinib for inflammatory bowel disease treatment: a hub for multiple inflammatory cytokines, Am. J. Physiol. Gastrointest. Liver Physiol. 310(3), G155-62 (2016); W. Strober, et al., Proinflammatory cytokines in the pathogenesis of inflammatory bowel diseases, Gastroenterology 140, 1756-1767 (2011)), allergic diseases, vitiligo, atopic dermatitis (R. Bissonnette, et al., Topical tofacitinib for atopic dermatitis: a phase IIa randomized trial, Br. J. Dermatol. 175(5), 902-911 (2016); W. Amano, et al., JAK inhibitor JTE-052 regulates contact hypersensitivity by downmodulating T cell activation and differentiation, J. Dermatol. Sci. 84, 258-265 (2016); T. Fukuyama, et al., Topically Administered Janus-Kinase Inhibitors Tofacitinib and Oclacitinib Display Impressive Antipruritic and Anti-Inflammatory Responses in a Model of Allergic Dermatitis, J. Pharmacol. Exp. Ther. 354(3), 394-405 (2015)), alopecia areata (A. K. Alves de Medeiros, et al., JAK3 as an Emerging Target for Topical Treatment of Inflammatory Skin Diseases, PLoS One 11(10) (2016); L. Xing, et al., Alopecia areata is driven by cytotoxic T lymphocytes and is reversed by JAK inhibition, Nat. Med. 20(9), 1043-9 (2014)), dermatitis scleroderma, acute or chronic immune disease associated with organ transplantation (P. S. Changelian, et al. Prevention of organ allograft rejection by a specific Janus kinase 3 inhibitor, Science 302, 875-878 (2003); F. Behbod, et al. Concomitant inhibition of Janus kinase 3 and calcineurin-dependent signaling pathways synergistically prolongs the survival of rat heart allografts, J. Immunol, 166, 3724-3732 (2001); S. Busque, et al., Calcineurin-inhibitor-free immunosuppression based on the JAK inhibitor CP-690,550: a pilot study in de novo kidney allograft recipients, Am. J. Transplant, 9, 1936-1945 (2009)), psoriatic arthropathy, ulcerative colitic arthropathy, autoimmune bullous disease, autoimmune haemolytic anaemia, rheumatoid arthritis (J. M. Kremer, et al., A randomized, double-blind placebo-controlled trial of 3 dose levels of CP-690,550 versus placebo in the treatment of active rheumatoid arthritis, Arthritis Rheum. 54 (annual meeting abstract), L40 (2006); W. Williams, et al., A randomized placebo-controlled study of INCBO 018424, a selective Janus kinase1&2 (JAK1&2) inhibitor in rheumatoid arthritis (RA), Arthritis Rheum. 58, S431 (2008); N. Nishimoto, et al., Study of active controlled monotherapy used for rheumatoid arthritis, an IL-6 inhibitor (SAMURAI): evidence of clinical and radiographic benefit from an x ray reader-blinded randomised controlled trial of tocilizumab, Ann. Rheum. Dis. 66(9), 1162-7 (2007)), rheumatoid arthritis associated interstitial lung disease, systemic lupus erythematosus (A. Goropevšek, et al., The Role of STAT Signaling Pathways in the Pathogenesis of Systemic Lupus Erythematosus, Clin. Rev. Allergy Immunol. (on-line pre-publication) <http://www.docguide.com/role-stat-signaling-pathways-pathogenesis-systemic-lupus-erythematosus?tsid=5> May 23, 2016; M. Kawasaki, et al., Possible role of the JAK/STAT pathways in the regulation of T cell-interferon related genes in systemic lupus erythematosus, Lupus. 20(12), 1231-9 (2011); Y. Furumoto, et al., Tofacitinib ameliorates murine lupus and its associated vascular dysfunction, Arthritis Rheumatol., (on-line pre-publication) <https://www.ncbi.nlm.nih.gov/pubmed/27429362> Jul. 18, 2016)), systemic lupus erythematosus associated lung disease, dermatomyositis/polymyositis associated lung disease, asthma (K. Vale, Targeting the JAK/STAT pathway in the treatment of 'Th2-high' severe asthma, Future Med. Chem. 8(4), 405-19 (2016)), ankylosing spondylitis (AS) (C. Thompson, et al., Anti cytokine therapy in chronic inflammatory arthritis, Cytokine 86, 92-9 (2016)), AS-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, psoriasis (C. L. Leonardi, et al., Efficacy and safety of ustekinumab, a human interleukin-12/23 monoclonal antibody, in patients with psoriasis: 76-week results from a randomised, double-blind, placebo-controlled trial (PHOENIX 1), Lancet 371, 1665-1674 (2008); G. Chan, et al., Dose-dependent reduction in psoriasis severity as evidence of immunosuppressive activity of an oral Jak3 inhibitor in humans, Am. J. Transplant. 6, S87 (2006); K. A. Papp, et al., Efficacy and safety of tofacitinib, an oral Janus kinase inhibitor, in the treatment of psoriasis: a phase 2b randomized placebo-controlled dose-ranging study, Br. J. Dermatol. 167, 668-677 (2012); M. Cargill, et al. A large-scale genetic association study confirms IL12B and leads to the identification of IL23R as psoriasis-risk genes, Am. J. Hum. Genet. 80, 273-290 (2007)), psoriasis type 1, psoriasis type 2, plaque psoriasis, moderate to severe chronic plaque psoriasis, autoimmune neutropaenia, sperm autoimmunity, multiple sclerosis (all subtypes, B. M. Segal, et al., Repeated subcutaneous injections of IL 12/23 p40 neutralising antibody, ustekinumab, in patients with relapsing-remitting multiple sclerosis: a phase II, double-blind, placebo-controlled, randomised, dose-ranging study, Lancet Neurol. 7, 796-804 (2008); Z. Yan, et al., Role of the JAK/STAT signaling pathway in regulation of innate immunity in neuroinflammatory diseases, Clin. Immunol. (online pre-publication) <https://www.ncbi.nlm.nih.gov/pubmed/27713030>, accessed Oct. 3, 2016; E. N. Benveniste, et al., Involvement of the janus kinase/signal transducer and activator of transcription signaling pathway in multiple sclerosis and the animal model of experimental autoimmune encephalomyelitis, J. Interferon Cytokine Res. 34(8), 577-88 (2014); Y. Liu, et al., Therapeutic efficacy of suppressing the Jak/STAT pathway in multiple models of experimental autoimmune encephalomyelitis, J. Immunol. 192(1), 59-72 (2014)), acute rheumatic fever, Sjögren's syndrome, Sjögren's syndrome/disease associated lung disease (T. Fujimura, et al., Significance of Interleukin-6/STAT Pathway for the Gene Expression of REG Iα, a New Autoantigen in Sjögren's Syndrome Patients, in Salivary Duct Epithelial Cells, Clin. Rev. Allergy Immunol. (online pre-publication) <https://www.ncbi.nlm.nih.gov/pubmed/27339601> Jun. 24, 2016), autoimmune thrombocytopaenia, neuroinflammation including Parkinson's disease (Z. Yan, et al., Oct. 3, 2016, cited above). JAK inhibitors have been reported as having therapeutic applications in cancer treatment in addition to inflammatory diseases. (S. J. Thomas, et al., The role of JAK/STAT signaling in the pathogenesis, prognosis and treatment of solid tumors, British J. Cancer 113, 365-71 (2015); A. Kontzias, et al., Jakinibs: A new class of kinase inhibitors in cancer and autoimmune disease, Current Opinion in Pharmacology, 12(4), 464-70 (August 2012); M. Pesu, et al., Therapeutic targeting of JANUS kinases, Immunological Reviews, 223, 132-42 (June 2008); P. Norman, Selective JAK inhibitors in development for rheumatoid arthritis, Expert Opinion on Investigational Drugs, 23(8), 1067-77 (August 2014)). In addition, JAK inhibitors could be useful in the prevention of colorectal cancer because inflammation reduction in the colon could lead to cancer prevention in such organ.

BRIEF SUMMARY OF THE INVENTION

Embodiments of the present invention relates to certain imidazopyrrolopyridine compounds, pharmaceutical compositions containing them, methods of making them, and methods of using them as JAK inhibitors and for the treatment of disease states, disorders, and conditions mediated by JAK.

Some embodiments of this invention are provided by compounds of Formula I. Further embodiments of this invention are provided by compounds of Formula II. The term "compounds of the invention" and "compound of the invention" is intended to encompass at least one compound selected from the below list of compounds, whether in a solvent-free form or in any one of hydrated and/or solvated forms as illustrated herein.

The present invention relates to compounds, pharmaceutical compositions containing them, methods of making and purifying them, methods of using them as JAK inhibitors and methods for using them the treatment of disease states, disorders, and conditions mediated by JAK.

Embodiments of this invention exhibit pan-JAK inhibition effects with local GI effects and low or negligible systemic effects. Furthermore, embodiments of this invention with such features can be orally administered.

An additional embodiment of the invention is a method of treating a subject suffering from or diagnosed with a disease, disorder, or medical condition mediated by JAK using compounds of the invention or active agents of the invention.

Additional embodiments, features, and advantages of the invention will be apparent from the following detailed description and through practice of the invention.

An embodiment of the invention is a compound of Formula I, or a pharmaceutically acceptable salt thereof

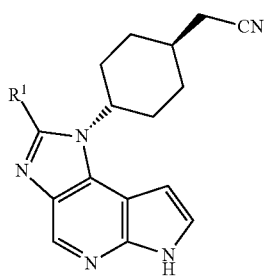

I wherein $R^1$ is selected from the group consisting of

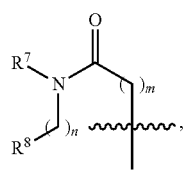

(a)

wherein
m is 0 or 1;
n is 0 or 1;

$R^7$ and $R^8$ are independently selected from the group consisting of H, $C_1$-$C_6$alkyl, $C_1$-$C_6$perhaloalkyl, $C_3$-$C_{10}$cycloalkyl, $C_3$-$C_7$heterocyclyl, phenyl, and 5- or 6-membered heteroaryl;
  wherein in each of said $R^7$ and $R^8$, each of $C_1$-$C_6$alkyl, $C_1$-$C_6$perhaloalkyl, $C_3$-$C_{10}$cycloalkyl, $C_3$-$C_7$heterocyclyl, phenyl, and 5- or 6-membered heteroaryl are optionally substituted with one or two substituents selected from the group consisting of halo, —OH, —CN, $C_1$-$C_4$alkyl, —$OC_1$-$C_6$alkyl, —$OC_1$-$C_4$perhaloalkyl, phenyl, —O-pyridine, —Si($CH_3$)$_3$, —($OCH_2CH_2$)$_2$—$NH_2$, —C(O)$NH_2$, —C(OH)(CF$_3$)$_2$, —(CH$_2$)P(O)(OCH$_2$CH$_3$)$_2$, $CH_2CN$ and $CH_2OH$; or $R^7$ and $R^8$ are taken together with the nitrogen to which they are attached to form a 4-to-7-membered heterocyclic ring,
  wherein said 4-to-7-membered heterocyclic ring contains 1-2 heteroatoms, wherein said heteroatoms are selected from the group consisting of O, N, and S(O)$_p$, p being 0, 1 or 2;
  said 4-to-7-membered heterocyclic ring is optionally substituted with one or two substituents selected from the group consisting of OH, CN, $CH_2OH$, —CH($CH_3$)$_2$OH, $CH_2CN$, —C(O)$CH_3$, $C_1$-$C_6$alkyl, morpholino, $C_1$-$C_3$perhaloalkyl, phenyl, benzyl, pyridyl, fluoro, and $OC_1$-$C_6$ alkyl;

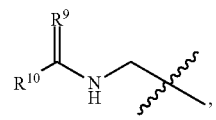

(b)

wherein $R^9$ is selected from the group consisting of NH, N—OH and O; and
$R^{10}$ is selected from the group consisting of $C_1$-$C_6$ alkyl, $C_3$-$C_{10}$cycloalkyl, phenyl, benzyl, pyrazolyl, $OC_1$-$C_6$ alkyl, phenoxy, NH$_2$, —NHCH$_2$—$C_3$-$C_{10}$cycloalkyl, —NHC$_1$-$C_6$alkyl, and —NHphenyl; wherein in said $R^{10}$, each of $C_1$-$C_6$ alkyl and phenyl is independently optionally substituted with one or two substituents selected from the group consisting of $C_3$-$C_{10}$cycloalkyl, piperidinyl, OH, CN and $OC_1$-$C_6$ alkyl;

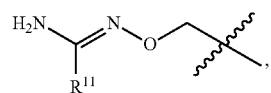

(c)

wherein $R^{11}$ is selected from the group consisting of phenyl, $C_3$-$C_{10}$cycloalkyl, and $C_1$-$C_6$ alkyl, wherein in said $R^{11}$, $C_1$-$C_6$ alkyl is optionally substituted with one or two substituents selected from the group consisting of $OC_1$-$C_6$ alkyl, $C_3$-$C_{10}$cycloalkyl and piperidinyl;

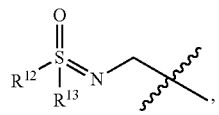

(d)

wherein $R^{12}$ and $R^{13}$ are independently selected from the group consisting of $C_1$-$C_3$alkyl and phenyl;

(e) $CH_2OR^{14}$,
wherein $R^{14}$ is selected from the group consisting of $C_1$-$C_6$ alkyl, —C(O)NHCH$_2$CH$_2$OCH$_3$,

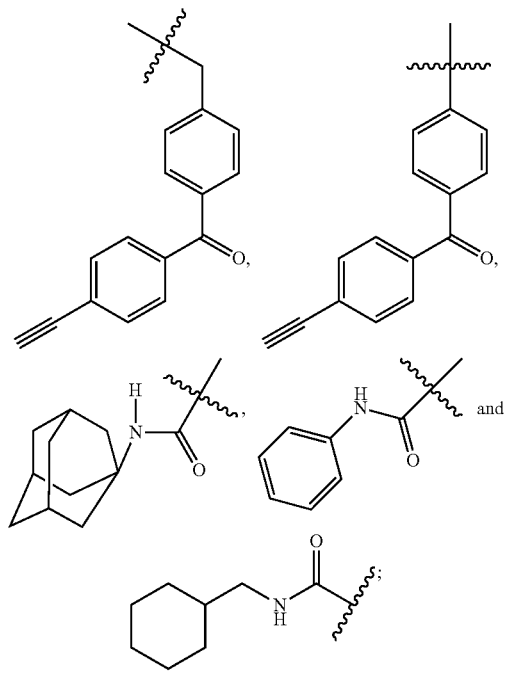

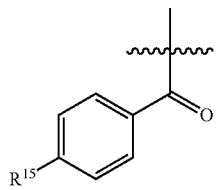

(f) either cyclohexyl that is optionally substituted with Si(CH$_3$)$_3$ or phenyl that is optionally substituted with one or two substituents selected from the group consisting of —CN, SF$_5$, -4-SO$_2$CH$_3$-phenyl, and

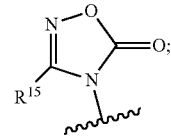

wherein $R^{15}$ is selected from the group consisting of H, —CN, CH$_2$OH and —C≡CH;
(g) 5- or 6-membered heteroaryl ring HR optionally containing 1-4 heteroatoms selected from the group consisting of O, N and S, said 5- or 6-membered heteroaryl ring HR being optionally substituted with one or two substituents selected from the group consisting of halo, $C_3$-$C_4$cycloalkyl, $C_1$-$C_6$alkyl, phenyl, —CH$_2$oxazolyl, —CH$_2$C(O)NHcyclopropyl, —CH$_2$C(O)$_2$CH$_2$CH$_3$, —CH$_2$C(CH$_3$)$_2$OH, CN, NH$_2$, NHCH$_3$ and SCH$_3$;
(h) $C_4$-$C_7$ heterocyclic ring, wherein said $C_4$-$C_7$ heterocyclic ring is optionally substituted with one or two substituents selected from the group consisting of —CO$_2$CH$_2$CH$_3$, —SO$_2$CH$_3$, —COCH$_3$, CH$_2$C(CH$_3$)$_3$, C(CH$_3$)$_3$, CH$_3$, C(O)CH$_2$CN, CH$_2$C(OH)(CH$_3$)$_2$ and 4-CN-phenyl;
(i) —CH$_2$—NR$^4$R$^5$, wherein each of R$^4$ and R$^5$ is independently selected from the group consisting of H and SO$_2$R$^6$, wherein R$^6$ is selected from the group consisting of cyclohexyl, phenyl optionally substituted with CN and $C_1$-$C_5$alkyl optionally substituted with CN;
(j) —CH$_2$-A, wherein A is selected from the group consisting of
5-membered heteroaryl ring selected from the group consisting of thiazolo, imidazolyl, pyrrolyl and pyrazolyl;
heterocyclic ring

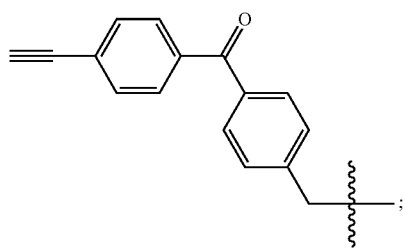

wherein $R^{15}$ is selected from the group consisting of phenyl, cyclopropyl and isopropyl; and

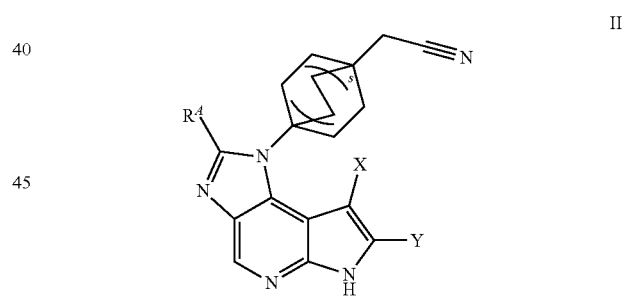

and
(k) —(CH$_2$)$_s$—(OCH$_2$CH$_2$)$_q$OCH$_3$, wherein s is 1 or 2, and q is 1, 2 or 3.

An additional embodiment of the invention is a compound of Formula II, or a pharmaceutically acceptable salt thereof

II

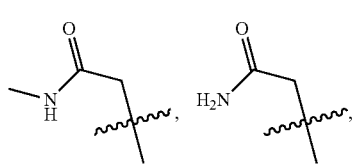

wherein s is 0 or 1, provided that
when s is 1, then X is selected from the group consisting of H, halo and
methyl;
when s is 0, then X is halo or methyl;
Y is CH$_3$ or H; and
R$^4$ is selected from the group consisting of

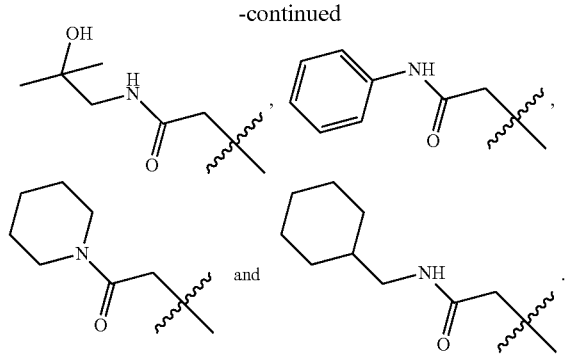

Figure 1:
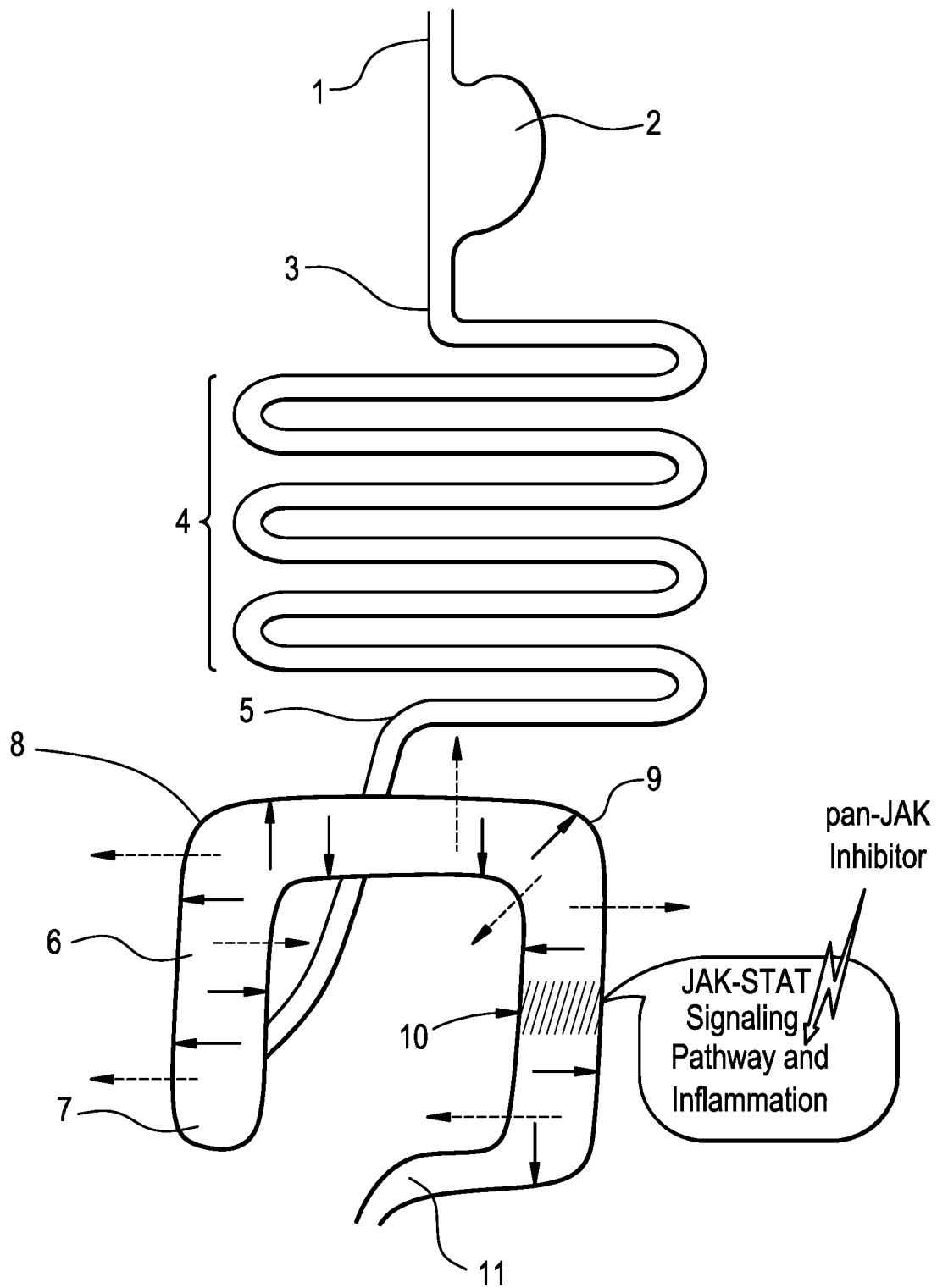
FIG. 1.

Schematic diagram of part of the human gastrointestinal tract, shown as a not-at-scale stretched rendering. The duodenum (3), jejunum (4), and ileum (5) (all schematically shown) form the small intestine after the stomach (2) and esophagus (1). The large intestine comprises the colon (6), in turn including the cecum (7) and appendix (not shown), ascending colon, transverse colon, descending colon, sigmoid colon (loop in the same not shown), and rectum (11). The transverse colon is the portion comprised between the right (8) and left (9) colonic flexures, the ascending colon extends from the cecum (7) to the right colonic flexure (8), and the descending colon extends from the left colonic flexure (9) to the rectum (11). Various distribution patterns are illustrated in reference to the colon for convenience, but they can also refer to other parts of the gastrointestinal tract. Systemic distribution is represented by dashed line arrows in FIG. 1 as permeating through the colon walls for simplified illustrative purposes, but such distribution is not limited to the colon walls, for it also can take place through the walls of other parts of the gastrointestinal tract shown in FIG. 1, such as those of the small intestine. Distribution with some tissue penetration is represented by solid line arrows in FIG. 1 as penetrating the colon tissue for simplified illustrative purposes, but such penetration is not limited to the colon tissue, for it also can take place in the tissue of other parts of the gastrointestinal tract shown in FIG. 1, such as the tissue of the small intestine. The effect of an embodiment of a JAK inhibitor according to this invention is illustratively shown as disrupting the JAK/STAT signaling pathway that otherwise would lead to inflammation associated with an inflammatory bowel disease ("IBD"), such as Crohn's disease or ulcerative colitis. By way of example, but not as a limitation, a disease site is illustratively shown as a colonic disease site (10) in the descending colon.

FIG. 2.

Schematic diagram showing the preparation/interconversion of embodiments of compound Ex. 1.

FIG. 3.

Overlay of high throughput X-ray powder diffraction (HT-XRPD) patterns for the following embodiments of compound Ex. 1, from bottom to top: 1s, 2 (obtained by equilibration at room temperature in 1,4-dioxane), 3b (obtained by thermocycling in cyclohexanone), 1b+4 (obtained by cooling crystallization at μL scale in methanol/water (50/50, v/v), 5 (obtained by thermocycling in chloroform), 6 (obtained by cooling crystallization at mL scale in acetonitrile), 7 (obtained of 1 s+7, in turn obtained by solvent equilibration in heptane), 7 (obtained by desolvation of 1 s+7, in turn obtained by solvent equilibration in heptane), 8 (obtained by desolvation of embodiment 5 by cycling differential scanning calorimetry)), and 9 (obtained by desolvation of embodiment 2 by cycling differential scanning calorimetry).

FIG. 4.

Overlay of high throughput X-ray powder diffraction (HT-XRPD) patterns for the following embodiments of compound Ex. 1, from bottom to top: is (starting material), 1a (obtained after exposure to accelerated aging conditions (AAC) (40° C. and 70% relative humidity) several forms of samples of embodiment 1s), 1b (obtained by solvent equilibration at room temperature in toluene), 1c (obtained by cooling crystallization at μL scale in ethyl acetate/1,4-dioxane (50/50, v/v)), 1d (obtained by cooling crystallization at μL scale in acetonitrile/chloroform (50/50, v/v)), 1e (obtained by cooling crystallization at μL scale in ethyl acetate/1,4-dioxane (50/50, v/v)), 1f (obtained by solvent equilibration at room temperature in p-xylene), 1 g (obtained by solvent equilibration at 50° C. in anisole), 1 h (obtained by cooling crystallization at μL scale in p-xylene).

FIG. 5.

Overlay of high throughput X-ray powder diffraction (HT-XRPD) patterns for the following embodiments of compound Ex. 1, from bottom to top: 1s, 3b (obtained by thermocycling in cyclohexanone), 3c (obtained by cooling crystallization at μL scale in 1,4-dioxane), 3d (obtained by cooling crystallization at μL screen in tetrahydrofuran), and 3e (obtained by thermocycling in isobutanol).

FIG. 6.

HR-XRPD diffractograms of embodiment 1s in its initial form ("1s"), after a four-day exposure to 40° C. and 70% relative humidity ("1s 70RH"), and after a four-day exposure to 25° C. and 100% relative humidity ("10").

DETAILED DESCRIPTION OF THE INVENTION

As used herein, the terms "including", "containing" and "comprising" are used in their open, non-limiting sense.

Unless qualified specifically in particular instances of use, the term "lower alkyl" or "low-alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_{1-4}$alkyl" refers to straight- or branched-chain alkyl group having from 1 to 4 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "aryl" refers to a monocyclic, aromatic carbocycle (ring structure having ring atoms that are all carbon) having 6 atoms per ring. (Carbon atoms in the aryl groups are $sp^2$ hybridized.)

The term "phenyl" represents the following moiety:

The term "heteroaryl" refers to a monocyclic heterocycle (ring structure having ring atoms selected from carbon atoms and up to four heteroatoms selected from nitrogen, oxygen, and sulfur) having from 5 to 6 ring atoms per heterocycle. Illustrative examples of heteroaryl groups include the following entities, in the form of properly bonded moieties:

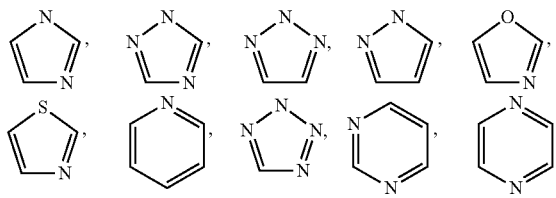

A "heterocycloalkyl" refers to a monocyclic ring structure that is saturated or partially saturated and has from 4 to 6 ring atoms per ring structure selected from carbon, oxygen and nitrogen. Illustrative entities, in the form of properly bonded moieties, include:

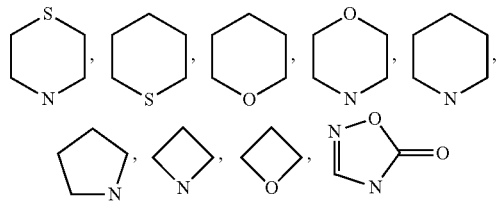

The term "cyano" refers to the group —CN.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

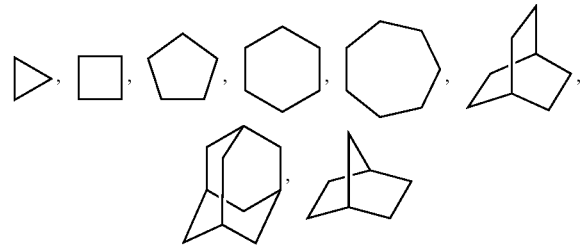

The term "halogen" represents chlorine, fluorine, bromine, or iodine. The term "halo" represents chloro, fluoro, bromo, or iodo.

The term "perhaloalkyl" or "haloalkyl" refers to a straight- or branched-chain alkyl group having from 1 to 6 carbon atoms in the chain optionally substituting hydrogens with halogens. The term "$C_{1-4}$haloalkyl" as used here refers to a straight- or branched-chain alkyl group having from 1 to 4 carbon atoms in the chain, optionally substituting hydrogens with halogens. The term "$C_{1-6}$haloalkyl" as used here refers to a straight- or branched-chain alkyl group having from 1 to 6 carbon atoms in the chain, optionally substituting hydrogens with halogens. Examples of "perhaloalkyl", "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

Those skilled in the art will recognize that the species of heteroaryl, cycloalkyl, and heterocycloalkyl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. Certain structures may exist as tautomers. Additionally, an amorphous form, hydrates, solvates, polymorphs and pseudopolymorphs of such compounds of this invention, and mixtures thereof, are also envisaged as parts of this invention.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—$COOH_{(s)}$, R—$COOH_{(sol)}$, and R—$COO^-_{(sol)}$. In this example, R—$COOH_{(s)}$ refers to the solid compound, as it could be for example in a tablet or some other solid pharmaceutical composition or preparation; R—$COOH_{(sol)}$ refers to the undissociated form of the compound in a solvent; and R—$COO^-_{(sol)}$ refers to the dissociated form of the compound in a solvent, such as the dissociated form of the compound in an aqueous environment, whether such dissociated form derives from R—COOH, from a salt thereof, or from any other entity that yields R—$COO^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—$COOH_{(aq)}$ and/or R—$COO^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, and oxygen such as $^2H$, $^3H$, $^{11}C$, $^{13}C$, $^{14}C$, $^{15}N$, $^{18}O$, and $^{17}O$, respectively. Such isotopically labeled compounds are useful in metabolic studies (preferably with $^{14}C$), reaction kinetic studies (with, for example deuterium (i.e., D or $^2H$); or tritium (i.e., T or $^3H$)), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased local in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The term $C_{n-m}$alkyl refers to an aliphatic chain, whether straight or branched, with a total number N of carbon members in the chain that satisfies $n \leq N \leq m$, with $m > n$.

"Tautomers" refer to compounds that are interchangeable forms of a particular compound structure, and that vary in the displacement of hydrogen atoms and electrons. Thus, two structures that have an H member in different positions may be in equilibrium while satisfying valency rules. For example, enols and ketones are tautomers because they are rapidly interconverted by treatment with either acid or base.

Certain examples contain chemical structures that are depicted as an (Z*) or (E*). When (Z*) or (E*) is used in the name of a compound, the absolute geometry of the corresponding double bond is unknown. The compound is a pure single isomer, but the absolute configuration has not been established. Thus, a compound designated as (Z*) refers to a compound with an absolute configuration of either (Z) or (E) and a compound designated as (E*) refers to a compound with an absolute configuration of either (Z) or (E). In cases where the absolute geometry has been confirmed, the structures are named using (Z) and (E).

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of Si and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of Si and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The nomenclature "$C_{i-j}$" with $j>i$, when applied herein to a class of substituents, is meant to refer to embodiments of this invention for which each and every one of the number of carbon members, from i to j including i and j, is independently realized. By way of example, the term $C_{1-4}$ refers independently to embodiments that have one carbon member ($C_1$), embodiments that have two carbon members ($C_2$), embodiments that have three carbon members ($C_3$), and embodiments that have four carbon members ($C_4$).

An embodiment of the invention is a compound of Formula I, or a pharmaceutically acceptable salt thereof

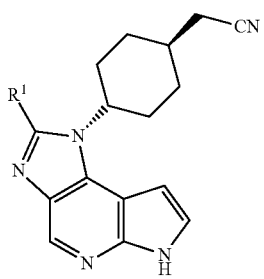

I wherein $R^1$ is selected from the group consisting of

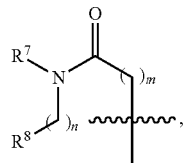

(a)

wherein
m is 0 or 1;
n is 0 or 1;
$R^7$ and $R^8$ are independently selected from the group consisting of H, $C_1$-$C_6$alkyl, $C_1$-$C_6$perhaloalkyl, $C_3$-$C_{10}$cycloalkyl, $C_3$-$C_7$heterocyclyl, phenyl, and 5- or 6-membered heteroaryl;
  wherein in each of said $R^7$ and $R^8$, each of $C_1$-$C_6$alkyl, $C_1$-$C_6$perhaloalkyl, $C_3$-$C_{10}$cycloalkyl, $C_3$-$C_7$heterocyclyl, phenyl, and 5- or 6-membered heteroaryl are optionally substituted with one or two substituents selected from the group consisting of halo, —OH, —CN, $C_1$-$C_4$alkyl, —O$C_1$-$C_6$alkyl, —O$C_1$-$C_4$perhaloalkyl, phenyl, —O-pyridine, —Si(CH$_3$)$_3$, —(OCH$_2$CH$_2$)$_2$—NH$_2$, —C(O)NH$_2$, —C(OH)(CF$_3$)$_2$, —(CH$_2$)P(O)(OCH$_2$CH$_3$)$_2$, CH$_2$CN and CH$_2$OH; or
$R^7$ and $R^8$ are taken together with the nitrogen to which they are attached to form a
4-to-7-membered heterocyclic ring,
  wherein said 4-to-7-membered heterocyclic ring contains 1-2 heteroatoms, wherein said heteroatoms are selected from the group consisting of O, N, and S(O)$_p$, p being 0, 1 or 2;

said 4-to-7-membered heterocyclic ring is optionally substituted with one or two substituents selected from the group consisting of OH, CN, CH$_2$OH, —CH(CH$_3$)$_2$OH, CH$_2$CN, —C(O)CH$_3$, $C_1$-$C_6$alkyl, morpholino, $C_1$-$C_3$perhaloalkyl, phenyl, benzyl, pyridyl, fluoro, and OC$_1$-$C_6$ alkyl;

(b)

wherein $R^9$ is selected from the group consisting of NH, N—OH and O; and
$R^{10}$ is selected from the group consisting of $C_1$-$C_6$ alkyl, $C_3$-$C_{10}$cycloalkyl, phenyl, benzyl, pyrazolyl, OC$_1$-$C_6$ alkyl, phenoxy, NH$_2$, —NHCH$_2$—$C_3$-$C_{10}$cycloalkyl, —NHC$_1$-$C_6$alkyl, and —NHphenyl; wherein in said $R^{10}$, each of $C_1$-$C_6$ alkyl and phenyl is independently optionally substituted with one or two substituents selected from the group consisting of $C_3$-$C_{10}$cycloalkyl, piperidinyl, OH, CN and OC$_1$-$C_6$ alkyl;

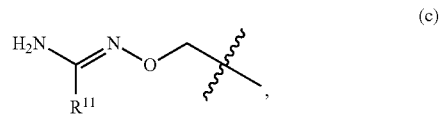

(c)

wherein $R^{11}$ is selected from the group consisting of phenyl, $C_3$-$C_{10}$cycloalkyl, and $C_1$-$C_6$ alkyl, wherein in said $R^{11}$, $C_1$-$C_6$ alkyl is optionally substituted with one or two substituents selected from the group consisting of OC$_1$-$C_6$ alkyl, $C_3$-$C_{10}$cycloalkyl and piperidinyl;

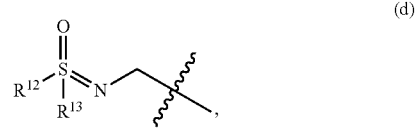

(d)

wherein $R^{12}$ and $R^{13}$ are independently selected from the group consisting of $C_1$-$C_3$alkyl and phenyl;
(e) CH$_2$OR$^{14}$,
wherein $R^{14}$ is selected from the group consisting of:
$C_1$-$C_6$ alkyl, —C(O)NHCH$_2$CH$_2$OCH$_3$,

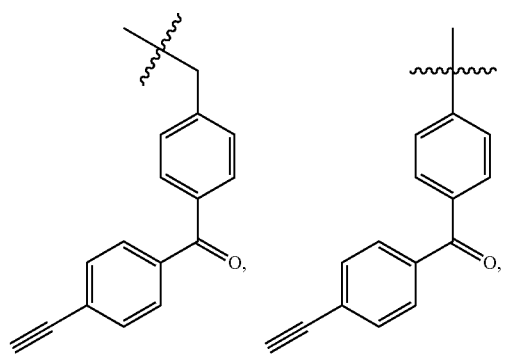

-continued

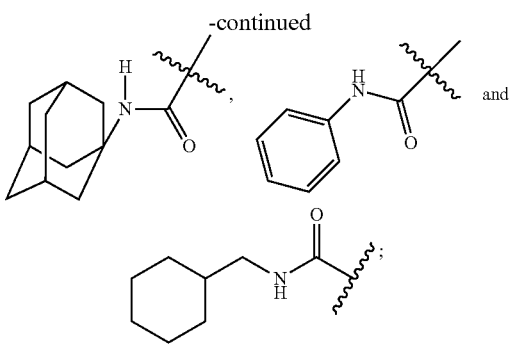 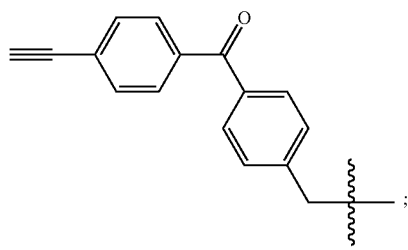 [SMILES: *Cc1ccc(C(=O)c2ccc(C#C)cc2)cc1]

(f) either cyclohexyl that is optionally substituted with Si(CH$_3$)$_3$ or phenyl that is optionally substituted with one or two substituents selected from the group consisting of —CN, SF$_5$, -4-SO$_2$CH$_3$-phenyl, and

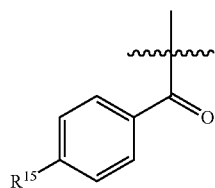

wherein R$^{15}$ is selected from the group consisting of H, —CN, CH$_2$OH and —C≡CH;

(g) 5- or 6-membered heteroaryl ring HR optionally containing 1-4 heteroatoms selected from the group consisting of O, N and S, said 5- or 6-membered heteroaryl ring HR being optionally substituted with one or two substituents selected from the group consisting of halo, C$_3$-C$_4$cycloalkyl, C$_1$-C$_6$alkyl, phenyl, —CH$_2$oxazolyl, —CH$_2$C(O)NHcyclopropyl, —CH$_2$C(O)$_2$CH$_2$CH$_3$, —CH$_2$C(CH$_3$)$_2$OH, CN, NH$_2$, NHCH$_3$ and SCH$_3$;

(h) C$_4$-C$_7$ heterocyclic ring, wherein said C$_4$-C$_7$ heterocyclic ring is optionally substituted with one or two substituents selected from the group consisting of —CO$_2$CH$_2$CH$_3$, —SO$_2$CH$_3$, —COCH$_3$, CH$_2$C(CH$_3$)$_3$, C(CH$_3$)$_3$, CH$_3$, C(O)CH$_2$CN, CH$_2$C(OH)(CH$_3$)$_2$ and 4-CN-phenyl;

(i) —CH$_2$—NR$^4$R$^5$, wherein each of R$^4$ and R$^5$ is independently selected from the group consisting of H and SO$_2$R$^6$, wherein R$^6$ is selected from the group consisting of cyclohexyl, phenyl optionally substituted with CN and C$_1$-C$_5$alkyl optionally substituted with CN;

(j) —CH$_2$-A, wherein A is selected from the group consisting of 5-membered heteroaryl ring selected from the group consisting of thiazolo, imidazolyl, pyrrolyl and pyrazolyl;

heterocyclic ring

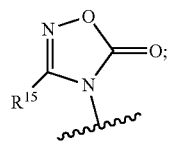

wherein R$^{15}$ is selected from the group consisting of phenyl, cyclopropyl and isopropyl; and and (k) —(CH$_2$)$_s$—(OCH$_2$CH$_2$)$_q$OCH$_3$, wherein s is 1 or 2, and q is 1, 2 or 3.

An additional embodiment of the invention is a compound of Formula II, or a pharmaceutically acceptable salt thereof

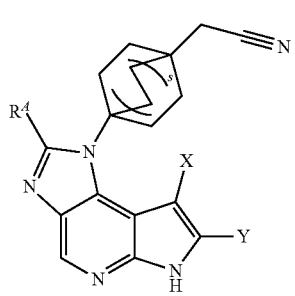

II wherein s is 0 or 1, provided that when s is 1, then X is selected from the group consisting of H, halo and methyl;

when s is 0, then X is halo or methyl;

Y is CH$_3$ or H; and

R$^A$ is selected from the group consisting of

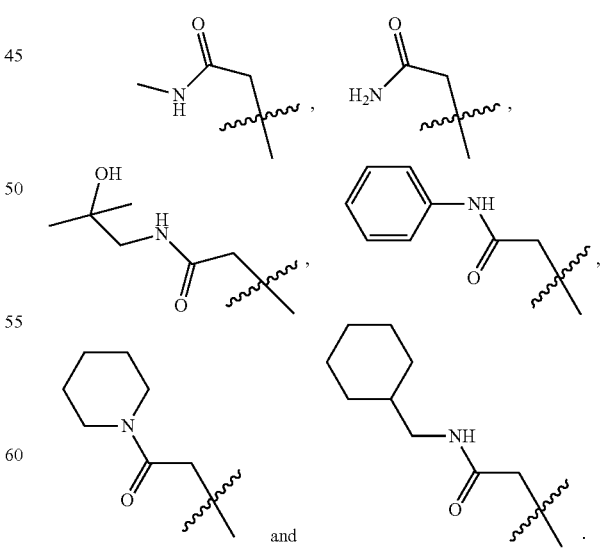

A further embodiment of the invention is a compound of Formula I, wherein R$^1$ is

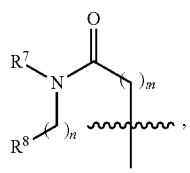

wherein
m is 0 or 1;
n is 0 or 1;
R[7] and R[8] are independently selected from the group consisting of H, $C_1$-$C_6$alkyl, $C_1$-$C_6$perhaloalkyl, $C_3$-$C_{10}$cycloalkyl, $C_3$-$C_7$heterocyclyl, phenyl, and 5- or 6-membered heteroaryl;
   wherein in each of said R[7] and R[8], each of $C_1$-$C_6$alkyl, $C_1$-$C_6$perhaloalkyl, $C_3$-$C_{10}$cycloalkyl, $C_3$-$C_7$heterocyclyl, phenyl, and 5- or 6-membered heteroaryl are optionally substituted with one or two substituents selected from the group consisting of halo, —OH, —CN, $C_1$-$C_4$alkyl, —O$C_1$-$C_6$alkyl, —O$C_1$-$C_4$perhaloalkyl, phenyl, —O-pyridine, —Si(CH$_3$)$_3$, —(OCH$_2$CH$_2$)$_2$—NH$_2$, —C(O)NH$_2$, —C(OH)(CF$_3$)$_2$, —(CH$_2$)P(O)(OCH$_2$CH$_3$)$_2$, CH$_2$CN and CH$_2$OH.

A further embodiment of the invention is a compound of Formula I, wherein R[1] is

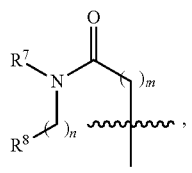

wherein
m is 0 or 1;
n is 0 or 1;
R[7] and R[8] are taken together with the nitrogen to which they are attached to form a 4-to-7-membered heterocyclic ring,
   wherein said 4-to-7-membered heterocyclic ring contains 1-2 heteroatoms,
   wherein said heteroatoms are selected from the group consisting of O, N, and S(O)$_p$, p being 0, 1 or 2;
   said 4-to-7-membered heterocyclic ring is optionally substituted with one or two substituents selected from the group consisting of OH, CN, CH$_2$OH, —CH(CH$_3$)$_2$OH, CH$_2$CN, —C(O)CH$_3$, $C_1$-$C_6$alkyl, morpholino, $C_1$-$C_3$perhaloalkyl, phenyl, benzyl, pyridyl, fluoro, and O$C_1$-$C_6$ alkyl.

A further embodiment of the invention is a compound of Formula I, wherein R[1] is

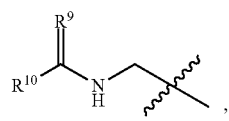

wherein R[9] is selected from the group consisting of NH, N—OH and O; and
R[10] is selected from the group consisting of $C_1$-$C_6$ alkyl, $C_3$-$C_{10}$cycloalkyl, phenyl, benzyl, pyrazolyl, O$C_1$-$C_6$ alkyl, phenoxy, NH$_2$, —NHCH$_2$—$C_3$-$C_{10}$cycloalkyl, —NH$C_1$-$C_6$alkyl, and —NHphenyl; wherein in said R[10], each of $C_1$-$C_6$ alkyl and phenyl is independently optionally substituted with one or two substituents selected from the group consisting of $C_3$-$C_{10}$cycloalkyl, piperidinyl, OH, CN and O$C_1$-$C_6$ alkyl.

A further embodiment of the invention is a compound of Formula I, wherein R[10] is selected from the group consisting of

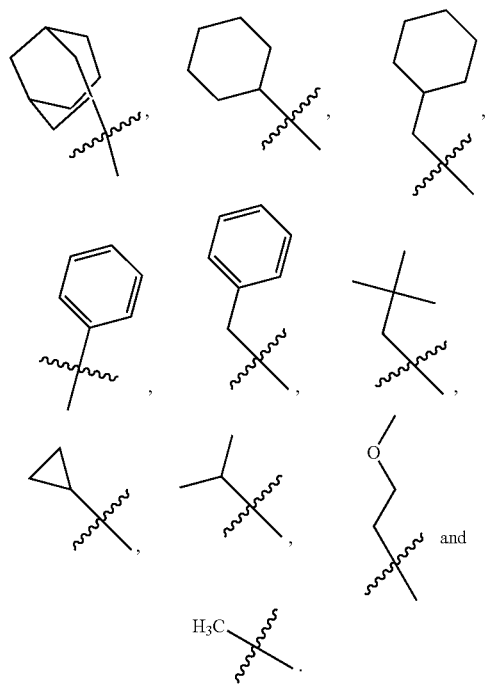

A further embodiment of the invention is a compound of Formula I, where R[9] is NH or N—OH and where R[10] is selected from the group consisting of

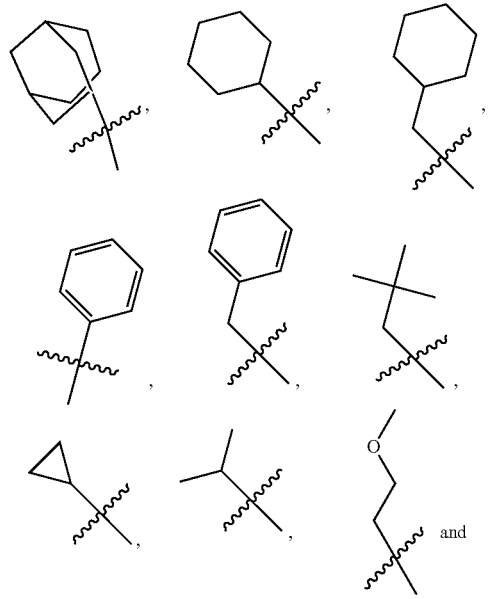

-continued

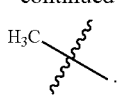

A further embodiment of the invention is a compound of Formula I, wherein R[1] is

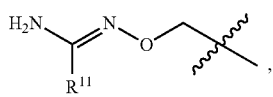

wherein R[11] is selected from the group consisting of phenyl, $C_3$-$C_{10}$cycloalkyl, and $C_1$-$C_6$ alkyl, wherein in said R[11], $C_1$-$C_6$ alkyl is optionally substituted with one or two substituents selected from the group consisting of $OC_1$-$C_6$ alkyl, $C_3$-$C_{10}$cycloalkyl and piperidinyl.

A further embodiment of the invention is a compound of Formula I, wherein R[11] is selected from the group consisting of

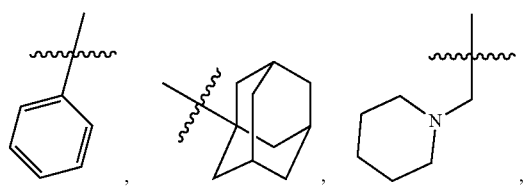


A further embodiment of the invention is a compound of Formula I, wherein R[1] is wherein R[12] and R[13] are independently selected from the group consisting of $C_1$-$C_3$alkyl and phenyl.

A further embodiment of the invention is a compound of Formula I, wherein R[1] is $CH_2OR^{14}$, wherein R[14] is selected from the group consisting of $C_1$-$C_6$ alkyl, —C(O)NHCH$_2$CH$_2$OCH$_3$, and A further embodiment of the invention is a compound of Formula I, wherein R[1] is either cyclohexyl that is optionally substituted with Si(CH$_3$)$_3$ or phenyl that is optionally substituted with one or two substituents selected from the group consisting of —CN, SF$_5$, -4-SO$_2$CH$_3$-phenyl, and R[15] wherein R[15] is selected from the group consisting of H, —CN, CH$_2$OH and —C≡CH;

A further embodiment of the invention is a compound of Formula I, wherein R[1] is 5- or 6-membered heteroaryl ring HR optionally containing 1-4 heteroatoms selected from the group consisting of O, N and S, said 5- or 6-membered heteroaryl ring HR being optionally substituted with one or two substituents selected from the group consisting of halo, $C_3$-$C_4$cycloalkyl, $C_1$-$C_6$alkyl, phenyl, —CH$_2$oxazolyl, —CH$_2$C(O)NHcyclopropyl, —CH$_2$C(O)$_2$CH$_2$CH$_3$, —CH$_2$C(CH$_3$)$_2$OH, CN, NH$_2$, NHCH$_3$ and SCH$_3$.

A further embodiment of the invention is a compound of Formula I, wherein R[1] is $C_4$-$C_7$ heterocyclic ring, wherein said $C_4$-$C_7$ heterocyclic ring is optionally substituted with one or two substituents selected from the group consisting of —CO$_2$CH$_2$CH$_3$, —SO$_2$CH$_3$, —COCH$_3$, CH$_2$C(CH$_3$)$_3$, C(CH$_3$)$_3$, CH$_3$, C(O)CH$_2$CN, CH$_2$C(OH)(CH$_3$)$_2$ and 4-CN-phenyl.

A further embodiment of the invention is a compound of Formula I, wherein R[1] is —CH$_2$—NR$^4$R$^5$, wherein each of R$^4$ and R$^5$ is independently selected from the group consisting of H and $SO_2R^6$, wherein $R^6$ is selected from the group consisting of cyclohexyl, phenyl optionally substituted with CN and $C_1$-$C_5$alkyl optionally substituted with CN.

A further embodiment of the invention is a compound of Formula I, wherein $R^1$ is —$CH_2$-A, wherein A is selected from the group consisting of 5-membered heteroaryl ring selected from the group consisting of thiazolo, imidazolyl, pyrrolyl and pyrazolyl;

heterocyclic ring

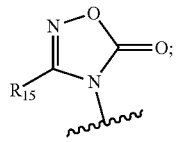

wherein $R^{15}$ is selected from the group consisting of phenyl, cyclopropyl and isopropyl; and

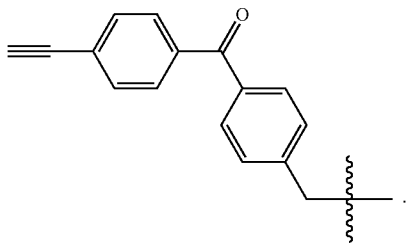 [SMILES: *Cc1ccc(C(=O)c2ccc(C#C)cc2)cc1]

A further embodiment of the invention is a compound of Formula I, wherein $R^1$ is —$(CH_2)_s$—$(OCH_2CH_2)_qOCH_3$, wherein s is 1 or 2, and q is 1, 2 or 3.

A further embodiment of the invention is a pharmaceutical composition for treating a disease, disorder, or medical condition mediated by JAK activity, comprising an effective amount of at least one chemical entity selected from compounds of Formula I.

A further embodiment of the invention is a compound of Formula II, wherein $R^4$ is

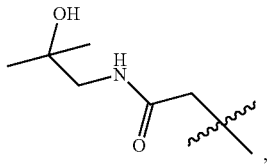

s is 1; Y is H; and X is Cl.

A further embodiment of the invention is a compound of Formula II, wherein $R^4$ is

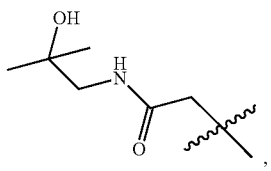 [SMILES: *CC(=O)NCC(C)(C)O]

s is 1; Y is H; and X is Br.
A further embodiment of the invention is a compound of Formula II, wherein $R^4$ is

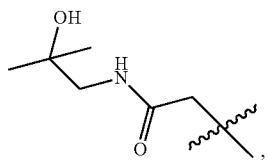 [SMILES: *CC(=O)NCC(C)(C)O]

s is 1; Y is H; and X is F.

A further embodiment of the invention is a compound of Formula II, wherein $R^4$ is

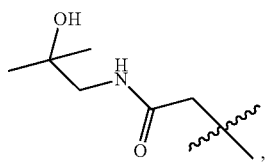 [SMILES: *CC(=O)NCC(C)(C)O]

s is 1; Y is $CH_3$; and X is H.

A further embodiment of the invention is a compound or a pharmaceutically acceptable salt thereof, selected from the group consisting of 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide;

2-((1r,4r)-4-(2-(1H-Imidazol-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide;

N-(2-Cyanoethyl)-2-(1-((1R,4R)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-pyran-4-yl)acetamide;

2-((1r,4r)-4-(2-(2-Oxo-2-(4-(trifluoromethyl)piperidin-1-yl)ethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)phenyl)acetamide;

2-(1-((1r,4r)-4-(Cyanomethyl)cyclohexyl)-1,6-dihydroimidazo[4,5-d]pyrrolo[2,3-b]pyridin-2-yl)-N-(4-(cyanomethyl)phenyl)acetamide;

2-((1r,4r)-4-(2-(1H-1,2,4-Triazol-3-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((tetrahydro-2H-pyran-4-yl)methyl)acetamide;

2-((1r,4r)-4-(2-(Oxazol-4-yl)imidazo[4,5-d]pyrrolo[2,3-b]pyridin-1(6H)-yl)cyclohexyl)acetonitrile;

2-((1r,4r)-4-(2-(2-(4-Hydroxypiperidin-1-yl)-2-oxoethyl)imidazo[4,5-d]pyrrolo[2,3-b]pyridin-1(6H)-yl)cyclohexyl)acetonitrile;

2-Cyano-N-((1-((1r,4r)-4-(cyanomethyl)cyclohexyl)-1,6-dihydroimidazo[4,5-d]pyrrolo[2,3-b]pyridin-2-yl)methyl)ethanesulfonamide;

2-(1-((1r,4r)-4-(Cyanomethyl)cyclohexyl)-1,6-dihydroimidazo[4,5-d]pyrrolo[2,3-b]pyridin-2-yl)-N-(pyrimidin-4-ylmethyl)acetamide;

2-(1-((1r,4r)-4-(Cyanomethyl)cyclohexyl)-1,6-dihydroimidazo[4,5-d]pyrrolo[2,3-b]pyridin-2-yl)-N-(3-hydroxy-2,2-dimethylpropyl)acetamide;

2-((1r,4r)-4-(2-(2H-1,2,3-Triazol-4-yl)imidazo[4,5-d]pyrrolo[2,3-b]pyridin-1(6H)-yl)cyclohexyl)acetonitrile;

(E)-N-((1-((1r,4r)-4-(Cyanomethyl)cyclohexyl)-1,6-dihydroimidazo[4,5-d]pyrrolo[2,3-b]pyridin-2-yl)methyl)-N'-hydroxybenzimidamide;

(Z)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxybenzimidamide;

2-((1r,4r)-4-(2-(2-(3-Hydroxyazetidin-1-yl)-2-oxoethyl)imidazo[4,5-d]pyrrolo[2,3-b]pyridin-1(6H)-yl)cyclohexyl)acetonitrile;

N-((1r,4r)-4-(Cyanomethyl)cyclohexyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-phenylacetamide;

2-(1-((1r,4r)-4-(Cyanomethyl)cyclohexyl)-1,6-dihydroimidazo[4,5-d]pyrrolo[2,3-b]pyridin-2-yl)-N-(((1S,3R,5R,7S)-3-hydroxyadamantan-1-yl)methyl)acetamide;

N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide;

N-(4-Cyanobicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((3-hydroxyoxetan-3-yl)methyl)acetamide;

2-((1r,4r)-4-(2-((1H-Pyrazol-5-yl)methyl)imidazo[4,5-d]pyrrolo[2,3-b]pyridin-1(6H)-yl)cyclohexyl)acetonitrile;

2-((1r,4r)-4-(2-(4-Morpholinopiperidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(hydroxymethyl)cyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-cyclohexylacetamide;

2-(1-((1r,4r)-4-(Cyanomethyl)cyclohexyl)-1,6-dihydroimidazo[4,5-d]pyrrolo[2,3-b]pyridin-2-yl)-N-(2-hydroxyethyl)acetamide;

N-((1-((1r,4r)-4-(Cyanomethyl)cyclohexyl)-1,6-dihydroimidazo[4,5-d]pyrrolo[2,3-b]pyridin-2-yl)methyl)benzimidamide;

2-((1r,4r)-4-(2-(4-Chloro-1H-pyrazol-3-yl)imidazo[4,5-d]pyrrolo[2,3-b]pyridin-1(6H)-yl)cyclohexyl)acetonitrile;

N-((3R,5R)-Adamantan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1r,4r)-4-hydroxycyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide;

2-(1-((1r,4r)-4-(Cyanomethyl)cyclohexyl)-1,6-dihydroimidazo[4,5-d]pyrrolo[2,3-b]pyridin-2-yl)-N-(pyrazin-2-ylmethyl)acetamide;

N-((1H-imidazol-2-yl)methyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1R,3R)-3-hydroxycyclobutyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide;

N-(4-Cyanobenzyl)-2-(1-((1r,4r)-4-(cyanomethyl)cyclohexyl)-1,6-dihydroimidazo[4,5-d]pyrrolo[2,3-b]pyridin-2-yl)acetamide;

1-((1-((1r,4r)-4-(Cyanomethyl)cyclohexyl)-1,6-dihydroimidazo[4,5-d]pyrrolo[2,3-b]pyridin-2-yl)methyl)urea;

2-((1r,4r)-4-(2-(Thiazol-4-ylmethyl)imidazo[4,5-d]pyrrolo[2,3-b]pyridin-1(6H)-yl)cyclohexyl)acetonitrile;

2-((1S,4r)-4-(2-(2-((S)-3-Hydroxypyrrolidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(2-(pyridin-4-yloxy)ethyl)acetamide;

2-(1-((1r,4r)-4-(Cyanomethyl)cyclohexyl)-1,6-dihydroimidazo[4,5-d]pyrrolo[2,3-b]pyridin-2-yl)-N-neopentylacetamide;

2-(1-((1r,4r)-4-(Cyanomethyl)cyclohexyl)-1,6-dihydroimidazo[4,5-d]pyrrolo[2,3-b]pyridin-2-yl)-N-(4-fluorobenzyl)acetamide;

Phenyl ((1-((1r,4r)-4-(cyanomethyl)cyclohexyl)-1,6-dihydroimidazo[4,5-d]pyrrolo[2,3-b]pyridin-2-yl)methyl)carbamate;

2-(1-((1r,4r)-4-(Cyanomethyl)cyclohexyl)-1,6-dihydroimidazo[4,5-d]pyrrolo[2,3-b]pyridin-2-yl)-N-((1S,4S)-4-hydroxycyclohexyl)acetamide;

N-Benzyl-2-(1-((1r,4r)-4-(cyanomethyl)cyclohexyl)-1,6-dihydroimidazo[4,5-d]pyrrolo[2,3-b]pyridin-2-yl)acetamide;

2-((1r,4r)-4-(2-(2-Oxo-2-(pyrrolidin-1-yl)ethyl)imidazo[4,5-d]pyrrolo[2,3-b]pyridin-1(6H)-yl)cyclohexyl)acetonitrile;

2-((1r,4r)-4-(2-(3-Hydroxy-3-phenylpyrrolidine-1-carbonyl)imidazo[4,5-d]pyrrolo[2,3-b]pyridin-1(6H)-yl)cyclohexyl)acetonitrile;

2-((1r,4r)-4-(2-(2-Aminopyrimidin-5-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1 s, 3r,5R,7S)-3-hydroxyadamantan-1-yl)acetamide;

2-((1r,4r)-4-(2-(2-Aminopyrimidin-4-yl)imidazo[4,5-d]pyrrolo[2,3-b]pyridin-1(6H)-yl)cyclohexyl)acetonitrile;

4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.1]heptane-1-carboxamide;

N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-((1r,4r)-4-(2-(1H-Imidazol-2-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(2,2,2-trifluoroethyl)acetamide;

4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.2]octane-1-carboxamide;

2-(1-((1r,4r)-4-(Cyanomethyl)cyclohexyl)-1,6-dihydroimidazo[4,5-d]pyrrolo[2,3-b]pyridin-2-yl)-N-(3-hydroxy-3-methylbutyl)acetamide;

2-((1r,4r)-4-(2-(1H-Pyrazol-3-yl)imidazo[4,5-d]pyrrolo[2,3-b]pyridin-1(6H)-yl)cyclohexyl)acetonitrile;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxyisobutyrimidamide;

2-(1-((1r,4r)-4-(Cyanomethyl)cyclohexyl)-1,6-dihydroimidazo[4,5-d]pyrrolo[2,3-b]pyridin-2-yl)-N-(1-isobutylpiperidin-4-yl)acetamide;

2-((1r,4r)-4-(2-(2H-Tetrazol-5-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(4,4-dimethylcyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-methylpiperidin-4-yl)acetamide;

2-((1r,4r)-4-(2-(2-(1,1-Dioxidothiomorpholino)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)benzyl)acetamide;

2-(1-((1r,4r)-4-(Cyanomethyl)cyclohexyl)-1,6-dihydroimidazo[4,5-d]pyrrolo[2,3-b]pyridin-2-yl)-N-(cyclohexylmethyl)acetamide;

1-((1-((1r,4r)-4-(Cyanomethyl)cyclohexyl)-1,6-dihydroimidazo[4,5-d]pyrrolo[2,3-b]pyridin-2-yl)methyl)-3-phenylurea;

2-(1-((1r,4r)-4-(Cyanomethyl)cyclohexyl)-1,6-dihydroimidazo[4,5-d]pyrrolo[2,3-b]pyridin-2-yl)-N-(2-methoxy-2-methylpropyl)acetamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)-3-methoxypropanimidamide;

2-((1r,4r)-4-(2-(2-(4-(Hydroxymethyl)piperidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(3,5-dimethylcyclohexyl)acetamide;

4-(4-(1-((1r,4r)-4-(Cyanomethyl)cyclohexyl)-1,6-dihydroimidazo[4,5-d]pyrrolo[2,3-b]pyridin-2-yl)piperidin-1-yl)benzonitrile;

N-((1-((1r,4r)-4-(Cyanomethyl)cyclohexyl)-1,6-dihydroimidazo[4,5-d]pyrrolo[2,3-b]pyridin-2-yl)methyl)benzenesulfonamide;

N-((1S,4R)-Bicyclo[2.2.1]heptan-2-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(cyanomethyl)cyclohexyl)-1,6-dihydroimidazo[4,5-d]pyrrolo[2,3-b]pyridin-2-yl)-N-(4-(difluoromethoxy)benzyl)acetamide;

1-((1r,4r)-4-(Cyanomethyl)cyclohexyl)-N-((3-hydroxyoxetan-3-yl)methyl)-1,6-dihydroimidazo[4,5-d]pyrrolo[2,3-b]pyridine-2-carboxamide;

2-((1r,4r)-4-(2-(3-Methyl-1H-pyrazol-5-yl)imidazo[4,5-d]pyrrolo[2,3-b]pyridin-1(6H)-yl)cyclohexyl)acetonitrile;

4-Cyano-N-((1-((1r,4r)-4-(cyanomethyl)cyclohexyl)-1,6-dihydroimidazo[4,5-d]pyrrolo[2,3-b]pyridin-2-yl)methyl)benzamide;

2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-thiopyran-4-yl)acetamide;

1-((1r,4r)-4-(Cyanomethyl)cyclohexyl)-N-(1-methylpiperidin-4-yl)-1,6-dihydroimidazo[4,5-d]pyrrolo[2,3-b]pyridine-2-carboxamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide;

N-((1-((1r,4r)-4-(Cyanomethyl)cyclohexyl)-1,6-dihydroimidazo[4,5-d]pyrrolo[2,3-b]pyridin-2-yl)methyl)acetimidamide;

2-((1r,4r)-4-(2-(2-(4-Benzylpiperidin-1-yl)-2-oxoethyl)imidazo[4,5-d]pyrrolo[2,3-b]pyridin-1(6H)-yl)cyclohexyl)acetonitrile;

2-((1r,4r)-4-(2-(4-Hydroxy-4-(pyridin-2-yl)piperidine-1-carbonyl)imidazo[4,5-d]pyrrolo[2,3-b]pyridin-1(6H)-yl)cyclohexyl)acetonitrile;

2-((1r,4r)-4-(2-(2-(Methylamino)pyrimidin-4-yl)imidazo[4,5-d]pyrrolo[2,3-b]pyridin-1(6H)-yl)cyclohexyl)acetonitrile;

2-((1r,4r)-4-(2-(2-Oxo-2-(piperidin-1-yl)ethyl)imidazo[4,5-d]pyrrolo[2,3-b]pyridin-1(6H)-yl)cyclohexyl)acetonitrile;

2-((1r,4r)-4-(2-(4'-(Methylsulfonyl)-[1,1'-biphenyl]-4-yl)imidazo[4,5-d]pyrrolo[2,3-b]pyridin-1(6H)-yl)cyclohexyl)acetonitrile;

2-((1r,4r)-4-(2-(4-Benzoylphenyl)imidazo[4,5-d]pyrrolo[2,3-b]pyridin-1(6H)-yl)cyclohexyl)acetonitrile;

2-((1r,4r)-4-(2-(4-(2-Hydroxypropan-2-yl)piperidin-1-yl)-2-oxoethyl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)-2-cyclopropylacetamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-2-cyclohexyl-N'-hydroxyacetimidamide;

4-(1-((1r,4r)-4-(Cyanomethyl)cyclohexyl)-1,6-dihydroimidazo[4,5-d]pyrrolo[2,3-b]pyridin-2-yl)benzonitrile;

4-Cyano-N-((1-((1r,4r)-4-(cyanomethyl)cyclohexyl)-1,6-dihydroimidazo[4,5-d]pyrrolo[2,3-b]pyridin-2-yl)methyl)benzenesulfonamide;

2-((1r,4r)-4-(2-(2-(Methylthio)pyrimidin-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((trimethylsilyl)methyl)acetamide;

2-((1r,4r)-4-(2-(4-(Trimethylsilyl)cyclohexyl)imidazo[4,5-d]pyrrolo[2,3-b]pyridin-1(6H)-yl)cyclohexyl)acetonitrile;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3,3-dimethylbutanimidamide;

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-phenylethyl)acetamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-2-phenylacetimidamide;

2-(1-((1r,4r)-4-(Cyanomethyl)cyclohexyl)-1,6-dihydroimidazo[4,5-d]pyrrolo[2,3-b]pyridin-2-yl)-N-(4-(1,1,1,3,3,3-hexafluoro-2-hydroxypropan-2-yl)phenyl)acetamide;

1-(2-(1-((1r,4r)-4-(Cyanomethyl)cyclohexyl)-1,6-dihydroimidazo[4,5-d]pyrrolo[2,3-b]pyridin-2-yl)acetyl)piperidine-4-carbonitrile;

2-(1-((1r,4r)-4-(Cyanomethyl)cyclohexyl)-1,6-dihydroimidazo[4,5-d]pyrrolo[2,3-b]pyridin-2-yl)-N-(2,3-dihydroxypropyl)acetamide;

2-((1r,4r)-4-(2-(2-(4,4-Difluoropiperidin-1-yl)-2-oxoethyl)imidazo[4,5-d]pyrrolo[2,3-b]pyridin-1(6H)-yl)cyclohexyl)acetonitrile;

Diethyl 4-(2-(1-((1r,4r)-4-(cyanomethyl)cyclohexyl)-1,6-dihydroimidazo[4,5-d]pyrrolo[2,3-b]pyridin-2-yl)acetamido)benzylphosphonate;

(1-((1r,4r)-4-(Cyanomethyl)cyclohexyl)-1,6-dihydroimidazo[4,5-d]pyrrolo[2,3-b]pyridin-2-yl)methyl phenylcarbamate;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclopropanecarboximidamide;

2-(1-((1r,4r)-4-(Cyanomethyl)cyclohexyl)-1,6-dihydroimidazo[4,5-d]pyrrolo[2,3-b]pyridin-2-yl)-N-(pyridin-3-yl)acetamide;

(Z)—N'-((1-((1r,4r)-4-(Cyanomethyl)cyclohexyl)-1,6-dihydroimidazo[4,5-d]pyrrolo[2,3-b]pyridin-2-yl)methoxy)-2-cyclopropylacetimidamide;

2-((1r,4r)-4-(2-(Methoxymethyl)imidazo[4,5-d]pyrrolo[2,3-b]pyridin-1(6H)-yl)cyclohexyl)acetonitrile;

1-((1r,4r)-4-(Cyanomethyl)cyclohexyl)-N-(2-hydroxyethyl)-1,6-dihydroimidazo[4,5-d]pyrrolo[2,3-b]pyridine-2-carboxamide;

5-(1-((1r,4r)-4-(Cyanomethyl)cyclohexyl)-1,6-dihydroimidazo[4,5-d]pyrrolo[2,3-b]pyridin-2-yl)picolinonitrile;

N-((1-((1r,4r)-4-(Cyanomethyl)cyclohexyl)-1,6-dihydroimidazo[4,5-d]pyrrolo[2,3-b]pyridin-2-yl)methyl)-3-hydroxy-3-methylbutanamide;

1-((1r,4r)-4-(Cyanomethyl)cyclohexyl)-N-(2-hydroxy-2-methylpropyl)-1,6-dihydroimidazo[4,5-d]pyrrolo[2,3-b]pyridine-2-carboxamide;

2-(1-((1r,4r)-4-(Cyanomethyl)cyclohexyl)-1,6-dihydroimidazo[4,5-d]pyrrolo[2,3-b]pyridin-2-yl)-N-(pyridin-4-yl)acetamide;

2-((1r,4r)-4-(2-(Thiazol-5-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(2-methoxyethyl)acetamide;

2-((1r,4r)-4-(2-(4-(4-(Hydroxymethyl)benzoyl)phenyl)imidazo[4,5-d]pyrrolo[2,3-b]pyridin-1(6H)-yl)cyclohexyl)acetonitrile;

1-((1r,4r)-4-(Cyanomethyl)cyclohexyl)-N-(oxetan-3-yl)-1,6-dihydroimidazo[4,5-d]pyrrolo[2,3-b]pyridine-2-carboxamide;

2-((1r,4r)-4-(2-(1H-pyrazol-4-yl)imidazo[4,5-d]pyrrolo[2,3-b]pyridin-1(6H)-yl)cyclohexyl)acetonitrile;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)benzimidamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3-methoxypropanimidamide;

2-((1r,4r)-4-(2-(((4-(4-Ethynylbenzoyl)benzyl)oxy)methyl)imidazo[4,5-d]pyrrolo[2,3-b]pyridin-1(6H)-yl)cyclohexyl)acetonitrile;

2-((1r,4r)-4-(2-(2-((R)-3-Hydroxypyrrolidin-1-yl)-2-oxoethyl)imidazo[4,5-d]pyrrolo[2,3-b]pyridin-1(6H)-yl)cyclohexyl)acetonitrile;

Ethyl 3-(1-((1r,4r)-4-(Cyanomethyl)cyclohexyl)-1,6-dihydroimidazo[4,5-d]pyrrolo[2,3-b]pyridin-2-yl)azetidine-1-carboxylate;

2-((1r,4r)-4-(2-((3-Isopropyl-5-oxo-1,2,4-oxadiazol-4(5H)-yl)methyl)imidazo[4,5-d]pyrrolo[2,3-b]pyridin-1(6H)-yl)cyclohexyl)acetonitrile;

2-((1r,4r)-4-(2-((4-(4-Ethynylbenzoyl)phenoxy)methyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)bicyclo[2.2.1]heptan-1-yl)acetamide;

2-(1-((1r,4r)-4-(Cyanomethyl)cyclohexyl)-8-fluoro-1,6-dihydroimidazo[4,5-d]pyrrolo[2,3-b]pyridin-2-yl)-N-(2-hydroxy-2-methylpropyl)acetamide;

1-((1r,4r)-4-(Cyanomethyl)cyclohexyl)-N-methyl-1,6-dihydroimidazo[4,5-d]pyrrolo[2,3-b]pyridine-2-carboxamide;

2-((1r,4r)-4-(2-(1-(Methyl sulfonyl)azetidin-3-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1S,4S)-4-(trimethylsilyl)cyclohexyl)acetamide;

1-((1r,4r)-4-(Cyanomethyl)cyclohexyl)-N-((1-hydroxycycloheptyl)methyl)-1,6-dihydroimidazo[4,5-d]pyrrolo[2,3-b]pyridine-2-carboxamide;

Isobutyl ((1-((1r,4r)-4-(Cyanomethyl)cyclohexyl)-1,6-dihydroimidazo[4,5-d]pyrrolo[2,3-b]pyridin-2-yl)methyl)carbamate;

N-(2-Cyanoethyl)-1-((1r,4r)-4-(cyanomethyl)cyclohexyl)-1,6-dihydroimidazo[4,5-d]pyrrolo[2,3-b]pyridine-2-carboxamide;

N-((1-((1r,4r)-4-(Cyanomethyl)cyclohexyl)-1,6-dihydroimidazo[4,5-d]pyrrolo[2,3-b]pyridin-2-yl)methyl)cyclohexanecarboxamide;

2-((1r,4r)-4-(2-(3-Cyclopropyl-4,5-dihydro-1,2,4-oxadiazol-5-yl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)cyclohexanesulfonamide;

2-((1r,4r)-4-(2-(((Dimethyl(oxo)-$\lambda^6$-sulfanylidene)amino)methyl)imidazo[4,5-d]pyrrolo[2,3-b]pyridin-1(6H)-yl)cyclohexyl)acetonitrile;

2-((1r,4r)-4-(2-(4-(Pentafluoro-$\lambda^6$-sulfanyl)phenyl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)-1H-pyrazole-4-carboxamide;

1-((1r,4r)-4-(Cyanomethyl)cyclohexyl)-N-(2-methoxyethyl)-1,6-dihydroimidazo[4,5-d]pyrrolo[2,3-b]pyridine-2-carboxamide;

(1-((1r,4r)-4-(Cyanomethyl)cyclohexyl)-1,6-dihydroimidazo[4,5-d]pyrrolo[2,3-b]pyridin-2-yl)methyl (cyclohexylmethyl)carbamate;

2-((1r,4r)-4-(2-(1-Acetylazetidin-3-yl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)benzamide;

2-((1r,4r)-4-(2-(2-((R)-2-(Hydroxymethyl)pyrrolidin-1-yl)-2-oxoethyl)imidazo[4,5-d]pyrrolo[2,3-b]pyridin-1(6H)-yl)cyclohexyl)acetonitrile;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)isobutyrimidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)cyclopropanecarboximidamide;

(3R,5R,7R,E*)—N'-((1-((1r,4r)-4-(Cyanomethyl)cyclohexyl)-1,6-dihydroimidazo[4,5-d]pyrrolo[2,3-b]pyridin-2-yl)methoxy)adamantane-1-carboximidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)-2-(piperidin-1-yl)acetimidamide;

Neopentyl ((1-((1r,4r)-4-(Cyanomethyl)cyclohexyl)-1,6-dihydroimidazo[4,5-d]pyrrolo[2,3-b]pyridin-2-yl)methyl)carbamate;

1-((1-((1r,4r)-4-(Cyanomethyl)cyclohexyl)-1,6-dihydroimidazo[4,5-d]pyrrolo[2,3-b]pyridin-2-yl)methyl)-3-(cyclohexylmethyl)urea;

(3R,5R,7R)—N-((1-((1r,4r)-4-(Cyanomethyl)cyclohexyl)-1,6-dihydroimidazo[4,5-d]pyrrolo[2,3-b]pyridin-2-yl)methyl)adamantane-1-carboximidamide;

3-Cyano-N-((1-((1r,4r)-4-(cyanomethyl)cyclohexyl)-1,6-dihydroimidazo[4,5-d]pyrrolo[2,3-b]pyridin-2-yl)methyl)propanamide;

tert-Butyl ((1-((1r,4r)-4-(Cyanomethyl)cyclohexyl)-1,6-dihydroimidazo[4,5-d]pyrrolo[2,3-b]pyridin-2-yl)methyl)carbamate;

2-((1r,4r)-4-(2-(Azetidin-3-yl)imidazo[4,5-d]pyrrolo[2,3-b]pyridin-1(6H)-yl)cyclohexyl)acetonitrile;

3-(3-(1-((1r,4r)-4-(Cyanomethyl)cyclohexyl)-1,6-dihydroimidazo[4,5-d]pyrrolo[2,3-b]pyridin-2-yl)azetidin-1-yl)-3-oxopropanenitrile;

(1-((1r,4r)-4-(Cyanomethyl)cyclohexyl)-1,6-dihydroimidazo[4,5-d]pyrrolo[2,3-b]pyridin-2-yl)methyl (2-methoxyethyl)carbamate;

2-((1r,4r)-4-(2-((((R)-Methyl(oxo)(phenyl)-λ⁶-sulfanylidene)amino)methyl)imidazo[4,5-d]pyrrolo[2,3-b]pyridin-1(6H)-yl)cyclohexyl)acetonitrile;

2-((1r,4r)-4-(2-((((S)-methyl(oxo)(phenyl)-λ⁶-sulfanylidene)amino)methyl)imidazo[4,5-d]pyrrolo[2,3-b]pyridin-1(6H)-yl)cyclohexyl)acetonitrile;

2-((1r,4r)-4-(2-(1-Acetylpiperidin-4-yl)imidazo[4,5-d]pyrrolo[2,3-b]pyridin-1(6H)-yl)cyclohexyl)acetonitrile;

2-((1r,4r)-4-(2-((3-Cyclopropyl-5-oxo-1,2,4-oxadiazol-4(5H)-yl)methyl)imidazo[4,5-d]pyrrolo[2,3-b]pyridin-1(6H)-yl)cyclohexyl)acetonitrile;

2-((1r,4r)-4-(2-(1-(Oxazol-4-ylmethyl)-1H-pyrazol-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(trimethylsilyl)cyclohexyl)acetamide;

2-((1r,4r)-4-(2-(1-(2-Hydroxy-2-methylpropyl)piperidin-4-yl)imidazo[4,5-d]pyrrolo[2,3-b]pyridin-1(6H)-yl)cyclohexyl)acetonitrile;

2-((1r,4r)-4-(2-(4-(4-Ethynylbenzoyl)phenyl)imidazo[4,5-d]pyrrolo[2,3-b]pyridin-1(6H)-yl)cyclohexyl)acetonitrile;

2-((1r,4r)-4-(2-(4-(4-Ethynylbenzoyl)phenethyl)imidazo[4,5-d]pyrrolo[2,3-b]pyridin-1(6H)-yl)cyclohexyl)acetonitrile;

1-((1-((1r,4r)-4-(Cyanomethyl)cyclohexyl)-1,6-dihydroimidazo[4,5-d]pyrrolo[2,3-b]pyridin-2-yl)methyl)-3-isopropylurea;

1-((1r,4r)-4-(Cyanomethyl)cyclohexyl)-N-isopropyl-1,6-dihydroimidazo[4,5-d]pyrrolo[2,3-b]pyridine-2-carboxamide;

1-((1r,4r)-4-(Cyanomethyl)cyclohexyl)-N-(3-methoxypropyl)-1,6-dihydroimidazo[4,5-d]pyrrolo[2,3-b]pyridine-2-carboxamide;

2-(1-((1r,4r)-4-Cyanocyclohexyl)-1,6-dihydroimidazo[4,5-d]pyrrolo[2,3-b]pyridin-2-yl)-N-(4-(methylsulfonyl)phenyl)acetamide;

1-((1r,4r)-4-(Cyanomethyl)cyclohexyl)-N-cyclopropyl-1,6-dihydroimidazo[4,5-d]pyrrolo[2,3-b]pyridine-2-carboxamide;

2-((1r,4r)-4-(2-(4-Methoxypiperidine-1-carbonyl)imidazo[4,5-d]pyrrolo[2,3-b]pyridin-1(6H)-yl)cyclohexyl)acetonitrile;

1-(1-((1r,4r)-4-(Cyanomethyl)cyclohexyl)-1,6-dihydroimidazo[4,5-d]pyrrolo[2,3-b]pyridine-2-carbonyl)piperidine-4-carbonitrile;

1-((1r,4r)-4-(Cyanomethyl)cyclohexyl)-N-(tetrahydro-2H-pyran-4-yl)-1,6-dihydroimidazo[4,5-d]pyrrolo[2,3-b]pyridine-2-carboxamide;

1-((1r,4r)-4-(Cyanomethyl)cyclohexyl)-N-(1-methoxypropan-2-yl)-1,6-dihydroimidazo[4,5-d]pyrrolo[2,3-b]pyridine-2-carboxamide;

2-((1r,4r)-4-(2-(Morpholine-4-carbonyl)imidazo[4,5-d]pyrrolo[2,3-b]pyridin-1(6H)-yl)cyclohexyl)acetonitrile;

2-((1r,4r)-4-(2-(4-Hydroxypiperidine-1-carbonyl)imidazo[4,5-d]pyrrolo[2,3-b]pyridin-1(6H)-yl)cyclohexyl)acetonitrile;

Ethyl 2-(4-(1-((1r,4r)-4-(cyanomethyl)cyclohexyl)-1,6-dihydroimidazo[4,5-d]pyrrolo[2,3-b]pyridin-2-yl)-1H-pyrazol-1-yl)acetate;

2-((1r,4r)-4-(2-(2,4-dimethyloxazol-5-yl)imidazo[4,5-d]pyrrolo[2,3-b]pyridin-1(6H)-yl)cyclohexyl)acetonitrile;

2-((1r,4r)-4-(2-(2,4-dimethylthiazol-5-yl)imidazo[4,5-d]pyrrolo[2,3-b]pyridin-1(6H)-yl)cyclohexyl)acetonitrile;

2-(4-(1-((1r,4r)-4-(Cyanomethyl)cyclohexyl)-1,6-dihydroimidazo[4,5-d]pyrrolo[2,3-b]pyridin-2-yl)-1H-pyrazol-1-yl)-N-cyclopropylacetamide;

2-((1r,4r)-4-(2-(2-aminopyridin-3-yl)imidazo[4,5-d]pyrrolo[2,3-b]pyridin-1(6H)-yl)cyclohexyl)acetonitrile;

2-((1r,4r)-4-(2-(1-(2-Hydroxy-2-methylpropyl)-1H-pyrazol-4-yl)imidazo[4,5-d]pyrrolo[2,3-b]pyridin-1(6H)-yl)cyclohexyl)acetonitrile;

2-(8-chloro-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;

2-(8-bromo-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;

2-(1-((1r,4r)-4-(cyanomethyl)cyclohexyl)-8-methyl-1,6-dihydroimidazo[4,5-d]pyrrolo[2,3-b]pyridin-2-yl)-N-(2-hydroxy-2-methylpropyl)acetamide;

2-(1-((1r,4r)-4-(Cyanomethyl)cyclohexyl)-7-methyl-1,6-dihydroimidazo[4,5-d]pyrrolo[2,3-b]pyridin-2-yl)-N-(2-hydroxy-2-methylpropyl)acetamide;

2-((1r,4r)-4-(2-(2,5,8,11-Tetraoxatridecan-13-yl)imidazo[4,5-d]pyrrolo[2,3-b]pyridin-1(6H)-yl)cyclohexyl)acetonitrile;

N-(2-(2-(2-Aminoethoxy)ethoxy)ethyl)-2-(1-((1r,4r)-4-(cyanomethyl)cyclohexyl)-1,6-dihydroimidazo[4,5-d]pyrrolo[2,3-b]pyridin-2-yl)acetamide;

2-((1r,4r)-4-(2-((2-(2-methoxyethoxy)ethoxy)methyl)imidazo[4,5-d]pyrrolo[2,3-b]pyridin-1(6H)-yl)cyclohexyl)acetonitrile;

2-((1S,4r)-4-(2-(2-((S)-2-(hydroxymethyl)pyrrolidin-1-yl)-2-oxoethyl)imidazo[4,5-d]pyrrolo[2,3-b]pyridin-1(6H)-yl)cyclohexyl)acetonitrile;

(1-((1R4R)-4-(Cyanomethyl)cyclohexyl)-1,6-dihydroimidazo[4,5-d]pyrrolo[2,3-b]pyridin-2-yl)methyl (3S,5S,7S)-adamantan-1-ylcarbamate;

2-((1r,4r)-4-(2-(2-(4-Methoxypiperidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-methylacetamide;

N-((3R,5R,7R)-Adamantan-1-ylmethyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimi-
dazo[4,5-d]pyrrolo[2,3-b]pyridin-2-yl)-N-(4-cyanophe-
nyl)acetamide;
2-(1-((1r,4r)-4-(Cyanomethyl)cyclohexyl)-1,6-dihydroimi-
dazo[4,5-d]pyrrolo[2,3-b]pyridin-2-yl)acetamide;
2-((1r,4r)-4-(2-(tert-Butoxymethyl)imidazo[4,5-d]pyrrolo
[2,3-b]pyridin-1(6H)-yl)cyclohexyl)acetonitrile;
2-((1r,4r)-4-(2-((5-Oxo-3-phenyl-1,2,4-oxadiazol-4(5H)-yl)
methyl)imidazo[4,5-d]pyrrolo[2,3-b]pyridin-1(6H)-yl)
cyclohexyl)acetonitrile;
(N-((1-((1r,4r)-4-(Cyanomethyl)cyclohexyl)-1,6-dihydro-
imidazo[4,5-d]pyrrolo[2,3-b]pyridin-2-yl)methyl)-N'-hy-
droxycyclohexanecarboximidamide;
2-(4-(2-(2-Oxo-2-(piperidin-1-yl)ethyl)imidazo[4,5-d]pyr-
rolo[2,3-b]pyridin-1(6H)-yl)bicyclo[2.2.2]octan-1-yl)ac-
etonitrile;
2-(1-(4-(Cyanomethyl)bicyclo[2.2.2]octan-1-yl)-1,6-dihy-
droimidazo[4,5-d]pyrrolo[2,3-b]pyridin-2-yl)acetamide;
2-(1-(4-(Cyanomethyl)bicyclo[2.2.2]octan-1-yl)-1,6-dihy-
droimidazo[4,5-d]pyrrolo[2,3-b]pyridin-2-yl)-N-pheny-
lacetamide;
2-(1-(4-(Cyanomethyl)bicyclo[2.2.2]octan-1-yl)-1,6-dihy-
droimidazo[4,5-d]pyrrolo[2,3-b]pyridin-2-yl)-N-(cyclo-
hexylmethyl)acetamide; and
2-(1-(4-(Cyanomethyl)bicyclo[2.2.2]octan-1-yl)-1,6-dihy-
droimidazo[4,5-d]pyrrolo[2,3-b]pyridin-2-yl)-N-methyl-
acetamide.

A further embodiment of the invention is a compound or a pharmaceutically acceptable salt thereof, selected from the group consisting of
2-(1-((1r,4r)-4-(Cyanomethyl)cyclohexyl)-1,6-dihydroimi-
dazo[4,5-d]pyrrolo[2,3-b]pyridin-2-yl)-N-(2-hydroxy-2-
methylpropyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-(cyclopropyl-
methyl)acetamide;
N-(2-Cyanoethyl)-2-(1-((1R,4R)-4-(cyanomethyl)cyclo-
hexyl)-1,6-dihydroimidazo[4,5-d]pyrrolo[2,3-b]pyridin-
2-yl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-(tetrahydro-
2H-pyran-4-yl)acetamide;
2-((1r,4r)-4-(2-(2-Oxo-2-(4-(trifluoromethyl)piperidin-1-yl)
ethyl)imidazo[4,5-d]pyrrolo[2,3-b]pyridin-1(6H)-yl)cy-
clohexyl)acetonitrile;
2-(1-((1r,4r)-4-(Cyanomethyl)cyclohexyl)-1,6-dihydroimi-
dazo[4,5-d]pyrrolo[2,3-b]pyridin-2-yl)-N-(4-(hydroxym-
ethyl)phenyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-(4-(cyanom-
ethyl)phenyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-((tetrahydro-
2H-pyran-4-yl)methyl)acetamide;
2-((1r,4r)-4-(2-(2-(4-Hydroxypiperidin-1-yl)-2-oxoethyl)
imidazo[4,5-d]pyrrolo[2,3-b]pyridin-1(6H)-yl)cyclo-
hexyl)acetonitrile;
2-(1-((1r,4r)-4-(Cyanomethyl)cyclohexyl)-1,6-dihydroimi-
dazo[4,5-d]pyrrolo[2,3-b]pyridin-2-yl)-N-(pyrimidin-4-
ylmethyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-(3-hydroxy-2,
2-dimethylpropyl)acetamide;
2-((1S,4r)-4-(2-(3-Hydroxyazetidin-1-yl)-2-oxoethyl)
imidazo[4,5-d]pyrrolo[2,3-b]pyridin-1(6H)-yl)cyclo-
hexyl)acetonitrile;

N-((1r,4r)-4-(Cyanomethyl)cyclohexyl)-2-(1-((1r,4r)-4-
(cyanomethyl)cyclohexyl)-1,6-dihydroimidazo[4,5-d]
pyrrolo[2,3-b]pyridin-2-yl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-phenylacet-
amide;
2-(1-((1r,4r)-4-(Cyanomethyl)cyclohexyl)-1,6-dihydroimi-
dazo[4,5-d]pyrrolo[2,3-b]pyridin-2-yl)-N-(((1S,3R,5R,
7S)-3-hydroxyadamantan-1-yl)methyl)acetamide;
N-(2-Cyano-2-methylpropyl)-2-(1-((1r,4r)-4-(cyanomethyl)
cyclohexyl)-1,6-dihydroimidazo[4,5-d]pyrrolo[2,3-b]
pyridin-2-yl)acetamide;
N-(4-Cyanobicyclo[2.2.1]heptan-1-yl)-2-(1-((1r,4r)-4-(cya-
nomethyl)cyclohexyl)-1,6-dihydroimidazo[4,5-d]pyrrolo
[2,3-b]pyridin-2-yl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-((3-hy-
droxyoxetan-3-yl)methyl)acetamide;
2-((1r,4r)-4-(2-(2-(4-Morpholinopiperidin-1-yl)-2-oxo-
ethyl)imidazo[4,5-d]pyrrolo[2,3-b]pyridin-1(6H)-yl)cy-
clohexyl)acetonitrile;
2-(1-((1r,4r)-4-(Cyanomethyl)cyclohexyl)-1,6-dihydroimi-
dazo[4,5-d]pyrrolo[2,3-b]pyridin-2-yl)-N-((1r,4r)-4-(hy-
droxymethyl)cyclohexyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-cyclohexylac-
etamide;
2-(1-((1r,4r)-4-(Cyanomethyl)cyclohexyl)-1,6-dihydroimi-
dazo[4,5-d]pyrrolo[2,3-b]pyridin-2-yl)-N-(2-hydroxy-
ethyl)acetamide;
N-((3R,5R)-Adamantan-1-yl)-2-(1-((1r,4r)-4-(cyanom-
ethyl)cyclohexyl)-1,6-dihydroimidazo[4,5-d]pyrrolo[2,3-
b]pyridin-2-yl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-((1r,4r)-4-hy-
droxycyclohexyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-((1-hydroxycy-
clobutyl)methyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-(pyrazin-2-yl-
methyl)acetamide;
N-((1H-imidazol-2-yl)methyl)-2-(1-((1r,4r)-4-(cyanom-
ethyl)cyclohexyl)-1,6-dihydroimidazo[4,5-d]pyrrolo[2,3-
b]pyridin-2-yl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-((1R,3R)-3-hy-
droxycyclobutyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-(1-methyl-1H-
pyrazol-4-yl)acetamide;
N-(4-Cyanobenzyl)-2-(1-((1r,4r)-4-(cyanomethyl)cyclo-
hexyl)-1,6-dihydroimidazo[4,5-d]pyrrolo[2,3-b]pyridin-
2-yl)acetamide;
1-((1-((1r,4r)-4-(Cyanomethyl)cyclohexyl)-1,6-dihydroimi-
dazo[4,5-d]pyrrolo[2,3-b]pyridin-2-yl)methyl)urea;
2-((1S,4r)-4-(2-(2-((S)-3-Hydroxypyrrolidin-1-yl)-2-oxo-
ethyl)imidazo[4,5-d]pyrrolo[2,3-b]pyridin-1(6H)-yl)cy-
clohexyl)acetonitrile;
2-(1-((1r,4r)-4-(Cyanomethyl)cyclohexyl)-1,6-dihydroimi-
dazo[4,5-d]pyrrolo[2,3-b]pyridin-2-yl)-N-(2-(pyridin-4-
yloxy)ethyl)acetamide;
2-(1-((1r,4r)-4-(Cyanomethyl)cyclohexyl)-1,6-dihydroimi-
dazo[4,5-d]pyrrolo[2,3-b]pyridin-2-yl)-N-neopentylacet-
amide;

2-(1-((1r,4r)-4-(Cyanomethyl)cyclohexyl)-1,6-dihydroimidazo[4,5-d]pyrrolo[2,3-b]pyridin-2-yl)-N-(4-fluorobenzyl)acetamide;

2-(1-((1r,4r)-4-(Cyanomethyl)cyclohexyl)-1,6-dihydroimidazo[4,5-d]pyrrolo[2,3-b]pyridin-2-yl)-N-((1S,4S)-4-hydroxycyclohexyl)acetamide;

N-Benzyl-2-(1-((1r,4r)-4-(cyanomethyl)cyclohexyl)-1,6-dihydroimidazo[4,5-d]pyrrolo[2,3-b]pyridin-2-yl)acetamide;

2-((1r,4r)-4-(2-(2-Oxo-2-(pyrrolidin-1-yl)ethyl)imidazo[4,5-d]pyrrolo[2,3-b]pyridin-1(6H)-yl)cyclohexyl)acetonitrile;

2-((1r,4r)-4-(2-(3-Hydroxy-3-phenylpyrrolidine-1-carbonyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1s,3r,5R,7S)-3-hydroxyadamantan-1-yl)acetamide;

4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.1]heptane-1-carboxamide;

N-(4-(Cyanomethyl)bicyclo[2.2.1]heptan-1i-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(2,2,2-trifluoroethyl)acetamide;

4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.2]octane-1-carboxamide;

2-(1-((1r,4r)-4-(Cyanomethyl)cyclohexyl)-1,6-dihydroimidazo[4,5-d]pyrrolo[2,3-b]pyridin-2-yl)-N-(3-hydroxy-3-methylbutyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-isobutylpiperidin-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(4,4-dimethylcyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-methylpiperidin-4-yl)acetamide;

2-((1r,4r)-4-(2-(2-(1,1-Dioxidothiomorpholino)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)benzyl)acetamide;

2-(1-((1r,4r)-4-(Cyanomethyl)cyclohexyl)-1,6-dihydroimidazo[4,5-d]pyrrolo[2,3-b]pyridin-2-yl)-N-(cyclohexylmethyl)acetamide;

2-(1-((1r,4r)-4-(Cyanomethyl)cyclohexyl)-1,6-dihydroimidazo[4,5-d]pyrrolo[2,3-b]pyridin-2-yl)-N-(2-methoxy-2-methylpropyl)acetamide;

2-((1r,4r)-4-(2-(2-(4-(Hydroxymethyl)piperidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(3,5-dimethylcyclohexyl)acetamide;

N-((1S,4R)-Bicyclo[2.2.1]heptan-2-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(cyanomethyl)cyclohexyl)-1,6-dihydroimidazo[4,5-d]pyrrolo[2,3-b]pyridin-2-yl)-N-(4-(difluoromethoxy)benzyl)acetamide;

1-((1r,4r)-4-(Cyanomethyl)cyclohexyl)-N-((3-hydroxyoxetan-3-yl)methyl)-1,6-dihydroimidazo[4,5-d]pyrrolo[2,3-b]pyridine-2-carboxamide;

4-Cyano-N-((1-((1r,4r)-4-(cyanomethyl)cyclohexyl)-1,6-dihydroimidazo[4,5-d]pyrrolo[2,3-b]pyridin-2-yl)methyl)benzamide;

2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-thiopyran-4-yl)acetamide;

1-((1r,4r)-4-(Cyanomethyl)cyclohexyl)-N-(1-methylpiperidin-4-yl)-1,6-dihydroimidazo[4,5-d]pyrrolo[2,3-b]pyridine-2-carboxamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide;

2-((1r,4r)-4-(2-(2-(4-Benzylpiperidin-1-yl)-2-oxoethyl)imidazo[4,5-d]pyrrolo[2,3-b]pyridin-1(6H)-yl)cyclohexyl) acetonitrile;

2-((1r,4r)-4-(2-(4-Hydroxy-4-(pyridin-2-yl)piperidine-1-carbonyl)imidazo[4,5-d]pyrrolo[2,3-b]pyridin-1(6H)-yl)cyclohexyl)acetonitrile;

2-((1r,4r)-4-(2-(2-Oxo-2-(piperidin-1-yl)ethyl)imidazo[4,5-d]pyrrolo[2,3-b]pyridin-1(6H)-yl)cyclohexyl)acetonitrile;

2-((1r,4r)-4-(2-(2-(4-(2-Hydroxypropan-2-yl)piperidin-1-yl)-2-oxoethyl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)-2-cyclopropylacetamide;

2-(1-((1r,4r)-4-(Cyanomethyl)cyclohexyl)-1,6-dihydroimidazo[4,5-d]pyrrolo[2,3-b]pyridin-2-yl)-N-((trimethylsilyl)methyl)acetamide;

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-phenylethyl)acetamide;

2-(1-((1r,4r)-4-(Cyanomethyl)cyclohexyl)-1,6-dihydroimidazo[4,5-d]pyrrolo[2,3-b]pyridin-2-yl)-N-(4-(1,1,1,3,3,3-hexafluoro-2-hydroxypropan-2-yl)phenyl)acetamide;

1-(2-(1-((1r,4r)-4-(Cyanomethyl)cyclohexyl)-1,6-dihydroimidazo[4,5-d]pyrrolo[2,3-b]pyridin-2-yl)acetyl)piperidine-4-carbonitrile;

2-(1-((1r,4r)-4-(Cyanomethyl)cyclohexyl)-1,6-dihydroimidazo[4,5-d]pyrrolo[2,3-b]pyridin-2-yl)-N-(2,3-dihydroxypropyl)acetamide;

2-((1r,4r)-4-(2-(2-(4,4-Difluoropiperidin-1-yl)-2-oxoethyl)imidazo[4,5-d]pyrrolo[2,3-b]pyridin-1(6H)-yl)cyclohexyl)acetonitrile;

Diethyl 4-(2-(1-((1r,4r)-4-(cyanomethyl)cyclohexyl)-1,6-dihydroimidazo[4,5-d]pyrrolo[2,3-b]pyridin-2-yl)acetamido)benzylphosphonate;

2-(1-((1r,4r)-4-(Cyanomethyl)cyclohexyl)-1,6-dihydroimidazo[4,5-d]pyrrolo[2,3-b]pyridin-2-yl)-N-(pyridin-3-yl)acetamide;

1-((1r,4r)-4-(Cyanomethyl)cyclohexyl)-N-(2-hydroxyethyl)-1,6-dihydroimidazo[4,5-d]pyrrolo[2,3-b]pyridine-2-carboxamide;

N-((1-((1r,4r)-4-(Cyanomethyl)cyclohexyl)-1,6-dihydroimidazo[4,5-d]pyrrolo[2,3-b]pyridin-2-yl)methyl)-3-hydroxy-3-methylbutanamide;

1-((1r,4r)-4-(Cyanomethyl)cyclohexyl)-N-(2-hydroxy-2-methylpropyl)-1,6-dihydroimidazo[4,5-d]pyrrolo[2,3-b]pyridine-2-carboxamide;
2-(1-((1r,4r)-4-(Cyanomethyl)cyclohexyl)-1,6-dihydroimidazo[4,5-d]pyrrolo[2,3-b]pyridin-2-yl)-N-(pyridin-4-yl)acetamide;
2-(1-((1r,4r)-4-(Cyanomethyl)cyclohexyl)-1,6-dihydroimidazo[4,5-d]pyrrolo[2,3-b]pyridin-2-yl)-N-(2-methoxyethyl)acetamide;
1-((1r,4r)-4-(Cyanomethyl)cyclohexyl)-N-(oxetan-3-yl)-1,6-dihydroimidazo[4,5-d]pyrrolo[2,3-b]pyridine-2-carboxamide;
2-((1r,4r)-4-(2-(2-((R)-3-Hydroxypyrrolidin-1-yl)-2-oxoethyl)imidazo[4,5-d]pyrrolo[2,3-b]pyridin-1(6H)-yl)cyclohexyl)acetonitrile;
2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)bicyclo[2.2.1]heptan-1-yl)acetamide;
1-((1r,4r)-4-(Cyanomethyl)cyclohexyl)-N-methyl-1,6-dihydroimidazo[4,5-d]pyrrolo[2,3-b]pyridine-2-carboxamide;
2-(1-((1r,4r)-4-(Cyanomethyl)cyclohexyl)-1,6-dihydroimidazo[4,5-d]pyrrolo[2,3-b]pyridin-2-yl)-N-((1S,4S)-4-(trimethylsilyl)cyclohexyl)acetamide;
1-((1r,4r)-4-(Cyanomethyl)cyclohexyl)-N-((1-hydroxycycloheptyl)methyl)-1,6-dihydroimidazo[4,5-d]pyrrolo[2,3-b]pyridine-2-carboxamide;
N-(2-Cyanoethyl)-1-((1r,4r)-4-(cyanomethyl)cyclohexyl)-1,6-dihydroimidazo[4,5-d]pyrrolo[2,3-b]pyridine-2-carboxamide;
1-((1r,4r)-4-(Cyanomethyl)cyclohexyl)-N-(2-methoxyethyl)-1,6-dihydroimidazo[4,5-d]pyrrolo[2,3-b]pyridine-2-carboxamide;
2-((1r,4r)-4-(2-(2-((R)-2-(Hydroxymethyl)pyrrolidin-1-yl)-2-oxoethyl)imidazo[4,5-d]pyrrolo[2,3-b]pyridin-1(6H)-yl)cyclohexyl)acetonitrile;
2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(trimethylsilyl)cyclohexyl)acetamide;
1-((1r,4r)-4-(Cyanomethyl)cyclohexyl)-N-isopropyl-1,6-dihydroimidazo[4,5-d]pyrrolo[2,3-b]pyridine-2-carboxamide;
1-((1r,4r)-4-(Cyanomethyl)cyclohexyl)-N-(3-methoxypropyl)-1,6-dihydroimidazo[4,5-d]pyrrolo[2,3-b]pyridine-2-carboxamide;
2-(1-((1r,4r)-4-Cyanocyclohexyl)-1,6-dihydroimidazo[4,5-d]pyrrolo[2,3-b]pyridin-2-yl)-N-(4-(methylsulfonyl)phenyl)acetamide;
1-((1r,4r)-4-(Cyanomethyl)cyclohexyl)-N-cyclopropyl-1,6-dihydroimidazo[4,5-d]pyrrolo[2,3-b]pyridine-2-carboxamide;
2-((1r,4r)-4-(2-(4-Methoxypiperidine-1-carbonyl)imidazo[4,5-d]pyrrolo[2,3-b]pyridin-1(6H)-yl)cyclohexyl)acetonitrile;
1-(1-((1r,4r)-4-(Cyanomethyl)cyclohexyl)-1,6-dihydroimidazo[4,5-d]pyrrolo[2,3-b]pyridine-2-carbonyl)piperidine-4-carbonitrile;
1-((1r,4r)-4-(Cyanomethyl)cyclohexyl)-N-(tetrahydro-2H-pyran-4-yl)-1,6-dihydroimidazo[4,5-d]pyrrolo[2,3-b]pyridine-2-carboxamide;
1-((1r,4r)-4-(Cyanomethyl)cyclohexyl)-N-(1-methoxypropan-2-yl)-1,6-dihydroimidazo[4,5-d]pyrrolo[2,3-b]pyridine-2-carboxamide;
2-((1r,4r)-4-(2-(Morpholine-4-carbonyl)imidazo[4,5-d]pyrrolo[2,3-b]pyridin-1(6H)-yl)cyclohexyl)acetonitrile;
2-((1r,4r)-4-(2-(4-Hydroxypiperidine-1-carbonyl)imidazo[4,5-d]pyrrolo[2,3-b]pyridin-1(6H)-yl)cyclohexyl)acetonitrile;
2-((1r,4r)-4-(2-(2-((S)-2-(Hydroxymethyl)pyrrolidin-1-yl)-2-oxoethyl)imidazo[4,5-d]pyrrolo[2,3-b]pyridin-1(6H)-yl)cyclohexyl)acetonitrile;
2-((1r,4r)-4-(2-(2-(4-Methoxypiperidin-1-yl)-2-oxoethyl)imidazo[4,5-d]pyrrolo[2,3-b]pyridin-1(6H)-yl)cyclohexyl)acetonitrile;
2-(1-((1r,4r)-4-(Cyanomethyl)cyclohexyl)-1,6-dihydroimidazo[4,5-d]pyrrolo[2,3-b]pyridin-2-yl)-N-methylacetamide;
N-((3R,5R,7R)-Adamantan-1-ylmethyl)-2-(1-((1r,4r)-4-(cyanomethyl)cyclohexyl)-1,6-dihydroimidazo[4,5-d]pyrrolo[2,3-b]pyridin-2-yl)acetamide;
2-(1-((1r,4r)-4-(Cyanomethyl)cyclohexyl)-1,6-dihydroimidazo[4,5-d]pyrrolo[2,3-b]pyridin-2-yl)-N-(4-cyanophenyl)acetamide;
2-(1-((1r,4r)-4-(Cyanomethyl)cyclohexyl)-1,6-dihydroimidazo[4,5-d]pyrrolo[2,3-b]pyridin-2-yl)acetamide; and
2-(1-(4-(Cyanomethyl)bicyclo[2.2.2]octan-1-yl)-1,6-dihydroimidazo[4,5-d]pyrrolo[2,3-b]pyridin-2-yl)-N-methylacetamide.

A further embodiment of the invention is a compound or a pharmaceutically acceptable salt thereof, selected from the group consisting of N-((1-((1r,4r)-4-(Cyanomethyl)cyclohexyl)-1,6-dihydroimidazo[4,5-d]pyrrolo[2,3-b]pyridin-2-yl)methyl)benzimidamide;
Phenyl ((1-((1r,4r)-4-(cyanomethyl)cyclohexyl)-1,6-dihydroimidazo[4,5-d]pyrrolo[2,3-b]pyridin-2-yl)methyl)carbamate;
(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxyisobutyrimidamide;
1-((1-((1r,4r)-4-(Cyanomethyl)cyclohexyl)-1,6-dihydroimidazo[4,5-d]pyrrolo[2,3-b]pyridin-2-yl)methyl)-3-phenylurea;
N-((1-((1r,4r)-4-(Cyanomethyl)cyclohexyl)-1,6-dihydroimidazo[4,5-d]pyrrolo[2,3-b]pyridin-2-yl)methyl)acetimidamide;
(EZ)—N-((1-((1r,4r)-4-(Cyanomethyl)cyclohexyl)-1,6-dihydroimidazo[4,5-d]pyrrolo[2,3-b]pyridin-2-yl)methyl)-2-cyclohexyl-N'-hydroxyacetimidamide;
(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3,3-dimethylbutanimidamide;
(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-2-phenylacetimidamide;
(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclopropanecarboximidamide;
(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3-methoxypropanimidamide;
Isobutyl ((1-((1r,4r)-4-(Cyanomethyl)cyclohexyl)-1,6-dihydroimidazo[4,5-d]pyrrolo[2,3-b]pyridin-2-yl)methyl)carbamate;
N-((1-((1r,4r)-4-(Cyanomethyl)cyclohexyl)-1,6-dihydroimidazo[4,5-d]pyrrolo[2,3-b]pyridin-2-yl)methyl)cyclohexanecarboxamide;
N-((1-((1r,4r)-4-(Cyanomethyl)cyclohexyl)-1,6-dihydroimidazo[4,5-d]pyrrolo[2,3-b]pyridin-2-yl)methyl)-1H-pyrazole-4-carboxamide;
N-((1-((1r,4r)-4-(Cyanomethyl)cyclohexyl)-1,6-dihydroimidazo[4,5-d]pyrrolo[2,3-b]pyridin-2-yl)methyl)benzamide;

Neopentyl ((1-((1r,4r)-4-(Cyanomethyl)cyclohexyl)-1,6-dihydroimidazo[4,5-d]pyrrolo[2,3-b]pyridin-2-yl)methyl)carbamate;

1-((1-((1r,4r)-4-(Cyanomethyl)cyclohexyl)-1,6-dihydroimidazo[4,5-d]pyrrolo[2,3-b]pyridin-2-yl)methyl)-3-(cyclohexylmethyl)urea;

(3R,5R,7R)—N-((1-((1r,4r)-4-(Cyanomethyl)cyclohexyl)-1,6-dihydroimidazo[4,5-d]pyrrolo[2,3-b]pyridin-2-yl)methyl)adamantane-1-carboximidamide;

3-Cyano-N-((1-((1r,4r)-4-(cyanomethyl)cyclohexyl)-1,6-dihydroimidazo[4,5-d]pyrrolo[2,3-b]pyridin-2-yl)methyl)propanamide;

tert-Butyl ((1-((1r,4r)-4-(Cyanomethyl)cyclohexyl)-1,6-dihydroimidazo[4,5-d]pyrrolo[2,3-b]pyridin-2-yl)methyl)carbamate;

1-((1-((1r,4r)-4-(Cyanomethyl)cyclohexyl)-1,6-dihydroimidazo[4,5-d]pyrrolo[2,3-b]pyridin-2-yl)methyl)-3-isopropylurea;

(N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclohexanecarboximidamide;

2-((1r,4r)-4-(2-(((Dimethyl(oxo)-$\lambda^6$-sulfanylidene)amino)methyl)imidazo[4,5-d]pyrrolo[2,3-b]pyridin-1(6H)-yl)cyclohexyl)acetonitrile;

2-((1r,4r)-4-(2-((((R)-Methyl(oxo)(phenyl)-$\lambda^6$-sulfanylidene)amino)methyl)imidazo[4,5-d]pyrrolo[2,3-b]pyridin-1(6H)-yl)cyclohexyl)acetonitrile;

2-((1r,4r)-4-(2-((((S)-methyl(oxo)(phenyl)-$\lambda^6$-sulfanylidene)amino)methyl)imidazo[4,5-d]pyrrolo[2,3-b]pyridin-1(6H)-yl)cyclohexyl)acetonitrile;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)-3-methoxypropanimidamide;

(Z)—N'-((1-((1r,4r)-4-(Cyanomethyl)cyclohexyl)-1,6-dihydroimidazo[4,5-d]pyrrolo[2,3-b]pyridin-2-yl)methoxy)-2-cyclopropylacetimidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)benzimidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)isobutyrimidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)cyclopropanecarboximidamide;

(3R,5R,7R,E*)-N'-((1-((1r,4r)-4-(Cyanomethyl)cyclohexyl)-1,6-dihydroimidazo[4,5-d]pyrrolo[2,3-b]pyridin-2-yl)methoxy)adamantane-1-carboximidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)-2-(piperidin-1-yl)acetimidamide;

2-Cyano-N-((1-((1r,4r)-4-(cyanomethyl)cyclohexyl)-1,6-dihydroimidazo[4,5-d]pyrrolo[2,3-b]pyridin-2-yl)methyl)ethanesulfonamide;

N-((1-((1r,4r)-4-(Cyanomethyl)cyclohexyl)-1,6-dihydroimidazo[4,5-d]pyrrolo[2,3-b]pyridin-2-yl)methyl)benzenesulfonamide;

4-Cyano-N-((1-((1r,4r)-4-(cyanomethyl)cyclohexyl)-1,6-dihydroimidazo[4,5-d]pyrrolo[2,3-b]pyridin-2-yl)methyl)benzenesulfonamide; and N-((1-((1r,4r)-4-(Cyanomethyl)cyclohexyl)-1,6-dihydroimidazo[4,5-d]pyrrolo[2,3-b]pyridin-2-yl)methyl)cyclohexanesulfonamide.

A further embodiment of the invention is a compound or a pharmaceutically acceptable salt thereof, selected from the group consisting of N-((1-((1r,4r)-4-(Cyanomethyl)cyclohexyl)-1,6-dihydroimidazo[4,5-d]pyrrolo[2,3-b]pyridin-2-yl)methyl)benzimidamide;

Phenyl ((1-((1r,4r)-4-(cyanomethyl)cyclohexyl)-1,6-dihydroimidazo[4,5-d]pyrrolo[2,3-b]pyridin-2-yl)methyl)carbamate;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxyisobutyrimidamide;

1-((1-((1r,4r)-4-(Cyanomethyl)cyclohexyl)-1,6-dihydroimidazo[4,5-d]pyrrolo[2,3-b]pyridin-2-yl)methyl)-3-phenylurea;

N-((1-((1r,4r)-4-(Cyanomethyl)cyclohexyl)-1,6-dihydroimidazo[4,5-d]pyrrolo[2,3-b]pyridin-2-yl)methyl)acetimidamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-2-cyclohexyl-N'-hydroxyacetimidamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3,3-dimethylbutanimidamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-2-phenylacetimidamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclopropanecarboximidamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3-methoxypropanimidamide;

Isobutyl ((1-((1r,4r)-4-(Cyanomethyl)cyclohexyl)-1,6-dihydroimidazo[4,5-d]pyrrolo[2,3-b]pyridin-2-yl)methyl)carbamate;

N-((1-((1r,4r)-4-(Cyanomethyl)cyclohexyl)-1,6-dihydroimidazo[4,5-d]pyrrolo[2,3-b]pyridin-2-yl)methyl)cyclohexanecarboxamide;

N-((1-((1r,4r)-4-(Cyanomethyl)cyclohexyl)-1,6-dihydroimidazo[4,5-d]pyrrolo[2,3-b]pyridin-2-yl)methyl)-1H-pyrazole-4-carboxamide;

N-((1-((1r,4r)-4-(Cyanomethyl)cyclohexyl)-1,6-dihydroimidazo[4,5-d]pyrrolo[2,3-b]pyridin-2-yl)methyl)benzamide;

Neopentyl ((1-((1r,4r)-4-(Cyanomethyl)cyclohexyl)-1,6-dihydroimidazo[4,5-d]pyrrolo[2,3-b]pyridin-2-yl)methyl)carbamate;

1-((1-((1r,4r)-4-(Cyanomethyl)cyclohexyl)-1,6-dihydroimidazo[4,5-d]pyrrolo[2,3-b]pyridin-2-yl)methyl)-3-(cyclohexylmethyl)urea;

(3R,5R,7R)—N-((1-((1r,4r)-4-(Cyanomethyl)cyclohexyl)-1,6-dihydroimidazo[4,5-d]pyrrolo[2,3-b]pyridin-2-yl)methyl)adamantane-1-carboximidamide;

3-Cyano-N-((1-((1r,4r)-4-(cyanomethyl)cyclohexyl)-1,6-dihydroimidazo[4,5-d]pyrrolo[2,3-b]pyridin-2-yl)methyl)propanamide;

tert-Butyl ((1-((1r,4r)-4-(Cyanomethyl)cyclohexyl)-1,6-dihydroimidazo[4,5-d]pyrrolo[2,3-b]pyridin-2-yl)methyl)carbamate;

1-((1-((1r,4r)-4-(Cyanomethyl)cyclohexyl)-1,6-dihydroimidazo[4,5-d]pyrrolo[2,3-b]pyridin-2-yl)methyl)-3-isopropylurea; and (N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclohexanecarboximidamide.

A further embodiment of the invention is a compound or a pharmaceutically acceptable salt thereof, selected from the group consisting of 2-((1r,4r)-4-(2-(((Dimethyl(oxo)-λ⁶-sulfanylidene)amino)methyl)imidazo[4,5-d]pyrrolo[2,3-b]pyridin-1(6H)-yl)cyclohexyl)acetonitrile;

2-((1r,4r)-4-(2-((((R)-Methyl(oxo)(phenyl)-λ⁶-sulfanylidene)amino)methyl)imidazo[4,5-d]pyrrolo[2,3-b]pyridin-1(6H)-yl)cyclohexyl)acetonitrile; and 2-((1r,4r)-4-(2-((((S)-methyl(oxo)(phenyl)-λ⁶-sulfanylidene)amino)methyl)imidazo[4,5-d]pyrrolo[2,3-b]pyridin-1(6H)-yl)cyclohexyl)acetonitrile.

A further embodiment of the invention is a compound or a pharmaceutically acceptable salt thereof, selected from the group consisting of (Z*)—N'-((1-((1r,4r)-4-(Cyanomethyl)cyclohexyl)-1,6-dihydroimidazo[4,5-d]pyrrolo[2,3-b]pyridin-2-yl)methoxy)-3-methoxypropanimidamide;

(Z)—N'-((1-((1r,4r)-4-(Cyanomethyl)cyclohexyl)-1,6-dihydroimidazo[4,5-d]pyrrolo[2,3-b]pyridin-2-yl)methoxy)-2-cyclopropylacetimidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)benzimidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)isobutyrimidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)cyclopropanecarboximidamide;

(3R,5R,7R,E*)-N'-((1-((1r,4r)-4-(Cyanomethyl)cyclohexyl)-1,6-dihydroimidazo[4,5-d]pyrrolo[2,3-b]pyridin-2-yl)methoxy)adamantane-1-carboximidamide; and (Z*)—N'-((1-((1r,4r)-4-(Cyanomethyl)cyclohexyl)-1,6-dihydroimidazo[4,5-d]pyrrolo[2,3-b]pyridin-2-yl)methoxy)-2-(piperidin-1-yl)acetimidamide.

A further embodiment of the invention is a compound or a pharmaceutically acceptable salt thereof, selected from the group consisting of 2-Cyano-N-((1-((1r,4r)-4-(cyanomethyl)cyclohexyl)-1,6-dihydroimidazo[4,5-d]pyrrolo[2,3-b]pyridin-2-yl)methyl)ethanesulfonamide;

N-((1-((1r,4r)-4-(Cyanomethyl)cyclohexyl)-1,6-dihydroimidazo[4,5-d]pyrrolo[2,3-b]pyridin-2-yl)methyl)benzenesulfonamide;

4-Cyano-N-((1-((1r,4r)-4-(cyanomethyl)cyclohexyl)-1,6-dihydroimidazo[4,5-d]pyrrolo[2,3-b]pyridin-2-yl)methyl)benzenesulfonamide; and N-((1-((1r,4r)-4-(Cyanomethyl)cyclohexyl)-1,6-dihydroimidazo[4,5-d]pyrrolo[2,3-b]pyridin-2-yl)methyl)cyclohexanesulfonamide.

A further embodiment of the invention is a pharmaceutical composition comprising a compound or a pharmaceutically acceptable salt thereof, selected from the group consisting of 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide;

2-((1r,4r)-4-(2-(1H-Imidazol-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide;

N-(2-Cyanoethyl)-2-(1-(((1R,4R)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-pyran-4-yl)acetamide;

2-((1r,4r)-4-(2-(2-Oxo-2-(4-(trifluoromethyl)piperidin-1-yl)ethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)phenyl)acetamide;

2-(1-((1r,4r)-4-(Cyanomethyl)cyclohexyl)-1,6-dihydroimidazo[4,5-d]pyrrolo[2,3-b]pyridin-2-yl)-N-(4-(cyanomethyl)phenyl)acetamide;

2-((1r,4r)-4-(2-(1H-1,2,4-Triazol-3-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((tetrahydro-2H-pyran-4-yl)methyl)acetamide;

2-((1r,4r)-4-(2-(Oxazol-4-yl)imidazo[4,5-d]pyrrolo[2,3-b]pyridin-1(6H)-yl)cyclohexyl)acetonitrile;

2-((1r,4r)-4-(2-(2-(4-Hydroxypiperidin-1-yl)-2-oxoethyl)imidazo[4,5-d]pyrrolo[2,3-b]pyridin-1(6H)-yl)cyclohexyl)acetonitrile;

2-Cyano-N-((1-((1r,4r)-4-(cyanomethyl)cyclohexyl)-1,6-dihydroimidazo[4,5-d]pyrrolo[2,3-b]pyridin-2-yl)methyl)ethanesulfonamide;

2-(1-((1r,4r)-4-(Cyanomethyl)cyclohexyl)-1,6-dihydroimidazo[4,5-d]pyrrolo[2,3-b]pyridin-2-yl)-N-(pyrimidin-4-ylmethyl)acetamide;

2-(1-((1r,4r)-4-(Cyanomethyl)cyclohexyl)-1,6-dihydroimidazo[4,5-d]pyrrolo[2,3-b]pyridin-2-yl)-N-(3-hydroxy-2,2-dimethylpropyl)acetamide;

2-((1r,4r)-4-(2-(2H-1,2,3-Triazol-4-yl)imidazo[4,5-d]pyrrolo[2,3-b]pyridin-1(6H)-yl)cyclohexyl)acetonitrile;

(E)-N-((1-((1r,4r)-4-(Cyanomethyl)cyclohexyl)-1,6-dihydroimidazo[4,5-d]pyrrolo[2,3-b]pyridin-2-yl)methyl)-N'-hydroxybenzimidamide;

(Z)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxybenzimidamide;

2-((1r,4r)-4-(2-(2-(3-Hydroxyazetidin-1-yl)-2-oxoethyl)imidazo[4,5-d]pyrrolo[2,3-b]pyridin-1(6H)-yl)cyclohexyl)acetonitrile;

N-((1r,4r)-4-(Cyanomethyl)cyclohexyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-phenylacetamide;

2-(1-((1r,4r)-4-(Cyanomethyl)cyclohexyl)-1,6-dihydroimidazo[4,5-d]pyrrolo[2,3-b]pyridin-2-yl)-N-(((1S,3R,5R,7S)-3-hydroxyadamantan-1-yl)methyl)acetamide;

N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide;

N-(4-Cyanobicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((3-hydroxyoxetan-3-yl)methyl)acetamide;

2-((1r,4r)-4-(2-((1H-Pyrazol-5-yl)methyl)imidazo[4,5-d]pyrrolo[2,3-b]pyridin-1(6H)-yl)cyclohexyl)acetonitrile;

2-((1r,4r)-4-(2-(2-(4-Morpholinopiperidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(hydroxymethyl)cyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-cyclohexylacetamide;

2-(1-((1r,4r)-4-(Cyanomethyl)cyclohexyl)-1,6-dihydroimidazo[4,5-d]pyrrolo[2,3-b]pyridin-2-yl)-N-(2-hydroxyethyl)acetamide;

N-((1-((1r,4r)-4-(Cyanomethyl)cyclohexyl)-1,6-dihydroimidazo[4,5-d]pyrrolo[2,3-b]pyridin-2-yl)methyl)benzimidamide;

2-((1r,4r)-4-(2-(4-Chloro-1H-pyrazol-3-yl)imidazo[4,5-d]pyrrolo[2,3-b]pyridin-1(6H)-yl)cyclohexyl)acetonitrile;

N-((3R,5R)-Adamantan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1r,4r)-4-hydroxycyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide;

2-(1-((1r,4r)-4-(Cyanomethyl)cyclohexyl)-1,6-dihydroimidazo[4,5-d]pyrrolo[2,3-b]pyridin-2-yl)-N-(pyrazin-2-ylmethyl)acetamide;

N-((1H-imidazol-2-yl)methyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1R,3R)-3-hydroxycyclobutyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide;

N-(4-Cyanobenzyl)-2-(1-((1r,4r)-4-(cyanomethyl)cyclohexyl)-1,6-dihydroimidazo[4,5-d]pyrrolo[2,3-b]pyridin-2-yl)acetamide;

1-((1-((1r,4r)-4-(Cyanomethyl)cyclohexyl)-1,6-dihydroimidazo[4,5-d]pyrrolo[2,3-b]pyridin-2-yl)methyl)urea;

2-((1r,4r)-4-(2-(Thiazol-4-ylmethyl)imidazo[4,5-d]pyrrolo[2,3-b]pyridin-1(6H)-yl)cyclohexyl)acetonitrile;

2-((1S,4r)-4-(2-(2-((S)-3-Hydroxypyrrolidin-1l-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(2-(pyridin-4-yloxy)ethyl)acetamide;

2-(1-((1r,4r)-4-(Cyanomethyl)cyclohexyl)-1,6-dihydroimidazo[4,5-d]pyrrolo[2,3-b]pyridin-2-yl)-N-neopentylacetamide;

2-(1-((1r,4r)-4-(Cyanomethyl)cyclohexyl)-1,6-dihydroimidazo[4,5-d]pyrrolo[2,3-b]pyridin-2-yl)-N-(4-fluorobenzyl)acetamide;

Phenyl ((1-((1r,4r)-4-(cyanomethyl)cyclohexyl)-1,6-dihydroimidazo[4,5-d]pyrrolo[2,3-b]pyridin-2-yl)methyl)carbamate;

2-(1-((1r,4r)-4-(Cyanomethyl)cyclohexyl)-1,6-dihydroimidazo[4,5-d]pyrrolo[2,3-b]pyridin-2-yl)-N-((1S,4S)-4-hydroxycyclohexyl)acetamide;

N-Benzyl-2-(1-((1r,4r)-4-(cyanomethyl)cyclohexyl)-1,6-dihydroimidazo[4,5-d]pyrrolo[2,3-b]pyridin-2-yl)acetamide;

2-((1r,4r)-4-(2-(2-Oxo-2-(pyrrolidin-1-yl)ethyl)imidazo[4,5-d]pyrrolo[2,3-b]pyridin-1(6H)-yl)cyclohexyl)acetonitrile;

2-((1r,4r)-4-(2-(3-Hydroxy-3-phenylpyrrolidine-1-carbonyl)imidazo[4,5-d]pyrrolo[2,3-b]pyridin-1(6H)-yl)cyclohexyl)acetonitrile;

2-((1r,4r)-4-(2-(2-Aminopyrimidin-5-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1 s, 3r,5R, 7S)-3-hydroxyadamantan-1-yl)acetamide;

2-((1r,4r)-4-(2-(2-Aminopyrimidin-4-yl)imidazo[4,5-d]pyrrolo[2,3-b]pyridin-1(6H)-yl)cyclohexyl)acetonitrile;

4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.1]heptane-1-carboxamide;

N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-((1r,4r)-4-(2-(1H-Imidazol-2-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(2,2,2-trifluoroethyl)acetamide;

4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.2]octane-1-carboxamide;

2-(1-((1r,4r)-4-(Cyanomethyl)cyclohexyl)-1,6-dihydroimidazo[4,5-d]pyrrolo[2,3-b]pyridin-2-yl)-N-(3-hydroxy-3-methylbutyl)acetamide;

2-((1r,4r)-4-(2-(1H-Pyrazol-3-yl)imidazo[4,5-d]pyrrolo[2,3-b]pyridin-1(6H)-yl)cyclohexyl)acetonitrile;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxyisobutyrimidamide;

2-(1-((1r,4r)-4-(Cyanomethyl)cyclohexyl)-1,6-dihydroimidazo[4,5-d]pyrrolo[2,3-b]pyridin-2-yl)-N-(1-isobutylpiperidin-4-yl)acetamide;

2-((1r,4r)-4-(2-(2H-Tetrazol-5-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(4,4-dimethylcyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-methylpiperidin-4-yl)acetamide;

2-((1r,4r)-4-(2-(1,1-Dioxidothiomorpholino)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)benzyl)acetamide;

2-(1-((1r,4r)-4-(Cyanomethyl)cyclohexyl)-1,6-dihydroimidazo[4,5-d]pyrrolo[2,3-b]pyridin-2-yl)-N-(cyclohexylmethyl)acetamide;

1-((1-((1r,4r)-4-(Cyanomethyl)cyclohexyl)-1,6-dihydroimidazo[4,5-d]pyrrolo[2,3-b]pyridin-2-yl)methyl)-3-phenylurea;

2-(1-((1r,4r)-4-(Cyanomethyl)cyclohexyl)-1,6-dihydroimidazo[4,5-d]pyrrolo[2,3-b]pyridin-2-yl)-N-(2-methoxy-2-methylpropyl)acetamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)-3-methoxypropanimidamide;

2-((1r,4r)-4-(2-(2-(4-(Hydroxymethyl)piperidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(3, 5-dimethylcyclohexyl)acetamide;

4-(4-(1-((1r,4r)-4-(Cyanomethyl)cyclohexyl)-1,6-dihydroimidazo[4,5-d]pyrrolo[2,3-b]pyridin-2-yl)piperidin-1-yl)benzonitrile;

N-((1-((1r,4r)-4-(Cyanomethyl)cyclohexyl)-1,6-dihydroimidazo[4,5-d]pyrrolo[2,3-b]pyridin-2-yl)methyl)benzenesulfonamide;

N-((1S,4R)-Bicyclo[2.2.1]heptan-2-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(cyanomethyl)cyclohexyl)-1,6-dihydroimidazo[4,5-d]pyrrolo[2,3-b]pyridin-2-yl)-N-(4-(difluoromethoxy)benzyl)acetamide;

1-((1r,4r)-4-(Cyanomethyl)cyclohexyl)-N-((3-hydroxyoxetan-3-yl)methyl)-1,6-dihydroimidazo[4,5-d]pyrrolo[2,3-b]pyridine-2-carboxamide;

2-((1r,4r)-4-(2-(3-Methyl-1H-pyrazol-5-yl)imidazo[4,5-d]pyrrolo[2,3-b]pyridin-1(6H)-yl)cyclohexyl)acetonitrile;

4-Cyano-N-((1-((1r,4r)-4-(cyanomethyl)cyclohexyl)-1,6-dihydroimidazo[4,5-d]pyrrolo[2,3-b]pyridin-2-yl)methyl)benzamide;

2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-thiopyran-4-yl)acetamide;

1-((1r,4r)-4-(Cyanomethyl)cyclohexyl)-N-(1-methylpiperidin-4-yl)-1,6-dihydroimidazo[4,5-d]pyrrolo[2,3-b]pyridine-2-carboxamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide;

N-((1-((1r,4r)-4-(Cyanomethyl)cyclohexyl)-1,6-dihydroimidazo[4,5-d]pyrrolo[2,3-b]pyridin-2-yl)methyl)acetimidamide;

2-((1r,4r)-4-(2-(2-(4-Benzylpiperidin-1-yl)-2-oxoethyl)imidazo[4,5-d]pyrrolo[2,3-b]pyridin-1(6H)-yl)cyclohexyl)acetonitrile;

2-((1r,4r)-4-(2-(4-Hydroxy-4-(pyridin-2-yl)piperidine-1-carbonyl)imidazo[4,5-d]pyrrolo[2,3-b]pyridin-1(6H)-yl)cyclohexyl)acetonitrile;

2-((1r,4r)-4-(2-(2-(Methylamino)pyrimidin-4-yl)imidazo[4,5-d]pyrrolo[2,3-b]pyridin-1(6H)-yl)cyclohexyl)acetonitrile;

2-((1r,4r)-4-(2-(2-Oxo-2-(piperidin-1-yl)ethyl)imidazo[4,5-d]pyrrolo[2,3-b]pyridin-1(6H)-yl)cyclohexyl)acetonitrile;

2-((1r,4r)-4-(2-(4'-(Methylsulfonyl)-[1,1'-biphenyl]-4-yl)imidazo[4,5-d]pyrrolo[2,3-b]pyridin-1(6H)-yl)cyclohexyl)acetonitrile;

2-((1r,4r)-4-(2-(4-Benzoylphenyl)imidazo[4,5-d]pyrrolo[2,3-b]pyridin-1(6H)-yl)cyclohexyl)acetonitrile;

2-((1r,4r)-4-(2-(2-(4-(2-Hydroxypropan-2-yl)piperidin-1-yl)-2-oxoethyl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)-2-cyclopropylacetamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-2-cyclohexyl-N'-hydroxyacetimidamide;

4-(1-((1r,4r)-4-(Cyanomethyl)cyclohexyl)-1,6-dihydroimidazo[4,5-d]pyrrolo[2,3-b]pyridin-2-yl)benzonitrile;

4-Cyano-N-((1-((1r,4r)-4-(cyanomethyl)cyclohexyl)-1,6-dihydroimidazo[4,5-d]pyrrolo[2,3-b]pyridin-2-yl)methyl)benzenesulfonamide;

2-((1r,4r)-4-(2-(2-(Methylthio)pyrimidin-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((trimethylsilyl)methyl)acetamide;

2-((1r,4r)-4-(2-(4-(Trimethylsilyl)cyclohexyl)imidazo[4,5-d]pyrrolo[2,3-b]pyridin-1(6H)-yl)cyclohexyl)acetonitrile;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3,3-dimethylbutanimidamide;

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-phenylethyl)acetamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-2-phenylacetimidamide;

2-(1-((1r,4r)-4-(Cyanomethyl)cyclohexyl)-1,6-dihydroimidazo[4,5-d]pyrrolo[2,3-b]pyridin-2-yl)-N-(4-(1,1,1,3,3,3-hexafluoro-2-hydroxypropan-2-yl)phenyl)acetamide;

1-(2-(1-((1r,4r)-4-(Cyanomethyl)cyclohexyl)-1,6-dihydroimidazo[4,5-d]pyrrolo[2,3-b]pyridin-2-yl)acetyl)piperidine-4-carbonitrile;

2-(1-((1r,4r)-4-(Cyanomethyl)cyclohexyl)-1,6-dihydroimidazo[4,5-d]pyrrolo[2,3-b]pyridin-2-yl)-N-(2,3-dihydroxypropyl)acetamide;

2-((1r,4r)-4-(2-(2-(4,4-Difluoropiperidin-1-yl)-2-oxoethyl)imidazo[4,5-d]pyrrolo[2,3-b]pyridin-1(6H)-yl)cyclohexyl)acetonitrile;

Diethyl 4-(2-(1-((1r,4r)-4-(cyanomethyl)cyclohexyl)-1,6-dihydroimidazo[4,5-d]pyrrolo[2,3-b]pyridin-2-yl)acetamido)benzylphosphonate;

(1-((1r,4r)-4-(Cyanomethyl)cyclohexyl)-1,6-dihydroimidazo[4,5-d]pyrrolo[2,3-b]pyridin-2-yl)methyl phenylcarbamate;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclopropanecarboximidamide;

2-(1-((1r,4r)-4-(Cyanomethyl)cyclohexyl)-1,6-dihydroimidazo[4,5-d]pyrrolo[2,3-b]pyridin-2-yl)-N-(pyridin-3-yl)acetamide;

(Z)—N'-((1-((1r,4r)-4-(Cyanomethyl)cyclohexyl)-1,6-dihydroimidazo[4,5-d]pyrrolo[2,3-b]pyridin-2-yl)methoxy)-2-cyclopropylacetimidamide;

2-((1r,4r)-4-(2-(Methoxymethyl)imidazo[4,5-d]pyrrolo[2,3-b]pyridin-1(6H)-yl)cyclohexyl)acetonitrile;

1-((1r,4r)-4-(Cyanomethyl)cyclohexyl)-N-(2-hydroxyethyl)-1,6-dihydroimidazo[4,5-d]pyrrolo[2,3-b]pyridine-2-carboxamide;

5-(1-((1r,4r)-4-(Cyanomethyl)cyclohexyl)-1,6-dihydroimidazo[4,5-d]pyrrolo[2,3-b]pyridin-2-yl)picolinonitrile;

N-((1-((1r,4r)-4-(Cyanomethyl)cyclohexyl)-1,6-dihydroimidazo[4,5-d]pyrrolo[2,3-b]pyridin-2-yl)methyl)-3-hydroxy-3-methylbutanamide;

1-((1r,4r)-4-(Cyanomethyl)cyclohexyl)-N-(2-hydroxy-2-methylpropyl)-1,6-dihydroimidazo[4,5-d]pyrrolo[2,3-b]pyridine-2-carboxamide;

2-(1-((1r,4r)-4-(Cyanomethyl)cyclohexyl)-1,6-dihydroimidazo[4,5-d]pyrrolo[2,3-b]pyridin-2-yl)-N-(pyridin-4-yl)acetamide;

2-((1r,4r)-4-(2-(Thiazol-5-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(2-methoxyethyl)acetamide;

2-((1r,4r)-4-(2-(4-(4-(Hydroxymethyl)benzoyl)phenyl)imidazo[4,5-d]pyrrolo[2,3-b]pyridin-1(6H)-yl)cyclohexyl)acetonitrile;

1-((1r,4r)-4-(Cyanomethyl)cyclohexyl)-N-(oxetan-3-yl)-1,6-dihydroimidazo[4,5-d]pyrrolo[2,3-b]pyridine-2-carboxamide;

2-((1r,4r)-4-(2-(1H-pyrazol-4-yl)imidazo[4,5-d]pyrrolo[2,3-b]pyridin-1(6H)-yl)cyclohexyl)acetonitrile;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)benzimidamide;

(EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxy-3-methoxypropanimidamide;

2-((1r,4r)-4-(2-(((4-(4-Ethynylbenzoyl)benzyl)oxy)methyl)imidazo[4,5-d]pyrrolo[2,3-b]pyridin-1(6H)-yl)cyclohexyl)acetonitrile;

2-((1r,4r)-4-(2-(2-((R)-3-Hydroxypyrrolidin-1-yl)-2-oxoethyl)imidazo[4,5-d]pyrrolo[2,3-b]pyridin-1(6H)-yl)cyclohexyl)acetonitrile;

Ethyl 3-(1-((1r,4r)-4-(Cyanomethyl)cyclohexyl)-1,6-dihydroimidazo[4,5-d]pyrrolo[2,3-b]pyridin-2-yl)azetidine-1-carboxylate;

2-((1r,4r)-4-(2-((3-Isopropyl-5-oxo-1,2,4-oxadiazol-4(5H)-yl)methyl)imidazo[4,5-d]pyrrolo[2,3-b]pyridin-1(6H)-yl)cyclohexyl)acetonitrile;

2-((1r,4r)-4-(2-((4-(4-Ethynylbenzoyl)phenoxy)methyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)bicyclo[2.2.1]heptan-1-yl)acetamide;

2-(1-((1r,4r)-4-(Cyanomethyl)cyclohexyl)-8-fluoro-1,6-dihydroimidazo[4,5-d]pyrrolo[2,3-b]pyridin-2-yl)-N-(2-hydroxy-2-methylpropyl)acetamide;

1-((1r,4r)-4-(Cyanomethyl)cyclohexyl)-N-methyl-1,6-dihydroimidazo[4,5-d]pyrrolo[2,3-b]pyridine-2-carboxamide;

2-((1r,4r)-4-(2-(1-(Methyl sulfonyl)azetidin-3-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1S,4S)-4-(trimethylsilyl)cyclohexyl)acetamide;

1-((1r,4r)-4-(Cyanomethyl)cyclohexyl)-N-((1-hydroxycycloheptyl)methyl)-1,6-dihydroimidazo[4,5-d]pyrrolo[2,3-b]pyridine-2-carboxamide;

Isobutyl ((1-((1r,4r)-4-(Cyanomethyl)cyclohexyl)-1,6-dihydroimidazo[4,5-d]pyrrolo[2,3-b]pyridin-2-yl)methyl)carbamate;

N-(2-Cyanoethyl)-1-((1r,4r)-4-(cyanomethyl)cyclohexyl)-1,6-dihydroimidazo[4,5-d]pyrrolo[2,3-b]pyridine-2-carboxamide;

N-((1-((1r,4r)-4-(Cyanomethyl)cyclohexyl)-1,6-dihydroimidazo[4,5-d]pyrrolo[2,3-b]pyridin-2-yl)methyl)cyclohexanecarboxamide;

2-((1r,4r)-4-(2-(3-Cyclopropyl-4,5-dihydro-1,2,4-oxadiazol-5-yl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)cyclohexanesulfonamide;

2-((1r,4r)-4-(2-(((Dimethyl(oxo)-$\lambda^6$-sulfanylidene)amino)methyl)imidazo[4,5-d]pyrrolo[2,3-b]pyridin-1(6H)-yl)cyclohexyl)acetonitrile;

2-((1r,4r)-4-(2-(4-(Pentafluoro-$\lambda^6$-sulfanyl)phenyl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)-1H-pyrazole-4-carboxamide;

1-((1r,4r)-4-(Cyanomethyl)cyclohexyl)-N-(2-methoxyethyl)-1,6-dihydroimidazo[4,5-d]pyrrolo[2,3-b]pyridine-2-carboxamide;

(1-((1r,4r)-4-(Cyanomethyl)cyclohexyl)-1,6-dihydroimidazo[4,5-d]pyrrolo[2,3-b]pyridin-2-yl)methyl (cyclohexylmethyl)carbamate;

2-((1r,4r)-4-(2-(1-Acetyl azetidin-3-yl)imidazo[4,5-d]pyrrolo[2,3-b]pyridin-1(6H)-yl)cyclohexyl)acetonitrile;

N-((1-((1r,4r)-4-(Cyanomethyl)cyclohexyl)-1,6-dihydroimidazo[4,5-d]pyrrolo[2,3-b]pyridin-2-yl)methyl)benzamide;

2-((1r,4r)-4-(2-(2-((R)-2-(Hydroxymethyl)pyrrolidin-1-yl)-2-oxoethyl)imidazo[4,5-d]pyrrolo[2,3-b]pyridin-1(6H)-yl)cyclohexyl)acetonitrile;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)isobutyrimidamide;

(Z*)—N'-((1-((1-((1r,4r)-4-(Cyanomethyl)cyclohexyl)-1,6-dihydroimidazo[4,5-d]pyrrolo[2,3-b]pyridin-2-yl)methoxy)cyclopropanecarboximidamide;

(3R,5R,7R,E*)-N'-((1-((1r,4r)-4-(Cyanomethyl)cyclohexyl)-1,6-dihydroimidazo[4,5-d]pyrrolo[2,3-b]pyridin-2-yl)methoxy)adamantane-1-carboximidamide;

(Z*)—N'-((1-((1r,4r)-4-(Cyanomethyl)cyclohexyl)-1,6-dihydroimidazo[4,5-d]pyrrolo[2,3-b]pyridin-2-yl)methoxy)-2-(piperidin-1-yl)acetimidamide;

Neopentyl ((1-((1r,4r)-4-(Cyanomethyl)cyclohexyl)-1,6-dihydroimidazo[4,5-d]pyrrolo[2,3-b]pyridin-2-yl)methyl)carbamate;

1-((1-((1r,4r)-4-(Cyanomethyl)cyclohexyl)-1,6-dihydroimidazo[4,5-d]pyrrolo[2,3-b]pyridin-2-yl)methyl)-3-(cyclohexylmethyl)urea;

(3R,5R,7R)—N-((1-((1r,4r)-4-(Cyanomethyl)cyclohexyl)-1,6-dihydroimidazo[4,5-d]pyrrolo[2,3-b]pyridin-2-yl)methyl)adamantane-1-carboximidamide;

3-Cyano-N-((1-((1r,4r)-4-(cyanomethyl)cyclohexyl)-1,6-dihydroimidazo[4,5-d]pyrrolo[2,3-b]pyridin-2-yl)methyl)propanamide;

tert-Butyl ((1-((1r,4r)-4-(Cyanomethyl)cyclohexyl)-1,6-dihydroimidazo[4,5-d]pyrrolo[2,3-b]pyridin-2-yl)methyl)carbamate;

2-((1r,4r)-4-(2-(Azetidin-3-yl)imidazo[4,5-d]pyrrolo[2,3-b]pyridin-1(6H)-yl)cyclohexyl)acetonitrile;

3-(3-(1-((1r,4r)-4-(Cyanomethyl)cyclohexyl)-1,6-dihydroimidazo[4,5-d]pyrrolo[2,3-b]pyridin-2-yl)azetidin-1-yl)-3-oxopropanenitrile;

(1-((1r,4r)-4-(Cyanomethyl)cyclohexyl)-1,6-dihydroimidazo[4,5-d]pyrrolo[2,3-b]pyridin-2-yl)methyl (2-methoxyethyl)carbamate;

2-((1r,4r)-4-(2-((((R)-Methyl(oxo)(phenyl)-$\lambda^6$-sulfanylidene)amino)methyl)imidazo[4,5-d]pyrrolo[2,3-b]pyridin-1(6H)-yl)cyclohexyl)acetonitrile;

2-((1r,4r)-4-(2-((((S)-methyl(oxo)(phenyl)-$\lambda^6$-sulfanylidene)amino)methyl)imidazo[4,5-d]pyrrolo[2,3-b]pyridin-1(6H)-yl)cyclohexyl)acetonitrile;

2-((1r,4r)-4-(2-(1-Acetylpiperidin-4-yl)imidazo[4,5-d]pyrrolo[2,3-b]pyridin-1(6H)-yl)cyclohexyl)acetonitrile;

2-((1r,4r)-4-(2-((3-Cyclopropyl-5-oxo-1,2,4-oxadiazol-4(5H)-yl)methyl)imidazo[4,5-d]pyrrolo[2,3-b]pyridin-1(6H)-yl)cyclohexyl)acetonitrile;

2-((1r,4r)-4-(2-(1-(Oxazol-4-ylmethyl)-1H-pyrazol-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(trimethylsilyl)cyclohexyl)acetamide;
2-((1r,4r)-4-(2-(1-(2-Hydroxy-2-methylpropyl)piperidin-4-yl)imidazo[4,5-d]pyrrolo[2,3-b]pyridin-1(6H)-yl)cyclohexyl)acetonitrile;
2-((1r,4r)-4-(2-(4-(4-Ethynylbenzoyl)phenyl)imidazo[4,5-d]pyrrolo[2,3-b]pyridin-1(6H)-yl)cyclohexyl)acetonitrile;
2-((1r,4r)-4-(2-(4-(4-Ethynylbenzoyl)phenethyl)imidazo[4,5-d]pyrrolo[2,3-b]pyridin-1(6H)-yl)cyclohexyl)acetonitrile;
1-((1-((1r,4r)-4-(Cyanomethyl)cyclohexyl)-1,6-dihydroimidazo[4,5-d]pyrrolo[2,3-b]pyridin-2-yl)methyl)-3-isopropylurea;
1-((1r,4r)-4-(Cyanomethyl)cyclohexyl)-N-isopropyl-1,6-dihydroimidazo[4,5-d]pyrrolo[2,3-b]pyridine-2-carboxamide;
1-((1r,4r)-4-(Cyanomethyl)cyclohexyl)-N-(3-methoxypropyl)-1,6-dihydroimidazo[4,5-d]pyrrolo[2,3-b]pyridine-2-carboxamide;
2-(1-((1r,4r)-4-Cyanocyclohexyl)-1,6-dihydroimidazo[4,5-d]pyrrolo[2,3-b]pyridin-2-yl)-N-(4-(methylsulfonyl)phenyl)acetamide;
1-((1r,4r)-4-(Cyanomethyl)cyclohexyl)-N-cyclopropyl-1,6-dihydroimidazo[4,5-d]pyrrolo[2,3-b]pyridine-2-carboxamide;
2-((1r,4r)-4-(2-(4-Methoxypiperidine-1-carbonyl)imidazo[4,5-d]pyrrolo[2,3-b]pyridin-1(6H)-yl)cyclohexyl)acetonitrile;
1-(1-((1r,4r)-4-(Cyanomethyl)cyclohexyl)-1,6-dihydroimidazo[4,5-d]pyrrolo[2,3-b]pyridine-2-carbonyl)piperidine-4-carbonitrile;
1-((1r,4r)-4-(Cyanomethyl)cyclohexyl)-N-(tetrahydro-2H-pyran-4-yl)-1,6-dihydroimidazo[4,5-d]pyrrolo[2,3-b]pyridine-2-carboxamide;
1-((1r,4r)-4-(Cyanomethyl)cyclohexyl)-N-(1-methoxypropan-2-yl)-1,6-dihydroimidazo[4,5-d]pyrrolo[2,3-b]pyridine-2-carboxamide;
2-((1r,4r)-4-(2-(Morpholine-4-carbonyl)imidazo[4,5-d]pyrrolo[2,3-b]pyridin-1(6H)-yl)cyclohexyl)acetonitrile;
2-((1r,4r)-4-(2-(4-Hydroxypiperidine-1-carbonyl)imidazo[4,5-d]pyrrolo[2,3-b]pyridin-1(6H)-yl)cyclohexyl)acetonitrile;
Ethyl 2-(4-(1-((1r,4r)-4-(cyanomethyl)cyclohexyl)-1,6-dihydroimidazo[4,5-d]pyrrolo[2,3-b]pyridin-2-yl)-1H-pyrazol-1-yl)acetate;
2-((1r,4r)-4-(2-(2,4-dimethyloxazol-5-yl)imidazo[4,5-d]pyrrolo[2,3-b]pyridin-1(6H)-yl)cyclohexyl)acetonitrile;
2-((1r,4r)-4-(2-(2,4-dimethylthiazol-5-yl)imidazo[4,5-d]pyrrolo[2,3-b]pyridin-1(6H)-yl)cyclohexyl)acetonitrile;
2-(4-(1-((1r,4r)-4-(Cyanomethyl)cyclohexyl)-1,6-dihydroimidazo[4,5-d]pyrrolo[2,3-b]pyridin-2-yl)-1H-pyrazol-1-yl)-N-cyclopropylacetamide;
2-((1r,4r)-4-(2-(2-aminopyridin-3-yl)imidazo[4,5-d]pyrrolo[2,3-b]pyridin-1(6H)-yl)cyclohexyl)acetonitrile;
2-((1r,4r)-4-(2-(1-(2-Hydroxy-2-methylpropyl)-1H-pyrazol-4-yl)imidazo[4,5-d]pyrrolo[2,3-b]pyridin-1(6H)-yl)cyclohexyl)acetonitrile;
2-(8-chloro-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;
2-(8-bromo-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;
2-(1-((1r,4r)-4-(cyanomethyl)cyclohexyl)-8-methyl-1,6-dihydroimidazo[4,5-d]pyrrolo[2,3-b]pyridin-2-yl)-N-(2-hydroxy-2-methylpropyl)acetamide;
2-(1-((1r,4r)-4-(Cyanomethyl)cyclohexyl)-7-methyl-1,6-dihydroimidazo[4,5-d]pyrrolo[2,3-b]pyridin-2-yl)-N-(2-hydroxy-2-methylpropyl)acetamide;
2-((1r,4r)-4-(2-(2,5,8,11-Tetraoxatridecan-13-yl)imidazo[4,5-d]pyrrolo[2,3-b]pyridin-1(6H)-yl)cyclohexyl)acetonitrile;
N-(2-(2-(2-Aminoethoxy)ethoxy)ethyl)-2-(1-((1r,4r)-4-(cyanomethyl)cyclohexyl)-1,6-dihydroimidazo[4,5-d]pyrrolo[2,3-b]pyridin-2-yl)acetamide;
2-((1r,4r)-4-(2-((2-(2-methoxyethoxy)ethoxy)methyl)imidazo[4,5-d]pyrrolo[2,3-b]pyridin-1(6H)-yl)cyclohexyl)acetonitrile;
2-((1S,4r)-4-(2-(2-((S)-2-(hydroxymethyl)pyrrolidin-1-yl)-2-oxoethyl)imidazo[4,5-d]pyrrolo[2,3-b]pyridin-1(6H)-yl)cyclohexyl)acetonitrile;
(1-((1R4R)-4-(Cyanomethyl)cyclohexyl)-1,6-dihydroimidazo[4,5-d]pyrrolo[2,3-b]pyridin-2-yl)methyl (3S,5S,7S)-adamantan-1-ylcarbamate;
2-((1r,4r)-4-(2-(2-(4-Methoxypiperidin-1-yl)-2-oxoethyl)imidazo[4,5-d]pyrrolo[2,3-b]pyridin-1(6H)-yl)cyclohexyl)acetonitrile;
2-(1-((1r,4r)-4-(Cyanomethyl)cyclohexyl)-1,6-dihydroimidazo[4,5-d]pyrrolo[2,3-b]pyridin-2-yl)-N-methylacetamide;
N-((3R,5R,7R)-Adamantan-1-ylmethyl)-2-(1-((1r,4r)-4-(cyanomethyl)cyclohexyl)-1,6-dihydroimidazo[4,5-d]pyrrolo[2,3-b]pyridin-2-yl)acetamide;
2-(1-((1r,4r)-4-(Cyanomethyl)cyclohexyl)-1,6-dihydroimidazo[4,5-d]pyrrolo[2,3-b]pyridin-2-yl)-N-(4-cyanophenyl)acetamide;
2-(1-((1r,4r)-4-(Cyanomethyl)cyclohexyl)-1,6-dihydroimidazo[4,5-d]pyrrolo[2,3-b]pyridin-2-yl)acetamide;
2-((1r,4r)-4-(2-(tert-Butoxymethyl)imidazo[4,5-d]pyrrolo[2,3-b]pyridin-1(6H)-yl)cyclohexyl)acetonitrile;
2-((1r,4r)-4-(2-((5-Oxo-3-phenyl-1,2,4-oxadiazol-4(5H)-yl)methyl)imidazo[4,5-d]pyrrolo[2,3-b]pyridin-1(6H)-yl)cyclohexyl)acetonitrile;
(N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclohexanecarboximidamide;
2-(4-(2-(2-Oxo-2-(piperidin-1-yl)ethyl)imidazo[4,5-d]pyrrolo[2,3-b]pyridin-1(6H)-yl)bicyclo[2.2.2]octan-1-yl)acetonitrile;
2-(1-(4-(Cyanomethyl)bicyclo[2.2.2]octan-1-yl)-1,6-dihydroimidazo[4,5-d]pyrrolo[2,3-b]pyridin-2-yl)acetamide;
2-(1-(4-(Cyanomethyl)bicyclo[2.2.2]octan-1-yl)-1,6-dihydroimidazo[4,5-d]pyrrolo[2,3-b]pyridin-2-yl)-N-phenylacetamide;
2-(1-(4-(Cyanomethyl)bicyclo[2.2.2]octan-1-yl)-1,6-dihydroimidazo[4,5-d]pyrrolo[2,3-b]pyridin-2-yl)-N-(cyclohexylmethyl)acetamide; and
2-(1-(4-(Cyanomethyl)bicyclo[2.2.2]octan-1-yl)-1,6-dihydroimidazo[4,5-d]pyrrolo[2,3-b]pyridin-2-yl)-N-methylacetamide;

A "pharmaceutically acceptable salt" is a salt of a compound that is non-toxic, biologically tolerable, or otherwise biologically suitable for administration to the subject. See, generally, S. M. Berge, et al., "Pharmaceutical Salts", J. Pharm. Sci., 66, 1-19 (1977), and *Handbook of Pharmaceutical Salts, Properties, Selection, and Use*, Stahl and Wermuth, Eds., Wiley-VCH and VHCA, Zurich, 2002. Compounds of the invention may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propane-sulfonates, naphthalene-1-sulfonates, naphthalene-2-sulfonates, and mandelates.

If the compound of the invention contains at least one basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, and phosphoric acid, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Not all the embodiments of pharmaceutically acceptable salts of compounds according to this invention may be equally suitable for their development, for compounds that are sufficiently weakly basic (e.g., $pK_a$ of about 4) might not form sufficiently stable salts for development purposes. See, e.g., G. A. Stephenson, et al., J. Pharm. Sciences 100(5), 1607-17 (2011) "Physical stability of salts of weak bases in the solid state". Some embodiments of this invention are envisaged to encompass co-crystallized forms of a compound according to this invention with a suitable co-crystal former. Design and properties of co-crystals for pharmaceutical use and methods of making and characterizing them have been given in, for example, N. Shan, et al., Drug Discovery Today, 13(9/10), 440-46 (2008) "The role of cocrystals in pharmaceutical science"; N. Qiao, et al., Intl. J. Pharmaceutics, 419, 1-11 (2011) "Pharmaceutical cocrystals: An overview"; R. Thakuria, et al., Intl. J. Pharmaceutics, 453, 101-25 (2013) "Pharmaceutical cocrystals and poorly soluble drugs".

The compounds of the invention, including their pharmaceutically acceptable salts, whether alone or in combination, (collectively, "active agent" or "active agents") of the present invention are useful as JAK inhibitors in the methods of the invention. Such methods for modulating JAK activity comprise exposing JAK to an effective amount of at least one chemical compound of the invention. Embodiments of this invention inhibit JAK activity.

In some embodiments, the JAK inhibitor is used in a subject diagnosed with or suffering from a disease, disorder, or medical condition mediated through JAK activity, such as those described herein. Symptoms or disease states are intended to be included within the scope of "disease, disorders or medical conditions."

Accordingly, the invention relates to methods of using the active agents described herein to treat subjects diagnosed with or suffering from a disease, disorder, or medical condition mediated through JAK. The term "treat" or "treating" as used herein is intended to refer to administration of an active agent or composition of the invention to a subject for the purpose of affecting a therapeutic or prophylactic benefit through modulation of JAK. Treating includes reversing, ameliorating, alleviating, inhibiting the progress of, lessening the severity of, or preventing a disease, disorder, or condition, or one or more symptoms of such disease, disorder or condition mediated through modulation of JAK activity. The term "subject" refers to a mammalian patient in need of such treatment, such as a human. The term "inhibitors" or "inhibitor" refers to compounds that decrease, prevent, inactivate, desensitize or down-regulate JAK expression or activity.

Embodiments of this invention provide JAK inhibitors for the prevention and/or control of excessive inflammatory response. Embodiments of JAK inhibitors according to this invention are pan-JAK inhibitors.

Unless indicated otherwise, the term "JAK inhibitor physico-chemical properties" refers to the corresponding named properties as follows:

as given in the description for compounds Ex. 1-5, 10, 22, 34, 38, 55, 74, and 85, in the case of molar masses;

as determined according to the respective definitions, in the case of numbers of H bond donors, acceptors and rotatable bonds; and as measured in reference to Table 1a, column 2, in case of plasma concentrations, and Table 7, columns 3 and 4, in case of the A-B permeability coefficients in the presence of P-gp inhibitor and B-A permeability coefficients.

Embodiments of this invention provide methods of inhibiting JAK, comprising exposing a JAK receptor to a JAK inhibitor that is characterized by having the following JAK inhibitor physico-chemical properties: a plasma concentration in the range from about 0.1 ng/mL to about 60 ng/mL, c Log P in the range from about 0.1 to about 2.8, A-B permeability coefficients in the presence of a P-gp inhibitor in the range from about 0.1 to about 2.5, B-A permeability coefficients in the range from about 0.5 to about 20, tPSA in the range from about 85 to about 120.

In other embodiments of methods of inhibiting JAK according to this invention, the plasma concentration is in the range from about 10 ng/mL to about 20 ng/mL.

In other embodiments of methods of inhibiting JAK according to this invention, c Log P is in the range from about 0.8 to about 1.4.

In other embodiments of methods of inhibiting JAK according to this invention, the A-B permeability coefficient in the presence of a P-gp inhibitor is in the range from about 0.6 to about 1.5.

In other embodiments of methods of inhibiting JAK according to this invention, the B-A permeability coefficient is in the range from about 0.5 to about 5.

In other embodiments of methods of inhibiting JAK according to this invention, the tPSA is in the range from about 100 to about 120.

Further embodiments of this invention provide methods of inhibiting JAK, comprising exposing a JAK receptor to a JAK inhibitor that is further characterized by having the following JAK inhibitor physico-chemical properties: A molar mass in the range from about 300 g mol$^{-1}$ to about 500 g mol$^{-1}$, a number of hydrogen bond donors in the range from about 2 to about 3, a number of hydrogen bond acceptors in the range from about 4 to about 5, and a number of rotatable bonds in the range from about 3 to about 6, in addition to the plasma concentrations, c log P values, permeability coefficients, and tPSA values described above for methodologies of inhibiting JAK according to this invention.

In other embodiments of methods of inhibiting JAK according to this invention, the molar mass is in the range from about 340 g mol$^{-1}$ to about 430 g mol$^{-1}$.

In other embodiments of methods of inhibiting JAK according to this invention, the number of rotatable bonds is in the range from about 5 to about 6.

Embodiments of this invention provide methods for treating inflammation in the gastrointestinal tract of a subject, comprising administering to a subject a pharmaceutically effective amount of a JAK inhibitor that is characterized by having the following JAK inhibitor physico-chemical properties: A plasma concentration in the range from about 0.1 ng/mL to about 60 ng/mL, c Log P in the range from about 0.1 to about 2.8, A-B permeability coefficients in the presence of a P-gp inhibitor in the range from about 0.1 to about 2.5, B-A permeability coefficients in the range from about 0.5 to about 20, tPSA in the range from about 85 to about 120.

In other embodiments of methods of treating inflammation in the gastrointestinal tract according to this invention, the plasma concentration is in the range from about 10 ng/mL to about 20 ng/mL.

In other embodiments of methods of treating inflammation in the gastrointestinal tract according to this invention, c Log P is in the range from about 0.8 to about 1.4.

In other embodiments of methods of treating inflammation in the gastrointestinal tract according to this invention, the A-B permeability coefficient is in the presence of a P-gp inhibitor is in the range from about 0.6 to about 1.5.

In other embodiments of methods of treating inflammation in the gastrointestinal tract according to this invention, the B-A permeability coefficient is in the range from about 0.5 to about 5.

In other embodiments of methods of treating inflammation in the gastrointestinal tract according to this invention, the tPSA is in the range from about 100 to about 120.

Further embodiments of this invention provide methods for treating inflammation in the gastrointestinal tract of a subject wherein the JAK inhibitor physico-chemical properties are further characterized by having the following JAK inhibitor physico-chemical properties: A molar mass in the range from about 300 g mol$^{-1}$ to about 500 g mol$^{-1}$, a number of hydrogen bond donors in the range from about 2 to about 3, a number of hydrogen bond acceptors in the range from about 4 to about 5, and a number of rotatable bonds in the range from about 3 to about 6, in addition to the plasma concentrations, c Log P values, permeability coefficients, and tPSA values described above for methodologies of treating inflammation according to this invention.

In other embodiments of methods of treating inflammation in the gastrointestinal tract according to this invention, the molar mass is in the range from about 350 g mol$^{-1}$ to about 430 g mol$^{-1}$.

In other embodiments of methods of treating inflammation in the gastrointestinal tract according to this invention, the number of rotatable bonds is in the range from about 5 to about 6.

Embodiments of JAK inhibitors according to this invention have the following JAK physico-chemical properties: a plasma concentration in the range from about 0.1 ng/mL to about 60 ng/mL, a c Log P in the range from 0.1 to about 2.8, an A-B permeability coefficient in the presence of a P-gp inhibitor in the range from about 0.1 to about 2.5, a B-A permeability coefficient in the range from about 0.5 to about 20, and a tPSA in the range from about 85 to about 120.

Further embodiments of JAK inhibitors according to this invention have a plasma concentration is in the range from about 10 ng/mL to about 20 ng/mL.

Further embodiments of JAK inhibitors according to this invention have c Log P values in the range from about 0.8 to about 1.4.

Further embodiments of JAK inhibitors according to this invention have A-B permeability coefficient in the presence of a P-gp inhibitor in the range from about 0.6 to about 1.5.

Further embodiments of JAK inhibitors according to this invention have B-A permeability coefficient in the range from about 0.5 to about 5.

Further embodiments of JAK inhibitors according to this invention have tPSA values in the range from about 100 to about 120.

Other embodiments of JAK inhibitors according to this invention have the following JAK inhibitor physico-chemical properties: A molar mass in the range from about 300 g mol$^{-1}$ to about 500 g mol$^{-1}$, a number of hydrogen bond donors in the range from about 2 to about 3, a number of hydrogen bond acceptors in the range from about 4 to about 5, and a number of rotatable bonds in the range from about 3 to about 6 in addition to the plasma concentrations, c Log P values, permeability coefficients, and tPSA values described above for JAK inhibitors according to this invention.

Further embodiments of JAK inhibitors according to this invention have a molar mass is in the range from about 350 g mol$^{-1}$ to about 430 g mol$^{-1}$.

Further embodiments of JAK inhibitors according to this invention have a number of rotatable bonds is in the range from about 5 to about 6.

In treatment methods according to the invention, an effective amount of at least one active agent according to the invention is administered to a subject suffering from or diagnosed as having such a disease, disorder, or medical condition. An "effective amount" means an amount or dose sufficient to generally bring about the desired therapeutic or prophylactic benefit in patients in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units.

Embodiments of this invention are new JAK inhibitors as active substances for the prevention and/or control of excessive inflammatory response and whose systemic effects are eliminated or reduced. Further embodiments of this invention are JAK inhibitors with local effects on gastro-intestinal tissues for the treatment of conditions such as, but not limited to IBD, without causing systemic effects or with such systemic effects acceptably reduced.

Embodiments of this invention are low permeability JAK inhibitors. Further embodiments of this invention are JAK inhibitors that have aqueous solubility.

Once improvement of the patient's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention are envisaged for use alone, in combination with one or more of other compounds of this invention, or in combination with additional active ingredients in the treatment of the conditions discussed below. The additional active ingredients may be co-administered separately with at least one compound of the invention, with active agents of the invention or included with such an agent in a pharmaceutical composition according to the invention. In an illustrative embodiment, additional active ingredients are those that are known or discovered to be effective in the treatment of conditions, disorders, or diseases mediated by JAK activity, such as another JAK inhibitor or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to inhibiting the target, an "effective amount" means an amount sufficient to affect the activity of at least one of the JAK family of proteins. Measuring the activity of the target may be performed by routine analytical methods. Target inhibition is in a variety of settings, including several assays.

The active agents of the invention are envisaged for use, alone or in combination with one or more additional active ingredients, to formulate pharmaceutical compositions of the invention. A pharmaceutical composition of the invention comprises an effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, topical administration, or oral administration. Preferably, the compositions may be formulated for oral administration.

For oral administration, the active agents of the invention can be provided in the form of tablets or capsules, or as a solution, emulsion, or suspension. To prepare the oral compositions, the active agents may be formulated to yield a dosage of, e.g., for a 70-kg human, an illustrative range for a suitable dosage amount is from about 1 to 1000 mg/day in single or multiple dosage units.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 rig/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

In a further embodiment, the invention is directed to a method of treating a subject suffering from or diagnosed with a disease, disorder, or medical condition mediated by JAK, comprising administering to the subject in need of such treatment an effective amount of the active agent.

In certain embodiments of the inventive method, the disease, disorder, or medical condition is an inflammatory bowel disease, such as Crohn's disease and ulcerative colitis.

Other embodiments of this invention provide for a method for modulating JAK activity, including when such kinase is in a subject, comprising exposing JAK to an effective amount of at least one compound selected from compounds of the invention.

The compounds of the invention are useful as JAK inhibitors that can be dosed orally and specifically distribute to intestinal tissue while maintaining low systemic exposures. This is in contrast to most known JAK inhibitors which are dosed orally and distribute to many tissues due to the fact that they have extensive systemic exposure.

Table 1a and Table 1b show results of in vivo experiments. These results comprise plasma and colon tissue concentrations for fifteen compounds that had been administered to mice as described in Protocols 1, 2 or 3. Plasma and colon concentration results were obtained by following Protocol 1 using venipuncture of dorsal metatarsal vein bleed for Compounds (B), (C), and Examples 10 and 74. Plasma and colon concentration results were obtained by following Protocol 2 using retro-orbital bleed for Compounds (A), and Examples 1, and 3-5 and Protocol 2 using venipuncture of the dorsal metatarsal vein for Examples 2, 22, 34, 38, 55, and 85. The results of Protocols 1 and 2 are shown in Table 1a. Plasma and colon concentration results were obtained by following Protocol 3 for Examples 1, 3 and 4. The results of Protocol 3 are shown in Table 1b. These protocols are described below under the heading In vivo Studies.

TABLE 1a

Results of In Vivo Experiments After p.o. Dosing - Mean Concentration of Test Compounds

| | Plasma Concentration After p.o. Dosing (ng/mL) | | | | | | Colon Concentration After p.o. Dosing (ng/g) | |
|---|---|---|---|---|---|---|---|---|
| | Time = 0.5 h | | Time = 2 h | | Time = 4 h | | Time = 4 h | |
| Test Compound | Mean* | Standard Deviation | Mean* | Standard Deviation | Mean* | Standard Deviation | Mean* | Standard Deviation |
| A | 347.0 | 78.5 | 69.1 | 40.8 | 84.5 | 25.5 | 895.0 | 260.6 |
| B | 352.7 | 85.7 | 66.3 | 26.2 | 11.3 | 3.7 | 6076.7 | 3125.8 |
| C | 547.0 | 71.4 | 130.2 | 63.7 | 16.7 | 5.9 | 7776.7 | 3500.2 |
| Ex. 1 | 13.4 | 1.5 | 6.1 | 3.7 | 3.3 | 1.2 | 8591.7 | 10245.7 |
| Ex. 2 | 24.5 | 3.6 | 4.2 | 1.8 | 1.3 | 0.1 | 7600.0 | 983.6 |
| Ex. 3 | 41.4 | 15.1 | 3.9 | 0.7 | 1.5** | *** | 2147.2 | 1821.6 |
| Ex. 4 | 12.9 | 1.6 | 7.5 | 2.8 | 3.3 | 1.5 | 4448.3 | 989.3 |
| Ex. 5 | 31.9 | 5.1 | 8.8 | 1.7 | 6.0 | 1.2 | 5328.3 | 986.0 |
| Ex. 10 | 18.8 | 20.6 | 3.0 | 0.9 | 1.7[#] | [##] | 11706.7 | 11305.2 |
| Ex. 22 | 47.0 | 3.8 | 9.6 | 4.4 | 5.0 | 1.2 | 12008.3 | 9461.1 |
| Ex. 34 | 43.1 | 8.7 | 5.4 | 0.6 | 2.6 | 0.6 | 7396.7 | 3037.3 |
| Ex. 38 | 15.1 | 1.8 | 6.2 | 4.5 | 3.9 | 0.9 | 7683.3 | 230.9 |
| Ex. 55 | 26.6 | 4.0 | 3.2 | 1.0 | 3.1 | 0.7 | 3005.0 | 1347.2 |
| Ex. 74 | 1.6** | *** | ^ | ^^ | ^ | ^^ | 4785.0 | 1059.9 |
| Ex. 85 | 15.6 | 8.7 | 4.2 | 1.4 | 2.3 | 1.0 | 5885.0 | 3154.1 |

*Mean calculated from the values obtained from three mice unless otherwise noted.

**Mean was calculated with values obtained from two mice as the values obtained from the third mouse were below the lower limit of quantitation.

*** No standard deviation calculated as the mean was calculated from only two values.

[#]Mean given as the value obtained from one mouse as the values obtained from the second and third mice were below the lower limit of quantitation.

[##] No standard deviation calculated in light of note [#] in this table.

^ Mean was not calculated as the values for all three mice were below the lower limit of quantitation.

^^ No standard deviation calculated in light of note ^ in this table.

TABLE 1b

Results of In Vivo Experiments After i.c. Dosing - Mean Concentration of Test Compounds

| Test Compound | Plasma Concentration After i.c. Dosing (ng/mL) | | | | | | Colon Concentration After i.c. Dosing (ng/g) | |
|---|---|---|---|---|---|---|---|---|
| | Time = 0.5 h | | Time = 2 h | | Time = 4 h | | Time = 4 h | |
| | Mean* | Standard Deviation | Mean* | Standard Deviation | Mean* | Standard Deviation | Mean* | Standard Deviation |
| Ex. 1 | 2.5# | ## | ^ | ^^ | ^ | ^^ | 681.0 | 437.0 |
| Ex. 3 | 1.5# | ## | ^ | ^^ | ^ | ^^ | 227.8 | 254.1 |
| Ex. 4 | 3.8** | *** | 2.5# | ## | ^ | ^^ | 26.1# | ## |

*Mean calculated from the values obtained from three mice unless otherwise noted.
**Mean was calculated with values obtained from two mice as the values obtained from the third mouse were below the lower limit of quantitation.
*** No standard deviation calculated as the mean was calculated from only two values.
Mean given as the value obtained from one mouse as the values obtained from the second and third mice were below the lower limit of quantitation.
No standard deviation calculated in light of note # in this table.
^ Mean was not calculated as the values for all three mice were below the lower limit of quantitation.
^^ No standard deviation calculated in light of note ^ in this table.

Compounds (A)-(C) are the following reference compounds that have been disclosed in WO2013/007765 or WO2011/086053 for their use as inhibitors of Janus kinases:

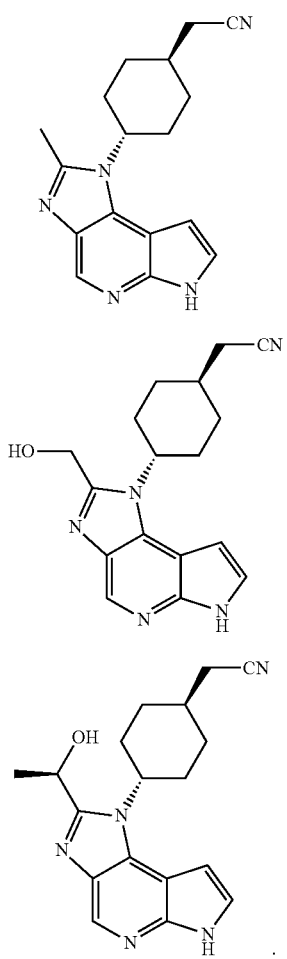

Compounds Ex. 1-5, 10, 22, 34, 38, 55, 74, and 85 in Tables 1a and 1b are embodiments of this invention given in the respective Examples.

As evinced in Table 1a, colon concentrations for compounds Ex. 1-5, 10, 22, 34, 38, 55, 74, and 85 were found to be much higher than the respective plasma concentrations, with [colon (4 h)]: [plasma (0.5 h)] concentration ratios ranging from about 52 to about 3,000. In contrast, such ratios for compounds (A)-(C) ranged from about 3 to about 17. Table 1b also provides supportive data that Examples 1, 3 and 4 have low systemic exposures after i.c. dosing. The contrast between properties of some embodiments of this invention with respect to reference compounds is much more accentuated when the comparison is referred to the 4 h plasma concentration values. In this regard, the [colon (4 h)]:[plasma (4 h)] concentration ratios for compounds Ex. 1-5, 10, 22, 34, 38, 55, 74, and 85 range from about 888 to about 6886. In contrast, such ratios for compounds (A)-(C) range from about 11 to about 538. These colon-to-plasma concentration ratios are indicative of compounds Ex. 1-5, 10, 22, 34, 38, 55, 74, and 85 having low systemic effects at any time post oral dose, while compounds (A)-(C) have comparatively high systemic effects. This is an unexpected finding of local GI effects for compounds 1-5, 10, 22, 34, 38, 55, 74, and 85.

As shown in Table 4, the data given therein for compounds Ex. 1-209 and (A)-(C) demonstrate inhibition of enzyme activity for all JAK proteins by these compounds.

There is no known reference teaching or suggestion indicating that the marked lack of systemic effects for some embodiments of this invention in comparison with those of reference compounds (A)-(C) can be inferred and/or predicted on the basis of structural comparisons. In contrast, one would envisage some embodiments of this invention as presenting similar systemic effects as those of reference compounds (A)-(C) in light of the structural similarities that one can find in comparing the respective chemical structures.

In addition, there is no known reference teaching or suggestion indicating that the low permeability feature for some embodiments of this invention in comparison with those of reference compounds (A)-(C) can be inferred and/or predicted on the basis of structural comparisons. In contrast, one would envisage some embodiments of this invention as presenting similar low permeability features as those of reference compounds (A)-(C) in light of the structural similarities that one can find in comparing the respective chemical structures.

The following specific examples are provided to further illustrate the invention and various embodiments.

In obtaining the compounds described in the examples below and the corresponding analytical data, the following experimental and analytical protocols were followed unless otherwise indicated.

Abbreviations and acronyms used herein include the following:

| Abbreviations and acronyms defined | |
|---|---|
| Acronym | Term |
| AAC | Accelerated aging conditions (40° C. and 70% RH) |
| ACN | Acetonitrile |
| AIBN | Azobisisobutyronitrile |
| aq | Aqueous |
| Boc | tert-Butylcarbamoyl |
| (Boc)$_2$O | Di-tert-butyl dicarbonate |
| BOP | Benzotriazol-1-yloxy-tris(dimethylamino)phosphonium hexafluorophosphate |
| n-BuOH | n-Butanol |
| br | Broad |
| CDI | 1,1'-Carbonyldiimidazole |
| CBz-Cl | Benzyl chloroformate |
| Celite ® | Diatomaceous Earth |
| CV | Column volume |
| DCC | N,N'-Dicyclohexylcarbodiimide |
| DCM | Dichloromethane |
| DIPEA or DIEA | Diisopropylethylamine |
| DMA | Dimethylacetamide |
| DMAP | 4-Dimethylaminopyridine |
| DME | 1,2-Dimethoxyethane |
| DMF | N,N-Dimethylformamide |
| DMSO | Dimethylsulfoxide |
| EDCI or EDC | 1-Ethyl-3-(3-dimethylaminopropyl)carbodiimide |
| Ether, Et$_2$O | Diethyl ether |
| EtOAc, or EA | Ethyl Acetate |
| EtOH | Ethanol |
| ESI | Electrospray ionization |
| FCC | Normal-phase silica gel chromatography |
| g | Gram |
| h | Hours |
| HATU | 1-[Bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl)uronium hexafluorophosphate |
| HOBt | Hydroxybenzotriazole |
| HPLC | High-pressure liquid chromatography |
| HR-XRPD | High resolution X-ray powder diffraction |
| HT-XRPD | High throughput X-ray powder diffraction |
| Hz | Hertz |
| IPA | isopropanol |
| i.c. | intra-colonic |
| LCMS | Liquid chromatography and mass spectrometry |
| M | Molar |
| m/z | Mass to charge ratio |
| mCPBA | meta-Chloroperoxybenzoic acid |
| MeI | Methyl Iodide |
| MeOH | Methanol |
| mesyl | CH$_3$SO$_3$— |
| mg | Milligrams |
| min | Minute |
| mL | Milliliter |
| µL | Microliter |
| mmol | Millimoles |
| MS | Mass spectrometry |
| MTBE | Methyl tert-butyl ether |
| N | Normal |
| NBS | N-Bromosuccinimide |
| NCS | N-Chlorosuccinimide |
| NIS | N-Iodosuccinimide |
| NMR | Nuclear magnetic resonance |

-continued

| Abbreviations and acronyms defined | |
|---|---|
| Acronym | Term |
| OTf or triflate | CF$_3$SO$_3$— |
| Pd(PPh$_3$)$_2$Cl$_2$ | Palladium(II)bis(triphenylphosphine) dichloride |
| Pd(PPh$_3$)$_4$ | Tetrakis(triphenylphosphine)palladium(0) |
| PdCl$_2$(dtbpf) or Pd(dtbpf)$_2$Cl$_2$ | [1,1'-Bis(di-tert-butylphosphino)ferrocene]dichloropalladium(II) |
| p.o. | per os or by mouth |
| ppm | Parts per million |
| PG | Protecting Group |
| PyBOP | Benzotriazol-1-yl-oxytripyrrolidinophosphonium hexafluorophosphate |
| PyBroP ® | Bromotripyrrolidinophosphonium hexafluorophosphate |
| R$_t$ | Retention time |
| Rt or RT | Room temperature |
| Selectfluor ® | 1-Chloromethyl-4-fluoro-1,4-diazoniabicyclo[2.2.2]octane bis(tetrafluoroborate) |
| SEM | [2-(Trimethylsilyl)ethoxy]methyl acetal |
| SFC | Supercritical Fluid Chromatography |
| Me$_3$Si | Trimethylsilyl |
| TBAF | Tetra-n-butylammonium fluoride |
| TEA | Triethylamine |
| TFA | Trifluoroacetic acid |
| tosyl | p-toluenesulfonyl |
| T$_3$P | 2,4,6-Tripropyl-1,3,5,2,4,6-trioxatriphosphorinane-2,4,6-trioxide |
| THF | Tetrahydrofuran |
| TLC | Thin layer chromatography |

Illustrative compounds useful in methods of this invention are described below by reference to the illustrative synthetic schemes ("Schemes") and specific examples for their preparation. One of ordinary skill in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula I or Formula II. If no temperature or temperature range is stated, it is to be understood that the reaction is to be run at room temperature. Schemes given below describe general preparation procedures. The term PG is used in the Schemes to represent a protecting group such as benzene sulfonyl, 4-bromobenzene sulfonyl or 4-methylbenzene sulfonyl. These groups are removed from the compounds at various stages and the conditions that are used to remove these protecting groups are deprotection include (i) treating with a strong base, such as KOH, in a solvent such as dioxane; (ii) treating with a strong acid, such as HBr in acetic acid; or (iii) treating with sodium naphthalide in THF. In the forgoing examples, these deprotection conditions will be referred to as "benzene sulfonyl type group deprotection conditions".

Scheme 1

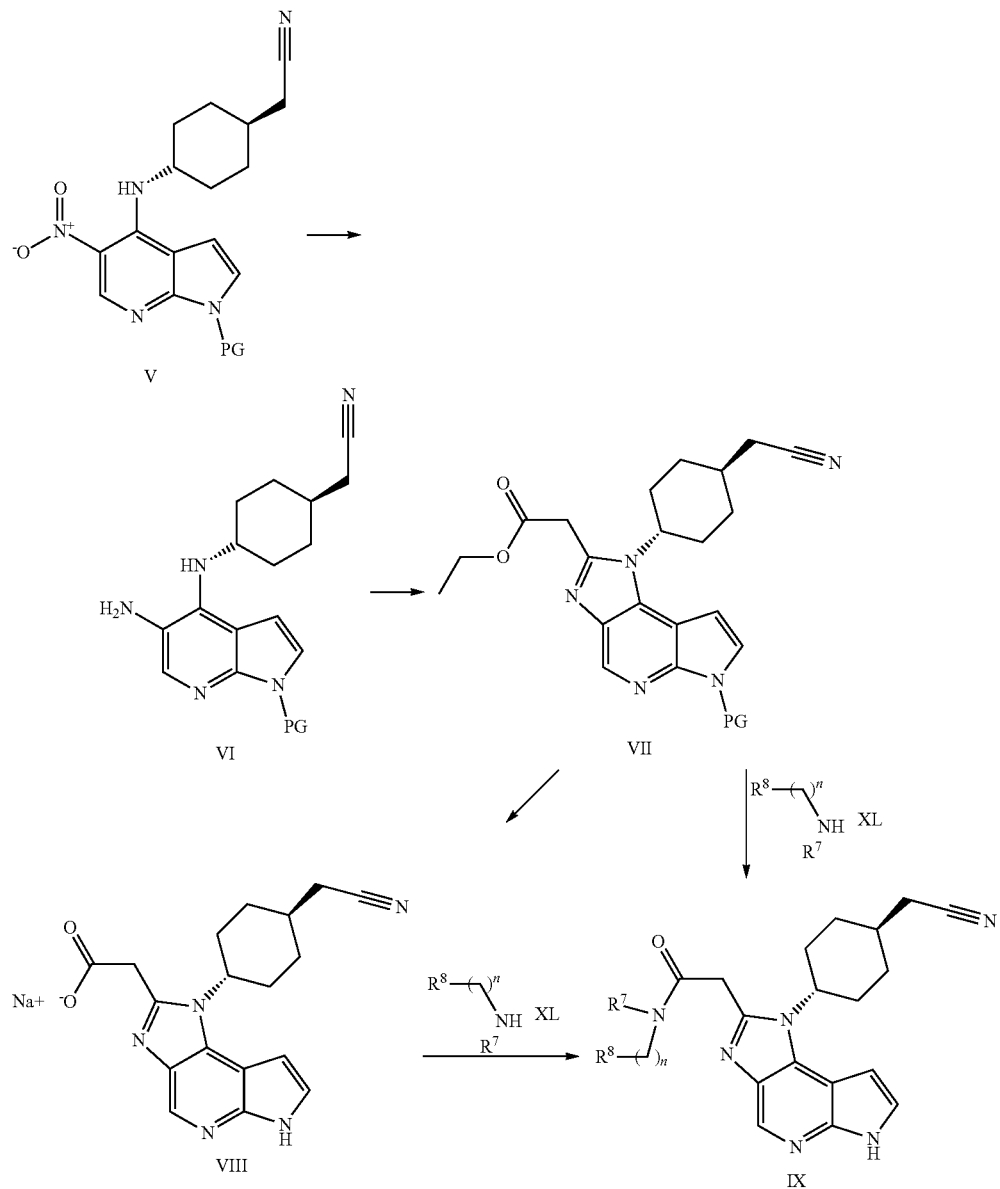

As shown in Scheme 1, compound V is converted to compound VI through a reduction of the nitro group. This reduction can be accomplished through a variety of methods including catalytic hydrogenation conditions such as $H_2$ gas and a catalytic amount of a metal catalyst such as Pd or Pt, wherein the Pd and Pt used may be 5-10% Pd on carbon and 5-10% Pt on carbon, respectively. This reduction may be run in the conventional manner in a flask wherein the atmosphere above the reaction mixture is $H_2$ gas or wherein $H_2$ gas is bubbled through the solution. Alternatively, the reaction may be run through a continuous hydrogenation flow reactor. The nitro group can also be reduced with Fe, Zn or $SnCl_2$ in solvents such as methanol, ethanol, isopropanol or THF. Compound VI is converted to compound VII through a condensation reaction with ethyl 3-ethoxy-3-iminopropanoate (structure not shown) in a solvent such as ethanol, methanol or isopropanol at about the reflux temperature of the solvent for a time from about 1 to 12 hours. Compound VII is converted to compound VIII by treating with a base such as NaOH or KOH in a solvent such as methanol, ethanol or tetrahydrofuran or mixture of such solvents. Compound VII is converted to compound IX via a two-step process, wherein the first step is a transamination reaction wherein compound VII is reacted with compound XL in a solvent such as DMF or DMA, and heated to a temperature of about 50° C. to 125° C., for 1-12 hours. This reaction may be run using conventional heating or run in a microwave reactor and $NH_4NO_3$ may be added as a catalyst. In the second step of this two-step process, the PG is removed to provide compound IX and the conditions for that are dependent on the PG that is used. When the PG is benzene sulfonyl, 4-bromobenzene sulfonyl or 4-methylbenzene sulfonyl, then PG is removed using the benzene sulfonyl type group deprotection conditions. Compound VIII is converted to compound IX by reacting it with compound XL and an appropriate activating reagent, for example (i) a carbodiimide, such as DCC, (ii) EDCI optionally in the presence of HOBt and/or a catalyst such as DMAP, (iii) a halotrisaminophosphonium salt such as BOP, PyBOP, or PyBroP, and (iv) a suitable pyridinium salt such as 2-chloro-1-methyl pyridinium chloride; or another suitable coupling agent such as HBTU, HATU, 2,4,6-tripropyl-1,3,5,2,4,6-trioxatriphosphorinane-2,4,6-trioxide (T3P®), in a suitable solvent such as DCM, THF, or DMF, optionally in the presence of a tertiary amine such as N-methylmorpholine, diisopropylethyl amine, or triethylamine, at a temperature ranging from about 0° C. to rt.

sodium hydrosulfite, in a solvent mixture wherein the solvent mixture comprises at least two of the following solvents: DMSO, methanol and water, at a temperature of about 100° C. for a time ranging from 1-18 hours. Compound V is converted to compound X by reaction with tert-butyl (2-oxo-ethyl)carbamate (structure not shown), a reducing agent such as sodium hydrosulfite, in a solvent mixture wherein the solvent mixture comprises at least two of the following solvents: DMSO, methanol and water, at a temperature of about 100° C. for a time ranging from 1-18 hours. Compound X is converted to compound XI by treating with (i) 1.0 M to 4.0 M HCl in dioxane or ethyl acetate wherein the

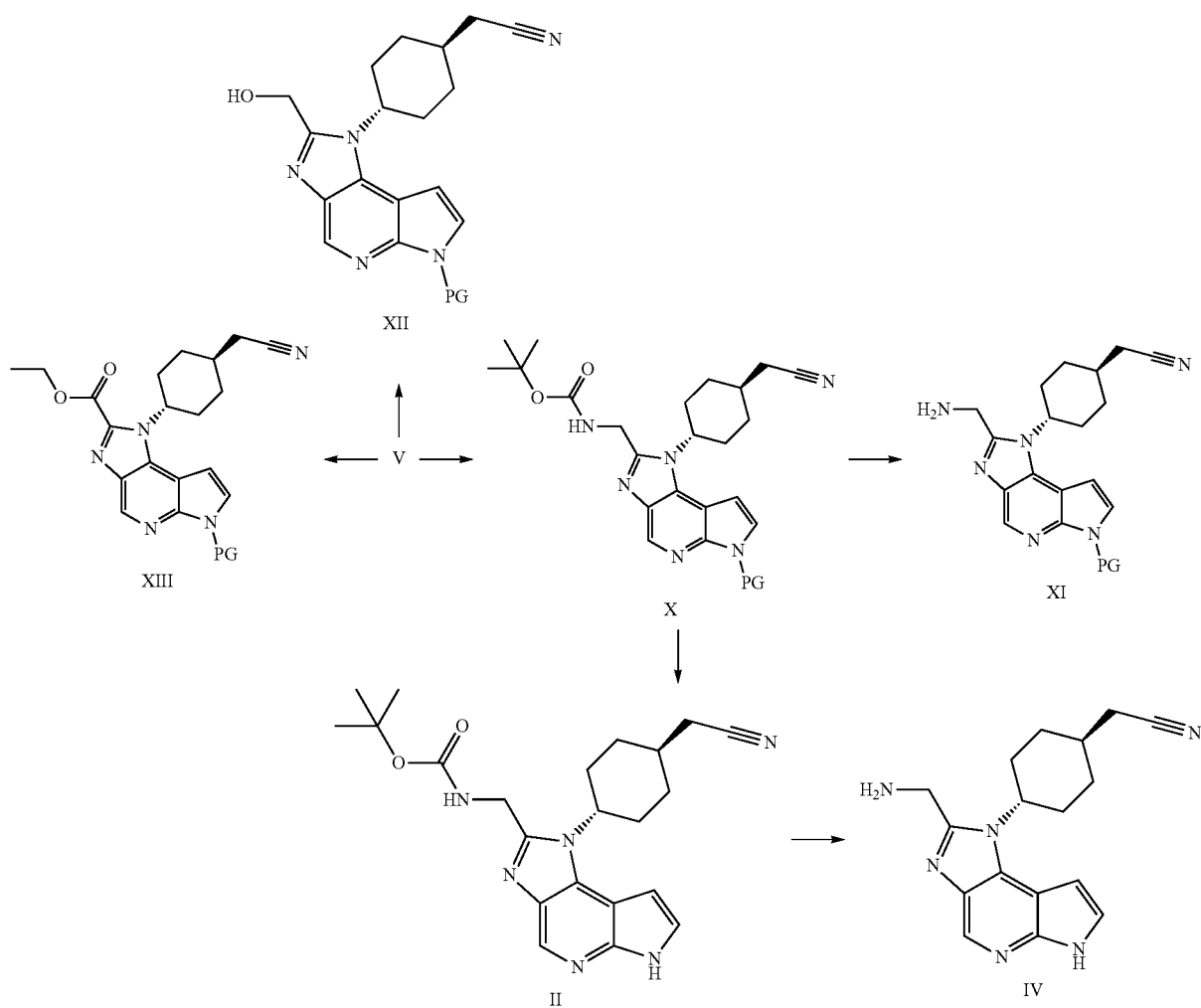

Scheme 2

As shown in Scheme 2, compound V is converted to compound XIII via a condensation reaction wherein compound V, ethyl glyoxalate (structure not shown) and a reducing agent such as sodium hydrosulfite [CAS #7775-14-6], are reacted in a solvent mixture wherein the solvent mixture comprises at least two of the following solvents: DMSO, methanol and water, at a temperature of about 100° C. for a time ranging from 1-18 hours. Compound V is converted to compound XII by treating with 1,4-dioxane-2,5-diol (structure not shown), a reducing agent such as reaction solvent is $CH_2Cl_2$ or ethyl acetate or (ii) TFA in $CH_2Cl_2$. In these cases, compound XI is understood to be produced as a hydrochloride salt or a trifluoroacetate salt. Alternatively, other acids could be used to convert compound X to compound XI, and it is understood that the salt form of compound XI would reflect the acid used. Compound X is converted to compound II using benzene sulfonyl type group deprotection conditions, and compound II is converted to compound IV by treating with an acid such as 1.0 M to 4.0 M HCl in dioxane.

Scheme 3

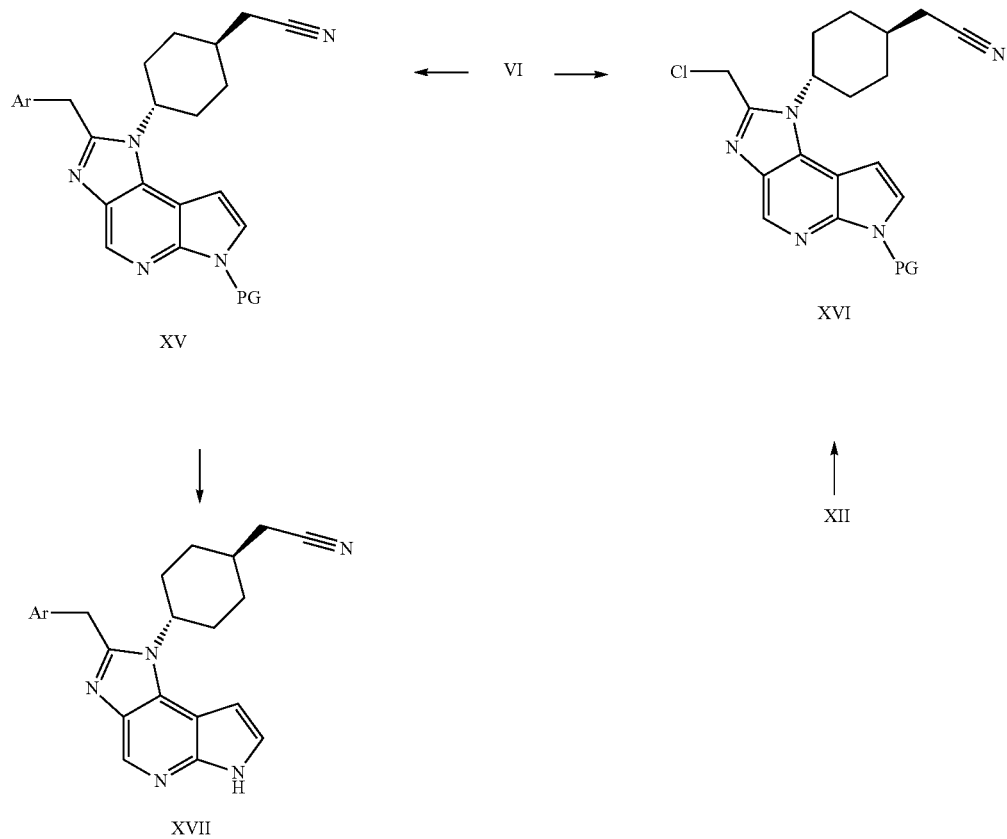

As described in Scheme 3, compound VI is converted to compound XVI by treating with 2-chloro-1,1,1-triethoxyethane (structure not shown) in acetic acid at a temperature of about 125° C. Compound XII is converted to compound XVI by treating with thionyl chloride, in a solvent such as CH₂Cl₂, dichloroethane or chloroform. Compound VI is converted to compound XV in a two-step reaction wherein in the first step, compound VI is treated with Ar—CH₂—CO₂H, with an appropriate activating reagent, for example (i) a carbodiimide, such as DCC, (ii) EDCI optionally in the presence of HOBt and/or a catalyst such as DMAP, (iii) a halotrisaminophosphonium salt such as BOP, PyBOP, or PyBroP, and (iv) a suitable pyridinium salt such as 2-chloro-1-methyl pyridinium chloride; or another suitable coupling agent such as HBTU, HATU, 2,4,6-tripropyl-1,3,5,2,4,6-trioxatriphosphorinane-2,4,6-trioxide (T3P®), in the presence of a base such as TEA, DIPEA or pyridine in a solvent such as DMF, DMA or DMSO. In the second step of the two step process, the resulting amide intermediate (structure not shown) is then cyclized to form compound XV by treating with an acid such as acetic acid at a temperature of about 100° C. for 1-18 hours. Compound XV is converted to compound XVII by deprotection of the PG. When the PG is benzene sulfonyl, 4-bromobenzene sulfonyl or 4-methylbenzene sulfonyl, this group is removed using the benzene sulfonyl type group deprotection conditions.

Scheme 4

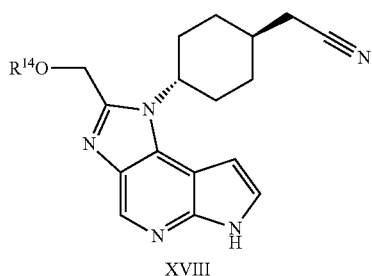

XVIII

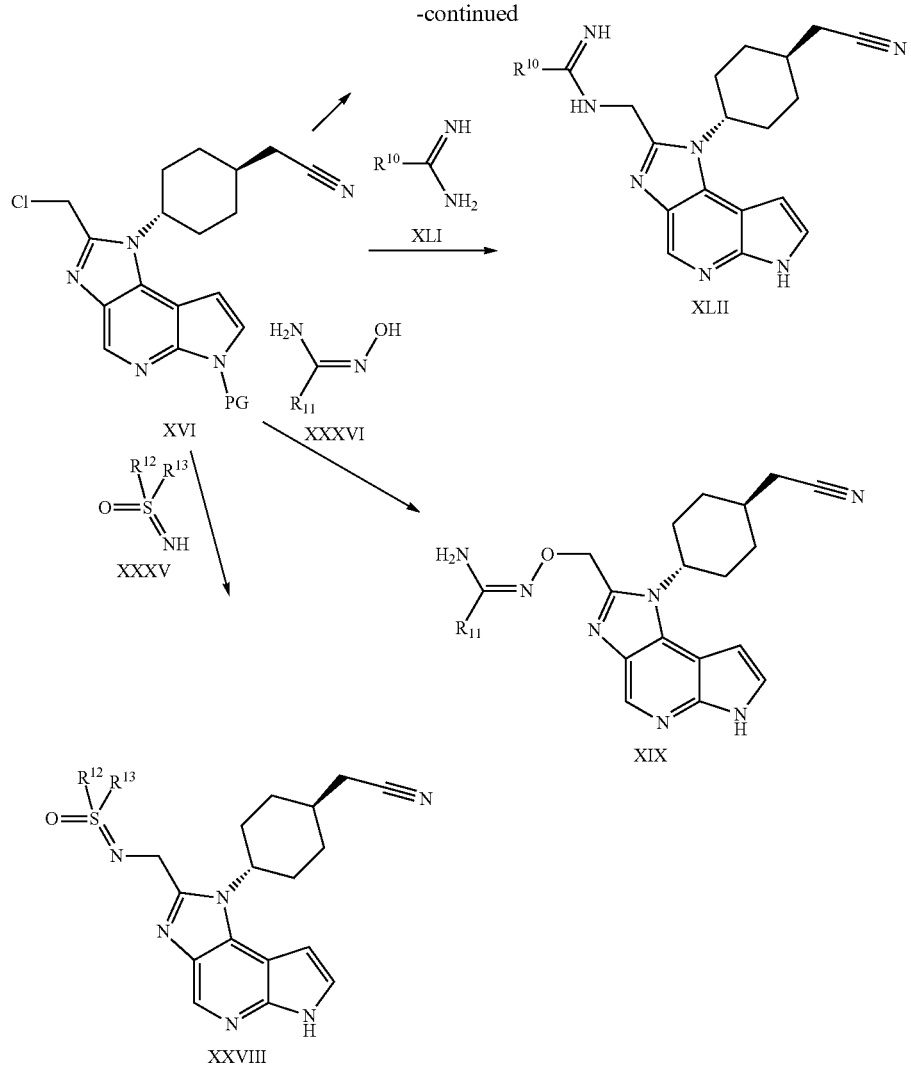

Compound XVI with certain R[14] assignments is transformed to compound XVIII as illustratively described in processes (a) and (b) below.

(a) When compound XVIII is desired in the form where R[14] is a substituted or unsubstituted phenyl, then compound XVI is reacted with the appropriately substituted phenol (structure not shown) in a solvent such as DMF, DMA or THF, with a base such as NaOH, KOH, $Cs_2CO_3$ or $K_2CO_3$ and KI at a temperature between 50° C. and 80° C. for 1-12 hours.

(b) When compound XVIII is desired in the form where R[14] is $C_1$-$C_6$ alkyl then compound XVI is treated with R[14]ONa or R[14]OK where R[14] is $C_1$-$C_6$ alkyl, in a solvent such as R[14]OH or THF.

When compound XLII is desired in the form in which, R[10] is $C_1$-$C_6$ alkyl, $C_3$-$C_{10}$cycloalkyl, phenyl, benzyl, pyrazolyl, then compound XVI is treated with compound XLI in a solvent such as DMF, DMA or THF with a base such as NaOH, KOH, $Cs_2CO_3$ or $K_2CO_3$, for a period of between 1-12 hours.

Compound XVI is converted to compound XIX by treatment with compound XXXVI and a base such as NaOH, KOH, $Cs_2CO_3$ or $K_2CO_3$ in a solvent such as DMF, DMA or THF for a period of between 1-12 hours.

Compound XVI is converted to compound XXVIII by treating it with sulfoximine (XXXV) in the presence of a base such as $NaHCO_3$ or $K_2CO_3$ in a solvent such as THF or $CH_3CN$.

Scheme 5

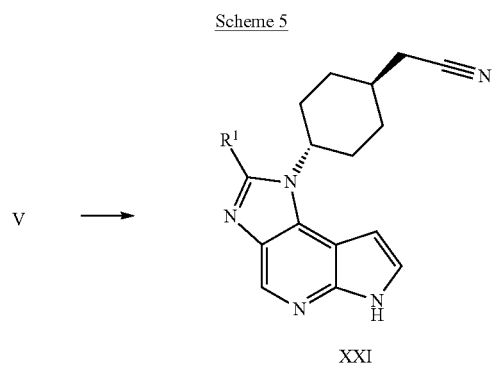

As shown in Scheme 5, when compound XXI is desired in the form in which, R[1] is an optionally substituted phenyl group, an optionally substituted 5-6 membered heteroaromatic ring, an optionally substituted $C_4$-$C_7$ heterocyclic ring or —$(CH_2)_q$—$(OCH_2CH_2)_q OCH_3$ then compound V is treated with the appropriately substituted aldehyde and a reducing agent such as $Na_2S_2O_4$ in a solvent mixture of at least two of the following solvents: DMSO, methanol and water, at a temperature of about 100° C. for a time ranging from 1-18 hours. In cases where the protecting group is not removed when using the above conditions, this protecting group is removed using the benzene sulfonyl type group deprotection conditions.

Scheme 6

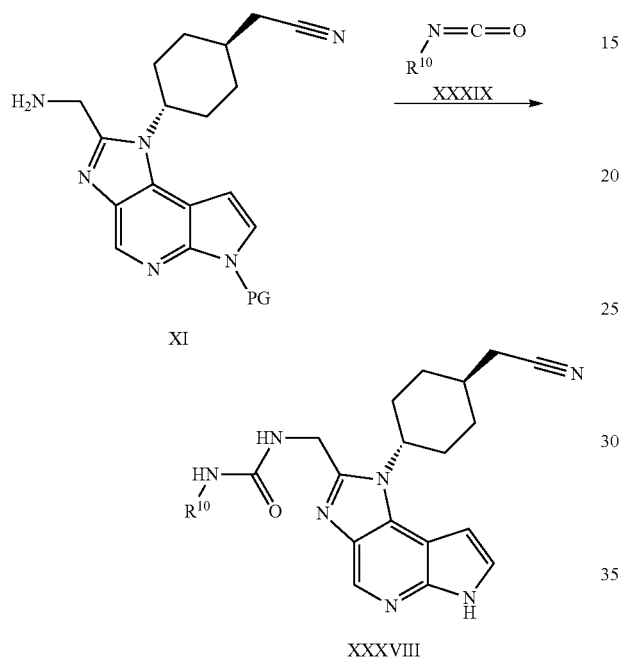

XI

XXXVIII

When compound XXXVIII is desired in the form in which $R^{10}$ is —$CH_2$-cylcohexyl, —$CH(CH_3)_2$, and -phenyl, compound XI is subjected to a two-step process. In the first step, compound XI is reacted with compound XXXIX in a solvent such as DMF, DMA or DMSO in the presence of a base such as trimethylamine, DIPEA or pyridine. In the second step, the PG is removed by treating it with a base such as aqueous KOH or aqueous NaOH in a solvent such as dioxane with heating to a temperature of about 50-100° C., for a time from 1-10 hours.

Scheme 7

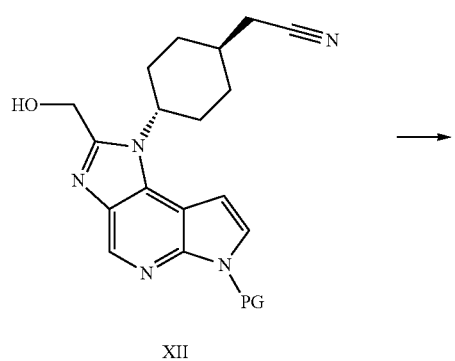

XII

-continued

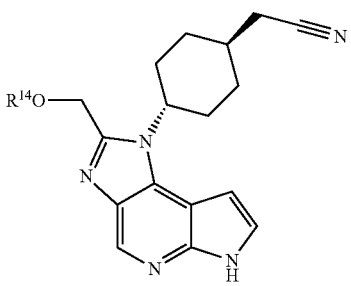

XVIII

When compound XVIII is desired in the form where $R^{14}$ is

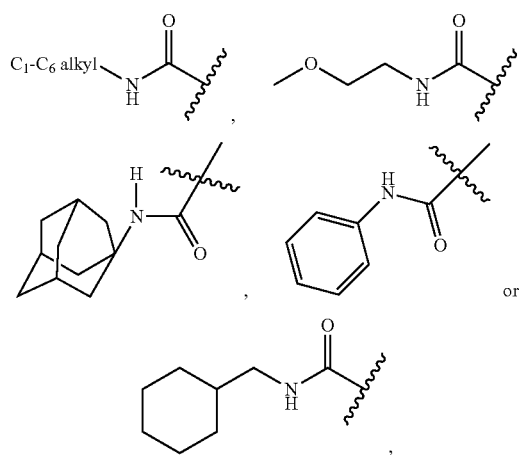

compound XII is treated with the appropriately substituted isocyanate, in a solvent such as DMF or DMA, in the presence of a base such as trimethylamine or diisopropyl-ethylamine, wherein the reaction may be run at room temperature or may be heated to a temperature from about 60° C. to 100° C. for a time period ranging from 0.25 hours to 72 hours. The final step of this transformation is removal of PG. When the PG is a benzenesulfonyl group, it is removed by treating it with a base such as aqueous KOH or aqueous NaOH in a solvent such as dioxane with heating to a temperature of about 50-100° C., for a time from 1-10 hours.

Scheme 8

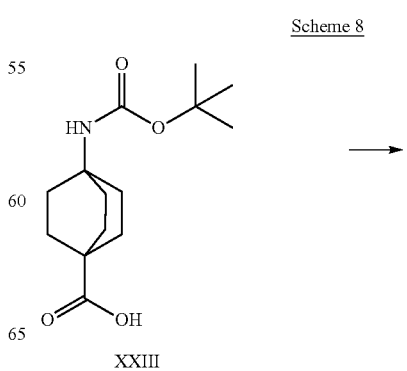

XXIII

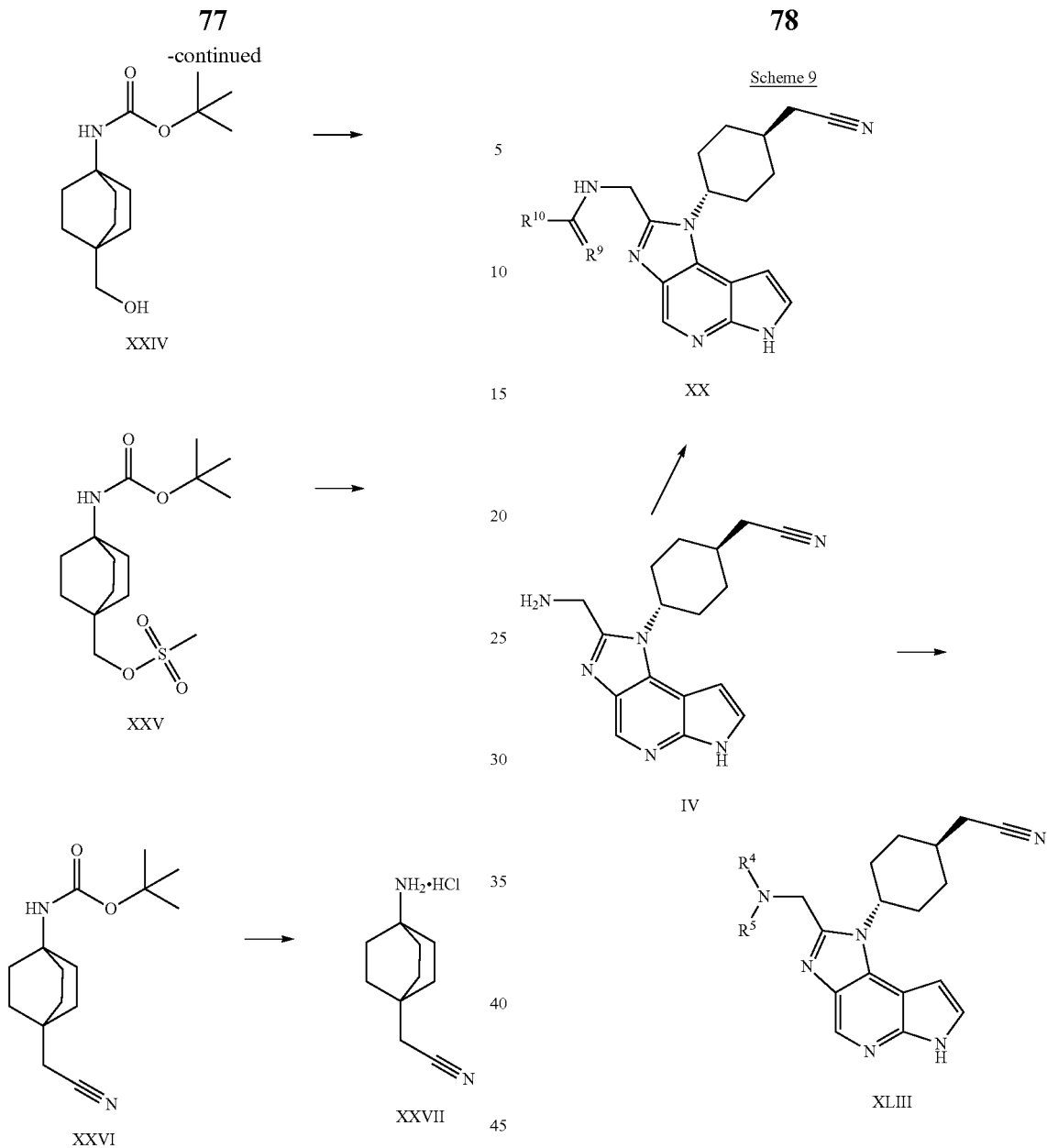

Scheme 8 describes the synthesis of compound XXVII (Intermediate 9). Compound XXIII is converted to compound XXIV by treating compound XXIII with a reducing agent such as borane/THF complex in a solvent such as THF or ether. Other suitable reducing agents include $BH_3/Me_2S$ complex or $NaBH_4/BF_3$-etherate. Compound XXIV is converted to compound XXV by treating with mesyl-chloride in a solvent such as $CH_2Cl_2$ or THF in the presence of a base such as pyridine, trimethylamine or DIPEA at a temperature ranging from 0° C. to room temperature. One of ordinary skill in the art will recognize that many different leaving groups could be prepared in place of the mesylate, including the triflate and the tosylate. Compound XXV is converted to compound XXVI by treating with NaCN or KCN in a solvent such as DMSO, DMF or DMA at a temperature ranging from room temperature to about 125° C., for about 18 hours. Compound XXVI is converted to compound XXVII by treating with (i) 1.0 M to 4.0 M HCl in dioxane or ethyl acetate, wherein the reaction solvent is $CH_2Cl_2$ or ethyl acetate or (ii) TFA in $CH_2Cl_2$.

When compound XLIII is desired in the form in which one of $R^4$ and $R^5$ is H and the other is $SO_2R^6$, compound IV is treated with an appropriately substituted sulfonyl chloride, in a solvent such as $CH_2Cl_2$, THF or DMF, in the presence of a base such as TEA, DIPEA, NMO or pyridine.

When compound XX is desired in the form in which $R^9$ is N—OH and $R^{10}$ is $C_1$-$C_6$ alkyl, $C_2$-$C_3$ alkyl ether, $C_3$-$C_{10}$cycloalkyl, phenyl, or benzyl compound IV is treated with the appropriately substituted chloroximine in a solvent such as DMF or DMA in the presence of a base such as TEA, DIPEA, pyridine or NMO.

When compound XX is desired in the form in which $R^9$ is O and $R^{10}$ is $OC_1$-$C_6$ alkyl or O-phenyl, compound IV is treated with the appropriately substituted chloroformate or anhydride in a solvent such as $CH_2Cl_2$ or THF in the presence of a base such as TEA, DIPEA, pyridine or NMO.

When compound XX is desired in the form in which, $R^9$ is O and $R^{10}$ is $C_1$-$C_6$ alkyl, $C_3$-$C_{10}$cycloalkyl, phenyl, benzyl or 5-membered heteroaryl, compound IV is treated with the appropriately substituted carboxylic acid and an activating agent such as a carbodiimide, such as DCC or EDCI optionally in the presence of HOBt and/or a catalyst such as DMAP; a halotrisaminophosphonium salt such as PyBroP; a suitable pyridinium salt such as 2-chloro-1-methyl pyridinium chloride; or another suitable coupling agent such as BOP, PyBOP, HBTU, HATU, 2,4,6-tripropyl-1,3,5,2,4,6-trioxatriphosphorinane-2,4,6-trioxide (T3P®) in a suitable solvent such as DCM, THF, DMF, optionally in the presence of a tertiary amine such as N-methylmorpholine, diisopropylethylamine, or triethylamine, at a temperature ranging from about 0° C. to rt. Alternatively, compound IV is treated with the appropriately substituted acid chloride or acid anhydride. This reaction may be run in a solvent such as $CH_2Cl_2$, THF or DCM in the presence of a base such as TEA, DIPEA, pyridine or NMO.

When compound XX is desired in the form in which $R^9$ is O and $R^{10}$ is $NH_2$, compound IV is treated with KOCN [CAS #590-28-3] in water in the presence of a base such as $NaHCO_3$ at a temperature ranging from room temperature to reflux for a time period between 15 min and 24 hours.

methanol, ethanol or isopropanol, in the presence of a base such as TEA, DIPEA, pyridine or NMO, at a temperature between room temperature and the reflux temperature of the solvent and for a time period between 1 hour and 24 hours. Compound XXX is converted to compound XXXI through reduction conditions including catalytic hydrogenation conditions such as $H_2$ gas and a catalytic amount of a metal catalyst such as Pd or Pt, wherein the Pd and Pt used may be 5-10% Pd on carbon and 5-10% Pt on carbon, respectively. This reduction may be run in the conventional manner in a flask wherein the atmosphere above the reaction mixture is $H_2$ gas or wherein $H_2$ gas is bubbled through the solution. Alternatively, the reaction may be run through a continuous hydrogenation flow reactor or using zinc dust in the presence of $NH_4Cl$ and EtOH. Other reaction conditions include iron in acetic acid; and sodium dithionate in DMSO, methanol and water. Compound XXXI is converted to compound XXXII through a reaction with ethyl 3-(ethoxyimino)propanoate hydrochloride (structure not shown), in a solvent Scheme 10

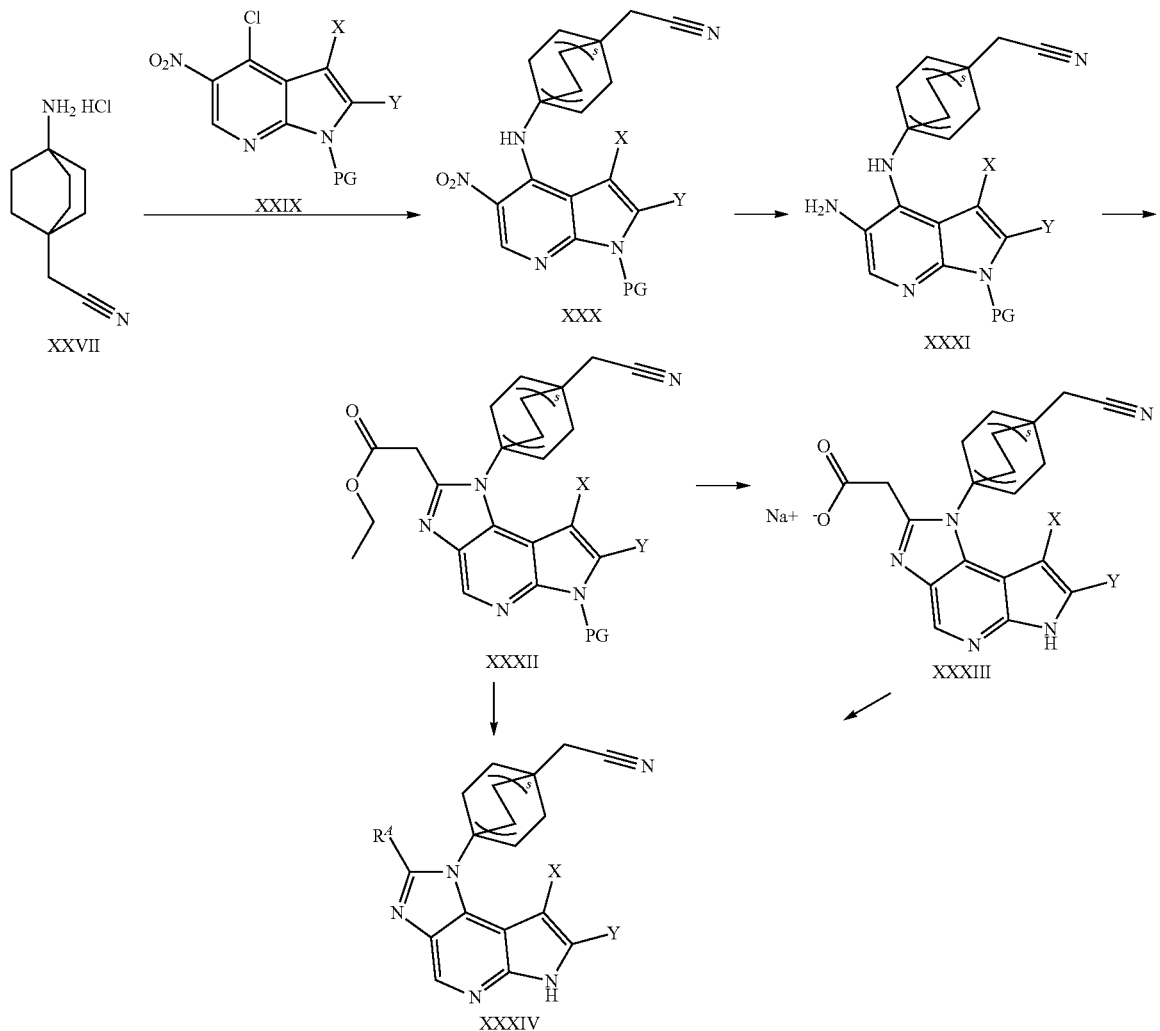

Scheme 10 illustrates the preparation of compound XXXIV. Compound XXVII is converted to compound XXX upon treatment with compound XXIX, in a solvent such as such as methanol, ethanol or isopropanol, at a temperature between room temperature and the reflux temperature of the solvent for a time period between 1 hour and 48 hours. When compound XXXIV is desired where $R^A$ is $C(O)NH_2$, then compound XXXII is treated with aqueous $NH_4OH$ in a solvent such as THF. The resulting compound is then subjected to the benzene sulfonyl type group deprotection conditions as discussed previously. Compound XXXII is converted to compound XXXIII by treating with a base such as NaOH or KOH in a solvent or mixture thereof of the following solvents: methanol, ethanol, isopropanol, THF and ether. When compound XXXIV is desired in the form where $R^A$ is one of the following:

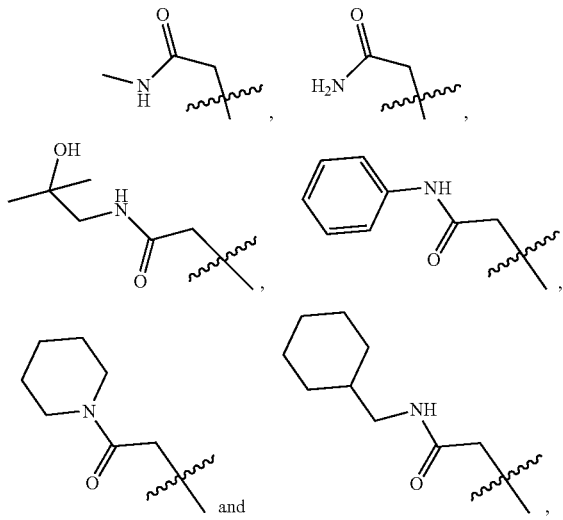

then compound XXXIII is treated with the appropriately substituted amine (structure not shown) an activating reagent, for example a carbodiimide, such as DCC or EDCI optionally in the presence of HOBt and/or a catalyst such as DMAP; a halotrisaminophosphonium salt such as BOP, PyBOP, or PyBroP; a suitable pyridinium salt such as 2-chloro-1-methyl pyridinium chloride; or another suitable coupling agent such as HBTU, HATU, 2,4,6-tripropyl-1,3,5,2,4,6-trioxatriphosphorinane-2,4,6-trioxide (T3P®). Coupling reactions are conducted in a suitable solvent such as DCM, THF, or DMF, optionally in the presence of a tertiary amine such as N-methylmorpholine, diisopropylethylamine, or triethylamine, at a temperature ranging from about 0° C. to rt.

Scheme 11

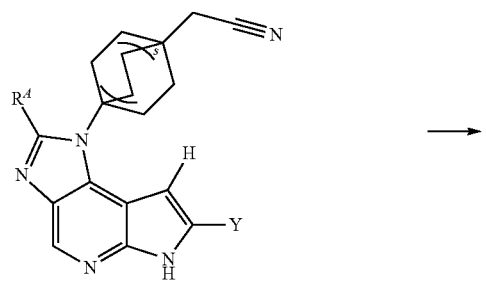

XXXV

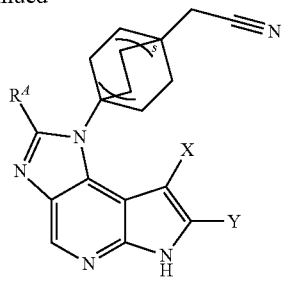

XXXIV

When compound XXXIV is desired in the form where X is Cl, compound XXXV is treated with a chlorinating agent such as 2-Chloro-1,3-bis(methoxycarbonyl)guanidine or NCS in a solvent such as $CH_3CN$ in the presence of a base such as $NaHCO_3$, $Cs_2CO_3$. When compound XXXIV is desired in the form where X is Br, compound XXXV is treated with NBS in a solvent such as dioxane. When Compound XXXIV is desired in the form in which X is methyl then compound XXXIV in the form in which X is Br is treated with 2-dicyclohexylphosphino-2',4',6'-triisopropylbiphenyl, (2-dicyclohexylphosphino-2',4',6'-triisopropyl-1,1'-biphenyl)[2-(2'-amino-1,1'-biphenyl)]palladium(II) methanesulfonate, and dimethyl zinc in a solvent such as THF, at a temperature of about 75-85° C. for a time period between 15 min and 3 hours.

Compounds of the invention may be converted to their corresponding salts using methods described in the art. For example, a compound of the invention is treated with trifluoroacetic acid, HCl, or citric acid in a solvent such as $Et_2O$, $CH_2Cl_2$, THF, MeOH, or isopropanol to provide the corresponding salt form. Crystalline forms of pharmaceutically acceptable salts of compounds of the invention may be obtained in crystalline form by recrystallization from polar solvents (including mixtures of polar solvents and aqueous mixtures of polar solvents) or from non-polar solvents (including mixtures of non-polar solvents).

The following examples are provided to further illustrate aspects of the invention and various preferred embodiments.

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography was performed using Merck silica gel 60 $F_{254}$ 2.5 cm×7.5 cm, 250 µm or 5.0 cm×10.0 cm, 250 µm pre-coated silica gel plates.

Normal-phase flash column chromatography (FCC) was performed on silica gel ($SiO_2$) eluting with $MeOH/CH_2Cl_2$ (0-10%), unless otherwise noted.

Mass spectra (MS) were obtained on an Agilent series 1100 MSD using electrospray ionization (ESI) in positive mode unless otherwise indicated. Calculated (calcd.) mass corresponds to the exact mass.

High Performance Liquid Chromatography was performed as described for the individual compounds. The following endcapped columns used were Varian Pursuit $XR_s5$ Diphenyl (pore size 100 Å, surface area 440 m²/g, carbon load of 14.6%), Waters Xbridge Prep OBD C$_{18}$ (pore size 130 Å, surface area 185 m$^2$/g, carbon load of 18%), Boston Green ODS (pore size 100 Å, surface area 450 m$^2$/g, carbon load of 21.7%), Kromasil, (pore size 100 Å, surface area 340 m$^2$/g, carbon load of 19%), Agela DuraShell (pore size 150 Å, surface area 380 m$^2$/g, carbon load of 21%), Xtimate C$_{18}$, (pore size 200 Å, surface area 320 m$^2$/g, carbon load of 14%), Diamonsil (pore size 100 Å, surface area 440 m$^2$/g, carbon load of 17%), Phenomenex Luna C$_{18}$, (pore size 100 Å, surface area 440 m$^2$/g, carbon load of 19%), Phenomenex Synergi C$_{18}$ (pore size 100 Å, surface area 475 m$^2$/g, carbon load of 11-19%) and Phenomenex Gemini (pore size 110 Å, surface area 375 m$^2$/g, carbon load of 14%).

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated by either by using ChemDraw (CambridgeSoft, Cambridge, Mass.) or ACD/ Name Version 9 (Advanced Chemistry Development, Toronto, Ontario, Canada).

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently.

Intermediate 1 Synthesis and Characterization 2-((1r,4r)-4-((5-Nitro-1-(phenylsulfonyl)-1H-pyrrolo [2,3-b]pyridin-4-yl)amino)cyclohexyl)acetonitrile

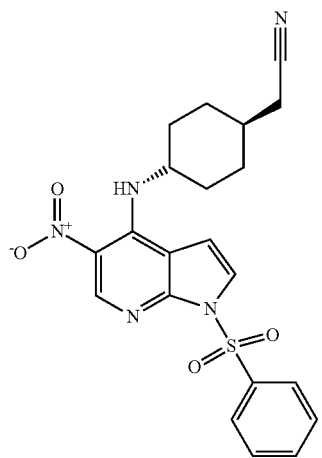

Step A: tert-butyl N-[(1r,4r)-4-(Hydroxymethyl)cyclohexyl]carbamate. To a 20-L 4-necked round-bottom flask purged and maintained with an inert atmosphere of nitrogen was placed (1r,4r)-4-[[(tert-butoxy)carbonyl]amino]cyclohexane-1-carboxylic acid (1066 g, 4.38 mol, 1.00 equiv) and THF (10 L). This was followed by the dropwise addition of BH$_3$-Me$_2$S (10 M, 660 mL) at −10° C. over 1 h. The resulting solution was stirred for 3 h at 15° C. This reaction was performed three times in parallel and the reaction mixtures were combined. The reaction was then quenched by the addition of methanol (2 L). The resulting mixture was concentrated under vacuum. This resulted in of tert-butyl N-[(1r,4r)-4-(hydroxymethyl)cyclohexyl]carbamate (3000 g, 99.6%) as a white solid. MS (ESI): mass calcd. for C$_{12}$H$_{23}$NO$_3$, 229.32; m/z found, 215.2 [M-tBu+MeCN+H]$^+$; $^1$H NMR: (300 MHz, CDCl$_3$): δ 4.40 (s, 1H), 3.45 (d, J=6.3 Hz, 2H), 3.38 (s, 1H), 2.05-2.02 (m, 2H), 1.84-1.81 (m, 2H), 1.44 (s, 11H), 1.17-1.01 (m, 4H).

Step B: tert-butyl N-[(1r,4r)-4-[(Methanesulfonyloxy) methyl]cyclohexyl]carbamate. To a 20 L 4-necked round-bottom flask purged and maintained with an inert atmosphere of nitrogen, was placed tert-butyl N-[(1r,4r)-4-(hydroxymethyl)cyclohexyl]carbamate (1000 g, 4.36 mol, 1.00 equiv.), dichloromethane (10 L), pyridine (1380 g, 17.5 mol, 4.00 equiv.). This was followed by the dropwise addition of MsCl (1000 g, 8.73 mol, 2.00 equiv.) at −15° C. The resulting solution was stirred overnight at 25° C. This reaction was performed in parallel for 3 times and the reaction mixtures were combined. The reaction was then quenched by the addition of 2 L of water. The water phase was extracted with ethyl acetate (1×9 L). The organic layer was separated and washed with 1 M HCl (3×10 L), NaHCO$_3$ (saturated aq.) (2×10 L), water (1×10 L) and brine (1×10 L). The mixture was dried over anhydrous sodium sulfate, filtered and concentrated under vacuum. This resulted in of tert-butyl N-[(1r,4r)-4-[(methanesulfonyloxy)methyl]cyclohexyl]carbamate (3300 g, 82%) as a white solid. LC-MS: MS (ESI): mass calcd. for C$_{13}$H$_{25}$NO$_5$S, 307.15; m/z found 292.1, [M-tBu+MeCN+H]$^+$; $^1$H NMR: (300 MHz, CDCl$_3$): δ 4.03 (d, J=6.6 Hz, 2H), 3.38 (s, 1H), 3.00 (s, 3H), 2.07-2.05 (m, 2H), 1.87-1.84 (m, 2H), 1.72-1.69 (m, 1H), 1.44 (s, 9H), 1.19-1.04 (m, 4H).

Step C: tert-butyl N-[(1r,4r)-4-(Cyanomethyl)cyclohexyl] carbamate. To a 10 L 4-necked round-bottom flask, was placed tert-butyl N-[(1r,4r)-4-[(methanesulfonyloxy) methyl]cyclohexyl]carbamate (1100 g, 3.58 mol, 1.00 equiv.), DMSO (5500 mL) and NaCN (406 g, 8.29 mol, 2.30 equiv.). The resulting mixture was stirred for 5 h at 90° C. This reaction was performed in parallel 3 times and the reaction mixtures were combined. The reaction was then quenched by the addition of 15 L of water/ice. The solids were collected by filtration. The solids were washed with water (3×10 L). This resulted in tert-butyl N-[(1r,4r)-4-(cyanomethyl)cyclohexyl]carbamate (2480 g, 97%) as a white solid. MS (ESI): mass calcd. for C$_{13}$H$_{22}$N$_2$O$_2$, 238.17; m/z found 224 [M-tBu+MeCN+H]$^+$; $^1$H NMR: (300 MHz, CDCl$_3$): δ 4.39 (s, 1H), 3.38 (s, 1H), 2.26 (d, J=6.9 Hz, 2H), 2.08-2.04 (m, 2H), 1.92-1.88 (m, 2H), 1.67-1.61 (m, 1H), 1.44 (s, 9H), 1.26-1.06 (m, 4H).

Step D: 2-[(1r,4r)-4-Aminocyclohexyl]acetonitrile hydrochloride. To a 10-L round-bottom flask was placed tert-butyl N-[(1r,4r)-4-(cyanomethyl)cyclohexyl]carbamate (620 g, 2.60 mol, 1.00 equiv.), and 1,4-dioxane (2 L). This was followed by the addition of a solution of HCl in 1,4-dioxane (5 L, 4 M) dropwise with stirring at 10° C. The resulting solution was stirred overnight at 25° C. This reaction was performed for 4 times and the reaction mixtures were combined. The solids were collected by filtration. The solids were washed with 1,4-dioxane (3×3 L), ethyl acetate (3×3 L) and hexane (3×3 L). This resulted in 2-[(1r,4r)-4-aminocyclohexyl]acetonitrile hydrochloride (1753 g, 96%) as a white solid. MS (ESI): mass calcd. for $C_8H_{14}N_2$, 138.12; m/z found 139.25, [M+H]$^+$; $^1$H NMR: (300 MHz, DMSO-d$_6$): δ 8.14 (s, 3H), 2.96-2.84 (m, 1H), 2.46 (d, J=6.3 Hz, 2H), 1.98 (d, J=11.1 Hz, 2H), 1.79 (d, J=12.0 Hz, 2H), 1.64-1.49 (m, 1H), 1.42-1.29 (m, 2H), 1.18-1.04 (m, 2H).

Step E: 2-((1r,4r)-4-((5-Nitro-1-(phenylsulfonyl)-1H-pyrrolo[2,3-b]pyridin-4-yl)amino)cyclohexyl)acetonitrile. To a 1000 mL round bottom flask containing 2-[(1r,4r)-4-aminocyclohexyl]acetonitrile hydrochloride (29.10 g, 166.6 mmol) was added DMA (400 mL). The resulting suspension was treated with 4-chloro-5-nitro-1-(phenylsulfonyl)-1H-pyrrolo[2,3-b]pyridine (51.53 g, 152.6 mmol), followed by DIPEA (63.0 mL, 366 mmol). The reaction mixture was placed under N$_2$ and heated at 80° C. for 4 h. The crude reaction mixture was cooled to room temperature and slowly poured into a vigorously stirred 2 L flask containing 1.6 L water. The resulting suspension was stirred for 15 minutes at room temperature, then filtered and dried for 16 h in a vacuum oven with heating at 70° C. to provide the title compound (63.37 g, 95%) as a yellow solid. MS (ESI): mass calcd. for $C_{21}H_{21}N_5O_4S$, 439.1; m/z found, 440.1 [M+H]$^+$. $^1$H NMR (500 MHz, CDCl$_3$): δ 9.10 (s, 1H), 8.99 (d, J=7.8 Hz, 1H), 8.23-8.15 (m, 2H), 7.66-7.59 (m, 2H), 7.56-7.49 (m, 2H), 6.67 (d, J=4.2 Hz, 1H), 3.95-3.79 (m, 1H), 2.38 (d, J=6.2 Hz, 2H), 2.32-2.21 (m, 2H), 2.08-1.98 (m, 2H), 1.88-1.76 (m, 1H), 1.60-1.32 (m, 4H).

Intermediate 2 Synthesis and Characterization:

2-((1r,4r)-4-((5-Amino-1-(phenylsulfonyl)-1H-pyrrolo[2,3-b]pyridin-4-yl)amino)cyclohexyl)acetonitrile

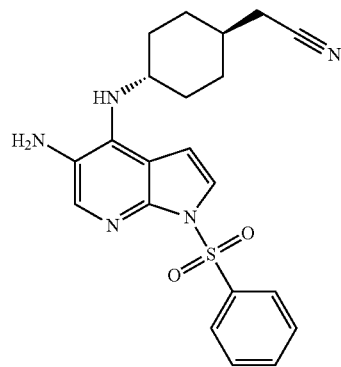 [SMILES: N#CC[C@H]1CC[C@H](Nc2c(N)cnc3c2ccn3S(=O)(=O)c2ccccc2)CC1]

2-((1r,4r)-4-((5-Nitro-1-(phenylsulfonyl)-1H-pyrrolo[2,3-b]pyridin-4-yl)amino)cyclohexyl)acetonitrile (Intermediate 1, 58.60 g, 133.3 mmol) was dissolved in THF/MeOH (1:1, 4800 mL). The mixture was passed through a continuous-flow hydrogenation reactor (10% Pd/C), such as a Thales Nano H-Cube®, at 10 mL/min with 100% hydrogen (atmospheric pressure, 80° C.), then the solution was concentrated to provide the product as a purple solid. The solid was triturated with EtOAc (400 mL) and then triturated again with MeOH (200 mL) then filtered and dried under vacuum to provide the title compound (50.2 g, 91.9% yield). MS (ESI): mass calcd. for $C_{21}H_{23}N_5O_2S$, 409.2; m/z found, 410.2 [M+H]$^+$. $^1$H NMR (400 MHz, CDCl$_3$) δ 8.10-8.03 (m, 2H), 7.76 (s, 1H), 7.51-7.43 (m, 1H), 7.43-7.34 (m, 3H), 6.44 (d, J=4.2 Hz, 1H), 4.61 (d, J=8.5 Hz, 1H), 3.65-3.51 (m, 1H), 2.74 (s, 2H), 2.26 (d, J=6.4 Hz, 2H), 2.19-2.05 (m, 2H), 1.97-1.86 (m, 2H), 1.76-1.59 (m, 1H), 1.33-1.12 (m, 4H).

Intermediate 3 Synthesis and Characterization

Ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate

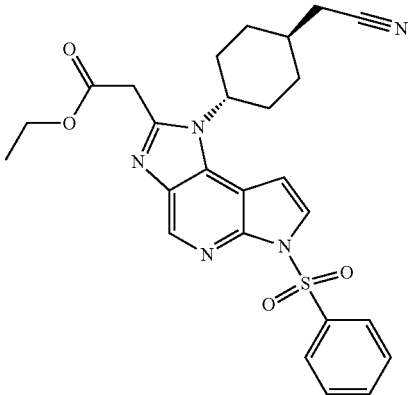 [SMILES: CCOC(=O)Cc1nc2cnc3c(ccn3S(=O)(=O)c3ccccc3)c2n1[C@H]1CC[C@H](CC#N)CC1]

To a 1 L round bottom flask containing a stir bar and 2-((1r,4r)-4-((5-amino-1-(phenylsulfonyl)-1H-pyrrolo[2,3-b]pyridin-4-yl)amino)cyclohexyl)acetonitrile (Intermediate 2, 58.31 g, 142.4 mmol) was added ethyl 3-ethoxy-3-iminopropanoate (60.51 g, 309.3 mmol), followed by EtOH (600 mL, dried over 3 Å molecular sieves for 48 h). A reflux condenser was attached to the reaction flask, the reaction was purged with N$_2$, and was heated at 90° C. for 9 h. The reaction mixture was cooled to room temperature and left to stand for 30 h where the product crystallized out as brown needles. The solids were broken up with a spatula and the reaction mixture was transferred to a 2 L flask. Water (1.4 L) was added slowly via separatory funnel with vigorous stirring. After addition of the water was complete, the suspension was stirred for 30 minutes. The brown needles were isolated by filtration and then dried by pulling air through the filter for 1 h. The product was transferred to a 500 mL flask and treated with EtOAc (200 mL). A small quantity of seed crystals were added, which induced the formation of a white solid precipitate. The suspension was stirred for 30 minutes at room temperature, filtered, rinsed with EtOAc (25 mL), and dried under vacuum to provide the product as a white solid (48.65 g, 68% yield). MS (ESI): mass calcd. for $C_{26}H_{27}N_5O_4S$, 505.2; m/z found, 506.2 [M+H]$^+$. $^1$H NMR (400 MHz, CDCl$_3$) δ 8.85 (s, 1H), 8.28-8.19 (m, 2H), 7.84 (d, J=4.0 Hz, 1H), 7.61-7.53 (m, 1H), 7.52-7.43 (m, 2H), 6.84 (d, J=4.1 Hz, 1H), 4.32 (s, 1H), 4.20 (q, J=7.1 Hz, 2H), 4.09 (s, 2H), 2.44 (d, J=6.2 Hz, 2H), 2.40-2.27 (m, 2H), 2.16 (d, J=13.3 Hz, 2H), 2.12-1.96 (m, 3H), 1.54-1.38 (m, 2H), 1.27 (t, J=7.1 Hz, 3H).

Intermediate 4 Synthesis and Characterization

Sodium 2-(1-((1r,4r)-4-(cyanomethyl)cyclohexyl)-1,6-dihydroimidazo[4,5-d]pyrrolo[2,3-b]pyridin-2-yl)acetate

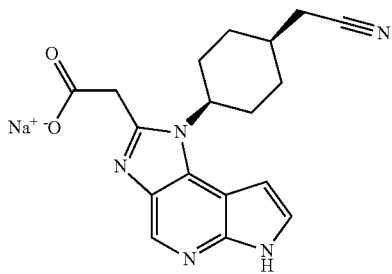

To a solution of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 9.50 g, 18.8 mmol) in MeOH (30 mL) and THF (30 mL) was added aq sodium hydroxide (56.4 mL, 56.4 mmol, 1 M) and was stirred at room temperature for 14 hours. The solvent was removed under reduced pressure at room temperature to provide the title compound (7 g) as a brown solid, which was used in the next step without further purification. MS (ESI): mass calcd. for $C_{18}H_{18}N_5NaO_2$, 359.1; m/z found, 337.9 [M+H-Na]$^+$. $^1$H NMR (400 MHz, CD$_3$OD) δ 8.52-8.47 (m, 1H), 7.85-7.81 (m, 2H), 7.46-7.41 (m, 4H), 6.85-6.81 (m, 1H), 4.60-4.46 (m, 1H), 3.96 (s, 2H), 2.59-2.49 (m, 4H), 2.19-2.05 (m, 6H), 1.56-1.43 (m, 2H) (a 1:1 mixture of the title compound and benzenesulfonic acid).

Intermediate 5 Synthesis and Characterization 2-((1r,4r)-4-(2-(Aminomethyl)imidazo[4,5-d]pyrrolo[2,3-b]pyridin-1(6H)-yl)cyclohexyl)acetonitrile hydrochloride

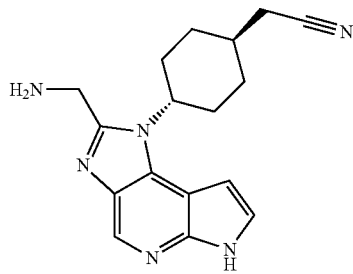 [SMILES: N#CC[C@H]1CC[C@H](n2c(CN)nc3cnc4[nH]ccc4c32)CC1]

Step A: tert-Butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate and 2-((1r,4r)-4-(2-(aminomethyl)-6-(phenylsulfonyl)imidazo[4,5-d]pyrrolo[2,3-b]pyridin-1(6H)-yl)cyclohexyl)acetonitrile. A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 1.50 g, 3.41 mmol), tert-butyl (2-oxoethyl)carbamate (1.47 g, 7.85 mmol), sodium hydrosulfite (2.97 g, 17.1 mmol), DMSO (3 mL), methanol (10 mL), and water (5 mL) was stirred for 2.5 h at 100° C. A mixture of two products, tert-butyl ((1-((1r,4r)-4-(cyanomethyl)cyclohexyl)-1,6-dihydroimidazo[4,5-d]pyrrolo[2,3-b]pyridin-2-yl)methyl)carbamate and 2-((1r,4r)-4-(2-(aminomethyl)imidazo[4,5-d]pyrrolo[2,3-b]pyridin-1(6H)-yl)cyclohexyl)acetonitrile, were found. The reaction mixture was used to the next step directly.

Step B: tert-Butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate. (Boc)$_2$O (1.04 g, 4.78 mmol) was added to a mixture of tert-butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate and 2-((1r,4r)-4-(2-(aminomethyl)-6-(phenylsulfonyl)imidazo[4,5-d]pyrrolo[2,3-b]pyridin-1(6H)-yl)cyclohexyl)acetonitrile (36 mL reaction mixture, 6.826 mmol), Na$_2$CO$_3$ (2.17 g, 20.5 mmol), and methanol (50 mL) and was stirred for 2 hours at 12° C. The reaction was concentrated under vacuum to dryness and the aqueous layer was diluted with water (30 mL) and extracted with ethyl acetate (50 mL×2). The combined organic extracts were dried over anhydrous Na$_2$SO$_4$, filtered, and concentrated to dryness. The residue was purified by flash column chromatography to provide the title compound (2.4 g, 63% over two steps) as a light yellow solid. $^1$H NMR (400 MHz, CDCl$_3$): δ 8.83 (s, 1H), 8.23 (d, J=7.6 Hz, 2H), 7.84 (d, J=4.0 Hz, 1H), 7.60-7.52 (m, 1H), 7.52-7.44 (m, 2H), 6.83 (d, J=4.0 Hz, 1H), 5.36 (br s, 1H), 4.67 (d, J=5.6 Hz, 2H), 4.65-4.59 (m, 1H), 2.40 (d, J=6.4 Hz, 2H), 2.37-2.22 (m, 2H), 2.20-2.09 (m, 2H), 2.04-1.87 (m, 3H), 1.53-1.39 (m, 11H).

Step C: tert-Butyl ((1-((1r,4r)-4-(cyanomethyl)cyclohexyl)-1,6-dihydroimidazo[4,5-d]pyrrolo[2,3-b]pyridin-2-yl)methyl)carbamate. Aqueous KOH (4.37 mL, 13.1 mmol) was added to a solution consisting of tert-butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate (2.40 g, 4.37 mmol) and dioxane (25 mL) and was stirred for 2 hours at 80° C. The reaction mixture was adjusted to pH=7-8 with 1 M HCl and the volatile solvents were removed under vacuum. The aqueous phase was diluted with water (20 mL) and extracted with ethyl acetate (50 mL×2). The combined organic extracts were dried over anhydrous Na$_2$SO$_4$, filtered, and concentrated to dryness to provide the title compound (2 g, 100% yield) as a light yellow solid, which was used in the next step without further purification. MS (ESI): mass calcd. for $C_{22}H_{28}N_6O_2$, 408.2; m/z found, 409.1 [M+H]$^+$. $^1$H NMR (400 MHz, DMSO-d$_6$): δ 11.86 (s, 1H), 8.51 (s, 1H), 7.56-7.49 (m, 1H), 7.47 (t, J=2.8 Hz, 1H), 6.74-6.68 (m, 1H), 4.66-4.58 (m, 1H), 4.53 (d, J=5.6 Hz, 2H), 2.58 (d, J=5.6 Hz, 2H), 2.41-2.28 (m, 2H), 2.08-1.94 (m, 3H), 1.93-1.83 (m, 2H), 1.54-1.23 (m, 11H).

Step D: 2-((1r,4r)-4-(2-(Aminomethyl)imidazo[4,5-d]pyrrolo[2,3-b]pyridin-1(6H)-yl)cyclohexyl)acetonitrile hydrochloride. HCl/dioxane (10 mL, 40 mmol, 4 M) was added to a solution of tert-butyl ((1-((1r,4r)-4-(cyanomethyl)cyclohexyl)-1,6-dihydroimidazo[4,5-d]pyrrolo[2,3-b]pyridin-2-yl)methyl)carbamate (2.0 g, 4.9 mmol) in CH$_2$Cl$_2$ (20 mL) at 0° C. and was stirred for 30 minutes at 10° C. The reaction was concentrated to dryness to provide the title compound (1.7 g, 100% yield) as a pale white solid, which was used without further purification. MS (ESI): mass calcd. for $C_{17}H_{20}ClN_6$, 308.2; m/z found, 308.9 [M+H]$^+$, $^1$H NMR (400 MHz, DMSO-d$_6$) δ 12.53 (s, 1H), 8.88 (s, 1H), 8.86 (br. s, 3H), 7.67 (t, J=3.2 Hz, 1H), 6.93 (s, 1H), 4.71-4.63 (m, 2H), 4.60-4.42 (m, 1H), 2.60 (d, J=6.0 Hz, 2H), 2.36-2.21 (m, 2H), 2.12-1.93 (m, 5H), 1.56-1.42 (m, 2H).

Intermediate 6 Synthesis and Characterization

Ethyl 1-((1r,4r)-4-(cyanomethyl)cyclohexyl)-6-(phenylsulfonyl)-1,6-dihydroimidazo[4,5-d]pyrrolo[2,3-b]pyridine-2-carboxylate

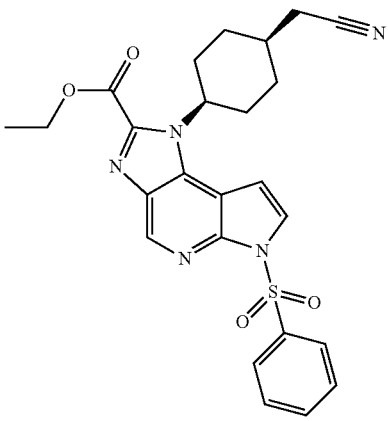 [SMILES: CCOC(=O)c1nc2cnc3c(ccn3S(=O)(=O)c3ccccc3)c2n1[C@H]1CC[C@@H](CC#N)CC1]

To 2-((1r,4r)-4-((5-Nitro-1-(phenylsulfonyl)-1H-pyrrolo[2,3-b]pyridin-4-yl)amino)cyclohexyl)acetonitrile (Intermediate 1, 440 mg, 1 mmol) in DMSO (2.5 mL) and $H_2O$ (0.15 mL), ethyl glyoxalate (307 mg, 3 mmol) was added followed by the addition of sodium hydrosulfite (523 mg, 3 mmol). The reaction mixture was heated at 100° C. for 15 h. The reaction was cooled to room temperature. $H_2O$ (20 mL) added. Solids formed and collected via filtration. The solids were purified by flash column chromatography (10% acetone/$CH_2Cl_2$) to provide ethyl 1-((1r,4r)-4-(cyanomethyl)cyclohexyl)-6-(phenylsulfonyl)-1,6-dihydroimidazo[4,5-d]pyrrolo[2,3-b]pyridine-2-carboxylate (410 mg, 83%). MS (ESI): mass calcd. for $C_{25}H_{25}N_5O_4S$, 491.16; m/z found, 492.2 [M+H]$^+$, $^1H$ NMR (500 MHz, CDCl$_3$) δ 9.02-8.85 (m, 1H), 8.21-8.08 (m, 2H), 7.90-7.77 (m, 1H), 7.55-7.46 (m, 1H), 7.47-7.36 (m, 2H), 6.93-6.79 (m, 1H), 5.58-5.25 (m, 1H), 4.50-4.02 (m, 2H), 2.41-2.34 (m, 3H), 2.10 (d, J=13.2 Hz, 2H), 2.02-1.95 (m, 2H), 1.48-1.37 (m, 2H), 1.29-1.14 (m, 5H).

Intermediate 7 Synthesis and Characterization 2-((1r,4r)-4-(2-(Hydroxymethyl)-6-(phenylsulfonyl)imidazo[4,5-d]pyrrolo[2,3-b]pyridin-1(6H)-yl)cyclohexyl)acetonitrile

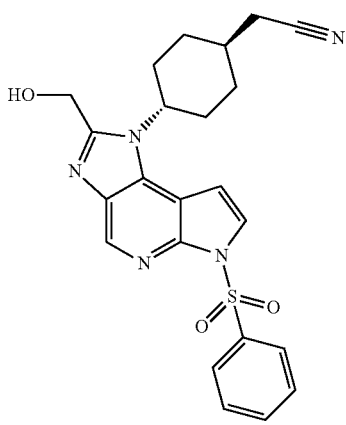 [SMILES: N#CC[C@H]1CC[C@H](n2c(CO)nc3cnc4c(ccn4S(=O)(=O)c4ccccc4)c32)CC1]

A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 900 mg, 2.05 mmol), 1,4-dioxane-2,5-diol (400 mg, 3.33 mmol), and sodium hydrosulfite (1.05 g, 5.12 mmol) in DMSO (6 mL), MeOH (20 mL), and distilled water (4 mL) in a pressure tube was heated at 100° C. for 12 h. The reaction was filtered, and the white solid was washed with water, MeOH and EtOAc, and dried to give the title compound (654 mg, 71%). The filtrate was concentrated and water was added to form a light brown precipitate. The precipitated light brown solid was filtered, washed with water and EtOAc, and dried over anhydrous $MgSO_4$ to provide 150 mg of a light brown solid. The filtrate from the washing of the light brown precipitate were extracted with EtOAc (3×) to provide extracts A. Extracts A were washed with water to provide aqueous layer A. The aqueous layer A was back extracted with EtOAc (2×) to provide extracts B. Extracts B were dried over anhydrous $MgSO_4$, filtered, and concentrated to dryness to provide 50 mg of an oil, which was combined with the above brown solid to provide the second portion of the title compound (200 mg, 22% yield), which was used as is in the next reaction without further purification. MS (ESI): mass calcd. for $C_{23}H_{23}N_5O_3S$ 449.15; m/z found, 450.1 [M+H]$^+$, $^1H$ NMR (400 MHz, CDCl$_3$) δ=8.85 (s, 1H), 8.26-8.22 (m, 2H), 7.85 (d, J=4.0 Hz, 1H), 7.60-7.54 (m, 1H), 7.53-7.46 (m, 2H), 6.83 (d, J=4.0 Hz, 1H), 4.95 (s, 2H), 4.55 (br s, 1H), 2.44 (d, J=6.6 Hz, 2H), 2.32 (br s, 2H), 2.17 (d, J=13.6 Hz, 2H), 2.13-1.97 (m, 3H), 1.53-1.43 (m, 2H).

Intermediate 8 Synthesis and Characterization 2-((1r,4r)-4-(2-(Chloromethyl)-6-(phenylsulfonyl)imidazo[4,5-d]pyrrolo[2,3-b]pyridin-1(6H)-yl)cyclohexyl)acetonitrile

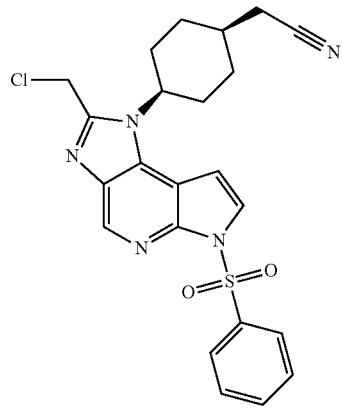 [SMILES: N#CC[C@H]1CC[C@@H](n2c(CCl)nc3cnc4c(ccn4S(=O)(=O)c4ccccc4)c32)CC1]

A solution of 2-((1r,4r)-4-((5-amino-1-(phenylsulfonyl)-1H-pyrrolo[2,3-b]pyridin-4-yl)amino)cyclohexyl)acetonitrile (Intermediate 2, 818 mg, 2.00 mmol) and 2-chloro-1,1,1-triethoxyethane (786 mg, 4.00 mmol) in acetic acid (5 mL) in 50 mL flask was lowered into a bath at 125° C. and heated for 20 minutes. The reaction mixture was cooled, diluted with $CH_2Cl_2$ (200 mL) and stirred over saturated sodium bicarbonate until the bubbling stopped. The organic layer was collected and washed with water, brine, dried over anhydrous $Na_2SO_4$, and concentrated to dryness. The residue was purified by flash column chromatography to provide the title compound (800 mg, 85% yield). MS (ESI): mass calcd. for $C_{23}H_{22}ClN_5O_2S$, 467.12; m/z found, 468.0 [M+H]$^+$. $^1$H NMR (400 MHz, DMSO-d$_6$): δ 8.72 (s, 1H), 8.13 (d, J=8.0 Hz, 2H), 7.99 (d, J=4.0 Hz, 1H), 7.73-7.65 (m, 1H), 7.63-7.55 (m, 2H), 7.14 (d, J=4.0 Hz, 1H), 5.19 (s, 2H), 4.65-4.53 (m, 1H), 2.57 (d, J=5.6 Hz, 2H), 2.27-2.12 (m, 2H), 2.11-1.88 (m, 5H), 1.49-1.35 (m, 2H).

Intermediate 9 Synthesis and Characterization 2-(4-Aminobicyclo[2.2.2]octan-1-yl)acetonitrile Hydrochloride

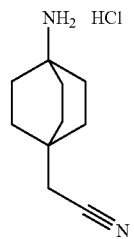 [SMILES: Cl ; N#CCC12CCC(N)(CC1)CC2]

Step A: tert-Butyl (4-(hydroxymethyl)bicyclo[2.2.2]octan-1-yl)carbamate. Borane-tetrahydrofuran complex (22.3 mL, 22.3 mmol, 1M) was added drop-wise to a solution at 0° C. of 4-((tert-butoxycarbonyl)amino)bicyclo[2.2.2]octane-1-carboxylic acid (3.0 g, 11 mmol) and anhydrous THF (5 mL). The resulting mixture was stirred at room temperature for 3 hours before slowly quenching with H$_2$O (10 mL) and extracting with ethyl acetate (50 mL×3). The combined organic extracts were washed with brine (35 mL), dried over anhydrous MgSO$_4$, filtered, concentrated to dryness under reduced pressure, and purified by flash column chromatography (eluent: petroleum ether:ethyl acetate=1:1) to afford the title compound (2.8 g, 98%) as a colorless, sticky oil. $^1$H NMR (400 MHz, DMSO-d$_6$) δ 6.27 (br s, 1H), 4.28 (t, J=5.2 Hz, 1H), 2.97 (d, J=5.2 Hz, 1H), 1.74-1.59 (m, 6H), 1.42-1.25 (m, 15H).

Step B: (4-((tert-Butoxycarbonyl)amino)bicyclo[2.2.2]octan-1-yl)methyl methane sulfonate. Methansulfonyl chloride (3.5 mL, 44 mmol) was added drop-wise to a solution at 0° C. of tert-butyl (4-(hydroxymethyl)bicyclo[2.2.2]octan-1-yl)carbamate (2.8 g, 11 mmol), pyridine (3.5 mL, 44 mmol), and anhydrous methylene chloride (20 mL). The mixture was stirred at room temperature for 5 hours before diluting with methylene chloride (100 mL) and quenching with H$_2$O (50 mL). The organic layer was separated, washed with brine (25 mL), dried over anhydrous MgSO$_4$, filtered, concentrated to dryness under reduced pressure, and purified by flash column chromatography (eluent: petroleum ether: ethyl acetate=5:1 to 1:1) to afford the title compound (2.95 g, 84%) as a white solid.

Step C: tert-Butyl (4-(cyanomethyl)bicyclo[2.2.2]octan-1-yl)carbamate. A solution of (4-((tert-butoxycarbonyl)amino)bicyclo[2.2.2]octan-1-yl)methyl methane sulfonate (2.95 g, 8.85 mmol) and DMSO (25 mL) was added to a suspension of sodium cyanide (1.30 g, 26.5 mmol) and DMSO (5 mL). The mixture was heated at 100° C. overnight before diluting with H$_2$O (80 mL) and extracting with ethyl acetate (60 mL×3). The combined organic extracts were washed with brine, dried over anhydrous MgSO$_4$, filtered, and concentrated to dryness under reduced pressure. The residue was triturated with MTBE (10 mL), and the white solid was filtered and dried under reduced pressure to afford the title compound (1.7 g, 73%). The filtrate was concentrated and purified by flash column chromatography (eluent: petroleum:ethyl acetate=10:1) to afford the second batch of the title compound (500 mg, 21%) as a white solid. $^1$H NMR (400 MHz, DMSO-d$_6$) δ 6.39 (br s, 1H), 2.32 (s, 2H), 1.78-1.68 (m, 6H), 1.54-1.44 (m, 6H), 1.35 (s, 9H)

Step D: 2-(4-Aminobicyclo[2.2.2]octan-1-yl)acetonitrile hydrochloride. A suspension of tert-butyl (4-(cyanomethyl)bicyclo[2.2.2]octan-1-yl)carbamate (2.2 g, 8.3 mmol) and ethyl acetate (10 mL) at 0° C. was treated with HCl in ethyl acetate (20 mL, 80 mmol, 4.0 M). After the addition of HCl solution, the suspension turned to a clear solution. The mixture was stirred at room temperature for 4 hours before concentrating to dryness under reduced pressure. The residue was triturated with MTBE (10 mL), and the solid was filtered, washed with MTBE (3 mL×2), and dried under reduced pressure to afford the title compound (1.55 g, 93%). MS (ESI): mass calcd. for $C_{10}H_{16}N_2$ 164.13; m/z found, 165.1 [M+H]$^+$. $^1$H NMR (400 MHz, DMSO-d$_6$) δ 8.11 (br s, 3H), 2.40 (s, 2H), 1.78-1.67 (m, 6H), 1.62-1.51 (m, 6H).

Intermediate 10 Synthesis and Characterization

Ethyl 2-(1-(4-(cyanomethyl)bicyclo[2.2.2]octan-1-yl)-6-(phenylsulfonyl)-1,6-dihydroimidazo[4,5-d]pyrrolo[2,3-b]pyridin-2-yl)acetate

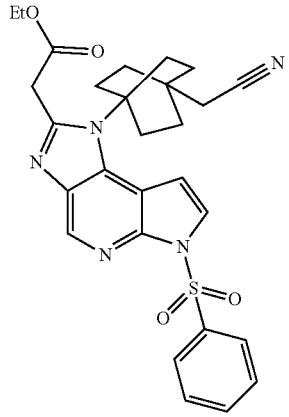 [SMILES: CCOC(=O)Cc1nc2cnc3c(ccn3S(=O)(=O)c3ccccc3)c2n1C12CCC(CC#N)(CC1)CC2]

Step A: 2-(4-((5-Nitro-1-(phenylsulfonyl)-1H-pyrrolo[2,3-b]pyridin-4-yl)amino)bicyclo[2.2.2]octan-1-yl)acetonitrile. A mixture of 4-chloro-5-nitro-1-(phenylsulfonyl)-1H-pyrrolo[2,3-b]pyridine (500 mg, 1.48 mmol), 2-(4-aminobicyclo[2.2.2]octan-1-yl)acetonitrile hydrochloride (Intermediate 9, 357 mg, 1.77 mmol), N,N-diisopropylethylamine (574 mg, 4.4 mmol), and propan-2-ol (20 mL) was stirred at reflux for 16 hours. After cooling to room temperature, the suspension was isolated via filtration. The filter cake was washed with propan-2-ol (5 mL) and dried under reduced pressure to afford the title compound (450 mg, 65%) as a yellow solid, which was used in the next step without further purification. MS (ESI): mass calcd. for $C_{23}H_{23}N_5O_4S$, 465.2; m/z found, 466.1 [M+H]$^+$.

Step B: 2-(4-((5-Amino-1-(phenylsulfonyl)-1H-pyrrolo[2,3-b]pyridin-4-yl)amino)bicyclo[2.2.2]octan-1-yl)acetonitrile. Zinc dust (279 mg, 4.29 mmol) was added to a 50 mL round-bottomed flask containing a mixture of 2-(4-((5-nitro-1-(phenylsulfonyl)-1H-pyrrolo[2,3-b]pyridin-4-yl)amino)bicyclo[2.2.2]octan-1-yl)acetonitrile (200 mg, 0.430 mmol), sat. NH$_4$Cl (0.6 mL), and EtOH (20 mL). After stirring at room temperature for 16 hours, the mixture was concentrated under reduced pressure and diluted with ethyl acetate (20 mL). The suspension was filtered through a pad of Celite® and washed with ethyl acetate (5 mL). The filtrate was concentrated to dryness under reduced pressure to afford the title compound (160 mg, 85.5%) as a brown solid, which was used in the next step without purification. MS (ESI): mass calcd. for $C_{23}H_{25}N_5O_2S$, 435.15; m/z found, 436.1 [M+H]$^+$.

Step C: Ethyl 2-(1-(4-(cyanomethyl)bicyclo[2.2.2]octan-1-yl)-6-(phenylsulfonyl)-1,6-dihydroimidazo[4,5-d]pyrrolo[2,3-b]pyridin-2-yl)acetate. A mixture of 2-(4-((5-amino-1-(phenylsulfonyl)-1H-pyrrolo[2,3-b]pyridin-4-yl)amino)bicyclo[2.2.2]octan-1-yl)acetonitrile (160 mg, 0.36 mmol), ethyl 3-(ethoxyimino)propanoate hydrochloride (180 mg, 0.918 mmol), and EtOH (25 mL) was stirred at reflux for 24 hours. After cooling to room temperature, EtOH was removed under reduced pressure, and the residue was purified by preparative TLC (eluent: ethyl acetate) to afford the title compound (120 mg, 61%). MS (ESI): mass calcd. for $C_{28}H_{29}N_5O_4S$, 531.19; m/z found, 532.0 [M+H]$^+$.

Intermediate 11 Synthesis and Characterization

Sodium 2-(1-(4-(cyanomethyl)bicyclo[2.2.2]octan-1-yl)-1,6-dihydroimidazo[4,5-d]pyrrolo[2,3-b]pyridin-2-yl)acetate

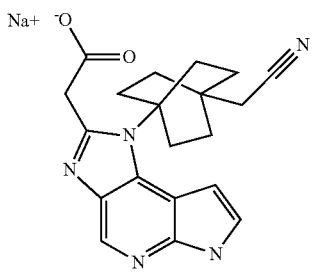

1 N NaOH aqueous solution (2.8 mL, 2.8 mmol) was added to a solution of ethyl 2-(1-(4-(cyanomethyl)bicyclo[2.2.2]octan-1-yl)-6-(phenylsulfonyl)-1,6-dihydroimidazo[4,5-d]pyrrolo[2,3-b]pyridin-2-yl)acetate (Intermediate 10, 500 mg, 0.941 mmol), MeOH (5 mL), and THF (5 mL). After stirring at room temperature for 24 hours, the mixture was concentrated to dryness under reduced pressure to afford the title compound (600 mg) as a brown solid, which was used in the next step without purification. MS (ESI): mass calcd. for $C_{20}H_{20}N_5NaO_2$, 385.1; m/z found, 364.0 (minus Na) [M+H]$^+$.

Example 1 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide

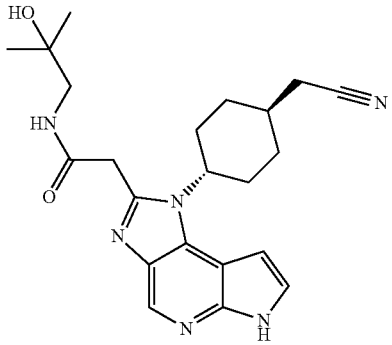

(Ex. 1)

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. To ensure dry starting material, ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3) was heated under vacuum at 50° C. for 18 h prior to the reaction. In a 1 L flask, ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 52.585 g, 104.01 mmol) was suspended in DMA (50 mL). 1-Amino-2-methylpropan-2-ol (50 mL) was added and the reaction was heated to 110° C. for 45 minutes, then to 125° C. for 5 hours. The reaction was cooled to room temperature and diluted with EtOAc (800 mL). The organic layer was extracted three times with a solution of water/brine wherein the solution was made up of 1 L water plus 50 mL brine. The aqueous layers were back extracted with EtOAc (2×600 mL). The combined organic layers were dried over anhydrous MgSO$_4$, concentrated to dryness, and then dried for 3 days under vacuum to provide the title compound (65.9 g, 98% yield) as a yellow foam. The product was taken to the next step with no further purification. MS (ESI): mass calcd. for $C_{28}H_{32}N_6O_4S$, 548.22; m/z found, 549.2 [M+H]$^+$. $^1$H NMR (400 MHz, CDCl$_3$): δ 8.76 (s, 1H), 8.26-8.19 (m, 2H), 7.84 (d, J=4.1 Hz, 1H), 7.60-7.53 (m, 1H), 7.50-7.44 (m, 2H), 6.84 (d, J=4.2 Hz, 1H), 4.76-4.61 (m, 1H), 3.97 (s, 2H), 3.45 (s, 1H), 3.27 (d, J=5.9 Hz, 2H), 2.41 (d, J=6.5 Hz, 2H), 2.38-2.25 (m, 2H), 2.23-2.12 (m, 2H), 2.09-1.94 (m, 4H), 1.48 (qd, J=13.6, 4.0 Hz, 2H), 1.21 (s, 6H).

Step B: 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide. 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide (65.90 g, 102.1 mmol) was added to a 1 L flask containing a stir bar. 1,4-dioxane (300 mL) was added, followed by aq KOH (3 M, 150 mL). The reaction was heated at 80° C. for 2 h. The reaction was cooled to room temperature and the solvent volume was reduced to about 200 mL on a rotovap. The residue was treated with a solution of water/brine (100 mL/100 mL), then extracted with 10% MeOH in CH$_2$Cl$_2$ (2×1 L). The organic layers were combined, dried over anhydrous MgSO$_4$, and concentrated to dryness to provide a yellow solid. The solid was suspended in CH$_2$Cl$_2$ (200 mL), stirred vigorously for 30 minutes, and then collected by filtration. The solid was rinsed with CH$_2$Cl$_2$ (100 mL), dried by pulling air through the filter, and then further dried under vacuum at room temperature for 16 h to provide the title compound (41.59 g, 89% yield) as a white solid. MS (ESI): mass calcd. for C$_{22}$H$_{28}$N$_6$O$_2$, 408.23; m/z found, 409.2 [M+H]$^+$. $^1$H NMR (600 MHz, DMSO-d$_6$): δ 11.85 (s, 1H), 8.50 (s, 1H), 8.21-8.10 (m, 1H), 7.49-7.43 (m, 1H), 6.74-6.65 (m, 1H), 4.53-4.42 (m, 2H), 4.07 (s, 2H), 3.08 (d, J=6.0 Hz, 2H), 2.58 (d, J=6.1 Hz, 2H), 2.41-2.28 (m, 2H), 2.09-1.92 (m, 5H), 1.42-1.31 (m, 2H), 1.09 (s, 6H).

Example 2 Synthesis and Characterization 2-((1r,4r)-4-(2-(1H-Imidazol-4-yl)imidazo[4,5-d]pyrrolo[2,3-b]pyridin-1(6H)-yl)cyclohexyl)acetonitrile

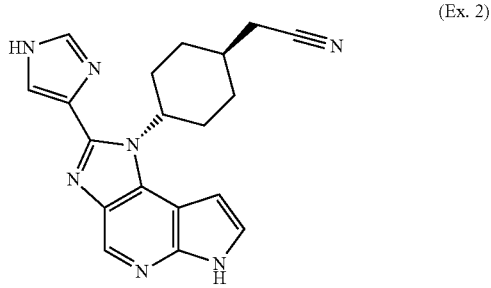

(Ex. 2)

Step A: 2-((1r,4r)-4-(2-(1H-Imidazol-4-yl)-6-(phenylsulfonyl)imidazo[4,5-d]pyrrolo[2,3-b]pyridin-1(6H)-yl)cyclohexyl)acetonitrile. 2-((1r,4r)-4-((5-Nitro-1-(phenylsulfonyl)-1H-pyrrolo[2,3-b]pyridin-4-yl)amino)cyclohexyl)acetonitrile (Intermediate 1, 23.3 g, 53.0 mmol) was added into a 1 L round-bottomed flask containing a magnetic stir-bar followed by the addition of DMSO (200 mL) and methanol (200 mL). 1H-Imidazole-4-carbaldehyde (8.56 g, 89.1 mmol) was added as a solid, followed by the addition of sodium hydrosulfite (32.7 g, 188 mmol) as a solution in water (100 mL). The reaction vessel was equipped with a reflux condenser and heated to 90° C. in a heating block for 15 h. The reaction mixture was then cooled to room temperature and added to a flask containing water (2000 mL) with stirring, which resulted in formation of a white precipitate. The mixture was stirred for 30 minutes and the solids were collected by filtration. The solids were dried by pulling air through the filter for 6 h and then further dried in a vacuum oven heating at 60° C. for 3 days to provide the title compound (22.7 g, 88% yield) as a yellow solid. MS (ESI): mass calcd. for C$_{25}$H$_{23}$N$_7$O$_2$S, 485.16; m/z found, 486.1 [M+H]$^+$. $^1$H NMR (400 MHz, CDCl$_3$): δ 8.74 (s, 1H), 8.29 (s, 1H), 8.20-8.11 (m, 2H), 8.04-7.96 (m, 2H), 7.76-7.68 (m, 1H), 7.68-7.60 (m, 2H), 7.19 (d, J=4.2 Hz, 1H), 5.56 (s, 1H), 2.58 (d, J=6.3 Hz, 2H), 2.38-2.24 (m, 2H), 2.07 (s, 1H), 1.98 (d, J=10.8 Hz, 5H), 1.35 (q, J=12.3 Hz, 2H).

Step B: 2-((1r,4r)-4-(2-(1H-Imidazol-4-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(2-(1H-imidazol-4-yl)-6-(phenylsulfonyl)imidazo[4,5-d]pyrrolo[2,3-b]pyridin-1(6H)-yl)cyclohexyl)acetonitrile (222 mg, 0.46 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and the residue was purified by flash column chromatography (0-15% 2 N NH$_3$-MeOH/EA) to provide the title compound (97 mg, 69% yield). MS (ESI): mass calcd. for C$_{19}$H$_{19}$N$_7$, 345.17; m/z found, 346.0 [M+H]$^+$. $^1$H NMR (400 MHz, DMSO-d$_6$): δ 12.61 (s, 1H), 11.86 (s, 1H), 8.55 (s, 1H), 7.92 (d, J=1.3 Hz, 1H), 7.83 (s, 1H), 7.48 (t, J=3.0 Hz, 1H), 6.76 (dd, J=3.5, 1.8 Hz, 1H), 5.85 (s, 1H), 2.60 (d, J=6.0 Hz, 2H), 2.57-2.41 (m, 2H), 2.14-1.88 (m, 5H), 1.45-1.27 (m, 2H).

Example 3 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide

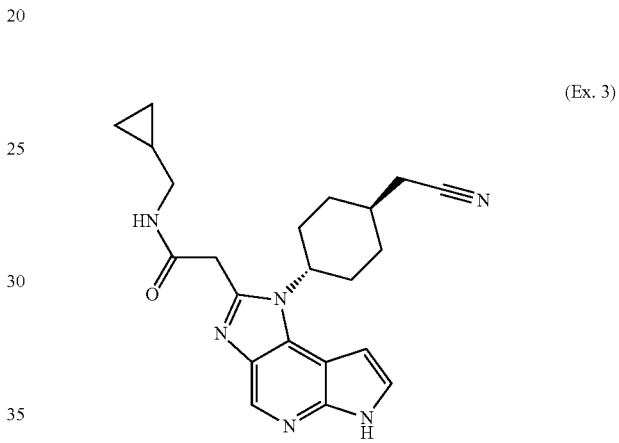

(Ex. 3)

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(cyclopropylmethyl)acetamide. A mixture of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 555 mg, 1.06 mmol) and cyclopropylmethylamine (1.87 mL, 21.1 mmol) was heated at 125° C. for 1 h in a microwave reactor. The residue was treated with water then extracted with ethyl acetate. The organic layers were combined, dried over sodium sulfate, passed through a silica plug, and concentrated to dryness using a rotovap to provide the title compound (642 mg). MS (ESI): mass calcd. for C$_{28}$H$_{30}$N$_6$O$_3$S, 530.21; m/z found, 531.2 [M+H]$^+$. $^1$H NMR (400 MHz, CD$_3$OD): δ 8.64 (s, 1H), 8.19-8.11 (m, 2H), 7.95 (d, J=4.1 Hz, 1H), 7.66-7.57 (m, 1H), 7.57-7.48 (m, 2H), 7.11 (d, J=4.1 Hz, 1H), 4.53 (s, 1H), 4.08 (s, 2H), 3.07 (d, J=7.1 Hz, 2H), 2.53 (d, J=5.9 Hz, 2H), 2.45-2.30 (m, 2H), 2.14-2.03 (m, 5H), 1.55-1.42 (m, 2H), 1.02-0.94 (m, 1H), 0.54-0.47 (m, 2H), 0.24-0.18 (m, 2H).

Step B: 2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide. To a mixture of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(cyclopropylmethyl)acetamide (560 mg, 1.05 mmol) in 1,4-dioxane (4.22 mL) was added 3N KOH (2.81 mL). The mixture was heated at 80° C. for 1 hr, then purified with basic HPLC: Xbridge Prep OBD C$_{18}$ 50 mm×100 mm, 5 μm column (eluent 0-100% aq NH$_4$OH/ACN (10 min)) to provide the title compound (187 mg, 46% yield). MS (ESI): mass calcd. for $C_{22}H_{26}N_6O$, 390.22; m/z found, 391.2 $[M+H]^+$. $^1H$ NMR (400 MHz, $CD_3OD$): δ 8.57 (s, 1H), 7.50 (d, J=3.5 Hz, 1H), 6.86 (d, J=3.5 Hz, 1H), 4.57 (s, 1H), 4.11 (s, 2H), 3.13 (d, J=7.0 Hz, 2H), 2.67-2.52 (m, 4H), 2.20-2.03 (m, 5H), 1.58-1.44 (m, 2H), 1.12-0.97 (m, 1H), 0.60-0.48 (m, 2H), 0.31-0.22 (m, 2H).

Example 4 Synthesis and Characterization

N-(2-Cyanoethyl)-2-(1-((1r,4r)-4-(cyanomethyl) cyclohexyl)-1,6-dihydroimidazo[4,5-d]pyrrolo[2,3-b]pyridin-2-yl)acetamide

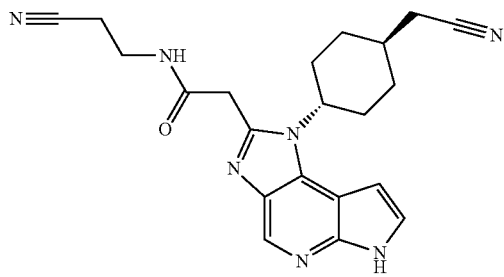

(Ex. 4)

To a solution of sodium 2-(1-((1r,4r)-4-(cyanomethyl) cyclohexyl)-1,6-dihydroimidazo[4,5-d]pyrrolo[2,3-b]pyridin-2-yl)acetate (Intermediate 4, 400 mg, 1.11 mmol) and 3-aminopropanenitrile (320 mg, 2.24 mmol) in DMF (5 mL) was added PyBOP (870 mg, 1.67 mmol) and DIPEA (0.60 mL, 3.5 mmol). The reaction mixture was stirred at room temperature for 40 h. After removal of the DMF in vacuo, the residue was purified by flash column chromatography using 50-100% ethyl acetate in heptane. The collected fractions were concentrated in vacuo to a small volume and white solid which had precipitated out was filtered off, washed with 10% MeOH in $CH_2Cl_2$, and dried to provide to provide the title compound (75 mg, 17% yield). The filtrate was concentrated to dryness and purified by reverse phase-HPLC using a Varian Pursuit $XR_s5$ Diphenyl 100 mm×30 mm column (eluent 10-90% $CH_3CN$ in water, 0.1% TFA) to provide a clear oil. This material was dissolved in 10% MeOH in $CH_2Cl_2$, passed through three 500 mg columns of SILICYCLE SPE-R66030B-03P Carbonate (SiliaBond acid scavenger solid phase extraction cartridge) to remove the TFA and eluted with 10% MeOH in $CH_2Cl_2$ to provide an additional fraction of the title compound (88 mg, 20% yield). The two fractions were combined to provide the final product (163 mg, 37% yield) as a white solid. MS (ESI): mass calcd. for $C_{21}H_{23}N_7O$, 389.20; m/z found, 390.3 $[M+H]^+$. $^1H$ NMR (400 MHz, $CD_3OD$): δ 8.53 (s, 1H), 7.48 (d, J=3.0 Hz, 1H), 6.84 (d, J=3.5 Hz, 1H), 4.51 (br s, 1H), 4.12 (s, 2H), 3.50 (t, J=6.6 Hz, 2H), 2.71 (t, J=6.6 Hz, 2H), 2.45-2.63 (m, 4H), 2.03-2.19 (m, 5H), 1.44-1.57 (m, 2H).

Example 5 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-pyran-4-yl)acetamide

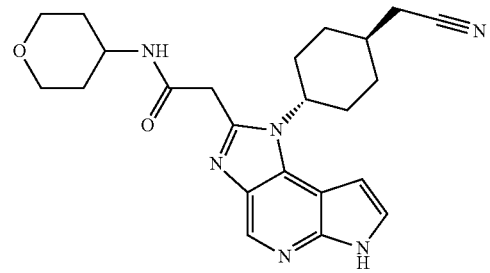 [SMILES: N#CC[C@H]1CC[C@H](n2c(CC(=O)NC3CCOCC3)nc3cnc4[nH]ccc4c32)CC1]

A mixture of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 309 mg, 0.61 mmol) and 4-aminotetrahydropyran (195 mg, 1.93 mmol) in 1,4-dioxane (0.5 mL) was heated in a microwave reactor at 180° C. for 1 hr. The reaction mixture was then diluted with 1,4-dioxane (1.5 mL), treated with aq 3N KOH (2 mL), and heated at 80° C. for 1.5 hr. The residue was then treated with water (10 mL) and extracted with $CH_2Cl_2$ (3×50 mL). The organic layers were combined, dried over $MgSO_4$ and concentrated in vacuo. The crude material was purified using flash column chromatography (5-10% MeOH/$CH_2Cl_2$) to yield the title compound (146 mg, 57% yield). MS (ESI): mass calcd. for $C_{23}H_{28}N_6O_2$, 420.23; m/z found, 421.2 $[M+H]^+$. $^1H$ NMR (600 MHz, DMSO-$d_6$): δ 11.84 (s, 1H), 8.49 (s, 1H), 8.36 (d, J=7.5 Hz, 1H), 7.46 (t, J=3.0 Hz, 1H), 6.73-6.67 (m, 1H), 4.54-4.41 (m, 1H), 3.98 (s, 2H), 3.86-3.81 (m, 2H), 3.81-3.74 (m, 1H), 3.40-3.34 (m, 2H), 2.60 (d, J=6.0 Hz, 2H), 2.41-2.29 (m, 2H), 2.10-2.01 (m, 1H), 2.00-1.93 (m, 4H), 1.77-1.70 (m, 2H), 1.49-1.33 (m, 4H).

Example 6 Synthesis and Characterization 2-((1r,4r)-4-(2-(2-Oxo-2-(4-(trifluoromethyl)piperidin-1-yl)ethyl)imidazo[4,5-d]pyrrolo[2,3-b]pyridin-1 (6H)-yl)cyclohexyl)acetonitrile

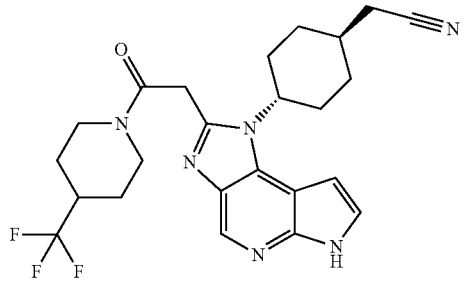 [SMILES: N#CC[C@H]1CC[C@H](n2c(CC(=O)N3CCC(C(F)(F)F)CC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), 4-(trifluoromethyl)piperidine (85.0 mg, 0.557 mmol), DIPEA (144 mg, 1.11 mmol), and DMF (5 mL) was stirred at 0° C. for 1 h. Then PyBrOP (311 mg, 0.668 mmol) was added and stirred at room-temperature overnight. The mixture was quenched with 10 mL water and was purified by preparative HPLC using a Boston Green ODS 150 mm×30 mm, 5 μm column (eluent: water (0.05% HCl)-ACN from 18% to 48%, v/v) to provide the title compound (81 mg, 30% yield) as a light brown solid. MS (ESI): mass calcd. for $C_{24}H_{27}F_3N_6O$, 472.2; m/z found, 473.2 [M+H]$^+$. $^1$H NMR (400 MHz, DMSO-d$_6$): δ 12.69 (s, 1H), 8.88 (s, 1H), 7.79-7.76 (m, 1H), 6.99-6.96 (m, 1H), 4.77-4.63 (m, 2H), 4.50-4.43 (m, 1H), 4.17-4.10 (m, 1H), 3.29-3.20 (m, 1H), 2.77-2.66 (m, 2H), 2.58 (d, J=6.0 Hz, 2H), 2.53-2.47 (m, 4H) 2.13-1.85 (m, 6H), 1.66-1.53 (m, 1H), 1.45-1.22 (m, 3H).

Example 7 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)phenyl)acetamide

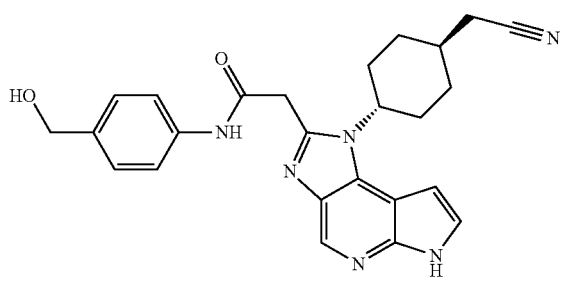 [SMILES: N#CC[C@H]1CC[C@H](n2c(CC(=O)Nc3ccc(CO)cc3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), (4-aminophenyl)methanol hydrochloride (133 mg, 0.835 mmol), DIPEA (216 mg, 1.67 mmol), and DMF (5 mL) was stirred at 0° C. for 1 h. PyBrOP (467 mg, 1.00 mmol) was added and stirred at rt for overnight. The mixture was quenched with 10 mL water and was purified by preparative C$_{18}$ HPLC using a Waters Xbridge Prep OBD C$_{18}$ 150 mm×30 mm, 5 μm column (eluent: water (0.05% ammonia hydroxide v/v)-MeOH from 44% to 55%, v/v) to provide the title compound (43 mg, 11% yield) as a white solid. MS (ESI): mass calcd. for $C_{25}H_{26}N_6O_2$, 442.2; m/z found, 443.2 [M+H]$^+$. $^1$H NMR (400 MHz, DMSO-d$_6$): δ 11.86 (br s, 1H), 10.40 (s, 1H), 8.52 (s, 1H), 7.55 (d, J=8.4 Hz, 2H), 7.49-7.45 (m, 1H), 7.26 (d, J=8.0 Hz, 2H), 6.75-6.71 (m, 1H), 5.15-5.08 (m, 1H), 4.65-4.54 (m, 1H), 4.46-4.41 (m, 2H), 4.24 (s, 2H), 2.58 (d, J=6.0 Hz, 2H), 2.45-2.30 (m, 2H), 2.11-1.93 (m, 5H), 1.48-1.33 (m, 2H).

Example 8 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4-(cyanomethyl)phenyl)acetamide

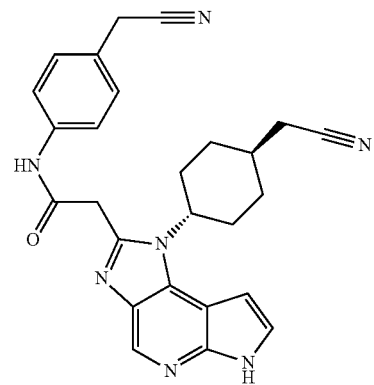 [SMILES: N#CCc1ccc(NC(=O)Cc2nc3cnc4[nH]ccc4c3n2[C@H]2CC[C@H](CC#N)CC2)cc1]

A mixture of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), 2-(4-aminophenyl)acetonitrile hydrochloride (93.8 mg, 0.557 mmol), DIPEA (144 mg, 1.11 mmol), and DMF (5 mL) was stirred at 0° C. for 1 h. PyBrOP (311 mg, 0.668 mmol) was added and stirred at room temperature overnight. The mixture was quenched with 10 mL water and was purified by preparative HPLC using a Kromasil 150 mm×25 mm, 10 μm column (eluent: water (0.05% ammonia hydroxide v/v)-ACN from 27% to 37%, v/v) and then by preparative TLC (CH$_2$Cl$_2$:MeOH=10:1) to provide the title compound (12 mg, 4% yield) as a white solid. MS (ESI): mass calcd. for $C_{26}H_{25}N_7O$, 451.2; m/z found, 452.2 [M+H]$^+$. $^1$H NMR (400 MHz, CD$_3$OD): δ 8.55 (s, 1H), 7.62 (d, J=8.8 Hz, 2H), 7.49 (d, J=3.6 Hz, 1H), 7.33 (d, J=8.4 Hz, 2H), 6.86 (d, J=3.6 Hz, 1H), 4.68-4.54 (m, 2H), 4.31-4.25 (m, 1H), 3.86 (s, 2H), 2.67-2.49 (m, 4H), 2.20-2.05 (m, 5H), 1.55-1.41 (m, 2H).

Example 9 Synthesis and Characterization 2-((1r,4r)-4-(2-(1H-1,2,4-Triazol-3-yl)imidazo[4,5-d]pyrrolo[2,3-b]pyridin-1(6H)-yl)cyclohexyl)acetonitrile

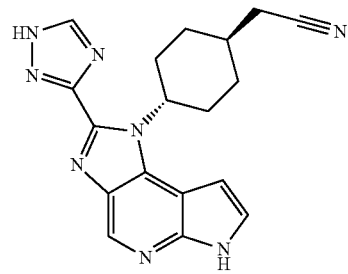 [SMILES: N#CC[C@H]1CC[C@H](n2c(-c3nc[nH]n3)nc3cnc4[nH]ccc4c32)CC1]

Step A: 2-((1r,4r)-4-(6-(Phenylsulfonyl)-2-(1H-1,2,4-triazol-3-yl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo

[2,3-b]pyridin-4-yl)amino)cyclohexyl)acetonitrile (Intermediate 1, 152 mg, 0.346 mmol) and 1H-pyrazole-3-carbaldehyde (74 mg, 0.762 mmol) as solids. DMSO (1.7 mL), MeOH (1.7 mL), and distilled water (0.9 mL) were added resulting a yellow mixture. Sodium hydrosulfite (183 mg, 1.05 mmol) was added as a solid and the vial sealed. The vial was placed into a preheated 100° C. heating block and heated for 3 h. The reaction mixture was then cooled to room temperature and added to a flask containing 50 mL water with stirring, which resulted in a white precipitate forming. The mixture was stirred for 30 minutes and the solids were collected by filtration. The solids retained a large amount of water, so they were initially dried by pulling air through the filter for 6 h and then further dried in a vacuum oven heating at 60° C. to provide the title compound (154 mg, 91% yield), which was used in the next reaction without further purification. MS (ESI): mass calcd. for $C_{24}H_{22}N_8O_2S$, 486.16; m/z found, 487.2 [M+H]$^+$.

Step B: 2-((1r,4r)-4-(2-(1H-1,2,4-Triazol-3-yl)imidazo[4,5-d]pyrrolo[2,3-b]pyridin-1(6H)-yl)cyclohexyl)acetonitrile. To a 10 mL microwave vial was added 2-((1r,4r)-4-(6-(phenylsulfonyl)-2-(1H-1,2,4-triazol-3-yl)imidazo[4,5-d]pyrrolo[2,3-b]pyridin-1(6H)-yl)cyclohexyl)acetonitrile (154 mg, 0.317 mmol) as a solid, followed by addition of dioxane (2 mL) and KOH (aqueous) (1.5 mL, 3 M, 4.5 mmol). The vial was sealed and heated to 80° C. using a heating block for 1 h. The reaction was cooled to room temperature and was purified by basic HPLC using a Waters Xbridge $C_{18}$ OBD 50 mm×100 mm, 5 μm column (eluent 0-100% aq NH$_4$OH/ACN (10 min) to provide the title compound (18 mg, 16% yield). MS (ESI): mass calcd. for $C_{18}H_{18}N_8$, 346.17; m/z found, 347.2 [M+H]$^+$. $^1$H NMR (500 MHz, DMSO-d$_6$): δ 12.04 (s, 1H), 8.69 (s, 1H), 8.54 (s, 1H), 7.54 (t, J=3.0 Hz, 1H), 6.88-6.74 (m, 1H), 5.68 (s, 1H), 2.60 (d, J=6.1 Hz, 2H), 2.49-2.41 (m, 2H), 2.13-1.91 (m, 6H), 1.43-1.29 (m, 2H).

Example 10 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((tetrahydro-2H-pyran-4-yl)methyl)acetamide

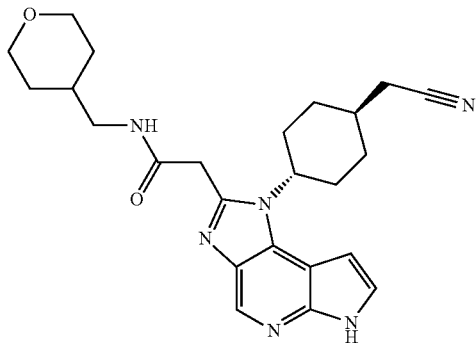 [SMILES: N#CC[C@H]1CC[C@H](n2c(CC(=O)NCC3CCOCC3)nc3cnc4[nH]ccc4c32)CC1]

To a microwave vial were added ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 300 mg, 0.593 mmol) and 4-aminomethyltetrahydropyran (683 mg, 5.93 mmol). The resulting solution was stirred at 125° C. for 1 h. Next were added dioxane (2.37 mL) and KOH (3 M in water, 1.58 mL, 4.75 mmol) and the reaction was stirred in the microwave at 80° C. for 1 h. The reaction was purified over basic HPLC using a Waters Xbridge Prep OBD $C_{18}$ 150 mm×30 mm, 5 μm column (eluent 0-100% water (0.5% NH$_4$OH)/ACN (10 min)) to provide the title compound (97 mg, 38% yield). MS (ESI): mass calcd. for $C_{24}H_{30}N_6O_2$, 434.24; m/z found, 435.2 [M+H]$^+$. $^1$H NMR (500 MHz, CD$_3$OD): δ 8.43 (s, 1H), 7.38 (d, J=3.5 Hz, 1H), 6.74 (d, J=3.5 Hz, 1H), 4.43 (s, 1H), 4.03-3.96 (m, 2H), 3.89-3.79 (m, 2H), 3.34-3.25 (m, 2H), 3.04 (d, J=6.8 Hz, 2H), 2.54-2.38 (m, 4H), 2.08-1.96 (m, 5H), 1.74-1.63 (m, 1H), 1.59-1.54 (m, 2H), 1.46-1.33 (m, 2H), 1.25-1.14 (m, 2H).

Example 11 Synthesis and Characterization 2-((1r,4r)-4-(2-(Oxazol-4-yl)imidazo[4,5-d]pyrrolo[2,3-b]pyridin-1(6H)-yl)cyclohexyl)acetonitrile

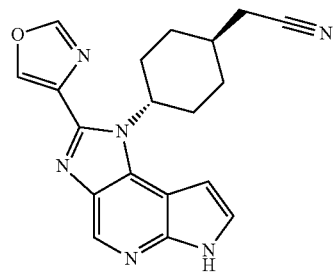 [SMILES: N#CC[C@H]1CC[C@H](n2c(-c3cocn3)nc3cnc4[nH]ccc4c32)CC1]

Step A: 2-((1r,4r)-4-(2-(Oxazol-4-yl)-6-(phenylsulfonyl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 190 mg, 0.432 mmol) and oxazole-4-carbaldehyde (94 mg, 0.968 mmol) as solids. DMSO (2 mL), MeOH (2 mL), and distilled water (0.9 mL) were added resulting in a yellow mixture. Next, sodium hydrosulfite (184 mg, 1.06 mmol) was added as a solid and the vial sealed. The vial was placed into a preheated 100° C. heating block. The reaction progress was followed by NMR and when all of Intermediate 1 had been consumed, the reaction mixture was cooled to room temperature and added to a flask containing 50 mL water with stirring, which resulted in a white precipitate forming. The mixture was stirred for 30 minutes and the solids were collected by filtration. The solids retained a large amount of water, so they were initially dried by pulling air through the filter for 6 h and then further dried in a vacuum oven heating at 60° C. to provide the title compound (178 mg, 84% yield) as a tan amorphous solid, which was used in the next step without further purification. MS (ESI): mass calcd. for $C_{25}H_{22}N_6O_3S$, 486.15; m/z found, 486.9 [M+H]$^+$.

Step B: 2-((1r,4r)-4-(2-(Oxazol-4-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(2-(Oxazol-4-yl)-6-(phenylsulfonyl)imidazo[4,5-d]pyrrolo[2,3-b]pyridin-1(6H)-yl)cyclohexyl)acetonitrile (178 mg, 0.37 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and purified by basic HPLC: using a Waters Xbridge Prep OBD $C_{18}$ 50 mm×100 mm, 5 μm column (eluent 0-100% aq NH$_4$OH/ACN (10 min)) to provide the title compound (38 mg, 30% yield). MS (ESI): mass calcd. for $C_{19}H_{18}N_6O$, 346.15; m/z found, 346.9 [M+H]$^+$. $^1$H NMR (500 MHz, DMSO-d$_6$): δ 11.99 (s, 1H), 8.83 (d, J=1.1 Hz, 1H), 8.70 (d, J=1.0 Hz, 1H), 8.62 (s, 1H), 7.52 (d, J=3.4 Hz, 1H), 6.79 (d, J=3.5 Hz, 1H), 5.33-5.17 (m, 1H), 2.58 (d, J=6.1 Hz, 2H), 2.50-2.40 (m, 2H), 2.11-1.91 (m, 5H), 1.35 (tt, J=13.7, 7.2 Hz, 2H).

Example 12 Synthesis and Characterization 2-((1r,4r)-4-(2-(2-(4-Hydroxypiperidin-1-yl)-2-oxo-ethyl)imidazo[4,5-d]pyrrolo[2,3-b]pyridin-1(6H)-yl)cyclohexyl)acetonitrile

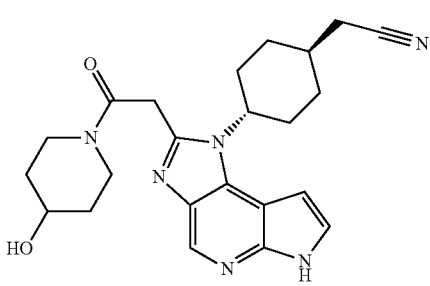 [SMILES: N#CC[C@H]1CC[C@H](n2c(CC(=O)N3CCC(O)CC3)nc3cnc4[nH]ccc4c32)CC1]

A mixture of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), piperidin-4-ol (56 mg, 0.557 mmol), DIPEA (144 mg, 1.11 mmol), and DMF (5 mL) was stirred at 0° C. for 1 h. PyBrOP (311 mg, 0.668 mmol) was added and the reaction mixture stirred overnight at room temperature. The reaction mixture was quenched with 10 mL water, extracted with CH$_2$Cl$_2$ (2×10 mL), and concentrated under reduced pressure. The resulting residue was purified by preparative acidic HPLC (Gemini 150×25 5 μm (eluent: water (0.05% HCl)-ACN from 0% to 33%, v/v). and then by preparative basic HPLC using a Kromasil 150 mm×25 mm, 10 μm column (eluent: water (0.05% ammonia hydroxide v/v)-ACN from 5% to 35%, v/v). to provide the title compound (21 mg, 9% yield) as a white solid. MS (ESI): mass calcd. for $C_{23}H_{28}N_6O_2$, 420.23; m/z found, 421.2 [M+H]$^+$. $^1$H NMR (400 MHz, DMSO-d$_6$): δ 11.85 (br s, 1H), 8.50 (s, 1H), 7.49-7.43 (m, 1H), 6.70 (br s, 1H), 4.76 (d, J=4.0 Hz, 1H), 4.44-4.32 (m, 1H), 4.25 (s, 2H), 3.95-3.83 (m, 2H), 3.76-3.66 (m, 1H), 3.11-3.02 (m, 1H), 2.58 (d, J=6.0 Hz, 3H), 2.41-2.26 (m, 2H), 2.09-1.89 (m, 5H), 1.79-1.65 (m, 2H), 1.42-1.18 (m, 4H).

Example 13 Synthesis and Characterization

2-Cyano-N-((1-((1r,4r)-4-(cyanomethyl)cyclohexyl)-1,6-dihydroimidazo[4,5-d]pyrrolo[2,3-b]pyridin-2-yl)methyl)ethanesulfonamide

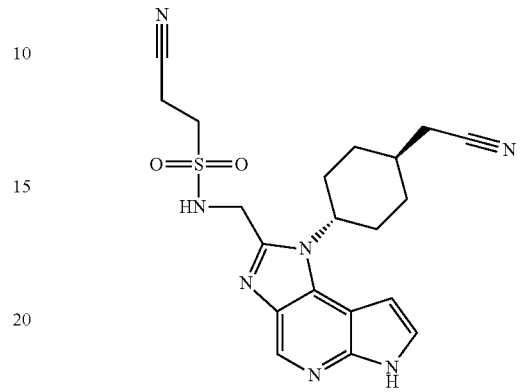

2-Cyanoethanesulfonyl chloride (133 mg, 0.435 mmol, purity 50%) was added drop-wise to a solution of 2-((1r,4r)-4-(2-(aminomethyl)imidazo[4,5-d]pyrrolo[2,3-b]pyridin-1(6H)-yl)cyclohexyl)acetonitrile (Intermediate 5, 150 mg, 0.435 mmol), triethylamine (0.30 mL, 2.2 mmol), and CH$_2$Cl$_2$ (5 mL) and was stirred for 30 minutes at 15° C. The reaction mixture was diluted with CH$_2$Cl$_2$ (10 mL), washed with water (10 mL), dried over anhydrous Na$_2$SO$_4$, filtered, and concentrated to dryness. The residue was purified by preparative HPLC using a Agela DuraShell 150 mm×25 mm, 5 μm column (eluent: 16% to 46% (v/v) CH$_3$CN and H$_2$O with 10 mM NH$_4$HCO$_3$) to provide the title compound (30 mg, 16% yield) as a white solid. MS (ESI): mass calcd. for $C_{20}H_{23}N_7O_2S$, 425.16; m/z found, 426.2 [M+H]$^+$. $^1$H NMR (400 MHz, CDCl$_3$): δ 9.76 (s, 1H), 8.69 (s, 1H), 8.01 (br s, 1H), 7.37-7.29 (m, 1H), 6.59 (s, 1H), 4.73 (s, 2H), 4.51-4.36 (m, 1H), 3.47 (t, J=7.6 Hz, 2H), 3.07 (t, J=7.6 Hz, 2H), 2.41 (d, J=6.4 Hz, 2H), 2.36-2.20 (m, 2H), 2.20-2.09 (m, 2H), 2.06-1.96 (m, 1H), 1.89-1.73 (m, 2H), 1.52-1.38 (m, 2H).

Example 14 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(pyrimidin-4-ylmethyl)acetamide

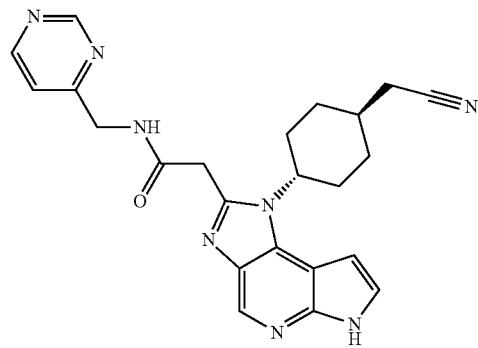 [SMILES: N#CC[C@H]1CC[C@H](n2c(CC(=O)NCc3ccncn3)nc3cnc4[nH]ccc4c32)CC1]

le;2qTo a 10 mL microwave vial was added sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 151 mg, 0.420 mmol) as a solid followed by DMF (1.7 mL). PyBOP (329 mg, 0.632 mmol) was added in one portion and immediately a canary yellow color formed. The reaction was stirred for 15 minutes prior to the addition of DIPEA (0.29 mL, 1.7 mmol), followed by 2-aminomethylpyrazine hydrochloride (120 mg, 0.824 mmol). Following completion, the reaction was diluted with MeOH (4 mL) and purified by basic HPLC: using a Waters Xbridge 50 mm×100 mm, 5 μm column (eluent 0-100% aq NH$_4$OH/ACN (10 min)) to provide the title compound (12 mg, 7% yield). MS (ESI): mass calcd. for $C_{23}H_{24}N_8O$, 428.21; m/z found, 429.0 [M+H]$^+$. $^1$H NMR (500 MHz, CDCl$_3$): δ 10.79 (s, 1H), 9.10 (d, J=1.4 Hz, 1H), 8.72 (s, 1H), 8.63 (d, J=5.2 Hz, 1H), 7.45 (dd, J=3.5, 2.5 Hz, 1H), 7.29-7.26 (m, 1H), 6.72 (dd, J=3.7, 1.8 Hz, 1H), 4.71-4.47 (m, 3H), 4.13 (s, 2H), 2.70-2.47 (m, 2H), 2.42 (d, J=6.5 Hz, 2H), 2.18 (d, J=13.3 Hz, 2H), 2.14-1.97 (m, 3H), 1.93-1.70 (m, 2H), 1.58-1.37 (m, 3H).

Example 15 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(3-hydroxy-2,2-dimethylpropyl)acetamide

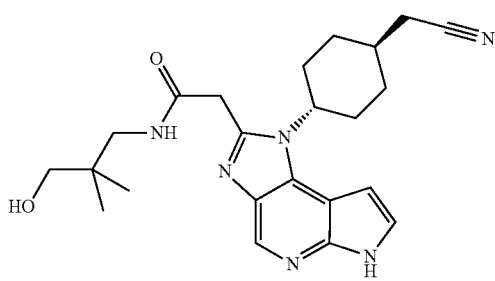 [SMILES: CC(C)(CO)CNC(=O)Cc1nc2cnc3[nH]ccc3c2n1[C@H]1CC[C@H](CC#N)CC1]

A mixture of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 3-amino-2,2-dimethylpropan-1-ol (86 mg, 0.84 mmol), DIPEA (216 mg, 1.67 mmol), and DMF (5 mL) was stirred at 0° C. for 1 h. PyBrOP (467 mg, 1.00 mmol) was added and the reaction was stirred overnight at room temperature. The mixture was quenched with 10 mL water and concentrated under reduced pressure to dryness. The residue was purified by preparative basic HPLC using a Kromasil 150 mm×25 mm 10 μm column (eluent: water (0.05% ammonia hydroxide v/v)-ACN from 20% to 30%, v/v) twice to provide the title compound (35 mg, 10% yield) as a white solid. MS (ESI): mass calcd. for $C_{23}H_{30}N_6O_2$, 422.24; m/z found, 423.2 [M+H]$^+$. $^1$H NMR (400 MHz, CD$_3$OD): δ 8.53 (s, 1H), 7.48 (d, J=3.6 Hz, 1H), 6.84 (d, J=3.2 Hz, 1H), 4.65-4.47 (m, 1H), 4.16-4.08 (m, 2H), 3.25 (s, 2H), 3.15 (s, 2H), 2.69-2.48 (m, 4H), 2.21-2.00 (m, 5H), 1.58-1.42 (m, 2H), 0.98-0.85 (m, 6H).

Example 16 Synthesis and Characterization 2-((1r,4r)-4-(2-(2H-1,2,3-Triazol-4-yl)imidazo[4,5-d]pyrrolo[2,3-b]pyridin-1(6H)-yl)cyclohexyl)acetonitrile

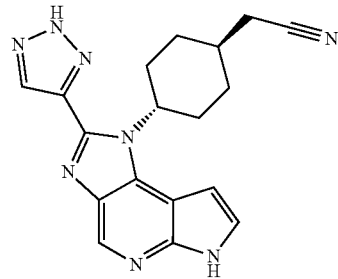 [SMILES: N#CC[C@H]1CC[C@H](n2c(-c3cn[nH]n3)nc3cnc4[nH]ccc4c32)CC1]

Step A: 2-((1r,4r)-4-(6-(Phenylsulfonyl)-2-(2H-1,2,3-triazol-4-yl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 135 mg, 0.307 mmol) and 1H-[1,2,3]triazole-4-carbaldehyde (59 mg, 0.61 mmol) as solids. DMSO (1.5 mL), MeOH (1.5 mL), and distilled water (0.8 mL) were added resulting a yellow mixture. Sodium hydrosulfite (134 mg, 0.768 mmol) was added as a solid and the vial sealed. The vial was placed into a preheated 100° C. heating block and heated for 3 h. the reaction mixture was cooled to room temperature and added to a flask containing 50 mL water with stirring, which resulted in a white precipitate forming. The mixture was stirred for 30 minutes and the solids were collected by filtration. The solids retained a large amount of water, so they were initially dried by pulling air through the filter for 6 h and then further dried in a vacuum oven heating at 60° C. to provide the title compound (122 mg, 81% yield), which was used in the next reaction without further purification. MS (ESI): mass calcd. for $C_{24}H_{22}N_8O_2S$, 486.16; m/z found, 487.2 [M+H]$^+$. $^1$H NMR (500 MHz, DMSO-d$_6$): δ 8.79 (s, 1H), 8.20-8.11 (m, 2H), 8.02 (d, J=4.1 Hz, 1H), 7.76-7.68 (m, 1H), 7.67-7.60 (m, 2H), 7.22 (d, J=4.2 Hz, 1H), 5.44 (s, 1H), 3.68-3.39 (m, 2H), 2.59 (d, J=6.4 Hz, 2H), 2.54 (s, 1H), 2.32 (q, J=12.6 Hz, 2H), 2.15-1.90 (m, 4H), 1.35 (q, J=12.2 Hz, 2H).

Step B: 2-((1r,4r)-4-(2-(2H-1,2,3-Triazol-4-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(6-(phenylsulfonyl)-2-(2H-1,2,3-triazol-4-yl)imidazo[4,5-d]pyrrolo[2,3-b]pyridin-1(6H)-yl)cyclohexyl)acetonitrile (122 mg, 0.25 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide to provide the title compound (32 mg, 35% yield). MS (ESI): mass calcd. for $C_{18}H_{18}N_8$, 346.17; m/z found, 347.1 [M+H]$^+$. $^1$H NMR (500 MHz, DMSO-d$_6$) δ 11.96 (s, 1H), 8.62 (s, 1H), 8.44 (s, 1H), 7.59-7.45 (m, 1H), 6.85-6.73 (m, 1H), 5.82-5.34 (m, 1H), 2.60 (d, J=6.1 Hz, 2H), 2.54 (s, 1H), 2.02 (q, J=16.1 Hz, 5H), 1.46-1.31 (m, 2H), 1.04 (d, J=6.1 Hz, 2H).

Examples 17A & B

Example 17A Synthesis and Characterization (E)-N-((1-((1r,4r)-4-(Cyanomethyl)cyclohexyl)-1,6-dihydroimidazo[4,5-d]pyrrolo[2,3-b]pyridin-2-yl)methyl)-N-hydroxybenzimidamide and Example 17B Synthesis and Characterization (Z)—N-((1-((1r,4r)-4-(Cyanomethyl)cyclohexyl)-1,6-dihydroimidazo[4,5-d]pyrrolo[23-b]pyridin-2-yl)methyl)-N-hydroxybenzimidamide

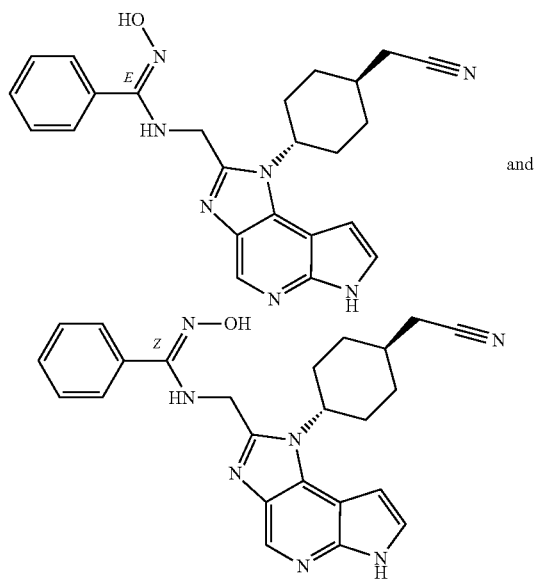

A solution of 2-((1r,4r)-4-(2-(aminomethyl)imidazo[4,5-d]pyrrolo[2,3-b]pyridin-1(6H)-yl)cyclohexyl)acetonitrile (Intermediate 5, 250 mg, 0.725 mmol), N-hydroxybenzimidoyl chloride (113 mg, 0.725 mmol), triethylamine (0.51 mL, 3.6 mmol), and DMF (5 mL) was stirred for 2 h at 15° C. Water (20 mL) was added and a brown precipitate formed which was isolated by filtration, washed with water (3 mL×2), and dried under high vacuum to provide a brown solid (190 mg). A portion of the (E)/(Z) mixture was reserved for later use as a mixture and a portion (130 mg) of the E)/(Z) mixture was subjected to preparative HPLC using a Phenomenex Gemini 150 mm×25 mm, 10 µm column (eluent: 13% to 43% (v/v) $CH_3CN$ and aqueous HCl (0.006 N) to purify and separate the (E) and (Z) isomers. The fractions for each isomer were collected and treated with saturated aqueous $NaHCO_3$ until pH=7-8. The volatile organic components were removed under reduced pressure and the precipitate was isolated via filtration and washed with water (2 mL×3). The filter cake was suspended in water (10 mL) and $CH_3CN$ (2 mL), the mixture was frozen using dry ice/acetone, and then lyophilized to dryness to provide (E)-N-((1-((1r,4r)-4-(cyanomethyl)cyclohexyl)-1,6-dihydroimidazo[4,5-d]pyrrolo[2,3-b]pyridin-2-yl)methyl)-N-hydroxybenzimidamide as the trans-(E) conformation (5 mg, 2% yield) as an off-white solid. MS (ESI): mass calcd. for $C_{24}H_{25}N_7O$, 427.21; m/z found, 428.1 $[M+H]^+$. $^1H$ NMR (400 MHz, DMSO-$d_6$): δ 11.89 (s, 1H), 8.91 (s, 1H), 8.55 (s, 1H), 7.48 (d, J=3.2 Hz, 1H), 7.46-7.40 (m, 2H), 7.27-7.20 (m, 2H), 6.97-6.87 (m, 2H), 6.73 (d, J=3.2 Hz, 1H), 4.72 (d, J=5.2 Hz, 2H), 4.67-4.53 (m, 1H), 2.58 (d, J=6.0 Hz, 2H), 2.43-2.28 (m, 2H), 2.08-1.89 (m, 5H), 1.54-1.37 (m, 2H). The following compound was also isolated: (Z)—N-((1-((1r,4r)-4-(Cyanomethyl)cyclohexyl)-1,6-dihydroimidazo[4,5-d]pyrrolo[2,3-b]pyridin-2-yl)methyl)-N-hydroxybenzimidamide as the cis-(Z)-isomer (7 mg, 2% yield). MS (ESI): mass calcd. for $C_{24}H_{25}N_7O$, 427.21; m/z found, 428.0 $[M+H]^+$. $^1H$ NMR (400 MHz, DMSO-$d_6$): δ 11.87 (s, 1H), 9.93 (br. s., 1H), 8.52 (s, 1H), 7.52-7.44 (m, 3H), 7.44-7.35 (m, 3H), 6.69 (d, J=2.8 Hz, 1H), 6.41 (t, J=5.6 Hz, 1H), 4.57 (d, J=5.6 Hz, 2H), 4.40-4.20 (m, 1H), 2.58 (d, J=5.2 Hz, 2H), 2.37-2.16 (m, 2H), 2.04-1.83 (m, 5H), 1.46-1.32 (m, 2H).

Example 18 Synthesis and Characterization 2-((1r,4r)-4-(2-(2-(3-Hydroxyazetidin-1-yl)-2-oxoethyl)imidazo[4,5-d]pyrrolo[2,3-b]pyridin-1(6H)-yl)cyclohexyl)acetonitrile

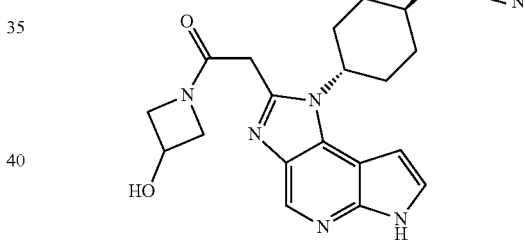

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), azetidin-3-ol (67 mg, 0.92 mmol), DIPEA (0.290 mL, 1.67 mmol), and DMF (5 mL) was added PyBrOP (428 mg, 0.918 mmol) at 0° C. and was stirred at room-temperature for 3.5 h. The mixture was quenched with 10 mL water and extracted with EtOAc (3×20 mL). Both the organic and water phases were concentrated and purified by preparative HPLC using a Xtimate $C_{18}$ 150×25 mm×5 µm column (eluent: 12% to 32% (v/v) $CH_3CN$ and $H_2O$ with 10 mM $NH_4HCO_3$) to provide the title compound (62 mg, 18% yield) as a yellow solid. MS (ESI): mass calcd. for $C_{21}H_{24}N_6O_2$, 392.20; m/z found, 393.1 $[M+H]^+$. $^1H$ NMR (400 MHz, DMSO-$d_6$): δ 11.84 (br s, 1H), 8.50 (s, 1H), 7.47 (br s, 1H), 6.74-6.68 (m, 1H), 5.80 (br s, 1H), 4.53-4.37 (m, 3H), 4.16-3.94 (m, 4H), 3.66-3.59 (m, 1H), 2.64-2.55 (m, 2H), 2.42-2.26 (m, 2H), 2.10-1.83 (m, 5H), 1.47-1.35 (m, 2H).

Example 19 Synthesis and Characterization

N-((1r,4r)-4-(Cyanomethyl)cyclohexyl)-2-(1-((1r,4r)-4-(cyanomethyl)cyclohexyl)-1,6-dihydroimidazo[4,5-d]pyrrolo[2,3-b]pyridin-2-yl)acetamide

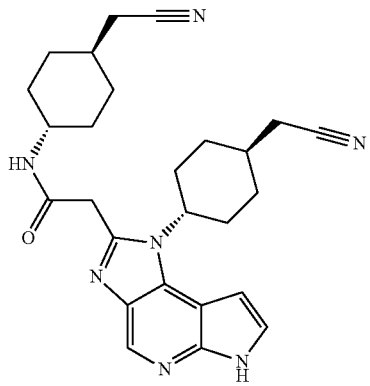 [SMILES: N#CC[C@H]1CC[C@H](NC(=O)Cc2nc3cnc4[nH]ccc4c3n2[C@H]2CC[C@H](CC#N)CC2)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 2-((1r,4r)-4-aminocyclohexyl)acetonitrile (145 mg, 0.835 mmol), DIPEA (324 mg, 2.50 mmol), DMF (10 mL), and PyBrOP (467 mg, 1.00 mmol) was stirred at room-temperature for 3 h. The reaction was quenched with 5 mL water and concentrated to dryness. The residue was purified preparative basic HPLC using a Kromasil 150 mm×25 mm, 10 μm column (eluent: 14% to 44% (v/v) CH$_3$CN and H$_2$O with 0.05% NH$_3$) to provide the title compound (35 mg, 9% yield) as a white solid. MS (ESI): mass calcd. for C$_{26}$H$_{31}$N$_7$O, 457.26; m/z found, 458.2 [M+H]$^+$. $^1$H NMR (400 MHz, DMSO-d$_6$): δ 11.83 (br s, 1H), 8.49 (s, 1H), 8.29-8.20 (m, 1H), 7.49-7.43 (m, 1H), 6.75-6.66 (m, 1H), 4.56-4.10 (m, 2H), 3.95 (s, 2H), 2.63-2.56 (m, 2H), 2.45-2.40 (m, 2H), 2.37-2.27 (m, 2H), 2.07-1.92 (m, 4H), 1.90-1.72 (m, 4H), 1.67-1.52 (m, 2H), 1.46-1.31 (m, 2H), 1.31-1.17 (m, 2H), 1.17-1.03 (m, 2H).

Example 20 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-phenylacetamide

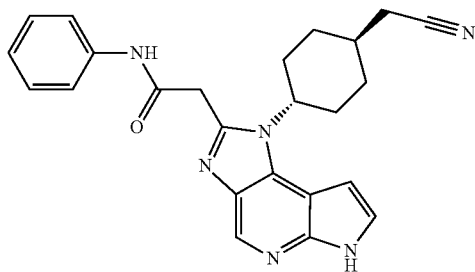 [SMILES: N#CC[C@H]1CC[C@H](n2c(CC(=O)Nc3ccccc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 50 mg, 0.14 mmol) and aniline (48 mg, 0.52 mmol) in DMF (2 mL) were added HATU (180 mg, 0.47 mmol) and DIPEA (0.12 mL, 0.70 mmol) and was stirred at room temperature for 18 h. The reaction was concentrated to dryness, water was added, and the aqueous layer was extracted with EtOAc. The combined organic extracts were dried over anhydrous Na$_2$SO$_4$, filtered, concentrated to dryness, and purified by reverse phase HPLC using a Phenomenex Luna C$_{18}$ 100 mm×30 mm, 5 μm column (mobile phase gradient 5-95% ACN in H$_2$O (both with 0.1% TFA), v/v) to provide the title compound (27 mg, 37% yield). MS (ESI): mass calcd. for C$_{24}$H$_{24}$N$_6$O, 412.20; m/z found, 413.3 [M+H]$^+$. $^1$H NMR (400 MHz, CDCl$_3$): δ 9.64 (br s, 1H), 8.79 (s, 1H), 7.55 (d, J=7.72 Hz, 2H), 7.43 (t, J=3.03 Hz, 1H), 7.32 (t, J=7.67 Hz, 2H), 7.12 (t, J=7.50 Hz, 1H), 6.74 (dd, J=2.02, 3.54 Hz, 1H), 4.54 (br s, 1H), 4.13-4.17 (m, 2H), 2.55 (br s, 1H), 2.44 (d, J=6.57 Hz, 2H), 2.21 (br d, J=13.14 Hz, 2H), 2.01-2.13 (m, 3H), 1.45-1.58 (m, 3H).

Example 21 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(((1S,3R,5R,7S)-3-hydroxyadamantan-1-yl)methyl)acetamide

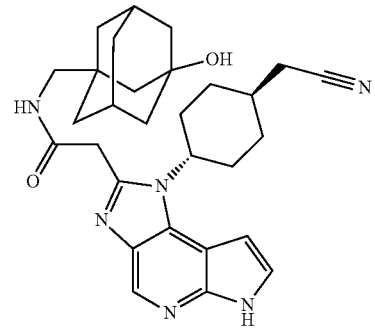 [SMILES: N#CC[C@H]1CC[C@H](n2c(CC(=O)NCC34CC5CC(CC(O)(C5)C3)C4)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), (1S,3R,5R,7S)-3-(aminomethyl)adamantan-1-ol hydrochloride (182 mg, 0.835 mmol), DIPEA (216 mg, 1.67 mmol), and DMF (5 mL) was stirred at 0° C. for 1 h. Then PyBrOP (467 mg, 1.00 mmol) was added and stirred at room-temperature overnight. The mixture was quenched with 10 mL water and was purified by preparative basic HPLC using a DuraShell 150 mm×25 mm, 5 μm column (eluent: water (0.05% ammonia hydroxide v/v)-ACN from 16% to 46%, v/v) and by preparative TLC (CH$_2$Cl$_2$:MeOH=10:1) to provide the title compound (64 mg, 15% yield) as a white solid. MS (ESI): mass calcd. for C$_{29}$H$_{36}$N$_6$O$_2$, 500.29; m/z found, 501.2 [M+H]$^+$. $^1$H NMR (400 MHz, DMSO-d$_6$): δ 11.84 (br s, 1H), 8.49 (s, 1H), 8.20-8.14 (m, 1H), 7.47-7.44 (m, 1H), 6.72-6.69 (m, 1H), 4.52-4.41 (br s, 1H), 4.39 (s, 1H), 4.03 (s, 2H), 2.87 (d, J=6.4 Hz, 2H), 2.57 (d, J=6.0 Hz, 2H), 2.41-2.27 (m, 2H), 2.11-1.93 (m, 7H), 1.56-1.44 (m, 6H), 1.41-1.29 (m, 8H).

Example 22 Synthesis and Characterization

N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide

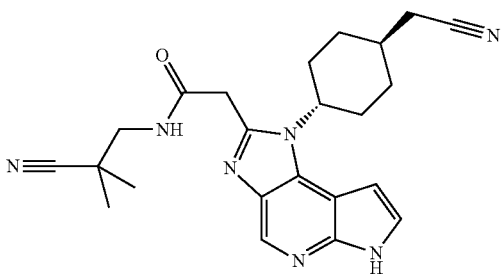 [SMILES: CC(C)(C#N)CNC(=O)Cc1nc2cnc3[nH]ccc3c2n1[C@H]1CC[C@H](CC#N)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 3-amino-2,2-dimethylpropanenitrile (82.0 mg, 0.835 mmol), DIPEA (216 mg, 1.67 mmol), and DMF (5 mL) was stirred at 0° C. for 1 h. Then PyBrOP (467 mg, 1.00 mmol) was added and the reaction mixture stirred overnight at room temperature. The mixture was quenched with 10 mL water and was purified by preparative HPLC using a Waters Xbridge Prep OBD $C_{18}$ 150 mm×30 mm 5 μm column (eluent: 28% water (0.05% ammonia hydroxide v/v)-ACN to provide the title compound (58 mg, 16% yield) as a white solid. MS (ESI): mass calcd. for $C_{23}H_{27}N_7O$, 417.23; m/z found, 418.2 $[M+H]^+$. $^1H$ NMR (400 MHz, DMSO-$d_6$): δ 11.86 (br s, 1H), 8.71-8.66 (m, 1H), 8.50 (s, 1H), 7.48-7.45 (m, 1H), 6.73-6.69 (m, 1H), 4.53-4.42 (m, 1H), 4.10 (s, 2H), 3.33-3.31 (m, 1H), 2.57 (d, J=5.6 Hz, 2H), 2.41-2.27 (m, 2H), 2.05-1.93 (m, 5H), 1.45-1.26 (m, 9H).

Example 23 Synthesis and Characterization

N-(4-Cyanobicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide

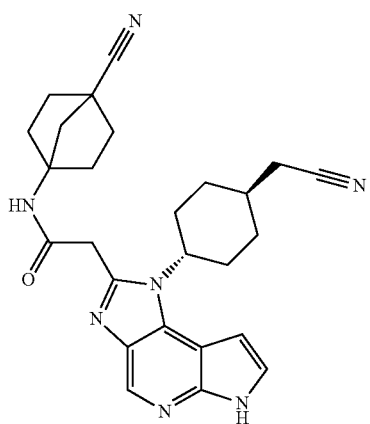 [SMILES: N#CC[C@H]1CC[C@H](n2c(CC(=O)NC34CCC(C#N)(CC3)C4)nc3cnc4[nH]ccc4c32)CC1]

Step A: tert-Butyl (4-(chlorocarbonyl)bicyclo[2.2.1]heptan-1-yl)carbamate. To a solution of 4-((tert-butoxycarbonyl)amino)bicyclo[2.2.1]heptane-1-carboxylic acid (1.00 g, 3.92 mmol) in $CH_2Cl_2$ (5 mL) was added oxalyl chloride (0.75 g, 5.9 mmol) at 0° C. dropwise, then DMF (0.1 mL) was added. The mixture was stirred at 0° C. for 1 h. The reaction was concentrated to dryness to provide the title compound (1.05 g, 97.9% yield) as a yellow oil, which was used in the next step without further purification.

Step B: tert-Butyl (4-carbamoylbicyclo[2.2.1]heptan-1-yl)carbamate. To a solution of tert-butyl (4-(chlorocarbonyl)bicyclo[2.2.1]heptan-1-yl)carbamate (1.05 g, 3.84 mmol) in methanol (5 mL) was added ammonia (0.10 g, 5.8 mmol) and was stirred at room temperature for 1 h. The reaction was concentrated to dryness to provide the title compound (200 mg, 20.5% yield) as a yellow oil.

Step C: tert-Butyl (4-cyanobicyclo[2.2.1]heptan-1-yl)carbamate and tert-butyl (4-cyanobicyclo[2.2.1]heptan-1-yl)(2,2,2-trifluoroacetyl)carbamate. To a solution of tert-butyl (4-carbamoylbicyclo[2.2.1]heptan-1-yl)carbamate (200 mg, 0.79 mmol), triethylamine (0.031 mL, 2.4 mmol) and dry $CH_2Cl_2$ (5 mL) at 0° C. was added trifluoroacetic anhydride (248 mg, 1.18 mmol). After the addition was complete, the solution was allowed to warm to room temperature and the stirring was continued overnight. The reaction was diluted with $CH_2Cl_2$ (10 mL), washed with saturated aqueous $NaHCO_3$ (5 mL×2), water (5 mL), brine (3 mL), dried over anhydrous $MgSO_4$, filtered, and concentrated to dryness to provide the title compound as a mixture of two compounds (120 mg, 56% yield) as a yellow oil, which was used in the next step without further purification. TLC of title compound: (petroleum ether:ethyl acetate=5:1), $R_f$=0.4.

Step D: tert-Butyl (4-cyanobicyclo[2.2.1]heptan-1-yl)carbamate. Sodium methoxide (34 mg, 0.63 mmol) was added to a solution of tert-butyl (4-cyanobicyclo[2.2.1]heptan-1-yl)(2,2,2-trifluoroacetyl)carbamate (60 mg, 0.18 mmol) and tert-butyl (4-cyanobicyclo[2.2.1]heptan-1-yl)carbamate (60 mg, 0.25 mmol) in methanol (4 mL) at 0° C. (ice/water) and was stirred for 3 hours at 0° C. The reaction was diluted with ethyl acetate (15 mL) and water (10 mL). The organic layer was separated and the aqueous layer was extracted with ethyl acetate (10 mL×2). The combined organic extracts were washed with brine (10 mL), dried over anhydrous $MgSO_4$, filtered, and concentrated to dryness to provide the title compound (30 mg, 70% yield) as a yellow oil, which was used without further purification. TLC of title compound: (petroleum ether:ethyl acetate=5:1), $R_f$=0.4.

Step E: 4-Aminobicyclo[2.2.1]heptane-1-carbonitrile. To a solution of tert-butyl (4-cyanobicyclo[2.2.1]heptan-1-yl)carbamate (90 mg, 0.38 mmol) was added HCl (4 M in EtOAc, 0.48 mL) and ethyl acetate (4 mL) and was stirred at room temperature for 3 h. The reaction was filtered to provide the title compound (50 mg, 96% yield) as a white solid, which was used without further purification. TLC of title compound: (dichloromethane:methanol=10:1), Rf=0.4.

Step F: N-(4-Cyanobicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide. A solution of 4-aminobicyclo[2.2.1]heptane-1-carbonitrile (50 mg, 0.29 mmol), sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 104 mg, 0.290 mmol), PyBrOP (162 mg, 0.348 mmol), and DIPEA (112 mg, 0.869 mmol) in DMF (5 mL) was stirred overnight. The reaction was quenched with water (20 mL) and extracted with ethyl acetate (3×20 mL). The combined organic layers were dried over anhydrous $MgSO_4$, filtered, and concentrated to dryness. The residue was purified by preparative basic HPLC using a DuraShell 150 mm×25 mm 5 μm column (eluent: 20% to 50% (v/v) $CH_3CN$ and $H_2O$ with 0.05% $NH_3$) to provide the title compound (9 mg, 7% yield) as a white solid. MS (ESI): mass calcd. for $C_{26}H_{29}N_7O$, 455.24; m/z found, 456.2 [M+H]$^+$. $^1$H NMR (400 MHz, DMSO-d$_6$): δ 11.57 (br s, 1H), 8.50 (s, 1H), 8.45-8.34 (m, 1H), 7.46-7.40 (m, 1H), 6.75-6.69 (m, 1H), 4.53-4.42 (m, 1H), 3.96 (s, 2H), 2.59-2.56 (m, 2H), 2.41-2.30 (m, 3H), 2.12-1.91 (m, 10H), 1.89-1.81 (m, 2H), 1.78-1.68 (m, 2H), 1.50-1.34 (m, 2H).

Example 24 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((3-hydroxyoxetan-3-yl)methyl)acetamide

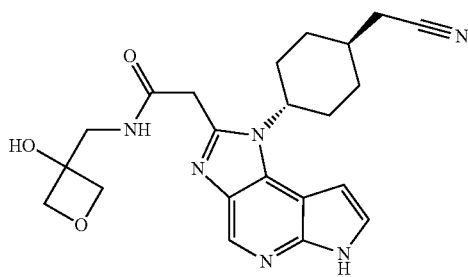 [SMILES: N#CC[C@H]1CC[C@H](n2c(CC(=O)NCC3(O)COC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 3-(aminomethyl)oxetan-3-ol (86.0 mg, 0.835 mmol), DIPEA (216 mg, 1.67 mmol), and DMF (5 mL) was stirred at 0° C. for 1 h. Then PyBrOP (467 mg, 1.00 mmol) was added and the reaction mixture was stirred at overnight at room-temperature. The mixture was quenched with 10 mL water and was purified by preparative HPLC using a Waters Xbridge Prep OBD C$_{18}$ 150 mm×30 mm, 5 μm column (eluent: water (0.05% ammonia hydroxide v/v)-MeOH from 25% to 55%, v/v) to provide the title compound (75 mg, 21% yield) as a white solid. MS (ESI): mass calcd. for $C_{22}H_{26}N_6O_3$, 422.21; m/z found, 423.2 [M+H]$^+$. $^1$H NMR (400 MHz, DMSO-d$_6$): δ 11.84 (br s, 1H), 8.49 (s, 1H), 8.46-8.39 (m, 1H), 7.48-7.44 (m, 1H), 6.73-6.69 (m, 1H), 5.92 (s, 1H), 4.53-4.43 (m, 1H), 4.42-4.35 (m, 4H), 4.06 (br s, 2H), 3.46-3.42 (m, 2H), 2.58 (d, J=6.0 Hz, 2H), 2.42-2.26 (m, 2H), 2.08-1.93 (m, 5H), 1.45-1.30 (m, 2H).

Example 25 Synthesis and Characterization 2-((1r,4r)-4-(2-((1H-Pyrazol-5-yl)methyl)imidazo[4,5-d]pyrrolo[2,3-b]pyridin-1(6H)-yl)cyclohexyl)acetonitrile

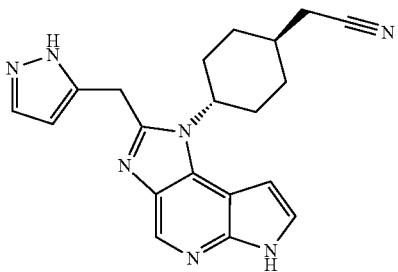 [SMILES: N#CC[C@H]1CC[C@H](n2c(Cc3ccn[nH]3)nc3cnc4[nH]ccc4c32)CC1]

Step A: N-(4-(((1r,4r)-4-(Cyanomethyl)cyclohexyl) amino)-1-(phenylsulfonyl)-1H-pyrrolo[2,3-b]pyridin-5-yl)-2-(1H-pyrazol-5-yl)acetamide. HATU (696 mg, 1.83 mmol) was added to a solution of 2-((1r,4r)-4-((5-amino-1-(phenylsulfonyl)-1H-pyrrolo[2,3-b]pyridin-4-yl)amino)cyclohexyl)acetonitrile (Intermediate 2, 500 mg, 1.22 mmol), 2-(1H-pyrazol-5-yl)acetic acid hydrochloride (238 mg, 1.46 mmol), DIPEA (1.2 mL, 6.5 mmol), and DMF (5 mL) and was stirred at room temperature for 16 hours. The reaction was concentrated to dryness, water (50 mL) was added, and was extracted three times with CH$_2$Cl$_2$ (50 mL×3). The organic layers were combined, dried over anhydrous MgSO$_4$, filtered, and concentrated to dryness. The residue was purified by flash column chromatography to provide the title compound (600 mg, 90% yield) as a brown oil. MS (ESI): mass calcd. for $C_{26}H_{27}N_7O_3S$, 517.60; m/z found, 518.1 [M+H]$^+$.

Step B: 2-((1r,4r)-4-(2-((1H-Pyrazol-5-yl)methyl)-6-(phenylsulfonyl)imidazo[4,5-d]pyrrolo[2,3-b]pyridin-1(6H)-yl)cyclohexyl)acetonitrile. A solution of N-(4-(((1r,4r)-4-(cyanomethyl)cyclohexyl)amino)-1-(phenylsulfonyl)-1H-pyrrolo[2,3-b]pyridin-5-yl)-2-(1H-pyrazol-5-yl) acetamide (350 mg, 0.676 mmol) and HOAc (20 mL) was stirred at 100° C. for 16 hours. The reaction was concentrated to dryness, washed with saturated NaHCO$_3$(50 mL), and extracted with chloromethane (50 mL×2). The organic extracts were dried over anhydrous Na$_2$SO$_4$, filtered, and concentrated to dryness. The residue was purified by flash column chromatography to provide the title compound (300 mg, 68% yield) as a yellow oil. MS (ESI): mass calcd. for $C_{26}H_{25}N_7O_2S$, 499.59; m/z found, 499.9 [M+H]$^+$.

Step C: 2-((1r,4r)-4-(2-((1H-Pyrazol-5-yl)methyl)imidazo[4,5-d]pyrrolo[2,3-b]pyridin-1(6H)-yl)cyclohexyl)acetonitrile. The title compound (63.6 mg, 29% yield) was prepared using conditions analogous to those described in Example 1, Step B using 2-((1r,4r)-4-(2-((1H-Pyrazol-5-yl) methyl)-6-(phenylsulfonyl)imidazo[4,5-d]pyrrolo[2,3-b] pyridin-1(6H)-yl)cyclohexyl)acetonitrile (300 mg, 0.600 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. Purification was performed on a preparative HPLC using the following conditions: Gemini 150 mm×25 mm, 10 μm column (eluent: water (0.05% ammonia hydroxide v/v)-ACN from 20% to 50%, v/v). MS (ESI): mass calcd. for $C_{20}H_{21}N_7$, 359.19; m/z found, 360.1 [M+H]$^+$. $^1$H NMR (400 MHz, DMSO-d$_6$): δ 11.80 (br s, 1H), 8.49 (s, 1H), 7.61-7.54 (m, 1H), 7.42 (d, J=3.1 Hz, 1H), 6.64 (d, J=3.5 Hz, 1H), 6.13-5.93 (m, 2H), 4.62-4.49 (m, 1H), 4.36 (s, 2H), 2.55-2.48 (m, 2H), 2.33-2.15 (m, 2H), 2.03-1.82 (m, 3H), 1.71-1.53 (m, 2H), 1.5-1.18 (m, 2H).

Example 26 Synthesis and Characterization 2-((1r,4r)-4-(2-(2-(4-Morpholinopiperidin-1-yl)-2-oxoethyl)imidazo[4,5-d]pyrrolo[2,3-b]pyridin-1(6H)-yl)cyclohexyl)acetonitrile

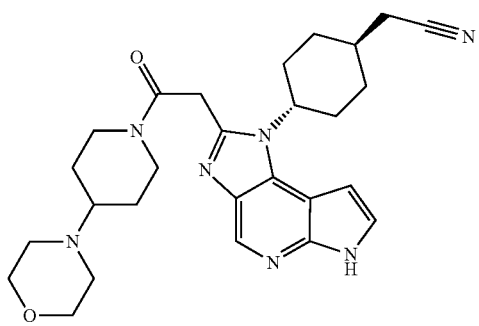 [SMILES: N#CC[C@H]1CC[C@H](n2c(CC(=O)N3CCC(N4CCOCC4)CC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), 4-(piperidin-4-yl)morpholine (94.8 mg, 0.557 mmol), DIPEA (144 mg, 1.11 mmol), and DMF (5 mL) was stirred at 0° C. for 1 h. Then PyBrOP (311 mg, 0.668 mmol) was added and stirred at room-temperature overnight. The mixture was quenched with 10 mL water and was purified by preparative acidic HPLC using a Boston Green ODS 150 mm×30 mm, 5 μm column (eluent: water (0.05% HCl)-ACN from 0% to 30%, v/v) and then by preparative basic HPLC using a Kromasil 150 mm×25 mm, 10 μm column (eluent: water (0.05% ammonia hydroxide v/v)-ACN from 10% to 40%, v/v) to provide the title compound (25 mg, 9% yield) as a white solid. MS (ESI): mass calcd. for $C_{27}H_{35}N_7O_2$, 489.29; m/z found, 490.3 [M+H]$^+$. $^1$H NMR (400 MHz, DMSO-d$_6$): δ 11.85 (br s, 1H), 8.51-8.47 (m, 1H), 7.48-7.44 (m, 1H), 6.72-6.68 (m, 1H), 4.42-4.29 (m, 2H), 4.25 (d, J=8.4 Hz, 2H), 4.16-4.07 (m, 1H), 3.59-3.52 (m, 4H), 3.15-3.05 (m, 1H), 2.69-2.63 (m, 1H), 2.58 (d, J=6.0 Hz, 3H), 2.47-2.41 (m, 5H), 2.07-1.90 (m, 6H), 1.85-1.74 (m, 2H), 1.42-1.27 (m, 3H), 1.27-1.13 (m, 1H).

Example 27 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(hydroxymethyl)cyclohexyl)acetamide

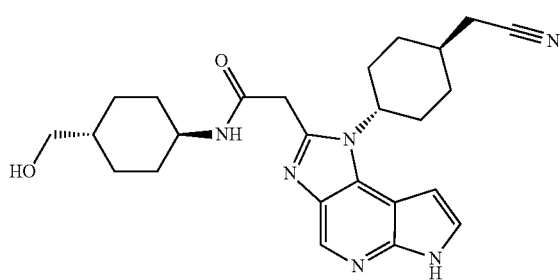 [SMILES: N#CC[C@H]1CC[C@H](n2c(CC(=O)N[C@H]3CC[C@H](CO)CC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), ((1r,4r)-4-aminocyclohexyl)methanol (71.9 mg, 0.557 mmol), PyBrOP (311 mg, 0.668 mmol), DIPEA (144 mg, 1.11 mmol), and DMF (10 mL) was stirred at room-temperature overnight. The mixture was quenched with 20 mL water and was extracted with EtOAc (3×20 mL). The combined organic layers were dried over anhydrous MgSO$_4$ and concentrated to dryness. The residue was purified by preparative basic HPLC using a DuraShell 150 mm×25 mm, 5 μm column (eluent: 13% to 43% (v/v) CH$_3$CN and H$_2$O with 0.05% NH$_3$) to provide the title compound (32.7 mg, 13% yield) as a white solid. MS (ESI): mass calcd. for $C_{25}H_{32}N_6O_2$, 448.26; m/z found, 449.2 [M+H]$^+$. $^1$H NMR (400 MHz, DMSO-d$_6$): δ 11.87-11.76 (m, 1H), 8.52-8.42 (m, 1H), 8.25-8.14 (m, 1H), 7.47-7.42 (m, 1H), 6.73-6.65 (m, 1H), 4.55-4.24 (m, 3H), 3.93 (br s, 2H), 3.21-3.11 (m, 2H), 2.63-2.55 (m, 2H), 2.36-2.25 (m, 2H), 2.08-1.88 (m, 4H), 1.87-1.75 (m, 2H), 1.77-1.66 (m, 2H), 1.44-1.10 (m, 5H), 0.98-0.78 (m, 3H).

Example 28 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-cyclohexylacetamide

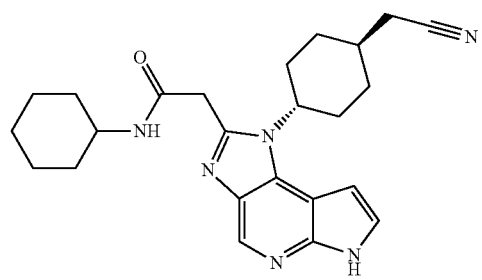 [SMILES: N#CC[C@H]1CC[C@H](n2c(CC(=O)NC3CCCCC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), cyclohexylamine (55.2 mg, 0.557 mmol), PyBrOP (311 mg, 0.668 mmol), DIPEA (144 mg, 1.11 mmol), and DMF (3 mL) was stirred at room-temperature overnight. The mixture was quenched with 20 mL water and was extracted with EtOAc (3×20 mL). The combined organic layers were dried over anhydrous MgSO$_4$ and concentrated to dryness. The residue was purified by preparative basic HPLC using a Gemini 150 mm×25 mm, 5 μm column (eluent: 12% to 42% (v/v) CH$_3$CN and H$_2$O with 0.05% NH$_3$) to provide the title compound (37.5 mg, 16% yield) as a white solid. MS (ESI): mass calcd. for $C_{24}H_{30}N_6O$, 418.25; m/z found, 419.2 [M+H]$^+$. $^1$H NMR (400 MHz, DMSO-d$_6$): δ 12.55 (br s, 1H), 8.81 (s, 1H), 8.56-8.47 (m, 1H), 7.77-7.70 (m, 1H), 6.93 (br s, 1H), 4.64 (br s, 1H), 4.29 (s, 2H), 2.61 (d, J=5.7 Hz, 2H), 2.43-2.26 (m, 2H), 2.14-1.95 (m, 4H), 1.83-1.75 (m, 2H), 1.72-1.69 (m, 2H), 1.61-1.51 (m, 1H), 1.49-1.35 (m, 2H), 1.34-1.07 (m, 7H).

Example 29 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2-hydroxyethyl)acetamide

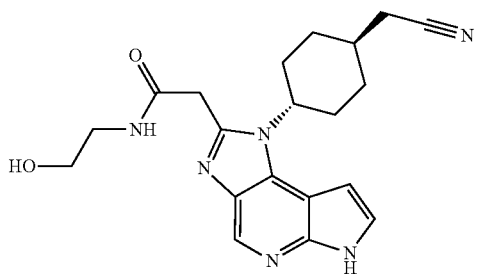 [SMILES: N#CC[C@H]1CC[C@H](n2c(CC(=O)NCCO)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835), 2-aminoethanol (51.0 mg, 0.835 mmol), DIPEA (216 mg, 1.67 mmol), and DMF (5 mL) was stirred at 0° C. for 1 h. Then PyBrOP (311 mg, 0.668 mmol) was added and was stirred at room-temperature overnight. The musing a DuraShell 150 mm×25 mm, 5 μm column (eluent: water (0.05% ammonia hydroxide v/v)-ACN from 14% to 44%, v/v) to provide the title compound (78 mg, 24% yield) as a yellow solid. MS (ESI): mass calcd. for $C_{20}H_{24}N_6O_2$, 380.20; m/z found, 381.2 [M+H]$^+$. $^1$H NMR (400 MHz, DMSO-d$_6$): δ 11.85 (br s, 1H), 8.50 (s, 1H), 8.35-8.29 (m, 1H), 7.49-7.45 (m, 1H), 6.74-6.70 (m, 1H), 4.79-4.72 (m, 1H), 4.56-4.45 (m, 1H), 4.00 (s, 2H), 3.49-3.42 (m, 2H), 3.22-3.15 (m, 2H), 2.59 (d, J=6.0 Hz, 2H), 2.43-2.27 (m, 2H), 2.07-1.93 (m, 5H), 1.46-1.33 (m, 2H).

Example 30 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)benzimidamide

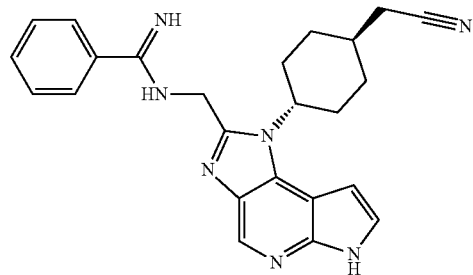 [SMILES: N#CC[C@H]1CC[C@H](n2c(CNC(=N)c3ccccc3)nc3cnc4[nH]ccc4c32)CC1]

Step A: N-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl)benzimidamide. A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 49 mg, 0.11 mmol), benzimidamide (42 mg, 0.27 mmol), K$_2$CO$_3$ (85 mg, 0.62 mmol), and DMF (2 mL) was stirred at room temperature for 15 h. LCMS showed a small amount of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile left, so more benzimidamide (16 mg), K$_2$CO$_3$ (45 mg, 0.33 mmol), and DMF (1 mL) were added, and the mixture was stirred at room temperature overnight. After the solid was filtered off, the filtrate was concentrated to dryness. The filtrate residue was purified by flash column chromatography to provide the title compound (50 mg, 86% yield). MS (ESI): mass calcd. for $C_{30}H_{29}N_7O_2S$, 551.21; m/z found, 552.3 [M+H]$^+$.

Step B: N-((1-((1r,4r)-4-(Cyanomethyl)cyclohexyl)-1,6-dihydroimidazo[4,5-d]pyrrolo[2,3-b]pyridin-2-yl)methyl)benzimidamide. A mixture of N-((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)benzimidamide (50 mg, 0.091 mmol), 1 M NaOH (0.20 mL, 0.20 mmol), MeOH (0.7 mL), and THF (0.7 mL) was stirred at room temperature for 18 h, and concentrated in vacuo. The residue was purified by reverse phase HPLC (10-90% CH$_3$CN in H$_2$O, 0.1% TFA) to give a clear oil. This material was dissolved in EtOAc, and washed with aqueous NaHCO$_3$ solution. The aqueous layer was extracted with EtOAc (×4). The combined extracts were dried over Na$_2$SO$_4$, filtered, and concentrated to give the title compound as an off-white solid (29 mg, 78% yield). MS (ESI): mass calcd. for $C_{24}H_{25}N_7$, 411.22; m/z found, 412.4 [M+H]$^+$. $^1$H NMR (400 MHz, CDCl$_3$) δ=9.77 (br s, 1H), 8.70 (s, 1H), 7.70 (br d, J=7.1 Hz, 2H), 7.57-7.44 (m, 3H), 7.41 (br s, 1H), 6.74 (d, J=3.0 Hz, 1H), 5.08 (br s, 2H), 4.91-4.77 (m, 1H), 2.58-2.45 (m, 2H), 2.40 (d, J=6.6 Hz, 2H), 2.16 (br d, J=11.6 Hz, 3H), 2.12-1.98 (m, 2H), 1.59-1.42 (m, 2H).

Example 31 Synthesis and Characterization 2-((1r,4r)-4-(2-(4-Chloro-1H-pyrazol-3-yl)imidazo[4,5-d]pyrrolo[2,3-b]pyridin-1(6H)-yl)cyclohexyl)acetonitrile

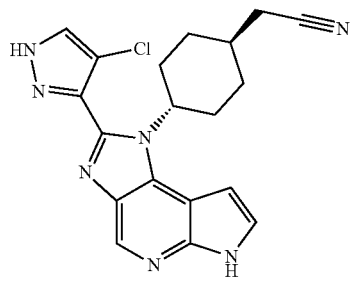 [SMILES: N#CC[C@H]1CC[C@H](n2c(-c3n[nH]cc3Cl)nc3cnc4[nH]ccc4c32)CC1]

Step A: 2-((1r,4r)-4-(2-(4-Chloro-1H-pyrazol-3-yl)-6-(phenylsulfonyl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 165 mg, 0.375 mmol) and 4-chloro-3-formylpyrazole (91 mg, 0.70 mmol) as solids. DMSO (1.87 mL), MeOH (1.87 mL), and distilled water (1.0 mL) were added next. Then sodium hydrosulfite (147 mg, 0.847 mmol) was added as a solid and the vial sealed. The vial was placed into a pre-heated 100° C. heating block for 7 h. The reaction was cooled to room temperature and was poured onto 30 mL of water, resulting in the formation of a precipitate. The mixture was stirred for 15 minutes, and then the yellow solids were collected by filtration and dried under high vacuum for 1 h. The residue was purified by flash column chromatography to provide the title compound (122 mg, 62.5% yield). MS (ESI): mass calcd. for $C_{25}H_{22}ClN_7O_2S$, 519.12; m/z found, 521.8 [M+H]$^+$.

Step B: 2-((1r,4r)-4-(2-(4-Chloro-1H-pyrazol-3-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(2-(4-Chloro-1H-pyrazol-3-yl)-6-(phenyl sulfonyl)imidazo[4,5-d]pyrrolo[2,3-b]pyridin-1(6H)-yl)cyclohexyl)acetonitrile (122 mg, 0.24 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and purified by basic HPLC: using a Waters Xbridge Prep OBD $C_{18}$ 150 mm×30 mm, 5 μm column, (eluent 0-100% aq NH$_4$OH/ACN (10 min) to provide the title compound (28 mg, 31% yield). MS (ESI): mass calcd. for $C_{19}H_{18}ClN_7$, 379.13; m/z found, 381.9 [M+H]$^+$. $^1$H NMR (400 MHz, CDCl$_3$) δ 10.12 (s, 1H), 8.91 (s, 1H), 7.77 (s, 1H), 7.43 (d, J=3.5 Hz, 1H), 6.78 (d, J=3.5 Hz, 1H), 4.74 (s, 1H), 2.68-2.47 (m, 2H), 2.40 (d, J=6.2 Hz, 2H), 2.25-1.94 (m, 6H), 1.41 (q, J=12.6, 11.5 Hz, 2H).

Example 32 Synthesis and Characterization

N-((3R,5R)-Adamantan-1-yl)-2-(1-((1r,4r)-4-(cyanomethyl)cyclohexyl)-1,6-dihydroimidazo[4,5-d]pyrrolo[2,3-b]pyridin-2-yl)acetamide

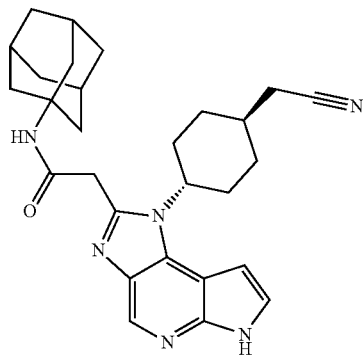 [SMILES: N#CC[C@H]1CC[C@H](n2c(CC(=O)NC34CC5CC(CC(C5)C3)C4)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), (3s,5s,7s)-adamantan-1-amine hydrochloride (104 mg, 0.557 mmol), DIPEA (144 mg, 1.11 mmol), and DMF (5 mL) was stirred at 0° C. for 1 h. Then PyBrOP (311 mg, 0.668 mmol) was added and stirred at room-temperature overnight. The mixture was quenched with 10 mL water and was purified by preparative basic HPLC using a Kromasil 150 mm×25 mm, 10 μm column (eluent: water (0.05% ammonia hydroxide v/v)-ACN from 30% to 60%) to provide the title compound (50 mg, 19% yield) as a white solid. MS (ESI): mass calcd. for $C_{28}H_{34}N_6O$, 470.28; m/z found, 471.3 [M+H]$^+$. $^1$H NMR (400 MHz, DMSO-d$_6$): δ 11.84 (br s, 1H), 8.49 (s, 1H), 7.86 (br s, 1H), 7.47-7.44 (m, 1H), 6.71-6.88 (m, 1H), 4.51-4.37 (m, 1H), 3.93 (s, 2H), 2.61 (d, J=5.6 Hz, 2H), 2.38-2.31 (m, 1H), 2.04-1.92 (m, 15H), 1.64-1.59 (m, 6H), 1.47-1.34 (m, 2H).

Example 33 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1r,4r)-4-hydroxycyclohexyl)acetamide

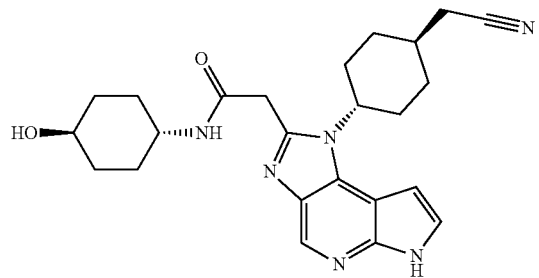 [SMILES: N#CC[C@H]1CC[C@H](n2c(CC(=O)N[C@H]3CC[C@H](O)CC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), (1r,4r)-4-aminocyclohexanol (64.1 mg, 0.557 mmol), PyBrOP (311 mg, 0.668 mmol), DIPEA (144 mg, 1.11 mmol), and DMF (10 mL) was stirred overnight. The mixture was quenched with 20 mL water and extracted with EtOAc (3×20 mL). The combined organic layers were dried over anhydrous MgSO$_4$ and concentrated to dryness. The residue was purified by preparative basic HPLC using a DuraShell 150 mm×25 mm, 5 μm column (eluent: 15% to 45% (v/v) CH$_3$CN and H$_2$O with 0.05% NH$_3$) to provide the title compound (27.9 mg, 11% yield) as a white solid. MS (ESI): mass calcd. for $C_{24}H_{30}N_6O_2$, 434.24; m/z found, 435.2 [M+H]$^+$. $^1$H NMR (400 MHz, DMSO-d$_6$): δ 11.85 (br s, 1H), 8.49 (s, 1H), 8.22-8.19 (m, 1H), 7.47-7.45 (m, 1H), 6.71 (br s, 1H), 4.59 (d, J=4.4 Hz, 1H), 4.55-4.39 (m, 1H), 3.95 (s, 2H), 2.60 (d, J=5.7 Hz, 2H), 2.42-2.33 (m, 2H), 2.08-1.92 (m, 5H), 1.89-1.71 (m, 5H), 1.48-1.31 (m, 2H), 1.31-1.12 (m, 5H).

Example 34 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide

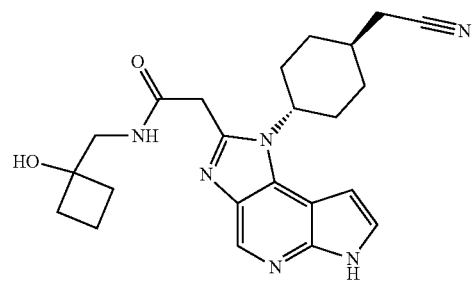 [SMILES: N#CC[C@H]1CC[C@H](n2c(CC(=O)NCC3(O)CCC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 1-(aminomethyl)cyclobutanol (84.4 mg, 0.835 mmol), DIPEA (216 mg, 1.67 mmol), and DMF (5 mL) was stirred at 0° C. for 1 h. Next, PyBrOP (467 mg, 1.00 mmol) was added and was stirred at room temperature overnight, then quenched with 10 mL water. The reaction was purified by preparative basic HPLC using a Kromasil 150 mm×25 mm, 10 μm column (eluent: water (0.05% ammonia hydroxide v/v)-ACN from 9% to 39%, v/v) to provide the title compound (90 mg, 26% yield) as a white solid. MS (ESI): mass calcd. for $C_{23}H_{28}N_6O_2$, 420.23; m/z found, 421.2 [M+H]$^+$. $^1$H NMR (400 MHz, DMSO-d$_6$): δ 11.58 (br s, 1H), 8.50 (s, 1H), 7.94-7.85 (m, 1H), 7.46-7.40 (m, 1H), 6.75-6.70 (m, 1H), 4.89 (br s, 1H), 4.57-4.47 (m, 1H), 4.04 (s, 2H), 3.27 (d, J=6.0 Hz, 2H), 2.55 (d, J=6.0 Hz, 2H), 2.45-2.31 (m, 2H), 2.10-1.88 (m, 9H), 1.71-1.60 (m, 1H), 1.54-1.35 (m, 3H).

Example 35 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(pyrazin-2-ylmethyl)acetamide

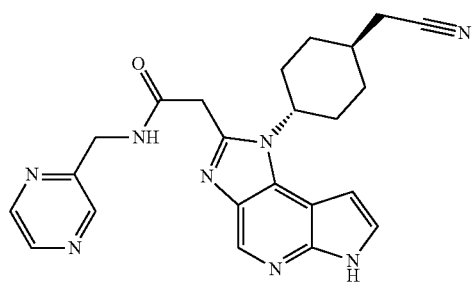 [SMILES: N#CC[C@H]1CC[C@H](n2c(CC(=O)NCc3cnccn3)nc3cnc4[nH]ccc4c32)CC1]

To a 10 mL microwave vial was added sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 154 mg, 0.429 mmol) as a solid followed by dissolution into DMF (1.7 mL). PyBOP (352 mg, 0.676 mmol) was added in one portion and immediately a canary yellow color formed. The resulting solution was stirred for 15 minutes prior to addition of DIPEA (0.295 mL, 1.71 mmol), followed by 2-aminomethylpyrazine (102 mg, 0.935 mmol) and was stirred at room temperature for 2 days. The reaction was added to water (20 mL), which resulted in a precipitate forming. The solids were collected by filtration. The filtrate was extracted with EtOAc and CH$_2$Cl$_2$ and the organic phases were combined and concentrated to dryness. The residue was purified by basic HPLC: using a Waters Xbridge Prep OBD C$_{18}$ 50 mm×100 mm, 5 mm (eluent=0-100% aq NH$_4$OH/ACN (10 min)) to provide the title compound (11 mg, 6% yield) as a fluffy white powder. MS (ESI): mass calcd. for $C_{23}H_{24}N_8O$, 428.21; m/z found, 429.0 [M+H]$^+$. $^1$H NMR (500 MHz, CDCl$_3$): δ 10.33 (s, 1H), 8.72 (s, 1H), 8.59 (d, J=1.0 Hz, 1H), 8.51-8.43 (m, 2H), 7.47-7.37 (m, 1H), 6.72 (m, J=3.5, 1.9 Hz, 1H), 4.73-4.53 (m, 3H), 4.10 (s, 2H), 2.53 (s, 2H), 2.41 (d, J=6.5 Hz, 2H), 2.26-2.12 (m, 2H), 2.12-1.93 (m, 3H), 1.57-1.37 (m, 2H).

Example 36 Synthesis and Characterization

N-((1H-imidazol-2-yl)methyl)-2-(1-((1r,4r)-4-(cyanomethyl)cyclohexyl)-1,6-dihydroimidazo[4,5-d]pyrrolo[2,3-b]pyridin-2-yl)acetamide

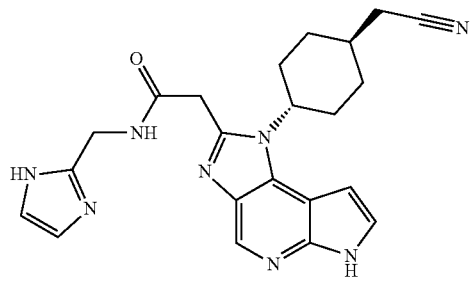 [SMILES: N#CC[C@H]1CC[C@H](n2c(CC(=O)NCc3ncc[nH]3)nc3cnc4[nH]ccc4c32)CC1]

To a 10 mL microwave vial was added sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 136 mg, 0.378 mmol) as a solid followed by dissolution into DMF (1.5 mL). PyBOP (304 mg, 0.584 mmol) was added in one portion. The solution was stirred for 15 minutes prior to addition of DIPEA (0.261 mL, 1.51 mmol), followed by (1H-imidazol-2-yl)methanamine dihydrochloride (151 mg, 0.870 mmol) and was stirred at room temperature for 72 h. The reaction was added to saturated NaHCO$_3$(20 mL), which resulted in a precipitate forming. The solids were collected by filtration. The solids were solubilized in EtOAc, and the aqueous phase was extracted with EtOAc and CH$_2$Cl$_2$, and the organic phases were combined, dried over anhydrous Na$_2$SO$_4$, and concentrated to dryness. The residue was purified by basic HPLC: Waters Xbridge Prep OBD C$_{18}$ 150 mm×30 mm 5 μm, eluent 0-100% aq NH$_4$OH/ACN (10 min) to provide the title compound (6 mg, 4% yield). MS (ESI): mass calcd. for $C_{22}H_{24}N_8O$, 416.21; m/z found, 418.0 [M+H]$^+$. $^1$H NMR (500 MHz, CD$_3$OD): δ 8.54 (s, 1H), 7.48 (d, J=3.5 Hz, 1H), 7.09-6.92 (m, 2H), 6.84 (d, J=3.6 Hz, 1H), 4.74-4.37 (m, 4H), 2.69-2.41 (m, 3H), 2.20-1.97 (m, 5H), 1.55-1.38 (m, 2H), 1.38-1.24 (m, 3H).

Example 37 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1R,3R)-3-hydroxycyclobutyl)acetamide

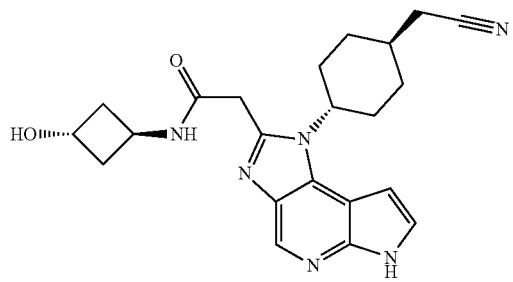 [SMILES: N#CC[C@H]1CC[C@H](n2c(CC(=O)N[C@H]3C[C@H](O)C3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), (1R,3R)-

3-aminocyclobutanol (72.7 mg, 0.835 mmol), DIPEA (216 mg, 1.67 mmol), and DMF (5 mL) was stirred at 0° C. for 1 h. Next, PyBrOP (467 mg, 1.00 mmol) was added and was stirred at room temperature overnight. The mixture was quenched with 10 mL water. The reaction was purified by preparative basic HPLC using a Kromasil 150 mm×25 mm, 10 μm column (eluent: water (0.05% ammonia hydroxide v/v)-ACN from 22% to 32%, v/v) and by preparative TLC (CH$_2$Cl$_2$: MeOH=10:1) to provide the title compound (36 mg, 11% yield) as a white solid. MS (ESI): mass calcd. for C$_{22}$H$_{26}$N$_6$O$_2$, 406.21; m/z found, 407.2 [M+H]$^+$. $^1$H NMR (400 MHz, DMSO-d$_6$): δ 11.83 (br s, 1H), 8.59 (d, J=6.8 Hz, 1H), 8.49 (s, 1H), 7.48-7.43 (m, 1H), 6.73-6.68 (m, 1H), 5.03 (d, J=5.6 Hz, 1H), 4.56-4.43 (m, 1H), 4.34-4.25 (m, 1H), 4.24-4.14 (m, 1H), 3.95 (s, 2H), 2.59 (d, J=5.6 Hz, 2H), 2.43-2.26 (m, 2H), 2.21-1.90 (m, 9H), 1.45-1.30 (m, 2H).

Example 38 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide

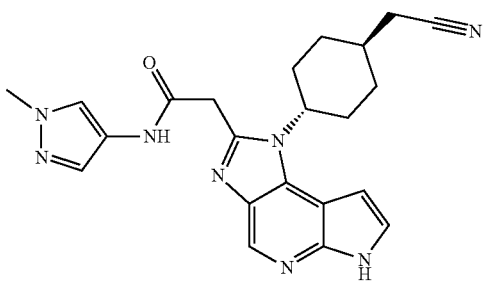 [SMILES: Cn1cc(NC(=O)Cc2nc3cnc4[nH]ccc4c3n2[C@H]2CC[C@H](CC#N)CC2)cn1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 100 mg, 0.278 mmol) and 1-methyl-1H-pyrazol-4-amine (54.0 mg, 0.557 mmol) in DMF (0.8 mL) were added PyBrOP (217 mg, 0.417 mmol) and DIPEA (0.144 mL, 0.835 mmol) and the mixture was stirred at room temperature overnight. The DMF was removed under reduced pressure and the residue was purified by flash column chromatography (50-100% EtOAc/heptanes, then 10% MeOH/DCM) and the subsequently by reverse phase HPLC using a Varian Pursuit XR$_s$5 Diphenyl 100 mm×30 mm column (eluent 10-90% CH$_3$CN in water, 0.1% TFA) to provide the product as the TFA salt. This material was dissolved in 10% MeOH in CH$_2$Cl$_2$ and passed through a 500 mg column of SILICYCLE SPE-R66030B-03P Carbonate (SiliaBond acid scavenger solid phase extraction cartridge) to remove the TFA to provide the title compound (34 mg, 29% yield) as a white solid. MS (ESI): mass calcd. for C$_{22}$H$_{24}$N$_8$O, 416.21; m/z found, 417.3 [M+H]$^+$. $^1$H NMR (400 MHz, CDCl$_3$) δ=12.77 (br s, 1H), 11.24 (br s, 1H), 7.94 (s, 1H), 7.89 (br s, 1H), 7.46 (s, 1H), 7.29-7.20 (m, 1H), 6.74 (br s, 1H), 4.85-4.65 (m, 1H), 4.23 (s, 2H), 3.85 (s, 3H), 2.80-2.55 (m, 1H), 2.45 (d, J=6.6 Hz, 2H), 2.32-1.98 (m, 6H), 1.62-1.44 (m, 2H).

Example 39 Synthesis and Characterization

N-(4-Cyanobenzyl)-2-(1-((1r,4r)-4-(cyanomethyl)cyclohexyl)-1,6-dihydroimidazo[4,5-d]pyrrolo[2,3-b]pyridin-2-yl)acetamide

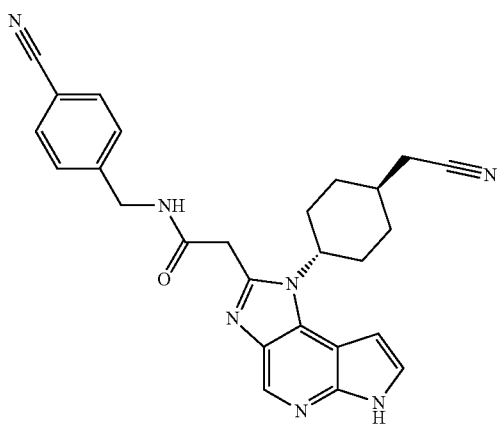 [SMILES: N#CC[C@H]1CC[C@H](n2c(CC(=O)NCc3ccc(C#N)cc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 100 mg, 0.278 mmol) and 4-(aminomethyl)benzonitrile (73.6 mg, 0.557 mmol) in DMF (0.8 mL) were added PyBrOP (217 mg, 0.417 mmol) and DIPEA (0.144 mL, 0.835 mmol) and was stirred at room temperature for 87 h. The DMF was removed under reduced pressure and the residue was purified by flash column chromatography and by reverse phase HPLC using a Phenomenex Luna C$_{18}$ 100 mm×30 mm, 5 μm column (mobile phase gradient 5-95% ACN in H$_2$O (both with 0.1% TFA), v/v) to provide the product as the TFA salt. This material was dissolved in MeOH and passed through a 500 mg column of SILICYCLE SPE-R66030B-03P Carbonate (SiliaBond acid scavenger solid phase extraction cartridge) to remove the TFA to provide the title compound (47 mg, 37% yield) as a white solid. MS (ESI): mass calcd. for C$_{26}$H$_{25}$N$_7$O, 451.21; m/z found, 452.1 [M+H]$^+$. $^1$H NMR (400 MHz, CD$_3$OD) δ=8.53 (s, 1H), 7.74-7.68 (m, 2H), 7.55-7.49 (m, 2H), 7.49-7.45 (m, 1H), 6.83 (d, J=4.0 Hz, 1H), 4.52-4.46 (m, 3H), 4.18-4.12 (m, 1H), 2.54 (d, J=5.6 Hz, 4H), 2.13-1.98 (m, 6H), 1.48-1.32 (m, 2H).

Example 40 Synthesis and Characterization 1-((1-((1r,4r)-4-(Cyanomethyl)cyclohexyl)-1,6-dihydroimidazo[4,5-d]pyrrolo[2,3-b]pyridin-2-yl)methyl)urea

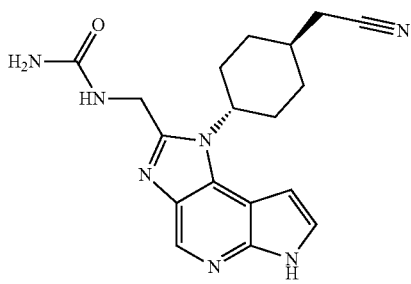 [SMILES: N#CC[C@H]1CC[C@H](n2c(CNC(N)=O)nc3cnc4[nH]ccc4c32)CC1]

Potassium cyanate (141 mg, 1.74 mmol) was added to a solution consisting of 2-((1r,4r)-4-(2-(aminomethyl)imidazo[4,5-d]pyrrolo[2,3-b]pyridin-1(6H)-yl)cyclohexyl)acetonitrile (Intermediate 5, 200 mg, 0.580 mmol), NaHCO$_3$ (49 mg, 0.58 mmol), dioxane (3 mL), and water (0.75 mL) and was stirred for 2 h at 90° C. The mixture was diluted with water (10 mL) and extracted with ethyl acetate (20 mL×2). The combined organic extracts were evaporated to dryness and were purified by preparative HPLC using a Boston Green ODS 150 mm×30 mm, 5 μm column (eluent: 5% to 30% (v/v) CH$_3$CN and aqueous HCl (0.006 N)). The pure fractions were collected and the volatile organic components were removed under reduced pressure. The remaining aqueous mixture was treated with saturated aqueous NaHCO$_3$ until pH=7-8, and extracted with mixed CH$_2$Cl$_2$ and ethyl acetate (1:1) (50 mL×2). The combined organic extracts were dried over anhydrous Na$_2$SO$_4$, filtered, and evaporated to dryness. The product was suspended in water (10 mL), the mixture was frozen using dry ice/acetone, and lyophilized to dryness to provide the title compound (35 mg, 17% yield) as a white solid. MS (ESI): mass calcd. for C$_{18}$H$_{21}$N$_7$O, 351.18; m/z found, 352.2 [M+H]$^+$. $^1$H NMR (400 MHz, DMSO-d$_6$): δ 11.87 (s, 1H), 8.53 (s, 1H), 7.50-7.43 (m, 1H), 6.72 (s, 1H), 6.65-6.57 (m, 1H), 5.70 (s, 2H), 4.66-4.51 (m, 3H), 2.58 (d, J=6.0 Hz, 2H), 2.40-2.27 (m, 2H), 2.08-1.87 (m, 5H), 1.48-1.33 (m, 2H).

Example 41 Synthesis and Characterization 2-((1r,4r)-4-(2-(Thiazol-4-ylmethyl)imidazo[4,5-d]pyrrolo[2,3-b]pyridin-1(6H)-yl)cyclohexyl)acetonitrile

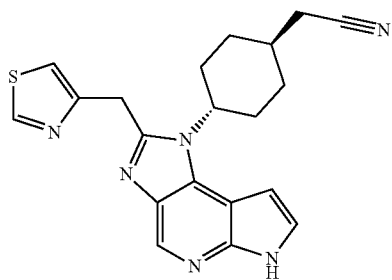 [SMILES: N#CC[C@H]1CC[C@H](n2c(Cc3cscn3)nc3cnc4[nH]ccc4c32)CC1]

Step A: N-(4-(((1r,4r)-4-(cyanomethyl)cyclohexyl)amino)-1-(phenylsulfonyl)-1H-pyrrolo[2,3-b]pyridin-5-yl)-2-(thiazol-4-yl)acetamide. HATU (2.12 g, 5.58 mmol) was added to a mixture containing of 2-((1r,4r)-4-((5-amino-1-(phenylsulfonyl)-1H-pyrrolo[2,3-b]pyridin-4-yl)amino)cyclohexyl)acetonitrile (Intermediate 2, 1.14 g, 2.78 mmol), 2-(thiazol-4-yl)acetic acid (400 mg, 2.79 mmol), DIPEA (722 mg, 5.59 mmol) and DMF (10 mL) at 0° C. (ice/water) and was stirred at room-temperature for 2 hours. The reaction was partitioned between EtOAc (100 mL) and water (100 mL), the aqueous phase was extracted with ethyl acetate (50 mL×3) and the combined organic extracts were dried over anhydrous Na$_2$SO$_4$, filtered, and concentrated to dryness. The residue was purified by flash column chromatography to provide the title compound (1.5 g, 95% yield) as a yellow solid. MS (ESI): mass calcd. for C$_{26}$H$_{26}$N$_6$O$_3$S$_2$, 534.65; m/z found, 534.9 [M+H]$^+$.

Step B: 2-((1r,4r)-4-(6-(Phenylsulfonyl)-2-(thiazol-4-ylmethyl)imidazo[4,5-d]pyrrolo[2,3-b]pyridin-1(6H)-yl)cyclohexyl)acetonitrile. Acetic acid (5 mL) was added to N-(1-((1r,4r)-4-(cyanomethyl)cyclohexyl)-6-(phenylsulfonyl)-1,6-dihydroimidazo[4,5-d]pyrrolo[2,3-b]pyridin-2-yl)-2-(thiazol-4-yl)acetamide (500 mg, 0.935 mmol) and was heated at 130° C. for 6 hours. Saturated NaHCO$_3$ solution (30 mL) was added to the reaction mixture and it was extracted with CH$_2$Cl$_2$ (30 mL×4). The combined extracts were dried over anhydrous Na$_2$SO$_4$, filtered, and concentrated to dryness. The residue was purified by flash column chromatography to provide the title compound (100 mg, 20% yield). MS (ESI): mass calcd. for C$_{26}$H$_{24}$N$_6$O$_2$S$_2$, 516.14; m/z found, 517.1 [M+H]$^+$.

Step C: 2-((1r,4r)-4-(2-(Thiazol-4-ylmethyl)imidazo[4,5-d]pyrrolo[2,3-b]pyridin-1(6H)-yl)cyclohexyl)acetonitrile. The title compound (85 mg, 27% yield) was prepared using conditions analogous to those described in Example 1, Step B using 2-((1r,4r)-4-(6-(phenylsulfonyl)-2-(thiazol-4-ylmethyl)imidazo[4,5-d]pyrrolo[2,3-b]pyridin-1(6H)-yl)cyclohexyl)acetonitrile (180 mg, 0.348 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The title compound was purified by HPLC using a Phenomenex Gemini 150 mm×25 mm, 10 μm (eluent: CH$_3$CN in H$_2$O (0.05% ammonia solution) from 20% to 50%, v/v). MS (ESI): mass calcd. for C$_{20}$H$_{20}$N$_6$S, 376.2; m/z found, 377.2 [M+H]$^+$. $^1$H NMR (400 MHz, DMSO-d$_6$): δ 11.80 (s, 1H), 9.03 (d, J=1.6 Hz, 1H), 8.49 (s, 1H), 7.51 (s, 1H), 7.44-7.40 (m, 1H), 6.68-6.62 (m, 1H), 4.62-4.53 (m, 3H), 2.55-2.51 (m, 2H), 2.35-2.20 (m, 2H), 2.02-1.94 (m, 1H), 1.96-1.86 (m, 2H), 1.75-1.58 (m, 2H), 1.37-1.20 (m, 2H).

Example 42 Synthesis and Characterization 2-((1S,4r)-4-(2-(2-((S)-3-Hydroxypyrrolidin-1-yl)-2-oxoethyl)imidazo[2,5-d]pyrrolo[2,3-b]pyridin-1(6H)-yl)cyclohexyl)acetonitrile

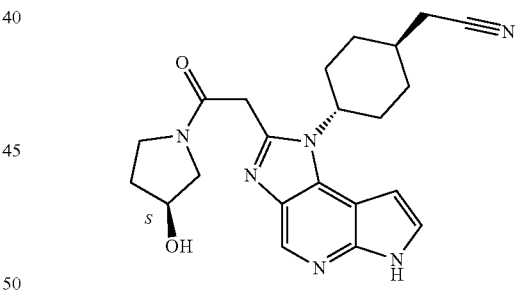

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), (S)-pyrrolidin-3-ol (48.5 mg, 0.557 mmol), DIPEA (144 mg, 1.11 mmol), and DMF (5 mL) was stirred at 0° C. for 1 h. Next, PyBrOP (311 mg, 0.668 mmol) was added and was stirred at room temperature for 4 h. The mixture was quenched with 10 mL water and extracted with CH$_2$Cl$_2$ (2×10 mL). The water layer was purified by preparative acidic HPLC using a Boston Green ODS 150 mm×30 mm, 5 μm column (eluent: water (0.05% HCl)-ACN from 5% to 35%, v/v), and the organic layer was purified by preparative acidic HPLC using a Boston Green ODS 150 mm×30 mm, 5 μm column (eluent: water (0.05% HCl)-ACN from 11% to 41%, v/v). The fractions containing the title compound were combined and purified again by preparative basic HPLC using a DuraShell 150 mm×25 mm, 5 μm column (eluent: water (0.05% ammonia hydroxide v/v)-ACN from 14% to 44%, v/v). Lastly the title compound was further purified by preparative TLC (CH$_2$Cl$_2$: MeOH=10:1) to provide the compound (10 mg, 4% yield) as a white solid. MS (ESI): mass calcd. for C$_{22}$H$_{26}$N$_6$O$_2$, 406.2; m/z found, 407.2 [M+H]$^+$. $^1$H NMR (400 MHz, DMSO-d$_6$): δ 11.84 (br s, 1H), 8.49 (s, 1H), 7.49-7.44 (m, 1H), 6.74-6.68 (m, 1H), 5.13-4.96 (m, 1H), 4.47-4.25 (m, 2H), 4.21-4.16 (m, 1H), 4.16-4.11 (m, 1H), 3.78-3.60 (m, 2H), 3.31-3.28 (m, 1H), 2.58 (d, J=5.6 Hz, 2H), 2.42-2.25 (m, 2H), 2.11-1.72 (m, 8H), 1.45-1.28 (m, 2H).

Example 43 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2-(pyridin-4-yloxy)ethyl)acetamide

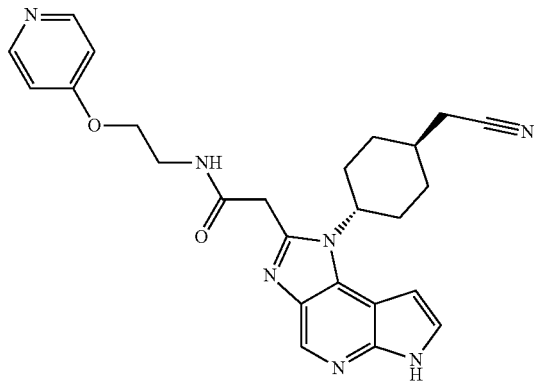 [SMILES: N#CC[C@H]1CC[C@H](n2c(CC(=O)NCCOc3ccncc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 70 mg, 0.19 mmol) and 2-(pyridin-4-yloxy)ethanamine (54 mg, 0.39 mmol) in DMF (2 mL) were added PyBOP (152 mg, 0.292 mmol) and DIPEA (0.101 mL, 0.584 mmol) and was stirred at room temperature for 18 h. The reaction was concentrated to dryness and the residue was purified by reverse phase acidic HPLC using a Varian Pursuit XR$_s$5 Diphenyl 100×30 mm column (eluent: 10-90% CH$_3$CN in H$_2$O, 0.1% TFA). The product was dissolved in n-BuOH and saturated NaHCO$_3$ (aqueous). The organic layer was separated and the aqueous layer was extracted with a 1:1 mixture of n-BuOH and CH$_2$Cl$_2$. The combined organic layers were dried over anhydrous MgSO$_4$, filtered, concentrated to dryness, and purified by flash column chromatography and again by reverse phase acidic HPLC using a Varian Pursuit XR$_s$5 Diphenyl 100×30 mm column (eluent: 10-90% CH$_3$CN in H$_2$O, 0.1% TFA) to provide the title compound that was still impure. The title compound was then dissolved in n-BuOH and saturated NaHCO$_3$(aqueous). The organic layer was separated and the aqueous layer was extracted with n-BuOH and then EtOAc. The extracts were dried over anhydrous MgSO$_4$, filtered, and concentrated to dryness. The residue was dissolved in 10% MeOH in CH$_2$Cl$_2$ and filtered through a syringe filter. The filtrate was concentrated to dryness to provide the title compound (18 mg, 20% yield). MS (ESI): mass calcd. for C$_{25}$H$_{27}$N$_7$O$_2$, 457.2; m/z found, 458.2 [M+H]$^+$. $^1$H NMR (400 MHz, CD$_3$OD) δ=8.52 (s, 1H), 8.32 (d, J=5.6 Hz, 2H), 7.48 (d, J=3.5 Hz, 1H), 6.97 (d, J=6.1 Hz, 2H), 6.81 (d, J=3.5 Hz, 1H), 4.51 (br s, 1H), 4.18 (t, J=5.1 Hz, 2H), 3.67 (t, J=5.1 Hz, 2H), 2.53 (br s, 2H), 2.44 (d, J=6.1 Hz, 2H), 2.11-1.99 (m, 6H), 1.47-1.34 (m, 3H).

Example 44 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-neopentylacetamide

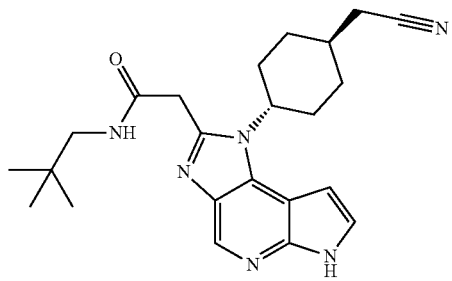 [SMILES: CC(C)(C)CNC(=O)Cc1nc2cnc3[nH]ccc3c2n1[C@H]1CC[C@H](CC#N)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), 2,2-dimethylpropan-1-amine (48.5 mg, 0.557 mmol), PyBrOP (311 mg, 0.668 mmol), DIPEA (144 mg, 1.11 mmol), and DMF (10 mL) was stirred at room temperature overnight. The mixture was quenched with 20 mL water and extracted with EtOAc (3×20 mL). The combined organic layers were dried over anhydrous MgSO$_4$ and concentrated to dryness. The residue was purified by preparative basic HPLC using a Phenomenex Synergi C$_{18}$ 250 mm×21.2 mm, 4 μm column (eluent: 15% to 45% (v/v) CH$_3$CN and H$_2$O with 0.05% NH$_3$) to provide the title compound (19.5 mg, 8% yield) as a white solid. MS (ESI): mass calcd. for C$_{23}$H$_{30}$N$_6$O, 406.25; m/z found, 407.2 [M+H]$^+$. $^1$H NMR (400 MHz, DMSO-d$_6$): δ 11.84 (br s, 1H), 8.50 (s, 1H), 8.26-8.19 (m, 1H), 7.50-7.45 (m, 1H), 6.74-6.69 (m, 1H), 4.57-4.42 (m, 1H), 4.06 (s, 2H), 2.99-2.92 (m, 2H), 2.59 (d, J=6.0 Hz, 2H), 2.41-2.29 (m, 2H), 2.11-1.92 (m, 5H), 1.46-1.30 (m, 2H), 0.88 (s, 9H).

Example 45 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4-fluorobenzyl)acetamide

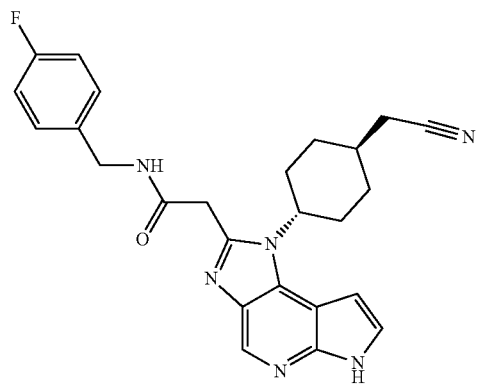 [SMILES: N#CC[C@H]1CC[C@H](n2c(CC(=O)NCc3ccc(F)cc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 100 mg, 0.278 mmol) and (4-fluorophenyl)methanamine (90 mg, 0.56 mmol) in DMF (1 mL) were added PyBOP (217 mg, 0.417 mmol) and DIPEA (0.192 mL, 1.11 mmol) and was stirred at room temperature for 87 h. The reaction was concentrated to dryness and the residue was purified by flash column chromatography (12 g silica gel column, 30-100% EtOAc in heptanes, then 10% MeOH in DCM) and by reverse phase acidic HPLC using a Varian Pursuit XR$_s$5 Diphenyl 100×30 mm column (eluent: 10-90% CH$_3$CN in H$_2$O, 0.1% TFA) to provide the title compound as the TFA salt. This material was dissolved in 10% MeOH in CH$_2$Cl$_2$ and loaded onto a 500 mg column of SILICYCLE SPE-R66030B-03P Carbonate (SiliaBond acid scavenger solid phase extraction cartridge) to remove the TFA and to provide the title compound (43 mg, 35% yield) as a white solid. MS (ESI): mass calcd. for C$_{25}$H$_{25}$FN$_6$O, 444.2 m/z found, 445.2 [M+H]$^+$. $^1$H NMR (400 MHz, CDCl$_3$) δ=11.70 (br s, 1H), 8.58 (br s, 1H), 8.33 (br s, 1H), 7.47 (br s, 1H), 7.20 (t, J=6.6 Hz, 2H), 6.98-6.87 (m, 2H), 6.78-6.71 (m, 1H), 4.71 (br s, 1H), 4.42 (d, J=5.6 Hz, 2H), 4.11 (br s, 2H), 2.68-2.47 (m, 2H), 2.43 (d, J=6.1 Hz, 2H), 2.25-1.82 (m, 5H), 1.58-1.40 (m, 2H).

Example 46 Synthesis and Characterization

Phenyl ((1-((1r,4r)-4-(cyanomethyl)cyclohexyl)-1,6-dihydroimidazo[4,5-d]pyrrolo[2,3-b]pyridin-2-yl)methyl)carbamate

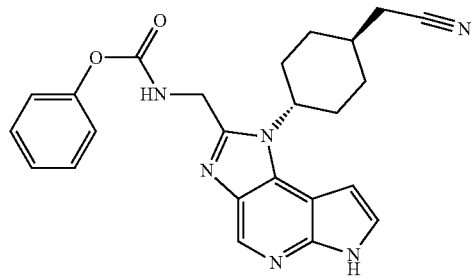 [SMILES: N#CC[C@H]1CC[C@H](n2c(CNC(=O)Oc3ccccc3)nc3cnc4[nH]ccc4c32)CC1]

A solution consisting of 2-((1r,4r)-4-(2-(aminomethyl)imidazo[4,5-d]pyrrolo[2,3-b]pyridin-1(6H)-yl)cyclohexyl)acetonitrile (Intermediate 5, 300 mg, 0.870 mmol), triethylamine (440 mg, 4.35 mmol), phenyl carbonochloridate (136 mg, 0.870 mmol), and CH$_2$Cl$_2$ (6 mL) was stirred at 10° C. for 0.5 hour. The reaction mixture was diluted with CH$_2$Cl$_2$ (10 mL), washed with water (10 mL), dried over anhydrous Na$_2$SO$_4$, filtered, and concentrated to dryness. The residue was purified by preparative HPLC using a Boston Green ODS 150 mm×30 mm, 5 m column (eluent: 20% to 50% (v/v) CH$_3$CN and H$_2$O with 10 mM NH$_4$HCO$_3$) to provide the title compound (52 mg, 14% yield) as a white solid. MS (ESI): mass calcd. for C$_{24}$H$_{24}$N$_6$O$_2$, 428.2; m/z found, 429.2 [M+H]$^+$. $^1$H NMR (400 MHz, DMSO-d$_6$): δ 11.90 (s, 1H), 8.56 (s, 1H), 8.49 (t, J=5.6 Hz, 1H), 7.48 (t, J=2.8 Hz, 1H), 7.43-7.35 (m, 2H), 7.25-7.18 (m, 1H), 7.11 (d, J=7.6 Hz, 2H), 6.76-6.70 (m, 1H), 4.70 (d, J=6.0 Hz, 2H), 4.64-4.51 (m, 1H), 2.59 (d, J=6.4 Hz, 2H), 2.43-2.31 (m, 2H), 2.06-1.92 (m, 5H), 1.48-1.33 (m, 2H).

Example 47 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1S,4S)-4-hydroxycyclohexyl)acetamide

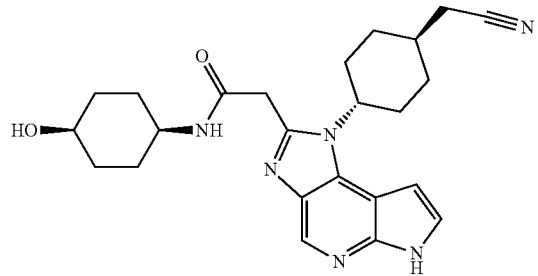 [SMILES: N#CC[C@H]1CC[C@H](n2c(CC(=O)N[C@H]3CC[C@@H](O)CC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), (1S,4S)-4-aminocyclohexanol (64.1 mg, 0.557 mmol), PyBrOP (311 mg, 0.668 mmol), DIPEA (144 mg, 1.11 mmol), and DMF (10 mL) was stirred at room temperature overnight. The mixture was quenched with 20 mL water and extracted with EtOAc (3×20 mL). The combined organic layers were dried over anhydrous MgSO$_4$ and concentrated to dryness. The residue was purified by preparative basic HPLC using a DuraShell 150 mm×25 mm, 5 μm column (eluent: 11% to 41% (v/v) CH$_3$CN and H$_2$O with 0.05% NH$_3$) to provide the title compound (29 mg, 12% yield) as a white solid. MS (ESI): mass calcd. for C$_{24}$H$_{30}$N$_6$O$_2$, 434.2; m/z found, 435.2 [M+H]$^+$. $^1$H NMR (400 MHz, DMSO-d$_6$): δ 11.82 (br s, 1H), 8.47 (s, 1H), 8.28-8.18 (m, 1H), 7.41-7.46 (m, 1H), 6.71-6.65 (m, 1H), 4.43-4.40 (m, 1H), 3.96-3.54 (m, 2H), 3.70-3.54 (m, 2H), 2.60-2.55 (m, 3H), 2.40-2.25 (m, 2H), 2.07-1.89 (m, 5H), 1.67-1.54 (m, 4H), 1.52-1.42 (m, 4H), 1.41-1.28 (m, 2H).

Example 48 Synthesis and Characterization

N-Benzyl-2-(1-((1r,4r)-4-(cyanomethyl)cyclohexyl)-1,6-dihydroimidazo[4,5-d]pyrrolo[2,3-b]pyridin-2-yl)acetamide

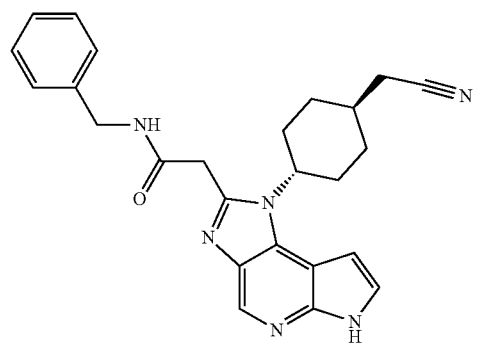 [SMILES: N#CC[C@H]1CC[C@H](n2c(CC(=O)NCc3ccccc3)nc3cnc4[nH]ccc4c32)CC1]

Step A: N-Benzyl-2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetamide. A mixture of ethyl 2-(1-((1r,4r)-4-(cyanomethyl)cyclohexyl)-6-(phenylsulfonyl)-1, 6-dihydroimidazo[4,5-d]pyrrolo[2,3-b]pyridin-2-yl)acetate (Intermediate 3, 65 mg, 0.13 mmol), phenylmethanamine (133 mg, 1.24 mmol), and NH$_4$NO$_3$ (26 mg, 0.33 mmol) was heated at 65° C. for 25 h. The mixture was purified by flash column chromatography (20-100% EtOAc in heptanes, then 10% MeOH in CH$_2$Cl$_2$) to provide the title compound (67 mg, 92%) as a light brown solid. MS (ESI): mass calcd. for C$_{31}$H$_{30}$N$_6$O$_3$S, 566.2; m/z found, 567.2 [M+H]-. $^1$H NMR (400 MHz, CDCl$_3$): δ 8.80 (s, 1H), 8.25-8.20 (m, 2H), 7.85 (d, J=4.0 Hz, 1H), 7.59-7.42 (m, 3H), 7.28-7.16 (m, 5H), 6.83 (d, J=4.0 Hz, 1H), 4.41 (d, J=6.1 Hz, 2H), 3.99 (s, 2H), 2.41 (d, J=6.57 Hz, 2H), 2.18-2.10 (m, 2H), 2.05 (s, 2H), 1.98 (br s, 2H), 1.81 (br s, 2H), 1.51-1.38 (m, 2H).

Step B: N-Benzyl-2-(1-((1r,4r)-4-(cyanomethyl)cyclohexyl)-1,6-dihydroimidazo[4,5-d]pyrrolo[2,3-b]pyridin-2-yl)acetamide. A solution of N-benzyl-2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetamide (75 mg, 0.13 mmol) in THF (1 mL) and MeOH (1 mL) was treated with 3N NaOH (0.10 mL, 0.30 mmol) overnight at room temperature. After removal of solvents in vacuo, the residue was purified by RF-HPLC (10-90% CH$_3$CN in H$_2$O, 0.1% TFA) to provide the title compound as a TFA salt. This material was dissolved in MeOH and passed through a column of StratoSpheres SPE PL-HCO$_3$ MP-Resin (a solid phase extraction acid scavenger cartridge) to remove the TFA to provide the title compound (32 mg, 56%) as an off-white solid. MS (ESI): mass calcd. for C$_{25}$H$_{26}$N$_6$O, 426.2; m/z found, 427.2 [M+H]$^+$. $^1$H NMR (400 MHz, CDCl$_3$) δ=11.25 (br s, 1H), 8.60 (br s, 1H), 8.00 (br s, 1H), 7.48-7.41 (m, 1H), 7.30-7.17 (m, 5H), 6.73 (d, J=2.0 Hz, 1H), 4.66 (br s, 1H), 4.47 (d, J=6.1 Hz, 2H), 4.08 (s, 2H), 2.54 (br s, 2H), 2.42 (d, J=6.6 Hz, 2H), 2.21-2.12 (m, 2H), 2.12-1.94 (m, 1H), 1.93-1.77 (m, 2H), 1.56-1.37 (m, 2H).

Example 49 Synthesis and Characterization 2-((1r,4r)-4-(2-(2-Oxo-2-(pyrrolidin-1-yl)ethyl)imidazo[4,5-d]pyrrolo[2,3-b]pyridin-1(6H)-yl)cyclohexyl)acetonitrile

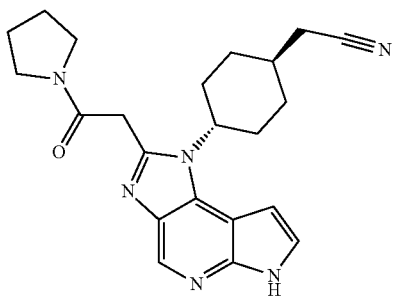 [SMILES: N#CC[C@H]1CC[C@H](n2c(CC(=O)N3CCCC3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (130 mg, 0.362 mmol) and pyrrolidine (17 mg, 0.11 mmol) in DMF (1 mL) were added PyBOP (288 mg, 0.553 mmol) and DIPEA (0.125 mL, 0.724 mmol) and the reaction mixture was stirred at room temperature for 42 h. After removal of the DMF in vacuo, the residue was purified by reverse phase HPLC to provide fractions containing the title compound. These fractions were dissolved in n-BuOH. To this solution was added NaHCO$_3$(aqueous) and the organic layer was separated and the aqueous layer was extracted with n-BuOH (2×) and EtOAc (1×). The organic extracts were dried, filtered, concentrated to dryness, and purified by flash column chromatography to provide the title compound (8 mg, 6% yield). MS (ESI): mass calcd. for C$_{22}$H$_{26}$N$_6$O, 390.2; m/z found, 391.2 [M+H]$^+$. $^1$H NMR (400 MHz, CD$_3$OD) δ=8.53 (s, 1H), 7.48 (d, J=3.5 Hz, 1H), 6.84 (d, J=3.5 Hz, 1H), 4.49 (br s, 1H), 4.26-4.20 (m, 2H), 3.70 (t, J=6.6 Hz, 2H), 3.47 (t, J=7.1 Hz, 2H), 2.65-2.48 (m, 4H), 2.16-1.88 (m, 9H), 1.56-1.42 (m, 2H).

Example 50 Synthesis and Characterization 2-((1r,4r)-4-(2-(3-Hydroxy-3-phenylpyrrolidine-1-carbonyl)imidazo[4,5-d]pyrrolo[2,3-b]pyridin-1(6H)-yl)cyclohexyl)acetonitrile

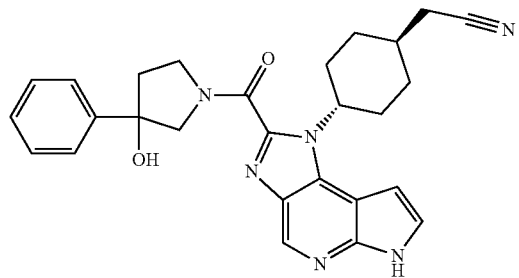 [SMILES: N#CC[C@H]1CC[C@H](n2c(C(=O)N3CCC(O)(c4ccccc4)C3)nc3cnc4[nH]ccc4c32)CC1]

Ethyl 1-((1r,4r)-4-(cyanomethyl)cyclohexyl)-6-(phenylsulfonyl)-1,6-dihydroimidazo[4,5-d]pyrrolo[2,3-b]pyridine-2-carboxylate (Intermediate 6, 100 mg, 0.203 mmol) was mixed with 3-phenylpyrrolin-3-ol (166 mg, 1.01 mmol), and heated at 80° C. After 3 h, the reaction mixture was concentrated. The residue was dissolved into MeOH/THF/NaOH (1 M) (3 mL/3 mL/3 mL) and was heated at 80° C. for 1 h. The reaction was concentrated to dryness and partitioned between CH$_2$Cl$_2$ and H$_2$O (10 mL/10 mL). The organic layer was concentrated to dryness and purified by flash column chromatography (10% MeOH in CH$_2$Cl$_2$) to provide the title compound (12 mg, 12% yield). MS (ESI): mass calcd. for C$_{27}$H$_{28}$N$_6$O$_2$, 468.2; m/z found, 469.3 [M+H]$^+$. $^1$H NMR (500 MHz, CDCl$_3$): δ 12.82-12.41 (m, 1H), 8.74 (d, J=1.3 Hz, 1H), 7.73-7.32 (m, 6H), 6.98-6.68 (m, 1H), 5.18-4.89 (m, 1H), 4.46-3.77 (m, 4H), 2.59-1.89 (m, 12H), 1.59-1.40 (m, 2H).

Example 51 Synthesis and Characterization 2-((1r,4r)-4-(2-(2-Aminopyrimidin-5-yl)imidazo[4,5-d]pyrrolo[2,3-b]pyridin-1(6H)-yl)cyclohexyl)acetonitrile

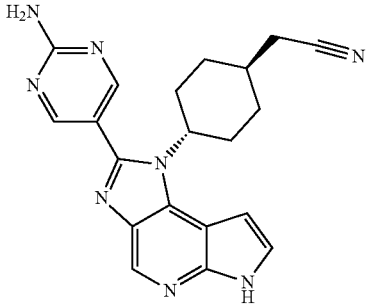 [SMILES: N#CC[C@H]1CC[C@H](n2c(-c3cnc(N)nc3)nc3cnc4[nH]ccc4c32)CC1]

A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 220 mg, 0.501 mmol), 2-aminopyrimidine-5-carbaldehyde (185 mg, 1.50 mmol), sodium dithionite (261 mg, 1.50 mmol), DMSO (2.5 mL), and water (0.15 mL) was heated to 100° C. for 3 hours. Water (20 mL) was added, which caused a precipitate to form and was filtered to collect the precipitate. The precipitate was recrystallized from 10% acetone/CH$_2$Cl$_2$ to provide a crude product (200 mg). This material was dissolved into MeOH/THF/NaOH (1 M) (3 mL/3 mL/3 mL) and was heated at 80° C. for 1 h. The reaction was concentrated to dryness and partitioned between CH$_2$Cl$_2$ and H$_2$O (10 mL/10 mL). The organic layer was concentrated to dryness and purified by flash column chromatography to provide the title compound (40 mg, 21% yield). MS (ESI): mass calcd. for C$_{20}$H$_{20}$N$_8$, 372.2; m/z found, 373.2 [M+H]$^+$. $^1$H NMR (500 MHz, DMSO-d$_6$): δ 11.96 (s, 1H), 8.80-8.38 (m, 3H), 7.52 (d, J=3.4 Hz, 1H), 7.26-7.04 (m, 2H), 6.77 (d, J=3.4 Hz, 1H), 4.54-4.15 (m, 1H), 2.63-2.35 (m, 4H), 2.24-1.85 (m, 5H), 1.52-1.24 (m, 2H).

Example 52 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1s,3r,5R,7S)-3-hydroxyadamantan-1-yl)acetamide

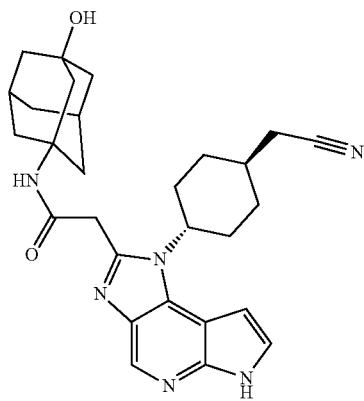 [SMILES: N#CC[C@H]1CC[C@H](n2c(CC(=O)NC34CC5CC(CC(O)(C5)C3)C4)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), (1S,3R,5R,7S)-3-aminoadamantan-1-ol hydrochloride (113 mg, 0.557 mmol), DIPEA (144 mg, 1.11 mmol), and DMF (5 mL) was stirred at 0° C. for 1 h. Then PyBrOP (311 mg, 0.668 mmol) was added and the reaction mixture was stirred at room temperature overnight. The reaction was quenched with 10 mL water and purified by preparative basic HPLC using a Kromasil 150 mm×25 mm, 10 μm column (eluent: water (0.05% ammonia hydroxide v/v)-ACN from 22% to 32%, v/v) to provide the title compound (30.1 mg, 11% yield) as a white solid. MS (ESI): mass calcd. for C$_{28}$H$_{34}$N$_6$O$_2$, 486.3; m/z found, 487.3 [M+H]$^+$. $^1$H NMR (400 MHz, DMSO-d$_6$): δ 11.84 (br s, 1H), 8.49 (s, 1H), 7.93 (br s, 1H), 7.47-7.44 (m, 1H), 6.72-6.68 (m, 1H), 4.51 (s, 1H), 4.49-4.39 (m, 1H), 3.93 (br s, 2H), 2.61 (d, J=5.6 Hz, 2H), 2.41-2.28 (m, 2H), 2.12 (br s, 2H), 2.05-1.92 (m, 5H), 1.89-1.77 (m, 6H), 1.58-1.34 (m, 8H).

Example 53 Synthesis and Characterization 2-((1r,4r)-4-(2-(2-Aminopyrimidin-4-yl)imidazo[4,5-d]pyrrolo[2,3-b]pyridin-1(6H)-yl)cyclohexyl)acetonitrile

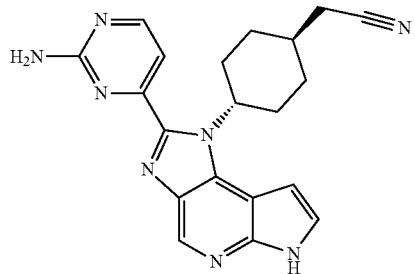 [SMILES: N#CC[C@H]1CC[C@H](n2c(-c3ccnc(N)n3)nc3cnc4[nH]ccc4c32)CC1]

Step A: 2-((1r,4r)-4-(2-(2-(Methylthio)pyrimidin-4-yl)imidazo[4,5-d]pyrrolo[2,3-b]pyridin-1(6H)-yl)cyclohexyl)acetonitrile. A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 400 mg, 1.00 mmol), 2-(methylthio)pyrimidine-4-carbaldehyde (463 mg, 3.00 mmol), sodium dithionite (523 mg, 3.00 mmol), DMSO (2.5 mL), and water (0.15 mL) was heated to 100° C. for 3 hours. Water (20 mL) was added, which caused a precipitate to form and was filtered to collect the precipitate. The precipitate was recrystallized from 10% acetone/CH$_2$Cl$_2$ to provide a crude product (200 mg). This material was dissolved into MeOH/THF/NaOH (1 M) (3 mL/3 mL/3 mL) and was heated at 80° C. for 1 h. The reaction was concentrated to dryness and partitioned between CH$_2$Cl$_2$ and H$_2$O (10 mL/10 mL). The organic layer was concentrated to dryness and purified by flash column chromatography to provide the title compound (40 mg, 21% yield). MS (ESI): mass calcd. for C$_{21}$H$_{21}$N$_7$S, 403.2; m/z found, 404.2 [M+H]$^+$.

Step B: 2-((1r,4r)-4-(2-(2-Aminopyrimidin-4-yl)imidazo[4,5-d]pyrrolo[2,3-b]pyridin-1(6H)-yl)cyclohexyl)acetonitrile. A solution of 2-((1r,4r)-4-(2-(2-(methylthio)pyrimidin-4-yl)imidazo[4,5-d]pyrrolo[2,3-b]pyridin-1(6H)-yl)cyclohexyl)acetonitrile (100 mg, 0.248 mmol) and 3-chlorobenzoperoxoic acid (85.5 mg, 0.496 mmol) in THF (10 mL) was stirred for 3 h. Then NH$_4$OH (5 M, 2 mL) was added and the reaction mixture was heated at 100° C. for 1 h. The reaction was concentrated to dryness and partitioned between CH$_2$Cl$_2$/H$_2$O (5 mL/5 mL). The organic layer was concentrated to dryness and the residue was purified by flash column chromatography (10% MeOH in CH$_2$Cl$_2$) to provide the title compound (10 mg, 11% yield). MS (ESI): mass calcd. for C$_{20}$H$_{20}$N$_8$, 372.2; m/z found, 373.2 [M+H]$^+$. $^1$H NMR (400 MHz, CD$_3$OD): δ 8.67 (s, 1H), 8.46 (d, J=5.1 Hz, 1H), 7.52 (d, J=3.5 Hz, 1H), 7.32 (d, J=5.1 Hz, 1H), 6.90 (d, J=3.5 Hz, 1H), 5.57-5.38 (m, 1H), 2.77-2.58 (m, 2H), 2.53 (d, J=6.3 Hz, 2H), 2.22-2.04 (m, 5H), 1.59-1.39 (m, 2H).

Example 54 Synthesis and Characterization 4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.1]heptane-1-carboxamide

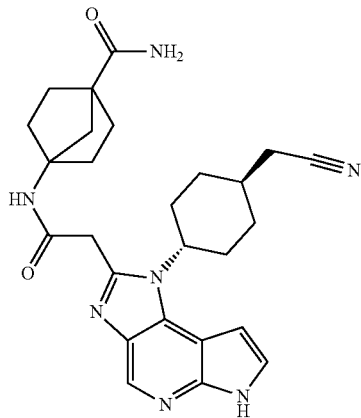 [SMILES: N#CC[C@H]1CC[C@H](n2c(CC(=O)NC34CCC(C(N)=O)(CC3)C4)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), 4-aminobicyclo[2.2.1]heptane-1-carboxamide hydrochloride (106 mg, 0.557 mmol), and DIPEA (0.291 mL, 1.67 mmol) in dry DMF (5 mL) was added PyBrOP (285 mg, 0.612 mmol) at 0° C. The reaction was stirred at room-temperature for 4 h. The mixture was quenched with 10 mL water and was extracted with EtOAc (3×20 mL). Both the organic and water phases were concentrated to provide the crud residue which was purified by preparative basic HPLC using a Waters Xbridge Prep OBD C18 150×30 mm×5 μm column (eluent: 14% to 44% (v/v) $CH_3CN$ and $H_2O$ with 0.05% $NH_3$) to provide the title compound (36.3 mg, 13% yield) as a yellow solid. MS (ESI): mass calcd. for $C_{26}H_{31}N_7O_2$, 473.3; m/z found, 474.2 [M+H]$^+$. $^1$H NMR (400 MHz, DMSO-d$_6$): δ 11.83 (br s, 1H), 8.53-8.46 (m, 2H), 7.48-7.44 (m, 1H), 7.07 (br s, 1H), 6.79 (br s, 1H), 6.70 (br s, 1H), 4.45 (br s, 1H), 3.96 (s, 2H), 2.62-2.57 (m, 2H), 2.40-2.28 (m, 2H), 2.09-1.91 (m, 5H), 1.91-1.74 (m, 6H), 1.73-1.61 (m, 2H), 1.61-1.51 (m, 2H), 1.45-1.32 (m, 2H).

Example 55 Synthesis and Characterization

N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide

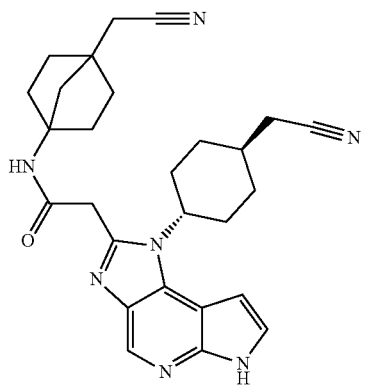 [SMILES: N#CCC12CCC(NC(=O)Cc3nc4cnc5[nH]ccc5c4n3[C@H]3CC[C@H](CC#N)CC3)(CC1)C2]

Step A: Dimethyl cyclopentane-1,3-dicarboxylate. A solution of cyclopentane-1,3-dicarboxylic acid (70.0 g, 443 mmol) and anhydrous methanol (300 mL) was cooled to 0° C. in an ice water bath. Concentrated sulfuric acid (14 mL) was added dropwise, maintaining the temperature at <15° C. After the addition, the reaction was heated to 90° C. and stirred overnight. The reaction was cooled to room temperature and concentrated to dryness. The residue was treated with MTBE (500 mL) and $H_2O$ (100 mL). The aqueous layer was separated and extracted with MTBE (2×100 mL). The combined organic extracts were washed with saturated sodium bicarbonate (2×100 mL), brine (100 mL), dried over anhydrous $MgSO_4$, filtered, and concentrated to dryness to provide the title compound (72.5 g, 88%) as a pale yellow oil. $^1$H NMR (400 MHz, CDCl$_3$) δ 3.65 (s, 6H), 2.84-2.72 (m, 2H), 2.26-2.17 (m, 1H), 2.11-2.02 (m, 1H), 1.96-1.88 (m, 4H).

Step B: Dimethyl bicyclo[2.2.1]heptane-1,4-dicarboxylate. n-Butyllithium (2.5 M in hexane, 419.0 mL, 1048 mmol) was added slowly to a solution of diisopropylamine (152 mL, 1090 mmol) and anhydrous THF (1000 mL) at −78° C. (dry ice/acetone) under $N_2$. Next, the reaction was stirred for 0.5 hours at 0° C. before cooling to −78° C. DMPU (404 mL, 3350 mmol) was added via an addition funnel. Then a solution of dimethyl cyclopentane-1,3-dicarboxylate (78.0 g, 419 mmol) and anhydrous THF (300 mL) was added slowly via an addition funnel. The reaction was warmed to 0° C. and stirred for 30 minutes, then cooled to −78° C. and treated with a solution of 1-bromo-2-chloroethane (59.0 mL, 712 mmol) and anhydrous THF (200 mL). The reaction was allowed to warm slowly to room-temperature and was stirred for 12 hours at room-temperature. The reaction was quenched with saturated aqueous ammonium chloride (400 mL). The reaction was diluted with ethyl acetate (500 mL), the organic layer separated, and the aqueous layer was further extracted with ethyl acetate (2×500 mL). The combined organic extracts were washed with brine (2×300 mL), dried over anhydrous $MgSO_4$, filtered, and concentrated to dryness. The residue was filtered through a pad of silica gel and washed with ethyl acetate (2000 mL). The filtrate was concentrated to dryness and the residue was purified by flash column chromatography (petroleum ether/ethyl acetate, 30:1 to 20:1, gradient elution) to provide the title compound (48.5 g, 54%) as white solid. $^1$H NMR (400 MHz, CDCl$_3$): δ 3.69 (s, 6H), 2.08-1.99 (m, 4H), 1.91 (s, 2H), 1.73-1.63 (m, 4H).

Step C: 4-(Methoxycarbonyl)bicyclo[2.2.1]heptane-1-carboxylic acid. A methanol (80 mL) solution of sodium hydroxide (5.145 g, 128.6 mmol) was added slowly to a solution of dimethyl bicyclo[2.2.1]heptane-1,4-dicarboxylate (27.3 g, 129 mmol) and THF (700 mL) at 0° C. and the reaction mixture was stirred at room temperature overnight. The reaction was concentrated to dryness and the residue was triturated with MTBE (15 mL). The precipitate was collected by filtration, washed with MTBE (5 mL), and dissolved in 100 mL of $H_2O$. The solution was acidified to pH=4 with 2 M HCl. The precipitate was collected by filtration and dried under vacuum to provide the title compound (13.0 g, 51.0%) as white solid. The filtrate was extracted with ethyl acetate (3×75 mL) and the combined organic extracts were washed with brine (50 mL), dried over anhydrous $MgSO_4$, filtered and concentrated to dryness to provide a second fraction of the title compound (8.0 g, 31%) as a white solid. $^1$H NMR (400 MHz, DMSO-d$_6$) δ 12.21 (br s, 1H), 3.59 (s, 3H), 1.94-1.86 (m, 4H), 1.74 (s, 2H), 1.61-1.54 (m, 4H).

Step D: Methyl 4-(((benzyloxy)carbonyl)amino)bicyclo[2.2.1]heptane-1-carboxylate. Diphenylphosphoryl azide (17.1 mL, 78.6 mmol) was added to a solution of 4-(methoxycarbonyl)bicyclo[2.2.1]heptane-1-carboxylic acid (13.0 g, 65.6 mmol), DIPEA (22.8 mL, 131 mmol), and anhydrous toluene (200 mL) and the reaction mixture was stirred at 110° C. for 2 hours. The reaction was cooled to 50° C. and benzyl alcohol (13.6 mL, 131 mmol) was added and the reaction mixture was stirred at 110° C. overnight. The reaction was concentrated to dryness, dissolved in MTBE (250 mL) and washed with $H_2O$ (150 mL). The organic layer was separated and the aqueous layer was extracted with MTBE (2×100 mL). The combined organic extracts were washed with brine (100 mL), dried over anhydrous $MgSO_4$, filtered, and concentrated to dryness. The residue was purified by flash column chromatography (petroleum ether/ethyl acetate, 10:1 to 5:1, gradient elution) to provide an impure product (28.5 g) as pale yellow oil. The product was further purified by preparative acidic HPLC using a Phenomenex Synergi Max-RP 250×50 mm x 10 μm column (eluent: 38% to 68% (v/v) $CH_3CN$ and $H_2O$ with 0.1% TFA). The pure fractions were combined and the volatiles were removed under vacuum. The residue was diluted with $H_2O$ (80 mL), the pH of the solution was adjusted to pH=8 with saturated aqueous $NaHCO_3$ solution, and the resulting solution was extracted with $CH_2Cl_2$ (3×100 mL). The combined organic extracts were washed with brine (75 mL), dried over anhydrous $MgSO_4$, filtered, and concentrated to dryness to provide the title compound (17.3 g, 85%) as a colorless oil. MS (ESI): mass calcd. for $C_{17}H_{21}NO_4$, 303.2; m/z found, 303.9 $[M+H]^+$. $^1H$ NMR (400 MHz, DMSO-$d_6$) δ 7.56 (br s, 1H), 7.37-7.30 (m, 5H), 4.97 (s, 2H), 3.58 (s, 3H), 1.90-1.80 (m, 6H), 1.65-1.59 (m, 4H).

Step E: Methyl 4-((tert-butoxycarbonyl)amino)bicyclo[2.2.1]heptane-1-carboxylate. A mixture of methyl 4-(((benzyloxy)carbonyl)amino)bicyclo[2.2.1]heptane-1-carboxylate (17 g, 56 mmol), di-tert-butyl dicarbonate (18.35 g, 84.06 mmol), MeOH (200 mL) and wet Pd/C (4 g, 10 wt. %, 50% $H_2O$) was added to a 500 mL round-bottom flask with a hydrogen balloon (13 psi) and was stirred at room temperature for 72 hours. The catalyst was filtered off and the filtrate was concentrated to dryness. The residue was purified by flash column chromatography (petroleum ether/ethyl acetate, 20:1 to 1:1, gradient elution) to provide the title compound (12.0 g, 79.5%) as a white solid. $^1H$ NMR (400 MHz, DMSO-$d_6$) δ 7.04 (br s, 1H), 3.57 (s, 3H), 1.93-1.78 (m, 4H), 1.77 (s, 2H), 1.63-1.53 (m, 4H), 1.35 (s, 9H).

Step F: 4-((tert-Butoxycarbonyl)amino)bicyclo[2.2.1]heptane-1-carboxylic acid. To a solution of methyl 4-((tert-butoxycarbonyl)amino)bicyclo[2.2.1]heptane-1-carboxylate (5.0 g, 19 mmol), THF (40 mL) and MeOH (20 mL) was added aqueous sodium hydroxide (1.0 M, 46.4 mL, 46.4 mmol) at room temperature and the reaction mixture was stirred at room temperature for 24 hours. The reaction was concentrated to dryness and the residue was diluted with $H_2O$ (20 mL), acidified to pH=4-5 with 2 M HCl to provide a precipitate. The precipitate was dissolved in 150 mL of ethyl acetate, washed with brine (45 mL), dried over anhydrous $Na_2SO_4$, filtered, and concentrated to dryness to provide the title compound (4.74 g, 100% yield) as white solid, which was used directly in the next step. $^1H$ NMR (400 MHz, DMSO-$d_6$) δ 12.06 (br s, 1H), 7.00 (br s, 1H), 1.87-1.73 (m, 6H), 1.58-1.50 (m, 4H), 1.35 (s, 9H).

Step G: tert-Butyl (4-(hydroxymethyl)bicyclo[2.2.1]heptan-1-yl)carbamate. A solution of borane-tetrahydrofuran complex (1.0 M, 37.1 mL, 37.1 mmol) was added slowly to a solution of 4-(((tert-butoxycarbonyl)amino)bicyclo[2.2.1]heptane-1-carboxylic acid (4.74 g, 18.6 mmol) and anhydrous THF (50 mL) at 0° C. under a nitrogen atmosphere. After the addition was complete, the reaction was stirred at room temperature overnight. Water (30 mL) was added to the mixture slowly and it was stirred for additional 30 minutes. The reaction was concentrated to dryness and the residue was diluted with ethyl acetate (50 mL), washed with $H_2O$ (15 mL) and brine (10 mL), dried over anhydrous $Na_2SO_4$, filtered, and concentrated to dryness. The residue was purified by flash column chromatography (petroleum ether/ethyl acetate, 2:1) to provide the title compound (4.0 g, 89% yield) as white solid. TLC (petroleum ether/ethyl acetate, 2:1), $R_f$=0.5. $^1H$ NMR (400 MHz, DMSO-$d_6$): 6.88 (br s, 1H), 4.38 (t, J=5.4 Hz, 1H), 3.36 (d, J=5.4 Hz, 2H), 1.73 (br s, 2H), 1.64-1.49 (m, 4H), 1.42 (s, 2H), 1.39-1.33 (m, 9H), 1.25-1.16 (m, 2H).

Step H: (4-((tert-Butoxycarbonyl)amino)bicyclo[2.2.1]heptan-1-yl)methyl methanesulfonate. Pyridine (2.7 mL, 33 mmol) was added to a solution of tert-butyl (4-(hydroxymethyl)bicyclo[2.2.1]heptan-1-yl)carbamate (2.0 g, 8.3 mmol) and anhydrous $CH_2Cl_2$ (30 mL). The reaction was cooled to 0° C. and methansulfonyl chloride (2.0 mL, 25.0 mmol) was added and the mixture was stirred for 3 hours at room temperature. The reaction was diluted with $CH_2Cl_2$ (50 mL) and water (30 mL). The organic layer was separated, washed with brine (15 mL), dried over anhydrous $MgSO_4$, filtered and concentrated to dryness. The residue was purified flash column chromatography (petroleum ether/ethyl acetate, 5:1 to 1:1, gradient elution) to provide the title compound (2.58 g, 97%) as white solid. TLC (petroleum ether/ethyl acetate, 1:1), $R_f$=0.85. $^1H$ NMR (400 MHz, $CDCl_3$) 4.73 (br s, 1H), 4.21 (s, 2H), 2.98 (s, 3H), 1.93-1.90 (m, 2H), 1.78-1.62 (m, 6H), 1.53-1.34 (m, 11H).

Step I: tert-Butyl (4-(cyanomethyl)bicyclo[2.2.1]heptan-1-yl)carbamate. To a solution of (4-((tert-butoxycarbonyl)amino)bicyclo[2.2.1]heptan-1-yl)methyl methanesulfonate (2.58 g, 8.07 mmol) and DMSO (25 mL) was added sodium cyanide (1.20 g, 24.5 mmol). The reaction was heated to 100° C. and stirred for 24 hours. The reaction was diluted with 50 mL of water and extracted with ethyl acetate (3×40 mL). The combined organic extracts were washed with brine (20 mL), dried over anhydrous $Na_2SO_4$, filtered, and concentrated to dryness. The residue was purified by flash column chromatography (petroleum ether/ethyl acetate, 5:1) to provide the title compound (1.8 g, 89% yield) as white solid. $^1H$ NMR (400 MHz, DMSO-$d_6$): δ 7.00 (br s, 1H), 2.67 (s, 2H), 1.82 (br s, 2H), 1.69-1.52 (m, 6H), 1.47-1.40 (m, 2H), 1.37 (s, 9H).

Step J: 2-(4-Aminobicyclo[2.2.1]heptan-1-yl)acetonitrile hydrochloride. To a suspension of tert-butyl (4-(cyanomethyl)bicyclo[2.2.1]heptan-1-yl)carbamate (850 mg, 3.40 mmol) and ethyl acetate (2 mL) at 0° C. was added a solution of HCl in ethyl acetate (4.0 M, 10 mL, 40 mmol). After stirring at room temperature for 2 hours, the mixture was concentrated under reduced pressure to dryness. The residue was triturated with MTBE (5 mL) and the suspension was isolated via filtration. The filter cake was washed with MTBE (1 mL) and dried under reduced pressure to afford the title compound (450 mg, 71%) as a white solid. MS (ESI): mass calcd. for $C_9H_{14}N_2$ 150.12 m/z, found 151.1 $[M+H]^+$. $^1H$ NMR (400 MHz, DMSO-$d_6$) δ 8.59 (br.s., 3H), 2.78 (s, 2H), 1.90-1.77 (m, 2H), 1.74-1.62 (m, 4H), 1.60 (s, 2H), 1.56-1.46 (m, 2H).

Step K: N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide. To a solution of sodium 2-(1-((1r,4r)-4-(cyanomethyl)cyclohexyl)-1, 6-dihydroimidazo[4,5-d]pyrrolo[2,3-b]pyridin-2-yl)acetate (Intermediate 4, 300 mg, 0.835 mmol), 2-(4-aminobicyclo[2.2.1]heptan-1-yl)acetonitrile hydrochloride (138 mg, 0.918 mmol), and DIPEA (0.291 mL, 1.67 mmol) in dry DMF (6 mL) was added PyBrOP (428 mg, 0.918 mmol) at 0° C. The reaction was stirred at room-temperature for 12 h. The mixture was quenched with 10 mL water and was extracted with EtOAc (3×20 mL). The combined organic phases were washed with brine, dried over anhydrous $Na_2SO_4$, filtered, and concentrated to dryness. The residue was purified by preparative HPLC using a Xtimate $C_{18}$ 150×25 mm×5 μm column (eluent: 23% to 33% (v/v) $CH_3CN$ and $H_2O$ with 10 mM $NH_4HCO_3$) and by preparative TLC (dichloromethane:methanol=15:1) to provide the title compound (36.6 mg, 9% yield) as a white solid. MS (ESI): mass calcd. for $C_{27}H_{31}N_7O$, 469.3; m/z found, 470.2 [M+H]$^+$. $^1$H NMR (400 MHz, $CD_3OD$): δ 8.53 (s, 1H), 7.48 (d, J=4.0 Hz, 1H), 6.84 (d, J=4.0 Hz, 1H), 4.47 (br s, 1H), 4.07-4.02 (m, 2H), 2.63 (s, 2H), 2.61-2.50 (m, 4H), 2.18-1.98 (m, 7H), 1.94-1.84 (m, 2H), 1.82 (s, 2H), 1.79-1.68 (m, 2H), 1.62-1.43 (m, 4H).

Example 56 Synthesis and Characterization 2-((1r,4r)-4-(2-(1H-Imidazol-2-yl)imidazo[4,5-d]pyrrolo[2,3-b]pyridin-1(6H)-yl)cyclohexyl)acetonitrile

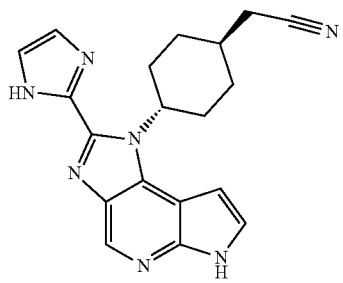 [SMILES: N#CC[C@H]1CC[C@H](n2c(-c3ncc[nH]3)nc3cnc4[nH]ccc4c32)CC1]

Step A. 2-((1r,4r)-4-(2-(1H-Imidazol-2-yl)-6-(phenylsulfonyl)imidazo[4,5-d]pyrrolo[2,3-b]pyridin-1(6H)-yl)cyclohexyl)acetonitrile. To a 20 mL microwave vial was added 2-((1r,4r)-4-((5-nitro-1-(phenylsulfonyl)-1H-pyrrolo[2,3-b]pyridin-4-yl)amino)cyclohexyl)acetonitrile (Intermediate 1, 215 mg, 0.489 mmol) and imidazole-2-carboxaldehyde (123 mg, 1.25 mmol) as solids. DMSO (2.4 mL), MeOH (2.4 mL), and distilled water (1.2 mL) were all added resulting a yellow mixture. Sodium hydrosulfite (282 mg, 1.62 mmol) was added as a solid and the vial was sealed. The vial was placed into a preheated 100° C. heating block for 2 h. The reaction was filtered to collect the solids, which were analyzed and shown to contain the product and a major impurity. The reaction was purified by flash column chromatography to provide the title compound (47 mg, 20% yield) as a tan colored solid. MS (ESI): mass calcd. for $C_{25}H_{23}N_7O_2S$, 485.2; m/z found, 486.2 [M+H]$^+$.

Step B: 2-((1r,4r)-4-(2-(1H-Imidazol-2-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(2-(1H-Imidazol-2-yl)-6-(phenylsulfonyl)imidazo[4,5-d]pyrrolo[2,3-b]pyridin-1(6H)-yl)cyclohexyl)acetonitrile (215 mg, 0.49 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and the residue was purified by flash column chromatography (eluent=0-5% 2 N $NH_3$ in MeOH/EA, 12 CV) to provide the title compound (15 mg, 45% yield). MS (ESI): mass calcd. for $C_{19}H_{19}N_7$, 345.2; m/z found, 346.2 [M+H]$^+$. $^1$H NMR (500 MHz, DMSO-$d_6$): δ 13.20 (s, 1H), 12.00 (s, 1H), 8.65 (s, 1H), 7.53 (t, J=3.0 Hz, 1H), 7.40-7.18 (m, 2H), 6.81 (dd, J=3.6, 1.9 Hz, 1H), 6.34 (s, 1H), 2.62 (d, J=6.2 Hz, 2H), 2.58-2.43 (m, 2H), 2.14-1.91 (m, 5H), 1.49-1.31 (m, 2H).

Example 57 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2,2,2-trifluoroethyl)acetamide

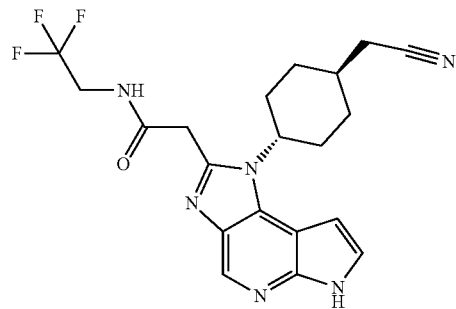 [SMILES: N#CC[C@H]1CC[C@H](n2c(CC(=O)NCC(F)(F)F)nc3cnc4[nH]ccc4c32)CC1]

PyBrOP (311 mg, 0.670 mmol) was added to a 0° C. (ice/water) solution consisting of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.560 mmol), 2,2,2-trifluoroethylamine (55 mg, 0.56 mmol), N,N-diisopropylethylamine (144 mg, 1.11 mmol), and dimethylformamide (10 mL). The mixture was stirred overnight with gradual warming to room temperature before quenching with $H_2O$ (10 mL) and extracting with ethyl acetate (20 mL×3). The combined organic extracts were dried over anhydrous $Na_2SO_4$, filtered, and concentrated to dryness under reduced pressure, purified by preparative HPLC using a DuraShell 150 mm×25 mm, 5 μm column (eluent: 20% to 50% (v/v) $CH_3CN$ and $H_2O$ with 0.05% $NH_3$) to afford pure product. The product was lyophilized to dryness to afford the title compound (14 mg, 6%) as a white solid. LCMS (ESI): RT=3.55 min, mass calcd. for $C_{20}H_{21}F_3N_6O$: 418.17 m/z, found 419.1 [M+H]$^+$. Analytical reverse phase LC-MS was carried out using a Phenomenex Luna-$C_{18}$, 50×2 mm×5 m column with a flow rate of 0.8 mL/min, eluting with a gradient of 0% to 85% acetonitrile containing 0.05% TFA (solvent B) and water containing 0.1% TFA (solvent A). The eluent composition was kept at 100% A for 1 minute, followed by increasing to 60% B over the course of 4 minutes. The eluent was further increased to 85% B over the course of 2.5 minutes before returning to 100% A over the course of 2 minutes. Total run time was 10 minutes. $^1$H NMR (400 MHz, DMSO-$d_6$) δ 11.86 (br s, 1H), 9.03-8.95 (m, 1H), 8.51 (s, 1H), 7.50-7.46 (m, 1H), 6.75-6.69 (m, 1H), 4.53-4.39 (m, 1H), 4.12 (s, 2H), 4.04-3.92 (m, 2H), 2.59 (d, J=6.0 Hz, 2H), 2.43-2.26 (m, 2H), 2.11-1.91 (m, 5H), 1.48-1.30 (m, 2H).

Example 58 Synthesis and Characterization 4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.2]octane-1-carboxamide

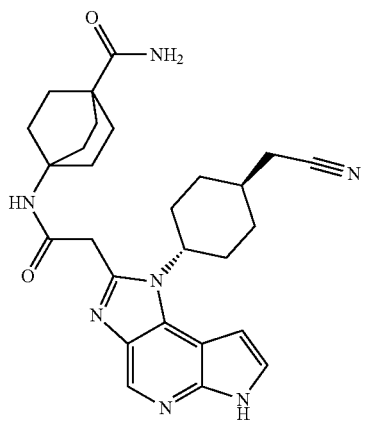 [SMILES: N#CC[C@H]1CC[C@H](n2c(CC(=O)NC34CCC(C(N)=O)(CC3)CC4)nc3cnc4[nH]ccc4c32)CC1]

Step A: tert-Butyl (4-(chlorocarbonyl)bicyclo[2.2.2]octan-1-yl)carbamate. Oxalyl chloride (0.61 mL, 7.2 mmol) was added slowly to a solution of 4-((tert-butoxycarbonyl)amino)bicyclo[2.2.2]octane-1-carboxylic acid (1.3 g, 4.8 mol) and anhydrous $CH_2Cl_2$ (30 mL) at 0° C. Then 4 drops of DMF was added and the reaction was stirred for 1.5 hours at 0° C. The reaction was concentrated to dryness under reduced pressure to provide the title compound (1.36 g, 98% yield) as a white solid, which was used in the next step without further purification.

Step B: tert-Butyl (4-carbamoylbicyclo[2.2.2]octan-1-yl)carbamate. tert-Butyl (4-(chlorocarbonyl)bicyclo[2.2.2]octan-1-yl)carbamate (1.36 g, 4.73 mmol) and anhydrous $CH_2Cl_2$ (40 mL) was added to a 100 mL three-neck flask and was cooled to 0° C. (ice/water). Ammonia gas was bubbled through the reaction for 25 minutes and it was stirred for 5 minutes at room-temperature before diluting with water (20 mL). The organic layer was separated and the aqueous layer was extracted with $CH_2Cl_2$ (15 mL×2). The combined organic extracts were washed with water (25 mL), brine (25 mL), dried over anhydrous $Na_2SO_4$, filtered, and concentrated to dryness to provide the title compound (260 mg, 20% yield), which was used without further purification. $^1H$ NMR (400 MHz, DMSO-$d_6$) δ 6.89 (br. s., 1H), 6.66 (br. s., 1H), 6.36 (br.s., 1H), 1.73-1.59 (m, 12H), 1.32 (s, 9H).

Step C: 4-Aminobicyclo[2.2.2]octane-1-carboxamide hydrochloride. To a solution of tert-butyl (4-carbamoylbicyclo[2.2.2]octan-1-yl)carbamate (260 mg, 0.969 mmol) in $CH_2Cl_2$ (5 mL) was added HCl in ethyl acetate (4 M, 4 mL) at 0° C. and was stirred at 0° C. for 1 hour. The reaction was concentrated to dryness, dissolved in water (5 mL), and washed with ethyl acetate (5 mL×2). The water phase was concentrated to dryness and lyophilized to provide the title compound (150 mg, 75% yield) as white solid. $^1H$ NMR (400 MHz, DMSO-$d_6$): δ 8.23 (br s, 3H), 7.05 (br s, 1H), 6.82 (br s, 1H), 1.71 (br s, 12H).

Step D: 4-(2-(1-((1r,4r)-4-(Cyanomethyl)cyclohexyl)-1,6-dihydroimidazo[4,5-d]pyrrolo[2,3-b]pyridin-2-yl)acetamido)bicyclo[2.2.2]octane-1-carboxamide. A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), 4-aminobicyclo[2.2.2]octane-1-carboxamide hydrochloride (114 mg, 0.557 mmol), and DIPEA (0.291 mL, 1.67 mmol) in dry DMF (5 mL) was added PyBrOP (285 mg, 0.612 mmol) at 0° C. The reaction was stirred at room-temperature for 15 h. The mixture was quenched with 10 mL water and was extracted with EtOAc (3×20 mL). Both the organic and water phases were concentrated and the resulting residue was purified by preparative basic HPLC using a Waters Xbridge Prep OBD C18 150×30 mm×5 μm column (eluent: 14% to 44% (v/v) MeOH and $H_2O$ with 0.05% $NH_3$) to provide the title compound (39.5 mg, 14% yield) as a yellow solid. MS (ESI): mass calcd. for $C_{27}H_{33}N_7O_2$, 487.3; m/z found, 488.2 $[M+H]^+$. $^1H$ NMR (400 MHz, DMSO-$d_6$): δ 11.83 (br s, 1H), 8.48 (s, 1H), 7.90 (br s, 1H), 7.48-7.44 (m, 1H), 6.94 (br s, 1H), 6.74-6.67 (m, 2H), 4.41 (br s, 1H), 3.92 (s, 2H), 2.63-2.57 (m, 2H), 2.39-2.28 (m, 2H), 2.08-1.91 (m, 5H), 1.90-1.78 (m, 6H), 1.78-1.66 (m, 6H), 1.44-1.32 (m, 2H).

Example 59 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(3-hydroxy-3-methylbutyl)acetamide

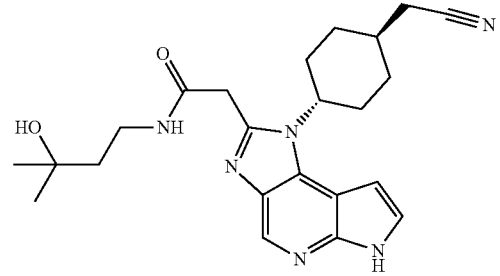 [SMILES: CC(C)(O)CCNC(=O)Cc1nc2cnc3[nH]ccc3c2n1[C@H]1CC[C@H](CC#N)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), 4-amino-2-methylbutan-2-ol (57.4 mg, 0.557 mmol), PyBrOP (311 mg, 0.668 mmol), DIPEA (144 mg, 1.11 mmol), and DMF (10 mL) was stirred at room temperature overnight. The mixture was quenched with 20 mL water and extracted with EtOAc (3×20 mL). The combined organic layers were dried over anhydrous $MgSO_4$ and concentrated to dryness. The residue was purified by preparative basic HPLC using a DuraShell 150 mm×25 mm, 5 μm column (eluent: 8% to 38% (v/v) $CH_3CN$ and $H_2O$ with 0.05% $NH_3$) to provide the title compound (15.2 mg, 6% yield) as a white solid. MS (ESI): mass calcd. for $C_{23}H_{30}N_6O_2$, 422.2; m/z found, 423.2 $[M+H]^+$. $^1H$ NMR (400 MHz, DMSO-$d_6$): δ 11.55 (br s, 1H), 8.50 (s, 1H), 8.01-7.53 (m, 1H), 7.47-7.41 (m, 1H), 6.76-6.71 (m, 1H), 4.59-4.48 (m, 1H), 4.05-3.97 (m, 1H), 3.98 (br s, 2H), 3.27-3.18 (m, 2H), 2.59-2.56 (m, 2H), 2.42-2.32 (m, 2H), 2.08-1.97 (m, 5H), 1.65-1.57 (m, 2H), 1.51-1.37 (m, 2H), 1.16-1.10 (m, 6H).

Example 60 Synthesis and Characterization 2-((1r,4r)-4-(2-(1H-Pyrazol-3-yl)imidazo[4,5-d]pyrrolo[2,3-b]pyridin-1(6H)-yl)cyclohexyl)acetonitrile

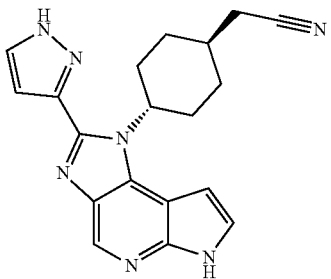 [SMILES: N#CC[C@H]1CC[C@H](n2c(-c3cc[nH]n3)nc3cnc4[nH]ccc4c32)CC1]

Step A: 2-((1r,4r)-4-(6-(Phenylsulfonyl)-2-(1H-pyrazol-3-yl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 150 mg, 0.341 mmol) and 1H-pyrazole-3-carbaldehyde (54 mg, 0.56 mmol) as solids. DMSO (1.7 mL), MeOH (1.7 mL) and distilled water (0.9 mL) were added resulting a yellow mixture. Sodium hydrosulfite (134 mg, 0.770 mmol) was added as a solid and the vial sealed. The vial was placed into a preheated 100° C. heating block and heated for 3 h. The vial was cooled to room temperature and the reaction was added to 50 mL of water with stirring. A brown solid formed and was collected by filtration and was dried overnight. The residue was purified by flash column chromatography to provide the title compound (84 mg, 51% yield). MS (ESI): mass calcd. for $C_{25}H_{23}N_7O_2S$, 485.57; m/z found, 485.9 [M+H]$^+$.

Step B: 2-((1r,4r)-4-(2-(1H-Pyrazol-3-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(6-(Phenylsulfonyl)-2-(1H-pyrazol-3-yl)imidazo[4,5-d]pyrrolo[2,3-b]pyridin-1(6H)-yl)cyclohexyl)acetonitrile (84 mg, 0.17 mmol) instead of 2-(1-((1r,4r)-4-(Cyanomethyl)cyclohexyl)-6-(phenyl sulfonyl)-1,6-dihydroimidazo[4,5-d]pyrrolo[2,3-b]pyridin-2-yl)-N-(2-hydroxy-2-methylpropyl)acetamide and the residue was purified by flash column chromatography (0-10% 2 N $NH_3$ in MeOH/DCM) to provide the title compound (21 mg, 35% yield). MS (ESI): mass calcd. for $C_{19}H_{19}N_7$, 345.4; m/z found, 345.9 [M+H]$^+$. $^1$H NMR (500 MHz, CD$_3$OD): δ 8.61 (s, 1H), 7.86 (d, J=2.4 Hz, 1H), 7.51 (d, J=3.5 Hz, 1H), 6.94 (d, J=2.4 Hz, 1H), 6.90 (d, J=3.5 Hz, 1H), 5.78-5.42 (m, 1H), 2.72-2.59 (m, 2H), 2.53 (d, J=6.0 Hz, 2H), 2.19-1.97 (m, 5H), 1.55-1.37 (m, 2H).

Example 61 Synthesis and Characterization

EZ)—N-((1-((1r,4r)-4-(Cyanomethyl)cyclohexyl)-1,6-dihydroimidazo[4,5-d]pyrrolo[2,3-b]pyridin-2-yl)methyl)-N-hydroxyisobutyrimidamide

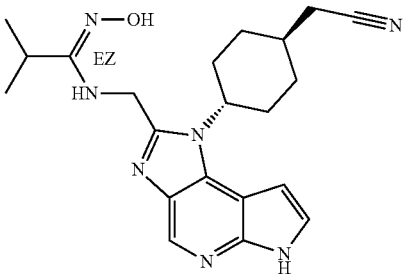 [SMILES: CC(C)/C(=N/O)NCc1nc2cnc3[nH]ccc3c2n1[C@H]1CC[C@H](CC#N)CC1]

Step A: Isobutyraldehyde oxime. A mixture of isobutyraldehyde (2.00 g, 27.7 mmol), hydroxylamine hydrochloride (5.78 g, 83.2 mmol), sodium acetate (6.83 g, 83.2 mmol), ethanol (100 mL), and water (20 mL) was stirred at 70° C. for 10 h. EtOH was removed under reduced pressure and water (20 mL) was added. The mixture was extracted with ethyl acetate (30 mL×2). The combined extracts were dried over anhydrous Na$_2$SO$_4$, filtered, and evaporated to dryness under reduced pressure to give the title compound as a colorless oil (2.00 g, 83% yield, contained 30% of isomer). $^1$H NMR (400 MHz, CDCl$_3$) δ 7.38 (d, J=5.6 Hz, 1H), 2.56-2.45 (m, 1H), 1.09 (d, J=7.2 Hz, 6H). Isomer: $^1$H NMR (400 MHz, CDCl$_3$) δ 6.54 (d, J=7.2 Hz, 1H), 3.27-3.16 (m, 1H), 1.07 (d, J=6.4 Hz, 6H).

Step B: N-Hydroxyisobutyrimidoyl chloride. A mixture of isobutyraldehyde oxime (2.0 g, 23 mmol), N-chlorosuccinimide (6.1 g, 46 mmol), and DMF (20 mL) was stirred for 2 h at 10° C. under N$_2$. Water (20 mL) was added, and the mixture was extracted with ethyl acetate (20 mL). The extract was dried over anhydrous Na$_2$SO$_4$, filtered, and evaporated to dryness under reduced pressure. The residue was purified by flash column chromatography (ethyl acetate in petroleum ether, 0-15%) to afford the title compound as a colorless oil (1.0 g, 32%). 1H NMR (400 MHz, CDCl$_3$) δ 7.70 (s, 1H), 2.87-2.75 (m, 1H), 1.21 (d, J=7.2 Hz, 6H).

Step C: (EZ)—N-((1-((1r,4r)-4-(Cyanomethyl)cyclohexyl)-1,6-dihydroimidazo[4,5-d]pyrrolo[2,3-b]pyridin-2-yl)methyl)-N-hydroxyisobutyrimidamide. A solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 200 mg, 0.580 mmol), N-hydroxyisobutyrimidoyl chloride (71 mg, 0.58 mmol), triethylamine (0.243 mL, 1.74 mmol), and DMF (5 mL) was stirred for 2 h at 10° C. The reaction was concentrated to dryness and the residue was washed with acetonitrile (5 mL) by filtration to provide the title compound as a white solid (15 mg, 6%). The filtrate was purified by preparative basic HPLC using a Gemini 150 mm×25 mm, 5 μm column (eluent: 20% to 50% (v/v) CH$_3$CN and H$_2$O with 0.05% NH$_3$) and then by preparative acidic HPLC with a Phenomenex Gemini 150 mm×25 mm, 10 μm column (eluent: 5% to 35% (v/v) CH$_3$CN and aqueous HCl (0.006 N). The pure fractions from the second HPLC purification were collected, adjusted to pH=7-8 with saturated aqueous NaHCO$_3$, and the volatiles were removed under reduced pressure. The precipitated white solid was filtered, washed with water (2 mL×3), and lyophilized to dryness to provide a second portion of the title compound (40 mg, 17% yield). MS (ESI): mass calcd. for $C_{21}H_{27}N_7O$, 393.23; m/z found, 394.1 [M+H]$^+$. $^1$H NMR (400 MHz, DMSO-d$_6$): δ 11.88 (s, 1H), 9.20 (br s, 1H), 8.56 (s, 1H), 7.47 (d, J=3.2 Hz, 1H), 6.72 (d, J=3.2 Hz, 1H), 6.23 (t, J=5.6 Hz, 1H), 4.74-4.59 (m, 3H), 2.89-2.80 (m, 1H), 2.60 (d, J=6.0 Hz, 2H), 2.42-2.25 (m, 2H), 2.07-1.87 (m, 5H), 1.56-1.42 (m, 2H), 1.00 (d, J=6.4 Hz, 6H).

Example 62 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(1-isobutylpiperidin-4-yl)acetamide

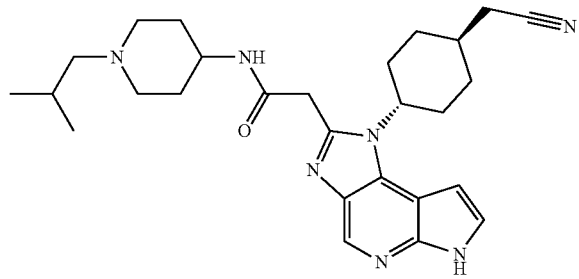 [SMILES: CC(C)CN1CCC(NC(=O)Cc2nc3cnc4[nH]ccc4c3n2[C@H]2CC[C@H](CC#N)CC2)CC1]

A mixture of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 300 mg, 0.59 mmol) and 1-isobutylpiperidin-4-amine (976 mg, 5.93 mmol) was heated at 125° C. in the microwave for 22 hr. The reaction was cooled to room temp, then 1,4-dioxane (2.37 mL) and 3N KOH (1.58 mL) was added. The vial was heated at 80° C. for 2 h in the microwave, then purified by basic HPLC using a Xbridge Prep OBD $C_{18}$ 50 mm×100 mm, 5 μm column (eluent=0-100% aq NH$_4$OH/ACN (10 min)) to yield the title compound (111 mg, 39% yield). MS (ESI): mass calcd. for $C_{27}H_{37}N_7O$, 475.31; m/z found, 476.3 [M+H]$^+$. $^1$H NMR (500 MHz, CD$_3$OD): δ 8.54 (s, 1H), 7.49 (d, J=3.5 Hz, 1H), 6.86 (d, J=3.5 Hz, 1H), 4.54 (s, 1H), 4.11-4.04 (m, 1H), 3.75-3.64 (m, 1H), 2.89 (d, J=11.8 Hz, 2H), 2.63-2.54 (m, 3H), 2.19-1.78 (m, 13H), 1.69-1.44 (m, 4H), 0.97-0.88 (m, 7H).

Example 63 Synthesis and Characterization 2-((1r,4r)-4-(2-(2H-Tetrazol-5-yl)imidazo[4,5-d]pyrrolo[2,3-b]pyridin-1(6H)-yl)cyclohexyl)acetonitrile

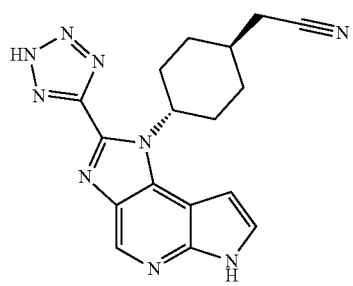

Step A: 2-((1r,4r)-4-(6-(Phenylsulfonyl)-2-(2H-tetrazol-5-yl)imidazo[4,5-d]pyrrolo[2,3-b]pyridin-1(6H)-yl)cyclohexyl)acetonitrile. To a 20 mL microwave vial was added 2-((1r,4r)-4-((5-nitro-1-(phenyl sulfonyl)-1H-pyrrolo[2,3-b]pyridin-4-yl)amino)cyclohexyl)acetonitrile (Intermediate 1, 200 mg, 0.455 mmol) and 2H-tetrazole-5-carbaldehyde (97 mg, 0.998 mmol) as solids. DMSO (2.2 mL), MeOH (2.2 mL), and distilled water (1.2 mL) were all added resulting a yellow mixture. Sodium hydrosulfite (285 mg, 1.64 mmol) was added as a solid and the vial was sealed. The vial was placed into a preheated 100° C. heating block for 4 h. The reaction was poured into water, resulting in a precipitate forming, which was filtered to provide the title compound (199 mg, 89% yield) as a tan colored solid, which was used without further purification. MS (ESI): mass calcd. for $C_{23}H_{21}N_9O_2S$, 487.15; m/z found, 488.2 [M+H]$^+$.

Step B: 2-((1r,4r)-4-(2-(2H-Tetrazol-5-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(6-(Phenylsulfonyl)-2-(2H-tetrazol-5-yl)imidazo[4,5-d]pyrrolo[2,3-b]pyridin-1(6H)-yl)cyclohexyl)acetonitrile (199 mg, 0.41 mmol) instead of 2-(1-((1r,4r)-4-(Cyanomethyl)cyclohexyl)-6-(phenyl sulfonyl)-1,6-dihydroimidazo[4,5-d]pyrrolo[2,3-b]pyridin-2-yl)-N-(2-hydroxy-2-methylpropyl)acetamide and the residue was purified by flash column chromatography (0-30% 2 N NH$_3$ in MeOH/EA to provide the title compound (12 mg, 8% yield). MS (ESI): mass calcd. for $C_{17}H_{17}N_9$, 347.16; m/z found, 348.2 [M+H]$^+$. $^1$H NMR (500 MHz, CD$_3$OD): δ 8.57 (s, 1H), 7.43 (t, J=2.8 Hz, 1H), 6.82 (t, J=3.0 Hz, 1H), 5.13-4.90 (m, 1H), 2.55-2.29 (m, 3H), 2.10-1.83 (m, 4H), 1.43-1.13 (m, 4H).

Example 64 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(1H-pyrazol-4-yl)acetamide

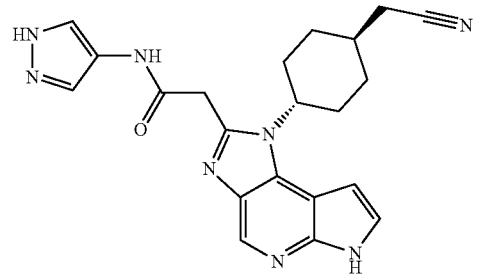 [SMILES: N#CC[C@H]1CC[C@H](n2c(CC(=O)Nc3cn[nH]c3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 100 mg, 0.278 mmol) and 1H-pyrazol-4-amine (50.0 mg, 0.602 mmol) in DMF (1.2 mL) were added PyBrOP (217 mg, 0.417 mmol) and DIPEA (0.144 mL, 0.835 mmol) and was stirred at room temperature overnight. The DMF was removed under reduced pressure and the residue was purified by flash column chromatography and by reverse phase HPLC to provide the product as the TFA salt. This material was dissolved in 10% MeOH in CH$_2$Cl$_2$ and passed through a 500 mg column of SILICYCLE SPE-R66030B-03P Carbonate (SiliaBond acid scavenger solid phase extraction cartridge) to remove the TFA to provide the title compound (37.0 mg, 33% yield) as a white solid. MS (ESI): mass calcd. for $C_{21}H_{22}N_8O$, 402.19; m/z found, 403.2 [M+H]$^+$. $^1$H NMR (400 MHz, CD$_3$OD) δ=8.55 (s, 1H), 7.92 (br s, 1H), 7.65 (br s, 1H), 7.48 (d, J=3.5 Hz, 1H), 6.83 (d, J=3.5 Hz, 1H), 4.59 (br s, 1H), 4.26-4.20 (m, 1H), 2.63-2.43 (m, 4H), 2.17-2.00 (m, 6H), 1.44 (q, J=11.8 Hz, 2H).

Example 65 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4,4-dimethylcyclohexyl)acetamide

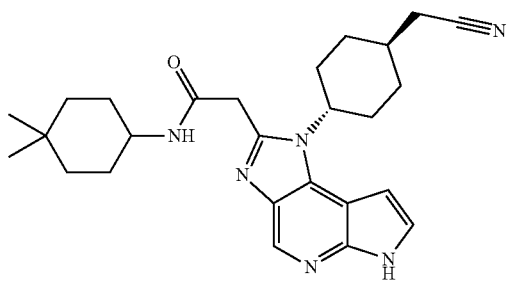 [SMILES: CC1(C)CCC(NC(=O)Cc2nc3cnc4[nH]ccc4c3n2[C@H]2CC[C@H](CC#N)CC2)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 800 mg, 2.23 mmol), 4,4-dimethylcyclohexanamine (283 mg, 2.23 mmol), and DIPEA (575 mg, 4.45 mmol) in dry DMF (10 mL) was stirred at 0° C. for 1 h. PyBrOP (1.25 g, 2.67 mmol) was added at 0° C. and was stirred at room-temperature overnight. The mixture was quenched with 60 mL water and was extracted with CH$_2$Cl$_2$ (3×80 mL). The organic phases were combined and concentrated to dryness. The residue was purified by preparative HPLC using a DuraShell 150 mm×25 mm, 5 µm column (eluent: H$_2$O (0.05% NH$_4$HCO$_3$)-ACN from 28% to 58%, v/v) and by preparative TLC (dichloromethane:methanol=12:1) to provide the title compound (135 mg, 13% yield) as a white solid. MS (ESI): mass calcd. for $C_{26}H_{34}N_6O$, 446.28; m/z found, 447.3 [M+H]$^+$. $^1$H NMR (400 MHz, DMSO-d$_6$): δ 11.83 (br s, 1H), 8.49 (s, 1H), 8.21 (d, J=7.5 Hz, 1H), 7.48-7.44 (m, 1H), 6.72-6.69 (m, 1H), 4.48 (br s, 1H), 3.96 (s, 2H), 3.57-3.45 (m, 1H), 2.60 (d, J=5.8 Hz, 2H), 2.43-2.27 (m, 2H), 2.09-1.93 (m, 5H), 1.67-1.58 (m, 2H), 1.47-1.32 (m, 6H), 1.28-1.16 (m, 2H), 0.91 (s, 3H), 0.89 (s, 3H).

Example 66 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(1-methylpiperidin-4-yl)acetamide

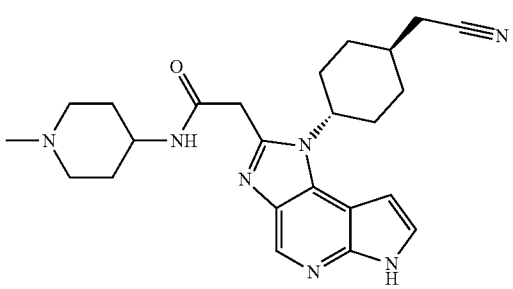 [SMILES: CN1CCC(NC(=O)Cc2nc3cnc4[nH]ccc4c3n2[C@H]2CC[C@H](CC#N)CC2)CC1]

The title compound (45 mg, 18% yield) was prepared using analogous conditions as described in Example 50, using 1-methylpiperidin-4-amine instead of 3-phenylpyrrolin-3-ol. MS (ESI): mass calcd. for $C_{24}H_{31}N_7O$, 433.26; m/z found, 434.2 [M+H]$^+$. $^1$H NMR (500 MHz, CDCl$_3$): δ 12.15-11.52 (m, 1H), 8.66 (s, 1H), 7.67 (s, 1H), 7.39 (dd, J=3.5, 1.9 Hz, 1H), 6.73-6.57 (m, 1H), 4.66 (s, 1H), 3.98 (s, 2H), 3.80-3.60 (m, 1H), 2.90-2.60 (m, 4H), 2.34 (d, J=6.5 Hz, 2H), 2.22-1.96 (m, 12H), 1.84-1.78 (m, 2H), 1.50-1.41 (m, 2H).

Example 67 Synthesis and Characterization 2-((1r,4r)-4-(2-(2-(1,1-Dioxidothiomorpholino)-2-oxoethyl)imidazo[4,5-d]pyrrolo[2,3-b]pyridin-1(6H)-yl)cyclohexyl)acetonitrile

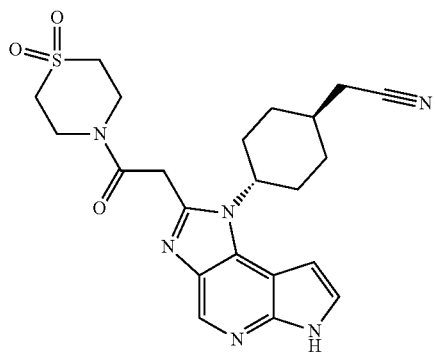 [SMILES: N#CC[C@H]1CC[C@H](n2c(CC(=O)N3CCS(=O)(=O)CC3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 66 mg, 0.18 mmol) and thiomorpholine 1,1-dioxide (63 mg, 0.37 mmol) in DMF (2 mL) were added PyBOP (190 mg, 0.37 mmol) and DIPEA (0.1 mL, 0.58 mmol) and was stirred at room-temperature for 64 h. The reaction was concentrated to dryness and the residue was purified by preparative reverse phase HPLC using a Varian Pursuit XR$_s$5 Diphenyl 100×30 mm column (eluent: 10-90% CH$_3$CN in H$_2$O, 0.1% TFA) to provide the title compound (20 mg, 19% yield) as a foam. MS (ESI): mass calcd. for $C_{22}H_{26}N_6O_3S$, 454.18; m/z found, 455.3 [M+H]$^+$. $^1$H NMR (400 MHz, CD$_3$OD) δ=8.84 (s, 1H), 7.75 (d, J=3.5 Hz, 1H), 7.12 (d, J=3.5 Hz, 1H), 4.62 (br s, 1H), 4.22-4.07 (m, 5H), 3.39-3.32 (m, 2H), 3.23-3.14 (m, 2H), 2.56 (d, J=6.1 Hz, 4H), 2.23-2.09 (m, 6H), 1.60-1.47 (m, 2H).

149

Example 68 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)benzyl)acetamide

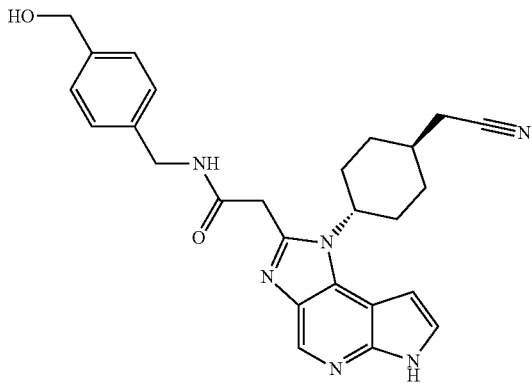 [SMILES: N#CC[C@H]1CC[C@H](n2c(CC(=O)NCc3ccc(CO)cc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 100 mg, 0.278 mmol) and (4-(aminomethyl)phenyl)methanol (76 mg, 0.56 mmol) in DMF (1 mL) were added PyBOP (217 mg, 0.417 mmol) and DIPEA (0.144 mL, 0.835 mmol) and was stirred at room temperature for 87 h. After removal of the DMF in vacuo, the residue was purified by flash column chromatography and by reverse phase HPLC to provide the compound as the TFA salt. This material was dissolved in 10% MeOH in $CH_2Cl_2$, loaded onto a 500 mg column of SILICYCLE SPE-R66030B-03P Carbonate (SiliaBond acid scavenger solid phase extraction cartridge) to remove the TFA and eluted with 10% MeOH in $CH_2Cl_2$ to provide the title compound (34 mg, 27% yield) as a white solid. MS (ESI): mass calcd. for $C_{26}H_{28}N_6O_2$, 456.23; m/z found, 457.2 [M+H]$^+$. $^1$H NMR (400 MHz, CDCl$_3$) δ=11.77 (br s, 1H), 8.53 (br s, 1H), 7.84 (br s, 1H), 7.49 (t, J=2.8 Hz, 1H), 7.27-7.18 (m, 4H), 6.76 (br s, 1H), 4.92 (t, J=12.1 Hz, 1H), 4.60 (s, 2H), 4.42 (d, J=5.1 Hz, 2H), 4.11 (s, 2H), 2.64-2.47 (m, 2H), 2.42 (d, J=6.1 Hz, 2H), 2.25-2.14 (m, 2H), 2.14-2.02 (m, 2H), 2.00-1.81 (m, 2H), 1.59-1.44 (m, 2H).

Example 69 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(cyclohexylmethyl)acetamide

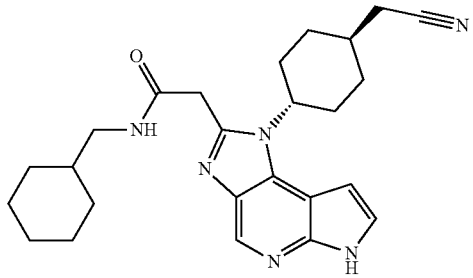 [SMILES: N#CC[C@H]1CC[C@H](n2c(CC(=O)NCC3CCCCC3)nc3cnc4[nH]ccc4c32)CC1]

150

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 1.00 g, 2.78 mmol), cyclohexylmethanamine (315 mg, 2.78 mmol), DIPEA (719 mg, 5.57 mmol), and DMF (10 mL) was stirred at 0° C. for 1 h. Then PyBrOP (1.56 g, 3.34 mmol) was added and stirred at room-temperature overnight. The mixture was quenched with 10 mL water and was purified by preparative basic HPLC using a Kromasil 150 mm×25 mm, 10 μm column (eluent: water (0.05% ammonia hydroxide v/v)-ACN from 33% to 43%, v/v) to provide the title compound (121 mg, 10% yield) as a white solid. MS (ESI): mass calcd. for $C_{25}H_{32}N_6O$, 432.26; m/z found, 433.2 [M+H]$^+$. $^1$H NMR (400 MHz, DMSO-d$_6$): δ 11.84 (br s, 1H), 8.49 (s, 1H), 8.28-8.21 (m, 1H), 7.48-7.44 (m, 1H), 6.73-6.67 (m, 1H), 4.54-4.42 (m, 1H), 3.99 (s, 2H), 2.98-2.91 (m, 2H), 2.58 (d, J=6.0 Hz, 2H), 2.42-2.27 (m, 2H), 2.10-1.92 (m, 5H), 1.74-1.56 (m, 5H), 1.46-1.29 (m, 3H), 1.25-1.06 (m, 3H), 0.95-0.82 (m, 2H).

Example 70 Synthesis and Characterization 1-((1-((1r,4r)-4-(Cyanomethyl)cyclohexyl)-1,6-dihydroimidazo[4,5-d]pyrrolo[2,3-b]pyridin-2-yl)methyl)-3-phenylurea and its Trifluoroacetate Salt

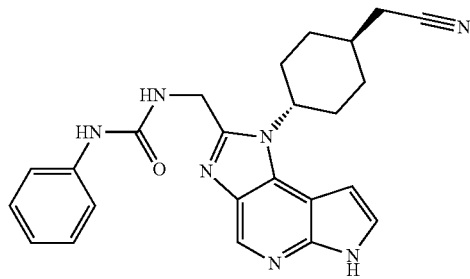 [SMILES: N#CC[C@H]1CC[C@H](n2c(CNC(=O)Nc3ccccc3)nc3cnc4[nH]ccc4c32)CC1]

Step A: tert-Butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate. A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 1.0 g, 2.3 mmol), tert-butyl (2-oxoethyl)carbamate (0.82 g, 5.2 mmol), sodium hydrosulfite (1.2 g, 5.7 mmol) in DMSO (3 mL), methanol (10 mL), and water (5 mL) was stirred for 15 h at 100° C. in a closed container. The reaction was concentrated to dryness and the residue was dissolved in water and $CH_2Cl_2$. The combined organic layer was washed with water and the aqueous phase was back-extracted with $CH_2Cl_2$. The combined organic phases were dried over anhydrous $Na_2SO_4$, filtered, and concentrated to dryness. The residue was purified by flash column chromatography to provide the title compound (750 mg, 60% yield) as a white solid. MS (ESI): mass calcd. for $C_{28}H_{32}N_6O_4S$, 548.22; m/z found, 549.3 [M+H]$^+$.

Step B: 2-((1r,4r)-4-(2-(Aminomethyl)-6-(phenylsulfonyl)imidazo[4,5-d]pyrrolo[2,3-b]pyridin-1(6H)-yl)cyclohexyl)acetonitrile 2,2,2-trifluoroacetate. A solution of tert-butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate (72 mg, 0.13 mmol) and $CH_2Cl_2$ (1 mL) was treated with TFA (0.10 mL) at room temperature for 3 h and concentrated in vacuo to dryness to provide the title compound (73 mg, 99% yield). MS (ESI): mass calcd. for $C_{23}H_{24}N_6O_2S$, 448.17; m/z found, 449.2 $[M+H]^+$.

Step C: 1-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl)-3-phenylurea. A solution of 2-((1r,4r)-4-(2-(aminomethyl)-6-(phenyl sulfonyl)imidazo[4,5-d]pyrrolo[2,3-b]pyridin-1(6H)-yl)cyclohexyl)acetonitrile (73 mg, 0.13 mmol), triethylamine (0.10 mL, 0.72 mmol), and isocyanatobenzene (60 mg, 0.50 mmol) in DMF (1.5 mL) was stirred at room temperature overnight. The reaction mixture was concentrated to dryness to provide the free base compound, 1-((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)-3-phenylurea. This free base compound was purified by flash column chromatography to provide the title compound as its trifluoroacetate salt (50 mg, 68% yield). $^1$H NMR (400 MHz, CDCl$_3$): δ 8.70 (s, 1H), 8.17 (d, J=7.6 Hz, 2H), 8.00 (s, 1H), 7.80 (d, J=4.0 Hz, 1H), 7.57-7.48 (m, 1H), 7.48-7.39 (m, 2H), 7.25 (d, J=8.59 Hz, 2H), 7.13 (t, J=7.3 Hz, 2H), 6.91 (br t, J=6.6 Hz, 1H), 6.80 (br d, J=3.5 Hz, 1H), 6.76 (br s, 1H), 4.88-4.76 (m, 2H), 4.62 (br s, 1H), 2.34 (br d, J=5.1 Hz, 2H), 2.29-2.02 (m, 5H), 1.95 (br s, 2H), 1.48-1.31 (m, 2H).

Step D: 1-((1-((1r,4r)-4-(Cyanomethyl)cyclohexyl)-1,6-dihydroimidazo[4,5-d]pyrrolo[2,3-b]pyridin-2-yl)methyl)-3-phenylurea. A solution of 1-((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)-3-phenylurea (50 mg, 0.088 mmol) in THF (0.8 mL) and MeOH (0.8 mL) was treated with 3 M NaOH (0.08 mL, 0.24 mmol) at room temperature for 3 h and concentrated in vacuo. The residue was purified by flash column chromatography (2-10% MeOH in CH$_2$Cl$_2$) to provide the title compound (30 mg, 80%) as a white solid. MS (ESI): mass calcd. for $C_{24}H_{25}N_7O$, 427.21; m/z found, 428.3 $[M+H]^+$. $^1$H NMR (400 MHz, CDCl$_3$) δ=11.91 (br s, 1H), 8.62 (s, 1H), 8.44 (br s, 1H), 7.35 (br s, 1H), 7.31-7.20 (m, 2H), 7.09 (br s, 2H), 6.88 (br s, 1H), 6.59 (br s, 1H), 4.87 (br s, 2H), 4.55 (br s, 1H), 2.39 (br s, 2H), 2.25 (br s, 2H), 2.11-1.75 (m, 5H), 1.43-1.28 (m, 2H).

Example 71 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2-methoxy-2-methylpropyl)acetamide

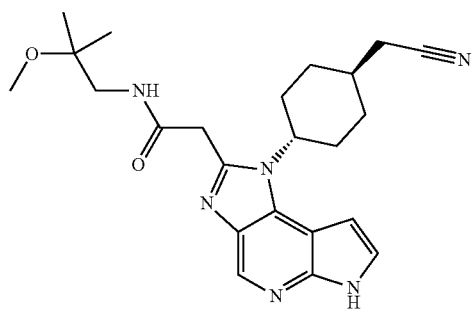 [SMILES: COC(C)(C)CNC(=O)Cc1nc2cnc3[nH]ccc3c2n1[C@H]1CC[C@H](CC#N)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 65 mg, 0.18 mmol) and 2-methoxy-2-methylpropan-1-amine (50 mg, 0.36 mmol) in DMF (2 mL) were added PyBOP (150 mg, 0.30 mmol) and DIPEA (0.10 mL, 0.58 mmol) and was stirred at room temperature for 64 h. The reaction was concentrated to dryness and the residue was purified by preparative reverse phase HPLC using a Varian Pursuit XR$_s$5 Diphenyl 100×30 mm column (eluent: 10-90% CH$_3$CN in H$_2$O, 0.1% TFA) to provide the title compound (23 mg, 24% yield) as a foam. MS (ESI): mass calcd. for $C_{23}H_{30}N_6O_2$, 422.24; m/z found, 423.3 $[M+H]^+$. $^1$H NMR (400 MHz, CD$_3$OD) δ=8.80 (s, 1H), 7.75 (d, J=3.0 Hz, 1H), 7.10 (d, J=3.5 Hz, 1H), 4.68 (br s, 1H), 3.35-3.32 (m, 3H), 3.25 (s, 3H), 2.56 (d, J=6.1 Hz, 4H), 2.29-2.04 (m, 6H), 1.63-1.44 (m, 2H), 1.20 (s, 6H).

Example 72 Synthesis and Characterization (Z*)—N-((1-((1r,4r)-4-(Cyanomethyl)cyclohexyl)-1,6-dihydroimidazo[4,5-d]pyrrolo[2,3-b]pyridin-2-yl)methoxy)-3-methoxypropanimidamide; the Structure being the (Z) or (E) Isomer, and the (Z) Notation and its Corresponding Structure Below is Chosen Arbitrarily

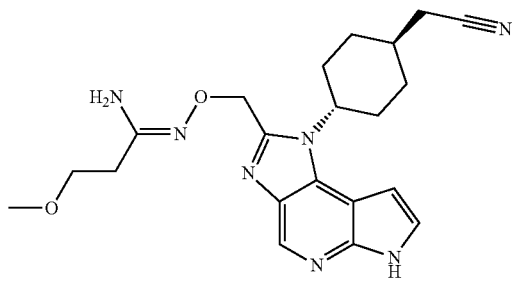 [SMILES: COCC/C(N)=N/OCc1nc2cnc3[nH]ccc3c2n1[C@H]1CC[C@H](CC#N)CC1]

Step A: (Z)—N-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methoxy)-3-methoxypropanimidamide. A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 300 mg, 0.641 mmol), N-hydroxy-3-methoxypropanimidamide (227 mg, 1.92 mmol), Cs$_2$CO$_3$ (1.04 g, 3.21 mmol), and DMF (5 mL) was stirred for 18 h at 10° C. The reaction was concentrated to dryness to provide the title compound (1.6 g, 100% yield), which was used in the next step without further purification. MS (ESI): mass calcd. for $C_{27}H_{31}N_7O_4S$, 549.22; m/z found, 550.1 $[M+H]^+$.

Step B: (Z*)—N-((1-((1r,4r)-4-(Cyanomethyl)cyclohexyl)-1,6-dihydroimidazo[4,5-d]pyrrolo[2,3-b]pyridin-2-yl)methoxy)-3-methoxypropanimidamide. The title compound was prepared using conditions analogous to those described in Example 1, Step B using (Z)—N-((1-((1r,4r)-4-(cyanomethyl)cyclohexyl)-6-(phenyl sulfonyl)-1,6-dihydroimidazo[4,5-d]pyrrolo[2,3-b]pyridin-2-yl)methoxy)-3-methoxypropanimidamide (1.6 g, 0.64 mmol, purity 22%) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide to provide the title compound (65 mg, 24% yield), which was first purified by flash column chromatography (DCM:methanol=100:0 to 85:15), and then purified by preparative HPLC using a Gemini 150 mm×25 mm, 5 µm column (eluent: 17% to 47% (v/v) CH$_3$CN and H$_2$O with 0.05% NH$_3$) MS (ESI): mass calcd. for $C_{21}H_{27}N_7O_2$, 409.22; m/z found, 410.3 $[M+H]^+$. MS (ESI): mass calcd. for $C_{21}H_{27}N_7O_2$, 409.5; m/z found, 410.3 $[M+H]^+$. $^1$H NMR (400 MHz, DMSO-d$_6$): δ

11.88 (s, 1H), 8.54 (s, 1H), 7.47 (s, 1H), 6.73 (s, 1H), 5.76 (s, 2H), 5.16 (s, 2H), 4.81-4.66 (m, 1H), 3.45 (t, J=6.4 Hz, 2H), 3.18 (s, 3H), 2.58 (d, J=4.8 Hz, 2H), 2.43-2.27 (m, 2H), 2.17 (t, J=6.4 Hz, 2H), 2.10-1.89 (m, 5H), 1.49-1.33 (m, 2H).

Example 73 Synthesis and Characterization 2-((1r,4r)-4-(2-(2-(4-(Hydroxymethyl)piperidin-1-yl)-2-oxoethyl)imidazo[4,5-d]pyrrolo[2,3-b]pyridin-1(6H)-yl)cyclohexyl)acetonitrile

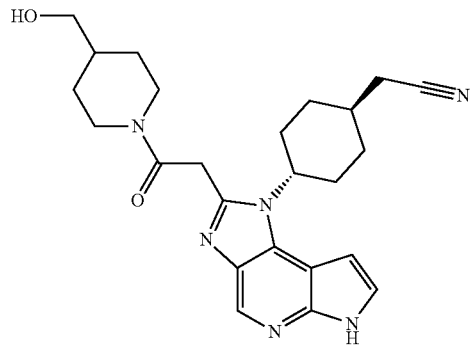 [SMILES: N#CC[C@H]1CC[C@H](n2c(CC(=O)N3CCC(CO)CC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 65 mg, 0.18 mmol) and piperidin-4-ylmethanol (55 mg, 0.36 mmol) in DMF (2 mL) were added PyBOP (150 mg, 0.30 mmol) and DIPEA (0.10 mL, 0.58 mmol) and was stirred at room-temperature for 64 h. The reaction was concentrated to dryness and the residue was purified by preparative reverse phase HPLC using a Varian Pursuit XR$_s$5 Diphenyl 100×30 mm column (eluent: 10-90% CH$_3$CN in H$_2$O, 0.1% TFA) to provide the title compound (11 mg, 11% yield) as a foam. MS (ESI): mass calcd. for C$_{24}$H$_{30}$N$_6$O$_2$, 434.24; m/z found, 435.3 [M+H]$^+$. $^1$H NMR (400 MHz, CD$_3$OD) δ=8.81 (d, J=1.5 Hz, 1H), 7.75 (d, J=3.5 Hz, 1H), 7.13-7.07 (m, 1H), 4.66-4.48 (m, 2H), 4.32 (d, J=6.1 Hz, 1H), 4.17 (br t, J=13.4 Hz, 1H), 3.47 (d, J=5.6 Hz, 1H), 3.36-3.24 (m, 2H), 2.78 (dq, J=2.5, 12.6 Hz, 1H), 2.56 (d, J=5.6 Hz, 4H), 2.25-2.08 (m, 6H), 1.99-1.77 (m, 3H), 1.61-1.14 (m, 4H).

Example 74 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide

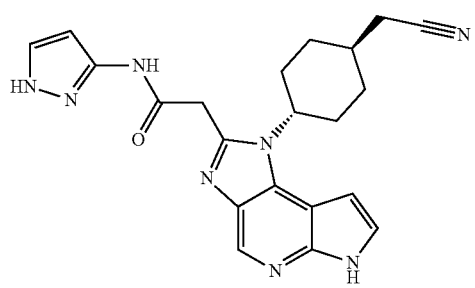 [SMILES: N#CC[C@H]1CC[C@H](n2c(CC(=O)Nc3cc[nH]n3)nc3cnc4[nH]ccc4c32)CC1]

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(1H-pyrazol-3-yl)acetamide. The title compound (383 mg, 70%) was prepared in a manner analogous to that described in Example 1, Step A using 1H-pyrazol-3-amine (465 mg, 5.48 mmol) instead of 1-amino-2-methylpropan-2-ol. MS (ESI): mass calcd. for C$_{27}$H$_{26}$N$_8$O$_3$S, 542.2; m/z found, 543.2 [M+H]$^+$. $^1$H NMR (500 MHz, DMSO-d$_6$) δ 12.36 (s, 1H), 11.36 (s, 1H), 10.81 (s, 1H), 8.65 (s, 1H), 8.14-8.10 (m, 2H), 7.96 (d, J=4.1 Hz, 1H), 7.72-7.68 (m, 1H), 7.63-7.60 (m, 2H), 7.30 (s, 1H), 7.13 (d, J=4.2 Hz, 1H), 6.44-6.41 (m, 1H), 5.41 (s, 1H), 4.57 (s, 1H), 4.44 (s, 2H), 4.24 (s, 2H), 2.56 (d, J=6.2 Hz, 2H), 2.23-2.13 (m, 2H), 2.02-1.95 (m, 1H), 1.41-1.32 (m, 2H).

Step B: 2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide. The title compound was prepared in a manner analogous to Example 1, Step B using 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(1H-pyrazol-3-yl)acetamide (270 mg, 0.500 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and purified by basic HPLC using a Xbridge Prep OBD C$_{18}$ 150 mm×30 mm, 5 μm, eluent 5% ACN/NH$_4$OH (aq) (10 min) to provide the title compound (15 mg, 7%). MS (ESI): mass calcd. for C$_{21}$H$_{22}$N$_8$O, 402.5; m/z found, 403.2 [M+H]$^+$. $^1$H NMR (500 MHz, DMSO-d$_6$): δ 12.35 (s, 1H), 11.85 (s, 1H), 10.84 (s, 1H), 8.50 (s, 1H), 7.58 (d, J=2.3 Hz, 1H), 7.46 (d, J=3.4 Hz, 1H), 6.72 (d, J=3.5 Hz, 1H), 6.47-6.39 (m, 1H), 4.64-4.46 (m, 1H), 4.21 (s, 2H), 2.57 (d, J=6.1 Hz, 2H), 2.45-2.26 (m, 2H), 2.08-1.88 (m, 5H), 1.39 (q, J=11.7 Hz, 2H).

Example 75 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(3,5-dimethylcyclohexyl)acetamide

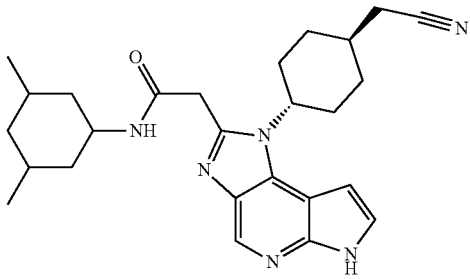 [SMILES: CC1CC(C)CC(NC(=O)Cc2nc3cnc4[nH]ccc4c3n2[C@H]2CC[C@H](CC#N)CC2)C1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (200 mg, 0.557 mmol), 3,5-dimethylcyclohexanamine (Intermediate 4, 70.8 mg, 0.557 mmol), and DIPEA (144 mg, 1.11 mmol) in DMF (5 mL) was added PyBOP (311 mg, 0.668 mmol) and was stirred at room-temperature overnight. The reaction was poured into water (60 mL) and extracted with CH$_2$Cl$_2$ (4×80 mL). The organic phases were combined and concentrated to dryness. The residue was purified by preparative basic HPLC using a Phenomenex Gemini 150 mm×25 mm, 10 μm column (eluent: ACN in water (0.05% NH$_4$OH) from 40% to 70%, v/v) to provide the title compound (79 mg, 32% yield) as a white solid. MS (ESI): mass calcd. for $C_{26}H_{34}N_6O$, 446.28; m/z found, 447.2 [M+H]⁺. ¹H NMR (400 MHz, DMSO-d₆): δ 11.84 (br s, 1H), 8.49 (s, 1H), 8.21-8.19 (m, 1H), 7.47-7.46 (m, 1H), 6.71 (s, 1H), 4.54-4.41 (m, 1H), 4.07-3.99 (m, 1H), 3.95 (s, 1H), 3.65-3.40 (m, 1H), 2.60 (t, J=5.6 Hz, 2H), 2.44-2.26 (m, 2H), 2.11-1.88 (m, 5H), 1.85-1.71 (m, 2H), 1.69-1.53 (m, 2H), 1.50-1.31 (m, 3H), 1.07-0.95 (m, 1H), 0.87 (t, J=6.0 Hz, 6H), 0.84-0.73 (m, 1H), 0.62-0.44 (m, 1H).

Example 76 Synthesis and Characterization 4-(4-(1-((1r,4r)-4-(Cyanomethyl)cyclohexyl)-1,6-dihydroimidazo[4,5-d]pyrrolo[2,3-b]pyridin-2-yl)piperidin-1-yl)benzonitrile

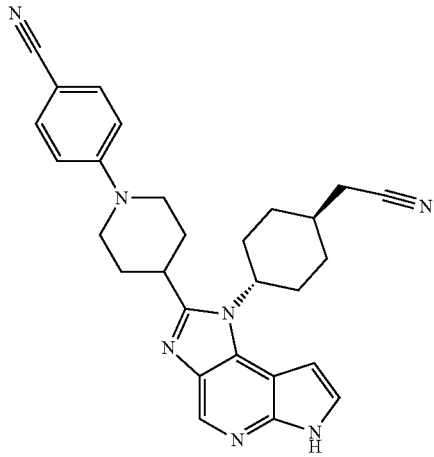 [SMILES: N#CC[C@H]1CC[C@H](n2c(C3CCN(c4ccc(C#N)cc4)CC3)nc3cnc4[nH]ccc4c32)CC1]

Step A: 4-(4-(1-((1r,4r)-4-(Cyanomethyl)cyclohexyl)-6-(phenylsulfonyl)-1,6-dihydroimidazo[4,5-d]pyrrolo[2,3-b]pyridin-2-yl)piperidin-1-yl)benzonitrile. A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 70 mg, 0.16 mmol), 4-(4-formylpiperidin-1-yl)benzonitrile (69 mg, 0.32 mmol), sodium hydrosulfite (82 mg, 0.40 mmol), DMSO (1 mL), methanol (1 mL), and water (0.5 mL) in a sealed tube was heated at 100° C. for 16 h. After cooling to room temperature, the mixture was extracted with EtOAc (3×) and CH₂Cl₂ (2×). The organic phases were combined, dried over anhydrous MgSO₄, filtered, and concentrated to dryness to provide the title compound (90 mg, 94% yield), which was used in the next reaction without further purification. MS (ESI): mass calcd. for $C_{34}H_{33}N_7O_2S$, 603.24; m/z found, 604.3 [M+H]⁺.

Step B: 4-(4-(1-((1r,4r)-4-(Cyanomethyl)cyclohexyl)-1,6-dihydroimidazo[4,5-d]pyrrolo[2,3-b]pyridin-2-yl)piperidin-1-yl)benzonitrile. A reaction mixture of 4-(4-(1-((1r,4r)-4-(cyanomethyl)cyclohexyl)-6-(phenylsulfonyl)-1,6-dihydroimidazo[4,5-d]pyrrolo[2,3-b]pyridin-2-yl)piperidin-1-yl)benzonitrile (90 mg, 0.15 mmol), 3 M NaOH aqueous solution (0.12 mL, 0.36 mmol), pyrrolidine (0.050 mL, 0.60 mmol), MeOH (1 mL), and THF (1 mL) was stirred at room temperature for 5 h, and concentrated in vacuo. The residue was purified by flash column chromatography (3-10% MeOH in CH₂Cl₂) to give the title compound as a white solid (15 mg, 22% yield). MS (ESI): mass calcd. for $C_{28}H_{29}N_7$, 463.25; m/z found, 464.2 [M+H]⁺. ¹H NMR (400 MHz, CDCl₃) δ=9.18 (br s, 1H), 8.77 (s, 1H), 7.54-7.50 (m, 2H), 7.39-7.36 (m, 1H), 6.94-6.91 (d, J=9.1 Hz, 2H), 6.72-6.70 (m, 1H), 4.39 (br s, 1H), 4.09-3.99 (m, 2H), 3.24-3.09 (m, 3H), 2.76-2.60 (m, 2H), 2.49 (d, J=6.1 Hz, 2H), 2.31-2.17 (m, 5H), 2.16-1.96 (m, 4H), 1.63-1.48 (m, 2H).

Example 77 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)benzenesulfonamide

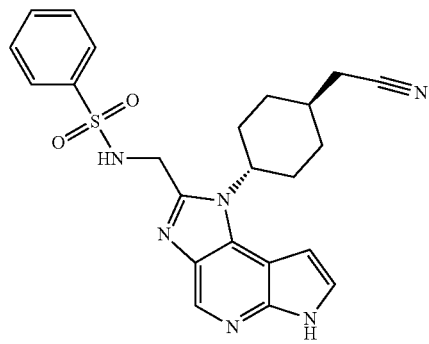 [SMILES: N#CC[C@H]1CC[C@H](n2c(CNS(=O)(=O)c3ccccc3)nc3cnc4[nH]ccc4c32)CC1]

Benzenesulfonyl chloride (69.9 mg, 0.396 mmol) was added dropwise to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.396 mmol, purity 91%), triethylamine (0.276 mL, 1.98 mmol), and CH₂Cl₂ (5 mL) and was stirred for 30 minutes at 10° C. The reaction was diluted with CH₂Cl₂ (10 mL), washed with water (10 mL), dried over anhydrous Na₂SO₄, filtered, and concentrated to dryness. The residue was purified by preparative TLC (eluent: CH₂Cl₂: methanol, 10:1) to provide the title compound (60 mg, 33% yield) as a white solid. MS (ESI): mass calcd. for $C_{23}H_{24}N_6O_2S$, 448.17; m/z found, 449.1 [M+H]⁺. ¹H NMR (400 MHz, DMSO-d₆): δ 11.91 (s, 1H), 8.52 (s, 1H), 8.42 (br s, 1H), 7.90-7.84 (m, 2H), 7.71-7.56 (m, 3H), 7.48 (t, J=2.8 Hz, 1H), 6.72 (d, J=0.8 Hz, 1H), 4.66-4.52 (m, 1H), 4.36 (s, 2H), 2.60 (d, J=5.6 Hz, 2H), 2.42-2.24 (m, 2H), 2.11-1.88 (m, 5H), 1.48-1.30 (m, 2H).

Example 78 Synthesis and Characterization

N-((1S,4R)-Bicyclo[2.2.1]heptan-2-yl)-2-(1-((1r,4r)-4-(cyanomethyl)cyclohexyl)-1,6-dihydroimidazo[4,5-d]pyrrolo[2,3-b]pyridin-2-yl)acetamide

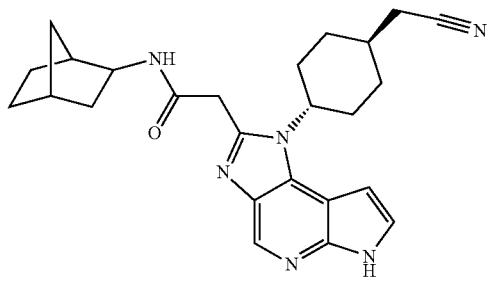 [SMILES: N#CC[C@H]1CC[C@H](n2c(CC(=O)NC3CC4CCC3C4)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 100 mg, 0.278 mmol) and (1S,4R)-bicyclo[2.2.1]heptan-2-amine (82.2 mg, 0.557 mmol) in DMF (0.8 mL) were added PyBOP (217 mg, 0.417 mmol) and DIPEA (0.192 mL, 1.11 mmol) and was stirred at room temperature for 42 h. The reaction was concentrated to dryness and the residue was purified by flash column chromatography (12 g silica gel column, 50-100% EtOAc in heptanes, and then 10% MeOH in DCM) and reverse phase acidic HPLC using a Varian Pursuit XR$_s$5 Diphenyl 100×30 mm column (eluent: 10-90% CH$_3$CN in H$_2$O, 0.1% TFA) to provide the TFA salt. This material was dissolved in 10% MeOH in CH$_2$Cl$_2$ and passed through a 500 mg column of SILICYCLE SPE-R66030B-03P Carbonate (SiliaBond acid scavenger solid phase extraction cartridge) to remove the TFA and eluted with 10% MeOH in CH$_2$Cl$_2$ to provide the title compound (61 mg, 51% yield) as a white solid. MS (ESI): mass calcd. for C$_{25}$H$_{30}$N$_6$O, 430.25; m/z found, 431.3 [M+H]$^+$. $^1$H NMR (400 MHz, CDCl$_3$) δ=11.90 (br s, 1H), 8.81 (s, 1H), 7.61 (br s, 1H), 7.52 (br s, 1H), 6.76 (d, J=3.0 Hz, 1H), 4.74 (br s, 1H), 4.18-3.99 (m, 2H), 2.71-2.48 (m, 1H), 2.46-2.35 (m, 3H), 2.31-1.95 (m, 9H), 1.58-1.22 (m, 7H), 1.18-1.05 (m, 1H), 0.75 (td, J=3.6, 13.0 Hz, 1H).

Example 79 Synthesis and Characterization 2-(1-((1r,4r)-4-(cyanomethyl)cyclohexyl)-1,6-dihydroimidazo[4,5-d]pyrrolo[2,3-b]pyridin-2-yl)-N-(4-(difluoromethoxy)benzyl)acetamide

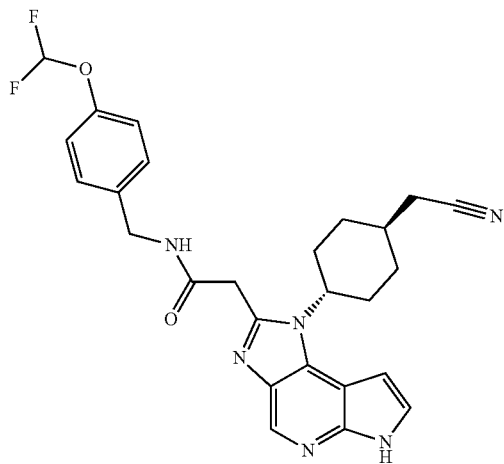 [SMILES: N#CC[C@H]1CC[C@H](n2c(CC(=O)NCc3ccc(OC(F)F)cc3)nc3cnc4[nH]ccc4c32)CC1]

Step A: 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(4-(difluoromethoxy)benzyl)acetamide. The title compound (90 mg, 71%) was prepared using condition analogous to those described in Example 48, Step A, using Intermediate 3 (100 mg, 0.200 mmol) and N-(4-(difluoromethoxy)benzyl amine (312 mg, 1.80 mmol) instead of phenylmethanamine. MS (ESI): mass calcd. for C$_{32}$H$_{30}$F$_2$N$_6$O$_4$S, 632.2; m/z found, 633.2 [M+H]$^+$.

Step B: 2-(1-((1r,4r)-4-(Cyanomethyl)cyclohexyl)-1,6-dihydroimidazo[4,5-d]pyrrolo[2,3-b]pyridin-2-yl)-N-(4-(difluoromethoxy)benzyl)acetamide. The title compound (53 mg, 75%) was prepared using analogous conditions as described in Example 48, Step B using 2-(1-((1R,4R)-4-(cyanomethyl)cyclohexyl)-6-(phenylsulfonyl)-1,6-dihydroimidazo[4,5-d]pyrrolo[2,3-b]pyridin-2-yl)-N-(4-(difluoromethoxy)benzyl)acetamide (90 mg, 0.14 mmol) instead of N-benzyl-2-(1-((1R,4R)-4-(cyanomethyl)cyclohexyl)-6-(phenylsulfonyl)-1,6-dihydroimidazo[4,5-d]pyrrolo[2,3-b]pyridin-2-yl)acetamide. The purification was performed by reverse phase HPLC using a Varian Pursuit XR$_s$5 Diphenyl 100×30 mm column (eluent: 10-90% CH$_3$CN in H$_2$O, 0.1% TFA). MS (ESI): mass calcd. for C$_{26}$H$_{26}$F$_2$N$_6$O$_2$, 492.21; m/z found, 493.2 [M+H]$^+$. $^1$H NMR (400 MHz, CD$_3$OD) δ=8.53 (s, 1H), 7.47 (d, J=3.5 Hz, 1H), 7.36 (d, J=8.5 Hz, 2H), 7.10 (d, J=8.6 Hz, 2H), 6.82 (d, J=3.6 Hz, 1H), 6.79 (s, 1H), 4.44 (br s, 1H), 4.39 (s, 2H), 4.12 (s, 2H), 2.62-2.48 (m, 2H), 2.50 (d, J=6.1 Hz, 2H), 2.09-1.97 (m, 5H), 1.44-1.28 (m, 2H).

Example 80 Synthesis and Characterization 1-((1r,4r)-4-(Cyanomethyl)cyclohexyl)-N-((3-hydroxyoxetan-3-yl)methyl)-1,6-dihydroimidazo[4,5-d]pyrrolo[2,3-b]pyridine-2-carboxamide

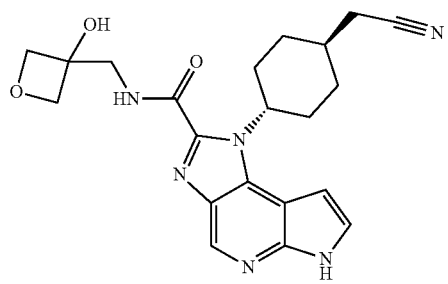 [SMILES: N#CC[C@H]1CC[C@H](n2c(C(=O)NCC3(O)COC3)nc3cnc4[nH]ccc4c32)CC1]

The title compound (37 mg, 45% yield) was prepared using Intermediate 6 and analogous conditions as described in Example 50, step A, and using 3-(aminomethyl)oxetan-3-ol instead of 3-phenylpyrrolin-3-ol. MS (ESI): mass calcd. for C$_{21}$H$_{24}$N$_6$O$_3$, 408.19; m/z found, 409.2 [M+H]$^+$. $^1$H NMR (400 MHz, CDCl$_3$): δ 10.40 (s, 1H), 8.67 (s, 1H), 8.17 (s, 1H), 7.36 (d, J=3.5 Hz, 1H), 6.72 (d, J=3.5 Hz, 1H), 6.03-5.53 (m, 1H), 5.33-5.06 (m, 1H), 4.62 (d, J=6.9 Hz, 2H), 4.55-4.38 (m, 2H), 3.86 (d, J=6.0 Hz, 2H), 2.66-2.42 (m, 2H), 2.35 (d, J=6.6 Hz, 2H), 2.05-1.95 (m, 5H), 1.51-1.32 (m, 2H).

Example 81 Synthesis and Characterization 2-((1r,4r)-4-(2-(3-Methyl-1H-pyrazol-5-yl)imidazo[4,5-d]pyrrolo[2,3-b]pyridin-1(6H)-yl)cyclohexyl)acetonitrile

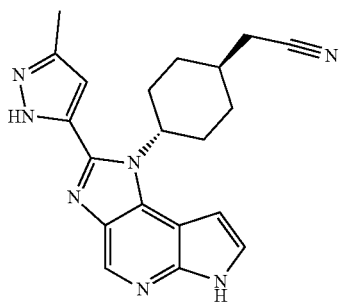 [SMILES: Cc1cc(-c2nc3cnc4[nH]ccc4c3n2[C@H]2CC[C@H](CC#N)CC2)[nH]n1]

Step A: 2-((1r,4r)-4-(2-(3-Methyl-1H-pyrazol-5-yl)-6-(phenylsulfonyl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 214 mg, 0.487 mmol) and 3-methyl-1H-pyrazole-5-carbaldehyde (120 mg, 1.09 mmol) as solids. DMSO (2.2 mL), MeOH (2.2 mL), and distilled water (1.1 mL) were added resulting a yellow mixture. Sodium hydrosulfite (298 mg, 1.71 mmol) was added as a solid and the vial sealed. The vial was placed into a preheated 100° C. heating block and heated for 3 h. The vial was cooled to room temperature and added to vigorously stirred water (75 mL), which resulted in an emulsion like mixture. The mixture was filtered through a micro porosity fritted funnel to trap any solids. The filter cake was rinsed with water and dried open to air overnight and then dried further under high vacuum for 1 h to provide the title compound (238 mg, 97% yield), which was used in the next reaction without further purification. MS (ESI): mass calcd. for $C_{26}H_{25}N_7O_2S$, 499.18; m/z found, 500.2 $[M+H]^+$. 1H NMR (500 MHz, Chloroform-d) δ 8.94 (s, 1H), 8.28-8.18 (m, 2H), 7.84 (d, J=4.0 Hz, 1H), 7.60-7.52 (m, 1H), 7.52-7.42 (m, 2H), 6.90 (d, J=4.1 Hz, 1H), 6.73 (s, 1H), 5.66 (s, 1H), 2.50-2.33 (m, 7H), 2.05 (dt, J=29.0, 12.9 Hz, 5H), 1.57-1.39 (m, 2H).

Step B: 2-((1r,4r)-4-(2-(3-Methyl-1H-pyrazol-5-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(2-(3-Methyl-1H-pyrazol-5-yl)-6-(phenylsulfonyl)imidazo[4,5-d]pyrrolo[2,3-b]pyridin-1(6H)-yl)cyclohexyl)acetonitrile (235 mg, 0.47 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and the residue was purified by flash column chromatography (0-8% 2 N $NH_3$-MeOH/EA, 10CV) to provide the title compound (143 mg, 81%). MS (ESI): mass calcd. for $C_{20}H_{21}N_7$, 359.19; m/z found, 360.2 $[M+H]^+$. $^1$H NMR (500 MHz, DMSO-$d_6$): δ 13.03 (s, 1H), 11.91 (s, 1H), 8.60 (s, 1H), 7.50 (t, J=3.0 Hz, 1H), 6.82-6.72 (m, 1H), 6.64 (s, 1H), 5.90-5.57 (m, 1H), 2.60 (d, J=6.0 Hz, 2H), 2.56-2.41 (m, 2H), 2.34 (s, 3H), 2.13-1.98 (m, 3H), 1.98-1.87 (m, 2H), 1.42-1.26 (m, 2H).

Example 82 Synthesis and Characterization

4-Cyano-N-((1-((1r,4r)-4-(cyanomethyl)cyclohexyl)-1,6-dihydroimidazo[4,5-d]pyrrolo[2,3-b]pyridin-2-yl)methyl)benzamide

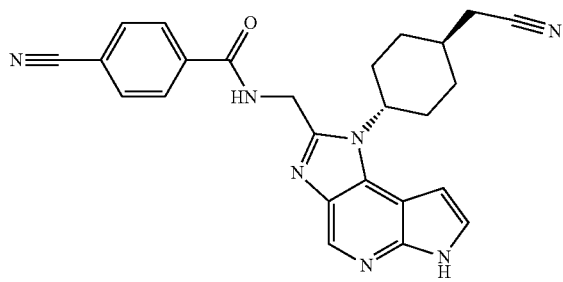 [SMILES: N#CC[C@H]1CC[C@H](n2c(CNC(=O)c3ccc(C#N)cc3)nc3cnc4[nH]ccc4c32)CC1]

HATU (155 mg, 0.409 mmol) was added to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.409 mmol, purity 94%), 4-cyanobenzoic acid (60.2 mg, 0.409 mmol), DIEA (0.356 mL, 2.04 mmol), and $CH_2Cl_2$ (5 mL) and was stirred for 1 h at 10° C. The reaction was diluted with $CH_2Cl_2$ (10 mL), washed with water (10 mL), and concentrated to dryness. The residue was purified by preparative HPLC using a Phenomenex Gemini 150 mm×25 mm, 10 μm column (eluent: 30% to 60% (v/v) $CH_3CN$ and $H_2O$ with 0.05% $NH_3$) to provide the title compound (130 mg, 71% yield) as a white solid. MS (ESI): mass calcd. for $C_{25}H_{23}N_7O$, 437.20; m/z found, 438.2 $[M+H]^+$. $^1$H NMR (400 MHz, DMSO-$d_6$): δ 11.89 (s, 1H), 9.47 (t, J=5.2 Hz, 1H), 8.55 (s, 1H), 8.07 (d, J=8.4 Hz, 2H), 7.98 (d, J=8.4 Hz, 2H), 7.47 (t, J=2.8 Hz, 1H), 6.72 (s, 1H), 4.93 (d, J=5.6 Hz, 2H), 4.69-4.56 (m, 1H), 2.57 (d, J=6.0 Hz, 2H), 2.43-2.28 (m, 2H), 2.06-1.84 (m, 5H), 1.43-1.27 (m, 2H).

Example 83 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-thiopyran-4-yl)acetamide

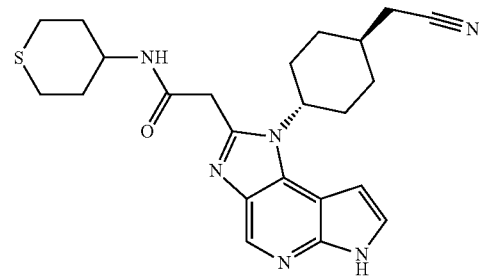 [SMILES: N#CC[C@H]1CC[C@H](n2c(CC(=O)NC3CCSCC3)nc3cnc4[nH]ccc4c32)CC1]

Step A: 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(tetrahydro-2H-thiopyran-4-yl)acetamide The title compound was prepared using analogous conditions as described in Example 48, step A using tetrahydro-2H-thiopyran-4-amine in place of phenylmethanamine to provide the title compound (85 mg, 75% yield). MS (ESI): mass calcd. for $C_{29}H_{32}N_6O_3S_2$, 576.20; m/z found, 577.2 $[M+H]^+$.

Step B: 2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-thiopyran-4-yl)acetamide. The title compound (30 mg, 47% yield) was prepared using conditions analogous to those described in Example 1, Step B using 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(tetrahydro-2H-thiopyran-4-yl)acetamide (85 mg, 0.15 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide.

The purification was performed by flash column chromatography (12 g silica gel column, 2-10% MeOH in DCM) and then reverse phase HPLC using a Varian Pursuit $XR_s5$ Diphenyl 100×30 mm column (eluent: 5-95% $CH_3CN$ in water, with 0.1% TFA). The fractions were concentrated and dissolved in 10% MeOH in DCM, passed through a 500 mg column of SILICYCLE SPE-R66030B-03P Carbonate to remove TFA, and eluted with 10% MeOH in DCM. MS (ESI): mass calcd. for $C_{23}H_{28}N_6OS$, 436.20; m/z found, 437.3 $[M+H]^+$. $^1$H NMR (400 MHz, CDCl$_3$) δ=11.35 (br s, 1H), 8.79 (s, 1H), 7.69 (br s, 1H), 7.50 (t, J=2.8 Hz, 1H), 6.79-6.73 (m, 1H), 4.69 (br s, 1H), 4.03 (s, 2H), 3.89-3.75 (m, 1H), 2.76-2.53 (m, 5H), 2.43 (d, J=6.6 Hz, 2H), 2.27-1.98 (m, 7H), 1.90 (br s, 1H), 1.65-1.44 (m, 4H).

Example 84 Synthesis and Characterization 1-((1r,4r)-4-(Cyanomethyl)cyclohexyl)-N-(1-methylpiperidin-4-yl)-1,6-dihydroimidazo[4,5-d]pyrrolo[2,3-b]pyridine-2-carboxamide

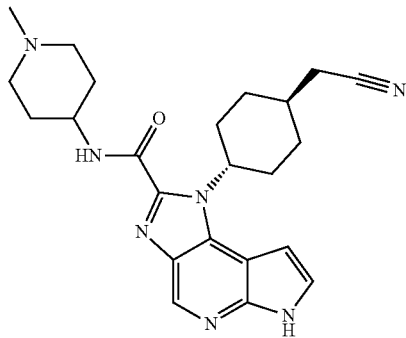 [SMILES: CN1CCC(NC(=O)c2nc3cnc4[nH]ccc4c3n2[C@H]2CC[C@H](CC#N)CC2)CC1]

The title compound (20 mg, 21% yield) was prepared using Intermediate 6 and analogous conditions as described in Example 50, step A using 1-methylpiperidin-4-amine instead of 3-phenylpyrrolin-3-ol. MS (ESI): mass calcd. for $C_{23}H_{29}N_7O$, 419.24; m/z found, 420.3 [M+H]$^+$. $^1$H NMR (500 MHz, CD$_3$OD): δ 8.66 (s, 1H), 7.53 (d, J=3.5 Hz, 1H), 6.89 (d, J=3.5 Hz, 1H), 5.54-5.44 (m, 1H), 4.05-3.83 (m, 1H), 2.93 (d, J=11.8 Hz, 2H), 2.71-2.50 (m, 4H), 2.37-2.19 (m, 5H), 2.18-1.99 (m, 7H), 1.82-1.69 (m, 2H), 1.57-1.39 (m, 2H).

Example 85 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide

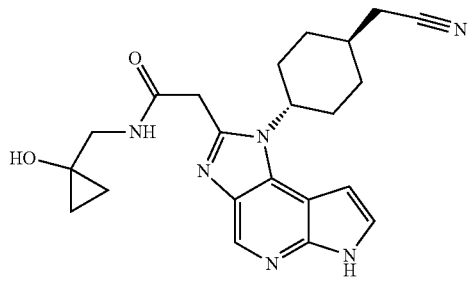 [SMILES: N#CC[C@H]1CC[C@H](n2c(CC(=O)NCC3(O)CC3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 1-(aminomethyl)cyclopropanol (72.7 mg, 0.835 mmol), DIPEA (216 mg, 1.67 mmol), and DMF (5 mL) was stirred at 0° C. for 1 h. Then PyBrOP (467 mg, 1.00 mmol) was added and stirred at room-temperature overnight. The mixture was quenched with 10 mL water and was purified by preparative basic HPLC using a Kromasil 150 mm×25 mm, 10 µm column (eluent: water (0.05% ammonia hydroxide v/v)-ACN from 5% to 35%, v/v) to provide the title compound (84 mg, 25% yield) as a white solid. MS (ESI): mass calcd. for $C_{22}H_{26}N_6O_2$, 406.21; m/z found, 407.2 [M+H]$^+$. $^1$H NMR (400 MHz, DMSO-d$_6$): δ 11.53 (br s, 1H), 8.50 (s, 1H), 8.03-7.93 (m, 1H), 7.44-7.40 (m, 1H), 6.74-6.71 (m, 1H), 5.04 (s, 1H), 4.58-4.49 (m, 1H), 4.02 (s, 2H), 3.29 (d, J=6.0 Hz, 2H), 2.55 (d, J=6.0 Hz, 2H), 2.45-2.31 (m, 2H), 2.10-1.97 (m, 5H), 1.50-1.37 (m, 2H), 0.62-0.55 (m, 2H), 0.55-0.48 (m, 2H).

Example 86 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)acetimidamide

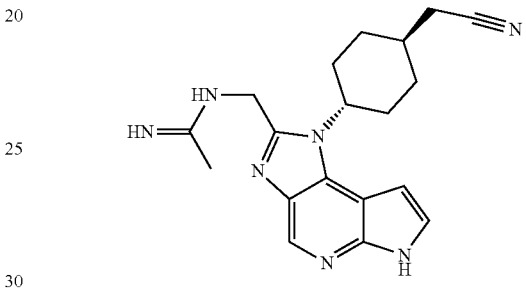

Step A: N-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl)acetimidamide. A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 52 mg, 0.11 mmol), acetimidamide hydrochloride (21 mg, 0.22 mmol), and K$_2$CO$_3$ (49 mg, 0.36 mmol) in DMF (1.4 mL) was stirred at room temperature for 15 h. The reaction was filtered to remove the solid and the filtrate was concentrated top dryness. The residue was partitioned between EtOAc and water. The organic phase was collected, dried over anhydrous Na$_2$SO$_4$, filtered, and concentrated to dryness to provide the title compound (47 mg, 86% yield) as a white solid. MS (ESI): mass calcd. for $C_{25}H_{27}N_7O_2S$, 489.19; m/z found, 490.2 [M+H]$^+$. MS (ESI): mass calcd. for $C_{25}H_{27}N_7O_2S$, 489.6; m/z found, 490.2 [M+H]$^+$. $^1$H NMR (400 MHz, CDCl$_3$) δ=8.82 (s, 1H), 8.23 (d, J=8.1 Hz, 2H), 7.83 (d, J=4.0 Hz, 1H), 7.60-7.53 (m, 1H), 7.52-7.44 (m, 2H), 6.84 (d, J=4.0 Hz, 1H), 4.56-4.52 (m, 3H), 2.41 (d, J=6.57 Hz, 2H), 2.39-2.25 (m, 2H), 2.20-2.09 (m, 2H), 2.05-1.90 (m, 6H), 1.56-1.41 (m, 2H).

Step B: N-((1-((1r,4r)-4-(Cyanomethyl)cyclohexyl)-1,6-dihydroimidazo[4,5-d]pyrrolo[2,3-b]pyridin-2-yl)methyl)acetimidamide. A solution of N-((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)acetimidamide (45 mg, 0.092 mmol) in THF (1 mL) and MeOH (1 mL) was treated with 3 N NaOH aqueous solution (0.15 mL, 0.45 mmol) at room temperature for 18 h and concentrated. The residue was purified by reverse phase HPLC (10-90% CH$_3$CN in H$_2$O, 0.1% TFA). The fractions were concentrated, and the residue was partitioned between NaHCO$_3$(aq) and n-BuOH (×3). The organic layer was dried (Na$_2$SO$_4$), filtered, and concentrated to a white solid. This solid was washed with CH$_2$Cl$_2$ and dried to give the title compound (31 mg, 97% yield). MS (ESI): mass calcd. for $C_{19}H_{23}N_7$, 349.20; m/z found, 350.3 [M+H]⁺. ¹H NMR (400 MHz, CD₃OD) δ=8.54 (s, 1H), 7.49 (d, J=3.5 Hz, 1H), 6.85 (d, J=3.5 Hz, 1H), 4.69 (s, 2H), 4.51 (br s, 1H), 2.55 (d, J=6.1 Hz, 4H), 2.19-2.02 (m, 8H), 1.56-1.42 (m, 2H).

Example 87 Synthesis and Characterization 2-((1r,4r)-4-(2-(2-(4-Benzylpiperidin-1-yl)-2-oxo-ethyl)imidazo[4,5-d]pyrrolo[2,3-b]pyridin-1(6H)-yl)cyclohexyl)acetonitrile and its Trifluoroacetic Acid Salt

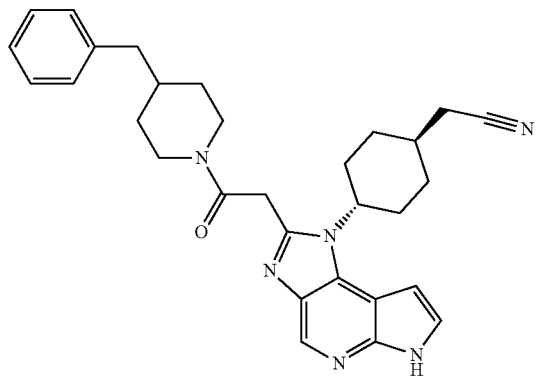 [SMILES: N#CC[C@H]1CC[C@H](n2c(CC(=O)N3CCC(Cc4ccccc4)CC3)nc3cnc4[nH]ccc4c32)CC1]

Step A: 2-((1r,4r)-4-(2-(2-(4-Benzylpiperidin-1-yl)-2-oxoethyl)-6-(phenylsulfonyl)imidazo[4,5-d]pyrrolo[2,3-b]pyridin-(6H)-yl)cyclohexyl)acetonitrile The title compound was prepared using analogous conditions as described in Example 48, step A using 4-benzylpiperidine in place of phenylmethanamine to provide the title compound (38 mg, 63% yield). MS (ESI): mass calcd. for C₃₆H₃₈N₆O₃S, 634.27; m/z found, 635.2 [M+H]⁺.

Step B: 2-((1r,4r)-4-(2-(2-(4-Benzylpiperidin-1-yl)-2-oxoethyl)imidazo[4,5-d]pyrrolo[2,3-b]pyridin-1(6H)-yl)cyclohexyl)acetonitrile as its trifluoroacetic acid salt. The free base compound was prepared using analogous conditions as described in Example 48, step B using 2-((1r,4r)-4-(2-(2-(4-benzylpiperidin-1-yl)-2-oxoethyl)-6-(phenylsulfonyl)imidazo[4,5-d]pyrrolo[2,3-b]pyridin-1(6H)-yl)cyclohexyl)acetonitrile in place of N-benzyl-2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetamide. Purification by reverse phase HPLC using a Varian Pursuit XRₛ5 Diphenyl 100×30 mm column (eluent: 10-90% CH₃CN in H₂O, 0.1% TFA) provided the title compound (11 mg, 38% yield) as its trifluoroacetic acid salt. MS (ESI): mass calcd. for C₃₀H₃₄N₆O, 494.28; m/z found, 495.3 [M+H]⁺. ¹H NMR (400 MHz, CD₃OD) δ=8.81 (br s, 1H), 7.74 (d, J=3.5 Hz, 1H), 7.30-7.21 (m, 2H), 7.20-7.14 (m, 3H), 7.08 (d, J=3.0 Hz, 1H), 4.56 (br s, 1H), 4.53-4.42 (m, 1H), 4.10 (br d, J=12.6 Hz, 1H), 3.28-3.16 (m, 1H), 2.77-2.66 (m, 1H), 2.64-2.48 (m, 6H), 2.22-2.08 (m, 6H), 1.95-1.68 (m, 4H), 1.59-1.44 (m, 2H), 1.37-1.11 (m, 2H).

Example 88 Synthesis and Characterization 2-((1r,4r)-4-(2-(4-Hydroxy-4-(pyridin-2-yl)piperidine-1-carbonyl)imidazo[4,5-d]pyrrolo[2,3-b]pyridin-1(6H)-yl)cyclohexyl)acetonitrile

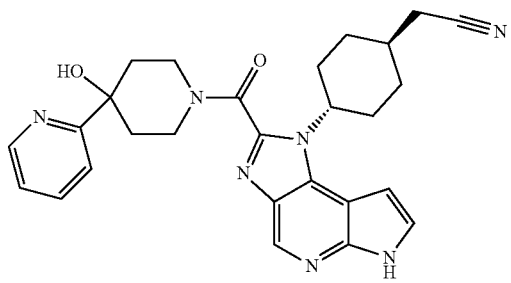 [SMILES: N#CC[C@H]1CC[C@H](n2c(C(=O)N3CCC(O)(c4ccccn4)CC3)nc3cnc4[nH]ccc4c32)CC1]

The title compound (11 mg, 11% yield) was prepared using Intermediate 6 and analogous conditions as described in Example 50, step A using 4-(pyridin-2-yl)piperidin-4-ol instead of 3-phenylpyrrolin-3-ol. MS (ESI): mass calcd. for C₂₇H₂₉N₇O₂, 483.24; m/z found, 484.3 [M+H]⁺. ¹H NMR (500 MHz, CD₃OD): δ 8.65 (s, 1H), 8.55 (d, J=4.8 Hz, 1H), 8.34 (d, J=4.6 Hz, 0.5H), 8.12 (d, J=7.7 Hz, 0.5H), 7.86 (t, J=7.7 Hz, 1H), 7.76 (d, J=7.9 Hz, 1H), 7.55 (d, J=3.5 Hz, 1H), 7.44 (dd, J=7.8, 4.8 Hz, 0.5H), 7.37-7.24 (m, 1H), 6.89 (d, J=3.5 Hz, 1H), 5.76 (s, 0.5H), 3.84-3.72 (m, 2H), 3.57-3.44 (m, 1H), 2.68 (s, 1H), 2.61-2.32 (m, 6H), 2.27-2.14 (m, 4H), 2.12-1.99 (m, 1H), 1.96-1.84 (m, 1H), 1.76-1.66 (m, 1H), 1.64-1.50 (m, 2H).

Example 89 Synthesis and Characterization 2-((1r,4r)-4-(2-(2-(Methylamino)pyrimidin-4-yl)imidazo[4,5-d]pyrrolo[2,3-b]pyridin-1(6H)-yl)cyclohexyl)acetonitrile

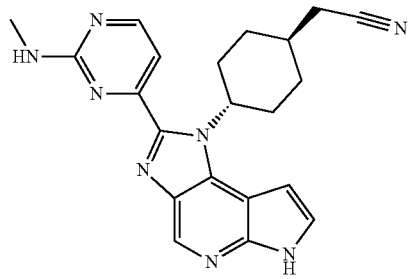

Step A: 2-((1r,4r)-4-(2-(2-(Methylthio)pyrimidin-4-yl)imidazo[4,5-d]pyrrolo[2,3-b]pyridin-1(6H)-yl)cyclohexyl)acetonitrile. A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 400 mg, 1.00 mmol), 2-(methylthio)pyrimidine-4-carbaldehyde (463 mg, 3.00 mmol), sodium dithionite (523 mg, 3.00 mmol), DMSO (2.5 mL), and water (0.15 mL) was heated to 100° C. for 3 hours. Water (20 mL) was added, which caused a precipitate to form and was filtered to collect the precipitate. The precipitate was recrystallized from 10% acetone/CH₂Cl₂ to provide a crude product (200 mg). This material was dissolved into MeOH/THF/NaOH (1 M) (3 mL/3 mL/3 mL)

and was heated at 80° C. for 1 h. The reaction was concentrated to dryness and partitioned between CH$_2$Cl$_2$ and H$_2$O (10 mL/10 mL). The organic layer was concentrated to dryness and purified by flash column chromatography (10% MeOH in CH$_2$Cl$_2$) to provide the title compound (100 mg). MS (ESI): mass calcd. for C$_{21}$H$_{21}$N$_7$S, 403.16; m/z found, 404.2 [M+H]$^+$.

Step B: 2-((1r,4r)-4-(2-(2-(Methylamino)pyrimidin-4-yl)imidazo[4,5-d]pyrrolo[2,3-b]pyridin-1(6H)-yl)cyclohexyl)acetonitrile. A solution of 2-((1r,4r)-4-(2-(2-(methylthio)pyrimidin-4-yl)imidazo[4,5-d]pyrrolo[2,3-b]pyridin-1(6H)-yl)cyclohexyl)acetonitrile (100 mg, 0.248 mmol) and 3-chlorobenzoperoxoic acid (128 mg, 0.743 mmol) in THF (10 mL) was stirred for 3 h. Then methylamine (2 M in MeOH, 2 mL) was added and was heated at 100° C. for 1 h. The reaction was concentrated to dryness and partitioned between CH$_2$Cl$_2$/water (5 mL/5 mL), the organic phase collected, and concentrated to dryness. The residue was purified by flash column chromatography to provide the title compound (9 mg, 9% yield). MS (ESI): mass calcd. for C$_{21}$H$_{22}$N$_8$, 386.20; m/z found, 387.1 [M+H]$^+$. $^1$H NMR (500 MHz, CDCl$_3$): δ 9.86 (s, 1H), 8.82 (s, 1H), 8.41 (d, J=5.1 Hz, 1H), 7.51-7.27 (m, 2H), 6.81-6.63 (m, 1H), 6.07-5.48 (br, 1H), 5.23 (s 1H), 3.03 (d, J=5.0 Hz, 3H), 2.71-2.50 (m, 2H), 2.37 (d, J=6.3 Hz, 2H), 2.18-2.01 (m, 5H), 1.48-1.31 (m, 2H).

Example 90 Synthesis and Characterization 2-((1r,4r)-4-(2-(2-Oxo-2-(piperidin-1-yl)ethyl)imidazo[4,5-d]pyrrolo[2,3-b]pyridin-1(6H)-yl)cyclohexyl)acetonitrile

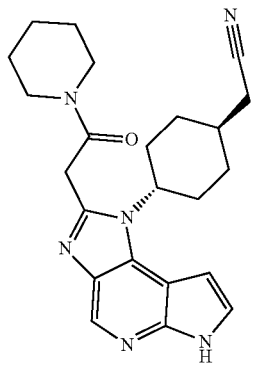 [SMILES: N#CC[C@H]1CC[C@H](n2c(CC(=O)N3CCCCC3)nc3cnc4[nH]ccc4c32)CC1]

Step A: 2-((1r,4r)-4-(2-(2-Oxo-2-(piperidin-1-yl)ethyl)-6-(phenylsulfonyl)imidazo[4,5-d]pyrrolo[2,3-b]pyridin-1(6H)-yl)cyclohexyl)acetonitrile as its trifluoroacetate salt. A solution of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 124 mg, 0.250 mmol), piperidine (1.0 mL, 10 mmol), and NH$_4$NO$_3$ (20 mg, 0.25 mmol) under Ar was microwaved at 50° C. for 5 h and 70° C. for 5 h. After concentration, the residue was purified by RF-HPLC using a Varian Pursuit XR$_s$5 Diphenyl 100×30 mm column (eluent: 10-100% CH$_3$CN in H$_2$O, 0.1% TFA) to provide the title compound (90.0 mg, 56%) as a clear oil. MS (ESI): mass calcd. for C$_{29}$H$_{32}$N$_6$O$_3$S, 544.23; m/z found, 545.3 [M+H]$^+$.

Step B: 2-((1r,4r)-4-(2-(2-Oxo-2-(piperidin-1-yl)ethyl)imidazo[4,5-d]pyrrolo[2,3-b]pyridin-1(6H)-yl)cyclohexyl)acetonitrile as its trifluoroacetate salt. A solution of 2-((1r,4r)-4-(2-(2-oxo-2-(piperidin-1-yl)ethyl)-6-(phenyl sulfonyl)imidazo[4,5-d]pyrrolo[2,3-b]pyridin-1(6H)-yl)cyclohexyl)acetonitrile as its trifluoroacetate salt (90 mg, 0.14 mmol) in THF (1 mL) and MeOH (1 mL) was treated with 3N NaOH (0.14 mL, 0.41 mmol) overnight at room temperature. A few drops of TFA were added, and the solvents were removed in vacuo to provide a clear oil. This residue was purified by RF-HPLC using a Varian Pursuit XR$_s$5 Diphenyl 100×30 mm column (eluent: 10-90% CH$_3$CN in H$_2$O, 0.1% TFA) to provide the title compound as a TFA salt, which was partitioned between CH$_2$Cl$_2$ and saturated aqueous NaHCO$_3$ solution. The organic layer was dried over Na$_2$SO$_4$, filtered, and concentrated to provide the title compound (19 mg, 47%) as an off-white solid. MS (ESI): mass calcd. for C$_{23}$H$_{28}$N$_6$O, 404.23; m/z found, 405.3 [M+H]$^+$. $^1$H NMR (400 MHz, CDCl$_3$) δ=11.67 (br s, 1H), 8.78 (s, 1H), 7.46 (br s, 1H), 6.73 (d, J=2.5 Hz, 1H), 4.82-4.72 (m, 1H), 4.22-4.16 (m, 1H), 3.75-3.67 (m, 2H), 3.60-3.50 (m, 2H), 2.64-2.46 (m, 2H), 2.40 (d, J=6.6 Hz, 2H), 2.33 (br s, 1H), 2.16 (d, J=14.7 Hz, 2H), 2.10-1.98 (m, 3H), 1.63-1.55 (m, 2H), 1.55-1.37 (m, 6H).

Example 91 Synthesis and Characterization 2-((1r,4r)-4-(2-(4'-(Methylsulfonyl)-[1,1'-biphenyl]-4-yl)imidazo[4,5-d]pyrrolo[2,3-b]pyridin-1(6H)-yl)cyclohexyl)acetonitrile

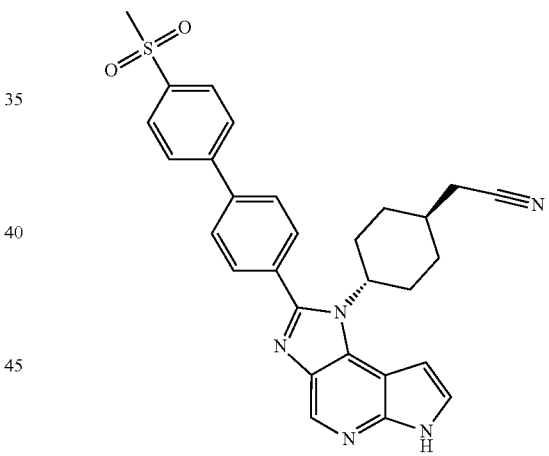

Step A: 2-((1r,4r)-4-(2-(4'-(Methylsulfonyl)-[1,1'-biphenyl]-4-yl)-6-(phenylsulfonyl)imidazo[4,5-d]pyrrolo[2,3-b]pyridin-1(6H)-yl)cyclohexyl)acetonitrile. To a solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 120 mg, 0.273 mmol) in DMSO (2.32 mL) and MeOH (0.465 mL) in a microwave vial was added 4'-(methylsulfonyl)[1,1'-biphenyl]-4-carbaldehyde (101 mg, 0.388 mmol), followed by sodium hydrosulfite (140 mg, 0.683 mmol). The vial was capped and heated to 100° C. over the weekend. After cooling to room temperature, the reaction was diluted with water (5 mL) and stirred for 5 minutes. The tan precipitate that formed was collected by filtration, washed with water (50 mL), and allowed to dry thoroughly. The precipitate was dissolved EtOAc, transferred to a round bottom flask and then concentrated to dryness to provide the title compound as a tan solid, which was used without further purification. MS (ESI): mass calcd. for $C_{35}H_{31}N_5O_4S_2$, 649.18; m/z found, 650.3 [M+H]⁺.

Step B: 2-((1r,4r)-4-(2-(4'-(Methylsulfonyl)-[1,1'-biphenyl]-4-yl)imidazo[4,5-d]pyrrolo[2,3-b]pyridin-1(6H)-yl)cyclohexyl)acetonitrile. The title compound (80 mg, 58% yield) was prepared using conditions analogous to those described in Example 1, Step B using 2-((1r,4r)-4-(2-(4'-(Methylsulfonyl)-[1,1'-biphenyl]-4-yl)-6-(phenylsulfonyl)imidazo[4,5-d]pyrrolo[2,3-b]pyridin-1(6H)-yl)cyclohexyl)acetonitrile (177 mg, 0.272 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The crude material was purified on a 12 gram silica gel column using 0 to 10% MeOH in DCM to provide the title compound. MS (ESI): mass calcd. for $C_{29}H_{27}N_5O_2S$, 509.19; m/z found, 510.1 [M+H]⁺. ¹H NMR (400 MHz, DMSO-d₆): δ 12.01 (s, 1H), 8.67 (s, 1H), 8.13-8.03 (m, 4H), 8.00 (d, J=7.9 Hz, 2H), 7.86 (d, J=7.9 Hz, 2H), 7.59-7.49 (m, 1H), 6.81 (d, J=3.3 Hz, 1H), 4.57-4.35 (m, 1H), 3.30 (s, 3H), 2.55 (d, J=6.2 Hz, 2H), 2.49-2.38 (m, 2H), 2.11-1.90 (m, 5H), 1.37-1.19 (m, 2H).

Example 92 Synthesis and Characterization 2-((1r,4r)-4-(2-(4-Benzoylphenyl)imidazo[4,5-d]pyrrolo[2,3-b]pyridin-1(6H)-yl)cyclohexyl)acetonitrile

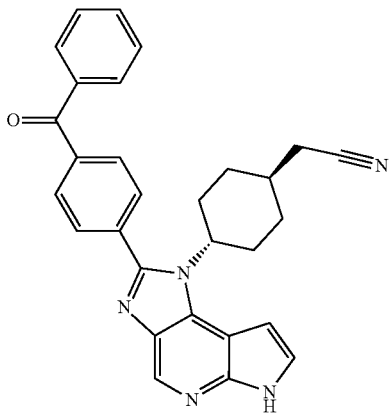 [SMILES: N#CC[C@H]1CC[C@H](n2c(-c3ccc(C(=O)c4ccccc4)cc3)nc3cnc4[nH]ccc4c32)CC1]

Step A: 2-((1r,4r)-4-(2-(4-Benzoylphenyl)-6-(phenylsulfonyl)imidazo[4,5-d]pyrrolo[2,3-b]pyridin-1(6H)-yl)cyclohexyl)acetonitrile. To a solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 121 mg, 0.275 mmol) in DMSO (2.34 mL) and MeOH (0.468 mL) in a microwave vial was added 4-benzoylbenzaldehyde (63.6 mg, 0.303 mmol), followed by sodium hydrosulfite (141 mg, 0.688 mmol). The vial was capped and heated to 100° C. over the weekend. After cooling to room temperature, the reaction was diluted with water (5 mL) and stirred for 5 minutes. The tan precipitate that formed was collected by filtration, washed with water (50 mL), and allowed to dry thoroughly. The solid was collected in a round bottom by dissolving it in EtOAc. The organic phase was then concentrated to dryness to provide the title compound as a tan solid, which was used without further purification. MS (ESI): mass calcd. for $C_{35}H_{29}N_5O_3S$, 599.20; m/z found, 600.3 [M+H]⁺.

Step B: 2-((1r,4r)-4-(2-(4-Benzoylphenyl)imidazo[4,5-d]pyrrolo[2,3-b]pyridin-1(6H)-yl)cyclohexyl)acetonitrile. The title compound (56 mg, 45% yield). was prepared using conditions analogous to those described in Example 1, Step B using 2-((1r,4r)-4-(2-(4-Benzoylphenyl)-6-(phenylsulfonyl)imidazo[4,5-d]pyrrolo[2,3-b]pyridin-1(6H)-yl)cyclohexyl)acetonitrile (165 mg, 0.275 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The crude material was purified on a 4 gram silica gel column using 0 to 100% EtOAc in heptane. The resulting material was then triturated with acetonitrile to provide the title compound. MS (ESI): mass calcd. for $C_{29}H_{25}N_5O$, 459.21; m/z found, 460.2 [M+H]⁺. ¹H NMR (400 MHz, DMSO-d₆): δ 12.03 (s, 1H), 8.68 (s, 1H), 7.96 (d, J=8.1 Hz, 2H), 7.91 (d, J=8.1 Hz, 2H), 7.84 (d, J=7.5 Hz, 2H), 7.76-7.71 (m, 1H), 7.67-7.59 (m, 2H), 7.58-7.52 (m, 1H), 6.84-6.79 (m, 1H), 4.52-4.37 (m, 1H), 2.59-2.51 (m, 4H), 2.05-1.94 (m, 5H), 1.39-1.20 (m, 2H).

Example 93 Synthesis and Characterization 2-((1r,4r)-4-(2-(2-(4-(2-Hydroxypropan-2-yl)piperidin-1-yl)-2-oxoethyl)imidazo[4,5-d]pyrrolo[2,3-b]pyridin-1(6H)-yl)cyclohexyl)acetonitrile

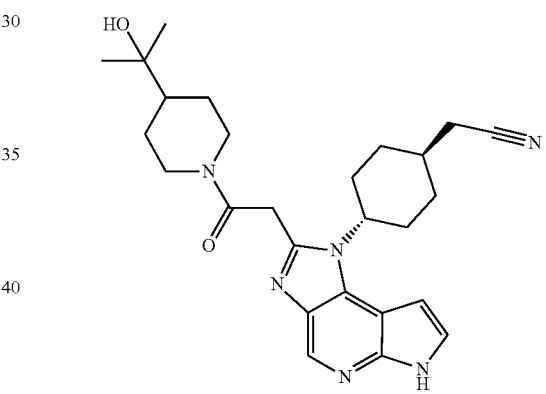

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 65 mg, 0.181 mmol) and 2-(piperidin-4-yl)propan-2-ol (65.0 mg, 0.362 mmol) in DMF (2 mL) were added PyBOP (152 mg, 0.292 mmol) and DIPEA (0.10 mL, 0.58 mmol) and was stirred at room temperature for 64 h. The reaction was concentrated to dryness and the residue was purified by reverse phase acidic HPLC to provide an impure product. This material was partitioned between $CH_2Cl_2$ and saturated $NaHCO_3$, collecting the organic layer. The organic layer was dried over anhydrous $MgSO_4$, filtered, and concentrated to dryness. This material was purified by flash column chromatography using 5-10% MeOH in DCM as eluent to provide the title compound (9 mg, 11% yield) as a foam. MS (ESI): mass calcd. for $C_{26}H_{34}N_6O_2$, 462.27; m/z found, 463.4 [M+H]⁺. ¹H NMR (400 MHz, CDCl₃) δ=10.72 (br s, 1H), 8.75 (s, 1H), 7.42 (t, J=2.8 Hz, 1H), 6.75-6.70 (m, 1H), 4.76-4.64 (m, 2H), 4.44 (d, J=12.6 Hz, 1H), 4.23-4.13 (m, 2H), 3.04 (dt, J=2.5, 13.1 Hz, 1H), 2.61-2.46 (m, 3H), 2.42 (d, J=6.6 Hz, 2H), 2.25-1.95 (m, 4H), 1.94-1.67 (m, 4H), 1.66-1.43 (m, 2H), 1.27-1.09 (m, 2H), 1.14 (d, J=3.5 Hz, 6H).

Example 94 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)-2-cyclopropylacetamide

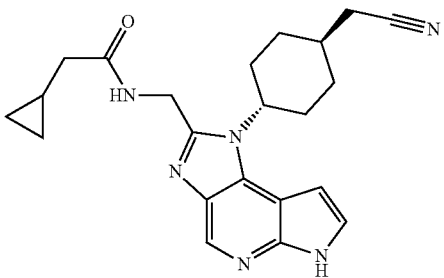 [SMILES: N#CC[C@H]1CC[C@H](n2c(CNC(=O)CC3CC3)nc3cnc4[nH]ccc4c32)CC1]

HATU (155 mg, 0.409 mmol) was added to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.409 mmol, purity 94%), cyclopropylacetic acid (40.9 mg, 0.409 mmol), DIEA (0.356 mL, 2.04 mmol), and $CH_2Cl_2$ (5 mL) and was stirred for 1 h at 10° C. The reaction was diluted with $CH_2Cl_2$ (10 mL), washed with water (10 mL), and concentrated to dryness. The residue was purified by preparative HPLC using a Gemini 150 mm×25 mm, 5 μm column (eluent: 20% to 50% (v/v) $CH_3CN$ and $H_2O$ with 0.05% $NH_3$) to provide the title compound (45 mg, 28% yield) as a white solid. MS (ESI): mass calcd. for $C_{22}H_{26}N_6O$, 390.22; m/z found, 391.2 [M+H]$^+$. $^1$H NMR (400 MHz, DMSO-d$_6$): δ 11.89 (s, 1H), 8.55 (s, 1H), 8.46 (t, J=5.6 Hz, 1H), 7.48 (t, J=2.4 Hz, 1H), 6.72 (s, 1H), 4.69 (d, J=5.6 Hz, 2H), 4.62-4.49 (m, 1H), 2.59 (d, J=6.0 Hz, 2H), 2.41-2.28 (m, 2H), 2.06 (d, J=6.8 Hz, 2H), 2.04-1.87 (m, 5H), 1.45-1.30 (m, 2H), 1.05-0.94 (m, 1H), 0.46-0.40 (m, 2H), 0.16-0.09 (m, 2H).

Example 95 Synthesis and Characterization (EZ)—N-((1-((1r,4r)-4-(Cyanomethyl)cyclohexyl)-1,6-dihydroimidazo[4,5-d]pyrrolo[2,3-b]pyridin-2-yl)methyl)-2-cyclohexyl-N-hydroxyacetimidamide

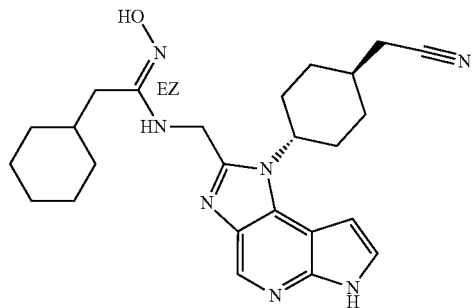 [SMILES: N#CC[C@H]1CC[C@H](n2c(CN/C(CC3CCCCC3)=N/O)nc3cnc4[nH]ccc4c32)CC1]

Step A: (EZ)-2-Cyclohexylacetaldehyde oxime. A solution of 2-cyclohexylacetaldehyde (1.0 g, 7.9 mmol), hydroxylamine hydrochloride (0.551 g, 7.92 mmol), sodium acetate (1.30 g, 15.8 mmol), and ethanol (20 mL) was stirred at room-temperature for 18 hours. The reaction was concentrated to dryness and treated with water (50 mL) and extracted with ethyl acetate (100 mL×3). The combined organic extracts were dried over anhydrous $Na_2SO_4$, filtered, and concentrated to dryness to provide the title compound (1.30 g, 116% yield), which was used in the next step without purification. 1H NMR (400 MHz, CDCl$_3$) δ 3.63 (qd, J=7.2, 9.2 Hz, 1H), 3.49 (qd, J=7.2 9.2 Hz, 1H), 2.15-2.04 (m, 1H), 1.76-1.62 (m, 4H), 1.50 (s, 1H), 1.20 (t, J=7.2 Hz, 4H), 1.10-0.80 (m, 2H).

Step B: (EZ)-2-Cyclohexyl-N-hydroxyacetimidoyl chloride. A solution of NCS (2.0 g, 15 mmol), (EZ)-2-cyclohexylacetaldehyde oxime (1.3 g, 9.2 mmol) and DMF (20 mL) was stirred for 2 hours at 10° C. under $N_2$. The reaction was treated with water (30 mL) and extracted with ethyl acetate (100 mL×3). The combined organic extracts were dried over anhydrous $Na_2SO_4$, filtered, and concentrated to dryness. The residue was purified by flash column chromatography to provide the title compound (300 mg, 19%) as a white solid. 1H NMR (400 MHz, CDCl$_3$) δ 8.42-8.09 (m, 1H), 2.38 (d, J=7.2 Hz, 2H), 1.72 (d, J=11.4 Hz, 5H), 1.35-1.08 (m, 4H), 1.01-0.89 (m, 2H).

Step C: (EZ)—N-((1-((1r,4r)-4-(Cyanomethyl)cyclohexyl)-1,6-dihydroimidazo[4,5-d]pyrrolo[2,3-b]pyridin-2-yl)methyl)-2-cyclohexyl-N-hydroxyacetimidamide. A solution of 2-((1r,4r)-4-(2-(aminomethyl)imidazo[4,5-d]pyrrolo[2,3-b]pyridin-1(6H)-yl)cyclohexyl)acetonitrile (Intermediate 5, 300 mg, 0.870 mmol), (EZ)-2-cyclohexyl-N-hydroxyacetimidoyl chloride (153 mg, 0.870 mmol), triethylamine (264 mg, 2.61 mmol) and DMF (25 mL) was stirred at room-temperature for 2 hours. The same reaction was carried out by using 2-((1r,4r)-4-(2-(aminomethyl)imidazo[4,5-d]pyrrolo[2,3-b]pyridin-1(6H)-yl)cyclohexyl)acetonitrile (Intermediate 5, 50 mg, 0.14 mmol), (EZ)-2-cyclohexyl-N-hydroxyacetimidoyl chloride (25 mg, 0.14 mmol), triethylamine (44 mg, 0.43 mmol), and DMF (2.5 mL), The two reactions were combined and purified by preparative HPLC using a Waters Xbridge Prep OBD $C_{18}$ 150 mm×30 mm, 5 μm column (eluent: 30% to 60% (v/v) $CH_3CN$ and $H_2O$ with 0.05% $NH_3$) to provide the title compound (10 mg, 2% yield). MS (ESI): mass calcd. for $C_{25}H_{33}N_7O$, 447.27; m/z found, 488.1 [M+H]$^+$. $^1$H NMR (400 MHz, DMSO-d$_6$): δ 11.88 (br s, 1H), 9.16 (br s, 0.7H), 8.73 (s, 0.3H), 8.54 (s, 1H), 7.47 (br s, 1H), 6.72 (s, 1H), 6.32-6.17 (m, 0.8H), 5.85-5.74 (m, 0.2H), 4.76-4.54 (m, 2.5H), 4.47-4.38 (m, 0.5H), 2.62-2.57 (m, 2H), 2.43-2.26 (m, 2H), 2.11-1.87 (m, 7H), 1.73-1.62 (m, 4H), 1.58-1.42 (m, 4H), 1.20-1.09 (m, 2H), 0.98-0.87 (m, 2H), 0.83-0.77 (m, 1H).

Example 96 Synthesis and Characterization 4-(1-((1r,4r)-4-(Cyanomethyl)cyclohexyl)-1,6-dihydroimidazo[4,5-d]pyrrolo[2,3-b]pyridin-2-yl)benzonitrile

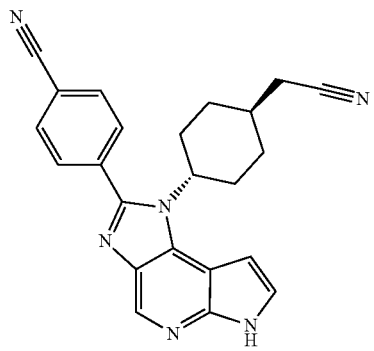 [SMILES: N#CC[C@H]1CC[C@H](n2c(-c3ccc(C#N)cc3)nc3cnc4[nH]ccc4c32)CC1]

Step A: 4-(1-((1r,4r)-4-(Cyanomethyl)cyclohexyl)-6-(phenylsulfonyl)-1,6-dihydroimidazo[4,5-d]pyrrolo[2,3-b]pyridin-2-yl)benzonitrile. A solution of 2-((1r,4r)-4-((5-nitro-1-(phenyl sulfonyl)-1H-pyrrolo[2,3-b]pyridin-4-yl)amino)cyclohexyl)acetonitrile (Intermediate 1, 151 mg, 0.344 mmol), 4-formylbenzonitrile (91 mg, 0.69 mmol), and sodium hydrosulfite (192 mg, 0.937 mmol) in DMSO (1 mL), MeOH (1 mL), and distilled water (0.5 mL) in a sealed tube was heated at 100° C. for 1 6 h. After cooling to room temperature, the reaction was concentrated and the residue was filtered. The yellow solid was washed with water and dried in the air to provide the title compound (150 mg), which was used in the next step without further purification. MS (ESI): mass calcd. for $C_{29}H_{24}N_6O_2S$, 520.17; m/z found, 521.3 [M+H]$^+$.

Step B: 4-(1-((1r,4r)-4-(Cyanomethyl)cyclohexyl)-1,6-dihydroimidazo[4,5-d]pyrrolo[2,3-b]pyridin-2-yl)benzonitrile. The title compound (64 mg, 58% yield) was prepared using conditions analogous to those described in Example 76, Step B using 4-(1-((1r,4r)-4-(Cyanomethyl)cyclohexyl)-6-(phenylsulfonyl)-1,6-dihydroimidazo[4,5-d]pyrrolo[2,3-b]pyridin-2-yl)benzonitrile (150 mg, 0.290 mmol) instead of 4-(4-(1-((1r,4r)-4-(cyanomethyl)cyclohexyl)-6-(phenylsulfonyl)-1,6-dihydroimidazo[4,5-d]pyrrolo[2,3-b]pyridin-2-yl)piperidin-1-yl)benzonitrile. The title compound was subjected to two flash column chromatography columns. The title compound was initially purified using the following conditions: 16 g silica gel column, 3-10% MeOH in DCM. The resulting compound was impure and subjected to an additional purification using the following conditions: 16 g silica gel column, 50-100% EtOAc in DCM. MS (ESI): mass calcd. for $C_{23}H_{20}N_6$, 380.17; m/z found, 381.1 [M+H]$^+$. $^1$H NMR (400 MHz, CDCl$_3$) δ=10.02 (br s, 1H), 8.89 (s, 1H), 7.88 (d, J=8.1 Hz, 2H), 7.84-7.81 (d, J=8.1 Hz, 2H), 7.52-7.43 (m, 1H), 6.78 (br s, 1H), 4.49-4.39 (m, 1H), 2.72-2.57 (m, 2H), 2.42 (d, J=6.1 Hz, 2H), 2.21-2.13 (m, 3H), 2.13-2.06 (m, 2H), 1.49-1.31 (m, 2H).

Example 97 Synthesis and Characterization

4-Cyano-N-((1-((1r,4r)-4-(cyanomethyl)cyclohexyl)-1,6-dihydroimidazo[4,5-d]pyrrolo[2,3-b]pyridin-2-yl)methyl)benzenesulfonamide

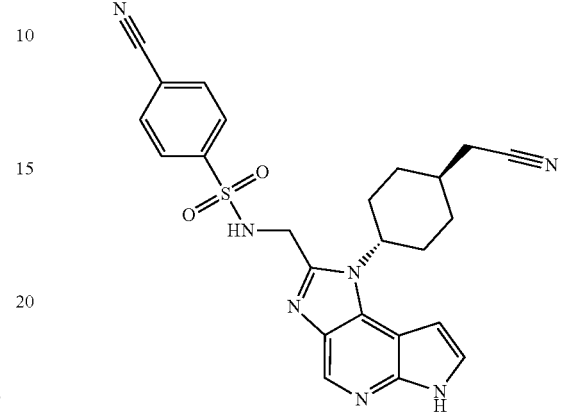

4-Cyanobenzenesulfonyl chloride (79.8 mg, 0.396 mmol) was added to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.396 mmol, purity 91%), triethylamine (0.276 mL, 1.98 mmol), and CH$_2$Cl$_2$ (5 mL) and was stirred for 1 h at 10° C. The reaction was diluted with CH$_2$Cl$_2$ (10 mL), washed with water (10 mL), dried over anhydrous Na$_2$SO$_4$, filtered, and concentrated to dryness. The residue was purified by preparative TLC (eluent: CH$_2$Cl$_2$: methanol 10:1) to provide the title compound (55 mg, 29% yield) as a white solid. MS (ESI): mass calcd. for $C_{24}H_{23}N_7O_2S$, 473.16; m/z found, 474.2 [M+H]$^+$. $^1$H NMR ((400 MHz, DMSO-d$_6$) ~85% major rotamer: δ 11.92 (s, 1H), 8.75 (br s, 1H), 8.49 (s, 1H), 8.08-8.03 (m, 2H), 8.02-7.98 (m, 2H), 7.48 (t, J=2.8 Hz, 1H), 6.74-6.70 (m, 1H), 4.62-4.51 (m, 1H), 4.46 (s, 2H), 2.61 (d, J=6.0 Hz, 2H), 2.41-2.26 (m, 2H), 2.06-1.91 (m, 5H), 1.47-1.32 (m, 2H).

Example 98 Synthesis and Characterization 2-((1r,4r)-4-(2-(2-(Methylthio)pyrimidin-4-yl)imidazo[4,5-d]pyrrolo[2,3-b]pyridin-1(6H)-yl)cyclohexyl)acetonitrile

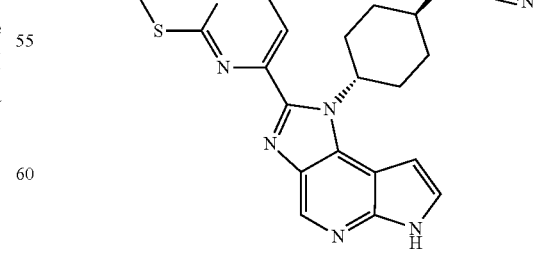

A solution of 2-((1R,4R)-4-((5-nitro-1-(phenylsulfonyl)-1H-pyrrolo[2,3-b]pyridin-4-yl)amino)cyclohexyl)acetonitrile (Intermediate 1, 440 mg, 1.00 mmol), 2-(methylthio)

pyrimidine-4-carbaldehyde (463 mg, 3.00 mmol), sodium dithionite (523 mg, 3.00 mmol), DMSO (2.5 mL), and water (0.15 mL) was heated to 100° C. for 3 hours. Water (20 mL) was added, which caused a precipitate to form. The precipitate was collected by filtration and was purified by flash column chromatography to obtain the intermediate, 2-((1r,4r)-4-(2-(2-(methylthio)pyrimidin-4-yl)-6-(phenylsulfonyl)imidazo[4,5-d]pyrrolo[2,3-b]pyridin-1(6H)-yl)cyclohexyl)acetonitrile (400 mg). 2-((1r,4r)-4-(2-(2-(Methylthio)pyrimidin-4-yl)-6-(phenylsulfonyl)imidazo[4,5-d]pyrrolo[2,3-b]pyridin-1(6H)-yl)cyclohexyl)acetonitrile (100 mg) was then dissolved into MeOH/THF/NaOH (1M) (3 mL/3 mL/3 mL) and was heated at 80° C. for 1 h. The reaction was concentrated to dryness and partitioned between $CH_2Cl_2$ (10 mL) and water (10 mL), collecting the organic phase. The organic layer was concentrated to dryness and purified flash column chromatography using 10% MeOH in $CH_2Cl_2$ as the eluent to provide the title compound (5 mg, 8% yield). MS (ESI): mass calcd. for $C_{21}H_{21}N_7S$, 403.16; m/z found, 404.2 $[M+H]^+$. $^1H$ NMR (500 MHz, $CDCl_3$): δ 10.66 (s, 1H), 8.89 (s, 1H), 8.70 (d, J=5.1 Hz, 1H), 7.95 (d, J=5.1 Hz, 1H), 7.47 (dd, J=3.4, 1.8 Hz, 1H), 6.91-6.70 (m, 1H), 5.79 (s, 1H), 2.79-2.56 (m, 5H), 2.44 (d, J=6.4 Hz, 2H), 2.25-2.13 (m, 5H), 1.62-1.35 (m, 2H).

Example 99 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((trimethyl silyl)methyl)acetamide

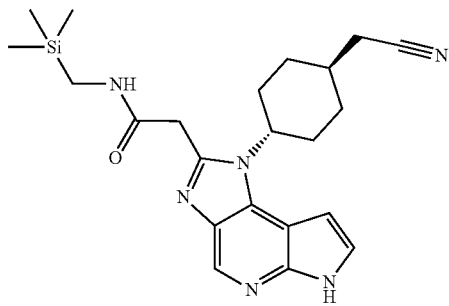 [SMILES: C[Si](C)(C)CNC(=O)Cc1nc2cnc3[nH]ccc3c2n1[C@H]1CC[C@H](CC#N)CC1]

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-((trimethylsilyl)methyl)acetamide. The title compound was prepared using analogous conditions as described in Example 48, step A using (trimethylsilyl)methanamine in place of phenylmethanamine to provide the title compound (84 mg, 75% yield). MS (ESI): mass calcd. for $C_{28}H_{34}N_6O_3SSi$, 562.22; m/z found, 563.3 $[M+H]^+$.

Step B: 2-(1-((1r,4r)-4-(Cyanomethyl)cyclohexyl)-1,6-dihydroimidazo[4,5-d]pyrrolo[2,3-b]pyridin-2-yl)-N-((trimethylsilyl)methyl)acetamide. The title compound (26 mg, 41% yield) was prepared as a white solid using analogous conditions as described in Example 48, step B using 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-((trimethylsilyl)methyl)acetamide in place of N-benzyl-2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetamide. The purification was performed by reverse phase-HPLC using a Varian Pursuit $XR_s5$ Diphenyl 100×30 mm column (eluent: 10-90% $CH_3CN$ in $H_2O$, 0.1% TFA). TFA was removed by dissolving the TFA salt in 10% MeOH in DCM and passing the solution through a 500 mg column of SILICYCLE SPE-R66030B-03P Carbonate and eluting with 10% MeOH in DCM. MS (ESI): mass calcd. for $C_{22}H_{30}N_6OSi$, 422.23; m/z found, 424.2 $[M+H]^+$. $^1H$ NMR (400 MHz, $CDCl_3$) δ=11.22 (br s, 1H), 8.75 (s, 1H), 7.61-7.43 (m, 2H), 6.77-6.71 (m, 1H), 4.68 (br s, 1H), 4.01 (d, J=6.6 Hz, 1H), 2.78 (d, J=5.6 Hz, 2H), 2.55 (br s, 2H), 2.41 (d, J=6.6 Hz, 2H), 2.24-2.11 (m, 2H), 2.14-1.96 (m, 2H), 1.94-1.82 (m, 2H), 1.56-1.41 (m, 2H), 0.00 (s, 9H).

Example 100 Synthesis and Characterization 2-((1r,4r)-4-(2-(4-(Trimethylsilyl)cyclohexyl)imidazo[4,5-d]pyrrolo[2,3-b]pyridin-1(6H)-yl)cyclohexyl)acetonitrile as its Trifluoroacetic Acid

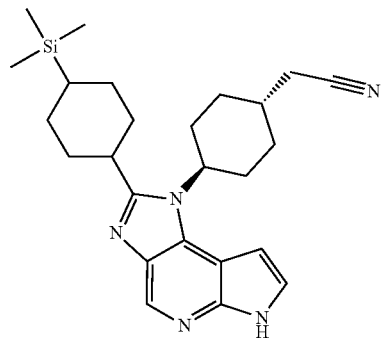 [SMILES: C[Si](C)(C)C1CCC(c2nc3cnc4[nH]ccc4c3n2[C@H]2CC[C@H](CC#N)CC2)CC1]

Step A: (4-Methoxyphenyl)trimethylsilane. To a solution consisting of 4-bromoanisole (9.4 g, 50 mmol) and anhydrous THF (200 mL) at 0° C. was added $Me_3SiCl$ (12.7 mL, 100 mmol) dropwise, followed by n-BuLi (40 mL, 2.5 M in hexanes, 100 mmol). The mixture was stirred at room temperature for 3 hours before quenching with water (150 mL) and extracting with ethyl acetate (100 mL×3). The combined organic extracts were washed with brine, dried over anhydrous $Na_2SO_4$, filtered, concentrated under reduced pressure, and purified by flash column chromatography (eluent: petroleum ether:ethyl acetate, 20:1) to afford the title compound (6.8 g, 69%). $^1H$ NMR (400 MHz, $CDCl_3$) δ 7.49-7.44 (m, 2H), 6.95-6.90 (m, 2H), 3.83 (s, 3H), 0.26 (s, 9H).

Step B: 4-(Trimethylsilyl)cyclohexanone. Ammonia (1 L) was condensed into a 3 L three-necked flask at −78° C. and then a solution of (4-methoxyphenyl)trimethylsilane (45.0 g, 250 mmol) and anhydrous THF (275 mL) was added, followed by EtOH (200 mL) and sodium (57.5 g, 2.50 mol) in portions. The resulting mixture was stirred at −40° C. for 2 hours and then treated with EtOH (130 mL). After stirring for 16 hours with gradual warming to room temperature and ammonia evaporating gradually, the remaining mixture was poured into water (600 mL) and extracted with ethyl acetate (600 mL×3). The combined organic extracts were washed with brine, dried over anhydrous $Na_2SO_4$, filtered, and concentrated to dryness under reduced pressure. The residue was dissolved in EtOH (400 mL) and $H_2O$ (48 mL) and then treated with oxalic acid (6.8 g, 76 mmol). The mixture was stirred at room temperature for 2 hours before pouring it into water (500 mL) and extracting with ethyl acetate (500 mL×3). The combined organic extracts were washed with brine, dried over anhydrous $Na_2SO_4$, filtered, concentrated to dryness under reduced pressure, and purified by flash column chromatography (eluent: petroleum ether:ethyl acetate=15:1) to afford the title compound (18 g, 41%). LCMS (ESI): RT=5.03 min, mass calcd. for $C_9H_{18}OSi$, 170.11; m/z found 171.2 [M+H]$^+$. Analytical reverse phase LC-MS was carried out using an Agilent TC-C18, 50×2.1 mm, 5 μm column with a flow rate of 0.8 mL/min, eluting with a gradient of 0% to 85% acetonitrile containing 0.05% TFA (solvent B) and water containing 0.1% TFA (solvent A). The eluent composition was kept at 100% A for 1 minute, followed by increasing to 40% B over the course of 4 minutes. The eluent was further increased to 85% B over the course of 2.5 minutes before returning to 100% A over the course of 2 minutes. Total run time was 9.5 minutes. $^1$H NMR (400 MHz, CDCl$_3$) δ 2.47-2.37 (m, 2H), 2.33-2.22 (m, 2H), 2.13-2.05 (m, 2H), 1.58-1.43 (m, 2H), 0.97-0.87 (m, 1H), 0.00 (s, 9H).

Step C: (4-(Methoxymethylene)cyclohexyl)trimethylsilane. n-Butyl lithium (10 mL, 2.5 M in hexane, 25 mmol) was added drop-wise to a solution consisting of diisopropylamine (3.5 mL, 25.1 mmol) and anhydrous THF (50 mL) −78° C. under N$_2$. After stirring for 30 minutes at 0° C., it was added drop-wise to a solution of (methoxymethyl)triphenylphosphonium chloride (8.60 g, 25.1 mmol) and anhydrous THF (50 mL) −78° C. The mixture was stirred at −78° C. for 10 minutes, and then warmed to 0° C. for 30 minutes and subsequently to room temperature for 30 minutes before being re-cooled to 0° C. and treating with a solution of 4-(trimethylsilyl)cyclohexanone (2.85 g, 16.7 mmol) and anhydrous THF (20 mL). The mixture was stirred for 2 hours with gradual warming to room-temperature before quenching with H$_2$O (50 mL) and extracting with ethyl acetate (75 mL×3). The combined organic extracts were washed with brine (30 mL), dried over anhydrous MgSO$_4$, filtered, concentrated to dryness, and purified by flash column chromatography (eluent: petroleum ether) to afford the title compound (3.00 g, 90%). $^1$H NMR (400 MHz, CDCl$_3$) δ 5.81 (s, 1H), 3.60 (s, 3H), 2.88-2.85 (m, 1H), 2.15-2.12 (m, 1H), 1.97-1.87 (m, 1H), 1.87-1.77 (m, 2H), 1.72-1.61 (m, 1H), 1.20-1.10 (m, 2H), 0.75-0.68 (m, 1H), 0.00 (s, 9H).

Step D: 4-(Trimethylsilyl)cyclohexanecarbaldehyde. To a solution of (4-(methoxymethylene)cyclohexyl)trimethylsilane (3.0 g, 15 mmol) and THF (100 mL) was added 2 N HCl (35 mL, 70 mmol). After stirring at room temperature for 16 hours, the mixture was quenched with H$_2$O (50 mL) and extracted with ethyl acetate (50 mL×3). The combined organic extracts were washed with brine, dried over anhydrous MgSO$_4$, filtered, concentrated to dryness under reduced pressure, and purified by flash column chromatography (eluent: petroleum ether:ethyl acetate=100:0 to 20:1) to afford the title compound (2.3 g, 82%). $^1$H NMR (400 MHz, CDCl$_3$ δ 9.83 (s, 0.3H), 9.68 (s, 0.7H), 2.59-2.53 (m, 0.3H), 2.33-2.24 (m, 1.2H), 2.14-2.06 (m, 1.3H), 1.94-1.91 (m, 1.3H), 1.72-1.59 (m, 1.4H), 1.36-1.15 (m, 3.5H), 0.67-0.56 (m, 1H), 0.08 (s, 6.5H), 0.00 (s, 2.5H).

Step E: 2-((1r,4r)-4-(6-(Phenylsulfonyl)-2-(4-(trimethylsilyl)cyclohexyl)imidazo[4,5-d]pyrrolo[2,3-b]pyridin-1 (6H)-yl)cyclohexyl)acetonitrile. The title compound (53 mg, 29%) was prepared from Intermediate 3 (130 mg) using analogous conditions as found in Example 1, Step A, and using 4-(trimethylsilyl)cyclohexanecarbaldehyde instead of ethyl 3-ethoxy-3-iminopropanoate. MS (ESI): mass calcd. for $C_{31}H_{39}N_5O_2SSi$, 573.26; m/z found, 574.3 [M+H]$^+$.

Step F: 2-((1r,4r)-4-(2-(4-(Trimethylsilyl)cyclohexyl)imidazo[4,5-d]pyrrolo[2,3-b]pyridin-1(6H)-yl)cyclohexyl)acetonitrile as its trifluoroacetic acid salt The title compound (11 mg, 22% yield) was prepared using analogous conditions as found in Example 197 step B using 2-((1R,4R)-4-(6-(phenylsulfonyl)-2-(4-(trimethylsilyl)cyclohexyl)imidazo[4,5-d]pyrrolo[2,3-b]pyridin-1(6H)-yl)cyclohexyl) acetonitrile instead of 2-((1R,4R)-4-(2-(2-(4-methoxypiperidin-1-yl)-2-oxoethyl)-6-(phenylsulfonyl) imidazo[4,5-d]pyrrolo[2,3-b]pyridin-1(6H)-yl)cyclohexyl) acetonitrile.). The title compound was subjected to two separate purification methods. It was purified initially by dry solid loading onto a flash column chromatography (16 g silica gel column, using 3-10% MeOH in DCM as the eluent). Second, the title compound was further purified by reverse phase-HPLC using a Varian Pursuit XR$_s$5 Diphenyl 100×30 mm column (eluent: 10-90% CH$_3$CN in H$_2$O, 0.1% TFA). MS (ESI): mass calcd. for $C_{25}H_{35}N_5Si$, 433.27; m/z found, 434.2 [M+H]$^+$. $^1$H NMR (400 MHz, CD$_3$OD) δ=8.69 (br s, 1H), 7.69 (d, J=3.0 Hz, 1H), 7.00 (d, J=3.5 Hz, 1H), 4.85-4.72 (m, 1H), 3.47 (br t, J=11.6 Hz, 1H), 2.70-2.58 (m, 2H), 2.53 (d, J=6.1 Hz, 2H), 2.21-2.00 (m, 7H), 2.02-1.88 (m, 2H), 1.78-1.66 (m, 2H), 1.64-1.43 (m, 4H), 0.71 (t, J=12.9 Hz, 1H), 0.00 (s, 9H).

Example 101 Synthesis and Characterization (EZ)—N-((1-((1r,4r)-4-(Cyanomethyl)cyclohexyl)-1,6-dihydroimidazo[4,5-d]pyrrolo[2,3-b]pyridin-2-yl)methyl)-N-hydroxy-3,3-dimethylbutanimidamide

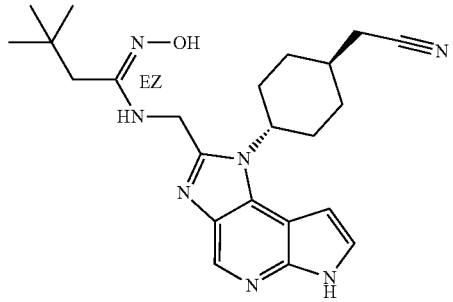 [SMILES: CC(C)(C)C/C(=N/O)NCc1nc2cnc3[nH]ccc3c2n1[C@H]1CC[C@H](CC#N)CC1]

Step A: (EZ)-3,3-Dimethylbutanal oxime. A solution of 3,3-dimethylbutanal (5.0 g, 50 mmol), hydroxylamine hydrochloride (10 g, 150 mmol), sodium acetate (12 g, 150 mmol), ethanol (150 mL), and water (30 mL) was stirred at room temperature for 24 h. The reaction was concentrated to dryness, the residue was diluted with water (40 mL), extracted with ethyl acetate (80 mL×3), dried over anhydrous Na$_2$SO$_4$, filtered, and concentrated to dryness to provide the title compound (4.0 g, 70% yield) as a colorless oil. $^1$H NMR (400 MHz, CDCl$_3$) δ 7.49 (t, J=6.8 Hz, 0.6H), 6.82 (t, J=5.8 Hz, 0.4H), 2.32 (d, J=5.6 Hz, 0.8H), 2.08 (d, J=6.8 Hz, 1.2H), 0.99 (s, 4H), 0.96 (s, 5H).

Step B: (EZ)—N-Hydroxy-3,3-dimethylbutanimidoyl chloride. A solution of NCS (5.80 g, 43.4 mmol), (EZ)-3,3-dimethylbutanal oxime (2.5 g, 22 mmol) and DMF (15 mL) was stirred for 2 hours at 10° C. under N$_2$. The reaction was diluted with ethyl acetate (180 mL) and washed with water (50 mL×3). The combined organic phases were dried over anhydrous Na$_2$SO$_4$, filtered, and concentrated to dryness. The residue was purified by flash column chromatography to provide the title compound (1.80 g, 55%) as a colorless oil. $^1$H NMR (400 MHz, CDCl$_3$) δ 8.90-8.68 (m, 1H), 2.45 (s, 2H), 1.03 (s, 9H).

Step C: (EZ)—N-((1-((1r,4r)-4-(Cyanomethyl)cyclohexyl)-1,6-dihydroimidazo[4,5-d]pyrrolo[2,3-b]pyridin-2- yl)methyl)-N-hydroxy-3,3-dimethylbutanimidamide. A solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 300 mg, 0.87 mmol), (EZ)—N-hydroxy-3,3-dimethylbutanimidoyl chloride (130 mg, 0.87 mmol), triethylamine (264 mg, 2.61 mmol), and DMF (12 mL) was stirred at room-temperature for 4 h. The reaction was filtered and the residue was purified by a preparative HPLC using a Kromasil 150 mm×25 mm, 10 μm column (eluent: 28% to 38% (v/v) CH$_3$CN and H$_2$O with 0.05% NH$_3$) to provide the title compound (99 mg, 27% yield) as a white solid. MS (ESI): mass calcd. for C$_{23}$H$_{31}$N$_7$O, 421.26; m/z found, 422.1 [M+H]$^+$. $^1$H NMR (400 MHz, DMSO-d$_6$): δ 11.88 (br s, 1H), 9.26 (s, 0.7H), 8.75 (s, 0.3H), 8.61-8.46 (m, 1H), 7.47 (br s, 1H), 6.72 (br s, 1H), 6.29-6.17 (m, 0.7H), 5.63-5.51 (m, 0.3H), 4.71-4.39 (m, 3H), 2.63-2.56 (m, 2H), 2.41-2.30 (m, 2H), 2.29-2.14 (m, 2H), 2.10-1.88 (m, 5H), 1.57-1.34 (m, 2H), 0.99 (s, 2.4H), 0.94 (s, 6.6H).

Example 102 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-phenylethyl)acetamide

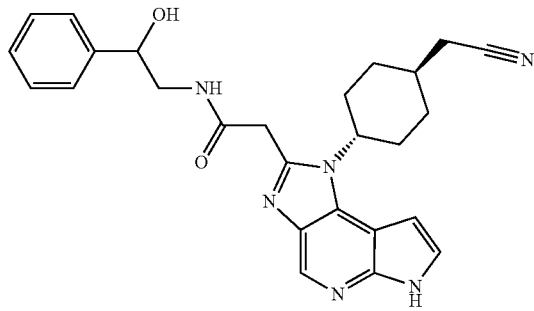 [SMILES: N#CC[C@H]1CC[C@H](n2c(CC(=O)NCC(O)c3ccccc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 66 mg, 0.18 mmol) and 2-amino-1-phenylethanol (51 mg, 0.37 mmol) in DMF (2 mL) were added PyBOP (190 mg, 0.37 mmol) and DIPEA (0.10 mL, 0.58 mmol) and the reaction mixture was stirred at room temperature for 18 h. The reaction was concentrated to dryness and the residue was purified by reverse phase HPLC using a Varian Pursuit XR$_s$5 Diphenyl 100×30 mm column (eluent: 10-90% CH$_3$CN in H$_2$O, 0.1% TFA) to provide the title compound (17 mg, 16% yield) as a foam. MS (ESI): mass calcd. for C$_{26}$H$_{28}$N$_6$O$_2$, 456.23; m/z found, 457.4 [M+H]$^+$. $^1$H NMR (400 MHz, CD$_3$OD) δ=8.81 (s, 1H), 7.75 (d, J=3.0 Hz, 1H), 7.44-7.34 (m, 5H), 7.09 (d, J=3.5 Hz, 1H), 5.65 (t, J=8.1 Hz, 1H), 4.80 (dd, J=4.5, 7.6 Hz, 1H), 4.67 (br s, 1H), 4.05-3.95 (m, 1H), 3.58-3.38 (m, 3H), 2.55 (d, J=6.1 Hz, 3H), 2.16-2.08 (m, 5H), 1.64-1.40 (m, 2H).

Example 103 Synthesis and Characterization (EZ)—N-((1-((1r,4r)-4-(Cyanomethyl)cyclohexyl)-1,6-dihydroimidazo[4,5-d]pyrrolo[2,3-b]pyridin-2-yl)methyl)-N-hydroxy-2-phenylacetimidamide

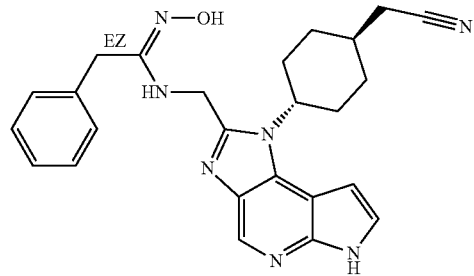 [SMILES: N#CC[C@H]1CC[C@H](n2c(CN/C(Cc3ccccc3)=N\O)nc3cnc4[nH]ccc4c32)CC1]

Step A: (EZ)-2-Phenylacetaldehyde oxime. A mixture of 2-phenylacetaldehyde (5.00 g, 41.6 mmol), hydroxylamine hydrochloride (2.89 g, 41.6 mmol), pyridine (3.29 g, 41.6 mmol), and methanol (50 mL) was stirred at room temperature for 18 hours. The reaction mixture was concentrated to dryness under reduced pressure, diluted with dichloromethane (200 mL), and washed with aq. HCl (1 M, 50 mL x 3) and water (100 mL×3). The organic layer was dried over anhydrous Na$_2$SO$_4$, filtered and concentrated to dryness under reduced pressure. The residue was purified by recrystallization (petroleum ether:ethyl acetate, 10:1) to afford the title compound (1.20 g, 21%) as a white solid. 1H NMR (400 MHz, CDCl$_3$) δ 7.97 (s, 1H), 7.37-7.30 (m, 2H), 7.26-7.22 (m, 3H), 6.90 (t, J=5.3 Hz, 1H), 3.75 (d, J=5.6 Hz, 2H).

Step B: (EZ)—N-Hydroxy-2-phenylacetimidoyl chloride. A mixture of NCS (2.37 g, 17.8 mmol), (EZ)-2-phenylacetaldehyde oxime (1.2 g, 8.9 mmol) and DMF (10 mL) was stirred for 2 hours at 10° C. under N$_2$. The reaction was diluted with water (20 mL) and extracted with ethyl acetate (100 mL×3). The combined organic phases were dried over anhydrous Na$_2$SO$_4$, filtered, and concentrated to dryness. The residue was purified by flash column chromatography (0-6% ethyl acetate in petroleum ether) to provide the title compound (750 mg, 50%) as a white solid. 1H NMR (400 MHz, CDCl$_3$) δ 7.82 (s, 1H), 7.38-7.25 (m, 5H), 3.81 (s, 2H).

Step C: (EZ)—N-((1-((1r,4r)-4-(Cyanomethyl)cyclohexyl)-1,6-dihydroimidazo[4,5-d]pyrrolo[2,3-b]pyridin-2-yl)methyl)-N-hydroxy-2-phenylacetimidamide. A solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 300 mg, 0.870 mmol), (EZ)—N-hydroxy-2-phenylacetimidoyl chloride (148 mg, 0.870 mmol), triethylamine (264 mg, 2.61 mmol) and DMF (25 mL) was stirred at room-temperature for 2 hours. The same reaction was carried out by using 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 50 mg, 0.14 mmol), (EZ)—N-hydroxy-2-phenylacetimidoyl chloride (25 mg, 0.14 mmol), triethylamine (44 mg, 0.43 mmol) and DMF (2.5 mL) The two reactions were combined and purified by preparative HPLC using a Waters Xbridge Prep OBD C$_{18}$ 150 mm×30 mm, 5 μm column (eluent: 30% to 60% (v/v) CH$_3$CN and H$_2$O with 0.05% NH$_3$) to provide the title compound (64 mg, 15% yield). MS (ESI): mass calcd. for C$_{25}$H$_{27}$N$_{7}$O, 441.23; m/z found, 442.2 [M+H]$^+$. $^1$H NMR (400 MHz, DMSO-d$_6$): δ 11.87 (br s, 1H), 9.42-9.26 (m, 0.7H), 9.06-8.93 (m, 0.2H), 8.62-8.49 (m, 1H), 7.50-7.41 (m, 1H), 7.39-7.27 (m, 4H), 7.25-7.16 (m, 1H), 6.74-6.64 (m, 1H), 6.34-6.26 (m, 0.8H), 6.11-6.05 (m, 0.3H), 4.57-4.41 (m, 3H), 3.65-3.55 (m, 2H), 2.61-2.57 (m, 2H), 2.39-2.16 (m, 1.3H), 2.10-1.77 (m, 5.6H), 1.48-1.37 (m, 1.6H), 1.25-1.14 (m, 0.5H).

Example 104 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4-(1,1,1,3,3,3-hexafluoro-2-hydroxypropan-2-yl)phenyl)acetamide

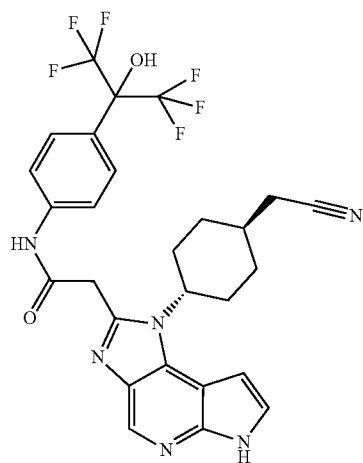 [SMILES: N#CC[C@H]1CC[C@H](n2c(CC(=O)Nc3ccc(C(O)(C(F)(F)F)C(F)(F)F)cc3)nc3cnc4[nH]ccc4c32)CC1]

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 2-(4-aminophenyl)-1,1,1,3,3,3-hexafluoropropan-2-ol hydrochloride (247 mg, 0.835 mmol), DIPEA (216 mg, 1.67 mmol), and DMF (5 mL) was stirred at 0° C. for 1 h. Then PyBrOP (467 mg, 1.00 mmol) was added and stirred at room-temperature overnight. The mixture was quenched with 10 mL water and was purified by preparative HPLC using a Diamonsil 150 mm×20 mm, 5 μm column (eluent: water (0.225% HCO$_2$H)-ACN from 28% to 58%, v/v) and by preparative TLC (CH$_2$Cl$_2$: MeOH=10:1) to provide the title compound (38 mg, 7% yield) as a white solid. MS (ESI): mass calcd. for C$_{27}$H$_{24}$F$_6$N$_6$O$_2$, 578.19; m/z found, 579.1 [M+H]$^+$. $^1$H NMR (400 MHz, CD$_3$OD): δ 8.55 (s, 1H), 7.73-7.66 (m, 4H), 7.49 (d, J=3.6 Hz, 1H), 6.86 (d, J=3.6 Hz, 1H), 4.66-4.55 (m, 1H), 4.34-4.28 (m, 2H), 2.68-2.49 (m, 4H), 2.21-2.05 (m, 5H), 1.56-1.41 (m, 2H).

Example 105 Synthesis and Characterization 1-(2-(1-((1r,4r)-4-(Cyanomethyl)cyclohexyl)-1,6-dihydroimidazo[4,5-d]pyrrolo[2,3-b]pyridin-2-yl)acetyl)piperidine-4-carbonitrile

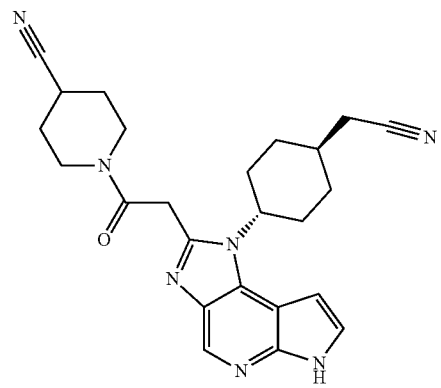 [SMILES: N#CC[C@H]1CC[C@H](n2c(CC(=O)N3CCC(C#N)CC3)nc3cnc4[nH]ccc4c32)CC1]

The title compound was prepared using analogous conditions as described in Example 52 using piperidine-4-carbonitrile in place of (1S,3R,5R,7S)-3-aminoadamantan-1-ol hydrochloride to provide the title compound (12 mg, 5% yield). This compound was purified initially by preparative acidic HPLC using a Boston Green ODS 150 mm×30 mm, 5 um column (eluent: water (0.05% HCl)-ACN from 11% to 41%, v/v). This compound was further purified by preparative basic HPLC using a DuraShell 150 mm×25 mm, 5 μm column (eluent: water (0.05% ammonia hydroxide v/v)-ACN from 20% to 50%, v/v). MS (ESI): mass calcd. for C$_{24}$H$_{27}$N$_7$O, 429.23; m/z found, 430.2 [M+H]$^+$. $^1$H NMR (400 MHz, CD$_3$OD) δ=8.82 (s, 1H), 7.75 (d, J=3.5 Hz, 1H), 7.10 (d, J=3.0 Hz, 1H), 4.57 (br s, 1H), 3.99-3.86 (m, 2H), 3.68-3.58 (m, 1H), 3.53-3.43 (m, 1H), 3.18-3.09 (m, 1H), 2.56 (br d, J=6.1 Hz, 4H), 2.24-2.06 (m, 7H), 2.05-1.91 (m, 3H), 1.88-1.74 (m, 1H), 1.62-1.43 (m, 2H).

Example 106 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2,3-dihydroxypropyl)acetamide

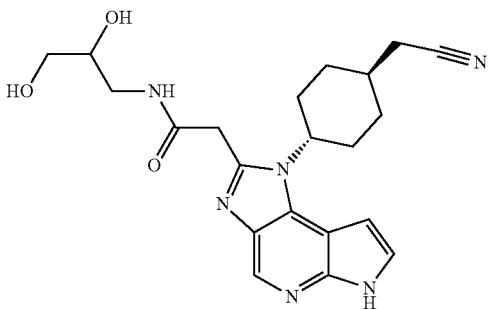 [SMILES: N#CC[C@H]1CC[C@H](n2c(CC(=O)NCC(O)CO)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 70 mg, 0.20 mmol) and 3-aminopropane-1,2-diol (50 mg, 0.39 mmol) in DMF (2 mL) were added PyBOP (150 mg, 0.30 mmol) and DIPEA (0.10 mL, 0.58 mmol) and was stirred at room temperature for 64 h. The reaction was concentrated to dryness and the residue was purified by reverse phase HPLC using a Varian Pursuit XR$_s$5 Diphenyl 100×30 mm column (eluent: 10-90% CH$_3$CN in H$_2$O, 0.1% TFA) to provide the title compound (2.0 mg, 2% yield). MS (ESI): mass calcd. for C$_{21}$H$_{26}$N$_6$O$_3$, 410.21; m/z found, 411.3 [M+H]$^+$. $^1$H NMR (400 MHz, CD$_3$OD) δ=8.92-8.74 (m, 1H), 7.80-7.72 (m, 1H), 7.14-7.04 (m, 1H), 4.69 (br s, 1H), 3.81-3.69 (m, 1H), 3.53 (d, J=5.1 Hz, 2H), 3.50-3.38 (m, 1H), 2.56 (d, J=6.1 Hz, 5H), 2.25-2.08 (m, 7H), 1.62-1.45 (m, 2H).

Example 107 Synthesis and Characterization 2-((1r,4r)-4-(2-(2-(4,4-Difluoropiperidin-1-yl)-2-oxoethyl)imidazo[4,5-d]pyrrolo[2,3-b]pyridin-1(6H)-yl)cyclohexyl)acetonitrile

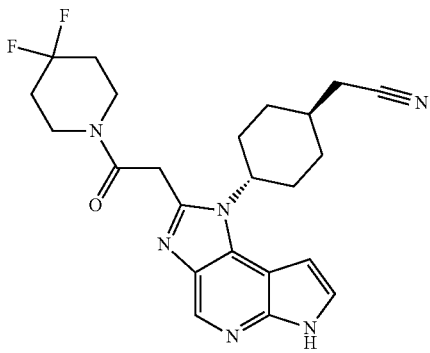 [SMILES: N#CC[C@H]1CC[C@H](n2c(CC(=O)N3CCC(F)(F)CC3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 66 mg, 0.18 mmol) and 4,4-difluoropiperidine (58 mg, 0.37 mmol) in DMF (2 mL) were added PyBOP (190 mg, 0.37 mmol) and DIPEA (0.16 mL, 0.92 mmol) and the reaction mixture was stirred at room temperature for 64 h. The reaction was concentrated to dryness and the residue was purified by reverse phase HPLC using a Varian Pursuit XR$_s$5 Diphenyl 100×30 mm column (eluent: 10-90% CH$_3$CN in H$_2$O, 0.1% TFA) to provide the title compound (24 mg, 24% yield) as a foam. MS (ESI): mass calcd. for C$_{23}$H$_{26}$F$_2$N$_6$O, 440.21; m/z found, 441.3 [M+H]$^+$. $^1$H NMR (400 MHz, CD$_3$OD) δ=8.82 (s, 1H), 7.74 (d, J=3.5 Hz, 1H), 7.10 (d, J=3.5 Hz, 1H), 4.61 (br s, 1H), 3.80 (td, J=5.8, 18.2 Hz, 4H), 2.56 (d, J=6.1 Hz, 4H), 2.24-2.10 (m, 8H), 2.10-1.96 (m, 3H), 1.65-1.40 (m, 2H).

Example 108 Synthesis and Characterization

Diethyl 4-(2-(1-((1r,4r)-4-(cyanomethyl)cyclohexyl)-1,6-dihydroimidazo[4,5-d]pyrrolo[2,3-b]pyridin-2-yl)acetamido)benzylphosphonate

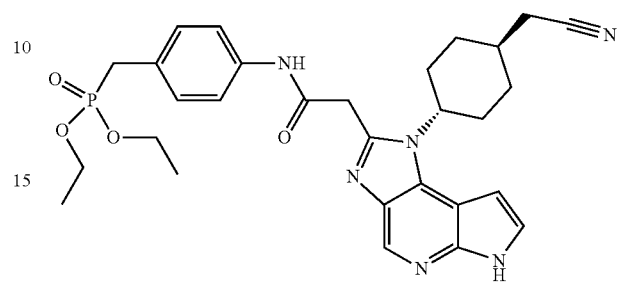

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 66 mg, 0.18 mmol) and diethyl 4-aminobenzylphosphonate (103 mg, 0.37 mmol) in DMF (2 mL) were added PyBOP (191 mg, 0.367 mmol) and DIPEA (0.10 mL, 0.58 mmol) and the reaction mixture was stirred at room temperature for 64 h. The reaction was concentrated to dryness and the residue was purified by reverse phase HPLC using a Varian Pursuit XR$_s$5 Diphenyl 100×30 mm column (eluent: 10-90% CH$_3$CN in H$_2$O, 0.1% TFA) to provide the title compound (12 mg, 10% yield) as a foam. MS (ESI): mass calcd. for C$_{29}$H$_{35}$N$_6$O$_4$P, 562.25; m/z found, 563.4 [M+H]$^+$. $^1$H NMR (400 MHz, CD$_3$OD) δ=8.81 (s, 1H), 7.74 (d, J=3.5 Hz, 1H), 7.56 (d, J=8.1 Hz, 2H), 7.29 (dd, J=2.3, 8.8 Hz, 2H), 7.10 (d, J=3.5 Hz, 1H), 4.76 (br s, 1H), 4.07-3.96 (m, 4H), 3.24 (s, 1H), 3.19 (s, 1H), 2.62-2.46 (m, 5H), 2.26-2.09 (m, 6H), 1.59-1.46 (m, 2H), 1.25 (t, J=7.1 Hz, 6H).

Example 109 Synthesis and Characterization (1-((1r,4r)-4-(Cyanomethyl)cyclohexyl)-1,6-dihydroimidazo[4,5-d]pyrrolo[2,3-b]pyridin-2-yl)methyl Phenylcarbamate

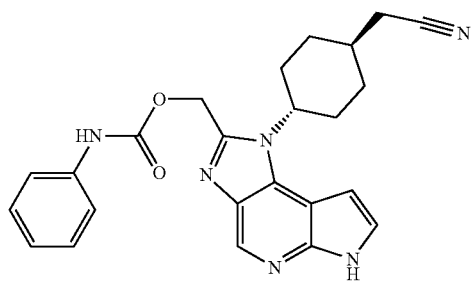 [SMILES: N#CC[C@H]1CC[C@H](n2c(COC(=O)Nc3ccccc3)nc3cnc4[nH]ccc4c32)CC1]

Step A: (1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl phenylcarbamate. A solution of 2-((1r,4r)-4-(2-(hydroxymethyl)-6-(phenyl sulfonyl)imidazo[4,5-d]pyrrolo[2,3-b]pyridin-1(6H)-yl)cyclohexyl)acetonitrile (Intermediate 7, 100 mg, 0.22 mmol), isocyanatobenzene (53 mg, 0.44 mmol), Et$_3$N (0.093 mL, 0.67 mmol), and DMF (1 mL) was heated at 60° C. for 40 h. The reaction had gone only about 50%, so more isocyanatobenzene (53 mg, 0.44 mmol) was added, and the mixture was heated at 60° C. for 18 h. The reaction was concentrated to dryness to provide the title compound (126 mg), which was used in the next reaction without further purification. MS (ESI): mass calcd. for $C_{30}H_{28}N_6O_4S$, 568.19; m/z found, 569.3 [M+H]$^+$.

Step B: (1-((1r,4r)-4-(Cyanomethyl)cyclohexyl)-1,6-dihydroimidazo[4,5-d]pyrrolo[2,3-b]pyridin-2-yl)methyl phenylcarbamate. A reaction mixture of (1-((1r,4r)-4-(cyanomethyl)cyclohexyl)-6-(phenylsulfonyl)-1,6-dihydroimidazo[4,5-d]pyrrolo[2,3-b]pyridin-2-yl)methyl phenylcarbamate (126 mg, 0.220 mmol), 3 M NaOH aqueous solution (0.27 mL, 0.81 mmol), MeOH (1.5 mL), and THF (1.5 mL) was stirred at room temperature for 6 h, and concentrated in vacuo. The residue was purified by flash column chromatography (0-10% MeOH in $CH_2Cl_2$) to give the title compound as a white solid (24 mg, 25% yield). MS (ESI): mass calcd. for $C_{24}H_{24}N_6O_2$, 428.20; m/z found, 429.2 [M+H]$^+$. $^1$H NMR (400 MHz, $CDCl_3$) δ=11.66 (br s, 1H), 8.71 (br s, 1H), 8.47 (br s, 1H), 7.52 (br s, 2H), 7.48-7.31 (m, 3H), 7.11 (t, J=7.0 Hz, 1H), 6.60 (br s, 1H), 5.52 (s, 2H), 4.42 (br s, 1H), 2.44-2.23 (m, 4H), 2.08-1.70 (m, 5H), 1.40-1.22 (m, 2H).

Example 110 Synthesis and Characterization (EZ)—N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclopropanecarboximidamide

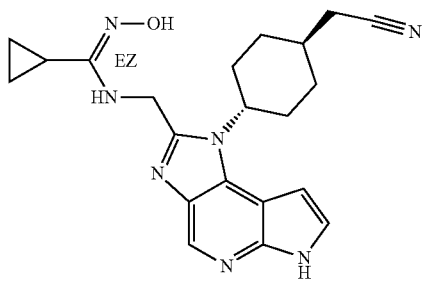 [SMILES: N#CC[C@H]1CC[C@H](n2c(CN/C(=N\O)C3CC3)nc3cnc4[nH]ccc4c32)CC1]

Step A: (EZ)-Cyclopropanecarbaldehyde oxime. A solution of cyclopropanecarboxaldehyde (3.00 g, 42.8 mmol), hydroxylamine hydrochloride (8.92 g, 128 mmol), sodium acetate (10.5 g, 128 mmol), ethanol (150 mL), and water (30 mL) was stirred at 70° C. for 10 h. The reaction was concentrated to dryness, extracted with ethyl acetate (50 mL×2), dried over anhydrous $Na_2SO_4$, filtered, and concentrated to dryness to provide the title compound (4.8 g) as a colorless oil. $^1$H NMR (400 MHz, $CDCl_3$): δ 8.80 (br s, 1H), 6.95 (d, J=8.4 Hz, 1H), 1.66-1.52 (m, 1H), 0.69-0.57 (m, 4H).

Step B: (EZ)—N-Hydroxycyclopropanecarbimidoyl chloride. NCS (11 g, 85 mmol) was added to a solution of (EZ)-cyclopropanecarbaldehyde oxime (4.8 g, 56 mmol) and DMF (50 mL) and the reaction mixture was stirred for 2 h at 15° C. Water (20 mL) was added, the reaction mixture was extracted with ethyl acetate (20 mL), dried over anhydrous $Na_2SO_4$, filtered, and concentrated to dryness. The residue was purified by flash column chromatography to provide the title compound (2.1 g, 28% yield) as a colorless oil. $^1$H NMR (400 MHz, $CDCl_3$): δ 7.84 (s, 1H), 1.97-1.84 (m, 1H), 1.00-0.93 (m, 2H), 0.89-0.81 (m, 2H).

Step C: (EZ)—N-((1-((1r,4r)-4-(Cyanomethyl)cyclohexyl)-1,6-dihydroimidazo[4,5-d]pyrrolo[2,3-b]pyridin-2-yl)methyl)-N-hydroxycyclopropanecarboximidamide. A solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 300 mg, 0.870 mmol), (EZ)-N-hydroxycyclopropanecarbimidoyl chloride (104 mg, 0.870 mmol), triethylamine (0.61 mL, 4.4 mmol), and DMF (5 mL) was stirred for 2 h at 15° C. Water (10 mL) was added and the reaction was extracted with ethyl acetate (20 mL) and dichloromethane (10 mL×2). The combined organic extracts were concentrated to dryness and the residue was initially purified by preparative basic HPLC using a Phenomenex Gemini 150 mm×25 mm, 5 μm column (eluent: 16% to 46% (v/v) $CH_3CN$ and $H_2O$ with 0.05% $NH_3$). The compound was then further purified by preparative acidic HPLC with a Phenomenex Gemini 150 mm×25 mm, 10 μm column (eluent: 10% to 30% (v/v) $CH_3CN$ and aqueous HCl (0.006 N)). The pure fractions from the preparative acidic HPLC were collected, adjusted to pH=7-8 with saturated aqueous $NaHCO_3$, and concentrated to dryness. The solid was filtered and washed with water (2 mL×3). The filter cake was suspended in water (10 mL) and $CH_3CN$ (2 mL), the mixture frozen using dry ice/acetone, and then lyophilized to dryness to provide the title compound (40 mg, 12% yield) as a white solid. MS (ESI): mass calcd. for $C_{21}H_{25}N_7O$, 391.21; m/z found, 392.0 [M+H]$^+$. $^1$H NMR (400 MHz, DMSO-$d_6$): δ 11.87 (br s, 1H), 9.05 (s, 1H), 8.55 (s, 1H), 7.47 (t, J=3.2 Hz, 1H), 6.75-6.68 (m, 1H), 6.33 (t, J=6.0 Hz, 1H), 4.80 (d, J=6.0 Hz, 2H), 4.75-4.62 (m, 1H), 2.60 (d, J=5.6 Hz, 2H), 2.42-2.27 (m, 2H), 2.06-1.85 (m, 5H), 1.71-1.61 (m, 1H), 1.57-1.41 (m, 2H), 0.63-0.50 (m, 4H).

Example 111 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(pyridin-3-yl)acetamide

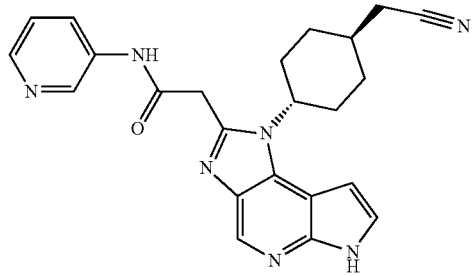 [SMILES: N#CC[C@H]1CC[C@H](n2c(CC(=O)Nc3cccnc3)nc3cnc4[nH]ccc4c32)CC1]

To a solution of sodium 2-(1-((1R,4R)-4-(cyanomethyl)cyclohexyl)-1,6-dihydroimidazo[4,5-d]pyrrolo[2,3-b]pyridin-2-yl)acetate (Intermediate 4, 66 mg, 0.18 mmol) and pyridin-3-amine (44 mg, 0.47 mmol) in DMF (2 mL) were added PyBOP (190 mg, 0.37 mmol) and DIPEA (0.10 mL, 0.58 mmol) and was stirred at room temperature for 18 h. The reaction was concentrated to dryness and the residue was purified by reverse phase HPLC using a Varian Pursuit XR$_s$5 Diphenyl 100×30 mm column (eluent: 10-90% $CH_3CN$ in $H_2O$, 0.1% TFA) to provide the title compound (14 mg, 14% yield) as a foam. MS (ESI): mass calcd. for $C_{23}H_{23}N_7O$, 413.20; m/z found, 414.3 [M+H]$^+$. $^1$H NMR (400 MHz, $CD_3OD$) δ=9.38 (s, 1H), 8.86 (s, 1H), 8.63-8.53

(m, 2H), 8.05 (dd, J=6.1, 8.6 Hz, 1H), 7.77 (d, J=3.5 Hz, 1H), 7.15 (d, J=3.5 Hz, 1H), 4.97 (s, 2H), 4.77 (br s, 1H), 2.65-2.45 (m, 4H), 2.25 (d, J=10.6 Hz, 2H), 2.20-2.08 (m, 3H), 1.62-1.47 (m, 2H).

Example 112 Synthesis and Characterization (Z)—N-((1-((1r,4r)-4-(Cyanomethyl)cyclohexyl)-1, 6-dihydroimidazo[4,5-d]pyrrolo[2,3-b]pyridin-2-yl) methoxy)-2-cyclopropylacetimidamide; the Structure being the (Z) or (E) Isomer, and the (Z) Notation and its Corresponding Structure Below is Chosen Arbitrarily

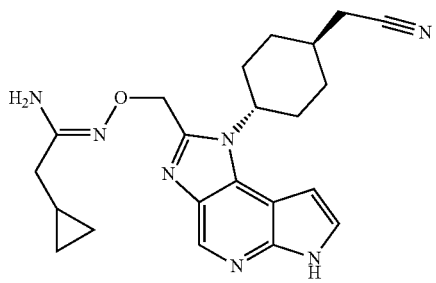 [SMILES: N#CC[C@H]1CC[C@H](n2c(CO/N=C(\N)CC3CC3)nc3cnc4[nH]ccc4c32)CC1]

Step A: (Z)-2-Cyclopropyl-N-hydroxyacetimidamide. A solution of cyclopropylacetonitrile (2.0 g, 25 mmol), hydroxylamine hydrochloride (3.4 g, 49 mmol), Na₂CO₃ (5.2 g, 49 mmol), ethanol (48 mL), and water (16 mL) was stirred for 12 h at 80° C. The reaction was concentrated to dryness and the residue was partitioned between ethyl acetate (50 mL) and water (50 mL). The organic phase was collected, dried over anhydrous Na₂SO₄, filtered, and concentrated to dryness to provide the title compound (2.4 g, 77% yield), which was used in the next step without further purification. ¹H NMR (400 MHz, DMSO-d₆): δ 8.76 (s, 1H), 5.31 (s, 2H), 1.83 (d, J=7.2 Hz, 2H), 1.00-0.82 (m, 1H), 0.43-0.33 (m, 2H), 0.13-0.05 (m, 2H).

Step B: (Z)—N-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methoxy)-2-cyclopropylacetimidamide. A solution of 2-((1r,4r)-4-(2-(chloromethyl)-6-(phenylsulfonyl)imidazo[4,5-d]pyrrolo[2,3-b]pyridin-1 (6H)-yl)cyclohexyl)acetonitrile (Intermediate 8, 300 mg, 0.641 mmol), (Z)-2-cyclopropyl-N-hydroxyacetimidamide (220 mg, 1.92 mmol), Cs₂CO₃ (1.0 g, 3.2 mmol), and DMF (5 mL) was stirred for 18 h at 10° C. The reaction was concentrated to dryness to provide the title compound (1.6 g, 100% yield), which was used in the next step without further purification. MS (ESI): mass calcd. for C₂₈H₃₁N₇O₃S, 545.22; m/z found, 546.1 [M+H]⁺.

Step C: (Z)—N-((1-((1r,4r)-4-(Cyanomethyl)cyclohexyl)-1,6-dihydroimidazo[4,5-d]pyrrolo[2,3-b]pyridin-2-yl)methoxy)-2-cyclopropylacetimidamide. The title compound (60 mg, 23% yield) was prepared using conditions analogous to those described in Example 1, Step B using (Z)—N-((1-((1r,4r)-4-(cyanomethyl)cyclohexyl)-6-(phenylsulfonyl)-1,6-dihydroimidazo[4,5-d]pyrrolo[2,3-b]pyridin-2-yl)methoxy)-2-cyclopropylacetimidamide (1.6 g, 0.65 mmol, purity 22%) instead of 2-(1-((1r,4r)-4-(cyanomethyl) cyclohexyl)-6-(phenylsulfonyl)-1,6-dihydroimidazo[4,5-d] pyrrolo[2,3-b]pyridin-2-yl)-N-(2-hydroxy-2-methylpropyl) acetamide. Purification was initially performed by flash column chromatography (eluent: DCM:methanol=100:0 to 85:15). The title compound was further purified by preparative HPLC using a Phenomenex Gemini 150 mm×25 mm, 10 μm column (eluent: 21% to 51% (v/v) CH₃CN and H₂O with 0.05% NH₃). MS (ESI): mass calcd. for C₂₂H₂₇N₇O, 405.23; m/z found, 406.3 [M+H]⁺. ¹H NMR (400 MHz, DMSO-d₆): δ 11.88 (s, 1H), 8.55 (s, 1H), 7.47 (s, 1H), 6.73 (s, 1H), 5.73 (s, 2H), 5.17 (s, 2H), 4.81-4.67 (m, 1H), 2.58 (d, J=5.6 Hz, 2H), 2.43-2.28 (m, 2H), 2.10-1.91 (m, 5H), 1.81 (d, J=6.4 Hz, 2H), 1.50-1.33 (m, 2H), 0.99-0.88 (m, 1H), 0.41-0.32 (m, 2H), 0.11-0.05 (m, 2H).

Example 113 Synthesis and Characterization 2-((1r,4r)-4-(2-(Methoxymethyl)imidazo[4,5-d]pyrrolo[2,3-b]pyridin-1(6H)-yl)cyclohexyl)acetonitrile

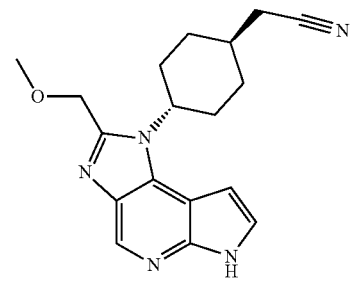 [SMILES: COCc1nc2cnc3[nH]ccc3c2n1[C@H]1CC[C@H](CC#N)CC1]

A solution of 2-((1r,4r)-4-(2-(chloromethyl)-6-(phenylsulfonyl)imidazo[4,5-d]pyrrolo[2,3-b]pyridin-1(6H)-yl) cyclohexyl)acetonitrile (Intermediate 12, 350 mg, 0.750 mmol) in THF (10 mL) was treated with a 0.5 M solution of NaOMe in MeOH (3.8 mL, 1.9 mmol) at RT for 2 h, and concentrated in vacuo. The residue was partitioned between CH₂Cl₂ and water. The extract was dried over Na₂SO₄, filtered, and concentrated. The residue was purified by flash column chromatography (50-100% EtOAc in heptanes, then 10% MeOH in CH₂Cl₂), and then reverse phase HPLC using a Varian Pursuit XR₅5 Diphenyl 100×30 mm column (eluent: 10-90% CH₃CN in H₂O, 0.1% TFA). The collected material was dissolved in 10% MeOH in CH₂Cl₂, passed through two 500 mg SILICYCLE SPE-R66030B-03P Carbonate to remove TFA, and eluted with 10% MeOH in CH₂Cl₂ to give the title compound as a white solid (98 mg, 41% yield). MS (ESI): mass calcd. for C₁₈H₂₁N₅O, 323.17; m/z found, 324.1 [M+H]⁺. ¹H NMR (400 MHz, CDCl₃) δ 13.45 (br s, 1H), 8.71 (s, 1H), 7.56 (d, J=3.5 Hz, 1H), 6.84 (d, J=3.0 Hz, 1H), 4.84 (s, 2H), 4.80-4.65 (m, 1H), 3.44 (s, 3H), 2.56-2.44 (m, 4H), 2.27-2.14 (m, 3H), 2.17-2.10 (m, 2H), 1.63-1.46 (m, 2H).

Example 114 Synthesis and Characterization 1-((1r,4r)-4-(Cyanomethyl)cyclohexyl)-N-(2-hydroxyethyl)-1,6-dihydroimidazo[4,5-d]pyrrolo[2,3-b]pyridine-2-carboxamide

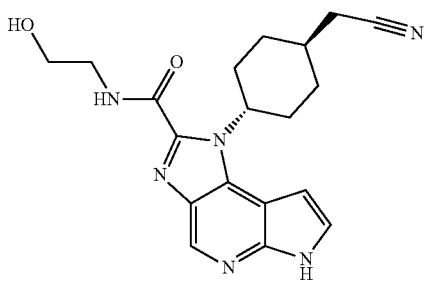 [SMILES: N#CC[C@H]1CC[C@H](n2c(C(=O)NCCO)nc3cnc4[nH]ccc4c32)CC1]

The title compound (21 mg, 28% yield) was prepared using analogous conditions as described in Example 50, Step A, and using 2-aminoethanol instead of 3-phenylpyrrolin-3-ol. MS (ESI): mass calcd. for $C_{19}H_{22}N_6O_2$, 366.18; m/z found, 367.2 [M+H]$^+$. $^1$H NMR (400 MHz, CD$_3$OD): δ 8.64 (s, 1H), 7.51 (d, J=4.2 Hz, 1H), 6.89 (d, J=4.1 Hz, 1H), 5.72-5.47 (m, 1H), 3.76 (d, J=5.3 Hz, 2H), 3.56 (d, J=5.2 Hz, 2H), 2.74-2.46 (m, 4H), 2.26-1.96 (m, 5H), 1.59-1.38 (m, 2H).

Example 115 Synthesis and Characterization 5-(1-((1r,4r)-4-(Cyanomethyl)cyclohexyl)-1,6-dihydroimidazo[4,5-d]pyrrolo[2,3-b]pyridin-2-yl)picolinonitrile

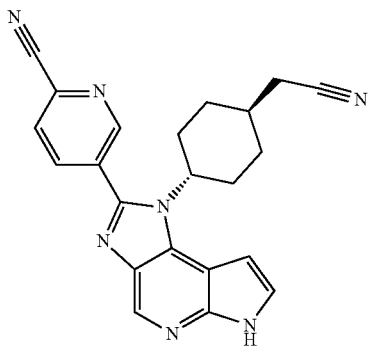

Step A: 5-(1-((r,4r)-4-(Cyanomethyl)cyclohexyl)-6-(phenylsulfonyl)-1,6-dihydroimidazo[4,5-d]pyrrolo[2,3-b]pyridin-2-yl)picolinonitrile. A solution of 2-((1r,4r)-4-((5-nitro-1-(phenyl sulfonyl)-1H-pyrrolo[2,3-b]pyridin-4-yl)amino)cyclohexyl)acetonitrile (Intermediate 1, 152 mg, 0.346 mmol), 5-formylpicolinonitrile (92 mg, 0.70 mmol), and sodium hydrosulfite (202 mg, 0.986 mmol) in DMSO (1 mL), MeOH (1 mL), and distilled water (0.5 mL) in a sealed tube was heated at 100° C. for 16 h. After cooling to room temperature, the reaction was concentrated and the residue was filtered. The yellow solid was washed with water and dried in air to provide the title compound (150 mg), which was taken to next step without further purification. MS (ESI): mass calcd. for $C_{28}H_{23}N_7O_2S$, 521.16; m/z found, 522.2 [M+H]$^+$.

Step B: 5-(1-((1r,4r)-4-(Cyanomethyl)cyclohexyl)-1,6-dihydroimidazo[4,5-d]pyrrolo[2,3-b]pyridin-2-yl)picolinonitrile. A mixture of 5-(1-((1r,4r)-4-(cyanomethyl)cyclohexyl)-6-(phenylsulfonyl)-1,6-dihydroimidazo[4,5-d]pyrrolo[2,3-b]pyridin-2-yl)picolinonitrile (150 mg, 0.29 mmol), pyrrolidine (0.10 mL, 1.2 mmol), 3 M of NaOH (aq) (0.24 mL, 0.72 mmol), THF (1.5 mL), and MeOH (1.5 mL) was stirred at RT for 5 h and concentrated in vacuo. The residue was purified by flash column chromatography (3-10% MeOH in CH$_2$Cl$_2$) to give the title compound as an off-white solid (8.0 mg, 7% yield). MS (ESI): mass calcd. for $C_{22}H_{19}N_7$, 381.17; m/z found, 382.2 [M+H]$^+$. $^1$H NMR (400 MHz, CDCl$_3$) δ=10.13 (br s, 1H), 9.02 (d, J=1.5 Hz, 1H), 8.91 (s, 1H), 8.23 (dd, J=2.0, 8.1 Hz, 1H), 7.93 (d, J=8.1 Hz, 1H), 7.49 (t, J=3.0 Hz, 1H), 6.79 (dd, J=2.0, 3.0 Hz, 1H), 4.46-4.37 (m, 1H), 2.73-2.59 (m, 2H), 2.42 (d, J=6.1 Hz, 2H), 2.25-2.15 (m, 2H), 2.15-2.03 (m, 3H), 1.40 (dq, J=3.5, 13.0 Hz, 2H)

Example 116 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)-3-hydroxy-3-methylbutanamide

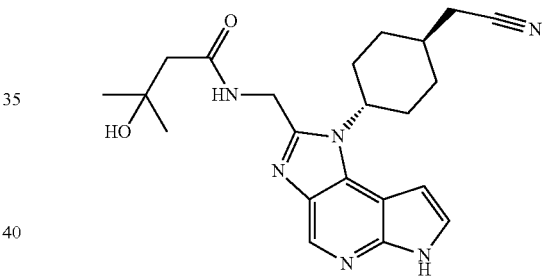

HATU (100 mg, 0.264 mmol) was added to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 100 mg, 0.264 mmol, purity 91%), beta-hydroxyisovaleric acid (31.2 mg, 0.264 mmol), DIEA (0.230 mL, 1.32 mmol), and CH$_2$Cl$_2$ (5 mL) and was stirred for 0.5 h at 10° C. The reaction was diluted with CH$_2$Cl$_2$ (10 mL), washed with water (10 mL), dried over anhydrous Na$_2$SO$_4$, filtered, and concentrated to dryness. The residue was initially purified by preparative TLC (eluent: CH$_2$Cl$_2$: methanol=10:1). The residue was then further purified by preparative HPLC using an Agela DuraShell 150 mm×25 mm, 5 µm column (eluent: 8% to 38% (v/v) CH$_3$CN and H$_2$O with 10 mM NH$_4$HCO$_3$) to provide the title compound (30 mg, 28% yield). MS (ESI): mass calcd. for $C_{22}H_{28}N_6O_2$, 408.23; m/z found, 409.2 [M+H]$^+$. $^1$H NMR (400 MHz, DMSO-d$_6$): δ 11.89 (s, 1H), 8.53 (s, 1H), 8.52-8.47 (m, 1H), 7.48 (t, J=2.8 Hz, 1H), 6.72 (s, 1H), 4.87 (s, 1H), 4.69 (d, J=5.2 Hz, 2H), 4.61-4.47 (m, 1H), 2.59 (d, J=6.0 Hz, 2H), 2.42-2.32 (m, 2H), 2.30 (s, 2H), 2.10-1.86 (m, 5H), 1.48-1.31 (m, 2H), 1.19 (s, 6H).

Example 117 Synthesis and Characterization 1-((1r,4r)-4-(Cyanomethyl)cyclohexyl)-N-(2-hydroxy-2-methylpropyl)-1,6-dihydroimidazo[4,5-d]pyrrolo[2,3-b]pyridine-2-carboxamide

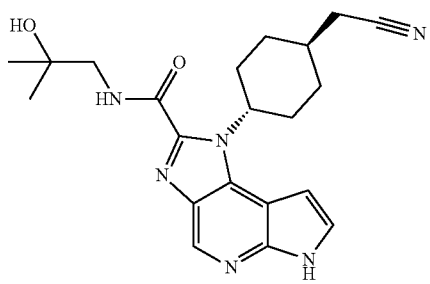 [SMILES: CC(C)(O)CNC(=O)c1nc2cnc3[nH]ccc3c2n1[C@H]1CC[C@H](CC#N)CC1]

The title compound (27 mg, 34% yield) was prepared using analogous conditions as described in Example 50, Step A, using 1-amino-2-methylpropan-2-ol instead of 3-phenylpyrrolin-3-ol. MS (ESI): mass calcd. for $C_{21}H_{26}N_6O_2$, 394.21; m/z found, 395.2 [M+H]$^+$. $^1$H NMR (500 MHz, CDCl$_3$): δ 10.79 (s, 1H), 8.82 (s, 1H), 8.24 (d, J=4.0 Hz, 1H), 7.55-7.37 (m, 1H), 6.89-6.65 (m, 1H), 6.30-5.56 (m, 1H), 3.52 (d, J=6.5 Hz, 2H), 3.10 (s, 1H), 2.63-2.53 (m, 2H), 2.39 (d, J=6.5 Hz, 2H), 2.25-1.96 (m, 5H), 1.64-1.43 (m, 2H), 1.36 (s, 6H).

Example 118 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(pyridin-4-yl)acetamide

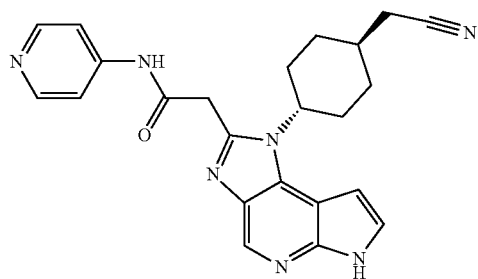 [SMILES: N#CC[C@H]1CC[C@H](n2c(CC(=O)Nc3ccncc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 66 mg, 0.18 mmol) and pyridin-4-amine (41 mg, 0.44 mmol) in DMF (2 mL) were added PyBOP (190 mg, 0.37 mmol) and DIPEA (0.10 mL, 0.58 mmol) and was stirred at room temperature for 18 h. The reaction was concentrated to dryness and the residue was purified by reverse phase HPLC using a Varian Pursuit XR$_s$5 Diphenyl 100×30 mm column (eluent: 10-90% CH$_3$CN in H$_2$O, 0.1% TFA) to provide the title compound (6 mg, 6% yield) as a foam. MS (ESI): mass calcd. for $C_{23}H_{23}N_7O$, 413.20; m/z found, 414.3 [M+H]$^+$. $^1$H NMR (400 MHz, CD$_3$OD) δ=8.86 (s, 1H), 8.66 (d, J=7.6 Hz, 2H), 8.19 (d, J=7.1 Hz, 2H), 7.77 (d, J=3.5 Hz, 1H), 7.17 (d, J=3.5 Hz, 1H), 4.73 (br s, 1H), 2.65-2.47 (m, 4H), 2.30-2.20 (m, 3H), 2.19-2.08 (m, 4H), 1.63-1.42 (m, 2H).

Example 119 Synthesis and Characterization 2-((1r,4r)-4-(2-(Thiazol-5-yl)imidazo[4,5-d]pyrrolo[2,3-b]pyridin-1(6H)-yl)cyclohexyl)acetonitrile

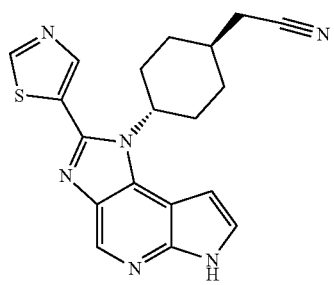 [SMILES: N#CC[C@H]1CC[C@H](n2c(-c3cncs3)nc3cnc4[nH]ccc4c32)CC1]

Step A: 2-((1r,4r)-4-(6-(Phenylsulfonyl)-2-(thiazol-5-yl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 197 mg, 0.448 mmol) and thiazole-5-carboxaldehyde (120 mg, 1.00 mmol) as solids. DMSO (2 mL), MeOH (2 mL), and distilled water (1 mL) were added resulting a yellow mixture. Next, sodium hydrosulfite (262 mg, 1.51 mmol) was added as a solid and the vial sealed. The vial was placed into a preheated 100° C. heating block for 1 h. The reaction was cooled to room temperature and added dropwise to 60 mL water with stirring. The precipitate that formed was collected by filtration and dried first in the open air and then under high vacuum for 3 h to provide the title compound (176 mg, 78% yield) as a canary yellow solid, which was used in the next step without further purification. MS (ESI): mass calcd. for $C_{25}H_{22}N_6O_2S_2$, 502.12; m/z found, 503.1 [M+H]$^+$.

Step B: 2-((1r,4r)-4-(2-(Thiazol-5-yl)imidazo[4,5-d]pyrrolo[2,3-b]pyridin-1(6H)-yl)cyclohexyl)acetonitrile. The title compound (68 mg, 54% yield) was prepared using conditions analogous to those described in Example 2, Step B using 2-((1r,4r)-4-(6-(Phenylsulfonyl)-2-(thiazol-5-yl)imidazo[4,5-d]pyrrolo[2,3-b]pyridin-1(6H)-yl)cyclohexyl)acetonitrile (176 mg, 0.35 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The residue was purified by flash column chromatography (40 g SiO$_2$, 0-5% 2 N NH$_3$-MeOH/EA) to afford the title compound. MS (ESI): mass calcd. for $C_{19}H_{18}N_6S$, 362.13; m/z found, 363.1 [M+H]$^+$. $^1$H NMR (500 MHz, DMSO-d$_6$): δ 12.04 (s, 1H), 9.36 (s, 1H), 8.65 (s, 1H), 8.36 (s, 1H), 7.55 (t, J=3.1 Hz, 1H), 6.80 (dd, J=3.5, 1.8 Hz, 1H), 4.74-4.54 (m, 1H), 2.57 (d, J=6.3 Hz, 2H), 2.49-2.40 (m, 2H), 2.12-1.94 (m, 5H), 1.49-1.34 (m, 2H).

Example 120 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2-methoxyethyl)acetamide

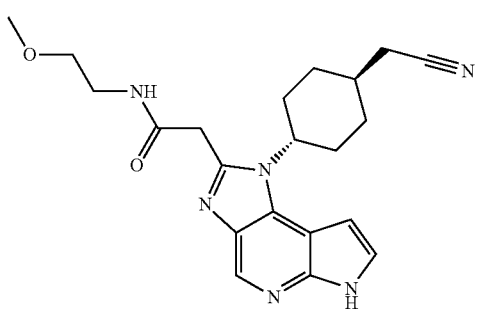 [SMILES: COCCNC(=O)Cc1nc2cnc3[nH]ccc3c2n1[C@H]1CC[C@H](CC#N)CC1]

Step A: 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-methoxyethyl)acetamide. A mixture of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 160 mg, 0.32 mmol), 2-methoxyethanamine (210 mg, 2.8 mmol), and $NH_4NO_3$ (50 mg, 0.63 mmol) was heated at 65° C. for 16 h. After standing at room temperature overnight, to the mixture $CH_2Cl_2$ and water were added. The precipitated white solid was filtered, washed with water, and dried to give the title compound (69 mg, 41%). The filtrate was extracted with $CH_2Cl_2$, the combined extracts were washed with water, and the aqueous layer was back extracted with $CH_2Cl_2$ (×1). The combined organic layers were dried over $Na_2SO_4$, filtered, and concentrated to provide the second portion of the title compound (90 mg, 53%) as an off-white solid. MS (ESI): mass calcd. for $C_{27}H_{30}N_6O_4S$, 534.6; m/z found, 535.2 $[M+H]^+$. $^1H$ NMR (400 MHz, $CDCl_3$) δ=8.84 (s, 1H), 8.23 (d, J=7.6 Hz, 2H), 7.85 (d, J=4.0 Hz, 1H), 7.60-7.54 (m, 1H), 7.52-7.45 (m, 2H), 6.85 (d, J=4.0 Hz, 2H), 4.63-4.52 (m, 1H), 3.96 (s, 2H), 3.42 (d, J=2.5 Hz, 4H), 3.29 (s, 3H), 2.42 (d, J=6.1 Hz, 2H), 2.38-2.25 (m, 2H), 2.16 (d, J=13.1 Hz, 2H), 2.10-1.96 (m, 3H), 1.54-1.40 (m, 2H).

Step B. 2-(1-((1r,4r)-4-(Cyanomethyl)cyclohexyl)-1,6-dihydroimidazo[4,5-d]pyrrolo[2,3-b]pyridin-2-yl)-N-(2-methoxyethyl)acetamide. The title compound was prepared using conditions analogous to those described in Example 1, Step B using 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-methoxyethyl)acetamide (90 mg, 0.17 mmol) and 3 N NaOH (aq) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and KOH in water to provide the title compound as a white solid (50 mg, 75% yield). MS (ESI): mass calcd. for $C_{21}H_{26}N_6O_2$, 394.21; m/z found, 395.2 $[M+H]^+$. $^1H$ NMR (400 MHz, $CDCl_3$) δ=11.38 (br s, 1H), 8.75 (s, 1H), 7.69 (br s, 1H), 7.47 (t, J=3.0 Hz, 1H), 6.77-6.70 (m, 1H), 4.67 (br s, 1H), 4.07 (s, 2H), 3.51-3.45 (m, 4H), 3.31 (s, 3H), 2.56 (br s, 2H), 2.42 (d, J=6.6 Hz, 2H), 2.19 (br d, J=12.6 Hz, 2H), 2.15-2.02 (m, 3H), 1.57-1.41 (m, 2H).

Example 121 Synthesis and Characterization 2-((1r,4r)-4-(2-(4-(4-(Hydroxymethyl)benzoyl)phenyl)imidazo[4,5-d]pyrrolo[2,3-b]pyridin-1(6H)-yl)cyclohexyl)acetonitrile

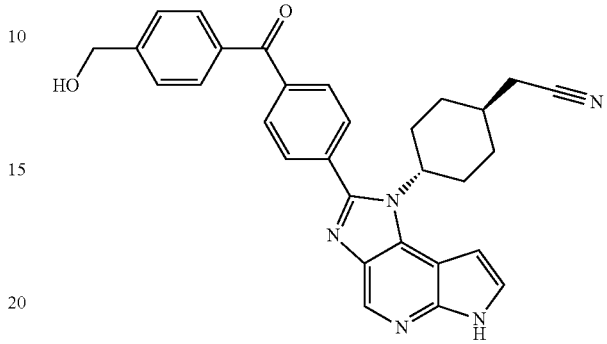

Step A: 2-((1r,4r)-4-(2-(4-(4-(Hydroxymethyl)benzoyl)phenyl)-6-(phenylsulfonyl)imidazo[4,5-d]pyrrolo[2,3-b]pyridin-1(6H)-yl)cyclohexyl)acetonitrile. To a solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 294 mg, 0.670 mmol) in DMSO (5.70 mL) and MeOH (1.14 mL) in a microwave vial was added 4-(4-(hydroxymethyl)benzoyl)benzaldehyde (177 mg, 0.737 mmol), followed by sodium hydrosulfite (343 mg, 1.67 mmol). The vial was capped and heated to 100° C. over the weekend. After cooling to room temperature, the reaction was diluted with water (5 mL) and stirred for 5 minutes. The tan precipitate that formed was collected by filtration, washed with water (50 mL), and allowed to dry thoroughly. The solid was eluted from the Büchner funnel using $CH_2Cl_2$/MeOH and collected in a round bottom flask. The organic phase was then concentrated to dryness to provide the title compound as a tan solid (421 mg, 99%), which was used without further purification. MS (ESI): mass calcd. for $C_{36}H_{31}N_5O_4S$, 629.21; m/z found, 630.3 $[M+H]^+$.

Step B: 2-((1r,4r)-4-(2-(4-(4-(Hydroxymethyl)benzoyl)phenyl)imidazo[4,5-d]pyrrolo[2,3-b]pyridin-1(6H)-yl)cyclohexyl)acetonitrile. The title compound (136 mg, 41% yield) was prepared using conditions analogous to those described in Example 1, Step B using 2-((1r,4r)-4-(2-(4-(4-(Hydroxymethyl)benzoyl)phenyl)-6-(phenylsulfonyl)imidazo[4,5-d]pyrrolo[2,3-b]pyridin-1(6H)-yl)cyclohexyl)acetonitrile (421 mg, 0.669 mmol) instead of 2-(1-((1r,4r)-4-(Cyanomethyl)cyclohexyl)-6-(phenyl sulfonyl)-1,6-dihydroimidazo[4,5-d]pyrrolo[2,3-b]pyridin-2-yl)-N-(2-hydroxy-2-methylpropyl)acetamide to provide the title compound. The crude material was purified on a 24 gram silica gel column using 0 to 10% MeOH in DCM as the eluent. To further purify the title compound, it was triturated with acetonitrile and collected by vacuum filtration to provide the title material as a white solid. MS (ESI): mass calcd. for $C_{30}H_{27}N_5O_2$, 489.22; m/z found, 490.2 $[M+H]^+$. $^1H$ NMR (400 MHz, DMSO-$d_6$): δ 12.03 (s, 1H), 8.68 (s, 1H), 7.94 (d, J=8.1 Hz, 2H), 7.90 (d, J=7.9 Hz, 2H), 7.81 (d, J=7.8 Hz, 2H), 7.58-7.49 (m, 3H), 6.82 (d, J=3.6 Hz, 1H), 5.44 (t, J=5.7 Hz, 1H), 4.64 (d, J=5.8 Hz, 2H), 4.53-4.39 (m, 1H), 2.54 (d, J=6.7 Hz, 2H), 2.47-2.38 (m, 2H), 2.11-1.92 (m, 5H), 1.37-1.21 (m, 2H).

Example 122 Synthesis and Characterization 1-((1r,4r)-4-(Cyanomethyl)cyclohexyl)-N-(oxetan-3-yl)-1,6-dihydroimidazo[4,5-d]pyrrolo[2,3-b]pyridine-2-carboxamide

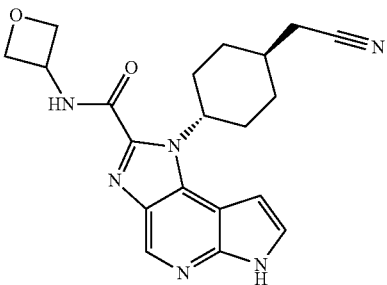 [SMILES: N#CC[C@H]1CC[C@H](n2c(C(=O)NC3COC3)nc3cnc4[nH]ccc4c32)CC1]

The title compound (25 mg, 24% yield) was prepared using analogous conditions as described in Example 50, and using oxetan-3-amine instead of 3-phenylpyrrolin-3-ol. MS (ESI): mass calcd. for $C_{20}H_{22}N_6O_2$, 378.18; m/z found, 379.2 [M+H]$^+$. $^1$H NMR (500 MHz, CDCl$_3$) δ 10.25 (s, 1H), 8.85 (s, 1H), 8.38 (d, J=7.8 Hz, 1H), 7.46 (dd, J=3.6, 1.8 Hz, 1H), 6.88-6.74 (br, 1H), 6.32-5.64 (m, 1H), 5.41-5.16 (m, 1H), 5.03 (t, J=7.2 Hz, 2H), 4.76 (dd, J=7.0, 6.3 Hz, 2H), 2.76-2.51 (m, 2H), 2.40 (d, J=6.6 Hz, 2H), 2.22-2.02 (m, 5H), 1.57-1.38 (m, 2H).

Example 123 Synthesis and Characterization 2-((1r,4r)-4-(2-(1H-pyrazol-4-yl)imidazo[4,5-d]pyrrolo[2,3-b]pyridin-1(6H)-yl)cyclohexyl)acetonitrile

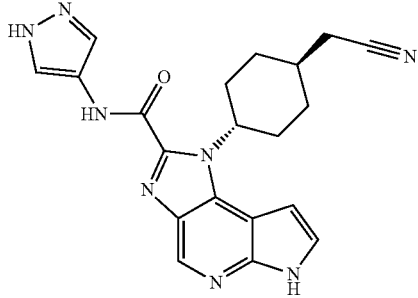 [SMILES: N#CC[C@H]1CC[C@H](n2c(C(=O)Nc3cn[nH]c3)nc3cnc4[nH]ccc4c32)CC1]

Step A: 2-((1r,4r)-4-(6-(Phenylsulfonyl)-2-(1H-pyrazol-4-yl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 1070 mg, 2.44 mmol) and 1H-pyrazole-4-carbaldehyde (444 mg, 4.62 mmol) as solids. DMSO (12 mL), MeOH (12 mL), and distilled water (6 mL) were added to the reaction mixture resulting in a yellow mixture. Next, sodium hydrosulfite (1060 mg, 6.09 mmol) was added as a solid and the vial sealed. The vial was placed into a preheated 100° C. heating block for 3 h. The reaction was cooled to room temperature and added dropwise to 60 mL water with stirring and continued stirring for 30 minutes. The white precipitate that formed was collected by filtration, washed with water (50 mL), and dried first in the open air and then under high vacuum overnight. A portion of the material (208 mg) was purified by flash column chromatography (24 g SiO$_2$, 0-15% 2 N NH$_3$-MeOH/EA) to provide the title compound (112 mg, 9% yield) as a white solid. MS (ESI): mass calcd. for $C_{25}H_{23}N_7O_2S$, 485.16; m/z found, 486.2 [M+H]$^+$.

Step B: 2-((1r,4r)-4-(2-(1H-pyrazol-4-yl)imidazo[4,5-d]pyrrolo[2,3-b]pyridin-1(6H)-yl)cyclohexyl)acetonitrile. To a 10 mL microwave vial was added 2-((1r,4r)-4-(6-(phenyl sulfonyl)-2-(1H-pyrazol-4-yl)imidazo[4,5-d]pyrrolo[2,3-b]pyridin-1(6H)-yl)cyclohexyl)acetonitrile (110 mg, 0.227 mmol) as a solid followed by addition of tetrabutylammonium fluoride (0.566 mL, 1 M, 0.566 mmol) and the vial was sealed and heated to 100° C. in a microwave for 30 minutes. The reaction was purified by flash column chromatography to provide the title compound (56 mg, 71% yield) as a white powder. MS (ESI): mass calcd. for $C_{19}H_{19}N_7$, 345.17; m/z found, 346.1 [M+H]$^+$. $^1$H NMR (500 MHz, DMSO-d$_6$): δ 13.38 (s, 1H), 11.89 (s, 1H), 8.57 (s, 1H), 8.43-7.81 (m, 2H), 7.49 (t, J=3.0 Hz, 1H), 6.75 (dd, J=3.5, 1.8 Hz, 1H), 4.67-4.46 (m, 1H), 2.56 (d, J=6.3 Hz, 2H), 2.49-2.39 (m, 2H), 2.13-1.91 (m, 5H), 1.45-1.30 (m, 2H).

Example 124 Synthesis and Characterization (Z*)—N-((1-((1r,4r)-4-(Cyanomethyl)cyclohexyl)-1,6-dihydroimidazo[4,5-d]pyrrolo[2,3-b]pyridin-2-yl)methoxy)benzimidamide; the Structure being the (Z) or (E) Isomer, and the (Z) Notation and its Corresponding Structure Below is Chosen Arbitrarily

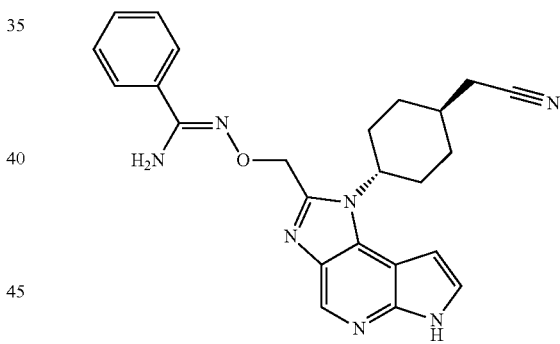

Step A: 2-((1r,4r)-4-(2-((((Z*)-2-Amino-2-phenylvinyl)oxy)methyl)-6-(phenyl sulfonyl)imidazo[4,5-d]pyrrolo[2,3-b]pyridin-1(6H)-yl)cyclohexyl)acetonitrile 2,2,2-trifluoroacetate. A mixture of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 13, 49 mg, 0.10 mmol), N-hydroxybenzimidamide (29 mg, 0.21 mmol), K$_2$CO$_3$ (23 mg, 0.17 mmol) in DMF (1 mL) was stirred at room temperature for 15 h. More N-hydroxybenzimidamide (16 mg, 0.12 mmol), K$_2$CO$_3$ (45 mg, 0.33 mmol), and DMF (1 mL) were added. After stirring overnight, the solid was filtered off and the filtrate was concentrated in vacuo. The residue was purified by reverse phase HPLC (10-90% CH$_3$CN in H$_2$O, 0.1% TFA) to give the title compound (50 mg, 70%), MS (ESI): mass calcd. for $C_{30}H_{29}N_7O_3S$, 567.2; m/z found, 568.3 [M+H]$^+$.

Step B: (Z*)—N-((1-((1r,4r)-4-(Cyanomethyl)cyclohexyl)-1,6-dihydroimidazo[4,5-d]pyrrolo[2,3-b]pyridin-2-yl)methoxy)benzimidamide. A mixture of 2-((1r,4r)-4-(2-

(((((Z)-2-amino-2-phenylvinyl)oxy)methyl)-6-(phenyl sulfonyl)imidazo[4,5-d]pyrrolo[2,3-b]pyridin-1(6H)-yl)cyclohexyl)acetonitrile 2,2,2-trifluoroacetate (50 mg, 0.073 mmol), 1 M NaOH (aq) (0.25 mL, 0.25 mmol), THF (0.7 mL), and MeOH (0.7 mL) was stirred at RT for 18 h and concentrated in vacuo. The residue was purified by reverse phase HPLC (10-90% CH$_3$CN in H$_2$O, 0.1% TFA). The fractions were collected and the solvents were removed under reduced pressure. The residue was partitioned between saturated NaHCO$_3$(aq) and EtOAc (×4). The combined organic layers were dried over Na$_2$SO$_4$, filtered, and concentrated to give the title compound as an off-white solid (30 mg, 95%). MS (ESI): mass calcd. for C$_{24}$H$_{25}$N$_7$O, 427.21; m/z found, 428.3 [M+H]$^+$. $^1$H NMR (400 MHz, CDCl$_3$) δ=10.92 (br s, 1H), 8.84 (br s, 1H), 7.67-7.57 (m, 2H), 7.46-7.36 (m, 4H), 6.72 (d, J=2.0 Hz, 1H), 4.94-4.79 (m, 3H), 2.65-2.45 (m, 2H), 2.37 (d, J=6.6 Hz, 2H), 2.21-1.98 (m, 5H), 1.51-1.34 (m, 2H).

Example 125 Synthesis and Characterization (EZ)—N-((1-((1r,4r)-4-(Cyanomethyl)cyclohexyl)-1,6-dihydroimidazo[4,5-d]pyrrolo[2,3-b]pyridin-2-yl)methyl)-N-hydroxy-3-methoxypropanimidamide

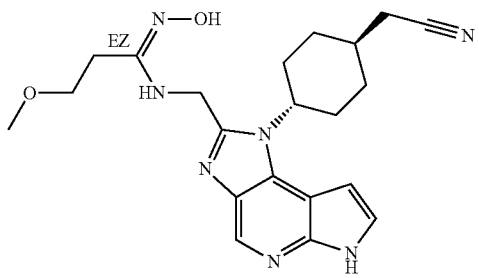 [SMILES: COCC/C(=N/O)NCc1nc2cnc3[nH]ccc3c2n1[C@H]1CC[C@H](CC#N)CC1]

A solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 300 mg, 0.870 mmol), N-hydroxy-3-methoxypropanimidoyl chloride (120 mg, 0.870 mmol), triethylamine (0.364 mL, 2.61 mmol), and DMF (6 mL) was stirred for 2 h at 20° C. The reaction mixture was concentrated to dryness and was purified by preparative HPLC using a Boston Green ODS 150 mm×30 mm, 5 m column (eluent: 4% to 34% (v/v) CH$_3$CN and H$_2$O with 0.1% TFA). The pure fractions from this HPLC run were collected, adjusted to pH=7-8 with saturated aqueous NaHCO$_3$, and the volatile solvents were removed under reduced pressure. The aqueous layer was extracted with ethyl acetate (20 mL×2). The combined organic extracts were dried over Na$_2$SO$_4$, filtered, and concentrated to dryness. The residue was further purified by preparative HPLC with a Kromasil 150 mm×25 mm, 10 μm column (eluent: 8% to 38% (v/v) CH$_3$CN and H$_2$O with 0.05% NH$_3$) to provide the title compound (30 mg, 8% yield) as a white solid. MS (ESI): mass calcd. for C$_{21}$H$_{27}$N$_7$O$_2$, 409.22; m/z found, 410.1 [M+H]$^+$. $^1$H NMR (400 MHz, DMSO-d$_6$): δ 11.88 (s, 1H), 9.21 (s, 1H), 8.56 (s, 1H), 7.49-7.45 (m, 1H), 6.74-6.69 (m, 1H), 6.33 (t, J=5.6 Hz, 1H), 4.72-4.60 (m, 3H), 3.43 (t, J=7.2 Hz, 2H), 3.19 (s, 3H), 2.60 (d, J=6.0 Hz, 2H), 2.43-2.24 (m, 2H), 2.11-1.84 (m, 7H), 1.57-1.43 (m, 2H).

Example 126 Synthesis and Characterization 2-((1r,4r)-4-(2-(((4-(4-Ethynylbenzoyl)benzyl)oxy) methyl)imidazo[4,5-d]pyrrolo[2,3-b]pyridin-1(6H)-yl)cyclohexyl)acetonitrile

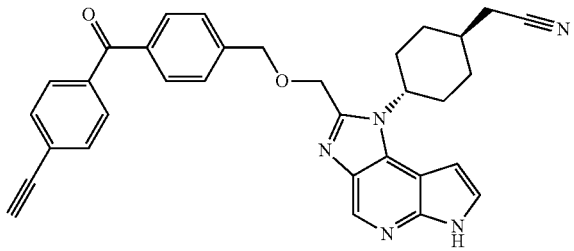 [SMILES: C#Cc1ccc(C(=O)c2ccc(COCc3nc4cnc5[nH]ccc5c4n3[C@H]3CC[C@H](CC#N)CC3)cc2)cc1]

Step A: (4-(Bromomethyl)phenyl)(4-bromophenyl) methanone. To a solution of 4-bromo-4'-methylbenzophenone (1.00 g, 3.64 mmol) in acetonitrile (5 mL) under nitrogen were added NBS (0.712 g, 4.00 mmol) and AIBN (0.060 mg, 0.36 mmol) and was stirred for 2 h at 90° C. to provide a white solution. The reaction was concentrated to dryness and the residue was purified by flash column chromatography to provide the title compound (1.3 g, 83% yield) as a white solid. $^1$H NMR (400 MHz, CDCl$_3$): δ 7.76 (d, J=7.6 Hz, 2H), 7.69-7.60 (m, 4H), 7.51 (d, J=8.0 Hz, 2H), 4.53 (s, 2H).

Step B: 2-((1r,4r)-4-(2-(((4-(4-Bromobenzoyl)benzyl) oxy)methyl)-6-(phenylsulfonyl)imidazo[4,5-d]pyrrolo[2,3-b]pyridin-1(6H)-yl)cyclohexyl)acetonitrile. A solution of 2-((1r,4r)-4-(2-(hydroxymethyl)-6-(phenylsulfonyl)imidazo [4,5-d]pyrrolo[2,3-b]pyridin-1(6H)-yl)cyclohexyl)acetonitrile (Intermediate 7, 500 mg, 0.80 mmol), (4-(bromomethyl)phenyl)(4-bromophenyl)methanone (515 mg, 1.20 mmol), silver oxide (742 mg, 3.20 mmol) and DMF (12 mL) was stirred at room-temperature for 18 h in the dark. The reaction was filtered through a pad of diatomaceous earth and concentrated to dryness, which was purified by flash column chromatography to provide the title compound as a yellow solid. MS (ESI): mass calcd. for C$_{37}$H$_{32}$BrN$_5$O$_4$S, 721.14; m/z found, 723.9 [M+H]$^+$. $^1$H NMR (400 MHz, CDCl$_3$): δ 8.90 (s, 1H), 8.25 (d, J=8.0 Hz, 2H), 7.86 (d, J=4 Hz, 1H), 7.76 (d, J=8.0 Hz, 2H), 7.66-7.63 (m, 4H), 7.58-7.55 (m, 1H), 7.51-7.47 (m, 2H), 7.43-7.40 (m, 2H), 6.84 (d, J=4.0 Hz, 1H), 4.93 (s, 2H), 4.65-4.59 (m, 3H), 2.44-2.41 (m, 2H), 2.38-2.30 (m, 2H), 2.15-2.07 (m, 5H), 1.51-1.43 (m, 2H).

Step C: 2-((1r,4r)-4-(6-(Phenylsulfonyl)-2-(((4-(4-((trimethyl silyl)ethynyl)benzoyl)benzyl)oxy)methyl)imidazo[4,5-d]pyrrolo[2,3-b]pyridin-1(6H)-yl)cyclohexyl)acetonitrile. 2-((1r,4r)-4-(2-(((4-(4-Bromobenzoyl)benzyl)oxy)methyl)-6-(phenylsulfonyl)imidazo[4,5-d]pyrrolo[2,3-b]pyridin-1 (6H)-yl)cyclohexyl)acetonitrile (40 mg, 0.037 mmol), Pd(PPh$_3$)$_4$ (4.2 mg, 0.0037 mmol), triethylamine (45 mg, 0.44 mmol), copper(I) iodide (0.42 mg, 0.0022 mmol) and DMF (1 mL) were added to a 2 mL microwave tube and purged with nitrogen for 10 minutes. The reaction was treated with trimethylsilylacetylene (36 mg, 0.37 mmol) and stirred while heating at 110° C. in a microwave for 1 hour before cooling to the room-temperature. The suspension was filtered through a pad of Celite® and the pad was washed with ethyl acetate (10 mL). The filtrate was concentrated to dryness and purified by preparative HPLC using a Phenomenex Synergi C$_{18}$ 150 mm×30 mm, 4 μm column (eluent:

77% to 95% (v/v) CH₃CN and aqueous HCl (0.006 N)). The pure fractions were collected, the pH adjusted to pH=7-8 with solid sodium bicarbonate and the volatiles were removed under vacuum. The residue was diluted with water (15 mL) and extracted with CH₂Cl₂ (45 mL×3), and the combined organic extracts were dried over anhydrous Na₂SO₄, filtered, and concentrated to dryness to provide the title compound as a yellow solid. MS (ESI): mass calcd. for $C_{42}H_{41}N_5O_4SSi$, 739.26; m/z found, 740.2 [M+H]⁺.

Step D: 2-((1r,4r)-4-(2-(((4-(4-Ethynylbenzoyl)benzyl)oxy)methyl)imidazo[4,5-d]pyrrolo[2,3-b]pyridin-1(6H)-yl)cyclohexyl)acetonitrile. The title compound (a light yellow solid, 800 mg, 8% yield)) was prepared using conditions analogous to those described in Example 1, Step B using 2-((1r,4r)-4-(6-(phenylsulfonyl)-2-(((4-(4-((trimethylsilyl)ethynyl)benzoyl)benzyl)oxy)methyl)imidazo[4,5-d]pyrrolo[2,3-b]pyridin-1(6H)-yl)cyclohexyl)acetonitrile (16 mg, 0.018 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. MS (ESI): mass calcd. for $C_{33}H_{29}N_5O_2$, 527.23; m/z found, 528.0 [M+H]⁺. ¹H NMR (400 MHz, DMSO-d₆): δ 11.93 (br s, 1H), 8.58 (s, 1H), 7.77-7.72 (m, 3H), 7.71 (s, 1H), 7.67-7.63 (m, 2H), 7.55 (d, J=8.0 Hz, 2H), 7.51-7.48 (m, 1H), 6.76-6.72 (m, 1H), 4.96 (s, 2H), 4.69 (s, 2H), 4.66-4.58 (m, 1H), 4.49 (s, 1H), 2.58 (d, J=6.0 Hz, 2H), 2.43-2.29 (m, 2H), 2.06-1.88 (m, 5H), 1.45-1.33 (m, 2H).

Example 127 Synthesis and Characterization 2-((1r,4r)-4-(2-(2-((R)-3-Hydroxypyrrolidin-1-yl)-2-oxoethyl)imidazo[4,5-d]pyrrolo[2,3-b]pyridin-1(6H)-yl)cyclohexyl)acetonitrile

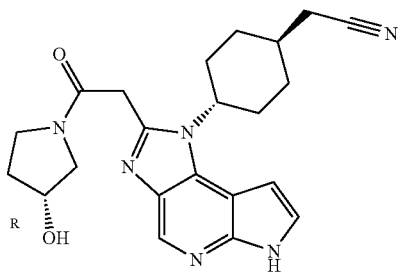

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), (R)-pyrrolidin-3-ol (114 mg, 0.918 mmol), DIPEA (0.29 mL, 1.67 mmol), and DMF (5 mL) was added PyBOP (428 mg, 0.918 mmol) at 0° C. and was stirred at room temperature for 3 h. The mixture was quenched with 10 mL water and extracted with EtOAc (3×20 mL). Both the organic phase and water phase were concentrated to provide a residue that was initially purified by preparative HPLC using a Xtimate Cis 150×25 mm x 5 μm column (eluent: 13% to 33% (v/v) CH₃CN and H₂O with 10 mM NH₄HCO₃). The resulting compound was then washed by 2-methoxy-2-methylpropane/methanol for further purification to provide the title compound (79 mg, 23% yield) as a white solid. MS (ESI): mass calcd. for $C_{22}H_{26}N_6O_2$, 406.21; m/z found, 407.2 [M+H]⁺. ¹H NMR (400 MHz, DMSO-d₆): δ 11.82 (br s, 1H), 8.49 (s, 1H), 7.47-7.44 (m, 1H), 6.72-6.69 (m, 1H), 5.15-4.98 (m, 1H), 4.47-4.25 (m, 2H), 4.23-4.07 (m, 2H), 3.77-3.62 (m, 2H), 3.51-3.42 (m, 1H), 3.33-3.25 (m, 1H), 2.59-2.54 (m, 2H), 2.41-2.27 (m, 2H), 2.08-1.73 (m, 7H), 1.44-1.28 (m, 2H).

Example 128 Synthesis and Characterization

Ethyl 3-(1-((1r,4r)-4-(Cyanomethyl)cyclohexyl)-1,6-dihydroimidazo[4,5-d]pyrrolo[2,3-b]pyridin-2-yl)azetidine-1-carboxylate

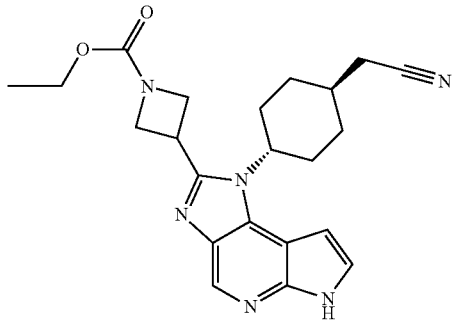 [SMILES: CCOC(=O)N1CC(c2nc3cnc4[nH]ccc4c3n2[C@H]2CC[C@H](CC#N)CC2)C1]

Step A: 2-((1r,4r)-4-((1-((4-Bromophenyl)sulfonyl)-5-nitro-1H-pyrrolo[2,3-b]pyridin-4-yl)amino)cyclohexyl)acetonitrile. The mixture of 2-((1r,4r)-4-aminocyclohexyl)acetonitrile hydrochloride (Intermediate 1, Step D, 437 mg, 2.50 mmol), 1-((4-bromophenyl)sulfonyl)-4-chloro-5-nitro-1H-pyrrolo[2,3-b]pyridine (932 mg, 2.24 mmol), DIEPA (1.30 mL, 7.94 mmol) in DMSO (3 mL) was heated at 100° C. for 1 h. The mixture was cooled down. H₂O (100 mL) was added. Solids were formed. After filtration, the solids were collected, re-dissolved into CH₂Cl₂ (50 mL), and washed with H₂O (50 mL). The organic layer was concentrated providing the title compound (1100 mg, 95% yield) which was used without further purification. MS (ESI): mass calcd. for $C_{21}H_{20}BrN_5O_4S$, 518.4; m/z found, 517.7/519.7 (Cl atom) [M+H]⁺.

Step B: 2-((1r,4r)-4-(2-(Azetidin-3-yl)-6-((4-bromophenyl)sulfonyl)imidazo[4,5-d]pyrrolo[2,3-b]pyridin-1(6H)-yl)cyclohexyl)acetonitrile. A solution of 2-((1r,4r)-4-((1-((4-bromophenyl)sulfonyl)-5-nitro-1H-pyrrolo[2,3-b]pyridin-4-yl)amino)cyclohexyl)acetonitrile (519 mg, 1.00 mmol), tert-butyl 3-formylazetidine-1-carboxylate (371 mg, 2.00 mmol), sodium dithionite (523 mg, 3.00 mmol), DMSO (2.5 mL), and water (0.15 mL) was heated to 100° C. for 16 hours. Water (20 mL) added. The precipitate that formed was collected by filtration and was purified by flash column chromatography. To this material was added CH₂Cl₂ (5 mL) and TFA (1 mL) and was stirred for 0.5 h. The reaction was concentrated to dryness. To the residue was added CH₂Cl₂ (10 mL) and saturated NaHCO₃(10 mL), the organic layer was collected and concentrated to dryness to provide the crude title compound (200 mg). MS (ESI): mass calcd. for $C_{25}H_{25}BrN_6O_2S$, 552.09; m/z found, 554.7 [M+H]⁺.

Step C: Ethyl 3-(1-((1r,4r)-4-(Cyanomethyl)cyclohexyl)-1,6-dihydroimidazo[4,5-d]pyrrolo[2,3-b]pyridin-2-yl)azetidine-1-carboxylate. To a solution of ethyl carbonochloridate (0.0362 mL, 0.379 mmol) and triethylamine (40 mg, 0.40 mmol) in CH$_2$Cl$_2$ (3 mL) was added 2-((1r,4r)-4-(2-(azetidin-3-yl)-6-((4-bromophenyl)sulfonyl)imidazo[4,5-d]pyrrolo[2,3-b]pyridin-1(6H)-yl)cyclohexyl)acetonitrile (200 mg, 0.361 mmol) in CH$_2$Cl$_2$ (0.5 mL) and was stirred at room temperature for 16 h. Water (10 mL) was added, the organic layer was collected, and concentrated to dryness. The residue was dissolved into THF/MeOH/NaOH (1M) (1 mL/1 mL/1 mL) and was heated at 80° C. for 1 h. The reaction was concentrated to dryness and the residue was purified by flash column chromatography to provide the title compound (16 mg, 11% yield). MS (ESI): mass calcd. for C$_{22}$H$_{26}$N$_6$O$_2$, 406.21; m/z found, 407.2 [M+H]$^+$. $^1$H NMR (400 MHz, CDCl$_3$): δ 8.69 (s, 1H), 7.40 (d, J=3.5 Hz, 1H), 6.67 (d, J=3.5 Hz, 1H), 4.70-4.35 (m, 4H), 4.26-4.01 (m, 3H), 3.88-3.42 (m, 1H), 2.68-2.40 (m, 4H), 2.29-1.92 (m, 5H), 1.59-1.38 (m, 2H), 1.28 (t, J=7.1 Hz, 3H).

Example 129 Synthesis and Characterization 2-((1r,4r)-4-(2-((3-Isopropyl-5-oxo-1,2,4-oxadiazol-4(5H)-yl)methyl)imidazo[4,5-d]pyrrolo[2,3-b]pyridin-1(6H)-yl)cyclohexyl)acetonitrile

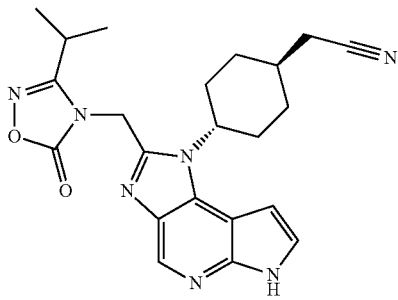 [SMILES: CC(C)c1noc(=O)n1Cc1nc2cnc3[nH]ccc3c2n1[C@H]1CC[C@H](CC#N)CC1]

A solution of (EZ)—N-((1-((1r,4r)-4-(cyanomethyl)cyclohexyl)-1,6-dihydroimidazo[4,5-d]pyrrolo[2,3-b]pyridin-2-yl)methyl)-N-hydroxyisobutyrimidamide (15 mg, 0.035 mmol), as prepared in Example 61, CDI (6.2 mg, 0.038 mmol), and THF (1 mL) was stirred for 1.5 h at 70° C. The reaction was concentrated to dryness and the residue was purified by preparative HPLC using a Phenomenex Gemini 150 mm×25 mm, 10 μm column (eluent: 25% to 55% (v/v) CH$_3$CN and H$_2$O with 0.05% NH$_3$) to provide the title compound (5 mg, 35% yield) as a white solid. MS (ESI): mass calcd. for C$_{22}$H$_{25}$N$_7$O$_2$, 419.21; m/z found, 420.1 [M+H]$^+$. $^1$H NMR (400 MHz, DMSO-d$_6$): δ 11.93 (s, 1H), 8.54 (s, 1H), 7.53-7.47 (m, 1H), 6.75 (s, 1H), 5.39 (s, 2H), 4.64-4.49 (m, 1H), 3.09-2.97 (m, 1H), 2.61 (d, J=6.0 Hz, 2H), 2.44-2.26 (m, 2H), 2.12-1.91 (m, 5H), 1.55-1.37 (m, 2H), 1.15 (d, J=6.8 Hz, 6H).

Example 130 Synthesis and Characterization 2-((1r,4r)-4-(2-((4-(4-Ethynylbenzoyl)phenoxy)methyl)imidazo[4,5-d]pyrrolo[2,3-b]pyridin-1(6H)-yl)cyclohexyl)acetonitrile

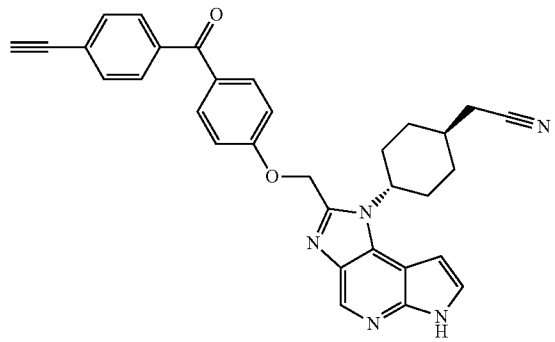 [SMILES: C#Cc1ccc(C(=O)c2ccc(OCc3nc4cnc5[nH]ccc5c4n3[C@H]3CC[C@H](CC#N)CC3)cc2)cc1]

Step A: 2-((1r,4r)-4-(2-((4-(4-Bromobenzoyl)phenoxy)methyl)-6-(phenylsulfonyl)imidazo[4,5-d]pyrrolo[2,3-b]pyridin-1(6H)-yl)cyclohexyl)acetonitrile. A solution of (4-bromophenyl)(4-hydroxyphenyl)methanone (289 mg, 0.968 mmol), 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 530 mg, 1.02 mmol), DMF (10 mL), K$_2$CO$_3$ (282 mg, 2.04 mmol), and KI (16.9 mg, 0.102 mmol) was stirred at 60° C. for 3 h. The reaction was quenched with water (250 mL) and washed with EtOAc (2×250 mL), the organic extracts were combined, washed with brine (150 mL), dried over anhydrous Na$_2$SO$_4$, and concentrated to dryness. The residue was purified by flash column chromatography (eluent: petroleum ether:ethyl acetate=100:0 to 36:64) to provide the title compound (330 mg, 44% yield) as a yellow solid. MS (ESI): mass calcd. for C$_{36}$H$_{30}$BrN$_5$O$_4$S, 707.12; m/z found, 710.0 [M+H]$^+$.

Step B: 2-((1r,4r)-4-(6-(Phenylsulfonyl)-2-((4-(4-((trimethylsilyl)ethynyl)benzoyl)phenoxy)methyl)imidazo[4,5-d]pyrrolo[2,3-b]pyridin-1(6H)-yl)cyclohexyl)acetonitrile. 2-((1r,4r)-4-(2-((4-(4-Bromobenzoyl)phenoxy)methyl)-6-(phenyl sulfonyl)imidazo[4,5-d]pyrrolo[2,3-b]pyridin-1(6H)-yl)cyclohexyl)acetonitrile (250 mg, 0.353 mmol), Pd(PPh$_3$)$_4$ (40.8 mg, 0.0353 mmol), triethylamine (428 mg, 4.23 mmol), copper(I) iodide (4.0 mg, 0.0.021 mmol) and DMF (6 mL) were added to a 10 mL microwave tube and purged with nitrogen for 10 minutes. The reaction was treated with trimethylsilylacetylene (347 mg, 3.53 mmol) and stirred while heating at 110° C. in a microwave for 1 hour before cooling to the room-temperature. The suspension was filtered through a pad of Celite® and the pad was washed with ethyl acetate (20 mL). The filtrate was concentrated to dryness and purified by flash column chromatography (eluent: petroleum ether:ethyl acetate=10:1 to 1:2) to provide the title compound as a yellow solid (212 mg, 68%). MS (ESI): mass calcd. for C$_{41}$H$_{39}$N$_5$O$_4$SSi, 725.25; m/z found, 726.2 [M+H]$^+$. $^1$H NMR (400 MHz, CDCl$_3$): δ 8.91 (s, 1H), 8.28-8.20 (m, 2H), 7.86 (d, J=4.0 Hz, 1H), 7.76 (d, J=8.8 Hz, 2H), 7.66 (d, J=8.4 Hz, 2H), 7.58-7.46 (m, 5H), 7.12 (d, J=8.8 Hz, 2H), 6.83 (d, J=4.0 Hz, 1H), 5.51 (s, 2H), 4.73-4.59 (m, 1H), 2.44 (d, J=6.0 Hz, 2H), 2.40-2.28 (m, 2H), 2.22-2.12 (m, 2H), 2.11-1.93 (m, 3H), 1.54-1.46 (m, 2H), 0.27 (s, 9H).

Step C: 2-((1r,4r)-4-(2-((4-(4-Ethynylbenzoyl)phenoxy)methyl)imidazo[4,5-d]pyrrolo[2,3-b]pyridin-1(6H)-yl)cyclohexyl)acetonitrile. The title compound (a light yellow solid, (42 mg, 27% yield)) as was prepared using conditions analogous to those described in Example 1, Step B using 2-((1r,4r)-4-(6-(Phenylsulfonyl)-2-((4-(4-((trimethylsilyl)ethynyl)benzoyl)phenoxy)methyl)imidazo[4,5-d]pyrrolo[2,3-b]pyridin-1(6H)-yl)cyclohexyl)acetonitrile (90 mg, 0.12 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. Purification was performed by preparative HPLC using a Phenomenex Gemini 150 mm×25 mm, 10 μm column (eluent: 45% to 75% (v/v) $CH_3CN$ and $H_2O$ with 0.05% $NH_3$). MS (ESI): mass calcd. for $C_{32}H_{27}N_5O_2$, 513.22; m/z found, 514.0 $[M+H]^+$. $^1H$ NMR (400 MHz, DMSO-$d_6$): δ 11.98 (br s, 1H), 8.62 (s, 1H), 7.78 (d, J=8.8 Hz, 2H), 7.71-7.67 (m, 2H), 7.66-7.62 (m, 2H), 7.53-7.49 (m, 1H), 7.30 (d, J=8.8 Hz, 2H), 6.79-6.73 (m, 1H), 5.67 (s, 2H), 4.70-4.57 (m, 1H), 4.46 (s, 1H), 2.59 (d, J=6.0 Hz, 2H), 2.44-2.28 (m, 2H), 2.07-1.94 (m, 5H), 1.49-1.31 (m, 2H).

Example 131 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)bicyclo[2.2.1]heptan-1-yl)acetamide

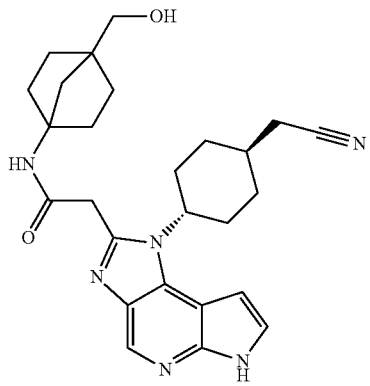 [SMILES: N#CC[C@H]1CC[C@H](n2c(CC(=O)NC34CCC(CO)(CC3)C4)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg crude, 0.557 mmol), (4-aminobicyclo[2.2.1]heptan-1-yl)methanol hydrochloride (109 mg, 0.612 mmol) and DIPEA (0.291 mL, 1.67 mmol) in dry DMF (6 mL) was added PyBrOP (285 mg, 0.612 mmol) at 0° C. and was stirred at room-temperature for 15 hours. The mixture was diluted with water (10 mL) and extracted with ethyl acetate (20 mL×3). The combined organic phases were washed with brine, dried over anhydrous $Na_2SO_4$, filtered, and concentrated to dryness. The residue was purified by preparative HPLC using a DuraShell 150×25 mm×5 μm column (eluent: 12% to 42% (v/v) $CH_3CN$ and $H_2O$ with 0.05% $NH_3$) to provide the title compound (37.2 mg, 14% yield) as yellow solid. MS (ESI): mass calcd. for $C_{26}H_{32}N_6O_2$, 460.26; m/z found, 461.2 $[M+H]^+$. $^1H$ NMR (400 MHz, $CD_3OD$): δ 8.53 (s, 1H), 7.48 (d, J=4.0 Hz, 1H), 6.84 (d, J=4.0 Hz, 1H), 4.04 (s, 2H), 3.56 (s, 2H), 2.66-2.51 (m, 4H), 2.18-2.05 (m, 5H), 2.00-1.82 (m, 5H), 1.77-1.65 (m, 4H), 1.57-1.47 (m, 2H), 1.44-1.35 (m, 2H).

Example 132 Synthesis and Characterization 2-(1-((1r,4r)-4-(Cyanomethyl)cyclohexyl)-8-fluoro-1,6-dihydroimidazo[4,5-d]pyrrolo[2,3-b]pyridin-2-yl)-N-(2-hydroxy-2-methylpropyl)acetamide

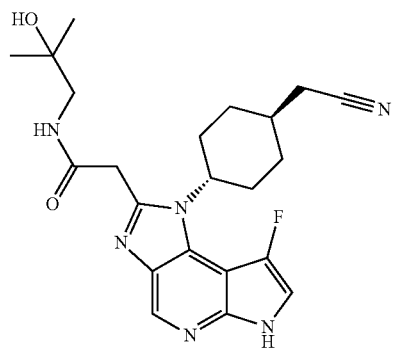 [SMILES: CC(C)(O)CNC(=O)Cc1nc2cnc3[nH]cc(F)c3c2n1[C@H]1CC[C@H](CC#N)CC1]

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide (55.4 mg, 0.136 mmol), as prepared in Example 1, was added to a 2 dram vial, then dissolved in $CH_3CN$ (1 mL) and water (1 mL). $NaHCO_3$ (34 mg, 0.41 mmol) was added with vigorous stirring. The reaction was treated slowly with 1-chloromethyl-4-fluoro-1,4-diazoniabicyclo[2.2.2]octane bis(tetrafluoroborate) (Selectfluor®) (72.1 mg, 0.203 mmol) as a solution in 1 mL $CH_3CN$. The reaction mixture was stirred at room temperature and was monitored by LCMS. The reaction was extracted with (2×10 mL) $CH_2Cl_2$. The combined organic layers were dried over anhydrous $MgSO_4$ and concentrated to dryness. The residue was initially purified by reverse phase acidic HPLC using a Xbridge 50 mm×250 mm, 10 μm column (10-70% $CH_3CN$-water with TFA as the eluent). The resulting compound was subjected to further purification by reverse phase basic HPLC using a Xbridge 50 mm×100 mm, 5 μm column ($CH_3CN$-water with $NH_4OH$ as the eluent) to provide the title compound (4 mg, 7% yield) as a white solid. MS (ESI): mass calcd. for $C_{22}H_{27}FN_6O_2$, 426.22; m/z found, 427.2 $[M+H]^+$. $^1H$ NMR (600 MHz, DMSO-$d_6$): δ 11.74 (s, 1H), 8.52 (s, 1H), 8.23-8.00 (m, 1H), 7.49 (s, 1H), 4.50 (s, 2H), 4.07 (s, 2H), 3.08 (d, J=5.9 Hz, 2H), 2.58-2.54 (m, 2H), 2.35 (d, J=14.8 Hz, 2H), 2.00-1.80 (m, 5H), 1.33 (d, J=12.7 Hz, 2H), 1.09 (s, 6H).

Example 133 Synthesis and Characterization 1-((1r,4r)-4-(Cyanomethyl)cyclohexyl)-N-methyl-1,6-dihydroimidazo[4,5-d]pyrrolo[2,3-b]pyridine-2-carboxamide

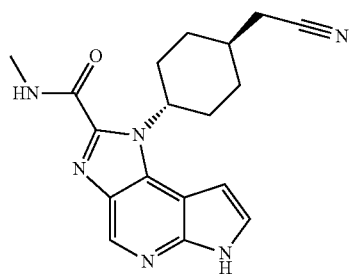 [SMILES: CNC(=O)c1nc2cnc3[nH]ccc3c2n1[C@H]1CC[C@H](CC#N)CC1]

The title compound (28 mg, 41% yield) was prepared using analogous conditions as described in Example 50, Step A using methylamine instead of 3-phenylpyrrolin-3-ol. MS (ESI): mass calcd. for $C_{18}H_{20}N_6O$, 336.17; m/z found, 337.2 [M+H]$^+$. $^1$H NMR (500 MHz, CDCl$_3$): δ 11.28 (s, 1H), 8.83 (s, 1H), 7.90 (d, J=5.1 Hz, 1H), 7.62-7.41 (m, 1H), 6.93-6.75 (m, 1H), 6.31-5.76 (br, 1H), 3.06 (d, J=5.1 Hz, 3H), 2.75-2.55 (m, 2H), 2.40 (d, J=6.6 Hz, 2H), 2.27-2.03 (m, 5H), 1.60-1.40 (m, 2H).

Example 134 Synthesis and Characterization 2-((1r,4r)-4-(2-(1-(Methylsulfonyl)azetidin-3-yl)imidazo[4,5-d]pyrrolo[2,3-b]pyridin-1(6H)-yl)cyclohexyl)acetonitrile

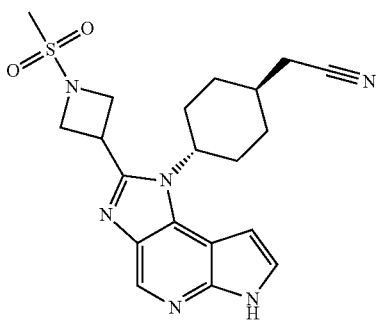 [SMILES: CS(=O)(=O)N1CC(c2nc3cnc4[nH]ccc4c3n2[C@H]2CC[C@H](CC#N)CC2)C1]

To a solution of 2-((1r,4r)-4-(2-(azetidin-3-yl)-6-((4-bromophenyl)sulfonyl)imidazo[4,5-d]pyrrolo[2,3-b]pyridin-1(6H)-yl)cyclohexyl)acetonitrile (50.0 mg, 0.0900 mmol), as prepared in Example 128, Step B, and DIPEA (3 equiv.) in CH$_2$Cl$_2$ (5 mL) was added methanesulfonyl chloride (10.3 mg, 0.0903 mmol) in THF (0.5 mL) and was stirred at room temperature for 1 h. Water (20 mL) was added, the organic phase collected, and concentrated to dryness. The residue was dissolved into THF/MeOH/NaOH (1M) (1 mL/1 mL/1 mL) and the mixture was heated to 80° C. for 1 h. The reaction was concentrated to dryness and the residue was purified by flash column chromatography to provide the title compound (7.00 mg, 19% yield). MS (ESI): mass calcd. for $C_{20}H_{24}N_6O_2S$, 412.17; m/z found, 413.2 [M+H]$^+$. $^1$H NMR (500 MHz, CDCl$_3$): δ 9.22 (s, 1H), 8.79 (s, 1H), 7.43-7.34 (m, 1H), 6.77-6.57 (m, 1H), 4.65-4.37 (m, 4H), 4.26-4.06 (m, 1H), 3.49 (d, J=5.1 Hz, 1H), 2.98 (s, 3H); 2.72-2.36 (m, 4H), 2.27-1.91 (m, 5H), 1.49-1.37 (m, 2H).

Example 135 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1S,4S)-4-(trimethylsilyl)cyclohexyl)acetamide

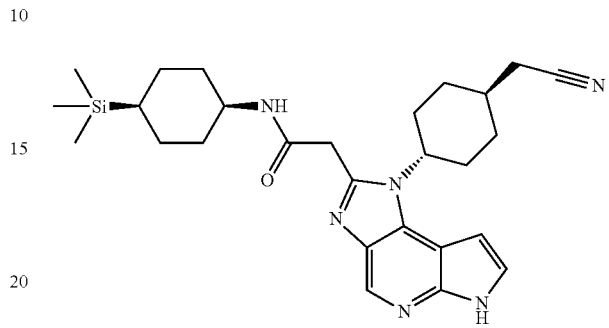

Step A: (4-methoxyphenyl)trimethylsilane. To a solution of 4-bromoanisole (50.0 g, 267 mmol) in dry THF (1000 mL) at 0° C. was added Me$_3$SiCl (68.0 mL, 535 mmol) followed by n-BuLi (2.50 M in hexanes, 200 mL, 0.500 mol). The reaction mixture was stirred at room-temperature for 3 hours. Water (500 mL) was added, the layers were separated, and the aqueous layer was extracted with ethyl acetate (400 mL×3). The combined organic extracts were dried over anhydrous Na$_2$SO$_4$, filtered, and concentrated to dryness. The residue was purified by flash column chromatography (eluent: petroleum ether:ethyl acetate=10:1) to provide the title compound (45.0 g, 69% yield). $^1$H NMR (400 MHz, CDCl$_3$): δ 7.51-7.44 (m, 2H), 6.97-6.90 (m, 2H), 3.84 (s, 3H), 0.27 (s, 9H).

Step B: 4-(Trimethylsilyl)cyclohexanone. Ammonia (700 mL) was condensed into a 2 L three-necked flask at −78° C. (4-Methoxyphenyl)trimethylsilane (27.0 g, 150 mmol) in anhydrous THF (165 mL) was added, followed by EtOH (120 mL) and sodium (34.5 g, 1.50 mol) in portions and was stirred at −40° C. for 2 hours. EtOH (80 mL) was added and the ammonia evaporated gradually overnight at room-temperature. Water (600 mL) was added to the reaction and was extracted with ethyl acetate (600 mL×3). The combined organic extracts were dried over anhydrous Na$_2$SO$_4$, filtered, and concentrated to dryness. The residue was dissolved in EtOH (300 mL) and water (36 mL), and oxalic acid (4.10 g, 46.0 mmol) was added and was stirred at room-temperature for 2 hours. Water (500 mL) was added and the reaction was extracted with ethyl acetate (500 mL×3). The combined organic extracts were washed with brine, dried over anhydrous Na$_2$SO$_4$, filtered and concentrated to dryness. The residue was purified by flash column chromatography (eluent: petroleum:ethyl acetate=15:1) to provide the title compound (11.0 g, 43% yield) as a light yellow sticky compound. $^1$H NMR (400 MHz, CDCl$_3$): δ 2.46-2.38 (m, 2H), 2.34-2.23 (m, 2H), 2.13-2.04 (m, 2H), 1.57-1.44 (m, 2H), 0.98-0.87 (m, 1H), 0.00 (s, 9H).

Step C: 4-(Trimethylsilyl)cyclohexanone oxime. 4-(Trimethylsilyl)cyclohexanone (4.0 g, 23 mmol), hydroxylamine hydrochloride (3.3 g, 47 mmol), CH$_3$COONa (4.0 g, 49 mmol), and ethanol (100 mL) were added to a 250 mL round-bottomed flask and was stirred at room-temperature for 16 hours. The mixture was diluted with water (50 mL), extracted with ethyl acetate (100 mL×3), the combined organic extracts were washed with brine (100 mL), dried over anhydrous Na$_2$SO$_4$, filtered, and concentrated to dryness to provide the title compound (4.0 g, 92%) as a light yellow solid. $^1$H NMR (400 MHz, CDCl$_3$): δ 3.44-3.33 (m, 1H), 2.49-2.37 (m, 1H), 2.14-1.99 (m, 2H), 1.97-1.86 (m, 2H), 1.76-1.62 (m, 1H), 1.39-1.18 (m, 2H), 0.81-0.69 (m, 1H), −0.03 (s, 9H).

Step D: 4-(Trimethylsilyl)cyclohexanamine. 4-(Trimethylsilyl)cyclohexanone oxime (4.0 g, 0.77 mmol), Raney Ni (100 mg), and MeOH/NH$_4$OH (4:1) (75 mL) were added to a 100 mL round-bottomed flask and was stirred at room-temperature under a H$_2$ atmosphere for 16 hours. The mixture was filtered through a pad of diatomite and the filtrate was concentrated to dryness to provide the title compound (3.0 g, 81% yield) as a colorless oil. MS (ESI): mass calcd. for C$_9$H$_{21}$NSi, 171.14; m/z found, 172.2 [M+H]$^+$.

Step E: Benzyl ((1S,4S)-4-(trimethylsilyl)cyclohexyl)carbamate. 4-(Trimethylsilyl)cyclohexanamine (500 mg, 2.92 mmol), Na$_2$CO$_3$ (928 mg, 8.76 mmol), and THF (30 mL) were added to a 100 mL round-bottomed flask and was stirred at 0° C. for 10 minutes. CbzCl (1.50 g, 8.80 mmol) was added at 0° C. and was stirred at room-temperature for 4 hours. The reaction was combined with two other reactions and the resulting mixture was poured into water (100 mL), extracted with CH$_2$Cl$_2$ (100 mL×4). The combined organic extracts were dried over anhydrous Na$_2$SO$_4$, filtered, and concentrated to dryness. The residue was purified by flash column chromatography (petroleum ether:ethyl acetate=15:1 to 6:1) to provide the title compound as a diastereomeric mixture (500 mg, 56% yield). The diastereomeric mixture was separated by Supercritical Fluid Chromatography (ChiralPak AD, Daicel Chemical Industries, Ltd, 250×30 mm, 5 μm; Mobile phase: A: Supercritical CO$_2$, B: ethanol (0.1% NH$_3$.H$_2$O), A:B=75:25 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and concentrated to dryness. The residue was dissolved in ethyl acetate (5 mL), washed with water (2 mL), and concentrated to dryness. The residue was partitioned between CH$_3$CN (1 mL) and water (5 mL) and lyophilized to dryness to provide the title compound as the (1S,4S)-analogue (190 mg, 21% yield). MS (ESI): mass calcd. for C$_{17}$H$_{27}$NO$_2$Si, 305.18; m/z found, 306.0 [M+H]$^+$. $^1$H NMR (400 MHz, CDCl$_3$): δ 7.43-7.30 (m, 5H), 5.17-5.07 (m, 2H), 4.94 (br s, 1H), 3.99-3.88 (m, 1H), 1.83-1.74 (m, 2H), 1.60-1.50 (m, 4H), 1.30-1.16 (m, 2H), 0.64-0.53 (m, 1H), −0.04 (s, 9H). The diastereomer (1r,4r)-4-(trimethylsilyl) cyclohexanamine was also isolated (280 mg, 31% yield). MS (ESI): mass calcd. for C$_{17}$H$_{27}$NO$_2$Si, 305.18; m/z found, 306.0 [M+H]$^+$. $^1$H NMR (400 MHz, CDCl$_3$) 7.41-7.29 (m, 5H), 5.09 (s, 2H), 4.57 (br. s., 1H), 3.43 (br. s., 1H), 2.11-2.02 (m, 2H), 1.80-1.71 (m, 2H), 1.26-1.12 (m, 2H), 1.10-0.98 (m, 2H), 0.47-0.37 (m, 1H), −0.05 (s, 9H).

Step F: (1S,4S)-4-(Trimethylsilyl)cyclohexanamine. Benzyl ((1s,4s)-4-(trimethylsilyl)cyclohexyl)carbamate (370 mg, 1.21 mmol), 10 wt. % Pd/C (Wet) (100 mg), and MeOH (30 mL) were added to 250 mL round-bottomed flask. The reaction was stirred at room temperature under a H$_2$ atmosphere for 6 hours. The mixture was filtrated through a pad of diatomite and the filtrate was concentrated to dryness to provide the title compound (177 mg, 85.0% yield) as a gray sticky compound. MS (ESI): mass calcd. for C$_9$H$_{21}$NSi, 171.14; m/z found, 172.2 [M+H]$^+$. $^1$H NMR (400 MHz, CD$_3$OD): δ 3.04-2.98 (m, 1H), 1.62-1.54 (m, 4H), 1.52-1.44 (m, 4H), 0.65-0.55 (m, 1H), −0.02−−0.06 (m, 9H).

Step G: 2-(1-((1r,4r)-4-(Cyanomethyl)cyclohexyl)-1,6-dihydroimidazo[4,5-d]pyrrolo[2,3-b]pyridin-2-yl)-N-((1S, 4S)-4-(trimethylsilyl)cyclohexyl)acetamide. To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 60 mg, 0.17 mmol) and (1S,4S)-4-(trimethylsilyl)cyclohexanamine (43 mg, 0.25 mmol) in DMF 3 mL) were added PyBOP (170 mg, 0.33 mmol) and DIPEA (0.10 mL, 0.58 mmol) and the reaction was stirred at room temperature for 18 h. After removal of the DMF in vacuo, water was added to the residue and the aqueous layer was extracted with EtOAc. The combined organic extracts were dried over anhydrous MgSO$_4$, filtered, and concentrated to dryness. The residue was purified by reverse phase HPLC using a Varian Pursuit XR$_s$5 Diphenyl 100×30 mm column (eluent: 10-90% CH$_3$CN in H$_2$O, 0.1% TFA) to provide the title compound (26 mg, 26% yield). MS (ESI): mass calcd. for C$_{27}$H$_{38}$N$_6$OSi, 490.29; m/z found, 491.4 [M+H]$^+$. $^1$H NMR (400 MHz, CD$_3$OD) δ=8.80 (s, 1H), 7.73 (d, J=3.5 Hz, 1H), 7.08 (d, J=2.5 Hz, 1H), 4.93 (s, 2H), 4.66 (br s, 1H), 4.04 (br s, 1H), 2.55 (br d, J=5.6 Hz, 4H), 2.25-2.08 (m, 5H), 1.82 (br d, J=10.1 Hz, 2H), 1.66-1.43 (m, 8H), 0.66 (br t, J=10.9 Hz, 1H), 0.00 (s, 9H).

Example 136 Synthesis and Characterization 1-((1r,4r)-4-(Cyanomethyl)cyclohexyl)-N-((1-hydroxycycloheptyl)methyl)-1,6-dihydroimidazo[4,5-d]pyrrolo[2,3-b]pyridine-2-carboxamide

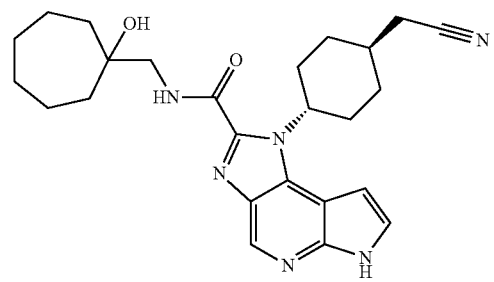 [SMILES: N#CC[C@H]1CC[C@H](n2c(C(=O)NCC3(O)CCCCCC3)nc3cnc4[nH]ccc4c32)CC1]

The title compound (61 mg, 70% yield) was prepared using analogous conditions as described in Example 50, Step A using 1-(aminomethyl)cycloheptanol instead of 3-phenylpyrrolin-3-ol. MS (ESI): mass calcd. for C$_{25}$H$_{32}$N$_6$O$_2$, 448.26; m/z found, 449.3 [M+H]$^+$. $^1$H NMR (500 MHz, CDCl$_3$): δ 12.29 (s, 1H), 8.78 (s, 1H), 8.40-8.15 (m, 1H), 7.55 (d, J=3.4 Hz, 1H), 6.83 (d, J=3.4 Hz, 1H), 6.30-5.33 (m, 2H), 3.69-3.40 (m, 2H) 2.62-2.21 (m, 4H), 2.16-1.87 (m, 5H), 1.81-1.33 (m, 14H).

Example 137 Synthesis and Characterization

Isobutyl ((1-((1r,4r)-4-(Cyanomethyl)cyclohexyl)-1,6-dihydroimidazo[4,5-d]pyrrolo[2,3-b]pyridin-2-yl)methyl)carbamate

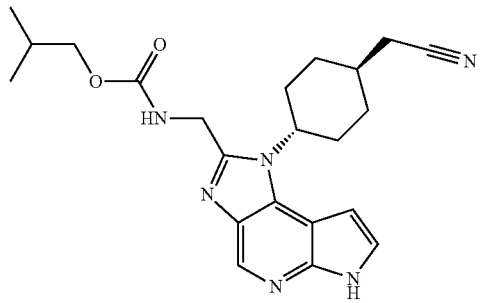 [SMILES: CC(C)COC(=O)NCc1nc2cnc3[nH]ccc3c2n1[C@H]1CC[C@H](CC#N)CC1]

Step A: Methyl 1-((2-(trimethylsilyl)ethoxy)methyl)-1H-pyrazole-4-carboxylate. A solution of methyl 1H-pyrazole-4-carboxylate (500 mg, 3.97 mmol) and dry THF (10 mL) was added to a 0° C. (ice/water) suspension of sodium hydride in mineral oil (317 mg, 60% purity, 7.93 mmol) and dry THF (10 mL) and was stirred for 1 h with gradual warming to 10° C. The reaction was then treated with a solution of SEM-Cl (793 mg, 4.76 mmol) and dry THF (5 mL) at 0° C. and was stirred overnight at 10° C. The reaction was quenched with saturated aqueous $NH_4C_1$ (20 mL) and concentrated to dryness. The aqueous phase was extracted with ethyl acetate (20 mL×2), dried over anhydrous $Na_2SO_4$, filtered, and concentrated to dryness. The residue was purified by flash column chromatography (gradient eluent: petroleum ether:ethyl acetate=100:0 to 85:15) to provide the title compound (400 mg, 39% yield) as a colorless oil. MS (ESI): mass calcd. for $C_{11}H_{20}N_2O_3Si$, 256.12; m/z found, 256.9 $[M+H]^+$. $^1H$ NMR (400 MHz, $CDCl_3$): δ 8.06 (s, 1H), 7.94 (s, 1H), 5.43 (s, 2H), 3.84 (s, 3H), 3.57 (t, J=8.0 Hz, 2H), 0.91 (t, J=8.0 Hz, 2H), −0.02 (s, 9H).

Step B: 1-((2-(Trimethylsilyl)ethoxy)methyl)-1H-pyrazole-4-carboxylic acid. A solution of NaOH (109 mg, 2.73 mmol) and water (1 mL) was added to a solution of methyl 1-((2-(trimethylsilyl)ethoxy)methyl)-1H-pyrazole-4-carboxylate (350 mg, 1.37 mmol), MeOH (1 mL), and THF (1 mL) and was stirred for 2.5 h at 20° C. The reaction was concentrated to dryness, diluted with water (5 mL) and adjusted to pH=2-3 with 1 M HCl. The precipitate that formed was filtered, washed with water (3 mL×2), and dried under high vacuum to provide the title compound (300 mg, 86% yield) as a white solid. MS (ESI): mass calcd. for $C_{10}H_{18}N_2O_3Si$, 242.11; m/z found, 243.0 $[M+H]^+$.

Step C: (Isobutyl carbonic) 1-((2-(trimethylsilyl)ethoxy)methyl)-1H-pyrazole-4-carboxylic anhydride. Isobutyl chloroformate (186 mg, 1.08 mmol) was added to a 0° C. (ice/water) solution of 1-((2-(trimethylsilyl)ethoxy)methyl)-1H-pyrazole-4-carboxylic acid (250 mg, 0.897 mmol), 4-methylmorpholine (136 mg, 1.35 mmol), and dry THF (5 mL) and was stirred for 1 h at 10° C. The reaction was concentrated to dryness and the residue was partitioned between water (10 mL) and $CH_2Cl_2$ (20 mL). The organic phase was separated, dried over anhydrous $Na_2SO_4$, filtered, and concentrated to dryness to provide the title compound (370 mg, 102% yield) as a light yellow oil. MS (ESI): mass calcd. for $C_{15}H_{26}N_2O_5Si$, 342.16; m/z found, 342.9 $[M+H]^+$. $^1H$ NMR (400 MHz, $CDCl_3$): δ 8.17 (s, 1H), 8.02 (s, 1H), 5.45 (s, 2H), 4.10 (d, J=6.8 Hz, 2H), 3.60 (t, J=8.4 Hz, 2H), 2.12-2.01 (m, 1H), 1.00 (d, J=6.8 Hz, 6H), 0.92 (t, J=8.4 Hz, 2H), 0.01--0.06 (m, 9H).

Step D: Isobutyl ((1-((1r,4r)-4-(Cyanomethyl)cyclohexyl)-1,6-dihydroimidazo[4,5-d]pyrrolo[2,3-b]pyridin-2-yl)methyl)carbamate. A solution of 2-((1r,4r)-4-(2-(Aminomethyl)imidazo[4,5-d]pyrrolo[2,3-b]pyridin-1(6H)-yl)cyclohexyl)acetonitrile hydrochloride (Intermediate 5, 170 mg, 0.493 mmol), (isobutyl carbonic) 1-((2-(trimethylsilyl)ethoxy)methyl)-1H-pyrazole-4-carboxylic anhydride (199 mg, 0.493 mmol), 4-methylmorpholine (150 mg, 1.48 mmol), and THF (5 mL) was stirred for 18 h at 25° C. The reaction was concentrated to dryness, dissolved in $CH_2Cl_2$ (20 mL), the organic phase washed with water (10 mL), dried over anhydrous $Na_2SO_4$, filtered, and concentrated to dryness. The residue was purified by preparative HPLC using an Agela DuraShell 150 mm×25 mm, 5 m column (eluent: 32% to 62% (v/v) $CH_3CN$ and $H_2O$ with 10 mM $NH_4HCO_3$) to provide the title compound (55 mg, 27% yield) as a white solid. MS (ESI): mass calcd. for $C_{22}H_{28}N_6O_2$, 408.23; m/z found, 409.3 $[M+H]^+$. $^1H$ NMR (400 MHz, DMSO-$d_6$): δ 11.88 (s, 1H), 8.53 (s, 1H), 7.84 (s, 1H), 7.47 (s, 1H), 6.71 (s, 1H), 4.73-4.42 (m, 3H), 3.92-3.66 (m, 2H), 2.67-2.57 (m, 2H), 2.43-2.23 (m, 2H), 2.19-1.65 (m, 6H), 1.54-1.29 (m, 2H), 1.12-0.63 (m, 6H).

Example 138 Synthesis and Characterization

N-(2-Cyanoethyl)-1-((1r,4r)-4-(cyanomethyl)cyclohexyl)-1,6-dihydroimidazo[4,5-d]pyrrolo[2,3-b]pyridine-2-carboxamide

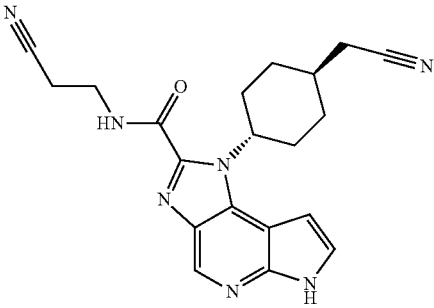 [SMILES: N#CCCNC(=O)c1nc2cnc3[nH]ccc3c2n1[C@H]1CC[C@H](CC#N)CC1]

The title compound (10 mg, 43% yield) was prepared using analogous conditions as described in Example 50, Step A, using 3-aminopropanenitrile instead of 3-phenylpyrrolin-3-ol. MS (ESI): mass calcd. for $C_{20}H_{21}N_7O$, 375.18; m/z found, 376.2 $[M+H]^+$. $^1H$ NMR (500 MHz, $CDCl_3$): δ 10.36 (s, 1H), 8.82 (s, 1H), 8.27 (t, J=6.4 Hz, 1H), 7.47 (t, J=2.9 Hz, 1H), 6.94-6.70 (m, 1H), 6.32-5.70 (m, 1H), 3.77 (q, J=6.6 Hz, 2H), 2.79 (t, J=6.6 Hz, 2H), 2.70-2.55 (m, 2H), 2.42 (d, J=6.6 Hz, 2H), 2.24-2.03 (m, 5H), 1.57-1.43 (m, 2H).

Example 139 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)cyclohexanecarboxamide

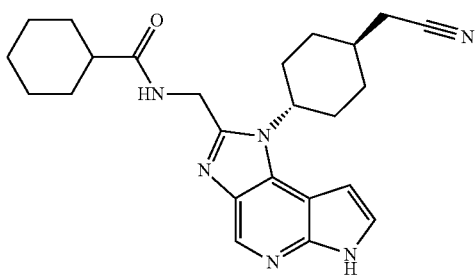 [SMILES: N#CC[C@H]1CC[C@H](n2c(CNC(=O)C3CCCCC3)nc3cnc4[nH]ccc4c32)CC1]

Cyclohexanecarbonyl chloride (58.0 mg, 0.396 mmol) was added drop-wise to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.396 mmol), triethylamine (0.276 mL, 1.98 mmol), and $CH_2Cl_2$ (5 mL) and was stirred for 1 h at 10° C. The reaction was diluted with $CH_2Cl_2$ (10 mL), washed with water (10 mL), dried over anhydrous $Na_2SO_4$, filtered, and concentrated to dryness. The residue was purified by preparative TLC (eluent: $CH_2Cl_2$: methanol=10:1) to provide the title compound (70 mg, 42% yield) as a white solid. MS (ESI): mass calcd. for $C_{24}H_{30}N_6O$, 418.25; m/z found, 419.3 $[M+H]^+$. $^1H$ NMR (400 MHz, $CDCl_3$): δ 10.54 (s, 1H), 8.76 (s, 1H), 7.45 (t, J=2.4 Hz, 1H), 6.88 (br s, 1H), 6.73 (s, 1H), 4.82 (d, J=4.8 Hz, 2H), 4.73-4.59 (m, 1H), 2.63-2.45 (m, 2H), 2.41 (d, J=6.8 Hz, 2H), 2.28-2.13 (m, 3H), 2.12-1.95 (m, 3H), 1.94-1.74 (m, 5H), 1.57-1.38 (m, 4H), 1.36-1.18 (m, 3H).

Example 140 Synthesis and Characterization 2-((1r,4r)-4-(2-(3-Cyclopropyl-4,5-dihydro-1,2,4-oxadiazol-5-yl)imidazo[4,5-d]pyrrolo[2,3-b]pyridin-1(6H)-yl)cyclohexyl)acetonitrile

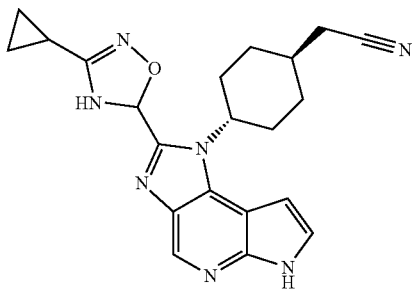 [SMILES: N#CC[C@H]1CC[C@H](n2c(C3NC(C4CC4)=NO3)nc3cnc4[nH]ccc4c32)CC1]

2-((1r,4r)-4-(2-(Aminomethyl)imidazo[4,5-d]pyrrolo[2,3-b]pyridin-1(6H)-yl)cyclohexyl)acetonitrile hydrochloride (Intermediate 5, 200 mg, 0.580 mmol), N-hydroxycyclopropanecarbimidoyl chloride (139 mg, 0.580 mmol), triethylamine (0.40 mL, 2.9 mmol), and DMF (5 mL) was stirred for 2 h at 20° C. The reaction was concentrated to dryness and the residue was partitioned between water (5 mL) and ethyl acetate (10 mL). The organic phase was collected, dried over anhydrous $Na_2SO_4$, filtered, and concentrated to dryness. The residue was initially purified by preparative HPLC using a Phenomenex Gemini 150 mm×25 mm, 5 μm column (eluent: 18% to 48% (v/v) $CH_3CN$ and $H_2O$ with 0.05% $NH_3$). The residue was then further purified by preparative HPLC using a Phenomenex Gemini 150 mm×25 mm, 10 μm column (eluent: 18% to 48% (v/v) $CH_3CN$ and $H_2O$ with 0.05% $NH_3$) to provide the title compound (8 mg, 3% yield) as a white solid. MS (ESI): mass calcd. for $C_{21}H_{23}N_7O$, 389.20; m/z found, 390.2 $[M+H]^+$. $^1H$ NMR (400 MHz, DMSO-$d_6$): δ 11.99 (s, 1H), 8.61 (s, 1H), 7.76 (s, 1H), 7.54-7.48 (m, 1H), 6.76 (s, 1H), 6.73 (s, 1H), 4.63-4.51 (m, 1H), 2.60 (d, J=5.6 Hz, 2H), 2.43-2.31 (m, 2H), 2.13-1.86 (m, 5H), 1.79-1.68 (m, 1H), 1.42-1.26 (m, 2H), 0.99-0.79 (m, 4H).

Example 141 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)cyclohexanesulfonamide

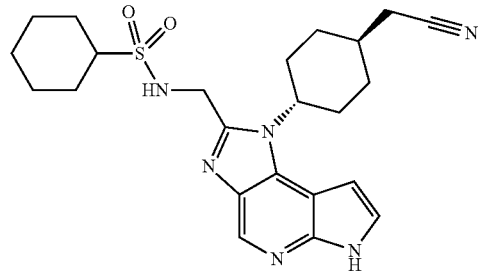 [SMILES: N#CC[C@H]1CC[C@H](n2c(CNS(=O)(=O)C3CCCCC3)nc3cnc4[nH]ccc4c32)CC1]

Cyclohexanesulfonyl chloride (482 mg, purity 15%, 0.396 mmol) was added drop-wise to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.396 mmol), triethylamine (0.276 mL, 1.98 mmol), and $CH_2Cl_2$ (5 mL) and was stirred for 1 h at 10° C. The reaction was diluted with $CH_2Cl_2$ (10 mL), washed with water (10 mL), dried over anhydrous $Na_2SO_4$, filtered, and concentrated to dryness. The residue was purified by flash column chromatography and by preparative HPLC twice using a Phenomenex Gemini 150 mm×25 mm, 5 μm column (eluent: 30% to 60% (v/v) $CH_3CN$ and $H_2O$ with 0.05% $NH_3$) to provide the title compound (5 mg, 3% yield) as a white solid. MS (ESI): mass calcd. for $C_{23}H_{30}N_6O_2S$, 454.22; m/z found, 455.2 $[M+H]^+$. $^1H$ NMR (400 MHz, DMSO-$d_6$): δ 11.91 (s, 1H), 8.55 (s, 1H), 7.86-7.74 (m, 1H), 7.51-7.42 (m, 1H), 6.73 (s, 1H), 4.76-4.62 (m, 1H), 4.56 (d, J=5.6 Hz, 2H), 3.14-3.03 (m, 1H), 2.60 (d, J=5.6 Hz, 2H), 2.43-2.32 (m, 2H), 2.09-1.94 (m, 7H), 1.82-1.70 (m, 2H), 1.65-1.55 (m, 1H), 1.51-1.29 (m, 4H), 1.25-1.08 (m, 3H).

Example 142 Synthesis and Characterization 2-((1r,4r)-4-(2-(((Dimethyl(oxo)-λ⁶-sulfanylidene)amino)methyl)imidazo[4,5-d]pyrrolo[2,3-b]pyridin-1(6H)-yl)cyclohexyl)acetonitrile

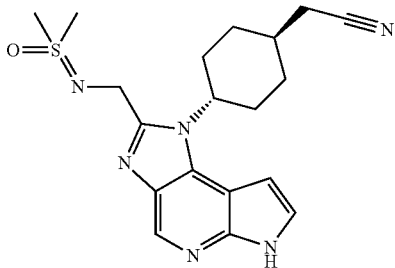 [SMILES: CS(C)(=O)=NCc1nc2cnc3[nH]ccc3c2n1[C@H]1CC[C@H](CC#N)CC1]

A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 91 mg, 0.19 mmol), (S-methylsulfonimidoyl)methane (48 mg, 0.52 mmol), and NaHCO₃(25 mg, 0.29 mmol) in CH₃CN (3 mL) was heated to 130° C. for 20 hours. The reaction was concentrated to dryness and the residue was dissolved into MeOH/THF/NaOH (1M) (1 mL/1 mL/1 mL) and was heated at 80° C. for 1 h. The reaction was concentrated to dryness and partitioned between CH₂Cl₂ (5 mL) and water (5 mL), the organic layer was collected, and concentrated to dryness. The residue was purified by flash column chromatography to provide the title compound (31 mg, 42% yield). MS (ESI): mass calcd. for C₁₉H₂₄N₆OS, 384.17; m/z found, 385.2 [M+H]⁺. ¹H NMR (400 MHz, CDCl₃): δ 11.76-11.30 (s, 1H), 8.95-8.49 (s, 1H), 7.52-7.31 (m, 1H), 6.85-6.49 (d, J=3.4 Hz, 1H), 4.93-4.41 (m, 3H), 3.16-2.94 (s, 6H), 2.62-2.30 (m, 4H), 2.20-2.00 (m, 5H), 1.53-1.36 (m, 2H).

Example 143 Synthesis and Characterization 2-((1r,4r)-4-(2-(4-(Pentafluoro-λ⁶-sulfanyl)phenyl)imidazo[4,5-d]pyrrolo[2,3-b]pyridin-1(6H)-yl)cyclohexyl)acetonitrile

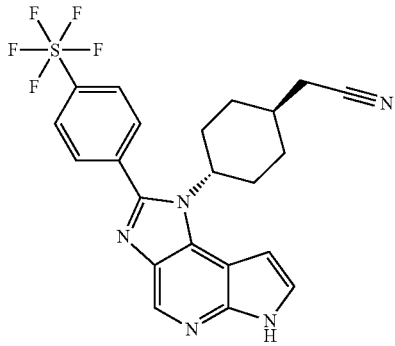 [SMILES: N#CC[C@H]1CC[C@H](n2c(-c3ccc(S(F)(F)(F)(F)F)cc3)nc3cnc4[nH]ccc4c32)CC1]

Step A: 2-((1r,4r)-4-(2-(4-(Pentafluoro-λ⁶-sulfanyl)phenyl)-6-(phenylsulfonyl)imidazo[4,5-d]pyrrolo[2,3-b]pyridin-1(6H)-yl)cyclohexyl)acetonitrile. 2-((1r,4r)-4-((5-Nitro-1-(phenylsulfonyl)-1H-pyrrolo[2,3-b]pyridin-4-yl)amino)cyclohexyl)acetonitrile (Intermediate 1, 120 mg, 0.273 mmol) was dissolved in DMSO (2.3 mL) and MeOH (0.5 mL) in a microwave vial. 4-(Pentafluorothio)benzaldehyde (139 mg, 0.599 mmol) was added followed by Na₂S₂O₄ (140 mg, 0.683 mmol) and the vial was capped and heated to 100° C. over the weekend. After cooling to room temperature, the mixture was diluted with water (5 mL) and stirred for 5 minutes. The tan precipitate that formed was collected by filtration, washed with water (50 mL), and allowed to dry thoroughly. The solid was collected in a round bottom flask by dissolving it in EtOAc. The organic phase was then concentrated to dryness to provide the title compound as a tan solid, which was used without further purification. MS (ESI): mass calcd. for C₂₈H₂₄F₅N₅O₂S₂, 621.13; m/z found, 622.2 [M+H]⁺.

Step B: 2-((1r,4r)-4-(2-(4-(Pentafluoro-λ⁶-sulfanyl)phenyl)imidazo[4,5-d]pyrrolo[2,3-b]pyridin-1(6H)-yl)cyclohexyl)acetonitrile. The title compound (94.6 mg, 72% yield) was prepared using conditions analogous to those described in Example 1, Step B using 2-((1r,4r)-4-(2-(4-(Pentafluoro-λ⁶-sulfanyl)phenyl)-6-(phenylsulfonyl)imidazo[4,5-d]pyrrolo[2,3-b]pyridin-1(6H)-yl)cyclohexyl)acetonitrile (169 mg, 0.272 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The crude material was triturated with heptane and DCM and then collected by vacuum filtration to provide the title compound. MS (ESI): mass calcd. for C₂₂H₂₀F₅N₅S, 481.14; m/z found, 482.1 [M+H]⁺. ¹H NMR (400 MHz, DMSO-d₆): δ 12.05 (s, 1H), 8.68 (s, 1H), 8.14 (d, J=8.3 Hz, 2H), 7.96 (d, J=8.4 Hz, 2H), 7.56 (d, J=3.0 Hz, 1H), 6.81 (d, J=3.3 Hz, 1H), 4.50-4.28 (m, 1H), 2.55 (d, J=6.3 Hz, 2H), 2.48-2.38 (m, 2H), 2.12-2.01 (m, 3H), 2.01-1.93 (m, 2H), 1.39-1.24 (m, 2H).

Example 144 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)-1H-pyrazole-4-carboxamide

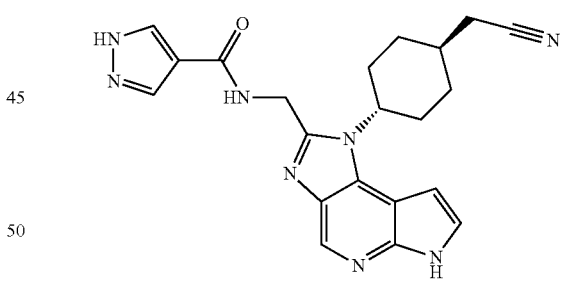

Step A: N-((1-((1r,4r)-4-(Cyanomethyl)cyclohexyl)-1,6-dihydroimidazo[4,5-d]pyrrolo[2,3-b]pyridin-2-yl)methyl)-1-((2-(trimethylsilyl)ethoxy)methyl)-1H-pyrazole-4-carboxamide. A solution of solution of 2-((1r,4r)-4-(2-(aminomethyl)imidazo[4,5-d]pyrrolo[2,3-b]pyridin-1(6H)-yl)cyclohexyl)acetonitrile (Intermediate 5, 170 mg, 0.493 mmol), (isobutyl carbonic) 1-((2-(trimethylsilyl)ethoxy)methyl)-1H-pyrazole-4-carboxylic anhydride, as prepared in Example 137, Step C, (199 mg, 0.493 mmol) 4-methylmorpholine (150 mg, 1.48 mmol), and dry THF (5 mL) and was stirred for 18 h at 25° C. The reaction was concentrated to dryness and the residue was dissolved in CH₂Cl₂ (20 mL). The organic phase was washed with water (10 mL), dried over anhydrous Na₂SO₄, filtered, and concentrated to dryness. The residue was purified by preparative HPLC using an Agela DuraShell 150 mm×25 mm, 5 μm column (eluent: 32% to 62% (v/v) CH$_3$CN and H$_2$O with 10 mM NH$_4$HCO$_3$) to provide the title compound (60 mg, 22% yield) as a white solid. MS (ESI): mass calcd. for C$_{27}$H$_{36}$N$_8$O$_2$Si, 532.27; m/z found, 533.1 [M+H]$^+$. $^1$H NMR (400 MHz, CDCl$_3$): δ 10.34 (s, 1H), 8.73 (s, 1H), 8.11 (s, 1H), 7.93 (s, 1H), 7.48-7.31 (m, 2H), 6.76-6.69 (m, 1H), 5.44 (s, 2H), 4.98 (d, J=5.2 Hz, 2H), 4.77-4.63 (m, 1H), 3.63-3.52 (m, 2H), 2.42 (d, J=6.8 Hz, 2H), 2.25-2.13 (m, 2H), 2.11-1.97 (m, 3H), 1.90-1.66 (m, 2H), 1.56-1.40 (m, 2H), 0.94-0.86 (m, 2H), −0.03 (s, 9H).

Step B: N-((1-((1r,4r)-4-(Cyanomethyl)cyclohexyl)-1,6-dihydroimidazo[4,5-d]pyrrolo[2,3-b]pyridin-2-yl)methyl)-1H-pyrazole-4-carboxamide. A solution of N-((1-((1r,4r)-4-(cyanomethyl)cyclohexyl)-1,6-dihydroimidazo[4,5-d]pyrrolo[2,3-b]pyridin-2-yl)methyl)-1-((2-(trimethylsilyl)ethoxy)methyl)-1H-pyrazole-4-carboxamide (50 mg, 0.094 mmol) and TFA (2 mL) was stirred for 0.5 h at 10° C. The reaction was concentrated to dryness, the residue was dissolved in water (5 mL), and the aqueous phase was adjusted to pH=7-8 with saturated aqueous NaHCO$_3$. The precipitate was filtered, washed with water (2 mL×3), and lyophilized to provide the title compound (38 mg, 99% yield) as an off-white solid. MS (ESI): mass calcd. for C$_{21}$H$_{22}$N$_8$O, 402.19; m/z found, 403.2 [M+H]$^+$. $^1$H NMR (400 MHz, DMSO-d$_6$): δ 13.15 (s, 1H), 11.88 (s, 1H), 8.77 (s, 1H), 8.55 (s, 1H), 8.24 (s, 1H), 7.95 (s, 1H), 7.46 (s, 1H), 6.71 (s, 1H), 4.84 (s, 2H), 4.69-4.49 (m, 1H), 2.63-2.55 (m, 2H), 2.40-2.21 (m, 2H), 2.09-1.71 (m, 4H), 1.45-1.09 (m, 3H).

Example 145: Synthesis and Characterization 1-((1r,4r)-4-(Cyanomethyl)cyclohexyl)-N-(2-methoxyethyl)-1,6-dihydroimidazo[4,5-d]pyrrolo[2,3-b]pyridine-2-carboxamide

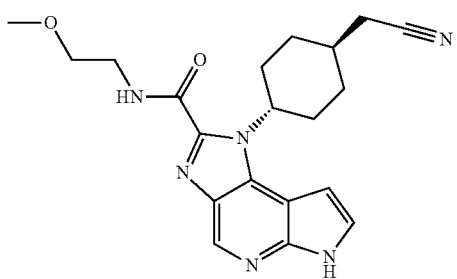

The title compound (40 mg, 52% yield) was prepared using analogous conditions as described in Example 50, Step A using 2-methoxyethanamine instead of 3-phenylpyrrolin-3-ol. MS (ESI): mass calcd. for C$_{20}$H$_{24}$N$_6$O$_2$, 380.20; m/z found, 381.2 [M+H]$^+$. $^1$H NMR (500 MHz, CDCl$_3$): δ 10.83 (s, 1H), 8.84 (s, 1H), 8.11 (t, J=5.8 Hz, 1H), 7.55-7.40 (m, 1H), 6.91-6.73 (m, 1H), 6.32-5.75 (m, 1H), 3.79-3.56 (m, 4H), 3.44 (s, 3H), 2.78-2.55 (m, 2H), 2.40 (d, J=6.6 Hz, 2H), 2.28-2.00 (m, 5H), 1.62-1.38 (m, 2H).

Example 146 Synthesis and Characterization (1-((1r,4r)-4-(Cyanomethyl)cyclohexyl)-1,6-dihydroimidazo[4,5-d]pyrrolo[2,3-b]pyridin-2-yl)methyl (cyclohexylmethyl)carbamate

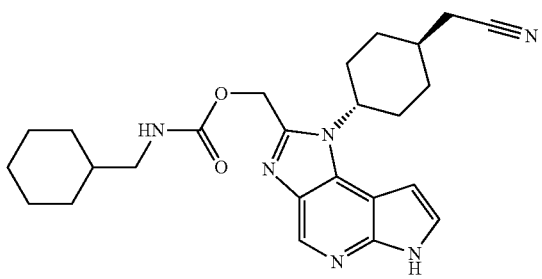 [SMILES: N#CC[C@H]1CC[C@H](n2c(COC(=O)NCC3CCCCC3)nc3cnc4[nH]ccc4c32)CC1]

Step A: (1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl (cyclohexylmethyl)carbamate. A solution of 2-((1r,4r)-4-(2-(hydroxymethyl)-6-(phenylsulfonyl)imidazo[4,5-d]pyrrolo[2,3-b]pyridin-1(6H)-yl)cyclohexyl)acetonitrile (Intermediate 7, 34 mg, 0.076 mmol), (isocyanatomethyl)cyclohexane (28 mg, 0.20 mmol), triethylamine (42 μL, 0.30 mmol), and DMF (1 mL) was heated at 80° C. for ~15 min, then stirred at room temperature over the weekend. The reaction was concentrated to dryness and the residue was purified by flash column chromatography (12 g silica gel column, 20-100% EtOAc in heptanes) to provide the title compound (42 mg, 94% yield) as a clear oil. MS (ESI): mass calcd. for C$_{31}$H$_{36}$N$_6$O$_4$S, 588.25; m/z found, 589.3 [M+H]$^+$.

Step B: (1-((1r,4r)-4-(Cyanomethyl)cyclohexyl)-1,6-dihydroimidazo[4,5-d]pyrrolo[2,3-b]pyridin-2-yl)methyl (cyclohexylmethyl)carbamate. A mixture of (1-((1r,4r)-4-(cyanomethyl)cyclohexyl)-6-(phenylsulfonyl)-1,6-dihydroimidazo[4,5-d]pyrrolo[2,3-b]pyridin-2-yl)methyl (cyclohexylmethyl)carbamate (42 mg, 0.071 mmol), 1 M NaOH (aq) (0.20 mL, 0.20 mmol), THF (1 mL), and MeOH (1 mL) was stirred at RT for 18 h and concentrated in vacuo. The residue was purified by flash column chromatography (2-10% MeOH in CH$_2$Cl$_2$) to give the title compound as an off-white solid (22 mg, 69% yield). MS (ESI): mass calcd. for C$_{25}$H$_{32}$N$_6$O$_2$, 448.26; m/z found, 449.3 [M+H]$^+$. $^1$H NMR (400 MHz, CDCl$_3$) δ=11.25 (br s, 1H), 8.85-8.77 (m, 1H), 7.47-7.43 (m, 1H), 6.75-6.68 (m, 1H), 5.48 (s, 2H), 5.23 (br s, 1H), 4.56 (br s, 1H), 3.08 (t, J=6.3 Hz, 2H), 2.53 (br s, 2H), 2.42 (d, J=7.1 Hz, 2H), 2.17 (d, J=12.1 Hz, 2H), 2.12-1.91 (m, 4H), 1.77-1.60 (m, 5H), 1.56-1.36 (m, 2H), 1.30-1.08 (m, 2H), 1.00-0.82 (m, 2H).

Example 147 Synthesis and Characterization 2-((1r,4r)-4-(2-(1-Acetylazetidin-3-yl)imidazo[4,5-d]pyrrolo[2,3-b]pyridin-1(6H)-yl)cyclohexyl)acetonitrile

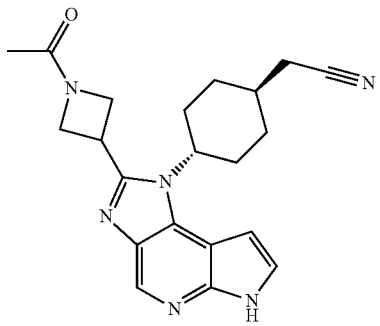 [SMILES: CC(=O)N1CC(c2nc3cnc4[nH]ccc4c3n2[C@H]2CC[C@H](CC#N)CC2)C1]

To a solution of 2-((1r,4r)-4-(2-(azetidin-3-yl)-6-((4-bromophenyl)sulfonyl)imidazo[4,5-d]pyrrolo[2,3-b]pyridin-1(6H)-yl)cyclohexyl)acetonitrile (50 mg, 0.090 mmol), as prepared in Example 128, Step B, and DIPEA (3 equiv.) in CH$_2$Cl$_2$ (5 mL) was added acetyl chloride (8.5 mg, 0.11 mmol) in THF (0.5 mL) and was stirred at room temperature for 1 h. Water (20 mL) added and the organic layer was collected and concentrated to dryness. The residue was dissolved into THF/MeOH/NaOH (1 M) (1 mL/1 mL/1 mL) and was heated at 80° C. for 1 h. The reaction was concentrated to dryness and the residue was purified by flash column chromatography to provide the title compound (15 mg, 44% yield). MS (ESI): mass calcd. for C$_{21}$H$_{24}$N$_6$O, 376.20; m/z found, 377.0 [M+H]$^+$. $^1$H NMR (500 MHz, CDCl$_3$): δ 10.64-10.47 (m, 1H), 8.81 (s, 1H), 7.43 (d, J=3.5 Hz, 1H), 6.69 (d, J=3.5 Hz, 1H), 5.02 (dd, J=8.2, 6.0 Hz, 1H), 4.64-4.44 (m, 2H), 4.32-4.07 (m, 2H), 3.54-3.41 (m, 1H), 2.64-2.39 (m, 4H), 2.27-2.14 (m, 2H), 2.12-1.88 (m, 6H), 1.55-1.41 (m, 1H), 1.32-1.17 (m, 1H).

Example 148 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)benzamide

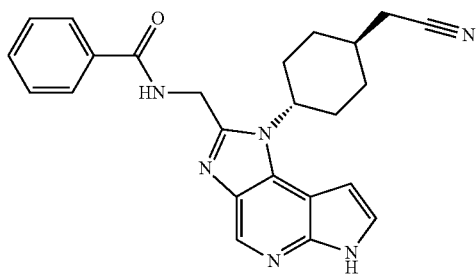 [SMILES: N#CC[C@H]1CC[C@H](n2c(CNC(=O)c3ccccc3)nc3cnc4[nH]ccc4c32)CC1]

Benzoyl chloride (55.6 mg, 0.396 mmol) was added drop-wise to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.396 mmol), triethylamine (0.276 mL, 1.98 mmol), and CH$_2$Cl$_2$ (5 mL) and the reaction mixture was stirred for 1 h at 10° C. The reaction was diluted with CH$_2$Cl$_2$ (10 mL), washed with water (10 mL), dried over anhydrous Na$_2$SO$_4$, filtered, and concentrated to dryness. The residue was purified by preparative TLC (eluent: CH$_2$Cl$_2$: methanol=10:1) twice to provide the title compound (20 mg, 12% yield) as a white solid. MS (ESI): mass calcd. for C$_{24}$H$_{24}$N$_6$O, 412.20; m/z found, 413.2 [M+H]$^+$. $^1$H NMR (400 MHz, DMSO-d$_6$): δ 11.88 (s, 1H), 9.19 (s, 1H), 8.55 (s, 1H), 7.92 (d, J=7.6 Hz, 2H), 7.58-7.51 (m, 1H), 7.51-7.37 (m, 3H), 6.71 (s, 1H), 4.91 (d, J=4.8 Hz, 2H), 4.72-4.58 (m, 1H), 2.57 (d, J=6.0 Hz, 2H), 2.41-2.27 (m, 2H), 2.07-1.80 (m, 5H), 1.43-1.28 (m, 2H).

Example 149: Synthesis and Characterization 2-((1r,4r)-4-(2-(2-((R)-2-(Hydroxymethyl)pyrrolidin-1-yl)-2-oxoethyl)imidazo[4,5-d]pyrrolo[2,3-b]pyridin-1(6H)-yl)cyclohexyl)acetonitrile

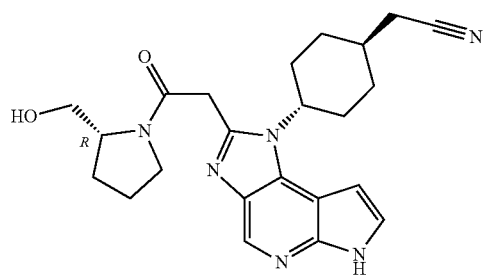

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg crude, 0.835 mmol), L-prolinol (126 mg, 0.918 mmol) and DIPEA (0.291 mL, 1.67 mmol) in dry DMF (5 mL) was added PyBrOP (428 mg, 0.918 mmol) at 0° C. and the reaction mixture was stirred at room-temperature for 4 hours. The mixture was diluted with water (10 mL) and extracted with ethyl acetate (20 mL×3). Both the organic and water phases were concentrated to provide a residue that was initially purified by preparative HPLC using a Xtimate C$_{18}$ 150×25 mm x 5 µm column (eluent: 16% to 36% (v/v) CH$_3$CN and H$_2$O with 10 mM NH$_4$HCO$_3$) and subsequently further purified by preparative TLC (dichloromethane:methanol=15:1) to provide the title compound (19 mg, 5% yield) as a white solid. MS (ESI): mass calcd. for C$_{23}$H$_{28}$N$_6$O$_2$, 420.23; m/z found, 421.2 [M+H]$^+$. $^1$H NMR (400 MHz, DMSO-d$_6$): δ 11.83 (br s, 1H), 8.49 (s, 1H), 7.48-7.44 (m, 1H), 6.71 (br s, 1H), 5.15 (t, J=4.0 Hz, 0.3H), 4.79 (t, J=4.0 Hz, 0.7H), 4.45-4.20 (m, 2H), 4.19-4.11 (m, 1H), 3.99-3.92 (m, 1H), 3.65-3.57 (m, 1H), 3.56-3.43 (m, 2H), 3.32-3.25 (m, 2H), 2.60-2.55 (m, 2H), 2.39-2.25 (m, 2H), 2.06-1.81 (m, 8H), 1.43-1.27 (m, 2H).

217

Example 150 Synthesis and Characterization (Z\*)—N-((1-((1r,4r)-4-(Cyanomethyl)cyclohexyl)-1,6-dihydroimidazo[4,5-d]pyrrolo[2,3-b]pyridin-2-yl)methoxy)isobutyrimidamide; the Structure being the (Z) or (E) Isomer, and the (Z) Notation and its Corresponding Structure Below is Chosen Arbitrarily

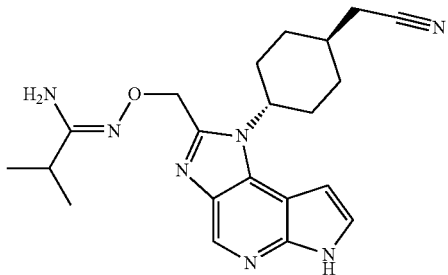 [SMILES: CC(C)/C(N)=N/OCc1nc2cnc3[nH]ccc3c2n1[C@H]1CC[C@H](CC#N)CC1]

Step A: (Z\*)—N-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methoxy)isobutyrimidamide. A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 250 mg, 0.534 mmol), N-hydroxy-2-methylpropanimidamide (164 mg, 1.60 mmol), $K_2CO_3$ (369 mg, 2.67 mmol), and DMF (4 mL) was stirred for 18 h at 50° C. The reaction mixture was concentrated to dryness to provide the title compound (780 mg, 95.8% yield), which was used in the next step without further purification. MS (ESI): mass calcd. for $C_{27}H_{31}N_7O_3S$, 533.22; m/z found, 534.0 $[M+H]^+$.

Step B: (Z\*)—N-((1-((1r,4r)-4-(Cyanomethyl)cyclohexyl)-1,6-dihydroimidazo[4,5-d]pyrrolo[2,3-b]pyridin-2-yl)methoxy)isobutyrimidamide. The title compound (50 mg, 24% yield) was prepared as a white solid using conditions analogous to those described in Example 1, Step B using (Z\*)—N-((1-((1r,4r)-4-(cyanomethyl)cyclohexyl)-6-(phenylsulfonyl)-1,6-dihydroimidazo[4,5-d]pyrrolo[2,3-b]pyridin-2-yl)methoxy)isobutyrimidamide (780 mg, 0.51 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The title compound was purified by preparative HPLC using a Phenomenex Gemini 150 mm×25 mm, 5 μm column (eluent: 20% to 50% (v/v) $CH_3CN$ and $H_2O$ with 0.05% $NH_3$). MS (ESI): mass calcd. for $C_{21}H_{27}N_7O$, 393.23; m/z found, 394.2 $[M+H]^+$. $^1H$ NMR (400 MHz, DMSO-$d_6$): δ 11.87 (s, 1H), 8.53 (s, 1H), 7.50-7.41 (m, 1H), 6.71 (d, J=1.6 Hz, 1H), 5.64 (s, 2H), 5.15 (s, 2H), 4.80-4.64 (m, 1H), 2.56 (d, J=6.4 Hz, 2H), 2.40-2.27 (m, 2H), 2.26-2.17 (m, 1H), 2.09-1.88 (m, 5H), 1.47-1.31 (m, 2H), 1.01 (d, J=6.8 Hz, 6H).

218

Example 151 Synthesis and Characterization (Z\*)—N-((1-((1r,4r)-4-(Cyanomethyl)cyclohexyl)-1,6-dihydroimidazo[4,5-d]pyrrolo[2,3-b]pyridin-2-yl)methoxy)cyclopropanecarboximidamide; the Structure being the (Z) or (E) Isomer, and the (Z) Notation and its Corresponding Structure Below is Chosen Arbitrarily

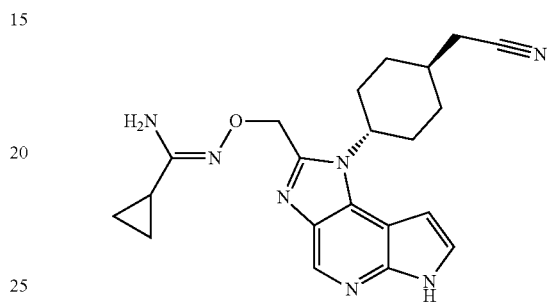

Step A: (Z\*)—N-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methoxy)cyclopropanecarboximidamide. A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 250 mg, 0.534 mmol), N-hydroxycyclopropanecarboximidamide (160 mg, 1.60 mmol), $K_2CO_3$ (369 mg, 2.67 mmol), and DMF (4 mL) was stirred for 18 h at 50° C. The reaction was concentrated to dryness to provide the title compound (780 mg, 96% yield), which was used in the next step without further purification. MS (ESI): mass calcd. for $C_{27}H_{29}N_7O_3S$, 531.21; m/z found, 532.1 $[M+H]^+$.

Step B: (Z\*)—N-((1-((1r,4r)-4-(Cyanomethyl)cyclohexyl)-1,6-dihydroimidazo[4,5-d]pyrrolo[2,3-b]pyridin-2-yl)methoxy)cyclopropanecarboximidamide. The title compound (35 mg, 17% yield). was prepared as a white solid using conditions analogous to those described in Example 1, Step B using (Z)—N'-((1-((1r,4r)-4-(cyanomethyl)cyclohexyl)-6-(phenylsulfonyl)-1,6-dihydroimidazo[4,5-d]pyrrolo[2,3-b]pyridin-2-yl)methoxy)cyclopropanecarboximidamide (780 mg, 0.51 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The title compound was purified by preparative HPLC using a Phenomenex Gemini 150 mm×25 mm, 5 μm column (eluent: 20% to 50% (v/v) $CH_3CN$ and $H_2O$ with 0.05% $NH_3$). MS (ESI): mass calcd. for $C_{21}H_{25}N_7O$, 391.21; m/z found, 392.2 $[M+H]^+$. $^1H$ NMR (400 MHz, DMSO-$d_6$): δ 11.88 (s, 1H), 8.54 (s, 1H), 7.47 (t, J=3.2 Hz, 1H), 6.73 (s, 1H), 5.57 (s, 2H), 5.15 (s, 2H), 4.80-4.67 (m, 1H), 2.58 (d, J=6.4 Hz, 2H), 2.42-2.27 (m, 2H), 2.09-1.90 (m, 5H), 1.50-1.35 (m, 2H), 1.35-1.26 (m, 1H), 0.69-0.55 (m, 4H).

Example 152 Synthesis and Characterization (3R,5R,7R,E*)-N'-((1-((1r,4r)-4-(Cyanomethyl)cyclohexyl)-1,6-dihydroimidazo[4,5-d]pyrrolo[2,3-b]pyridin-2-yl)methoxy)adamantane-1-carboximidamide; the Structure being the (Z) or (E) Isomer, and the (Z) Notation and its Corresponding Structure Below is Chosen Arbitrarily

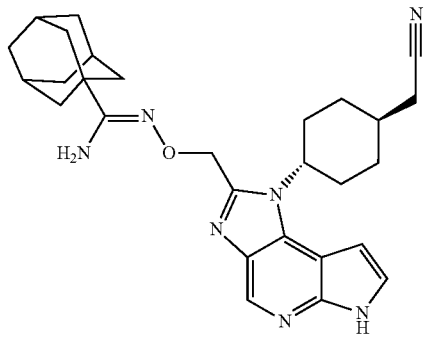 [SMILES: N#CC[C@H]1CC[C@H](n2c(CO/N=C(\N)C34CC5CC(CC(C5)C3)C4)nc3cnc4[nH]ccc4c32)CC1]

Step A: (3R,5R,7R,E*)-N'((1-((1r,4r)-4-(Cyanomethyl)cyclohexyl)-6-(phenylsulfonyl)-1,6-dihydroimidazo[4,5-d]pyrrolo[2,3-b]pyridin-2-yl)methoxy)adamantane-1-carboximidamide. A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 76 mg, 0.16 mmol), (3R,5R,7R,Z)—N'-hydroxyadamantane-1-carboximidamide (80 mg, 0.41 mmol), $K_2CO_3$ (82 mg, 0.59 mmol), and DMF (2 mL) was stirred at room temperature for 45 h. After the solid was filtered off, the filtrate was concentrated to dryness to provide the title compound (100 mg, 98% yield). MS (ESI): mass calcd. for $C_{34}H_{39}N_7O_3S$, 625.28; m/z found, 626.4 $[M+H]^+$.

Step B: (3R,5R,7R,E*)-N'-((1-((1r,4r)-4-(Cyanomethyl)cyclohexyl)-1,6-dihydroimidazo[4,5-d]pyrrolo[2,3-b]pyridin-2-yl)methoxy)adamantane-1-carboximidamide. A solution of (3R,5R,7R,E*)-N'-((1-((1r,4r)-4-(cyanomethyl)cyclohexyl)-6-(phenylsulfonyl)-1,6-dihydroimidazo[4,5-d]pyrrolo[2,3-b]pyridin-2-yl)methoxy)adamantane-1-carboximidamide (100 mg, 0.16 mmol) in THF (0.7 mL) and MeOH (0.7 mL) was treated with 3N NaOH (0.21 mL, 0.64 mmol) for 18 h at room temperature. After concentration in vacuo, the residue was purified by RF-HPLC (10-90% $CH_3CN$ in $H_2O$, 0.1% TFA). The collected fractions were concentrated, and the residue was partitioned between EtOAc and saturated $NaHCO_3$ aqueous solution. The aqueous layer was extracted with EtOAc (×4). The combined extracts were dried over anhydrous $Na_2SO_4$, filtered, and concentrated to provide the title compound (19 mg, 24%). MS (ESI): mass calcd. for $C_{28}H_{35}N_7O$, 485.29; m/z found, 486.3 $[M+H]^+$. $^1H$ NMR (400 MHz, $CDCl_3$) δ=11.04 (br s, 1H), 8.80 (s, 1H), 7.44 (br s, 1H), 6.75-6.69 (m, 1H), 5.82 (br s, 1H), 5.65 (br s, 1H), 4.83-4.67 (m, 1H), 4.49 (br s, 2H), 2.66-2.49 (m, 2H), 2.43 (d, J=6.1 Hz, 2H), 2.22-2.10 (m, 2H), 2.10-1.96 (m, 3H), 1.88 (d, J=3.0 Hz, 4H), 1.82 (d, J=2.5 Hz, 4H), 1.77-1.63 (m, 7H), 1.58-1.34 (m, 2H).

Example 153 Synthesis and Characterization (Z*)—N'-((1-((1r,4r)-4-(Cyanomethyl)cyclohexyl)-1,6-dihydroimidazo[4,5-d]pyrrolo[2,3-b]pyridin-2-yl)methoxy)-2-(piperidin-1-yl)acetimidamide; the Structure being the (Z) or (E) Isomer, and the (Z) Notation and its Corresponding Structure Below is Chosen Arbitrarily

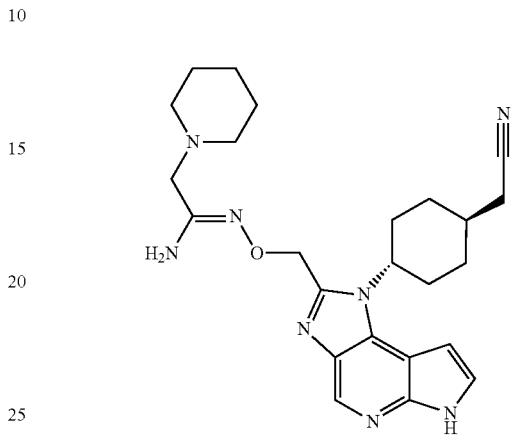

Step A: N-((1-((1r,4r)-4-(Cyanomethyl)cyclohexyl)-6-(phenyl sulfonyl)-1,6-dihydroimidazo[4,5-d]pyrrolo[2,3-b]pyridin-2-yl)methoxy)-2-(piperidin-1-yl)acetimidamide. The title compound was prepared using conditions analogous to those described in Example 152, Step A using N-hydroxy-2-(piperidin-1-yl)acetimidamide instead of (3R,5R,7R)—N-hydroxyadamantane-1-carboximidamide to provide the title compound (113 mg, 100%). MS (ESI): mass calcd. for $C_{30}H_{36}N_8O_3S$, 588.26; m/z found, 589.3 $[M+H]^+$.

Step B: N'-((1-((1r,4r)-4-(Cyanomethyl)cyclohexyl)-1,6-dihydroimidazo[4,5-d]pyrrolo[2,3-b]pyridin-2-yl)methoxy)-2-(piperidin-1-yl)acetimidamide. The title compound was prepared using conditions analogous to those described in Example 152, Step B using N'-((1-((1r,4r)-4-(cyanomethyl)cyclohexyl)-6-(phenylsulfonyl)-1,6-dihydroimidazo[4,5-d]pyrrolo[2,3-b]pyridin-2-yl)methoxy)-2-(piperidin-1-yl)acetimidamide (113 mg, 0.190 mmol) instead of (3R,5R,7R)—N'-((1-((1r,4r)-4-(cyanomethyl)cyclohexyl)-6-(phenylsulfonyl)-1,6-dihydroimidazo[4,5-d]pyrrolo[2,3-b]pyridin-2-yl)methoxy)adamantane-1-carboximidamide to provide the title compound (22 mg, 26%). The title compound was initially purified by flash column chromatography (12 g silica gel column, 2-20% MeOH in DCM). Subsequently it was further purified by reverse phase HPLC (5-95% $CH_3CN$ in $H_2O$, 0.1% TFA). The pure fractions from the HPLC purification were concentrated and dissolved in 10% MeOH in DCM, passed through a 500 mg column of SILICYCLE SPE-R66030B-03P Carbonate to remove TFA, and eluted with 10% MeOH in DCM. MS (ESI): mass calcd. for $C_{24}H_{32}N_8O$, 448.27; m/z found, 449.2 $[M+H]^+$. $^1H$ NMR (400 MHz, $CDCl_3$) δ=10.65 (br s, 1H), 8.81 (s, 1H), 7.45-7.42 (m, 1H), 6.73 (d, J=2.5 Hz, 1H), 5.40 (br s, 1H), 5.32 (s, 2H), 4.79-4.63 (m, 1H), 3.14 (br s, 2H), 2.73-2.47 (m, 5H), 2.44 (d, J=6.1 Hz, 2H), 2.28-2.11 (m, 3H), 2.11-1.89 (m, 3H), 1.71-1.59 (m, 4H), 1.59-1.39 (m, 4H).

Example 154 Synthesis and Characterization

Neopentyl ((1-((1r,4r)-4-(Cyanomethyl)cyclohexyl)-1,6-dihydroimidazo[4,5-d]pyrrolo[2,3-b]pyridin-2-yl)methyl)carbamate

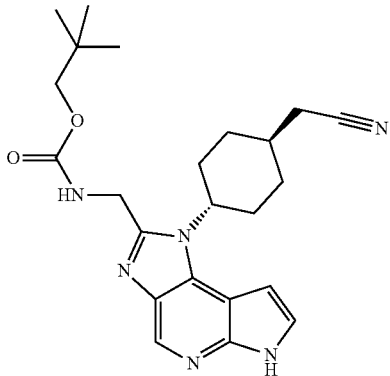 [SMILES: CC(C)(C)COC(=O)NCc1nc2cnc3[nH]ccc3c2n1[C@H]1CC[C@H](CC#N)CC1]

Neopentyl chloroformate (69.9 mg, 0.464 mmol) was added dropwise to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 160 mg, 0.422 mmol), triethylamine (0.294 mL, 2.11 mmol), and $CH_2Cl_2$ (5 mL) and was stirred for 30 minutes at 10° C. The reaction mixture was diluted with $CH_2Cl_2$ (10 mL), washed with water (10 mL), dried over anhydrous $Na_2SO_4$, filtered, and concentrated to dryness. The residue was purified by preparative TLC (eluent: $CH_2Cl_2$: methanol=10:1) to provide the title compound (50 mg, 28% yield) as a white solid. MS (ESI): mass calcd. for $C_{23}H_{30}N_6O_2$, 422.24; m/z found, 423.2 $[M+H]^+$. $^1H$ NMR (400 MHz, DMSO-$d_6$): δ 11.87 (s, 1H), 8.54 (s, 1H), 7.84 (s, 1H), 7.47 (t, J=2.8 Hz, 1H), 6.71 (s, 1H), 4.60 (d, J=5.6 Hz, 2H), 4.58-4.47 (m, 1H), 3.71 (s, 2H), 2.59 (d, J=5.6 Hz, 2H), 2.43-2.25 (m, 2H), 2.08-1.84 (m, 5H), 1.47-1.32 (m, 2H), 0.89 (s, 9H).

Example 155 Synthesis and Characterization 1-((1-((1r,4r)-4-(Cyanomethyl)cyclohexyl)-1,6-dihydroimidazo[4,5-d]pyrrolo[2,3-b]pyridin-2-yl)methyl)-3-(cyclohexylmethyl)urea

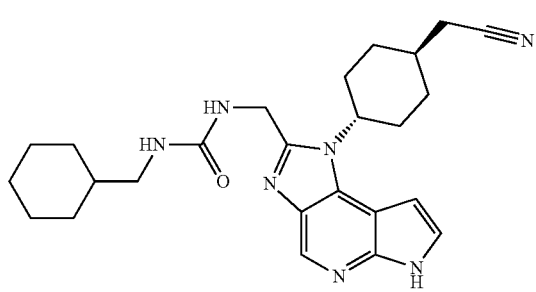 [SMILES: N#CC[C@H]1CC[C@H](n2c(CNC(=O)NCC3CCCCC3)nc3cnc4[nH]ccc4c32)CC1]

Step A: 1-((1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl)-3-(cyclohexylmethyl)urea. The title compound (185 mg) was prepared using conditions analogous to those described in Example 70, Step C using (isocyanatomethyl)cyclohexane (101 mg, 0.726 mmol) instead of isocyanatobenzene. The compound was purified by flash column chromatography (12 g silica gel column, 2-10% MeOH in DCM). MS (ESI): mass calcd. for $C_{31}H_{37}N_7O_3S$, 587.27; m/z found, 588.3 $[M+H]^+$.

Step B: 1-((1-((1r,4r)-4-(Cyanomethyl)cyclohexyl)-1,6-dihydroimidazo[4,5-d]pyrrolo[2,3-b]pyridin-2-yl)methyl)-3-(cyclohexylmethyl)urea. The title compound was prepared using the product of Step A (Example 155, Step A) using analogous conditions as described in Example 1, Step B (67 mg, 48% yield). The compound was purified by flash column chromatography (12 g silica gel column, 2-10% MeOH in DCM). MS (ESI): mass calcd. for $C_{25}H_{33}N_7O$, 447.27; m/z found, 448.4 $[M+H]^+$. $^1H$ NMR (400 MHz, $CDCl_3$) δ=11.95 (br s, 1H), 8.71 (s, 1H), 7.44 (t, J=2.8 Hz, 1H), 6.68 (br s, 2H), 5.44 (br s, 1H), 4.83 (br d, J=5.6 Hz, 2H), 4.65 (br s, 1H), 3.01 (t, J=6.1 Hz, 2H), 2.47 (br s, 2H), 2.32 (d, J=6.4 Hz, 2H), 2.14-1.87 (m, 5H), 1.67-1.52 (m, 5H), 1.44-1.23 (m, 3H), 1.17-0.98 (m, 2H), 0.88-0.73 (m, 2H).

Example 156 Synthesis and Characterization (3R,5R,7R)—N-((1-((1r,4r)-4-(Cyanomethyl)cyclohexyl)-1,6-dihydroimidazo[4,5-d]pyrrolo[2,3-b]pyridin-2-yl)methyl)adamantane-1-carboximidamide

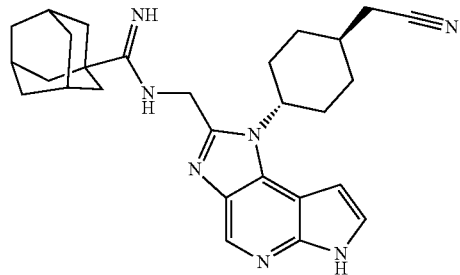 [SMILES: N#CC[C@H]1CC[C@H](n2c(CNC(=N)C34CC5CC(CC(C5)C3)C4)nc3cnc4[nH]ccc4c32)CC1]

Step A: (3R,5R,7R)—N-((1-((1r,4r)-4-(Cyanomethyl)cyclohexyl)-6-(phenyl sulfonyl)-1,6-dihydroimidazo[4,5-d]pyrrolo[2,3-b]pyridin-2-yl)methyl)adamantane-1-carboximidamide. A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 76 mg, 0.16 mmol), (3R,5R,7R)-adamantane-1-carboximidamide (88 mg, 0.41 mmol), $K_2CO_3$ (80 mg, 0.58 mmol), and DMF (2 mL) was stirred at room temperature overnight. After filtering off the solid, the filtrate was concentrated to dryness to provide the title compound (98 mg, 99% yield) as an oil, which was taken to next step without further purification. MS (ESI): mass calcd. for $C_{34}H_{39}N_7O_2S$, 609.29; m/z found, 610.3 $[M+H]^+$.

Step B: (3R,5R,7R)—N-((1-((1r,4r)-4-(Cyanomethyl)cyclohexyl)-1,6-dihydroimidazo[4,5-d]pyrrolo[2,3-b]pyridin-2-yl)methyl)adamantane-1-carboximidamide. A mixture of (3R,5R,7R)—N-((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)adamantane-1-carboximidamide (98 mg, 0.16 mmol), 3 M NaOH (aq) (0.11 mL, 0.33 mmol), THF (1 mL), and MeOH (1 mL) was stirred at RT for 18 h and concentrated in vacuo. The residue was purified by reverse phase HPLC (10-90% $CH_3CN$ in $H_2O$, 0.1% TFA) to give a clear oil. This material was partitioned between EtOAc and saturated $NaHCO_3$(aq). The aqueous layer was extracted with EtOAc (×4). The combined organic phases were dried over Na$_2$SO$_4$, filtered, and concentrated to give the title compound as an off-white solid (62 mg, 83%). MS (ESI): mass calcd. for C$_{28}$H$_{35}$N$_7$, 469.30; m/z found, 470.4 [M+H]$^+$. $^1$H NMR (400 MHz, CDCl$_3$) δ 9.64 (br s, 1H), 8.75 (s, 1H), 7.45-7.41 (m, 1H), 6.76 (d, J=2.0 Hz, 1H), 5.11 (br s, 2H), 4.74 (br s, 1H), 2.45 (br s, 2H), 2.39 (d, J=6.6 Hz, 2H), 2.25-2.09 (m, 6H), 2.05-1.94 (m, 6H), 1.90-1.47 (m, 10H).

Example 157 Synthesis and Characterization

3-Cyano-N-((1-((1r,4r)-4-(cyanomethyl)cyclohexyl)-1,6-dihydroimidazo[4,5-d]pyrrolo[2,3-b]pyridin-2-yl)methyl)propanamide

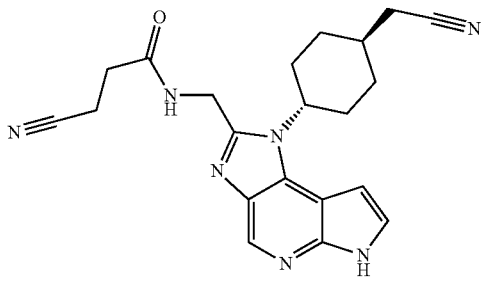 [SMILES: N#CCCC(=O)NCc1nc2cnc3[nH]ccc3c2n1[C@H]1CC[C@H](CC#N)CC1]

HATU (100 mg, 0.264 mmol) was added to a solution of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 100 mg, 0.264 mmol), 3-cyanopropanoic acid (26.1 mg, 0.264 mmol), DIEA (0.230 mL, 1.32 mmol), and CH$_2$Cl$_2$ (5 mL) and was stirred for 0.5 h at 10° C. The reaction was diluted with CH$_2$Cl$_2$ (10 mL), washed with water (10 mL), dried over anhydrous Na$_2$SO$_4$, filtered, and concentrated to dryness. The residue was purified by preparative TLC (eluent: CH$_2$Cl$_2$: methanol=10:1) to provide the title compound (30 mg, 29% yield) as a white solid. MS (ESI): mass calcd. for C$_{21}$H$_{23}$N$_7$O, 389.20; m/z found, 390.2 [M+H]$^+$. $^1$H NMR (400 MHz, DMSO-d$_6$): δ 11.90 (s, 1H), 8.76 (t, J=5.6 Hz, 1H), 8.55 (s, 1H), 7.48 (t, J=2.8 Hz, 1H), 6.73 (s, 1H), 4.72 (d, J=5.6 Hz, 2H), 4.62-4.47 (m, 1H), 2.69 (t, J=6.8 Hz, 2H), 2.57 (d, J=6.0 Hz, 2H), 2.55 (t, J=6.8 Hz, 2H), 2.43-2.24 (m, 2H), 2.11-1.87 (m, 5H), 1.47-1.30 (m, 2H).

Example 158 Synthesis and Characterization tert-Butyl ((1-((1r,4r)-4-(Cyanomethyl)cyclohexyl)-1,6-dihydroimidazo[4,5-d]pyrrolo[2,3-b]pyridin-2-yl)methyl)carbamate

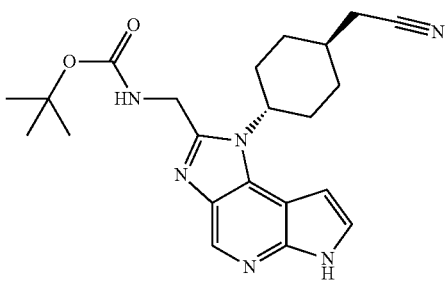 [SMILES: CC(C)(C)OC(=O)NCc1nc2cnc3[nH]ccc3c2n1[C@H]1CC[C@H](CC#N)CC1]

Step A: tert-Butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate. A solution of 2-((1r,4r)-4-((5-nitro-1-(phenyl sulfonyl)-1H-pyrrolo[2,3-b]pyridin-4-yl)amino)cyclohexyl)acetonitrile (Intermediate 1, 1.00 g, 2.28 mmol), tert-butyl (2-oxoethyl)carbamate (0.820 g, 5.20 mmol), and sodium hydrosulfite (1.17 g, 5.69 mmol) in DMSO (3 mL), MeOH (10 mL), and distilled water (5 mL) in a pressure tube was heated at 100° C. for 15 h. The reaction was concentrated to dryness and the residue was partitioned between CH$_2$Cl$_2$ and water. The organic layers were combined, washed with water, and the aqueous layer was back extracted with CH$_2$Cl$_2$. The combined organic phases were dried over anhydrous MgSO$_4$, filtered, and concentrated to dryness. The residue was purified by flash column chromatography (36 g silica gel column, 30-100% EtOAc in heptanes) to provide the title compound (748 mg, 60% yield) as a white solid, MS (ESI): mass calcd. for C$_{28}$H$_{32}$N$_6$O$_4$S, 548.2; m/z found, 549.3 [M+H]$^+$.

Step B: tert-Butyl ((1-((1r,4r)-4-(Cyanomethyl)cyclohexyl)-1,6-dihydroimidazo[4,5-d]pyrrolo[2,3-b]pyridin-2-yl)methyl)carbamate. The title compound (64 mg, 86%). was prepared as a white solid using conditions analogous to those described in Example 156, Step B using tert-butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate (100 mg, 0.18 mmol) instead of (3R,5R,7R)—N-((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)adamantane-1-carboximidamide. The title compound was initially purified by reverse phase HPLC (10-90% CH$_3$CN in H$_2$O, 0.1% TFA). The pure fractions were dissolved in 10% MeOH in DCM, passed through a 500 mg column of SILICYCLE SPE-R66030B-03P Carbonate to remove TFA, and eluted with 10% MeOH in DCM. MS (ESI): mass calcd. for C$_{22}$H$_{28}$N$_6$O$_2$, 408.23; m/z found, 409.2 [M+H]$^+$. $^1$H NMR (400 MHz, CDCl$_3$) δ=11.41-11.26 (m, 1H), 8.77 (s, 1H), 7.48 (t, J=3.0 Hz, 1H), 6.76-6.70 (m, 1H), 6.08 (br s, 1H), 4.75 (br d, J=6.1 Hz, 3H), 2.54 (br s, 2H), 2.42 (d, J=6.6 Hz, 2H), 2.24-2.09 (m, 3H), 2.09-1.95 (m, 3H), 1.87 (br s, 1H), 1.49 (m, 9H).

Example 159 Synthesis and Characterization 2-((1r,4r)-4-(2-(Azetidin-3-yl)imidazo[4,5-d]pyrrolo[2,3-b]pyridin-1(6H)-yl)cyclohexyl)acetonitrile

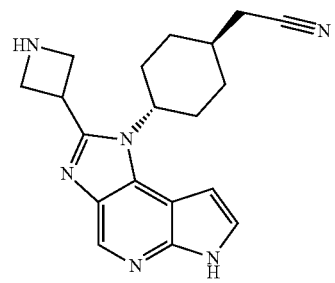 [SMILES: N#CC[C@H]1CC[C@H](n2c(C3CNC3)nc3cnc4[nH]ccc4c32)CC1]

A solution of 2-((1r,4r)-4-((1-((4-bromophenyl)sulfonyl)-5-nitro-1H-pyrrolo[2,3-b]pyridin-4-yl)amino)cyclohexyl)acetonitrile (519 mg, 1.00 mmol), as prepared in Example 128, Step A, tert-butyl 3-formylazetidine-1-carboxylate, (371 mg, 2.00 mmol), sodium dithionite (523 mg, 3.00 mmol), DMSO (2.5 mL), and water (0.15 mL) was heated to 100° C. for 16 hours. Water (20 mL) added. The precipitate that formed was collected by filtration and was purified by flash column chromatography. To this material was added $CH_2Cl_2$ (5 mL) and TFA (1 mL) and was stirred for 0.5 h. The reaction was concentrated to dryness. To the residue was added $CH_2Cl_2$ (10 mL) and saturated $NaHCO_3$ (10 mL), the organic layer was collected and concentrated to dryness. The residue was dissolved in NaOH (1 M)/THF/MeOH (1 mL/1 mL/1 mL) and was heated at 80° C. for 1 h. The reaction was concentrated to dryness and the residue was purified by flash column chromatography to provide the title compound (5.00 mg, 1% yield). MS (ESI): mass calcd. for $C_{19}H_{22}N_6$, 334.19; m/z found, 335.2 $[M+H]^+$. $^1H$ NMR (500 MHz, $CDCl_3$): δ 8.97 (s, 1H), 8.84-8.71 (m, 1H), 7.40-7.31 (m, 1H), 6.68 (d, J=3.6 Hz, 1H), 4.38-4.20 (m, 3H), 4.04-3.87 (m, 3H), 2.68-2.32 (m, 4H), 2.27-1.85 (m, 5H), 1.50-1.35 (m, 2H).

Example 160 Synthesis and Characterization 3-(3-(1-((1r,4r)-4-(Cyanomethyl)cyclohexyl)-1,6-dihydroimidazo[4,5-d]pyrrolo[2,3-b]pyridin-2-yl)azetidin-1-yl)-3-oxopropanenitrile

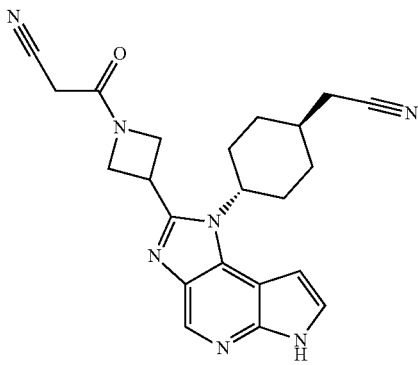 [SMILES: N#CCC(=O)N1CC(c2nc3cnc4[nH]ccc4c3n2[C@H]2CC[C@H](CC#N)CC2)C1]

A solution of 2-((1r,4r)-4-(2-(Azetidin-3-yl)imidazo[4,5-d]pyrrolo[2,3-b]pyridin-1(6H)-yl)cyclohexyl)acetonitrile (30.0 mg, 0.0900 mmol), as prepared in Example 159, and 2,5-dioxopyrrolidin-1-yl 2-cyanoacetate (32.7 mg, 0.179 mmol) in $CH_2Cl_2$ (2 mL) was stirred at room temperature for 4 h. Water (1 mL) was added and the organic layer was collected and concentrated to dryness. The residue was purified by flash column chromatography to provide the title compound (9 mg, 25% yield). MS (ESI): mass calcd. for $C_{22}H_{23}N_7O$, 401.2; m/z found, 402.2 $[M+H]^+$. $^1H$ NMR (400 MHz, $CDCl_3$): δ 9.45 (s, 1H), 8.79 (s, 1H), 7.49-7.34 (m, 1H), 6.81-6.54 (m, 1H), 5.21-5.02 (m, 1H), 4.77 (t, J=8.5 Hz, 1H), 4.57 (t, J=9.2 Hz, 1H), 4.47-4.29 (m, 1H), 4.32-4.12 (m, 1H), 3.78-3.52 (m, 1H), 3.37 (d, J=3.8 Hz, 2H), 2.54-2.40 (m, 4H), 2.33-1.91 (m, 5H), 1.53-1.37 (m, 2H).

Example 161 Synthesis and Characterization (1-((1r,4r)-4-(Cyanomethyl)cyclohexyl)-1,6-dihydroimidazo[4,5-d]pyrrolo[2,3-b]pyridin-2-yl)methyl (2-methoxyethyl)carbamate

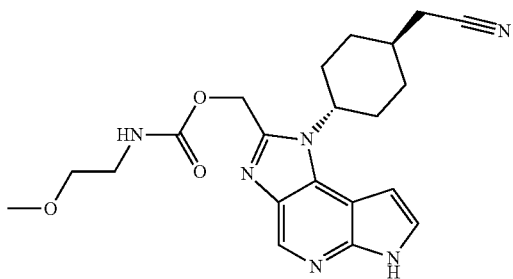 [SMILES: COCCNC(=O)OCc1nc2cnc3[nH]ccc3c2n1[C@H]1CC[C@H](CC#N)CC1]

Step A: (1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl (2-methoxyethyl)carbamate. A solution of 2-((1r,4r)-4-(2-(hydroxymethyl)-6-(phenylsulfonyl)imidazo[4,5-d]pyrrolo[2,3-b]pyridin-1(6H)-yl)cyclohexyl)acetonitrile (Intermediate 7, 100 mg, 0.222 mmol) and 1-isocyanato-2-methoxyethane (45 mg, 0.45 mmol) was heated at 60° C. for 16 h. LCMS showed starting material remained, so heating was continued for 24 h. After which additional 1-isocyanato-2-methoxyethane (45 mg, 0.45 mmol) was added and the reaction was heated at 60° C. for 18 h, then heated at 80° C. for 68 h. The reaction was concentrated to dryness and the residue was purified by flash column chromatography (12 g silica gel column, 0-100% EtOAc in heptanes, then 10% MeOH in DCM) to provide the title compound as an impure mixture (2:1 of product and starting material, 159 mg) as an off-white solid which was used as is in the subsequent reaction. MS (ESI): mass calcd. for $C_{27}H_{30}N_6O_5S$, 550.2; m/z found, 551.2 $[M+H]^+$.

Step B: (1-((1r,4r)-4-(Cyanomethyl)cyclohexyl)-1,6-dihydroimidazo[4,5-d]pyrrolo[2,3-b]pyridin-2-yl)methyl (2-methoxyethyl)carbamate. The title compound (30 mg, 25%) was prepared using conditions analogous to those described in Example 156, Step B using (1-((1r,4r)-4-(cyanomethyl)cyclohexyl)-6-(phenylsulfonyl)-1,6-dihydroimidazo[4,5-d]pyrrolo[2,3-b]pyridin-2-yl)methyl (2-methoxyethyl)carbamate (159 mg, 0.290 mmol) instead of (3R,5R,7R)—N-((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)adamantane-1-carboximidamide. The compound was purified by reverse phase HPLC using a Varian Pursuit $XR_s5$ Diphenyl 100×30 mm column (eluent: 5-95% $CH_3CN$ in $H_2O$, 0.1% TFA). The pure fractions were concentrated and dissolved in 10% MeOH in DCM, passed through a 500 mg column of SILICYCLE SPE-R66030B-03P Carbonate to remove TFA, and eluted with 10% MeOH in DCM. MS (ESI): mass calcd. for $C_{21}H_{26}N_6O_3$, 410.2; m/z found, 411.3 $[M+H]^+$. $^1H$ NMR (400 MHz, $CDCl_3$) δ=11.51 (br s, 1H), 8.82 (s, 1H), 7.46 (t, J=2.8 Hz, 1H), 6.74-6.64 (m, 1H), 5.70 (br s, 1H), 5.48 (s, 2H), 4.52 (br s, 1H), 3.53-3.47 (m, 2H), 3.47-3.40 (m, 1H), 3.38-3.29 (m, 3H), 2.52 (br s, 2H), 2.41 (d, J=6.6 Hz, 2H), 2.23-1.91 (m, 6H), 1.56-1.34 (m, 2H).

Example 162 Synthesis and Characterization 2-((1r,4r)-4-(2-((((R)-Methyl(oxo)(phenyl)-λ⁶-sulfanylidene)amino)methyl)imidazo[4,5-d]pyrrolo[2,3-b]pyridin-1(6H)-yl)cyclohexyl)acetonitrile

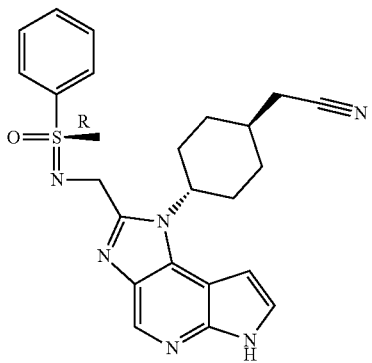

A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 91 mg, 0.19 mmol), (R)-(S-methylsulfonimidoyl)benzene (36 mg, 0.23 mmol), and NaHCO₃ (24.5 mg, 0.292 mmol) were mixed together in CH₃CN (3 mL), and heated to 130° C. for 20 hours. The reaction was concentrated to dryness and the residue was dissolved in MeOH/THF/NaOH (1M) (1 mL/1 mL/1 mL) and was heated at 80° C. for 1 h. The reaction was concentrated to dryness and the residue was partitioned between CH₂Cl₂ and water (5 mL/5 mL). The organic layer was collected, concentrated to dryness, and the residue purified by flash column chromatography to provide the title compound (10 mg, 12% yield). MS (ESI): mass calcd. for $C_{24}H_{26}N_6OS$, 446.2; m/z found, 447.2 [M+H]⁺. ¹H NMR (400 MHz, CDCl₃): δ 10.53-10.14 (m, 1H), 8.74-8.57 (m, 1H), 7.99-7.82 (m, 2H), 7.69-7.45 (m, 3H), 7.41-7.26 (m, 1H), 6.79-6.58 (m, 1H), 4.92-4.62 (m, 1H), 4.58-4.36 (m, 1H), 4.36-4.19 (m, 1H), 3.21-3.00 (m, 3H), 2.64-2.28 (m, 4H), 2.22-1.95 (m, 5H), 1.57-1.34 (m, 2H).

Example 163 Synthesis and Characterization 2-((1r,4r)-4-(2-((((S)-methyl(oxo)(phenyl)-λ⁶-sulfanylidene)amino)methyl)imidazo[4,5-d]pyrrolo[2,3-b]pyridin-1(6H)-yl)cyclohexyl)acetonitrile

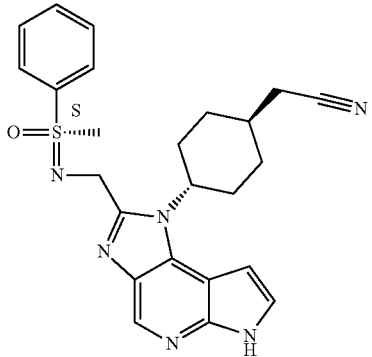

The title compound (42 mg, 48% yield) was prepared using analogous conditions in Example 163 using 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8, 91 mg, 0.19 mmol), and (S)-(S-methylsulfonimidoyl)benzene (36 mg, 0.23 mmol) instead of (R)-(S-methylsulfonimidoyl)benzene. MS (ESI): mass calcd. for $C_{24}H_{26}N_6OS$, 446.2; m/z found, 447.2 [M+H]⁺. ¹H NMR (500 MHz, CDCl₃) δ 11.41-11.18 (s, 1H), 8.93-8.57 (s, 1H), 8.10-7.82 (m, 2H), 7.74-7.46 (m, 3H), 7.42-7.29 (m, 1H), 6.91-6.55 (d, J=3.2 Hz, 1H), 5.04-4.68 (m, 1H), 4.62-4.38 (d, J=14.3 Hz, 1H), 4.38-4.19 (m, 1H), 3.32-2.92 (m, 3H), 2.58-2.32 (m, 4H), 2.20-1.98 (m, 5H), 1.58-1.35 (m, 2H).

Example 164 Synthesis and Characterization 2-((1r,4r)-4-(2-(1-Acetylpiperidin-4-yl)imidazo[4,5-d]pyrrolo[2,3-b]pyridin-1(6H)-yl)cyclohexyl)acetonitrile

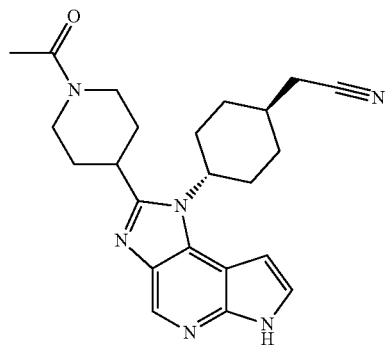 [SMILES: CC(=O)N1CCC(c2nc3cnc4[nH]ccc4c3n2[C@H]2CC[C@H](CC#N)CC2)CC1]

Step A: tert-Butyl 4-(1-((1r,4r)-4-(cyanomethyl)cyclohexyl)-6-(phenylsulfonyl)-1,6-dihydroimidazo[4,5-d]pyrrolo[2,3-b]pyridin-2-yl)piperidine-1-carboxylate. To a solution of 2-((1r,4r)-4-((5-amino-1-(phenylsulfonyl)-1H-pyrrolo[2,3-b]pyridin-4-yl)amino)cyclohexyl)acetonitrile (Intermediate 2, 250 mg, 0.569 mmol) in DMSO (5 mL) and MeOH (1 mL) in a microwave vial was added 1-Boc-4-piperidinecarboxaldehyde (146 mg, 0.683 mmol), followed by sodium hydrosulfite (291 mg, 1.42 mmol). The vial was capped and heated to 100° C. overnight. After cooling to room temperature, the mixture was diluted with water (5 mL) and stirred for 5 minutes. The white precipitate that formed was collected by filtration, washed with water (50 mL), and allowed to dry thoroughly. The solid was collected in a round bottom flask by dissolving it in EtOAc. The organic phase was concentrated to dryness to the title compound as a white solid, which was used without further purification. MS (ESI): mass calcd. for $C_{32}H_{38}N_6O_4S$, 602.3; m/z found, 603.3 [M+H]⁺.

Step B: 2-((1r,4r)-4-(6-(Phenylsulfonyl)-2-(piperidin-4-yl)imidazo[4,5-d]pyrrolo[2,3-b]pyridin-1(6H)-yl)cyclohexyl)acetonitrile hydrochloride. To a solution of tert-butyl 4-(1-((1r,4r)-4-(cyanomethyl)cyclohexyl)-6-(phenyl sulfonyl)-1,6-dihydroimidazo[4,5-d]pyrrolo[2,3-b]pyridin-2-yl)piperidine-1-carboxylate (336 mg, 0.557 mmol) in CH₂Cl₂ (3.9 mL) at room temperature was added 4 M HCl in dioxane (3.9 mL) and was stirred at room temperature for 10 minutes. The reaction was concentrated to dryness and then was dried under vacuum for 20 minutes to provide the title compound as the HCl salt as an off-white colored powder. MS (ESI): mass calcd. for $C_{27}H_{30}N_6O_2S$, 502.2; m/z found, 503.3 $[M+H]^+$.

Step C: 2-((1r,4r)-4-(2-(1-Acetylpiperidin-4-yl)-6-(phenylsulfonyl)imidazo[4,5-d]pyrrolo[2,3-b]pyridin-1(6H)-yl)cyclohexyl)acetonitrile. To a solution of 2-((1r,4r)-4-(6-(phenylsulfonyl)-2-(piperidin-4-yl)imidazo[4,5-d]pyrrolo[2,3-b]pyridin-1(6H)-yl)cyclohexyl)acetonitrile hydrochloride (100 mg, 0.185 mmol) in $CH_2Cl_2$ (2.7 mL) was added triethylamine (0.258 mL, 1.86 mmol) and was cooled to 0° C. Next, acetyl chloride (0.0158 mL, 0.223 mmol) was added and was stirred at 0° C. for 15 minutes. The reaction was quenched by addition of 1 mL of saturated aqueous $NaHCO_3$. The reaction was extracted with EtOAc (3×25 mL), dried over anhydrous sodium sulfate, filtered, and concentrated to dryness. The residue was purified by flash column chromatography. The purified product was further triturated with $CH_3CN$ and the solids were collected by filtration to provide the title compound as a white solid. MS (ESI): mass calcd. for $C_{29}H_{32}N_6O_3S$, 544.2; m/z found, 545.3 $[M+H]^+$.

Step D: 2-((1r,4r)-4-(2-(1-Acetylpiperidin-4-yl)imidazo[4,5-d]pyrrolo[2,3-b]pyridin-1(6H)-yl)cyclohexyl)acetonitrile. The title compound (27.5 mg, 37% yield) was prepared using conditions analogous to those described in Example 1, Step B using 2-((1r,4r)-4-(2-(1-Acetylpiperidin-4-yl)-6-(phenylsulfonyl)imidazo[4,5-d]pyrrolo[2,3-b]pyridin-1(6H)-yl)cyclohexyl)acetonitrile (101 mg, 0.185 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The crude material was purified on a 12 gram silica gel column using 0 to 10% (2N $NH_3$ in MeOH) in DCM to provide the title compound. MS (ESI): mass calcd. for $C_{23}H_{28}N_6O$, 404.2; m/z found, 405.3 $[M+H]^+$. $^1H$ NMR (400 MHz, DMSO-$d_6$): δ 11.84 (s, 1H), 8.50 (s, 1H), 7.56-7.34 (m, 1H), 6.71 (d, J=3.5 Hz, 1H), 4.63-4.52 (m, 1H), 4.52-4.42 (m, 1H), 3.98-3.88 (m, 1H), 3.55-3.42 (m, 1H), 3.31-3.22 (m, 1H), 2.86-2.73 (m, 1H), 2.61 (d, J=6.0 Hz, 2H), 2.47-2.38 (m, 2H), 2.05 (s, 3H), 2.03-1.96 (m, 3H), 1.96-1.80 (m, 5H), 1.73-1.58 (m, 1H), 1.58-1.43 (m, 2H).

Example 165 Synthesis and Characterization 2-((1r,4r)-4-(2-((3-Cyclopropyl-5-oxo-1,2,4-oxadiazol-4(5H)-yl)methyl)imidazo[4,5-d]pyrrolo[2,3-b]pyridin-1(6H)-yl)cyclohexyl)acetonitrile

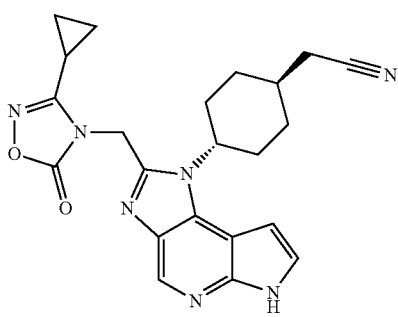 [SMILES: N#CC[C@H]1CC[C@H](n2c(Cn3c(C4CC4)noc3=O)nc3cnc4[nH]ccc4c32)CC1]

A solution of (EZ)—N-((1-((1r,4r)-4-(cyanomethyl)cyclohexyl)-1,6-dihydroimidazo[4,5-d]pyrrolo[2,3-b]pyridin-2-yl)methyl)-N-hydroxycyclopropanecarboximidamide, as prepared in Example 110, (73 mg, 0.17 mmol), CDI (30 mg, 0.19 mmol), and THF (2 mL) was stirred for 1.5 h at 70° C. The reaction was concentrated to dryness and the residue was purified by flash column chromatography and by preparative HPLC using a Phenomenex Gemini 150 mm×25 mm, 10 μm column (eluent: 23% to 53% (v/v) $CH_3CN$ and $H_2O$ with 0.05% $NH_3$) to provide the title compound (40 mg, 56% yield) as a white solid. MS (ESI): mass calcd. for $C_{22}H_{23}N_7O_2$, 417.2; m/z found, 418.0 $[M+H]^+$. $^1H$ NMR (400 MHz, DMSO-$d_6$): δ 11.93 (s, 1H), 8.55 (s, 1H), 7.54-7.46 (m, 1H), 6.79-6.71 (m, 1H), 5.44 (s, 2H), 4.67-4.53 (m, 1H), 2.61 (d, J=6.0 Hz, 2H), 2.43-2.28 (m, 2H), 2.12-1.89 (m, 6H), 1.55-1.38 (m, 2H), 0.94-0.78 (m, 4H).

Example 166 Synthesis and Characterization 2-((1r,4r)-4-(2-(1-(Oxazol-4-ylmethyl)-1H-pyrazol-4-yl)imidazo[4,5-d]pyrrolo[2,3-b]pyridin-1(6H)-yl)cyclohexyl)acetonitrile

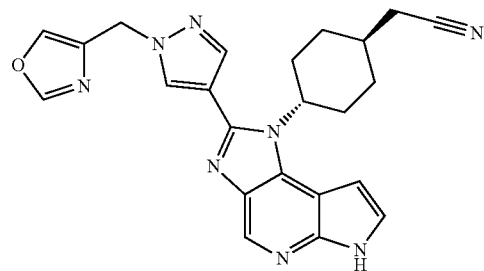 [SMILES: N#CC[C@H]1CC[C@H](n2c(-c3cnn(Cc4cocn4)c3)nc3cnc4[nH]ccc4c32)CC1]

Step A: 2-((1r,4r)-4-(2-(1-(Oxazol-4-ylmethyl)-1H-pyrazol-4-yl)-6-(phenylsulfonyl)imidazo[4,5-d]pyrrolo[2,3-b]pyridin-1(6H)-yl)cyclohexyl)acetonitrile. To a 10 mL microwave vial was added 2-((1r,4r)-4-(6-(phenylsulfonyl)-2-(1H-pyrazol-4-yl)imidazo[4,5-d]pyrrolo[2,3-b]pyridin-1(6H)-yl)cyclohexyl)acetonitrile (as prepared in Example 123, Step A, 189 mg, 0.389 mmol) as a solid, followed by the addition of DMF (0.833 mL), $Cs_2CO_3$ (588 mg, 1.81 mmol), and 4-(bromomethyl)oxazole hydrobromide (189 mg, 0.778 mmol). The vial was sealed and contents heated to 80° C. using a heating block for 4 h and then the reaction was allowed to slowly cool to room temperature. The reaction was added into 50 mL of water with stirring. The reaction was extracted with EtOAc (3×40 mL), dried over anhydrous $MgSO_4$, and concentrated to dryness. The residue was purified by flash column chromatography (40 g $SiO_2$, 0-5% 2 N $NH_3$-MeOH/EA over 7 CV) to provide the title compound (116 mg, 53% yield) as a dark brown solid. MS (ESI): mass calcd. for $C_{29}H_{26}N_8O_3S$, 566.2; m/z found, 567.2 $[M+H]^+$.

Step B: 2-((1r,4r)-4-(2-(1-(Oxazol-4-ylmethyl)-1H-pyrazol-4-yl)imidazo[4,5-d]pyrrolo[2,3-b]pyridin-1(6H)-yl)cyclohexyl)acetonitrile. The title compound was prepared using analogous conditions as described in Example 1, Step B. The residue was purified by flash column chromatography (24 g $SiO_2$, 0-10% 2 N $NH_3$-MeOH/EA over 12 CV) to afford the title compound (57 mg, 59% yield). MS (ESI): mass calcd. for $C_{23}H_{22}N_8O$, 426.2; m/z found, 427.2 $[M+H]^+$. $^1H$ NMR (500 MHz, DMSO-$d_6$): δ 11.90 (s, 1H), 8.57 (s, 1H), 8.41 (d, J=1.0 Hz, 1H), 8.34 (d, J=0.8 Hz, 1H), 8.19 (q, J=0.9 Hz, 1H), 7.90 (d, J=0.8 Hz, 1H), 7.49 (t, J=3.0 Hz, 1H), 6.75 (dd, J=3.5, 1.9 Hz, 1H), 5.40 (s, 2H), 4.63-4.44 (m, 1H), 2.58 (d, J=6.3 Hz, 2H), 2.49-2.39 (m, 2H), 2.13-1.91 (m, 5H), 1.47-1.30 (m, 2H).

Example 167 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(trimethylsilyl)cyclohexyl)acetamide

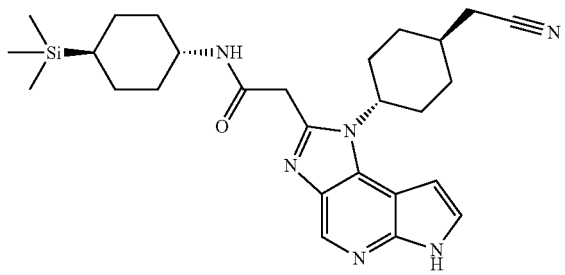 [SMILES: C[Si](C)(C)[C@H]1CC[C@H](NC(=O)Cc2nc3cnc4[nH]ccc4c3n2[C@H]2CC[C@H](CC#N)CC2)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 60.0 mg, 0.170 mmol) and (1r,4r)-4-(trimethylsilyl)cyclohexanamine (prepared in Example 135, Step E, 43 mg, 0.25 mmol) in DMF (3 mL) were added PyBOP (174 mg, 0.334 mmol) and DIPEA (0.10 mL, 0.58 mmol) and was stirred at room temperature for 18 h. The reaction was concentrated to dryness, the residue was added water, and the aqueous layer was extracted with EtOAc. The combined extracts were dried over anhydrous MgSO$_4$, filtered, and concentrated to dryness. The residue was purified by reverse phase HPLC using a Varian Pursuit XR$_s$5 Diphenyl 100×30 mm column (eluent: 10-90% CH$_3$CN in H$_2$O, 0.1% TFA) twice to provide the title compound (20 mg, 20% yield) as an off-white solid. MS (ESI): mass calcd. for C$_{27}$H$_{38}$N$_6$OSi, 490.3; m/z found 491.4, [M+H]$^+$. $^1$H NMR (400 MHz, CD$_3$OD) δ=8.84 (s, 1H), 7.78 (d, J=3.0 Hz, 1H), 7.13 (br d, J=3.0 Hz, 1H), 4.99 (s, 2H), 4.71 (br s, 1H), 3.70-3.58 (m, 1H), 2.70 (s, 1H), 2.61 (br d, J=5.6 Hz, 3H), 2.30-2.13 (m, 5H), 2.12-2.00 (m, 2H), 1.94-1.77 (m, 2H), 1.68-1.48 (m, 2H), 1.41-1.18 (m, 4H), 0.56 (br t, J=10.9 Hz, 1H), 0.00 (s, 9H).

Example 168 Synthesis and Characterization 2-((1r,4r)-4-(2-(1-(2-Hydroxy-2-methylpropyl)piperidin-4-yl)imidazo[4,5-d]pyrrolo[2,3-b]pyridin-1(6H)-yl)cyclohexyl)acetonitrile

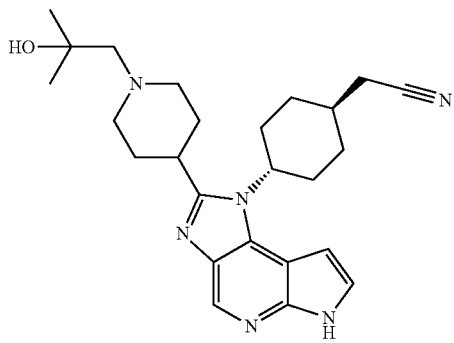 [SMILES: CC(C)(O)CN1CCC(c2nc3cnc4[nH]ccc4c3n2[C@H]2CC[C@H](CC#N)CC2)CC1]

Step A: 2-((1r,4r)-4-(2-(1-(2-Hydroxy-2-methylpropyl)piperidin-4-yl)-6-(phenylsulfonyl)imidazo[4,5-d]pyrrolo[2,3-b]pyridin-1(6H)-yl)cyclohexyl)acetonitrile. A solution of 2-((1r,4r)-4-(6-(phenylsulfonyl)-2-(piperidin-4-yl)imidazo[4,5-d]pyrrolo[2,3-b]pyridin-1(6H)-yl)cyclohexyl)acetonitrile, as prepared in Example 165, Step B, (100 mg, 0.185 mmol), isobutylene oxide (0.165 mL, 1.86 mmol), and Cs$_2$CO$_3$ (212 mg, 0.649 mmol)) in CH$_3$CN (1 mL) was heated to 130° C. in the microwave for 1 hour. The reaction was diluted with water (25 mL) and CH$_2$Cl$_2$ (5 mL), extracted with EtOAc (3×25 mL), dried over anhydrous sodium sulfate, filtered, and concentrated to dryness to provide the title compound as a clear oil, which was used without further purification. MS (ESI): mass calcd. for C$_{31}$H$_{38}$N$_6$O$_3$S, 574.3; m/z found, 575.2 [M+H]$^+$.

Step B: 2-((1r,4r)-4-(2-(1-(2-Hydroxy-2-methylpropyl)piperidin-4-yl)imidazo[4,5-d]pyrrolo[2,3-b]pyridin-1(6H)-yl)cyclohexyl)acetonitrile. The title compound (30.3 mg, 38% yield) was prepared using conditions analogous to those described in Example 1, Step B using 2-((1r,4r)-4-(2-(1-(2-Hydroxy-2-methylpropyl)piperidin-4-yl)-6-(phenylsulfonyl)imidazo[4,5-d]pyrrolo[2,3-b]pyridin-1(6H)-yl)cyclohexyl)acetonitrile (106 mg, 0.184 mmol) instead of 2-(1-((1r,4r)-4-(Cyanomethyl)cyclohexyl)-6-(phenyl sulfonyl)-1,6-dihydroimidazo[4,5-d]pyrrolo[2,3-b]pyridin-2-yl)-N-(2-hydroxy-2-methylpropyl)acetamide. The crude material was purified on a 12 gram silica gel column using 0 to 10% (2N NH$_3$ in MeOH) in DCM to provide the title compound. MS (ESI): mass calcd. for C$_{25}$H$_{34}$N$_6$O, 434.3; m/z found, 435.3 [M+H]$^+$. $^1$H NMR (400 MHz, DMSO-d$_6$): δ 11.82 (s, 1H), 8.50 (s, 1H), 7.49-7.42 (m, 1H), 6.70 (d, J=3.5 Hz, 1H), 4.61-4.40 (m, 1H), 4.08 (s, 1H), 3.12-2.98 (m, 3H), 2.60 (d, J=6.0 Hz, 2H), 2.39-2.30 (m, 4H), 2.25 (s, 2H), 2.07-1.92 (m, 4H), 1.94-1.85 (m, 3H), 1.85-1.76 (m, 2H), 1.58-1.41 (m, 2H), 1.11 (s, 6H).

Example 169 Synthesis and Characterization 2-((1r,4r)-4-(2-(4-(4-Ethynylbenzoyl)phenyl)imidazo[4,5-d]pyrrolo[2,3-b]pyridin-1(6H)-yl)cyclohexyl)acetonitrile

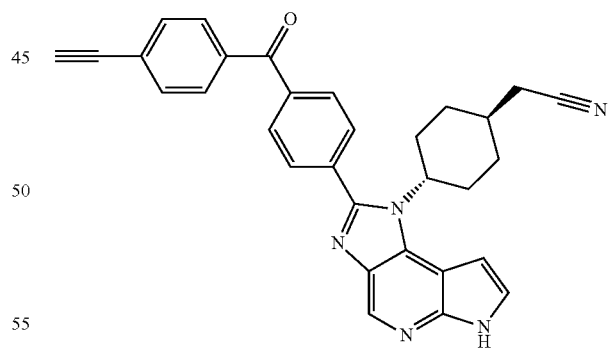

Step A: 2-((1r,4r)-4-(2-(4-(4-Formylbenzoyl)phenyl)imidazo[4,5-d]pyrrolo[2,3-b]pyridin-1(6H)-yl)cyclohexyl)acetonitrile. 2-((1r,4r)-4-(2-(4-(4-(Hydroxymethyl)benzoyl)phenyl)imidazo[4,5-d]pyrrolo[2,3-b]pyridin-1(6H)-yl)cyclohexyl)acetonitrile, as prepared in Example 121, (243 mg, 0.496 mmol) was dissolved in CH$_2$Cl$_2$ (13 mL) and DMF (4 mL) with gentle heating with a heat gun and then cooled to room temperature. Then Dess-Martin periodinane (234 mg, 0.550 mmol) was added in two 117 mg portions. After that last addition, the reaction was stirred for 15 more minutes. The reaction was concentrated to dryness and the residue was purified by flash column chromatography to provide the title compound (165 mg, 68.2% yield) as a light tan solid. MS (ESI): mass calcd. for $C_{30}H_{25}N_5O_2$, 487.2; m/z found, 488.2 [M+H]$^+$.

Step B: Dimethyl (2-oxo-1-(1λ$^4$,2λ$^4$-triaza-1,2-dien-1-ylidene)propyl)phosphonate. To a solution of dimethyl (2-oxopropyl)phosphonate (1000 mg, 6.02 mmol) in $CH_3CN$ (3.5 mL) was added tosyl azide (1.108 mL, 7.224 mmol) at room temperature. Then $K_2CO_3$ (1.165 g, 8.428 mmol)) was added and the reaction was stirred for 2 h. Next, 15 mL of saturated aqueous $NH_4Cl$ was added and the reaction was extracted with EtOAc (3×20 mL). The combined organics were dried over anhydrous sodium sulfate and concentrated to dryness. The material was dissolved in 6 mL of MeCN to make an approximately 1 M solution, which was used as is in the next reaction.

Step C: 2-((1r,4r)-4-(2-(4-(4-Ethynylbenzoyl)phenyl)imidazo[4,5-d]pyrrolo[2,3-b]pyridin-1(6H)-yl)cyclohexyl)acetonitrile. 2-((1r,4r)-4-(2-(4-(4-Formylbenzoyl)phenyl)imidazo[4,5-d]pyrrolo[2,3-b]pyridin-1(6H)-yl)cyclohexyl)acetonitrile (165 mg, 0.338 mmol) was dissolved in MeOH (20 mL) and a solution of dimethyl (2-oxo-1-(1λ$^4$,2λ$^4$-triaza-1,2-dien-1-ylidene)propyl)phosphonate (1 M in $CH_3CN$, 1.015 mL, 1.015 mmol) was added. To this solution was added $K_2CO_3$ (234 mg, 1.69 mmol) and the reaction was stirred at room temperature overnight. The reaction was quenched with saturated aqueous $NaHCO_3$ (2 mL), extracted with EtOAc (3×10 mL), dried over anhydrous $Na_2SO_4$, filtered, and concentrated to dryness. The crude material was purified on a 24 gram silica gel column using 0 to 10% MeOH in DCM to provide the title compound (33 mg, 20% yield) as a tan solid. MS (ESI): mass calcd. for $C_{31}H_{25}N_5O$, 483.2; m/z found, 484.2 [M+H]$^+$. $^1$H NMR (400 MHz, CDCl$_3$): δ 12.37 (s, 1H), 8.96 (s, 1H), 7.98 (d, J=8.2 Hz, 2H), 7.90-7.74 (m, 4H), 7.64 (d, J=8.2 Hz, 2H), 7.59-7.52 (m, 1H), 6.82-6.69 (m, 1H), 4.65-4.43 (m, 1H), 3.30 (s, 1H), 2.77-2.54 (m, 2H), 2.41 (d, J=6.0 Hz, 2H), 2.23-2.02 (m, 5H), 1.50-1.29 (m, 2H).

Example 170 Synthesis and Characterization 2-((1r,4r)-4-(2-(4-(4-Ethynylbenzoyl)phenethyl)imidazo[4,5-d]pyrrolo[2,3-b]pyridin-1(6H)-yl)cyclohexyl)acetonitrile

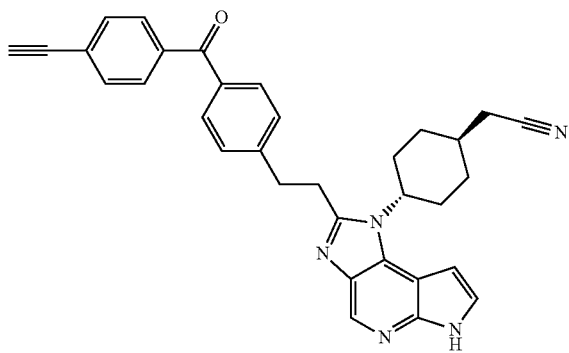 [SMILES: C#Cc1ccc(C(=O)c2ccc(CCc3nc4cnc5[nH]ccc5c4n3[C@H]3CC[C@H](CC#N)CC3)cc2)cc1]

Step A: (E)-3-(4-(4-Bromobenzoyl)phenyl)acrylaldehyde. Pd(OAc)$_2$ (0.033 g, 0.15 mmol) was added to a solution of 4,4'-dibromobenzophenone (1.00 g, 2.94 mmol), acrolein (0.247 g, 4.41 mmol), potassium carbonate (0.813 g, 5.88 mmol), benzyltriethylammonium chloride (0.670 g, 2.94 mmol), 4 Å molecular sieves (1 g), and dry DMF (14 mL) under N$_2$ and the reaction mixture was stirred for 4 h at 60° C. in a microwave tube. The solution was filtered, the filtrate was diluted with water (100 mL), and extracted with ethyl acetate (100 mL×2). The combined organic extracts were dried over anhydrous Na$_2$SO$_4$, filtered, and concentrated to dryness. The residue was purified by flash column chromatography to provide the title compound as a yellow solid. MS (ESI): mass calcd. for $C_{16}H_{11}BrO_2$, 313.99; m/z found, 317.2 [M+H]$^+$.

Step B: (4-Bromophenyl)(4-(3-hydroxypropyl)phenyl)methanone. A solution of (E)-3-(4-(4-bromobenzoyl)phenyl)acrylaldehyde (864 mg, 2.74 mmol), Pt/C (160 mg, 5%) and ethyl acetate (40 mL) was stirred for 12 h at 15° C. under H$_2$. TLC showed a small amount of (E)-3-(4-(4-bromobenzoyl)phenyl)acrylaldehyde remaining, so the reaction mixture was filtered and additional Pt/C (100 mg) was added and the reaction mixture was stirred for 6 h at 15° C. under H$_2$. The solution was filtered, and the filtrate was concentrated to dryness. The residue was purified by flash column chromatography to provide the title compound (266 mg, 30% yield) as white solid. 1H NMR (400 MHz, CDCl$_3$) 7.71 (d, J=8.0 Hz, 2H), 7.69-7.59 (m, 4H), 7.34-7.29 (m, 1H), 7.38-7.25 (m, 1H), 3.70 (t, J=6.4 Hz, 2H), 2.81 (t, J=7.6 Hz, 2H), 1.99-1.86 (m, 2H).

Step C: 3-(4-(4-Bromobenzoyl)phenyl)propanal. Dess-Martin periodinane (424 mg, 1.00 mmol) was added to a solution of (4-bromophenyl)(4-(3-hydroxypropyl)phenyl)methanone (266 mg, 0.833 mmol) and CH$_2$Cl$_2$ (14 mL) at 0° C. and was stirred for overnight at 15° C. TLC showed part of (4-bromophenyl)(4-(3-hydroxypropyl)phenyl)methanone remained, so more Dess-Martin periodinane (134 mg, 0.316 mmol) was added to the reaction mixture and it was stirred for an additional 3 h at 15° C. The reaction was quenched with saturated NaHCO$_3$ and saturated Na$_2$S$_2$O$_3$ (1:1, 30 mL) and the reaction was stirred for 30 minutes at 15° C. The reaction was extracted with CH$_2$Cl$_2$ (30 mL), the organic layer was washed with brine (40 mL), dried over anhydrous Na$_2$SO$_4$, filtered, and concentrated to dryness. The residue was purified by flash column chromatography (eluent: petroleum ether:ethyl acetate=100:0 to 12:88) to provide the title compound (120 mg, 45% yield) as a white solid. $^1$H NMR (400 MHz, CDCl$_3$): δ 9.84 (s, 1H), 7.75-7.69 (m, 2H), 7.68-7.60 (m, 4H), 7.31 (d, J=8.0 Hz, 2H), 3.09-2.99 (m, 2H), 2.89-2.80 (m, 2H).

Step D: 2-((1r,4r)-4-(2-(4-(4-Bromobenzoyl)phenethyl)-6-(phenylsulfonyl)imidazo[4,5-d]pyrrolo[2,3-b]pyridin-1(6H)-yl)cyclohexyl)acetonitrile. A solution of 3-(4-(4-bromobenzoyl)phenyl)propanal (303 mg, 0.956 mmol), 2-((1r,4r)-4-((5-nitro-1-(phenylsulfonyl)-1H-pyrrolo[2,3-b]pyridin-4-yl)amino)cyclohexyl)acetonitrile (Intermediate 1, 280 mg, 0.637 mmol), sodium hydrosulfite (555 mg, 3.19 mmol), DMSO (2.5 mL), MeOH (7.5 mL), and water (5 mL) was stirred for 7 h at 100° C. in a microwave tube. The mixture was concentrated to dryness, washed with water (10 mL×3), filtered, and dried under reduced pressure. The residue was purified by flash column chromatography to provide the title compound (360 mg, 74% yield). MS (ESI): mass calcd. for $C_{37}H_{32}BrN_5O_3S$, 705.14; m/z found, 707.9 [M+H]$^+$.

Step E: 2-((1r,4r)-4-(6-(Phenylsulfonyl)-2-(4-(4-((trimethylsilyl)ethynyl)benzoyl)phenethyl)imidazo[4,5-d]pyrrolo[2,3-b]pyridin-1(6H)-yl)cyclohexyl)acetonitrile. Trimethylsilylacetylene (348 mg, 3.54 mmol) was added to a solution of 2-((1r,4r)-4-(2-(4-(4-bromobenzoyl)phenethyl)-6-(phenyl sulfonyl)imidazo[4,5-d]pyrrolo[2,3-b]pyridin-1

(6H)-yl)cyclohexyl)acetonitrile (250 mg, 0.35 mmol), CuI (8.1 mg, 0.042 mmol), tetrakis(triphenylphosphine)palladium(0) (82 mg, 0.071 mmol), triethylamine (430 mg, 4.25 mmol), and DMF (6 mL) under Ar in a microwave vessel. The vessel was capped and irradiated at 110° C. for 40 minutes. The reaction mixture was concentrated to dryness and purified by flash column chromatography (eluent: petroleum ether:ethyl acetate=100:0 to 42:58) to provide the title compound. MS (ESI): mass calcd. for $C_{42}H_{41}N_5O_3SSi$, 723.27; m/z found, 724.3 $[M+H]^+$.

Step F: 2-((1r,4r)-4-(2-(4-(4-Ethynylbenzoyl)phenethyl) imidazo[4,5-d]pyrrolo[2,3-b]pyridin-1(6H)-yl)cyclohexyl) acetonitrile. The title compound (50 mg, 43% yield) was prepared as a light yellow solid using conditions analogous to those described in Example 1, Step B using 2-((1r,4r)-4-(6-(phenylsulfonyl)-2-(4-(4-((trimethylsilyl)ethynyl)benzoyl)phenethyl)imidazo[4,5-d]pyrrolo[2,3-b]pyridin-1(6H)-yl)cyclohexyl)acetonitrile (220 mg, 0.220 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The compound was initially purified by flash column chromatography (eluent: petroleum ether:ethyl acetate=100:0 to 0:100). The compound was further purified by preparative HPLC with a Boston Green ODS 150 mm×30 mm, 5 m column (eluent: 30% to 60% (v/v) $CH_3CN$ and $H_2O$ with 0.1% TFA). MS (ESI): mass calcd. for $C_{33}H_{29}N_5O$, 511.2; m/z found, 512.0 $[M+H]^+$. $^1H$ NMR (400 MHz, $CDCl_3$): δ 10.59 (s, 1H), 8.81 (s, 1H), 7.78-7.71 (m, 4H), 7.59 (d, J=8.0 Hz, 2H), 7.47-7.35 (m, 3H), 6.69 (s, 1H), 4.46-4.17 (m, 1H), 3.49-3.36 (m, 2H), 3.35-3.27 (m, 2H), 3.25 (s, 1H), 2.69-2.47 (m, 2H), 2.44 (d, J=6.0 Hz, 2H), 2.23-2.12 (m, 2H), 2.11-2.02 (m, 1H), 1.97-1.82 (m, 2H), 1.54-1.37 (m, 2H).

Example 171 Synthesis and Characterization 1-((1-((1r,4r)-4-(Cyanomethyl)cyclohexyl)-1,6-dihydroimidazo[4,5-d]pyrrolo[2,3-b]pyridin-2-yl) methyl)-3-isopropylurea

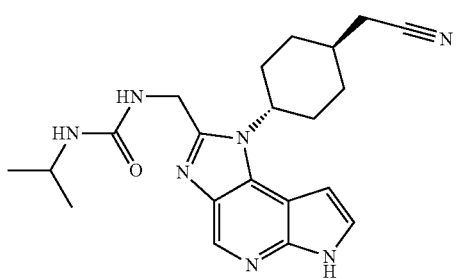 [SMILES: CC(C)NC(=O)NCc1nc2cnc3[nH]ccc3c2n1[C@H]1CC[C@H](CC#N)CC1]

Step A: 1-((1-((1r,4r)-4-(Cyanomethyl)cyclohexyl)-6-(phenylsulfonyl)-1,6-dihydroimidazo[4,5-d]pyrrolo[2,3-b] pyridin-2-yl)methyl)-3-isopropylurea. A solution of 2-((1r,4r)-4-(2-(aminomethyl)-6-(phenyl sulfonyl)imidazo[4,5-d] pyrrolo[2,3-b]pyridin-1(6H)-yl)cyclohexyl)acetonitrile (Intermediate 5, 136 mg, 0.242 mmol), 2-isocyanatopropane (110 mg, 1.29 mmol), and triethylamine (0.168 mL, 1.21 mmol) in DMF (1.5 mL) was stirred at room temperature for 24 h. The reaction was concentrated to dryness and the residue was purified by flash column chromatography to provide the title compound (200 mg). MS (ESI): mass calcd. for $C_{27}H_{31}N_7O_3S$, 533.2; m/z found, 534.3 $[M+H]^+$.

Step B: 1-((1-((1r,4r)-4-(Cyanomethyl)cyclohexyl)-1,6-dihydroimidazo[4,5-d]pyrrolo[2,3-b]pyridin-2-yl)methyl)-3-isopropylurea. A mixture of 1-((1-((1r,4r)-4-(cyanomethyl)cyclohexyl)-6-(phenylsulfonyl)-1,6-dihydroimidazo [4,5-d]pyrrolo[2,3-b]pyridin-2-yl)methyl)-3-isopropylurea (200 mg, 0.370 mmol), 3 M NaOH (aq) (0.25 mL, 0.75 mmol), THF (1 mL), and MeOH (1 mL) was stirred at RT for 15 h and concentrated in vacuo. The residue was partitioned between $CH_2Cl_2$ and water. The organic layer was dried over $Na_2SO_4$, filtered, concentrated, and purified by flash column chromatography (2-10% MeOH in $CH_2Cl_2$) to give the title compound as a white solid (54 mg, 37%). MS (ESI): mass calcd. for $C_{21}H_{27}N_7O$, 393.2; m/z found, 394.2 $[M+H]^+$. $^1H$ NMR (400 MHz, $CDCl_3$) δ 12.19 (br s, 1H), 8.72 (s, 1H), 7.44 (t, J=2.8 Hz, 1H), 6.67 (br s, 2H), 5.29 (br s, 1H), 4.82 (d, J=5.6 Hz, 2H), 4.66 (br s, 1H), 3.95-3.83 (m, 1H), 2.74 (br s, 1H), 2.46 (br s, 2H), 2.40-2.25 (m, 2H), 2.08 (br d, J=11.6 Hz, 2H), 1.97 (br s, 2H), 1.43-1.25 (m, 2H), 1.07 (d, J=6.6 Hz, 6H).

Example 172 Synthesis and Characterization 1-((1r,4r)-4-(Cyanomethyl)cyclohexyl)-N-isopropyl-1,6-dihydroimidazo[4,5-d]pyrrolo[2,3-b]pyridine-2-carboxamide

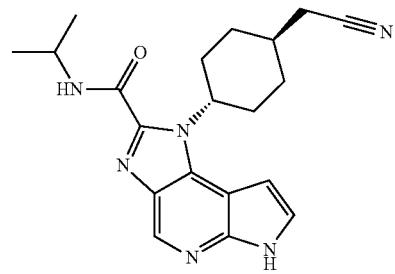 [SMILES: CC(C)NC(=O)c1nc2cnc3[nH]ccc3c2n1[C@H]1CC[C@H](CC#N)CC1]

The title compound (28 mg, 38% yield) was prepared using analogous conditions as described in Example 50, Step A using isopropylamine instead of 3-phenylpyrrolin-3-ol. MS (ESI): mass calcd. for $C_{20}H_{24}N_6O$, 364.2; m/z found, 365.2 $[M+H]^+$. $^1H$ NMR (500 MHz, $CDCl_3$) δ 10.22 (s, 1H), 8.82 (s, 1H), 7.65 (d, J=8.2 Hz, 1H), 7.45 (dd, J=3.5, 2.6 Hz, 1H), 6.81 (dd, J=3.6, 2.0 Hz, 1H), 6.29-5.84 (m, 1H), 4.41-4.17 (m, 1H), 2.77-2.52 (m, 2H), 2.40 (d, J=6.6 Hz, 2H), 2.23-2.00 (m, 5H), 1.58-1.43 (m, 2H), 1.34 (d, J=6.6 Hz, 6H).

Example 173 Synthesis and Characterization 1-((1r,4r)-4-(Cyanomethyl)cyclohexyl)-N-(3-methoxypropyl)-1,6-dihydroimidazo[4,5-d]pyrrolo[2,3-b]pyridine-2-carboxamide

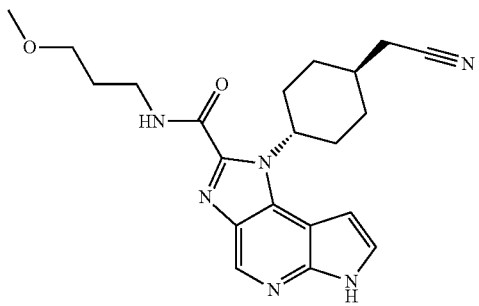 [SMILES: COCCCNC(=O)c1nc2cnc3[nH]ccc3c2n1[C@H]1CC[C@H](CC#N)CC1]

The title compound (30 mg, 37% yield) was prepared using analogous conditions as described in Example 50, Step A using 3-methoxypropan-1-amine instead of 3-phenylpyrrolin-3-ol. MS (ESI): mass calcd. for $C_{21}H_{26}N_6O_2$, 394.2; m/z found, 395.2 [M+H]$^+$. $^1$H NMR (500 MHz, CDCl$_3$): δ 11.38 (s, 1H), 8.85 (s, 1H), 8.31-8.10 (m, 1H), 7.59-7.35 (m, 1H), 6.90-6.71 (m, 1H), 6.31-5.63 (m, 1H), 3.77-3.47 (m, 4H), 3.41 (s, 3H), 2.78-2.51 (m, 2H), 2.40 (d, J=6.6 Hz, 2H), 2.26-2.01 (m, 5H), 2.02-1.88 (m, 2H), 1.61-1.38 (m, 2H).

Example 174 Synthesis and Characterization 1-((1r,4r)-4-(cyanomethyl)cyclohexyl)-N-(cyclopropylmethyl)-1,6-dihydroimidazo[4,5-d]pyrrolo[2,3-b]pyridine-2-carboxamide

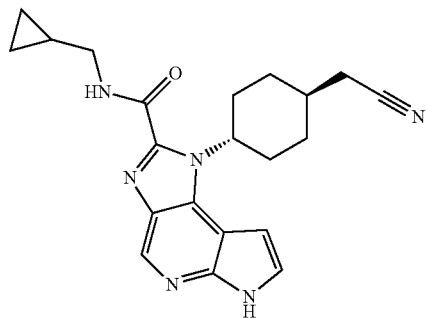 [SMILES: N#CC[C@H]1CC[C@H](n2c(C(=O)NCC3CC3)nc3cnc4[nH]ccc4c32)CC1]

The title compound (17 mg, 55% yield) was prepared using analogous conditions as described in Example 50, Step A and using cyclopropylmethylamine instead of 3-phenylpyrrolin-3-ol. MS (ESI): mass calcd. for $C_{21}H_{24}N_6O$, 376.2; m/z found, 377.2 [M+H]$^+$. $^1$H NMR (500 MHz, CDCl$_3$) δ 10.52 (s, 1H), 8.84 (s, 1H), 7.93 (t, J=5.7 Hz, 1H), 7.66-7.40 (m, 1H), 6.82 (d, J=3.5 Hz, 1H), 6.33-5.84 (m, 1H), 3.35 (dd, J=7.2, 5.7 Hz, 2H), 2.73-2.55 (m, 2H), 2.40 (d, J=6.6 Hz, 2H), 2.25-2.00 (m, 5H), 1.57-1.41 (m, 2H), 1.18-1.03 (m, 1H), 0.69-0.56 (m, 2H), 0.39-0.25 (m, 2H).

Example 175 Synthesis and Characterization 1-((1r,4r)-4-(Cyanomethyl)cyclohexyl)-N-cyclopropyl-1,6-dihydroimidazo[4,5-d]pyrrolo[2,3-b]pyridine-2-carboxamide

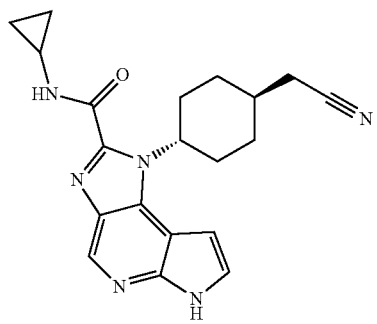 [SMILES: N#CC[C@H]1CC[C@H](n2c(C(=O)NC3CC3)nc3cnc4[nH]ccc4c32)CC1]

The title compound (34 mg, 47% yield) was prepared using analogous conditions as described in Example 50, Step A and using cyclopropylamine instead of 3-phenylpyrrolin-3-ol MS (ESI): mass calcd. for $C_{20}H_{22}N_6O$, 362.19; m/z found, 363.2 [M+H]$^+$. $^1$H NMR (500 MHz, CDCl$_3$) δ 10.77 (s, 1H), 8.81 (s, 1H), 7.90 (d, J=3.5 Hz, 1H), 7.59-7.39 (m, 1H), 6.96-6.71 (m, 1H), 6.43-5.80 (m, 1H), 3.03-2.80 (m, 1H), 2.74-2.46 (m, 2H), 2.40 (d, J=6.6 Hz, 2H), 2.25-2.00 (m, 5H), 1.61-1.38 (m, 2H), 1.05-0.86 (m, 2H), 0.81-0.62 (m, 2H).

Example 176 Synthesis and Characterization 2-((1r,4r)-4-(2-(4-Methoxypiperidine-1-carbonyl)imidazo[4,5-d]pyrrolo[2,3-b]pyridin-1(6H)-yl)cyclohexyl)acetonitrile

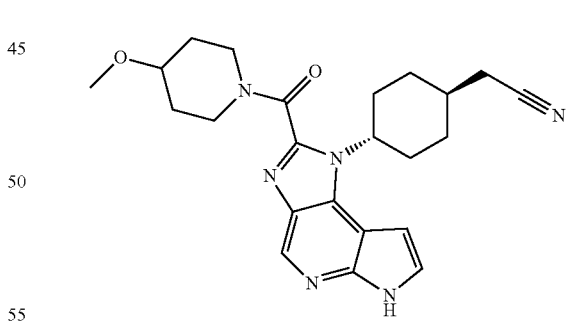

The title compound (30 mg, 35% yield) was prepared using analogous conditions as described in Example 50, Step A, and using 4-methoxypiperidine instead of 3-phenylpyrrolin-3-ol. MS (ESI): mass calcd. for $C_{23}H_{28}N_6O_2$, 420.2; m/z found, 421.3 [M+H]$^+$. $^1$H NMR (500 MHz, CDCl$_3$) δ 12.76-12.12 (m, 1H), 8.81 (s, 1H), 7.64 (d, J=3.3 Hz, 1H), 6.86 (d, J=3.4 Hz, 1H), 5.35-5.23 (m, 1H), 4.79-4.59 (m, 1H), 4.10-3.89 (m, 1H), 3.89-3.68 (m, 2H), 3.50 (s, 4H), 2.55-2.36 (m, 4H), 2.23-2.09 (m, 5H), 2.11-1.91 (m, 2H), 1.91-1.69 (m, 2H), 1.59-1.38 (m, 2H).

Example 177 Synthesis and Characterization 1-(1-((1r,4r)-4-(Cyanomethyl)cyclohexyl)-1,6-dihydroimidazo[4,5-d]pyrrolo[2,3-b]pyridine-2-carbonyl)piperidine-4-carbonitrile

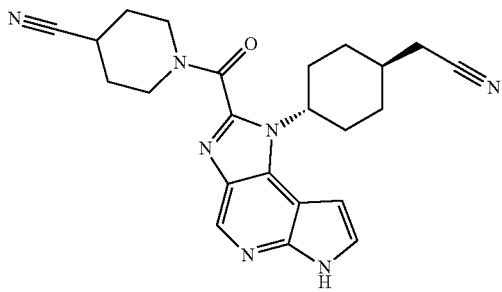 [SMILES: N#CC[C@H]1CC[C@H](n2c(C(=O)N3CCC(C#N)CC3)nc3cnc4[nH]ccc4c32)CC1]

The title compound (25 mg, 30% yield) was prepared using analogous conditions as described in Example 50, Step A and using piperidine-4-carbonitrile instead of 3-phenylpyrrolin-3-ol. MS (ESI): mass calcd. for $C_{23}H_{25}N_7O$, 415.2; m/z found, 416.2 [M+H]$^+$. $^1$H NMR (400 MHz, CDCl$_3$) δ 10.22 (s, 1H), 8.75 (s, 1H), 7.46-7.31 (m, 1H), 6.78-6.60 (m, 1H), 4.84-4.51 (m, 1H), 4.01-3.63 (m, 4H), 3.06-2.88 (m, 1H), 2.47-2.29 (m, 4H), 2.16-1.81 (m, 9H), 1.52-1.31 (m, 2H).

Example 178 Synthesis and Characterization 1-((1r,4r)-4-(Cyanomethyl)cyclohexyl)-N-(tetrahydro-2H-pyran-4-yl)-1,6-dihydroimidazo[4,5-d]pyrrolo[2,3-b]pyridine-2-carboxamide

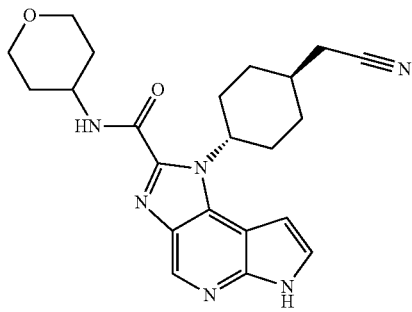 [SMILES: N#CC[C@H]1CC[C@H](n2c(C(=O)NC3CCOCC3)nc3cnc4[nH]ccc4c32)CC1]

The title compound (40 mg, 48% yield) was prepared using analogous conditions as described in Example 50, Step A and using tetrahydro-2H-pyran-4-amine in place of 3-phenylpyrrolin-3-ol. MS (ESI): mass calcd. for $C_{22}H_{26}N_6O_2$, 406.2; m/z found, 407.2 [M+H]$^+$. $^1$H NMR (500 MHz, CDCl$_3$) δ 10.72 (s, 1H), 8.77 (s, 1H), 7.72 (d, J=8.2 Hz, 1H), 7.40 (d, J=3.5 Hz, 1H), 6.75 (d, J=3.6 Hz, 1H), 6.36-5.51 (m, 1H), 4.36-3.79 (m, 3H), 3.56-3.36 (m, 2H), 2.75-2.46 (m, 2H), 2.33 (d, J=6.6 Hz, 2H), 2.23-1.92 (m, 7H), 1.76-1.53 (m, 2H), 1.55-1.24 (m, 2H).

Example 179 Synthesis and Characterization 1-((1r,4r)-4-(Cyanomethyl)cyclohexyl)-N-(1-methoxypropan-2-yl)-1,6-dihydroimidazo[4,5-d]pyrrolo[2,3-b]pyridine-2-carboxamide

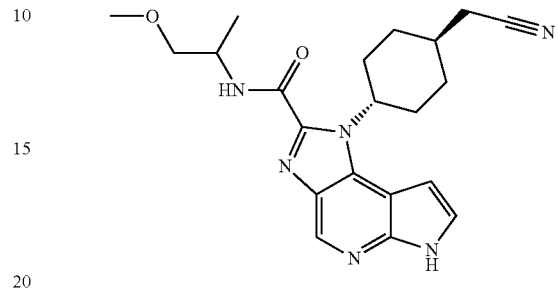

The title compound (21 mg, 16% yield) was prepared using analogous conditions as described in Example 50, Step A and using 1-methoxypropan-2-amine instead of 3-phenylpyrrolin-3-ol. MS (ESI): mass calcd. for $C_{21}H_{26}N_6O_2$, 394.2; m/z found, 395.2 [M+H]$^+$. $^1$H NMR (500 MHz, CDCl$_3$): δ 9.75 (s, 1H), 8.82 (s, 1H), 7.90 (d, J=8.5 Hz, 1H), 7.47-7.37 (m, 1H), 6.90-6.76 (m, 1H), 6.25-5.75 (m, 1H), 4.43-4.23 (m, 1H), 3.51 (dd, J=4.8, 1.9 Hz, 2H), 3.43 (s, 3H), 2.76-2.54 (m, 2H), 2.40 (d, J=6.6 Hz, 2H), 2.23-2.01 (m, 5H), 1.58-1.42 (m, 2H), 1.36 (d, J=6.8 Hz, 3H).

Example 180 Synthesis and Characterization 2-((1r,4r)-4-(2-(Morpholine-4-carbonyl)imidazo[4,5-d]pyrrolo[2,3-b]pyridin-1(6H)-yl)cyclohexyl)acetonitrile

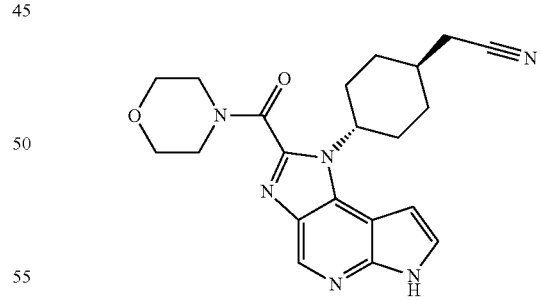

The title compound (21 mg, 26% yield) was prepared using analogous conditions as described in Example 50, Step A using 4-morpholine instead of 3-phenylpyrrolin-3-ol. MS (ESI): mass calcd. for $C_{21}H_{24}N_6O_2$, 392.2; m/z found, 393.2 [M+H]$^+$. $^1$H NMR (500 MHz, CDCl$_3$) δ 12.31 (s, 1H), 8.83 (s, 1H), 7.66 (d, J=3.5 Hz, 1H), 7.01-6.56 (m, 1H), 4.95-4.64 (m, 1H), 3.99-3.67 (m, 8H), 2.61-2.35 (m, 4H), 2.31-1.91 (m, 5H), 1.68-1.34 (m, 2H).

Example 181: Synthesis and Characterization 2-((1r,4r)-4-(2-(4-Hydroxypiperidine-1-carbonyl)imidazo[4,5-d]pyrrolo[2,3-b]pyridin-1(6H)-yl)cyclohexyl)acetonitrile

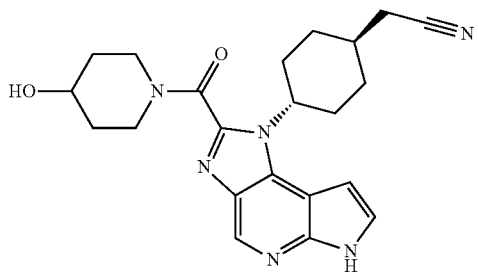 [SMILES: N#CC[C@H]1CC[C@H](n2c(C(=O)N3CCC(O)CC3)nc3cnc4[nH]ccc4c32)CC1]

The title compound (35 mg, 42% yield) was prepared using analogous conditions as described in Example 50, Step A and using 4-hydroxypiperidine instead of 3-phenylpyrrolin-3-ol. MS (ESI): mass calcd. for $C_{22}H_{26}N_6O_2$, 406.2; m/z found, 407.2 [M+H]$^+$. $^1$H NMR (500 MHz, CDCl$_3$) δ 11.09 (s, 1H), 8.82 (s, 1H), 7.46 (dd, J=3.6, 1.7 Hz, 1H), 6.74 (d, J=3.4 Hz, 1H), 4.81-4.59 (m, 1H), 4.36-4.19 (m, 1H), 4.16-4.03 (m, 1H), 4.01-3.86 (m, 1H), 3.64-3.43 (m, 2H), 2.58-1.92 (m, 12H), 1.82-1.61 (m, 2H), 1.57-1.34 (m, 2H).

Example 182 Synthesis and Characterization

Ethyl 2-(4-(1-((1r,4r)-4-(cyanomethyl)cyclohexyl)-1,6-dihydroimidazo[4,5-d]pyrrolo[2,3-b]pyridin-2-yl)-1H-pyrazol-1-yl)acetate

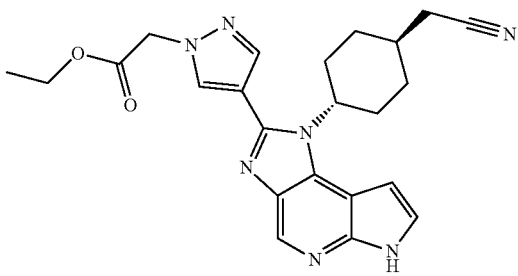 [SMILES: CCOC(=O)Cn1cc(-c2nc3cnc4[nH]ccc4c3n2[C@H]2CC[C@H](CC#N)CC2)cn1]

Step A: To a 10 mL microwave vial was added 2-((1r,4r)-4-(6-(Phenylsulfonyl)-2-(1H-pyrazol-4-yl)imidazo[4,5-d]pyrrolo[2,3-b]pyridin-1(6H)-yl)cyclohexyl)acetonitrile, as prepared in Example 123, Step A, (203 mg, 0.418 mmol) followed by ACN (1.00 mL), cesium carbonate (440 mg, 1.35 mmol), and ethyl bromoacetate (0.10 mL, 0.884 mmol). The vial was sealed and heated to 80° C. for 2 h. The contents were added on water/brine (1:1) then extracted with CH$_2$Cl$_2$ (2×40 mL). The organics were dried with Na$_2$SO$_4$ then conc to dryness. The crude material was purified by flash column chromatography (40 to 100% EA/hex) to provide the title compound (122 mg, 51%) as colorless residue. $^1$H NMR (500 MHz, CDCl$_3$) δ 8.89 (s, 1H), 8.29-8.19 (m, 2H), 7.97 (d, J=0.7 Hz, 1H), 7.86 (d, J=4.0 Hz, 1H), 7.80 (d, J=0.7 Hz, 1H), 7.62-7.53 (m, 1H), 7.53-7.43 (m, 2H), 6.86 (d, J=4.1 Hz, 1H), 5.02 (s, 2H), 4.72-4.57 (m, 1H), 4.29 (q, J=7.1 Hz, 2H), 2.52-2.37 (m, 4H), 2.23-2.13 (m, 2H), 2.10-1.97 (m, 2H), 1.49-1.35 (m, 2H), 1.32 (t, J=7.1 Hz, 3H).

Step B: Ethyl 2-(4-(1-((1r,4r)-4-(cyanomethyl)cyclohexyl)-1,6-dihydroimidazo[4,5-d]pyrrolo[2,3-b]pyridin-2-yl)-1H-pyrazol-1-yl)acetate. The title compound was prepared using analogous conditions as described in Example 123, step C (16.0 mg, 17% yield). The residue was purified by flash column chromatography (24 g SiO$_2$, 0-5% 2 N NH$_3$-MeOH/EA) to afford the title compound MS (ESI): mass calcd. for $C_{23}H_{25}N_7O_2$, 431.2; m/z found, 432.2 [M+H]$^+$. $^1$H NMR (500 MHz, DMSO-d$_6$) δ 11.91 (s, 1H), 8.58 (s, 1H), 8.33 (s, 1H), 7.95 (s, 1H), 7.50 (t, J=3.1 Hz, 1H), 6.76 (dd, J=3.4, 1.8 Hz, 1H), 5.21 (s, 2H), 4.68-4.45 (m, 1H), 4.20 (q, J=7.1 Hz, 2H), 2.58 (d, J=6.2 Hz, 2H), 2.53-2.40 (m, 2H), 2.14-1.90 (m, 5H), 1.48-1.30 (m, 2H), 1.24 (t, J=7.1 Hz, 3H).

Example 183 Synthesis and Characterization 2-((1r,4r)-4-(2-(2,4-dimethyloxazol-5-yl)imidazo[4,5-d]pyrrolo[2,3-b]pyridin-1(6H)-yl)cyclohexyl)acetonitrile

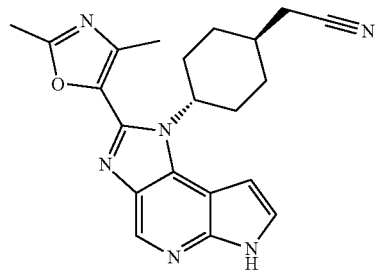 [SMILES: Cc1nc(C)c(-c2nc3cnc4[nH]ccc4c3n2[C@H]2CC[C@H](CC#N)CC2)o1]

Step A: 2-((1r,4r)-4-(2-(2,4-dimethyloxazol-5-yl)-6-(phenylsulfonyl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 192 mg, 0.437 mmol) and 2,4-dimethyloxazole-5-carbaldehyde (140 mg, 1.07 mmol) as solids. DMSO (2.20 mL), MeOH (2.20 mL), and distilled water (1.10 mL) were added next. Then sodium hydrosulfite (229 mg, 1.32 mmol) was added as a solid and the vial sealed. The vial was placed into a pre-heated 100° C. heating block for 1 h. The reaction was cooled to room temperature and was poured onto 30 mL of water, resulting in the formation of a precipitate. The mixture was stirred for 15 minutes, and then the solids were collected by filtration and dried under high vacuum for 1 h to provide the title compound (169 mg, 75.2% yield). MS (ESI): mass calcd. for $C_{27}H_{26}N_6O_3S$, 514.2; m/z found, 515.2 [M+H]$^+$.

Step B: 2-((1r,4r)-4-(2-(2,4-dimethyloxazol-5-yl)imidazo[4,5-d]pyrrolo[2,3-b]pyridin-1(6H)-yl)cyclohexyl)acetonitrile. The title compound (16.3 mg, 13% yield) was prepared using conditions analogous to those described in Example 2, Step B using 2-((1r,4r)-4-(2-(2,4-dimethyloxazol-5-yl)imidazo[4,5-d]pyrrolo[2,3-b]pyridin-1(6H)-yl)cyclohexyl)acetonitrile (169 mg, 0.33 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The residue was purified by flash column chromatography (12 g SiO$_2$, 0-8%

243

2 N NH$_3$-MeOH/EA over 12 CV) to afford the title compound. MS (ESI): mass calcd. for C$_{21}$H$_{22}$N$_6$O, 374.2; m/z found, 375.2 [M+H]$^+$. $^1$H NMR (500 MHz, DMSO-d$_6$) δ 12.01 (s, 1H), 8.65 (s, 1H), 7.53 (d, J=3.4 Hz, 1H), 6.80 (d, J=3.5 Hz, 1H), 4.70-4.54 (m, 1H), 2.55 (d, J=6.2 Hz, 2H), 2.52 (s, 3H), 2.39-2.29 (m, 5H), 2.08-1.86 (m, 5H), 1.38 (tt, J=13.6, 7.4 Hz, 2H).

Example 184 Synthesis and Characterization 2-((1r,4r)-4-(2-(2,4-dimethylthiazol-5-yl)imidazo[4,5-d]pyrrolo[2,3-b]pyridin-1(6H)-yl)cyclohexyl)acetonitrile

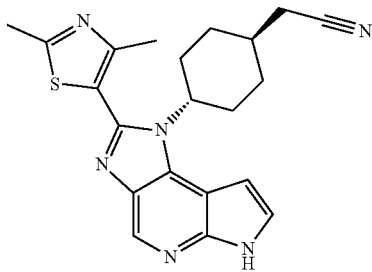 [SMILES: Cc1nc(C)c(-c2nc3cnc4[nH]ccc4c3n2[C@H]2CC[C@H](CC#N)CC2)s1]

Step A: 2-((1r,4r)-4-(2-(2,4-dimethylthiazol-5-yl)-6-(phenylsulfonyl)imidazo[4,5-d]pyrrolo[2,3-b]pyridin-1(6H)-yl)cyclohexyl)acetonitrile. To a 20 mL microwave vial were added 2-((1r,4r)-4-((5-nitro-1-(phenylsulfonyl)-1H-pyrrolo[2,3-b]pyridin-4-yl)amino)cyclohexyl)acetonitrile (Intermediate 1, 201 mg, 0.457 mmol) and 2,4-dimethyl-1,3-thioxazole-5-carbaldehyde (158 mg, 1.09 mmol) as solids. DMSO (2.10 mL), MeOH (2.10 mL), and distilled water (1.10 mL) were added next. Then sodium hydrosulfite (250 mg, 1.44 mmol) was added as a solid and the vial sealed. The vial was placed into a pre-heated 100° C. heating block for 1 h. The reaction was cooled to room temperature and was poured onto 60 mL of water, resulting in the formation of a precipitate. The mixture was stirred for 15 minutes, and then the solids were collected by filtration and dried under high vacuum for 1 h to provide the title compound (205 mg, 84% yield) as a faint yellow powder. MS (ESI): mass calcd. for C$_{27}$H$_{26}$N$_6$O$_2$S$_2$, 530.2; m/z found, 531.1 [M+H]$^+$.

Step B: 2-((1r,4r)-4-(2-(2,4-dimethylthiazol-5-yl)imidazo[4,5-d]pyrrolo[2,3-b]pyridin-1(6H)-yl)cyclohexyl)acetonitrile. The title compound (33.0 mg, 21% yield) was prepared using conditions analogous to those described in Example 1, Step B using 2-((1r,4r)-4-(2-(2,4-dimethylthiazol-5-yl)-6-(phenylsulfonyl)imidazo[4,5-d]pyrrolo[2,3-b]pyridin-1(6H)-yl)cyclohexyl)acetonitrile (205 mg, 0.39 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The residue was purified by flash column chromatography (24 g SiO$_2$, 0-10% 2 N NH$_3$-MeOH/EA) to afford the title compound. MS (ESI): mass calcd. for C$_{21}$H$_{22}$N$_6$S, 390.2; m/z found, 391.2 [M+H]$^+$. $^1$H NMR (500 MHz, DMSO-d$_6$) δ 12.00 (s, 1H), 8.64 (s, 1H), 7.53 (d, J=3.4 Hz, 1H), 6.78 (d, J=3.5 Hz, 1H), 4.50-4.10 (m, 1H), 2.73 (s, 3H), 2.53 (d, J=6.2 Hz, 2H), 2.45-2.34 (m, 2H), 2.32 (s, 3H), 2.09-1.85 (m, 5H), 1.40-1.23 (m, 2H).

244

Example 185 Synthesis and Characterization 2-(4-(1-((1r,4r)-4-(Cyanomethyl)cyclohexyl)-1,6-dihydroimidazo[4,5-d]pyrrolo[2,3-b]pyridin-2-yl)-1H-pyrazol-1-yl)-N-cyclopropylacetamide

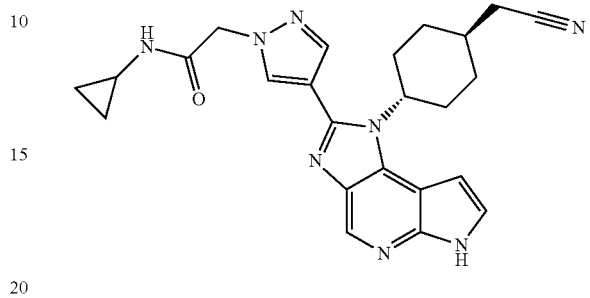

Step A: 2-(4-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-1H-pyrazol-1-yl)-N-cyclopropylacetamide. To a 10 mL microwave vial was added 2-((1r,4r)-4-(6-(phenylsulfonyl)-2-(1H-pyrazol-4-yl)imidazo[4,5-d]pyrrolo[2,3-b]pyridin-1(6H)-yl)cyclohexyl)acetonitrile, as prepared in Example 123, Step A (197 mg, 0.406 mmol) as a solid, followed by the addition of CH$_3$CN (1 mL), Cs$_2$CO$_3$ (423 mg, 1.81 mmol), and 2-bromo-N-cyclopropylacetamide (141 mg, 0.792 mmol). The vial was sealed and contents heated to 80° C. using a heating block for 1 h and then cooled the reaction to room temperature. The reaction was diluted with CH$_2$Cl$_2$ (30 mL) and poured into water (25 mL). The organic layer was removed and the aqueous layer was extracted with CH$_2$Cl$_2$ (30 mL). The combined organics were dried over anhydrous Na$_2$SO$_4$ and concentrated to dryness. The residue was purified by flash column chromatography (24 g SiO$_2$, 0-10% 2 N NH$_3$-MeOH/EA) to afford the title compound (103 mg, 43% yield) as a dark brown solid. No mass detectable by ESI MS.

Step B: 2-(4-(1-((1r,4r)-4-(Cyanomethyl)cyclohexyl)-1,6-dihydroimidazo[4,5-d]pyrrolo[2,3-b]pyridin-2-yl)-1H-pyrazol-1-yl)-N-cyclopropylacetamide. The title compound (6.4 mg, 8% yield) was prepared using conditions analogous to those described in Example 1, Step B using 2-(4-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-1H-pyrazol-1-yl)-N-cyclopropylacetamide (103 mg, 0.18 mmol) instead of 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. The residue was purified by flash column chromatography (12 g SiO$_2$, 0-10% 2 N NH$_3$-MeOH/EA over 12 CV) to afford the title compound. MS (ESI): mass calcd. for C$_{24}$H$_{26}$N$_8$O, 442.2; m/z found, 443.3 [M+H]$^+$. $^1$H NMR (500 MHz, DMSO-d$_6$): δ 11.90 (s, 1H), 8.57 (s, 1H), 8.35 (d, J=4.2 Hz, 1H), 8.26 (d, J=0.8 Hz, 1H), 7.90 (d, J=0.8 Hz, 1H), 7.50 (t, J=3.0 Hz, 1H), 6.80-6.72 (m, 1H), 4.86 (s, 2H), 4.68-4.49 (m, 1H), 2.75-2.63 (m, 1H), 2.57 (d, J=6.4 Hz, 2H), 2.50-2.40 (m, 2H), 2.18-1.92 (m, 5H), 1.50-1.33 (m, 2H), 0.74-0.62 (m, 2H), 0.56-0.42 (m, 2H).

Example 186 Synthesis and Characterization 2-((1r,4r)-4-(2-(2-aminopyridin-3-yl)imidazo[4,5-d]pyrrolo[2,3-b]pyridin-1(6H)-yl)cyclohexyl)acetonitrile

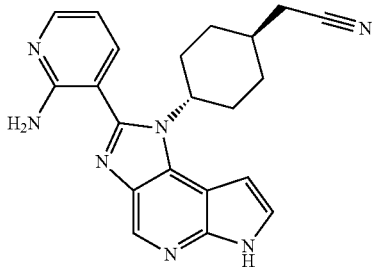 [SMILES: N#CC[C@H]1CC[C@H](n2c(-c3cccnc3N)nc3cnc4[nH]ccc4c32)CC1]

The title compound (27 mg, 15% yield) was prepared using analogous conditions in Example 51 and using 2-aminonicotinaldehyde instead of aminopyrimidine-5-carbaldehyde. MS (ESI): mass calcd. for $C_{21}H_{21}N_7$, 371.2; m/z found, 372.2 [M+H]$^+$. $^1$H NMR (500 MHz, Methanol-d4) δ 8.65 (s, 1H), 8.27-8.10 (m, 1H), 7.80-7.62 (m, 1H), 7.59-7.41 (m, 1H), 7.00-6.80 (m, 2H), 4.39-4.22 (m, 1H), 2.74-2.40 (m, 4H), 2.20-1.92 (m, 5H), 1.44-1.21 (m, 2H).

Example 187 Synthesis and Characterization 2-((1r,4r)-4-(2-(1-(2-Hydroxy-2-methylpropyl)-1H-pyrazol-4-yl)imidazo[4,5-d]pyrrolo[2,3-b]pyridin-1(6H)-yl)cyclohexyl)acetonitrile

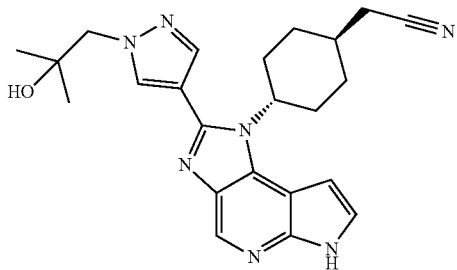 [SMILES: CC(C)(O)Cn1cc(-c2nc3cnc4[nH]ccc4c3n2[C@H]2CC[C@H](CC#N)CC2)cn1]

Step A: 2-((1r,4r)-4-(2-(1-(2-Hydroxy-2-methylpropyl)-1H-pyrazol-4-yl)-6-(phenyl sulfonyl)imidazo[4,5-d]pyrrolo[2,3-b]pyridin-1(6H)-yl)cyclohexyl)acetonitrile. To a 10 mL microwave vial was charged 2-((1r,4r)-4-(6-(phenylsulfonyl)-2-(1H-pyrazol-4-yl)imidazo[4,5-d]pyrrolo[2,3-b]pyridin-1(6H)-yl)cyclohexyl)acetonitrile, as prepared in Example 123, Step A, (227 mg, 0.467 mmol) as a solid followed by DMF (1 mL), Cs$_2$CO$_3$ (457 mg, 1.40 mmol), and isobutylene oxide (0.13 mL, 1.5 mmol). The vial was sealed and the contents heated to 110° C. for 30 minutes using a microwave reactor. The reaction was poured into 30 mL water with vigorous stirring causing a precipitated to form. The solution was stirred for 30 minutes, then the solids were collected by filtration. The solids were dried open to air for 30 minutes, then further under high vacuum overnight. The solid was purified by flash column chromatography (40 g SiO$_2$, 0-6% 2N NH$_3$-MeOH/EA) to provide the title compound (99 mg, 38% yield) as an off white solid. MS (ESI): mass calcd. for $C_{29}H_{31}N_7O_3S$, 557.2; m/z found, 558.3 [M+H]$^+$.

Step B: 2-((1r,4r)-4-(2-(1-(2-Hydroxy-2-methylpropyl)-1H-pyrazol-4-yl)imidazo[4,5-d]pyrrolo[2,3-b]pyridin-1(6H)-yl)cyclohexyl)acetonitrile. The title compound (52 mg, 68% yield) was prepared using conditions analogous to those described in Example 1, Step B using 2-((1r,4r)-4-(2-(1-(2-Hydroxy-2-methylpropyl)-1H-pyrazol-4-yl)-6-(phenylsulfonyl)imidazo[4,5-d]pyrrolo[2,3-b]pyridin-1(6H)-yl)cyclohexyl)acetonitrile (99 mg, 0.18 mmol) instead of 2-(1-((1r,4r)-4-(Cyanomethyl)cyclohexyl)-6-(phenyl sulfonyl)-1,6-dihydroimidazo[4,5-d]pyrrolo[2,3-b]pyridin-2-yl)-N-(2-hydroxy-2-methylpropyl)acetamide. The residue was purified by flash column chromatography (24 g SiO$_2$, 0-10% 2 N NH$_3$-MeOH/EA over 12 CV) to afford the title compound. MS (ESI): mass calcd. for $C_{23}H_{27}N_7O$, 417.2; m/z found, 418.3 [M+H]$^+$. $^1$H NMR (500 MHz, DMSO-d$_6$): δ 11.90 (s, 1H), 8.57 (s, 1H), 8.18 (d, J=0.8 Hz, 1H), 7.88 (d, J=0.8 Hz, 1H), 7.50 (t, J=3.0 Hz, 1H), 6.76 (dd, J=3.5, 1.9 Hz, 1H), 4.79 (s, 1H), 4.69-4.49 (m, 1H), 4.16 (s, 2H), 2.57 (d, J=6.2 Hz, 2H), 2.49-2.39 (m, 2H), 1.99 (m, J=12.1, 7.5 Hz, 5H), 1.45-1.25 (m, 2H), 1.14 (s, 6H).

Example 188 Synthesis and Characterization 2-(8-chloro-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide

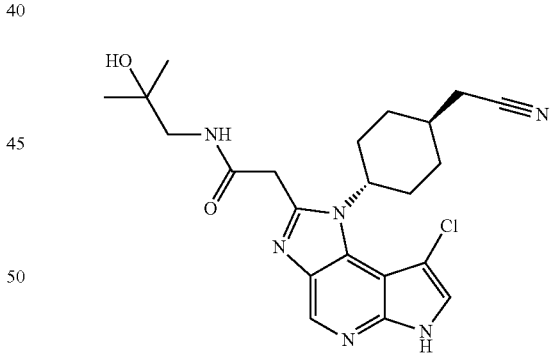

To a vial containing 2-(1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide, as prepared in Example 1, (52 mg, 0.13 mmol) was added CH$_3$CN (2.0 mL) and NaHCO$_3$ (62 mg, 0.74 mmol). 2-Chloro-1,3-bis(methoxycarbonyl)guanidine (54 mg, 0.26 mmol) was added as a solution in CH$_3$CN (2.0 mL) slowly over 5 minutes. The reaction mixture was stirred at rt under an atmosphere of N$_2$ for 25 min, then poured onto a vigorously stirred mixture of 0.1 N sodium thiosulfate (25 mL), saturated aqueous sodium bicarbonate (25 mL), and CH$_2$Cl$_2$ (50 mL). The organic layer was separated, and the aqueous layer was extracted with CH$_2$Cl$_2$ (2×50 mL). The combined organic layers were dried (MgSO$_4$) and concentrated. The residue was purified by flash column chromatography (2-10% MeOH/CH$_2$Cl$_2$). The resulting residue was dissolved in 3 CH$_2$Cl$_2$ (3 mL), the product was precipitated by the addition of hexanes (10 mL), and the resulting white solid was isolated by filtration to provide the title compound (35 mg, 62%). MS (ESI): mass calcd. for C$_{22}$H$_{27}$ClN$_6$O$_2$, 442.19; m/z found, 443.2 [M+H]-. $^1$H NMR (500 MHz, DMSO-d$_6$): δ 12.23 (s, 1H), 8.54 (s, 1H), 8.04-7.97 (m, 1H), 7.65 (d, J=2.9 Hz, 1H), 5.69-5.58 (m, 1H), 4.50 (s, 1H), 4.05 (s, 2H), 3.10 (d, J=5.9 Hz, 2H), 2.57 (d, J=6.3 Hz, 2H), 2.20-2.09 (m, 2H), 2.06-1.82 (m, 5H), 1.46-1.32 (m, 2H), 1.10 (s, 6H).

Example 189 Synthesis and Characterization 2-(8-bromo-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide

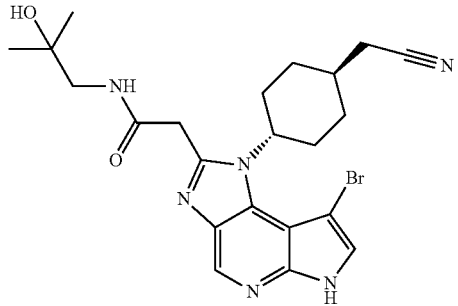 [SMILES: CC(C)(O)CNC(=O)Cc1nc2cnc3[nH]cc(Br)c3c2n1[C@H]1CC[C@H](CC#N)CC1]

To a vial containing 2-(1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide, as prepared in Example 1, (52 mg, 0.13 mmol) was added THF (20 mL) followed by N-bromosuccinimide (246 mg, 1.48 mmol) in a single portion. The reaction mixture was stirred under an atmosphere of N$_2$ at rt for 5 min, then poured onto a vigorously stirred mixture of 0.1 N sodium thiosulfate (25 mL) saturated aqueous sodium bicarbonate (25 mL) and CH$_2$Cl$_2$ (100 mL). The organic layer was separated, and the aqueous layer was extracted again with CH$_2$Cl$_2$ (100 mL). The combined organic layers were dried (MgSO$_4$) and concentrated. The residue was purified (FCC, 2-10% MeOH/CH$_2$Cl$_2$) and the fractions containing product were combined and concentrated. The residue was dissolved in 3 CH$_2$Cl$_2$ (3 mL), the product was precipitated by the addition of hexanes (10 mL), and the resulting white solid was isolate by filtration to provide the title compound (34.5 mg, 9%). MS (ESI): mass calcd. for C$_{22}$H$_{27}$BrN$_6$O$_2$, 486.14; m/z found, 487.1 [M+H]$^+$. $^1$H NMR (600 MHz, DMSO-d$_6$): δ 12.33 (s, 1H), 8.53 (s, 1H), 8.05-8.00 (m, 1H), 7.69 (d, J=2.7 Hz, 1H), 5.90-5.82 (m, 1H), 4.52 (s, 1H), 4.05 (s, 2H), 3.10 (d, J=5.9 Hz, 2H), 2.57 (d, J=6.3 Hz, 2H), 2.21-2.11 (m, 2H), 2.03-1.87 (m, 5H), 1.54-1.43 (m, 2H), 1.10 (s, 6H).

Example 190 Synthesis and Characterization 2-(1-((1r,4r)-4-(cyanomethyl)cyclohexyl)-8-methyl-1,6-dihydroimidazo[4,5-d]pyrrolo[2,3-b]pyridin-2-yl)-N-(2-hydroxy-2-methylpropyl)acetamide

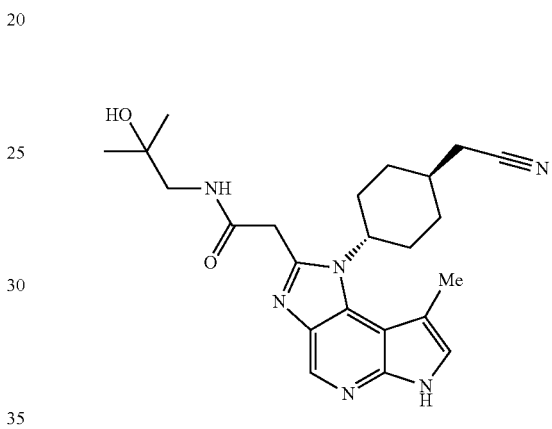

To a microwave vial containing 2-(8-bromo-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide, as prepared in Example 190, (52 mg, 0.13 mmol) was added (2-dicyclohexylphosphino-2',4',6'-triisopropyl-1,1'-biphenyl)[2-(2'-amino-1,1'-biphenyl)]palladium(II) methanesulfonate (5.6 mg, 0.0066 mmol) and 2-dicyclohexylphosphino-2',4',6'-triisopropylbiphenyl (3.1 mg, 0.0066 mmol). The vial was evacuated, treated with THF (4.0 ml) via syringe, then vented to N$_2$. Dimethyl zinc (68 μL, 0.66 mmol) was added via syringe, then the reaction mixture was heated at 75° C. for 30 min, then 85° C. for an additional 30 min. The reaction mixture was quenched with saturated aqueous sodium bicarbonate (10 mL) then extracted with CH$_2$Cl$_2$ (3×50 mL). The combined organic layers were dried (MgSO$_4$) and concentrated. The residue was purified (FCC 6-10% MeOH/CH$_2$Cl$_2$) to provide the title compound as a white solid. (29.5 mg, 53%). MS (ESI): mass calcd. for C$_{23}$H$_{30}$N$_6$O$_2$, 422.24; m/z found, 423.2 [M+H]$^+$. $^1$H NMR (600 MHz, DMSO-d$_6$): δ 11.51 (d, J=2.7 Hz, 1H), 8.43 (s, 1H), 8.00 (t, J=5.9 Hz, 1H), 7.27-7.19 (m, 1H), 5.09-4.98 (m, 1H), 4.52 (s, 1H), 4.03 (s, 2H), 3.10 (d, J=5.9 Hz, 2H), 2.60-2.55 (m, 5H), 2.21-2.10 (m, 2H), 2.05-1.85 (m, 5H), 1.40-1.29 (m, 2H), 1.09 (s, 6H).

Example 191 Synthesis and Characterization 2-(1-((1r,4r)-4-(Cyanomethyl)cyclohexyl)-7-methyl-1,6-dihydroimidazo[4,5-d]pyrrolo[2,3-b]pyridin-2-yl)-N-(2-hydroxy-2-methylpropyl)acetamide

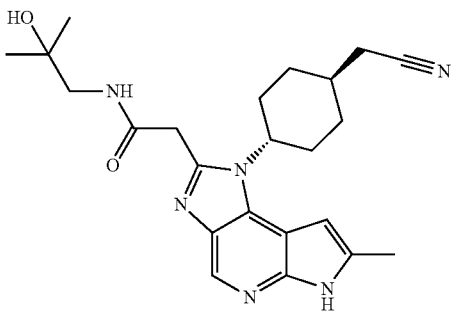 [SMILES: Cc1cc2c(ncc3nc(CC(=O)NCC(C)(C)O)n([C@H]4CC[C@H](CC#N)CC4)c32)[nH]1]

Step A: 4-Chloro-2-methyl-1-tosyl-1H-pyrrolo[2,3-b]pyridine. To a 250 mL round bottom flask was added NaH (60% dispersion in mineral oil, 1.39 g, 34.8 mmol) as a solid. The flask was evacuated and backfilled with $N_2$. DMF (25 mL) was added and the round bottom flask was placed into an ice/water bath and cooled to 3° C. A solution of 4-chloro-2-methyl-1H-pyrrolo[2,3-b]pyridine (4.07 g, 24.4 mmol) in DMF (34 mL) was then added slowly (over 45 minutes) via addition funnel and was stirred for 45 min. p-Toluenesulfonyl chloride (5.75 g, 29.9 mmol) was dissolved into DMF (33 mL) and the resulting solution was added dropwise over 20 minutes. Reaction progress was monitored by LCMS analysis. NOTE: attempts to add additional quantities of TsCl did not push reaction conversion further. The reaction was poured slowly onto 500 mL ice water while stirring vigorously, which caused a precipitate to form. Next was added 1 M NaOH (35 mL) and the reaction was stirred for 1 h. The solids were collected by suction filtration. The solids were crushed to a fine powder and dried under vacuum for 1 day using high vacuum (100 mTorr) to afford the title compound (7.82 g, 95%) as a tan powder. MS (ESI): mass calcd. for $C_{15}H_{13}ClN_2O_2S$, 320.0; m/z found, 321.0 [M+H]$^+$. $^1$H NMR (500 MHz, CDCl$_3$): δ 8.25 (d, J=5.3 Hz, 1H), 8.06-7.96 (m, 2H), 7.30-7.23 (m, 2H), 7.13 (d, J=5.3 Hz, 1H), 6.42-6.37 (m, 1H), 2.74 (s, 3H), 2.36 (s, 3H).

Step B: 4-Chloro-2-methyl-5-nitro-1-tosyl-1H-pyrrolo[2,3-b]pyridine. To a solution of 4-chloro-2-methyl-1-tosyl-1H-pyrrolo[2,3-b]pyridine (3.2 g, 10 mmol) in dry $CH_2Cl_2$ (300 mL) was added n-Bu$_4$NNO$_3$ (4.556 g, 14.96 mmol)) slowly at −10° C. Trifluoroacetic anhydride (2.812 mL, 19.95 mmol) was added drop-wise over 10 minutes. The reaction was stirred at room temperature for 16 h and then diluted with $CH_2Cl_2$, washed with saturated aqueous sodium bicarbonate (100 mL×2), and brine (100 mL). The organic phase was separated, dried over anhydrous $Na_2SO_4$, filtered, and concentrated to dryness to provide the title compound (3.1 g, 85% yield). MS (ESI): mass calcd. for $C_{15}H_{12}ClN_3O_4S$, 365.80; m/z found, 366.0 [M+H]$^+$.

Step C: Ethyl 2-(1-((1r,4r)-4-(cyanomethyl)cyclohexyl)-7-methyl-6-tosyl-1,6-dihydroimidazo[4,5-d]pyrrolo[2,3-b]pyridin-2-yl)acetate. A solution of 4-chloro-2-methyl-5-nitro-1-tosyl-1H-pyrrolo[2,3-b]pyridine (818 mg, 2.24 mmol) and 2-((1r,4r)-4-aminocyclohexyl)acetonitrile hydrochloride (Intermediate 1, Step D, 437 mg, 2.50 mmol) and DIPEA (5 mmol) in DMSO (3 mL) was stirred at 100° C. for 1 h. The reaction was cooled to room temperature and water (100 mL) added. A precipitate formed that was filtered, dissolved in $CH_2Cl_2$ (50 mL), the organics were washed with water (50 mL), and concentrated to dryness. To the residue was added ethyl 3-ethoxy-3-iminopropanoate (1.313 g, 6.711 mmol), sodium dithionate (1.168 g, 6.711 mmol), and DMSO (5 mL) and was heated to 100° C. for 3 hours. Water (20 mL) was added and the precipitate that formed was collected via filtration. The precipitate was washed with MeOH and the organics were concentrated to dryness to provide the crude title compound (1.0 g). MS (ESI): mass calcd. for $C_{28}H_{31}N_5O_4S$, 533.2; m/z found, 534.3 [M+H]$^+$.

Step D: 2-(1-((1r,4r)-4-(Cyanomethyl)cyclohexyl)-7-methyl-1,6-dihydroimidazo[4,5-d]pyrrolo[2,3-b]pyridin-2-yl)-N-(2-hydroxy-2-methylpropyl)acetamide. The title compound was prepared using analogous conditions as described in Example 30, Step B, and using ethyl 2-(1-((1r,4r)-4-(cyanomethyl)cyclohexyl)-7-methyl-6-tosyl-1,6-dihydroimidazo[4,5-d]pyrrolo[2,3-b]pyridin-2-yl)acetate in place of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate in step D (10 mg, 11% yield), with purification by flash column chromatography (10% MeOH in $CH_2Cl_2$) MS (ESI): mass calcd. for $C_{23}H_{30}N_6O_2$, 422.2; m/z found, 423.3 [M+H]$^+$. $^1$H NMR (500 MHz, CDCl$_3$): δ 10.50 (s, 1H), 8.67-8.30 (m, 1H), 7.72 (s, 1H), 7.31-7.06 (br, 1H), 6.34-6.16 (m, 1H), 4.81-4.47 (br, 1H), 3.93 (s, 2H), 3.23 (d, J=6.2 Hz, 2H), 2.59-2.27 (m, 7H), 2.20-1.91 (m, 5H), 1.53-1.05 (m, 8H).

Example 192 Synthesis and Characterization 2-((1r,4r)-4-(2-(2, 5,8,11-Tetraoxatridecan-13-yl)imidazo[4,5-d]pyrrolo[2,3-b]pyridin-1(6H)-yl)cyclohexyl)acetonitrile

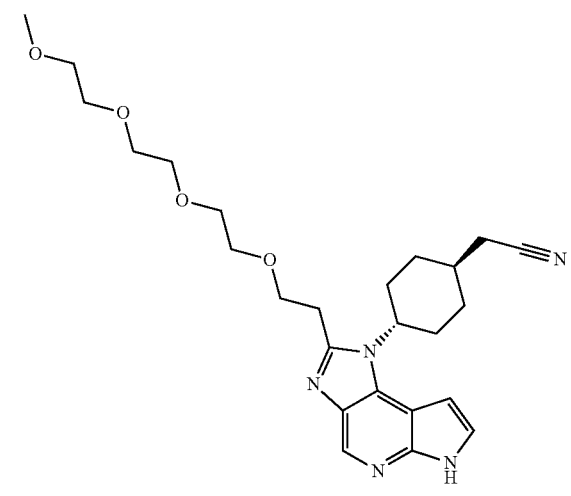 [SMILES: COCCOCCOCCOCCc1nc2cnc3[nH]ccc3c2n1[C@H]1CC[C@H](CC#N)CC1]

Step A: 2-((1r,4r)-4-(6-(Phenylsulfonyl)-2-(2,5,8,11-tetraoxatridecan-13-yl)imidazo[4,5-d]pyrrolo[2,3-b]pyridin-1

(6H)-yl)cyclohexyl)acetonitrile. A solution of 2-((1r,4r)-4-((5-nitro-1-(phenylsulfonyl)-1H-pyrrolo[2,3-b]pyridin-4-yl)amino)cyclohexyl)acetonitrile (Intermediate 1, 97 mg, 0.22 mmol), 2,5,8,11-tetraoxatetradecan-14-al (79 mg, 0.36 mmol), and sodium hydrosulfite (108 mg, 0.527 mmol) in DMSO (1 mL), MeOH (1 mL), and distilled water (0.5 mL) in a sealed tube was heated at 100° C. for 17 h. The reaction was filtered through a syringe filter, and the filtrate was purified by reverse phase HPLC to provide the title compound (95 mg, 59% yield) as an oil. MS (ESI): mass calcd. for $C_{31}H_{39}N_5O_6S$, 609.3; m/z found, 610.2 [M+H]$^+$.

Step B: 2-((1r,4r)-4-(2-(2,5,8,11-Tetraoxatridecan-13-yl)imidazo[4,5-d]pyrrolo[2,3-b]pyridin-1(6H)-yl)cyclohexyl)acetonitrile. The title compound was prepared using analogous conditions as described in Example 1, Step B (39 mg, 63% yield). The compound was purified by flash column chromatography (16 g silica gel column, 2-10% MeOH in DCM). MS (ESI): mass calcd. for $C_{25}H_{35}N_5O_4$, 469.3; m/z found, 470.2 [M+H]$^+$. $^1$H NMR (400 MHz, CDCl$_3$) δ=10.47 (br s, 1H), 8.76 (s, 1H), 7.41 (br s, 1H), 6.71 (br s, 1H), 4.54 (br s, 1H), 3.99 (br s, 2H), 3.68-3.55 (m, 10H), 3.55-3.46 (m, 2H), 3.35 (s, 3H), 3.33-3.25 (m, 2H), 2.56 (br s, 2H), 2.44 (d, J=6.4 Hz, 2H), 2.18 (d, J=13.0 Hz, 2H), 2.13-1.99 (m, 3H), 1.57-1.40 (m, 2H).

Example 193 Synthesis and Characterization

N-(2-(2-(2-Aminoethoxy)ethoxy)ethyl)-2-(1-((1r,4r)-4-(cyanomethyl)cyclohexyl)-1,6-dihydroimidazo[4,5-d]pyrrolo[2,3-b]pyridin-2-yl)acetamide

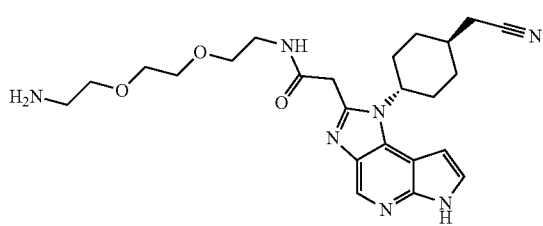 [SMILES: N#CC[C@H]1CC[C@H](n2c(CC(=O)NCCOCCOCCN)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 130 mg, 0.360 mmol) and 2,2'-(ethane-1,2-diylbis(oxy))diethanamine (17 mg, 0.11 mmol) in DMF (1 mL) were added PyBOP (288 mg, 0.550 mmol) and DIPEA (0.12 mL, 0.72 mmol) and was stirred at room temperature for 42 h. After removal of DMF in vacuo, the residue was purified by reverse phase HPLC (10-90% CH$_3$CN in H$_2$O, 0.1% TFA) to provide the title compound. This material was dissolved in n-BuOH and saturated aqueous NaHCO$_3$ solution. The organic layer was separated and the aqueous layer was extracted with n-BuOH (×3). The organic extracts were dried over Na$_2$SO$_4$, filtered, and concentrated. The residue was dissolved in 10% MeOH in CH$_2$Cl$_2$, and the solution was filtered through a syringe filter. The filtrate was concentrated to provide the title compound (12 mg, 7%). MS (ESI): mass calcd. for $C_{24}H_{33}N_7O_3$, 467.3; m/z found, 468.1 [M+H]$^+$. $^1$H NMR (400 MHz, CD$_3$OD) δ=8.53 (s, 1H), 7.52-7.44 (m, 1H), 6.85 (d, J=3.5 Hz, 1H), 4.63-4.44 (m, 1H), 4.14-4.04 (m, 1H), 3.68-3.47 (m, 9H), 3.44 (t, J=5.3 Hz, 2H), 2.78 (br s, 1H), 2.63-2.44 (m, 4H), 2.19-1.99 (m, 6H), 1.57-1.43 (m, 2H).

Example 194 Synthesis and Characterization 2-((1r,4r)-4-(2-((2-(2-methoxyethoxy)ethoxy)methyl)imidazo[4,5-d]pyrrolo[2,3-b]pyridin-1(6H)-yl)cyclohexyl)acetonitrile

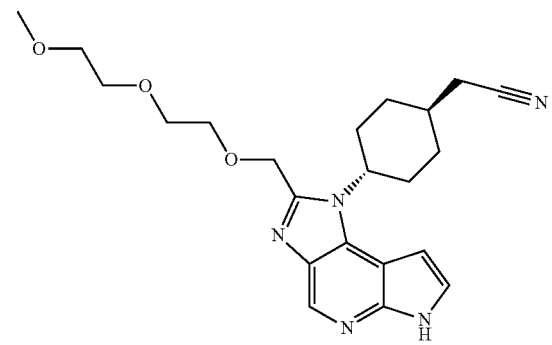 [SMILES: COCCOCCOCc1nc2cnc3[nH]ccc3c2n1[C@H]1CC[C@H](CC#N)CC1]

Step A: 2-((1r,4r)-4-(2-((2-(2-methoxyethoxy)ethoxy)methyl)-6-(phenylsulfonyl)imidazo[4,5-d]pyrrolo[2,3-b]pyridin-1(6H)-yl)cyclohexyl)acetonitrile. 2-((1r,4r)-4-((5-Nitro-1-(phenylsulfonyl)-1H-pyrrolo[2,3-b]pyridin-4-yl)amino)cyclohexyl)acetonitrile (Intermediate 1, 100 mg, 0.228 mmol) was dissolved in DMSO (1.9 mL) and MeOH (0.4 mL) in a 10 mL microwave vial. 2-(2-(2-methoxyethoxy)ethoxy)acetaldehyde (197 mg, 1.22 mmol) was added followed by sodium hydrosulfite (116 mg, 0.57 mmol). The vial was capped and heated to 100° C. for 18 hours. After cooling to room temperature, the mixture was diluted with water (5 mL) and ethyl acetate (5 mL) and then stirred for 5 minutes. The aqueous layer was then extracted with EtOAc (3×25 mL). The combined organic extracts were dried over sodium sulfate, filtered and then concentrated to dryness to provide a yellow solid that was used without further purification. MS (ESI): mass calcd. for $C_{28}H_{33}N_5O_5S$, 551.2; m/z found, 552.3 [M+H]$^+$.

Step B: 2-((1r,4r)-4-(2-((2-(2-methoxyethoxy)ethoxy)methyl)imidazo[4,5-d]pyrrolo[2,3-b]pyridin-1(6H)-yl)cyclohexyl)acetonitrile. The title compound was prepared using analogous conditions as described in Example 1, Step B (18.2 mg, 19% yield). The crude material was initially triturated with heptane/DCM and then purified on by HPLC using a Phenomonex Gemini 150 mm×30 mm, 5 μm column using a 5 to 95% gradient of MeCN in water (both phases containing 0.1% TFA) to provide the title compound. MS (ESI): mass calcd. for $C_{22}H_{29}N_5O_3$, 411.2; m/z found, 412.2 [M+H]$^+$. $^1$H NMR (400 MHz, CDCl$_3$): δ 11.78 (s, 1H), 8.83 (s, 1H), 7.54-7.41 (m, 1H), 6.78-6.69 (m, 1H), 4.94 (s, 2H), 4.79-4.66 (m, 1H), 3.71-3.67 (m, 2H), 3.67-3.64 (m, 2H), 3.64-3.60 (m, 2H), 3.54-3.51 (m, 2H), 3.36 (s, 3H), 2.65-2.48 (m, 2H), 2.43 (d, J=6.3 Hz, 2H), 2.24-2.04 (m, 5H), 1.56-1.42 (m, 2H).

Example 195 Synthesis and Characterization 2-((1S,4r)-4-(2-(2-((S)-2-(hydroxymethyl)pyrrolidin-1-yl)-2-oxoethyl)imidazo[4,5-d]pyrrolo[2,3-b]pyridin-1(6H)-yl)cyclohexyl)acetonitrile

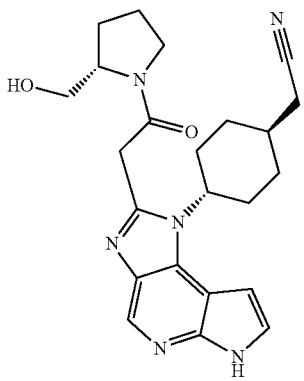 [SMILES: N#CC[C@H]1CC[C@H](n2c(CC(=O)N3CCC[C@H]3CO)nc3cnc4[nH]ccc4c32)CC1]

N,N-Diisopropylethylamine (144 mg, 1.11 mmol) was added to a 0° C. solution consisting of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 200 mg, 0.557 mmol), (S)-pyrrolidin-2-ylmethanol (56.3 mg, 0.557 mmol), and dimethylformamide (5 mL). After stirring at 0° C. for 1 hour, PyBOP (311 mg, 0.668 mmol) was added. The mixture was stirred for 4 hours with gradual warming to room temperature before quenching with H$_2$O (10 mL) and concentrating to dryness. The residue was purified by preparative HPLC using a DuraShell 150×25 mm×5 µm column (eluent: 18% to 48% (v/v) CH$_3$CN and H$_2$O with 0.05% NH$_3$), and lyophilized to dryness to afford the impure product, which was further purified by preparative TLC (eluent: methylene chloride:MeOH=10:1) to yield the title compound (5 mg, 2%) as a white solid. LCMS (ESI): RT=3.56 min, mass calcd. for C$_{23}$H$_{28}$N$_6$O$_2$, 420.23 m/z; m/z found, 421.2 [M+H]$^+$. Analytical reverse phase LC-MS was carried out using a X-Bridge Shield RP18, 50×2.1 mm×5 µm column with a flow rate of 0.8 mL/min., eluting with a gradient of 0% to 95% acetonitrile (solvent B) and water with 0.05% NH$_{3(aq)}$ (solvent A). The eluent composition was kept at 100% A for 1 minute, followed by increasing to 60% B over the course of 4 minutes. The eluent was increased to 95% B over the course of 2 minutes before returning to 100% A over the course of 2 minutes. Total run time was 9.5 minutes. MS (ESI): mass calcd. for C$_{23}$H$_{28}$N$_6$O$_2$, 420.2; m/z found, 421.2 [M+H]$^+$. $^1$H NMR (400 MHz, DMSO-d$_6$) δ 11.84 (br s, 1H), 8.49 (s, 1H), 7.49-7.43 (m, 1H), 6.74-6.68 (m, 1H), 5.17-5.12 (m, 0.3H), 4.82-4.76 (m, 0.7H), 4.49-4.28 (m, 1H), 4.27-4.20 (m, 0.3H), 4.00-3.91 (m, 0.7H), 3.68-3.58 (m, 2H), 3.33-3.31 (m, 2H), 2.60-2.57 (m, 2H), 2.42-2.26 (m, 2H), 2.10-1.79 (m, 11H), 1.43-1.27 (m, 2H).

Example 196 Synthesis and Characterization (1-((1r,4r)-4-(Cyanomethyl)cyclohexyl)-1,6-dihydroimidazo[4,5-d]pyrrolo[2,3-b]pyridin-2-yl)methyl (3S,5S,7S)-adamantan-1-ylcarbamate

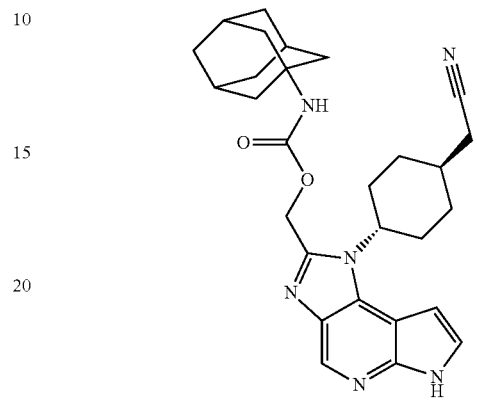

Step A: (1-((1r,4r)-4-(Cyanomethyl)cyclohexyl)-6-(phenylsulfonyl)-1,6-dihydroimidazo[4,5-d]pyrrolo[2,3-b]pyridin-2-yl)methyl (3S,5S,7S)-adamantan-1-ylcarbamate. A mixture of 2-((1r,4r)-4-(2-(hydroxymethyl)-6-(phenylsulfonyl)imidazo[4,5-d]pyrrolo[2,3-b]pyridin-1(6H)-yl)cyclohexyl)acetonitrile (Intermediate 7, 35 mg, 0.078 mmol), (3S,5S,7S)-1-isocyanatoadamantane (25 mg, 0.14 mmol), and Et$_3$N (0.030 mL, 0.22 mmol) in THF (1.5 mL) and DMF (0.5 mL) was heated at 80° C. for 5 h. Additional (3S,5S, 7S)-1-isocyanatoadamantane (15 mg, 0.085 mmol) and Et$_3$N (0.030 mL, 0.22 mmol) were added and the mixture was heated at 90° C. for 17 h. After concentration in vacuo, the residue was purified by flash chromatography (20-80% EtOAc in heptane) to provide the title compound (44 mg, 90%) as a white solid. MS (ESI): mass calcd. for C$_{34}$H$_{38}$N$_6$O$_4$S, 626.3; m/z found, 627.3 [M+H]$^+$.

Step B: (1-((1r,4r)-4-(Cyanomethyl)cyclohexyl)-1,6-dihydroimidazo[4,5-d]pyrrolo[2,3-b]pyridin-2-yl)methyl (3s,5S,7s)-adamantan-1-ylcarbamate. The title compound (25 mg, 73%) was prepared using analogous conditions as found in Example 152, step D. The compound was purified by reverse phase HPLC using a Varian Pursuit XR$_s$5 Diphenyl 100×30 mm column (eluent: 10-90% CH$_3$CN in H$_2$O, 0.1% TFA). The concentrated fractions were dissolved in DCM and NaHCO$_3$ aqueous solution. The aqueous portion was separated and extracted with DCM (×3) and EtOAc (×2). The combined organic extracts were dried, filtered, concentrated, and purified again by flash column chromatography (2-5% MeOH in DCM). MS (ESI): mass calcd. for C$_{28}$H$_{34}$N$_6$O$_2$, 486.3; m/z found, 487.4 [M+H]$^+$. $^1$H NMR (400 MHz, CDCl$_3$) δ=10.97 (br s, 1H), 8.82 (s, 1H), 7.44 (br s, 1H), 6.72 (br s, 1H), 5.43 (s, 2H), 4.84 (br s, 1H), 4.59 (br s, 1H), 2.67-2.45 (m, 1H), 2.43 (d, J=6.6 Hz, 2H), 2.27-2.14 (m, 2H), 2.15-2.00 (m, 3H), 1.95 (br s, 6H), 1.68 (br s, 6H), 1.60-1.41 (m, 2H), 1.35-1.19 (m, 2H), 0.92-0.84 (m, 2H).

Example 197 Synthesis and Characterization 2-((1r,4r)-4-(2-(2-(4-Methoxypiperidin-1-yl)-2-oxo-ethyl)imidazo[4,5-d]pyrrolo[2,3-b]pyridin-1(6H)-yl)cyclohexyl)acetonitrile and its Trifluoroacetic Acid Salt

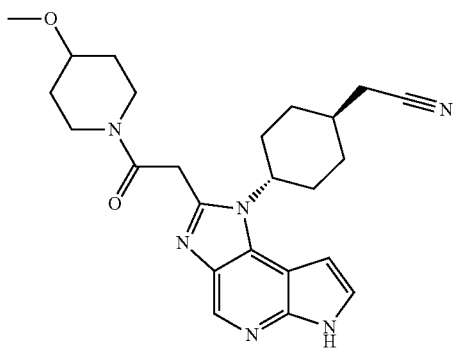 [SMILES: COC1CCN(C(=O)Cc2nc3cnc4[nH]ccc4c3n2[C@H]2CC[C@H](CC#N)CC2)CC1]

Step A: 2-((1r,4r)-4-(2-(2-(4-Methoxypiperidin-1-yl)-2-oxoethyl)-6-(phenylsulfonyl)imidazo[4,5-d]pyrrolo[2,3-b]pyridin-1(6H)-yl)cyclohexyl)acetonitrile. TFA. A solution of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 55 mg, 0.11 mmol, 4-methoxypiperidine (355 mg, 3.08 mmol), and $NH_4NO_3$ (20 mg, 0.25 mmol) under Ar was heated at 65° C. for 88 h. After concentration, the residue was purified by reverse phase HPLC (10-100% $CH_3CN$ in $H_2O$, 0.1% TFA) to provide the title compound (50 mg, 67%). MS (ESI): mass calcd. for $C_{30}H_{34}N_6O_4S$, 574.2; m/z found, 575.3 $[M+H]^+$.

Step B: 2-((1r,4r)-4-(2-(2-(4-Methoxypiperidin-1-yl)-2-oxoethyl)imidazo[4,5-d]pyrrolo[2,3-b]pyridin-1(6H)-yl)cyclohexyl)acetonitrile as its trifluoroacetic acid salt. A solution of 2-((1r,4r)-4-(2-(2-(4-methoxypiperidin-1-yl)-2-oxoethyl)-6-(phenylsulfonyl)imidazo[4,5-d]pyrrolo[2,3-b]pyridin-1(6H)-yl)cyclohexyl)acetonitrile (50 mg, 0.087 mmol) in THF (1 mL) and MeOH (1 mL) was treated with 3N NaOH (0.087 mL, 0.26 mmol) for 16 h at room temperature. After concentration in vacuo, the free base, 2-((1r,4r)-4-(2-(2-(4-methoxypiperidin-1-yl)-2-oxoethyl)imidazo[4,5-d]pyrrolo[2,3-b]pyridin-1(6H)-yl)cyclohexyl)acetonitrile was purified by reverse phase HPLC (10-90% $CH_3CN$ in $H_2O$, 0.1% TFA) to provide the title compound as the trifluoracetic acid salt (24 mg, 50%). MS (ESI): mass calcd. for $C_{24}H_{30}N_6O_2$, 434.2; m/z found, 435.3 $[M+H]^+$. $^1$H NMR (400 MHz, $CD_3OD$) δ=8.81 (s, 1H), 7.76-7.72 (m, 1H), 7.09 (br s, 1H), 4.74-4.49 (m, 1H), 3.95-3.83 (m, 2H), 3.60-3.48 (m, 2H), 3.47-3.37 (M, 1H), 3.40 (s, 3H), 2.56 (d, J=5.6 Hz, 2H), 2.25-2.07 (m, 5H), 2.08-1.99 (m, 2H), 1.96-1.85 (m, 2H), 1.85-1.66 (m, 2H), 1.63-1.45 (m, 4H).

Example 198 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-methylacetamide as its Trifluoroacetic Acid Salt

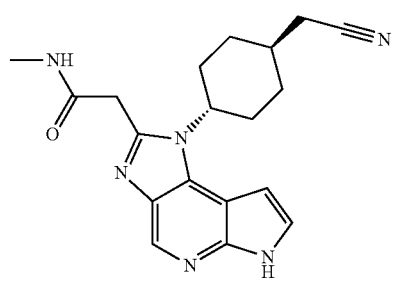 [SMILES: CNC(=O)Cc1nc2cnc3[nH]ccc3c2n1[C@H]1CC[C@H](CC#N)CC1]

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-methylacetamide trifluoroacetic acid salt. A solution of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 70 mg, 0.14 mmol), 40% methylamine in water (0.30 mL, 3.1 mmol), and EtOH (1 mL) under Ar was heated at 65° C. for 15 min, and then stirred at room temperature for 62 h. A few drops of TFA were added, and the solvents were removed in vacuo. The residue was purified by reverse phase HPLC (10-100% $CH_3CN$ in $H_2O$, 0.1% TFA) to provide the title compound (63 mg, 75%). MS (ESI): mass calcd. for $C_{25}H_{26}N_6O_3S$, 490.2; m/z found, 491.2 $[M+H]^+$.

Step B: 2-(1-((1r,4r)-4-(Cyanomethyl)cyclohexyl)-1,6-dihydroimidazo[4,5-d]pyrrolo[2,3-b]pyridin-2-yl)-N-methylacetamide trifluoroacetic acid salt. The title compound (15 mg, 31%) was prepared using analogous conditions as found in Example 198, step B wherein the free base compound, 2-(1-((1r,4r)-4-(Cyanomethyl)cyclohexyl)-1,6-dihydroimidazo[4,5-d]pyrrolo[2,3-b]pyridin-2-yl)-N-methylacetamide, was prepared and then upon purification with reverse phase HPLC using a Varian Pursuit $XR_s5$ Diphenyl 100×30 mm column (eluent: 10-90% $CH_3CN$ in $H_2O$, 0.1% TFA) was isolated as its trifluoroacetic acid salt. MS (ESI): mass calcd. for $C_{19}H_{22}N_6O$, 350.2; m/z found, 351.1 $[M+H]^+$. $^1$H NMR (400 MHz, $CD_3OD$) δ=8.80 (s, 1H), 7.75 (d, J=3.0 Hz, 1H), 7.09 (d, J=3.0 Hz, 1H), 4.71 (br s, 1H), 2.99 (s, 1H), 2.86 (s, 1H), 2.82 (s, 3H), 2.56 (d, J=6.1 Hz, 4H), 2.18-2.07 (m, 5H), 1.61-1.45 (m, 2H).

Example 199 Synthesis and Characterization

N-((3R,5R,7R)-Adamantan-1-ylmethyl)-2-(1-((1r,4r)-4-(cyanomethyl)cyclohexyl)-1,6-dihydroimidazo[4,5-d]pyrrolo[2,3-b]pyridin-2-yl)acetamide as its Trifluoroacetic Acid Salt

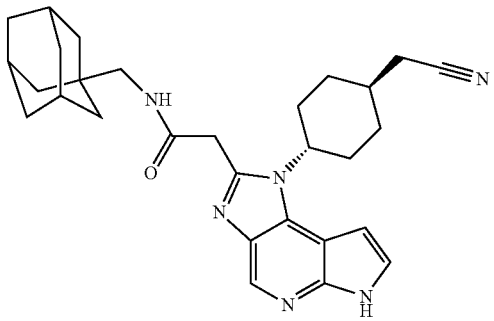 [SMILES: N#CC[C@H]1CC[C@H](n2c(CC(=O)NCC34CC5CC(CC(C5)C3)C4)nc3cnc4[nH]ccc4c32)CC1]

The title compound (25 mg, 86%) was prepared using analogous conditions as found in Example 198 and using (3R,5R,7R)-adamantan-1-ylmethanamine in place of 4-methoxypiperidine in step A. MS (ESI): mass calcd. for $C_{29}H_{36}N_6O$, 484.3; m/z found, 485.4 $[M+H]^+$. $^1H$ NMR (400 MHz, $CD_3OD$) δ 8.79 (s, 1H), 7.73 (d, J=3.5 Hz, 1H), 7.09 (d, J=3.5 Hz, 1H), 4.66 (br s, 1H), 4.37-4.32 (m, 1H), 3.00-2.93 (m, 2H), 2.56 (d, J=6.1 Hz, 4H), 2.28-2.06 (m, 6H), 2.03-1.92 (m, 3H), 1.77 (d, J=12.1 Hz, 3H), 1.68 (d, J=11.6 Hz, 3H), 1.61-1.49 (m, 8H).

Example 200 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(4-cyanophenyl)acetamide

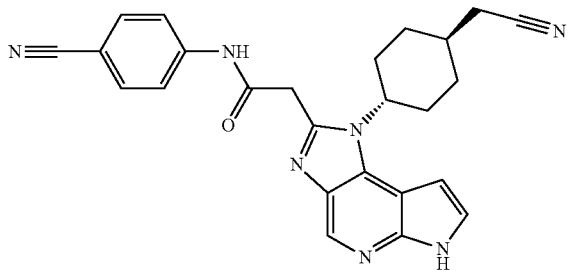 [SMILES: N#CC[C@H]1CC[C@H](n2c(CC(=O)Nc3ccc(C#N)cc3)nc3cnc4[nH]ccc4c32)CC1]

To a solution of sodium 2-(1-((1r,4r)-4-(cyanomethyl)cyclohexyl)-1,6-dihydroimidazo[4,5-d]pyrrolo[2,3-b]pyridin-2-yl)acetate (50 mg, 0.14 mmol) and 4-aminobenzonitrile (70 mg, 0.59 mmol) in DMF (2 mL) were added HATU (180 mg, 0.47 mmol) and DIPEA (0.12 mL, 0.72 mmol) and was stirred at room temperature for 18 h. After removal of DMF in vacuo, to the residue was added water, and the aqueous layer was extracted with EtOAc. The combined extracts were dried over $Na_2SO_4$, filtered, concentrated, and purified by reverse phase HPLC (10-90% $CH_3CN$ in $H_2O$, 0.1% TFA). The collected TFA salt was neutralized by partitioning it between saturated $NaHCO_3$ aqueous solution and $CH_2Cl_2$, and purified again by flash chromatography (4 g column, 0-20% MeOH in $CH_2Cl_2$ saturated with $NH_3$) to provide the title compound (10 mg, 16%) as a white solid. MS (ESI): mass calcd. for $C_{25}H_{23}N_7O$, 437.2; m/z found, 438.1 $[M+H]^+$. $^1H$ NMR (400 MHz, $CD_3OD$) δ 8.67 (br s, 1H), 7.80 (d, J=8.1 Hz, 2H), 7.68 (d, J=8.1 Hz, 2H), 7.61 (d, J=3.5 Hz, 1H), 6.97 (d, J=3.5 Hz, 1H), 4.66 (br s, 1H), 2.61-2.47 (m, 4H), 2.23-2.08 (m, 5H), 1.58-1.36 (m, 3H), 1.36-1.23 (m, 1H).

Example 201 Synthesis and Characterization 2-(1-((1r,4r)-4-(Cyanomethyl)cyclohexyl)-1,6-dihydroimidazo[4,5-d]pyrrolo[2,3-b]pyridin-2-yl)acetamide Trifluoroacetic Acid

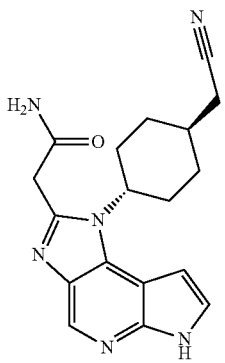 [SMILES: N#CC[C@H]1CC[C@H](n2c(CC(N)=O)nc3cnc4[nH]ccc4c32)CC1]

The title compound (40 mg, 83%) was prepared from ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3) using condition analogous to those in Example 199, using and using 28% $NH_4OH$ in water in place of 40% $NH_2Me$ in water in Example 199, step A. MS (ESI): mass calcd. for $C_{18}H_{20}N_6O$, 336.2; m/z found, 337.2 $[M+H]^+$. 1H NMR (400 MHz, $CD_3OD$) δ 8.81 (br s, 1H), 7.75 (d, J=3.5 Hz, 1H), 7.10 (d, J=3.5 Hz, 1H), 4.69 (br s, 1H), 2.56 (d, J=6.1 Hz, 4H), 2.27-2.09 (m, 6H), 1.66-1.45 (m, 3H).

Example 202 Synthesis and Characterization 2-((1r,4r)-4-(2-(tert-Butoxymethyl)imidazo[4,5-d]pyrrolo[2,3-b]pyridin-1(6H)-yl)cyclohexyl)acetonitrile and its Trifluoroacetic Acid Salt

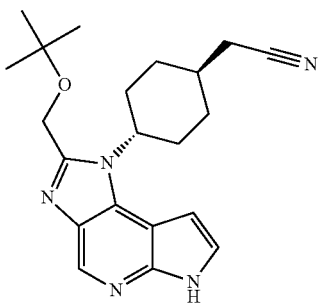 [SMILES: CC(C)(C)OCc1nc2cnc3[nH]ccc3c2n1[C@H]1CC[C@H](CC#N)CC1]

A solution of 2-((1r,4r)-4-(2-(chloromethyl)-6-(phenylsulfonyl)imidazo[4,5-d]pyrrolo[2,3-b]pyridin-1(6H)-yl)cyclohexyl)acetonitrile (Intermediate 8.42 mg, 0.090 mmol), 1M KOtBu in THF (0.38 mL, 0.38 mmol), and THF (1.5 mL) was heated at 50° C. for 20 min during which the mixture changed from cloudy to clear then to cloudy again. After concentration, the free base residue, 2-((1r,4r)-4-(2-(tert-Butoxymethyl)imidazo[4,5-d]pyrrolo[2,3-b]pyridin-1(6H)-yl)cyclohexyl)acetonitrile, was purified by reverse phase HPLC (10-90% $CH_3CN$ in $H_2O$, 0.1% TFA) to provide the title compound as its trifluoroacetic acid salt (15 mg, 35% yield). MS (ESI): mass calcd. for $C_{21}H_{27}N_5O$, 365.2; m/z found, 366.3 [M+H]$^+$. $^1$H NMR (400 MHz, $CD_3OD$) δ 8.82 (s, 1H), 7.75 (d, J=3.5 Hz, 1H), 7.08 (d, J=3.5 Hz, 1H), 5.02 (s, 2H), 4.80 (br s, 1H), 2.58 (d, J=6.6 Hz, 4H), 2.25-2.10 (m, 5H), 1.63-1.46 (m, 2H), 1.39 (s, 9H).

Example 203 Synthesis and Characterization 2-((1r,4r)-4-(2-((5-Oxo-3-phenyl-1,2,4-oxadiazol-4(5H)-yl)methyl)imidazo[4,5-d]pyrrolo[2,3-b]pyridin-1(6H)-yl)cyclohexyl)acetonitrile

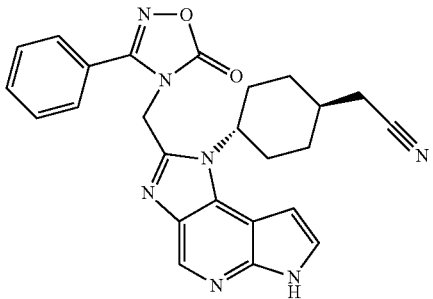 [SMILES: N#CC[C@H]1CC[C@H](n2c(Cn3c(-c4ccccc4)noc3=O)nc3cnc4[nH]ccc4c32)CC1]

A mixture of the (E)/(Z) isomers of N-((1-((1r,4r)-4-(cyanomethyl)cyclohexyl)-1,6-dihydroimidazo[4,5-d]pyrrolo[2,3-b]pyridin-2-yl)methyl)-N'-hydroxybenzimidamide (60 mg, 0.13 mmol, as prepared in Examples 17A &17B), CDI (23 mg, 0.14 mmol), and THF (2 mL) was stirred at 70° C. for 1.5 h. LC-MS showed 20% of starting material remained and 67% of desired product formed. Another portion of CDI (11 mg) was added. The mixture was stirred at 70° C. for additional 1 h. LC-MS showed 27% of starting material remained and 50% of desired product formed. The reaction mixture was concentrated to dryness under reduced pressure, purified by flash column chromatography (eluent: methylene chloride:methanol=100:0 to 85:15) and preparative HPLC using a Boston Green ODS 150×30 mm×5 μm column (eluent: 30% to 40% (v/v) $CH_3CN$ and $H_2O$ with 0.1% TFA). The pure fractions were combined and treated with saturated aqueous $NaHCO_3$ until pH=7-8. The volatile organic solvent was removed under reduced pressure. The precipitate was filtered, washed with water (3 mL×2), lyophilized to dryness to afford the title compound (10 mg, 17%). Reverse phase LC-MS was carried out using a Phenomenex Luna-C18, 50×2 mm×5 μm column with a flow rate of 0.8 mL/min, eluting with a gradient of 10% to 85% acetonitrile containing 0.05% TFA (solvent B) and water containing 0.1% TFA (solvent A). The eluent composition was kept at 90% A for 0.8 minutes, followed by increasing to 80% B over the course of 3.7 minutes. The eluent was then kept at 80% B for 3 minutes before returning to 10% B over the course of 2 minutes. Total run time was 10 minutes. MS (ESI): mass calcd. for $C_{25}H_{23}N_7O_2$, 453.19; m/z found, 454.0 [M+H]$^+$. $^1$H NMR (400 MHz, DMSO-$d_6$) δ 11.92 (s, 1H), 8.52 (s, 1H), 7.70-7.60 (m, 2H), 7.60-7.53 (m, 1H), 7.53-7.38 (m, 3H), 6.71 (s, 1H), 5.41 (s, 2H), 4.61-4.38 (m, 1H), 2.64-2.56 (m, 2H), 2.37-2.16 (m, 2H), 2.08-1.79 (m, 5H), 1.53-1.34 (m, 2H).

Example 204 Synthesis and Characterization

N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclohexanecarboximidamide

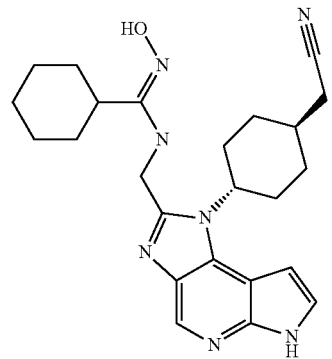 [SMILES: N#CC[C@H]1CC[C@H](n2c(CN/C(=N/O)C3CCCCC3)nc3cnc4[nH]ccc4c32)CC1]

Step A: Cyclohexanecarbaldehyde oxime. A solution consisting of cyclohexanecarbaldehyde (5.00 g, 44.6 mmol), hydroxylamine hydrochloride (9.29 g, 134 mmol), sodium acetate (10.97 g, 133.7 mmol), ethanol (150 mL), and water (30 mL) was stirred at 70° C. for 10 h. The mixture was concentrated under reduced pressure, and the residue was diluted with water (40 mL), and extracted with ethyl acetate (80 mL×3). The combined organic extracts were dried over anhydrous $Na_2SO_4$, filtered, and concentrated to dryness under reduced pressure to provide the title compound (5.1 g, 90%) as a colorless oil. $^1$H NMR (400 MHz, $CDCl_3$) δ 9.10 (br s, 1H), 7.33 (d, J=6.0 Hz, 0.6H), 6.54 (d, J=7.2 Hz, 0.3H), 3.04-2.91 (m, 0.3H), 2.29-2.16 (m, 0.7H), 1.88-1.59 (m, 5H), 1.42-1.11 (m, 5H).

Step B: N-Hydroxycyclohexanecarbimidoyl chloride. 1-Chloropyrrolidine-2,5-dione (6.30 g, 47.2 mmol) was added to a solution consisting of cyclohexanecarbaldehyde oxime (3.0 g, 24 mmol) and N,N-dimethylformamide (20 mL) and the mixture was stirred for 2 h at room temperature under nitrogen. The mixture was diluted with ethyl acetate (200 mL) and washed with water (50 mL×3). The organic layer was dried over anhydrous $Na_2SO_4$, filtered, and evaporated to dryness under vacuum to provide the crude product, which was purified by flash column chromatography (eluent: petroleum ether:ethyl acetate=100:0 to 100:20) to afford the title compound (2.1 g, 55%) as a colorless oil. $^1$H NMR (400 MHz, $CDCl_3$) δ 8.56-8.35 (m, 1H), 2.52-2.38 (m, 1H), 1.99-1.89 (m, 2H), 1.86-1.75 (m, 2H), 1.73-1.64 (m, 1H), 1.50-1.38 (m, 2H), 1.35-1.15 (m, 3H).

Step C: tert-Butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate. A solution consisting of 2-((1r,4r)-4-((5-nitro-1-(phenylsulfonyl)-1H-pyrrolo[2,3-b]pyridin-4-yl)amino)cyclohexyl)acetonitrile (Intermediate 1, 5.0 g, 11 mmol), tert-butyl (2-oxoethyl)carbamate (4.2 g, 26 mmol), sodium hydrosulfite (9.9 g, 57 mmol), DMSO (25 mL), methanol (75 mL), and water (50 mL) was stirred at 100° C. for 3 h. The mixture was diluted with water (50 mL) and extracted with dichloromethane (100 mL×2). The combined organic extracts were dried over Na₂SO₄, filtered, and concentrated under reduced pressure to provide the crude product, which was purified by flash column chromatography (eluent: petroleum ether: ethyl acetate=100:0 to 40:60) to afford the title compound as a light yellow solid (3.6 g, 52%). LCMS (ESI): RT=0.75 min, mass calcd. for $C_{28}H_{32}N_6O_4S$, 548.22; m/z found, 549.1 [M+H]⁺. Reverse phase LC-MS was carried out using a Merck RP-18e, 3 Lm x 25×2 mm column with a flow rate of 1.5 mL/min. The HPLC solvent system was a gradient starting with 95% water containing 0.038% TFA (solvent A) and 5% acetonitrile containing 0.02% TFA (solvent B), followed by a gradient up to 5% solvent A and 95% solvent B over the subsequent 0.7 minutes. This eluent composition was maintained for 0.4 minutes before returning to 95% solvent A and 5% solvent B over the ensuing 0.4 minutes. Total run time was 1.5 minutes. ¹H NMR (400 MHz, CDCl₃) δ 8.83 (s, 1H), 8.26-8.19 (m, 2H), 7.84 (d, J=4.0 Hz, 1H), 7.59-7.52 (m, 1H), 7.51-7.44 (m, 2H), 6.83 (d, J=4.0 Hz, 1H), 5.41 (br.s, 1H), 4.67 (d, J=5.6 Hz, 2H), 4.65-4.57 (m, 1H), 2.40 (d, J=6.4 Hz, 2H), 2.36-2.23 (m, 2H), 2.19-2.11 (m, 2H), 2.03-1.90 (m, 3H), 1.49-1.42 (m, 11H).

Step D: tert-Butyl ((1-((1r,4r)-4-(cyanomethyl)cyclohexyl)-1,6-dihydroimidazo[4,5-d]pyrrolo[2,3-b]pyridin-2-yl)methyl)carbamate. An aqueous KOH (3.6 mL, 11 mmol) solution was added to a solution consisting of tert-butyl ((1-((1r,4r)-4-(cyanomethyl)cyclohexyl)-6-(phenylsulfonyl)-1,6-dihydroimidazo[4,5-d]pyrrolo[2,3-b]pyridin-2-yl)methyl)carbamate (2.0 g, 3.6 mmol) and 1,4-dioxane (20 mL). The resulting mixture was stirred at 80° C. for 2 h. After cooling to room temperature, the reaction mixture was adjusted to pH=7-8 with 1N HCl. The volatiles were removed under reduced pressure, diluted with water (20 mL) and extracted with ethyl acetate (50 mL×2). The combined organic extracts were dried over anhydrous Na₂SO₄, filtered, and concentrated under reduced pressure to provide the title compound as a brown solid (crude, 1.6 g), which was used in the next step without purification. LCMS (ESI): RT=0.63 min, mass calcd. for $C_{22}H_{28}N_6O_2$, 408.23; m/z, found 409.0 [M+H]⁺. Reverse phase LC-MS was carried out using a Merck RP-18e, 3 μm×25×2 mm column with a flow rate of 1.5 mL/min. The HPLC solvent system was a gradient starting with 95% water containing 0.038% TFA (solvent A) and 5% acetonitrile containing 0.02% TFA (solvent B), followed by a gradient up to 5% solvent A and 95% solvent B over the subsequent 0.7 minutes. This eluent composition was maintained for 0.4 minutes before returning to 95% solvent A and 5% solvent B over the ensuing 0.4 minutes. Total run time was 1.5 minutes. ¹H NMR (400 MHz, DMSO-d₆) δ 11.87 (s, 1H), 8.52 (s, 1H), 7.56-7.49 (m, 1H), 7.47 (t, J=3.2 Hz, 1H), 6.73-6.69 (m, 1H), 4.68-4.58 (m, 1H), 4.54 (d, J=5.6 Hz, 2H), 2.59 (d, J=6.0 Hz, 2H), 2.42-2.28 (m, 2H), 2.07-1.95 (m, 3H), 1.94-1.84 (m, 2H), 1.46-1.35 (m, 11H).

Step E: 2-((1r,4r)-4-(2-(Aminomethyl)imidazo[4,5-d]pyrrolo[2,3-b]pyridin-1(6H)-yl)cyclohexyl)acetonitrile.HCl A solution of tert-Butyl ((1-((1r,4r)-4-(cyanomethyl)cyclohexyl)-1,6-dihydroimidazo[4,5-d]pyrrolo[2,3-b]pyridin-2-yl)methyl)carbamate (1.6 g, 3.9 mmol) and methylene chloride (15 mL) was treated with 4M HCl in 1,4-dioxane (8.0 mL, 32 mmol) at 15° C. for 30 min. The reaction mixture was concentrated to dryness under reduced pressure to provide the crude title compound as a brown solid, which was used in the next step without purification (crude, 1.5 g). LCMS (ESI): RT=0.16 min, mass calcd. for $C_{17}H_{20}N_6$, 308.17; m/z found 308.9 [M+H]⁺. Reverse phase LC-MS was carried out using a Merck RP-18e, 3 μm×25×2 mm column with a flow rate of 1.5 mL/min. The HPLC solvent system was a gradient starting with 95% water containing 0.038% TFA (solvent A) and 5% acetonitrile containing 0.02% TFA (solvent B), followed by a gradient up to 5% solvent A and 95% solvent B over the subsequent 0.7 minutes. This eluent composition was maintained for 0.4 minutes before returning to 95% solvent A and 5% solvent B over the ensuing 0.4 minutes. Total run time was 1.5 minutes. ¹H NMR (400 MHz, DMSO-d₆) δ 12.53 (s, 1H), 8.88 (s, 1H), 8.86 (br. s, 3H), 7.67 (t, J=3.2 Hz, 1H), 6.93 (s, 1H), 4.71-4.63 (m, 2H), 4.60-4.42 (m, 1H), 2.60 (d, J=6.0 Hz, 2H), 2.36-2.21 (m, 2H), 2.12-1.93 (m, 5H), 1.56-1.42 (m, 2H).

Step F: N-((1-((1r,4r)-4-(Cyanomethyl)cyclohexyl)-1,6-dihydroimidazo[4,5-d]pyrrolo[2,3-b]pyridin-2-yl)methyl)-N'-hydroxycyclohexanecarboximidamide. A solution consisting of 2-((1r,4r)-4-(2-(aminomethyl)imidazo[4,5-d]pyrrolo[2,3-b]pyridin-1(6H)-yl)cyclohexyl)acetonitrile hydrochloride (Intermediate 5, 150 mg, 0.440 mmol), N-hydroxycyclohexanecarbimidoyl chloride (70.3 mg, 0.440 mmol, Example 205, Step B), triethylamine (132 mg, 1.31 mmol), and N,N-dimethylformamide (7.5 mL) was stirred for 2 hours at room temperature. The mixture was filtered, and the filtrate was concentrated and purified by preparative HPLC using a Phenomenex Gemini 150×25 mm x 10 μm column (eluent: 26% to 56% (v/v) CH₃CN and H₂O with 0.05% NH₃). The pure fractions were collected and concentrated to dryness under reduced pressure to afford the title compound (53 mg, 28%) as a white solid. LCMS (ESI): RT=2.39 min, mass calcd. for $C_{24}H_{31}N_7O$, 433.26; m/z found 434.1 [M+H]⁺. Reverse phase LC-MS was carried out using a Phenomenex Luna-C18, 50×2 mm x 5 μm column with a flow rate of 0.8 mL/min, eluting with a gradient of 10% to 80% acetonitrile containing 0.05% TFA (solvent B) and water containing 0.1% TFA (solvent A). The eluent composition was kept at 10% B for 0.8 minutes, followed by increasing to 80% B over the course of 3.7 minutes. The eluent was kept at 80% B for 3 minutes before returning to 10% B over the course of 2 minutes. Total run time was 9.5 minutes. MS (ESI): mass calcd. for $C_{24}H_{31}N_7O$, 433.3; m/z found, 434.1 [M+H]⁺. ¹H NMR (400 MHz, DMSO-d₆) δ 11.91-11.83 (m, 1H), 9.16 (s, 1H), 8.57-8.50 (m, 1H), 7.49-7.44 (m, 1H), 6.74-6.67 (m, 1H), 6.25-6.17 (m, 1H), 4.74-4.57 (m, 3H), 2.60 (d, J=6.0 Hz, 2H), 2.53-2.51 (m, 1H), 2.44-2.26 (m, 2H), 2.06-1.89 (m, 5H), 1.68-1.40 (m, 7H), 1.30-1.07 (m, 5H).

Example 205 Synthesis and Characterization 2-(4-(2-(2-Oxo-2-(piperidin-1-yl)ethyl)imidazo[4,5-d]pyrrolo[2,3-b]pyridin-1(6H)-yl)bicyclo[2.2.2]octan-1-yl)acetonitrile

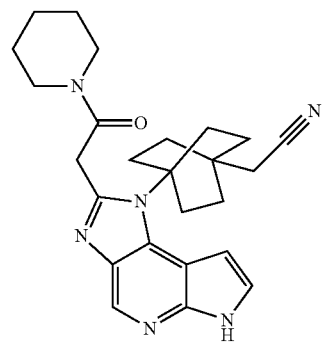 [SMILES: N#CCC12CCC(n3c(CC(=O)N4CCCCC4)nc4cnc5[nH]ccc5c43)(CC1)CC2]

A mixture of sodium 2-(1-(4-(cyanomethyl)bicyclo[2.2.2]octan-1-yl)-1,6-dihydroimidazo[4,5-d]pyrrolo[2,3-b]pyridin-2-yl)acetate (Intermediate 11, 200 mg, 0.518 mmol, crude), piperidine (49 mg, 0.57 mmol), PyBrOP (265 mg, 0.569 mmol), N,N-diisopropylethylamine (0.67 mL, 1.6 mmol), and anhydrous DMF (6 mL) was stirred at room temperature for 15 hours and diluted with $H_2O$ (20 mL). The mixture was extracted with ethyl acetate (20 mL×3). The combined organic extracts were washed with brine (20 mL), dried over anhydrous $Na_2SO_4$, filtered, and concentrated to dryness under reduced pressure. The residue was purified by preparative HPLC (eluent: 25% to 55% (v/v) $CH_3CN$ and $H_2O$ with 0.05% $NH_4HCO_3$) to afford the title compound (57 mg, 26%) as a white solid. MS (ESI): mass calcd. for $C_{25}H_{30}N_6O$, 430.3; m/z found, 431.2 $[M+H]^+$. $^1H$ NMR (400 MHz, DMSO-$d_6$) δ 11.88 (br s, 1H), 8.48 (s, 1H), 7.52 (d, J=3.2 Hz, 1H), 6.53 (d, J=3.2 Hz, 1H), 4.28 (s, 2H), 3.51-3.47 (m, 4H), 2.48-2.35 (m, 6H), 1.82-1.73 (m, 6H), 1.68-1.41 (m, 8H).

Example 206 Synthesis and Characterization 2-(1-(4-(Cyanomethyl)bicyclo[2.2.2]octan-1-yl)-1,6-dihydroimidazo[4,5-d]pyrrolo[2,3-b]pyridin-2-yl)acetamide

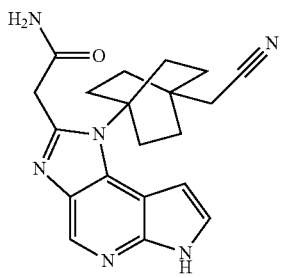 [SMILES: N#CCC12CCC(n3c(CC(N)=O)nc4cnc5[nH]ccc5c43)(CC1)CC2]

Step A: 2-(1-(4-(Cyanomethyl)bicyclo[2.2.2]octan-1-yl)-6-(phenylsulfonyl)-1,6-dihydroimidazo[4,5-d]pyrrolo[2,3-b]pyridin-2-yl)acetamide. A mixture of ethyl 2-(1-(4-(cyanomethyl)bicyclo[2.2.2]octan-1-yl)-6-(phenylsulfonyl)-1,6-dihydroimidazo[4,5-d]pyrrolo[2,3-b]pyridin-2-yl)acetate (Intermediate 10, 150 mg, 0.282 mmol), 28% ammonium hydroxide aqueous solution (2 mL), and EtOH (10 mL) in a 50 mL round-bottomed flask was stirred at room temperature overnight. More 28% ammonium hydroxide aqueous solution (18 mL) and THF (5 mL) were added. The mixture was stirred at room temperature for another 24 hours and concentrated to dryness under reduced. The residue was purified by preparative TLC (eluent: $CH_2Cl_2$:MeOH=20:1) to afford the title compound (80 mg, 56%) as a white solid. $R_f$ ($CH_2Cl_2$:MeOH=20:1), 0.3.

Step B: 2-(1-(4-(Cyanomethyl)bicyclo[2.2.2]octan-1-yl)-1,6-dihydroimidazo[4,5-d]pyrrolo[2,3-b]pyridin-2-yl)acetamide.2,2,2-trifluoroacetate. A solution of 2-(1-(4-(cyanomethyl)bicyclo[2.2.2]octan-1-yl)-6-(phenylsulfonyl)-1,6-dihydroimidazo[4,5-d]pyrrolo[2,3-b]pyridin-2-yl)acetamide (80 mg, 0.16 mmol), 1 N NaOH (aq) (0.5 mL, 0.5 mmol), THF (2 mL), and MeOH (2 mL) was stirred at room temperature for 12 hours and concentrated under reduced pressure. The residue was partitioned between water (5 mL) and ethyl acetate (20 mL×2). The combined organic phases were washed with $H_2O$ (10 mL) and brine (10 mL), dried over anhydrous $Na_2SO_4$, filtered, concentrated, and purified by preparative HPLC (eluent: 10% to 30% (v/v) $CH_3CN$ and $H_2O$ with 0.1% TFA) to afford the title compound (23 mg, 39%) as a white solid. MS (ESI): mass calcd. For $C_{20}H_{22}N_6O$, 362.2; m/z found, 363.1 $[M+H]^+$. $^1H$ NMR (400 MHz, $CD_3OD$) δ 8.77 (s, 1H), 7.77 (d, J=3.2 Hz, 1H), 6.91 (d, J=3.6 Hz, 1H), 4.46-4.44 (m, 2H), 2.69-2.65 (m, 6H), 2.51 (s, 2H), 2.03-2.00 (m, 6H).

Example 207 Synthesis and Characterization 2-(1-(4-(Cyanomethyl)bicyclo[2.2.2]octan-1-yl)-1,6-dihydroimidazo[4,5-d]pyrrolo[2,3-b]pyridin-2-yl)-N-phenylacetamide

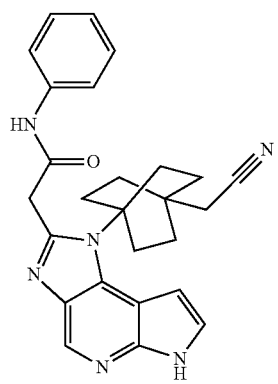 [SMILES: N#CCC12CCC(n3c(CC(=O)Nc4ccccc4)nc4cnc5[nH]ccc5c43)(CC1)CC2]

The title compound (7 mg, 99%) was prepared using analogous conditions as found in Example 205 and using sodium 2-(1-(4-(cyanomethyl)bicyclo[2.2.2]octan-1-yl)-1,6-dihydroimidazo[4,5-d]pyrrolo[2,3-b]pyridin-2-yl)acetate (Intermediate 11, 200 mg, 0.52 mmol) and aniline (53 mg, 0.57 mmol) instead of piperidine. MS (ESI): mass calcd. For $C_{26}H_{26}N_6O$, 438.2; m/z found, 439.2 $[M+H]^+$. $^1H$ NMR (400 MHz, $CD_3OD$) δ 8.55 (s, 1H), 7.59-7.55 (m, 2H), 7.53 (d, J=3.4 Hz, 1H), 7.36-7.30 (m, 2H), 7.15-7.09 (m, 1H), 6.73 (d, J=3.4 Hz, 1H), 3.35 (s, 2H), 2.70-2.60 (m, 6H), 2.45 (s, 2H), 2.00-1.92 (m, 6H).

Example 208 Synthesis and Characterization 2-(1-(4-(Cyanomethyl)bicyclo[2.2.2]octan-1-yl)-1,6-dihydroimidazo[4,5-d]pyrrolo[2,3-b]pyridin-2-yl)-N-(cyclohexylmethyl)acetamide

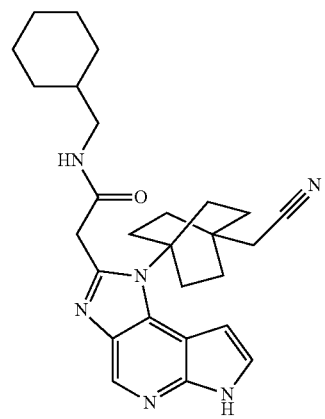 [SMILES: N#CCC12CCC(n3c(CC(=O)NCC4CCCCC4)nc4cnc5[nH]ccc5c43)(CC1)CC2]

The title compound (70 mg, 29%) was prepared using conditions analogous to those as found in Example 205 and using sodium 2-(1-(4-(cyanomethyl)bicyclo[2.2.2]octan-1-yl)-1,6-dihydroimidazo[4,5-d]pyrrolo[2,3-b]pyridin-2-yl)acetate (Intermediate 11, 200 mg, 0.52 mmol) and cyclohexylmethanamine (64 mg, 0.57 mmol) instead of piperidine. MS (ESI): mass calcd. for $C_{27}H_{34}N_6O$, 458.3; m/z found, 459.2 $[M+H]^+$. $^1$H NMR (400 MHz, $CD_3OD$) δ 8.53 (s, 1H), 7.51 (d, J=3.5 Hz, 1H), 6.71 (d, J=3.5 Hz, 1H), 4.22-4.18 (m, 2H), 3.08 (d, J=6.8 Hz, 2H), 2.63-2.56 (m, 6H), 2.46 (s, 2H), 1.97-1.91 (m, 6H), 1.80-1.73 (m, 4H), 1.72-1.65 (m, 1H), 1.57-1.46 (m, 1H), 1.34-1.17 (m, 3H), 1.03-0.91 (m, 2H).

Example 209 Synthesis and Characterization 2-(1-(4-(Cyanomethyl)bicyclo[2.2.2]octan-1-yl)-1,6-dihydroimidazo[4,5-d]pyrrolo[2,3-b]pyridin-2-yl)-N-methylacetamide

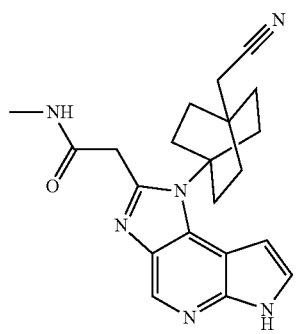 [SMILES: CNC(=O)Cc1nc2cnc3[nH]ccc3c2n1C12CCC(CC#N)(CC1)CC2]

The title compound (24 mg, 12%) was prepared using conditions analogous to those as found in Example 205 and using sodium 2-(1-(4-(cyanomethyl)bicyclo[2.2.2]octan-1-yl)-1,6-dihydroimidazo[4,5-d]pyrrolo[2,3-b]pyridin-2-yl)acetate (Intermediate 11, 200 mg, 0.52 mmol) and methanamine (0.78 mL, 0.57 mmol) instead of piperidine. MS (ESI): mass calcd. for $C_{21}H_{24}N_6O$, 376.2; m/z found 377.2 $[M+H]^+$. $^1$H NMR (400 MHz, $CD_3OD$) δ 8.52 (s, 1H), 7.50 (d, J=3.5 Hz, 1H), 6.71 (d, J=3.5 Hz, 1H), 4.19 (s, 2H), 2.77 (s, 3H), 2.62-2.55 (m, 6H), 2.45 (s, 2H), 1.97-1.91 (m, 6H).

Polymorph Screening Example

Some embodiments of compounds according to this invention as free bases present multiple crystalline configurations that have a complex solid-state behavior, some of which in turn can present distinguishing features among themselves due to different amounts of incorporated solvent. Some embodiments of compounds according to this invention are in the form of pseudopolymorphs, which are embodiments of the same compound that present crystal lattice compositional differences due to different amounts of solvent in the crystal lattice itself. In addition, channel solvation can also be present in some crystalline embodiments of compounds according to this invention, in which solvent is incorporated within channels or voids that are present in the crystal lattice. For example, the various crystalline configurations given in Table 2 were found for compound Ex. 1. Because of these features, non-stoichiometric solvates were often observed, as illustrated in Table 2. Furthermore, the presence of such channels or voids in the crystal structure of some embodiments according to this invention enables the presence of water and/or solvent molecules that are held within the crystal structure with varying degrees of bonding strength. Consequently, changes in the specific ambient conditions can readily lead to some loss or gain of water molecules and/or solvent molecules in some embodiments according to this invention. It is understood that "solvation" (third column in Table 2) for each of the embodiments listed in Table 2 is the formula solvation, and that the actual determination of the same as a stoichiometry number (fourth column in Table 2) can slightly vary from the formula solvation depending on the actual ambient conditions when it is experimentally determined. For example, if about half of the water molecules in an embodiment may be present as hydrogen-bonded to the active compound in the crystal lattice, while about the other half of water molecules may be in channels or voids in the crystal lattice, then changes in ambient conditions may alter the amount of such loosely contained water molecules in voids or channels, and hence lead to a slight difference between the formula solvation that is assigned according to, for example, single crystal diffraction, and the stoichiometry that is determined by, for example, thermogravimetric analysis coupled with mass spectroscopy.

TABLE 2

Embodiments of crystalline forms of compound Ex. 1

| Embodiment | Crystallization solvent | Solvation | Stoichiometry |
|---|---|---|---|
| 1s | — | monohydrate | 0.8 $H_2O$ |
| 1a | Water | monohydrate | 1.3 $H_2O$ |
| 1b | Toluene | Toluene solvate | 0.4 toluene |
| 1c | Ethyl acetate/ 1,4-dioxane | monohydrate | 1.1 $H_2O$ |
| 1d | Acetonitrile/ chloroform | 1.7 hydrate | 1.7 $H_2O$ |
| 1e | Ethyl acetate/ 1,4-dioxane | monohydrate | 1 $H_2O$ |
| 1f | p-xylene | p-xylene solvate | 0.3 p-xylene |
| 1f | Cumene | Cumene solvate | 0.3 cumene |
| 1g | Anisole | Anisole solvate | 0.3 anisole |
| 1h | p-xylene | p-xylene solvate | 0.2 p-xylene |
| 2 | 1,4-dioxane | 1,4-dioxane solvate | 1.2 1,4-dioxane |
| 3b | Cyclohexanone | Cyclohexanone solvate | 0.3 Cyclohexanone |
| 3c | 1,4-dioxane | 1,4-dioxane solvate | 0.5 1,4-dioxane |
| 3d | THF | THF solvate | 0.4 THF |
| 3e | Isobutanol | Isobutanol solvate | 0.7 isobutanol |
| 1b + 4 | Water/methanol | Mix hydrate/methanol solvate | — |
| 5 | Chloroform | Chloroform solvate | 0.5 chloroform |
| 6 | Acetonitrile | Anhydrous | 0.2 acetonitrile |
| 1s + 7 | Heptane | Heptane solvate | 0.1 hepatane |
| 7 | — | Non-solvated | — |
| 8 | — | Non-solvated | — |
| 9 | — | Non-solvated | — |
| 10 | | dihydrate | 1.8 $H_2O$ |

The compound that was obtained as described in Example 1 was further crystallized by preparing a slurry in DCM (1:3, for example 10 g of compound in 30 ml DCM) that was stirred at 40° C. for 4 hours, and further stirred for 14 hours at 25° C., then heptane was slowly added (1:2, for example 20 ml of heptane into the compound/DCM slurry/solution) at 25° C., stirred at 40° C. for 4 hours, cooled to 25° C. and stirred for further 14 hours at 25° C. Subsequent filtration lead to compound Ex. 1 in the form of an off-white solid, that was identified as a monohydrate, a 1s embodiment.

Figure 2:
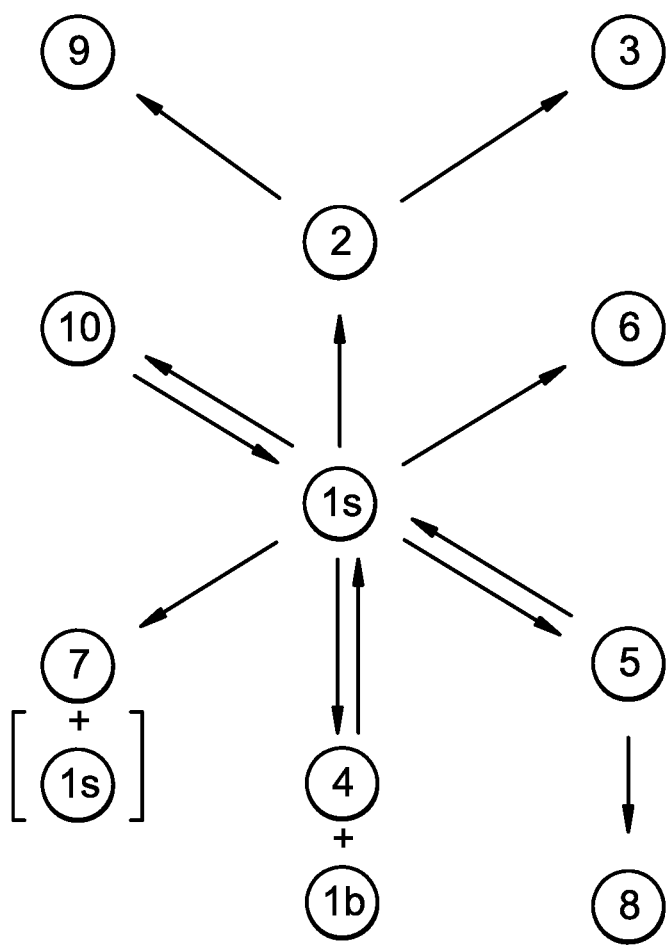

Embodiments 1-10 in Table 2 and FIG. 2 are crystalline. Embodiments 1s and 1a through 1 h are isostructural. Embodiment 1s crystallizes in a centro-symmetrical triclinic space group P-1. The term "embodiment 1" collectively refers to the isostructural embodiments is and 1a through 1h. Any one of such 1s and 1a through 1 h embodiments is sometimes referred to as an isostructural member of embodiment 1 or just as a member of embodiment 1. Embodiments 3b, 3c, 3d and 3e are isostructural and crystallize in the monoclinic system, space group C 2/c. The term "embodiment 3" collectively refers to the isostructural embodiments 3b, 3c, 3d and 3e. Any one of such 3b, 3c, 3d and 3e embodiments is sometimes referred to as an isostructural member of embodiment 3 or just as a member of embodiment 3. Isostructural embodiments are such that they possess similar crystal structure properties (same symmetries and similar unit cell parameters and crystal packing) while having different chemical compositions (i.e., different solvent and/or water molecules incorporated in the crystal lattice). Unit cell parameters in isostructural embodiments can slightly differ due to the different composition (solvent or water incorporated into the crystal structure). Embodiments referred to in Table 2 were prepared and/or interconverted as schematically shown in FIG. 2 and as described in more detail in the following screening techniques.

Screening included crystallization protocols such as solvent equilibration in neat solvents, evaporative crystallization, cooling crystallization with hot filtration, crash-crystallization with anti-solvent, and crystallization by thermocycling. Solids were analyzed by HT-XRPD. When applicable, mother liquors were evaporated completely and the remaining solids were also analyzed by HT-XRPD. The predominant solid form that was identified was the starting material embodiment 1s as a monohydrate.

Solvent equilibration at 25° C. and 50° C.

Long term slurry experiments were performed by suspending compound embodiment s in twenty neat solvents and stirred at room temperature for two weeks and at 50° C. for one week. Upon completion of the equilibration time, the residual solids were separated from the mother liquors. The solids were dried under ambient conditions and dried under vacuum (5mBar) before being analyzed by HT-XRPD. Subsequently, the solids were exposed to accelerated aging conditions (40° C./70% relative humidity) for two days and again analyzed by HT-XRPD.

From most of the crystallization solvents, the starting material as embodiment 1s was obtained. From several crystallization solvents, HT-XRPD patterns were found to be similar to those of the initial embodiment 1s. In most of these diffraction patterns peak shifts and/or additional peaks were identified. Each of these patterns corresponded to an embodiment that was labeled as one of 1a through 1 h, and based on the similarities in the HT-XRPD diffraction patterns for such embodiments, they are presented as embodiments that are isostructural members of embodiment 1. All isostructural members of embodiment 1 converted to embodiment 1a after exposure to 40° C. and 75% RH for two days.

Embodiment 1s converted to hydrated embodiment 10 when it was exposed to 100% RH at 25° C. Nevertheless, embodiment 10 was physically not stable at ambient conditions. Whereas embodiment 1s crystallized in the triclinic system, space group P-1, embodiment 10 was found to crystallize in the monoclinic system, space group C 2/c. Embodiment 10 had limited physical stability under ambient conditions and it converted to another embodiment such as 1s or 1a. This behavior is attributable to an unequally strong binding of all the hydration/solvation molecules. In this case, embodiment 10 would have a less strongly bound second water molecule that would be lost under ambient conditions. More precisely, the physical stability of embodiment 1s was investigated in climate chambers by exposing a 20 mg sample of such embodiment to 40° C. and 70% relative humidity for four days, and another 20 mg sample of the same embodiment was exposed also for four days to 25° C. and 100% relative humidity. After four days, the various solid samples were analyzed by HR-XRPD, the crystal cell parameters were determined and the diffractograms were indexed. Diffractograms are shown in FIG. 6. From bottom to top, the first diffractogram in FIG. 6 corresponds to embodiment 1s as starting material, and the second corresponds to the same form after a 4-day exposure to 40° C. and 70% relative humidity, noted as "1s 70 RH" in the same figure. This analysis revealed that the initial embodiment 1s had been recovered although with a small amount of a second crystalline form that was possibly another hydrated embodiment with a higher water content. Indexing for such form was not possible due to the small amount in which it was present. The third diffractogram corresponds to embodiment 1s after a 4-day exposure to 25° C. and 100% relative humidity, noted as "10" in the same figure. These conditions lead to the conversion of embodiment 1s into embodiment 10, with a small contamination of initial embodiment 1s, and solvation as characterized in Table 2. Upon dehydration, both embodiments 1s and 10 re-crystallized to the anhydrous form with a melting point of 148° C.

Solvent equilibration at room temperature yielded embodiment 1b out of toluene as the crystallization solvent, and embodiment 1f out of p-xylene as the crystallization solvent.

Three additional solid embodiments were identified and designated as embodiments 2, 3 and 7. Embodiment 2 was identified from the solvent equilibration experiment performed at room temperature in 1,4-dioxane while embodiment 7 was found as a mixture with embodiment 1s in the single solvent equilibration experiment at 50° C. from heptane. Several similar but not identical diffractograms were identified which were grouped as embodiments 3b, 3c, 3d and 3e that are isostructural members of embodiment 3. Isostructural members of embodiment 3 were found mixed with members of embodiment 1. The mixtures containing members of embodiment 3 transformed in some cases to embodiment 1a or to mixtures of embodiments 1a and 3e. Embodiment 7 appeared to be physically stable, but embodiment 2 converted to embodiment 3e after exposure to AAC for two days.

Evaporative Crystallization

The mother liquors saved from the solvent equilibration experiments performed at RT were used for slow evaporative crystallization experiments. The mother liquors were filtered to remove any particulate matter and allowed to slowly evaporate under ambient conditions. The obtained solids were analyzed by HT-XRPD and again after exposure to AAC for two days.

Due to the poor solubility of compound Ex. 1 in some of the solvents, no solids were recovered when such solvents were used. In the experiments where solids had precipitated, an amorphous residue or isostructural members of embodiments 1 or 3 were recovered. During the stability study, the different members of embodiment 1 converted to embodiment 1a whilst the sample of embodiment 3 seemed to be physically stable. The amorphous solids in some cases remained amorphous after the stability study, became deliquescent or showed some signs of crystallinity.

Cooling Crystallization

The mother liquors of the solvent equilibration experiments performed at 50° C. were filtered at 50° C. to remove any particulate matter. The suspensions at 50° C. were filtered using 0.2 μm PTFE filters, and the solutions were placed at 5° C. and aged for 72 hours. When solids had precipitated during aging these solids were separated from the liquid, dried under ambient conditions and under vacuum, and analyzed by HT-XRPD. The remaining mother liquors were allowed to slowly evaporate and the remaining solids were analyzed by HT-XRPD. The samples in which no precipitation occurred were placed under vacuum and the dried solids were analyzed by HT-XRPD. All the solids were then exposed to AAC (2 days at 40° C./70% RH) and re-analyzed by HT-XRPD.

Solids did not precipitate upon cooling in some of the solutions, in which cases the solutions were evaporated under ambient conditions. Due to the low solubility of compound Ex. 1 in some solvents, no solids were obtained from some solutions.

From four solvents (2-propanol, 2-butanone, acetonitrile, and methanol), precipitation occurred. Embodiment 6 was identified after evaporation of a single cooling crystallization experiment at mL scale in 800 μL acetonitrile, concentration of 25 mg/mL. Embodiment 6 seemed to be a stable solid form after 2 days AAC, and it appeared as a non-solvated embodiment.

Cooling/Evaporative Crystallization at μL Scale

The cooling/evaporative crystallization experiments at μL scale were performed in a 96-well plate, using 12 neat solvents and 12 solvent mixtures and applying four temperature profiles. In each well approximately 4 mg of embodiment 1s was solid dosed. Subsequently, the crystallization solvents (80 μL) and solvent mixtures were added to reach a concentration of 50 mg/mL, and the plate, with each well individually sealed, to subsequently undergo one of the four temperature profiles. Upon completion of the temperature profile the solvents were allowed to evaporate at low ambient pressure (24 hours) and the remaining solids were analyzed by HT-XRPD before and after exposure to AAC for 2 days (40° C./70% RH).

Members of embodiments 1 and 3 were found from most of the solvent systems and temperature profiles. However, a certain tendency of solid form versus temperature profile was observed. Embodiment 1b was mainly identified from the short temperature profiles (3 hours aging). Nevertheless, the same solvent systems with long aging times led to the identification of embodiment 1f, members of embodiment 3 or mixtures of members of embodiments 1 and 3. Embodiment 3c was obtained with 1,4-dioxane as crystallization solvent and a temperature profile of 50° C. as initial temperature, held for 60 min, followed by cooling at a rate of 1° C./h to a final temperature of 20° C., held for 48 h; embodiment 3d was obtained with tetrahydrofuran as crystallization solvent and the same temperature profile as for embodiment 3c.

Embodiment 4 was identified in experiments performed in methanol/water (50/50, v/v), THF and DCM/IPA (50/50, v/v) when short aging conditions were applied. Embodiment 4 was obtained by treating embodiment 1s with a mixture (50/50) of water and methanol and a temperature profile of 50° C. as initial temperature, held for 60 min, followed by cooling at a rate of 20° C./h to a final temperature of 5° C., held for 3 h, which yielded embodiment 4 together with embodiment 1b. Embodiment 4 together with embodiment 1b was also obtained by treating is with a mixture (50/50) of water and methanol and a temperature profile of 50° C. as initial temperature, held for 60 min, followed by cooling at a rate of 20° C./h to a final temperature of 20° C., held for 3 h. Embodiment 4 did not appear to be physically stable under ambient conditions. Cooling crystallization experiments yielded embodiment 1c out of ethyl acetate/1,4-dioxane (50/50, v/v) as the crystallization solvent and a temperature profile of 50° C. as initial temperature, held for 60 min, followed by cooling at a rate of 1° C./h to a final temperature of 5° C., held for 48 h; embodiment 1d out of acetonitrile/chloroform (50/50, v/v) as the crystallization solvent and a temperature profile of 50° C. as initial temperature, held for 60 min, followed by cooling at a rate of 1° C./h to a final temperature of 5° C., held for 48 h; and embodiment 1e out of ethyl acetate/1,4-dioxane (50/50, v/v) as the crystallization solvent and a temperature profile of 50° C. as initial temperature, held for 60 min, followed by cooling at a rate of 1° C./h to a final temperature of 20° C., held for 48 h.

Embodiment 5 was identified in experiments performed in chloroform as the crystallization solvent and a temperature profile of 50° C. as initial temperature, held for 60 min, followed by cooling at a rate of 1° C./h to a final temperature of 20° C., held for 48 h.

Similar conversions were seen during the stability study as previously observed in the other crystallization methods. In most cases all solid forms converted to embodiment 1a or to mixtures containing embodiment 1a.

Evaporative Crystallization from Solid Mixtures

In evaporative crystallization using solvent/anti-solvent mixtures, clear solutions of a compound are prepared from which the solvent evaporates first (high vapor pressure) causing the compound to precipitate to some extent in the form of crystals. These crystals then act as seeds when the anti-solvent (lower vapor pressure) is evaporated.

Compound Ex. 1 did not completely dissolve in each of the solvent systems. For that reason, all the experiments included filtration prior to evaporation.

The results of the HT-XRPD analysis demonstrated that compound Ex. 1 crystallized mainly as embodiment 1s upon evaporation of solvent mixtures. This was observed for the following solvent/anti-solvent systems: tetrahydrofuran/water, acetonitrile/water, chloroform/ethanol, methanol/ethyl acetate, 2-butanone/isopropanol, and heptane/acetone. From two systems, acetone/cumene and 1,4-dioxane/ethyl formate, the isostructural embodiments 3b and 3e were identified, which after AAC converted to different mixtures of embodiments 1a and 3d, and is and 3e, respectively.

Anti-Solvent Crystallization

Saturated solutions of compound Ex. 1 were prepared in neat solvents. The anti-solvent additions were performed in forward and reverse additions. In the forward addition, the anti-solvent was added in three aliquots to the compound solution. The reverse addition was performed by adding a volume of compound solution to a large excess of anti-solvent (20 mL).

After precipitation, the solids were separated from the liquids, dried under ambient conditions and dried under vacuum (5 mbar) before being analyzed by HT-XRPD. The experiments in which no precipitation occurred upon anti-solvent addition were stored at 5° C. for 48 hours to induce precipitation. The precipitated solids were afterwards separated and analyzed by HT-XRPD. When no solids were obtained, the solutions were evaporated under mild conditions and the residual solids were analyzed by HT-XRPD. All solids were exposed to AAC (2 days at 40° C./70% RH) and were re-analyzed by HT-XRPD.

The forward anti-solvent crystallization showed precipitation in all cases. All solids could be classified as isostructural members (1s, 1b, 1j, 1f) of embodiment 1 or of embodiment 3 (3b, 3d, 3f). After exposure to AAC, all solid samples converted to embodiment 1a, except one that converted to a mixture of embodiments 1a and 3e.

The reverse anti-solvent crystallization experiments performed in DMSO as solvent gave different solid forms depending on the anti-solvent used. With dichloromethane or p-xylene isostructural members (1s and 1b) of embodiment 1 were identified, while with MTBE an amorphous residue was obtained. Evaporation of two solutions with heptane and water as anti-solvents that had no precipitated upon anti-solvent addition led to an oil. Conversions to embodiment 1a were observed after AAC, and the amorphous residues became deliquescent.

Hot Filtration Experiments

The cooling crystallization experiments with hot filtration were performed from supersaturated solutions of compound Ex. 1 prepared at 50° C. in different solvent mixtures. The hot filtrated solutions underwent a 48-hour cooling profile. The vials in which solids had precipitated after the temperature profile were centrifuged and the solids were separated from the liquid and analyzed by HT-XRPD (after drying under vacuum). If no solids had precipitated the solutions were evaporated under vacuum and the solids analyzed by HT-XRPD. All the solids were exposed to AAC (2 days at 40° C./70% RH) and re-analyzed by HT-XRPD. In half of the hot filtration experiments precipitation did not occur and upon evaporation of the solvents, not enough solids were recovered due to the poor solubility of compound Ex. 1 in those solvent systems. In three experiments, an amorphous residue was recovered which after AAC crystallized to a mixture of members of embodiment 1 (is or 1a) and 3 (3e) or became deliquescent. Embodiment 5 was identified from the experiment in acetone/chloroform (50/50, v/v). This embodiment appeared to be physically unstable as conversion to embodiment 1a was observed after AAC.

Thermo-Cycling Experiments

Suspensions of about 6 mg of embodiment 1s were prepared in 10 solvents at room temperature. The suspensions were cycled between 5° C. and 50° C. Upon completion of the thermo-cycling, the solids were separated by centrifugation and dried under ambient conditions and under vacuum (5 mbar) before being analyzed by HT-XRPD. Subsequently, all solids were exposed to AAC for two days and again analyzed by HT-XRPD. Thermo-cycling experiments usually promote the formation of the more stable polymorphic form. With the exception of the experiment performed in cyclohexanone, all vials contained solids after the thermo profile. The cyclohexanone solution was slowly evaporated under mild vacuum. Members of embodiments 1, 3 or mixtures of them were identified mainly in the wet solids. Upon drying these solids, conversion to embodiment 1s was observed. Embodiments 3b and 3e were obtained from thermo-cycling in 300 µL of cyclohexanone at a concentration of 51 mg/mL (3b), and in 400 µL of isobutanol at a concentration of 37.3 mg/mL (3e). Embodiment 5 was obtained from thermo-cycling in 800 µL of chloroform at a concentration of 18.6 mg/mL.

Figure 3:
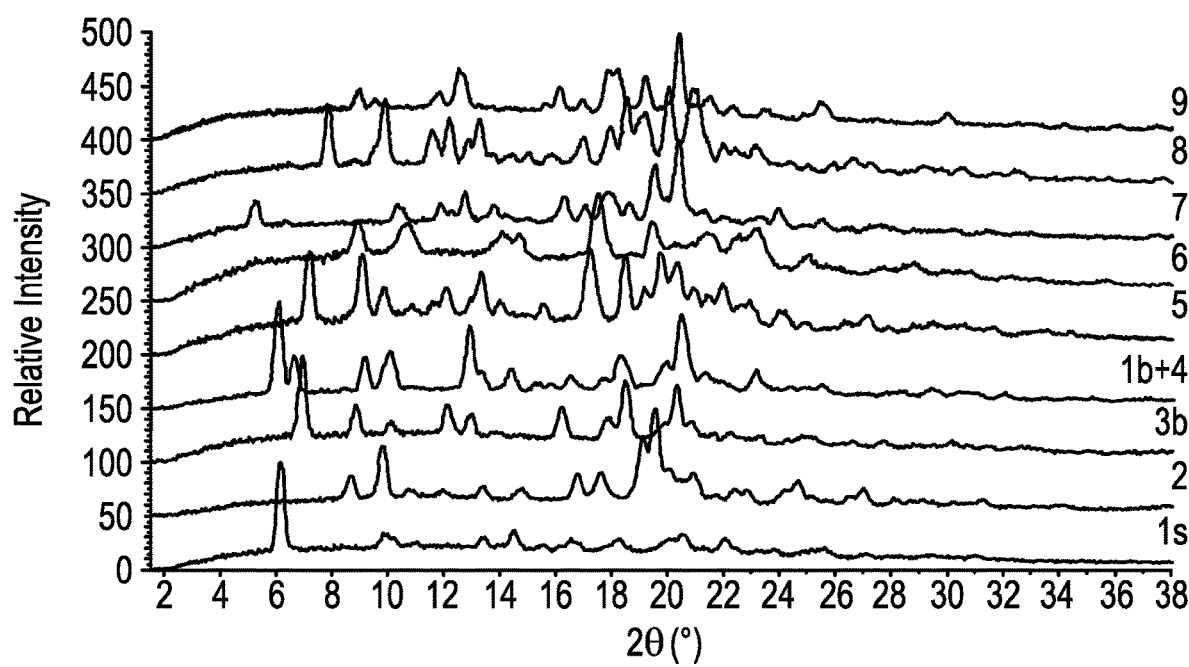
Figure 4:
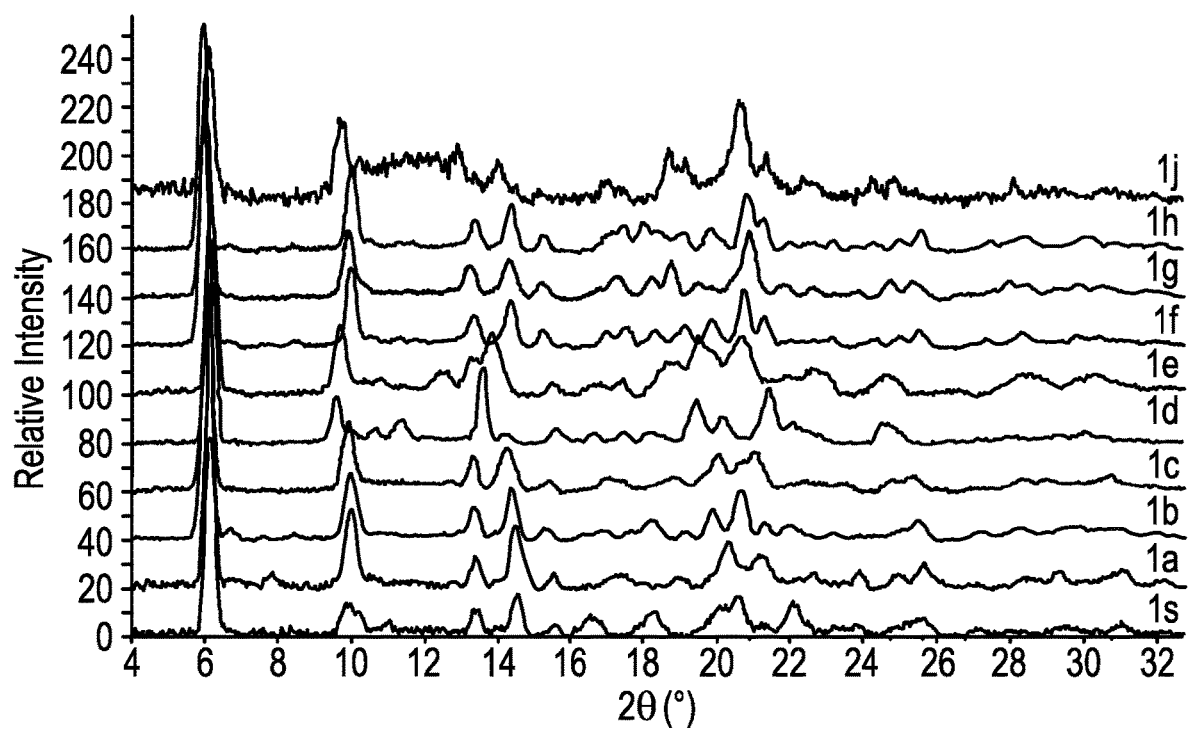
Figure 5:
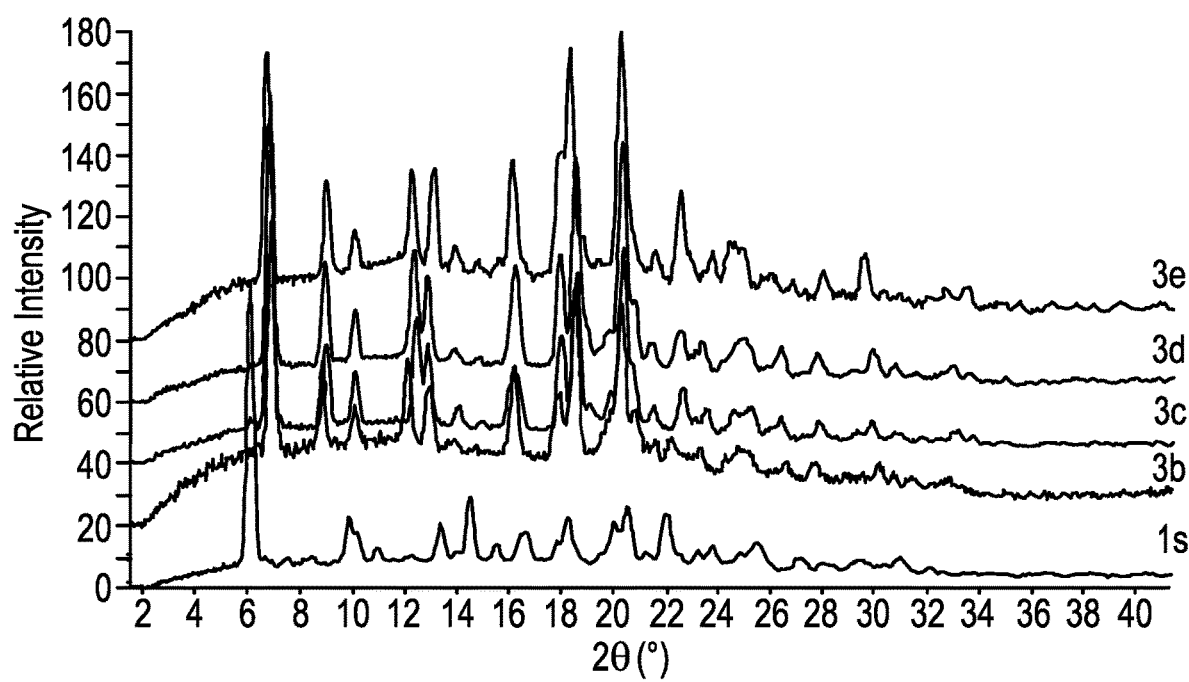

FIGS. 3, 4 and 5 show an overlay of HT-XRPD patterns for the embodiments listed in Table 2 and also referred to in the screenings described above.

Embodiment 1s was recovered from most of the crystallization experiments. It is a channel hydrate having a variable number of water molecules and/or other solvents incorporated depending on ambient conditions. Conversion to embodiment 1a was observed. This form contained slightly more water (1.3 molecules of water). All isostructural members of embodiment 1 converted to embodiment 1a after exposure to 40° C. and 75% RH for two days. The shifts of some diffraction peaks in XRPD patterns for members of embodiment 1 might be attributed to the different solvent or water molecules that were incorporated into the crystal lattice. FIG. 4 shows an overlay of HT-XRPD patters for members of embodiment 1. Diffractogram 1s corresponds to compound Ex. 1 as starting material in the form of embodiment 1s. Diffractogram 1a corresponds to embodiment 1a that was obtained after exposure to AAC of several embodiment 1s samples. Diffractogram 1b corresponds to embodiment 1b that was obtained from the solvent equilibration experiment at RT in toluene. Diffractogram 1c corresponds to embodiment 1c that was obtained from the cooling crystallization experiment at L scale in ethyl acetate/1,4-dioxane (50/50, v/v). Diffractogram 1c corresponds to embodiment 1d that was obtained from the cooling crystallization experiment at µL scale in acetonitrile/chloroform (50/50, v/v). Diffractogram 1e corresponds to embodiment 1e that was obtained from the cooling crystallization experiment at µL scale in ethyl acetate/1,4-dioxane (50/50, v/v). Diffractogram 1f corresponds to embodiment 1f that was obtained from the solvent equilibration experiment at RT in p-xylene. Diffractogram 1 g corresponds to embodiment 1 g that was obtained from the solvent equilibration experiment at 50° C. in anisole. Diffractogram 1 h corresponds to embodiment 1 h obtained from the cooling crystallization experiment at µL scale in p-xylene.

Diffractograms for members of embodiment 3 are shown in FIG. 5. The shifts observed in the different HT-XRPD patterns are most likely attributed to the different solvent molecules that were incorporated into the crystal lattice. Embodiment 3 was obtained by heating embodiment 2 to 40° C. at 70% RH for 4 days. Embodiments 3b through 3e were solvated forms containing a non-stoichiometric amount of solvent which varied depending on the solvent incorporated in the crystal structure (0.3-0.7 molecules). The mixtures containing members of embodiment 3 were unstable upon exposure to AAC and they transformed in some cases to embodiment 1a or to mixtures of embodiments 1a and 3e. Conversion to embodiment 1a is attributed to the exchange of solvent molecules by water molecules upon exposure to high relative humidity, and re-crystallization to the hydrated embodiment 1a.

Embodiment 9 was obtained by heating embodiment 2 to a temperature of about 200° C. followed by cooling to 25° C. and also by cyclic DSC 25-200-25-300° C.

Embodiment 8 was obtained by heating embodiment 5 to a temperature of about 175° C.

Embodiments of this invention include compound Ex. 1 in at least one of the forms is, 1a, 1b, 1c, 1d, 1e, 1f, 1 g, 1 h, 2, 3b, 3c, 3d, 3e, 5, 6, 7, 8, 9, and 10. Embodiments of this invention include compounds according to this invention in the form of pharmaceutically acceptable co-crystals.

Enzymatic Inhibition Assay

Materials

Substrate (NH2-KGGEEEEYFELVKK-CO2 (SEQ ID NO: 1)), internal standard peptide (NH2-SWGAIETD-KEYYTVKD-CO2 (SEQ ID NO: 2)) and product peptide (for standard curve only) (NH2-KGGEEEEY-Pi-FELVKK-CO2 (SEQ ID NO: 3)), were purchased from AnaSpec (Fremont, Calif., USA). JAK1-JH1JH2 (574-1154 with a His-GST Tag and a C-terminal tev (ENLYFQ-G (SEQ ID NO: 4)) cleavage site), JAK3-JH1JH2 (512-1124 with a GST Tag and a C-terminal tev (ENLYFQ-G (SEQ ID NO: 4)) cleavage site), and Tyk2-JH2JH1 (8H_tev_580-1182-C936A-C1142A with a C-terminal tev (ENLYFQ-G (SEQ ID NO: 4)) cleavage site) were purified internally. JAK2-JH1JH2 (532-1132 with a GST tag and C-terminal tev (ENLYFQ-G (SEQ ID NO: 4)) cleavage site), was purchased from Invitrogen. LC/MS grade Water and Acetonitrile (ACN), were purchased from HoneyWell, Burdick & Jackson (Muskegon, Mich., USA). Dimethylsulfoxide 99.8% (DMSO) and Trifluoroacetic Acid 99.5% (TFA) were purchased from EMD Chemical (Gibbstown, N.J., USA). Adenosine triphosphate (ATP), 4-Morpholinepropanesulfonic acid (MOPS), Magnesium chloride ($MgCl_2$), ethylenediaminetetraacetic acid (EDTA), dithiothreitol (DTT), formic acid >95% (FA) and Tween-20 were purchased from Sigma (St Louis, Mo., USA). 384-well polypropylene plates, Cat #781280 were purchased from Greiner (Monroe, N.C.), RapidFire™ cartridge A C4 Column (Agilent Technologies, Santa Clara, Calif.).

The HTMS experiments were performed in positive ionization mode on a RapidFire 300 instrument (Agilent Technologies, Santa Clara, Calif.), coupled with an ABSiex QTrap 4000 system with an Electrospray Ionization source (RF-MS) (Concord, ON, Canada). The RapidFire system was run with 3 Agilent 1200 series isocratic pumps Agilent Technologies (Santa Clara, Calif.) and one peristaltic pump model ISM832C from Ismatec (Wertheim, Germany). The entire system was operated using the RapidFire software interfaced with Analyst software for the mass spectrometer.

Assay Protocol 11-point dosing series were made for each compound by serially diluting 1:3 or 1:4 in DMSO, with point 12 being a DMSO control. From the serial dilution plates, sample was transferred to a 384 wells assay plate (#781280, Greiner, Monroe, N.C.) using Labcyte Echo (Sunnyvale, Calif.), or Biosero ATS (San Diego, Calif.). The compounds were tested in duplicate. Column 12 was used for positive controls, and column 24 contained negative controls with no enzyme added. A compound from our internal collection, with inhibitory activity for JAK isoforms, was used as a reference compound. The final concentration of DMSO was ≤0.25% in a 20 µL reaction. Assay conditions for each of the proteins are summarized in Table 3. The enzyme reaction was initiated by the addition of 10 µL of 2× enzyme and ATP mixture to 10 µL of 2× substrate solution prepared in reaction buffer (50 mM MOPS pH 7.5, 10 mM $MgCl_2$, 1 mM EDTA, 2 mM DTT, 0.002% Tween-20). The Tyk2 enzyme was pre-incubated with 2 mM ATP for 30 min prior to the reaction initiation. Immediately after the addition of the enzyme to the reaction mixture, the plate was centrifuged at 1000 rpm for 1 minute and incubated at 25° C. for 45 minutes for JAK 3 and 90 minutes for JAK1, JAK2 and Tyk2. The reaction was quenched by the addition of 20 µL of 0.5% TFA containing 0.15 µM of internal standard peptide using Multidrop Combi reagent dispenser (Thermo Scientific, Waltham, Mass.). Several wells in column 24 were typically used for the product standard curve. After the quench, the assay plate was centrifuged at 3000 rpm for 3 minutes and sealed with pierceable aluminum foil (Cat #06644-001, Agilent) using a PlateLoc (Agilent Technologies, Santa Clara, Calif.). The plates then were transferred on to the RapidFire for the MS analysis. Compound inhibition was assessed by a decrease of the phosphorylated product levels in sample wells compared to the non-inhibited enzyme reaction. The assay conditions for the above assays are shown in Table 3 and the results of Ex. 1-209 as tested in these assays are shown in Table 4.

TABLE 3

Assay conditions for JAK family enzyme assays*

| Enzyme | [p], nM | [ATP], µM | [Substrate], µM | [IS], nM |
|---|---|---|---|---|
| JAK1-JH1JH2 | 8.0 | 12.5 | 200 | 100 |
| JAK2-JH1JH2 | 7.0 or 3.6 | 30 | 40 | 100 |
| JAK3-JH1JH2 | 2.0 | 150 | 40 | 100 |
| Tyk2-JH1JH2 | 25 or 14.7 | 50 | 200 | 100 |

*Reaction buffer: 50 mM MOPS, pH 7.5 10 mM $MgCl_2$, 1 mM EDTA, 2 mM DTT, 0.002% Tween-20; "IS" stands for internal standard peptide; "p" stands for phospho-peptide (product); "Substrate" stands for peptide.

High-Throughput Mass Spectrometry Method

The sample analysis on the RapidFire was performed using a mobile phase A consisting of Water/TFA/FA (100: 0.01:0.1, v/v/v), a mobile phase B consisting of ACN/Water/TFA/FA (80:20:0.01:0.1, v/v/v). The following run parameters were used: state 1 (aspirate), 250 ms; state 2 (load/wash), 3000 ms; state 3 (elute), 4000 ms; state 4 (re-equilibrate), 1000 ms with a flow rate of 1.25 mL/min. The samples were aspirated directly from the 384 assay plate and delivered onto RF-MS microscale solid-phase C4 extraction cartridge (Type A). The undesired component such as salt, cofactor, detergent and large protein were washed out and the retained analytes (substrate, product and IS) were coeluted directly onto the ABSiex Qtrap 4000 system. The quantification of peptide (substrate), phospho-peptide (product) and internal standard peptide (IS) was performed by MRM using 562-136.0, 589.2-215.7 and 953.2-158.8 (or 974.2-158.8) transitions respectively.

TABLE 4

Results of Enzymatic Inhibition Assays

| Example # | JAK1-JH2JH1 $IC_{50}$ (nM) | JAK2-JH1JH2 $IC_{50}$ (nM) | JAK3-JH1JH2 $IC_{50}$ (nM) | Tyk2-JH1JH2 $IC_{50}$ (nM) |
|---|---|---|---|---|
| Ex. 1 | 0.3 | 8.2 | 87.8 | 6.9 |
| Ex. 2 | 0.2 | 1.0 | 33.9 | 1.5 |
| Ex. 3 | 0.2 | 6.2 | 82.8 | 11.6 |
| Ex. 4 | 0.1 | 6.6 | 96.2 | 2.2 |
| Ex. 5 | 0.3 | 2.1 | 23.1 | 4.1 |
| Ex. 6 | 0.0 | 4.3 | 49.4 | 0.4 |
| Ex. 7 | 0.1 | 0.6 | 13.3 | 0.9 |
| Ex. 8 | 0.1 | 0.5 | 12.9 | 0.7 |
| Ex. 9 | 0.1 | 0.3 | 48.9 | 1.6 |
| Ex. 10 | 0.1 | 1.4 | 28.2 | 1.1 |
| Ex. 11 | 0.1 | 0.8 | 33.5 | 1.2 |
| Ex. 12 | 0.1 | 9.2 | 99.4 | 1.4 |
| Ex. 13 | 0.1 | 7.1 | 651.2 | 3.3 |
| Ex. 14 | 0.1 | 1.8 | 43.7 | 2.8 |
| Ex. 15 | 0.1 | 3.9 | 54.5 | 4.1 |
| Ex. 16 | 0.1 | 1.2 | 37.7 | 3.7 |
| Ex. 17A | 0.1 | 1.2 | 65.8 | 1.4 |
| Ex. 17B | 0.5 | 4.5 | 102.0 | 2.9 |
| Ex. 18 | 0.1 | 35.3 | 539.9 | 6.4 |
| Ex. 19 | 0.1 | 2.4 | 31.8 | 4.4 |
| Ex. 20 | 0.1 | 1.2 | 20.5 | 1.9 |
| Ex. 21 | 0.1 | 1.3 | 55.1 | 3.5 |
| Ex. 22 | 0.1 | 5.4 | 93.6 | 4.1 |
| Ex. 23 | 0.1 | 1.4 | 38.1 | 3.5 |
| Ex. 24 | 0.1 | 4.9 | 57.5 | 3.3 |
| Ex. 25 | 0.1 | 4.7 | 77.9 | 5.3 |
| Ex. 26 | 0.1 | 6.1 | 106.0 | 2.7 |
| Ex. 27 | 0.1 | 2.9 | 36.9 | 7.2 |
| Ex. 28 | 0.1 | 2.4 | 32.7 | 3.5 |
| Ex. 29 | 0.1 | 7.3 | 67.2 | 3.8 |
| Ex. 30 | 0.2 | 6.6 | 996.3 | 1.6 |
| Ex. 31 | 0.2 | 5.5 | 120.9 | 3.7 |
| Ex. 32 | 0.2 | 1.3 | 59.3 | 2.8 |
| Ex. 33 | 0.2 | 2.3 | 38.0 | 3.8 |
| Ex. 34 | 0.2 | 3.1 | 42.5 | 3.1 |

TABLE 4-continued

Results of Enzymatic Inhibition Assays

| Example # | JAK1-JH2JH1 IC$_{50}$ (nM) | JAK2-JH1JH2 IC$_{50}$ (nM) | JAK3-JH1JH2 IC$_{50}$ (nM) | Tyk2-JH1JH2 IC$_{50}$ (nM) |
|---|---|---|---|---|
| Ex. 35 | 0.2 | 3.6 | 106.6 | 4.5 |
| Ex. 36 | 0.2 | 0.8 | 12.0 | 2.2 |
| Ex. 37 | 0.2 | 4.6 | 38.8 | 4.3 |
| Ex. 38 | 0.2 | 6.6 | 79.9 | 4.7 |
| Ex. 39 | 0.2 | 5.3 | 142.3 | 10.0 |
| Ex. 40 | <0.2 | 1.0 | 47.0 | 0.3 |
| Ex. 41 | <0.2 | 0.4 | 19.9 | 0.6 |
| Ex. 42 | 0.2 | 24.4 | 438.7 | 7.8 |
| Ex. 43 | 0.2 | 5.1 | 87.4 | 5.7 |
| Ex. 44 | 0.2 | 5.4 | 52.3 | 6.0 |
| Ex. 45 | 0.2 | 6.1 | 182.7 | 12.2 |
| Ex. 46 | 0.2 | 14.5 | 214.3 | 5.5 |
| Ex. 47 | 0.2 | 2.3 | 38.9 | 5.1 |
| Ex. 48 | 0.2 | 5.3 | 193.0 | 11.2 |
| Ex. 49 | 0.2 | 43.5 | 249.2 | 4.2 |
| Ex. 50 | 0.2 | 4.0 | 99.9 | 21.0 |
| Ex. 51 | 0.2 | 3.2 | 126.7 | 5.8 |
| Ex. 52 | 0.2 | 1.7 | 57.5 | 4.4 |
| Ex. 53 | 0.2 | 3.2 | 61.8 | 9.0 |
| Ex. 54 | 0.2 | 2.1 | 42.0 | 4.2 |
| Ex. 55 | 0.2 | 2.9 | 59.6 | 4.7 |
| Ex. 56 | 0.2 | 1.9 | 32.9 | 7.2 |
| Ex. 57 | 0.2 | 5.6 | 69.5 | 3.4 |
| Ex. 58 | 0.3 | 1.4 | 31.4 | 3.3 |
| Ex. 59 | 0.3 | 6.7 | 121.9 | 7.2 |
| Ex. 60 | 0.3 | 1.7 | 72.0 | 3.4 |
| Ex. 61 | 0.3 | 25.7 | 219.1 | 6.3 |
| Ex. 62 | 0.3 | 2.1 | 30.6 | 2.6 |
| Ex. 63 | 0.3 | 2.2 | 57.3 | 19.1 |
| Ex. 64 | 0.3 | 5.6 | 51.4 | 5.7 |
| Ex. 65 | 0.3 | 7.0 | 81.5 | 11.7 |
| Ex. 66 | 0.3 | 2.5 | 18.9 | 2.8 |
| Ex. 67 | 0.3 | 12.3 | 121.0 | 3.8 |
| Ex. 68 | 0.3 | 8.2 | 179.6 | 13.3 |
| Ex. 69 | 0.3 | 4.1 | 111.1 | 15.6 |
| Ex. 70 | 0.4 | 10.1 | 108.0 | 9.4 |
| Ex. 71 | 0.2 | 3.4 | 54.2 | 3.3 |
| Ex. 72 | 0.4 | 5.2 | 181.2 | 27.2 |
| Ex. 73 | 0.4 | 19.9 | 199.0 | 6.3 |
| Ex. 74 | 0.4 | 1.6 | 30.3 | 1.5 |
| Ex. 75 | 0.4 | 3.4 | 62.3 | 9.2 |
| Ex. 76 | 0.4 | 23.6 | 1213.9 | 16.8 |
| Ex. 77 | 0.4 | 39.4 | 1914.7 | 22.3 |
| Ex. 78 | 0.4 | 11.2 | 69.4 | 13.4 |
| Ex. 79 | 0.4 | 10.6 | 223.4 | 13.3 |
| Ex. 80 | 0.4 | 2.1 | 89.7 | 4.1 |
| Ex. 81 | 0.4 | 3.7 | 117.1 | 6.0 |
| Ex. 82 | 0.4 | 13.6 | 188.9 | 5.2 |
| Ex. 83 | 0.4 | 4.1 | 30.0 | 9.4 |
| Ex. 84 | 0.4 | 27.1 | 1117.9 | 10.4 |
| Ex. 85 | 0.4 | 6.2 | 68.2 | 5.4 |
| Ex. 86 | 0.4 | 14.0 | 2268.8 | 2.6 |
| Ex. 87 | <0.4 | 27.7 | 274.0 | 10.3 |
| Ex. 88 | 0.4 | 43.4 | 540.6 | 49.5 |
| Ex. 89 | 0.4 | 3.4 | 60.6 | 18.0 |
| Ex. 90 | <4.0 | 8.1 | 85.0 | ~2.4 |
| Ex. 91 | 0.4 | 30.1 | 850.9 | 35.5 |
| Ex. 92 | 0.4 | 11.7 | 874.4 | 33.6 |
| Ex. 93 | 0.5 | 12.0 | 181.0 | 4.5 |
| Ex. 94 | 0.5 | 20.5 | 263.5 | 12.1 |
| Ex. 95 | 0.5 | 0.6 | 18.7 | 1.4 |
| Ex. 96 | 0.5 | 33.8 | 459.9 | 49.6 |
| Ex. 97 | 0.5 | 45.1 | 3882.4 | 26.9 |
| Ex. 98 | 0.5 | 9.3 | 117.0 | 13.0 |
| Ex. 99 | 0.5 | 30.9 | 275.7 | 29.2 |
| Ex. 100 | 72.0 | 1930.2 | >6250.3 | 2279.8 |
| Ex. 101 | 0.5 | 29.7 | 182.4 | 6.7 |
| Ex. 102 | 0.5 | 11.5 | 201.0 | 7.4 |
| Ex. 103 | 0.5 | 25.1 | 458.9 | 11.3 |
| Ex. 104 | 0.5 | 17.5 | 298.5 | 12.6 |
| Ex. 105 | 0.6 | 19.4 | 203.9 | 6.9 |
| Ex. 106 | 0.6 | 14.3 | 149.0 | 11.2 |
| Ex. 107 | 0.6 | 18.2 | 142.0 | 5.1 |
| Ex. 108 | 0.6 | 3.8 | 32.9 | 7.1 |
| Ex. 109 | 0.6 | 7.5 | 135.4 | 11.3 |
| Ex. 110 | 0.6 | 29.0 | 416.2 | 17.4 |
| Ex. 111 | 0.6 | 4.0 | 68.0 | 6.3 |
| Ex. 112 | 0.6 | 3.6 | 161.0 | 40.8 |
| Ex. 113 | 0.6 | 10.2 | 322.3 | 11.2 |
| Ex. 114 | 0.6 | 4.8 | 102.2 | 12.7 |
| Ex. 115 | 0.6 | 73.2 | 754.1 | 86.2 |
| Ex. 116 | 0.6 | 86.7 | 1191.2 | 50.9 |
| Ex. 117 | 0.6 | 15.0 | 272.9 | 17.3 |
| Ex. 118 | 0.7 | 3.5 | 50.5 | 5.4 |
| Ex. 119 | 0.7 | 8.8 | 117.1 | 15.7 |
| Ex. 120 | 0.7 | 16.0 | 227.6 | 19.1 |
| Ex. 121 | 0.7 | 11.4 | 431.0 | 44.3 |
| Ex. 122 | 0.7 | 20.8 | 437.0 | 21.6 |
| Ex. 123 | 0.7 | 8.6 | 145.9 | 11.6 |
| Ex. 124 | 0.7 | 4.4 | 141.4 | 18.1 |
| Ex. 125 | 0.7 | 27.1 | 622.3 | 14.9 |
| Ex. 126 | 0.7 | 19.4 | 317.0 | 14.2 |
| Ex. 127 | 0.7 | 69.4 | 787.6 | 12.8 |
| Ex. 128 | 0.7 | 109.5 | 1088.4 | 64.4 |
| Ex. 129 | 0.8 | 150.0 | 2694.6 | 10.7 |
| Ex. 130 | 0.8 | 15.7 | 129.7 | 19.4 |
| Ex. 131 | 0.8 | 5.6 | 100.3 | 10.5 |
| Ex. 132 | 0.8 | 13.8 | 61.7 | 16.1 |
| Ex. 133 | 0.8 | 9.4 | 154.0 | 19.8 |
| Ex. 134 | 0.8 | 118.5 | 1289.7 | 91.2 |
| Ex. 135 | 0.8 | 4.0 | 54.3 | 8.7 |
| Ex. 136 | 0.9 | 6.0 | 65.9 | 19.1 |
| Ex. 137 | 0.9 | 25.1 | 279.5 | 14.2 |
| Ex. 138 | 0.9 | 18.9 | 195.0 | 18.7 |
| Ex. 139 | 0.9 | 66.9 | 745.6 | 53.5 |
| Ex. 140 | 0.9 | 4.5 | 56.8 | 14.9 |
| Ex. 141 | 0.9 | 95.8 | 4070.1 | 66.7 |
| Ex. 142 | 0.9 | 10.0 | 383.0 | 6.9 |
| Ex. 143 | 0.9 | 38.5 | 1271.5 | 117.2 |
| Ex. 144 | 1.0 | 43.1 | 376.1 | 16.2 |
| Ex. 145 | 1.1 | 9.5 | 175.2 | 19.4 |
| Ex. 146 | 1.1 | 18.0 | 319.0 | 11.3 |
| Ex. 147 | 1.1 | 314.6 | 1974.2 | 87.9 |
| Ex. 148 | 1.1 | 50.4 | 767.0 | 36.2 |
| Ex. 149 | 1.1 | 54.4 | 925.6 | 13.9 |
| Ex. 150 | 1.2 | 10.0 | 110.0 | 34.0 |
| Ex. 151 | 1.4 | 10.6 | 103.3 | 37.1 |
| Ex. 152 | 2.8 | 21.2 | 803.3 | 53.5 |
| Ex. 153 | 3.7 | 43.1 | 512.5 | 42.7 |
| Ex. 154 | 1.2 | 65.4 | 407.7 | 16.1 |
| Ex. 155 | 1.3 | 48.5 | 367.5 | 20.1 |
| Ex. 156 | 1.3 | 33.6 | 1324.6 | 2.9 |
| Ex. 157 | 1.4 | 74.9 | 1109.9 | 39.5 |
| Ex. 158 | 1.4 | 77.9 | 630.5 | 59.5 |
| Ex. 159 | 1.6 | 57.0 | 1230.0 | 19.0 |
| Ex. 160 | 1.5 | 87.1 | 1078.2 | 52.4 |
| Ex. 161 | 1.6 | 20.0 | 260.0 | 20.0 |
| Ex. 162 | 1.6 | 113.0 | 2265.2 | 81.7 |
| Ex. 163 | 3.2 | 21.2 | 864.0 | 60.8 |
| Ex. 164 | 1.6 | 125.0 | 2148.8 | 174.3 |
| Ex. 165 | 1.7 | 121.5 | 2703.3 | 30.5 |
| Ex. 166 | 1.8 | 17.0 | 143.6 | 37.3 |
| Ex. 167 | 1.9 | 20.8 | 468.5 | 25.5 |
| Ex. 168 | 2.0 | 34.2 | 1570.0 | 30.7 |
| Ex. 169 | 2.0 | 30.7 | 5640.3 | 104.5 |
| Ex. 170 | 1.5 | 80.9 | >12500.0 | 26.4 |
| Ex. 171 | 2.0 | 33.9 | 210.9 | 18.8 |
| Ex. 172 | 2.1 | 75.2 | 3059.9 | 53.5 |
| Ex. 173 | 1.3 | 28.0 | 731.5 | 55.9 |
| Ex. 174 | 2.2 | 57.2 | 604.2 | 55.2 |
| Ex. 175 | 2.5 | 27.8 | 839.1 | 49.5 |
| Ex. 176 | 2.6 | 156.9 | 3252.4 | 127.4 |
| Ex. 177 | 2.7 | 160.8 | 2373.6 | 101.8 |
| Ex. 178 | 3.1 | 60.0 | 1312.8 | 42.2 |
| Ex. 179 | 1.4 | 20.9 | 640.9 | 30.0 |
| Ex. 180 | 3.4 | 149.3 | 2294.0 | 129.4 |
| Ex. 181 | 5.4 | 330.8 | 6300.9 | 159.1 |
| Ex. 182 | 2.8 | 24.3 | 275.5 | 52.5 |

TABLE 4-continued

Results of Enzymatic Inhibition Assays

| Example # | JAK1-JH2JH1 IC$_{50}$ (nM) | JAK2-JH1JH2 IC$_{50}$ (nM) | JAK3-JH1JH2 IC$_{50}$ (nM) | Tyk2-JH1JH2 IC$_{50}$ (nM) |
|---|---|---|---|---|
| Ex. 183 | 4.3 | 52.9 | 644.6 | 118.3 |
| Ex. 184 | 25.5 | 229.6 | 1229.7 | 318.6 |
| Ex. 185 | 2.1 | 19.8 | 149.5 | 36.4 |
| Ex. 186 | 3.7 | 82.2 | 4647.3 | 253.7 |
| Ex. 187 | 1.3 | 24.6 | 179.9 | 60.0 |
| Ex. 188 | 3.2 | 36.7 | 13.1 | 121.9 |
| Ex. 189 | 3.4 | 42.3 | 16.6 | 181.8 |
| Ex. 190 | 12.4 | 149.5 | 102.3 | 457.5 |
| Ex. 191 | 1.3 | 57.3 | 1336.9 | 20.6 |
| Ex. 192 | 1.0 | 69.0 | 1118.9 | 25.8 |
| Ex. 193 | 0.2 | 10.1 | 69.5 | 5.3 |
| Ex. 194 | 9.4 | 132.6 | 1462.2 | 72.5 |
| Ex. 195 | 3.3 | 33.7 | 293.6 | 11.0 |
| Ex. 196 | 3.4 | 41.4 | 659.5 | 41.8 |
| Ex. 197 | <4.0 | 15.5 | 132.0 | 6.2 |
| Ex. 198 | <4.0 | 2.1 | 24.4 | 1.2 |
| Ex. 199 | <4.0 | 3.6 | 109.0 | 7.9 |
| Ex. 200 | <4.0 | <3.5 | 13.7 | 12.5 |
| Ex. 201 | <4.0 | 1.9 | 47.5 | 1.1 |
| Ex. 202 | 5.0 | 50.9 | 1039.9 | 50.9 |
| Ex. 203 | 8.5 | 152.0 | 4675.2 | 41.5 |
| Ex. 204 | 6.7 | 13.1 | 427.0 | 10.7 |
| Ex. 205 | 5.3 | 487.3 | 438.8 | 605.9 |
| Ex. 206 | 5.6 | 210.0 | 881.0 | 158.0 |
| Ex. 207 | 6.8 | 197.8 | 374.9 | 523.5 |
| Ex. 208 | 7.6 | 442.0 | 536.0 | 714.0 |
| Ex. 209 | 18.9 | 520.0 | 603.9 | 651.0 |

Cellular Assays

IL-2 pSTAT5 (JAK1/JAK3) Cellular Assay

The AlphaLISA assay (based on Alpha Technology from PerkinElmer) was performed by first plating freshly thawed PBMCs (Biological Specialty Corporation) in 384-well plates at 30,000 cells per 4 μL per well in HBSS (Hanks' Balanced Salt Solution) containing 0.1% IgG (immunoglobulin G)-free, protease-free BSA (bovine serum albumin) (Jackson ImmunoResearch Cat. No. 001-000-161). The cells were then treated with 2 μL/well of compounds diluted in DMSO at half-log titrated concentrations, with a highest test concentration of 10 μM and 0.5% final DMSO concentration, for thirty minutes at 37° C. Next, the cells were stimulated with 2 μL/well of IL-2 (R&D Systems Cat. No. 202-IL-050) at 5 ng/mL for thirty minutes at 37° C. The cellular reactions were terminated by the addition of 2 μL/well of lysis buffer (PerkinElmer Cat. No. ALSU-PST5-A (OK) followed by an incubation of five minutes at room temperature. 5 μL/well of acceptor mix (PerkinElmer Cat. No. ALSU-PST5-A10K) was added to the cells and incubated in the dark for one hour at room temperature. Then, 5 μL/well of donor mix (PerkinElmer Cat. No. ALSU-PST5-A 1 OK) was added to the cells and incubated in the dark overnight at room temperature. Finally, the plates were read on a PerkinElmer EnVision for detection of the time-resolved fluorescence signal. The percentage of IL-2-dependent pSTAT5 inhibition was determined at the compound test concentrations; and for each compound, a dose curve was generated and the IC$_{50}$ was calculated. Compound IC$_{50}$ was calculated by nonlinear regression, sigmoidal dose response analysis of the half-log dilution titration curve of the compound concentration vs. Alpha signal. The acronym "Alpha" stands for amplified luminescent proximity homogeneous assay; the Alpha signal is a luminescent/fluorescent signal.

IFNα pSTAT4 (JAK1/TYK2) Cellular Assay

The AlphaLISA assay (based on Alpha Technology from PerkinElmer) was performed by first plating freshly thawed PBMCs (Biological Specialty Corporation) in 384-well plates at 100,000 cells per 6 μL per well in DMEM (Dulbecco's Modified Eagle Medium) containing 10% FBS (fetal bovine serum) and 1,000 I.U./mL penicillin and 1,000 μg/mL streptomycin. The cells were then treated with 2 μL/well of compounds diluted in DMSO at half-log titrated concentrations, with a highest test concentration of 10 μM and 0.5% final DMSO concentration, for thirty minutes at 37° C. Next, the cells were stimulated with 2 μL/well of IFNα (PBL Assay Science Cat. No. 11101-2) at 4 ng/mL for thirty minutes at 37° C. The cellular reactions were terminated by the addition of 2 μL/well of lysis buffer (PerkinElmer Cat. No. ALSU-PST4-A10K) followed by an incubation of five minutes at room temperature. 4 μL/well of acceptor mix (PerkinElmer Cat. No. ALSU-PST4-A10K) was added to the cells and incubated in the dark for one hour at room temperature. Then, 4 μL/well of donor mix (PerkinElmer Cat. No. ALSU-PST4-A10K) was added to the cells and incubated in the dark overnight at room temperature. Finally, the plates were read on a PerkinElmer EnVision for detection of the time-resolved fluorescence signal. The percentage of IFNα-dependent pSTAT4 inhibition was determined at the compound test concentrations; and for each compound, a dose curve was generated and the IC$_{50}$ was calculated. Compound IC$_{50}$ was calculated by nonlinear regression, sigmoidal dose response analysis of the half-log dilution titration curve of the compound concentration vs. Alpha signal. The term "Alpha" is defined in the immediately preceding cellular assay description.

GM-CSF pSTAT5 (JAK2/JAK2) Cellular Assay

The AlphaLISA assay (based on Alpha Technology from PerkinElmer) was performed by first plating freshly thawed PBMCs (Biological Specialty Corporation) in 384-well plates at 30,000 cells per 4 L per well in HBSS containing 0.1% IgG-free, protease-free BSA (Jackson ImmunoResearch Cat. No. 001-000-161). The cells were then treated with 2 μL/well of compounds diluted in DMSO at half-log titrated concentrations, with a highest test concentration of 10 M and 0.5% final DMSO concentration, for thirty minutes at 37° C. Next, the cells were stimulated with 2 μL/well of GM-CSF (R&D Systems Cat. No. 215-GM-050) at 11 pg/mL for fifteen minutes at 37° C. The cellular reactions were terminated by the addition of 2 L/well of lysis buffer (PerkinElmer Cat. No. ALSU-PST5-A10K) followed by an incubation of five minutes at room temperature. 5 μL/well of acceptor mix (PerkinElmer Cat. No. ALSU-PST5-A10K) was added to the cells and incubated in the dark for one hour at room temperature. Then, 5 μL/well of donor mix (PerkinElmer Cat. No. ALSU-PST5-A10K) was added to the cells and incubated in the dark overnight at room temperature. Finally, the plates were read on a PerkinElmer EnVision for detection of the time-resolved fluorescence signal. The percentage of GM-CSF-dependent pSTAT5 inhibition was determined at the compound test concentrations; and for each compound, a dose curve was generated and the IC$_{50}$ was calculated. Compound IC$_{50}$ was calculated by nonlinear regression, sigmoidal dose response analysis of the half-log dilution titration curve of the compound concentration vs. Alpha signal. The term "Alpha" is defined in the IL-2 pSTAT5 (JAK1/JAK3) cellular assay description. Examples 1-5, 10, 22, 34, 38, 55, 74, and 85 were tested in this cellular assay and the results are shown in Table 5.

TABLE 5

Cell-Based Assay Data

| Test Compound | IL-2 pSTAT5 (JAK1/JAK3) $IC_{50}$ (nM) | IFNα pSTAT4 (JAK1/TYK2) $IC_{50}$ (nM) | GM-CSF pSTAT5 (JAK2/JAK2) $IC_{50}$ (nM) |
|---|---|---|---|
| Ex. 1 | 21.6 | 59.5 | 83.9 |
| Ex. 2 | 9.0 | 20.8 | 61.0 |
| Ex. 3 | 6.4 | 10.1 | 21.9 |
| Ex. 4 | 35.5 | 64.7 | 119.4 |
| Ex. 5 | 6.4 | 38.1 | 28.9 |
| Ex. 10 | 6.7 | 39.4 | 25.1 |
| Ex. 22 | 9.7 | 38.5 | 67.3 |
| Ex. 34 | 20.6 | 42.8 | 33.8 |
| Ex. 38 | 11.2 | 35.9 | 26.9 |
| Ex. 55 | 16.8 | 40.4 | 44.6 |
| Ex. 74 | 49.1 | 96.5 | 201.5 |
| Ex. 85 | 13.9 | 81.4 | 75.4 |

Examples 1-5, 10, 22, 34, 38, 55, 74, and 85 were tested in solubility and permeability assays. The results of the solubility assay are presented in Table 6 which is entitled Solubility Assay Data and the results of the permeability assay are presented in Table 7 entitled MDCK-MDR1 Permeability Data. These solubility and permeability assays are described below under the headings Solubility Assays and Permeability Assays, respectively.

Solubility Assays

Solubility measurements were conducted in the following solubility media: Simulated gastric (34.2 mM of sodium chloride and 100 mM of hydrochloric acid) or simulated intestinal fluids (fasted state [pH 6.5]: 3 mM of sodium taurocholate, 0.75 mM of lecithin, 28.4 mM of monobasic sodium phosphate, 8.7 mM of sodium hydroxide, and 105.9 mM of sodium chloride). Test compounds were dissolved in DMSO at a concentration of 10 mM. The test compounds were dispensed (20 µL) into Nunc 1-mL-96-Deep-Well-PP plates, and the DMSO was evaporated via nitrogen blow down from a TurboVap 96 for 6 hours or until a dry residue was produced. Then, 400 µL of solubility media was added to the well containing the dry solid. A Pre-Slit Well Cap was securely placed over the well plate block, and the samples were vigorously stirred for 2-5 days at ambient temperature. After the incubation period, the samples were filtered through an AcroPrep 1-mL-96-Filter plate into a new 2-mL-96-Deep-Well-PP plate, and the supernatants were quantified by UV-HPLC using a 3-point calibration ranging from 0.004-0.55 mM. The solubility for each compound was calculated from the following equation:

$$\text{Solubility} = \frac{\text{Sample Peak Area}}{\text{Average Responses Factor from 3 Standards}}.$$

The solubility values were in the range of 4-400 µM. Values outside of this range were reported as either <4 µM or >400 µM. Solubilities are reported as long as the compound under study was sufficiently stable to complete the corresponding solubility determination.

TABLE 6

Solubility Assay Data

| Test Compound | SGF solubility (µM) | SIF solubility (µM) |
|---|---|---|
| A | >400 | >400 |
| B | >400 | 75 |

TABLE 6-continued

Solubility Assay Data

| Test Compound | SGF solubility (µM) | SIF solubility (µM) |
|---|---|---|
| C | >400 | >400 |
| Ex. 1 | >400 | 387 |
| Ex. 2 | >400 | >400 |
| Ex. 3 | >400 | >400 |
| Ex. 4 | >400 | >400 |
| Ex. 5 | >400 | 198 |
| Ex. 10 | >400 | >400 |
| Ex. 22 | >400 | 81 |
| Ex. 34 | >400 | >400 |
| Ex. 38 | >400 | >400 |
| Ex. 55 | >400 | 359 |
| Ex. 74 | >400 | >400 |
| Ex. 85 | >400 | >400 |

Permeability Assays

Permeability measurements were conducted according to the Cyprotex protocol using the MDCK-MDR1 cell line obtained from the NIH (Rockville, Md., USA). Cells between passage numbers 6-30 were seeded onto a Multiscreen Plate™ (Millipore) at a cell density of $3.4 \times 10^5$ cells/cm$^2$ and cultured for three days before permeability studies were conducted. The cells in this assay form a cohesive sheet of a single cell layer filing the surface area of the culture dish, also known as a confluent monolayer, and on day four the test compound was added to the apical side of the membrane and the transport of the compound across the monolayer was monitored over a time period of 60 min.

In a simple and basic way of introducing "A" and "B" terms that are often used in these assays, the apical ("A") side or compartment of an entity is the side of such entity that is exposed to the lumen or exterior environment, whereas the basolateral ("B") side or compartment is the side or compartment of such entity that is exposed to the typically internal environment, encompassing the opposite side. For example, when such entity is illustratively an intestinal epithelium cell, the apical side of such intestinal cell would be the side of the cell exposed to the intestinal lumen, whereas the basolateral side would be the side that is exposed to the blood.

Test compounds were dissolved in DMSO at a concentration of 10 mM. The dosing solutions were prepared by diluting test compound with assay buffer (Hanks Balanced Salt Solution), pH 7.4, at a final concentration of 5 µM. For assessment of apical to basolateral ("A-B") permeability, buffer was removed from the apical compartment and replaced with test compound dosing solution with or without the permeability glycoprotein ("PgP", "P-gP", "Pgp" or "P-gp") inhibitor elacridar (2 µM). For assessment of basolateral to apical ("B-A") permeability, buffer was removed from the companion plate and replaced with test compound dosing solution. Incubations were carried out in duplicate at 37° C. in an atmosphere of 5% $CO_2$ with a relative humidity of 95%. Each assay included the reference markers propranolol (high permeability) and prazosin (PgP substrate). After incubation for 60 minutes, apical and basolateral samples were diluted and test compounds quantified by LC/MS/MS using an 8-point calibration in the range 0.0039 to 3 µM with appropriate dilution of the samples (receiver dilution factor=1; donor and $C_0$ dilution factor=10). The permeability coefficient ($P_{app}$) for each compound was calculated from the following equation: $P_{app} = (dQ/dt)/(C_0 \times S)$, where dQ/dt is the rate of permeation of the drug across the cells, $C_0$ is the donor compartment concentration at time zero, and S is the area of the cell monolayer.

The percent recovery was measured for all incubation conditions. These measurements did not reveal unacceptable compound/plate binding or compound accumulation in the cell monolayer.

The second and third columns in Table 7 show the values of $P_{app(A\text{-}B)}$ for the apical-to-basolateral compound transport without (second column) and with a P-gp inhibitor (third column, noted as $P^e_{app(A\text{-}B)}$) that was elacridar. $P_{app(A\text{-}B)}$ gives an indication of permeation extent across the cells in this assay, which is envisaged to model the transcellular transport across Pgp-expressing cells, such as Pgp-expressing gastrointestinal tract cells. $P^e_{app(A\text{-}B)}$ values ($P_{app(A\text{-}B)}$ in the presence of the P-gp inhibitor) given in column 3 are determined to confirm the role of P-gp in the compound efflux. The fourth column in Table 7 shows the values of $P_{app(B\text{-}A)}$ for the basolateral-to-apical compound transport. Test compound efflux ratios are given in the fifth column of Table 7 as $P_{app(B\text{-}A)}/P_{app(A\text{-}B)}$ by using the corresponding permeability coefficient values from the fourth and second columns in the same table. The efflux ratios (fifth column, Table 7) are consistently greater than 2 for compounds (A)-(C) and also for compounds Ex. 1-5, 10, 22, 34, 38, 55, 74, and 85, which indicates that compound efflux occurs for all such compounds.

$P_{app(A\text{-}B)}$ values in column 2 are generally low and comparable for reference compounds (A)-(C) and also for compounds Ex. 1-5, 10, 22, 34, 38, 55, 74, and 85. These low values indicate low permeability for all such compounds, which is due to the P-gp effects since all such compounds are P-gp substrates as indicated by the values given in column 5 being all greater than 2. To be characterized as having low permeability, the values given in the third and fourth columns for $P^e_{app(A\text{-}B)}$ and $P_{app(B\text{-}A)}$, respectively, should be low. However, these data show that the $P_{app(B\text{-}A)}$ values for compounds (A)-(C) are greater than the corresponding values compounds Ex. 1-5, 10, 22, 34, 38, 55, 74, and 85.

The integrity of each monolayer was monitored by examining the permeation of lucifer yellow by fluorimetric analysis. This examination revealed that the cells in this assay maintained a satisfactory confluent monolayer.

In Vivo Studies

Oral Dosing—Protocol 1

Three non-fasted female C57BL/6 mice were orally administered test compound at a dose of 25 mg/kg p.o. as a solution in 20% hydroxypropyl-beta-cyclodextrin (HPβCD) at a dose volume of 5 mL/kg. Blood samples were collected at 0.5, 2, and 4 h post dose via retro-orbital bleed or venipuncture of the dorsal metatarsal vein. Blood samples were collected into tubes containing anticoagulant (Heparin-Na) and placed on wet ice. The plasma fraction was separated by centrifugation and frozen at −20° C. for up to 4 h and −80° C. after 4 h unless analyzed shortly after sample collection. Colon samples were collected at 4 h post dose. From the beginning of the cecum, a 4-6 cm sample of the colon was dissected, cut open on the longitudinal axis, and the solid contents removed by flushing with 2 mL of saline. The colon was further washed by putting it in 5 mL of saline and shaken for 5 seconds. The colon sample was then patted dry, weighed, and homogenized as 1 part tissue (g) to 4 parts HPLC grade water (mL). Concentrations of the compound in plasma and colon homogenate were determined using a qualified liquid chromatography-triple quadrupole mass spectrometry (LC-MS/MS) method. This protocol was used to evaluate the following test compounds: Compounds (B) and (C) and Examples 10 and 74.

Oral Dosing Protocol 2

Three non-fasted female C57BL/6 mice were orally administered test compound at a dose of 25 mg/kg p.o. as a solution in 20% HPβCD at a dose volume of 5 mL/kg. Blood samples were collected at 0.5, 2, and 4 h post dose via retro-orbital bleed or dorsal metatarsal vein. Blood samples were collected into tubes containing anticoagulant (Heparin-Na) and placed on wet ice. The plasma fraction was separated by centrifugation and frozen at −20° C. for up to 4 h and −80° C. after 4 h unless analyzed shortly after sample collection. Colon samples were collected at 4 h post dose. From 2 cm below the cecum, a 4 cm sample of the colon was dissected, cut open on the longitudinal axis, and the solid contents removed by flushing with 2 mL of saline. The colon was further washed by putting it in 5 mL of saline and shaken for 5 seconds. The colon sample was then patted dry, weighed, and homogenized as 1 part tissue (g) to 4 parts HPLC grade water (mL). Concentrations of the compound

TABLE 7

MDCK-MDR1 Permeability Data

| Test Compound** | MDCK-MDR1 $P_{app(A\text{-}B)}$ ($10^{-6}$ cm/sec) @ 5 (μM) | MDCK-MDR1 $P^e_{app(A\text{-}B)}$ ($10^{-6}$ cm/sec) @ 5 (μM) | MDCK-MDR1 $P_{app(B\text{-}A)}$ ($10^{-6}$ cm/sec) @ 5 (μM) | $P_{app(B\text{-}A)}/P_{app(A\text{-}B)}$ |
|---|---|---|---|---|
| A | 1.3 | 22 | 55.3 | 43 |
| B | 0.4 | 1.7 | 23.5 | 59 |
| C | 0.5 | 2.5 | 23.1 | 46 |
| Ex. 1 | <0.5, 0.4 | <0.5, 1.1 | 0.9, 1.1 | >1.9, 3.3 |
| Ex. 2* | 1.1 | 1.6 | 4.8 | 4.4 |
| Ex. 3 | <0.4, <0.5 | 2.3, 1.6 | 17, 16 | >41, >33 |
| Ex. 4 | 0.1 | 0.5 | 1.3 | 8.7 |
| Ex. 5 | <0.4, <0.5 | 0.7, 0.5 | 1.8, 2.1 | >4.8, >4.5 |
| Ex. 10 | <0.3, <0.3 | 0.9, 1.1 | 2.5, 2.6 | >8.4, >8.7 |
| Ex. 22 | <0.4 | 1.2 | 3.6 | >9 |
| Ex. 34 | 0.1 | 0.5 | 1.7 | 11.5 |
| Ex. 38 | <0.4 | 0.6 | 1.8 | >4.2 |
| Ex. 55 | <0.4 | 1.1 | 7.1 | >16.9 |
| Ex. 74 | <0.4 | 0.8 | 1.1 | >2.9 |
| Ex. 85 | <0.5 | 0.6 | 1.1 | >2.2 |

*Starting concentration was measured to be >7 μM for A to B, A to B (with elacridar), and B to A conditions.
**Unless indicated otherwise, compounds (A)-(C) and Ex. 1 5, 10, 22, 34, 38, 55, 74 and 85 were tested at a concentration of 5 μM. For data shown in cells with two data points, compounds were tested twice.

in plasma and colon homogenate were determined using a qualified liquid chromatography-triple quadrupole mass spectrometry (LC-MS/MS) method. This protocol was used to evaluate the following test compounds: Compound (A) and Examples 1-5, 22, 34, 38, 55, and 85.

IC Dosing-Protocol 3

Intracolonic (IC) dose group: Following anesthesia with isoflurane by inhalation, three non-fasted female C57BL/6 mice were administered the compound intracolonically through a small incision in the abdominal wall using a syringe and needle at a dose of 5 mg/kg as a solution in 20% HPβCD at a dose volume of 1 mL/kg. Blood samples were collected at 0.5, 2, and 4 h post dose via retro-orbital bleed. Blood samples were collected into tubes containing anticoagulant (Heparin-Na) and placed on wet ice. The plasma fraction was separated by centrifugation and frozen at −20° C. for up to 4 h and −80° C. after 4 h unless analyzed shortly after sample collection. Colon samples were collected at 4 h post dose. From 2 cm below the cecum, a 4-cm sample of the colon was dissected, cut open on the longitudinal axis, and the solid contents removed by flushing with 2 mL of saline. The colon was further washed by putting it in 5 mL of saline and shaken for 5 seconds. The colon sample was then patted dry, weighed, and homogenized as 1 part tissue (g) to 4 parts HPLC grade water (mL). Concentrations of the compound in plasma and colon homogenate were determined using a qualified liquid chromatography-triple quadrupole mass spectrometry (LC-MS/MS) method. This protocol was used to evaluate IC dosing of the following test compounds: Examples 1, 3, and 4.

Compounds Ex. 1-5, 10, 22, 34, 38, 55, 74, and 85 are further characterized by the physico-chemical properties given in Table 8. c Log P and tPSA values were calculated by using ChemBioDraw Ultra 14.0, where P is the n-octanol—water partition coefficient. The topological polar surface area (tPSA) is calculated as the surface sum over all polar atoms, primarily oxygen and nitrogen, also including their attached hydrogens.

TABLE 8

Some physico-chemical properties of compounds Ex. 1-5, 10, 22, 34, 38, 55, 74, and 85

| Test Compound | cLog P | tPSA | # H bond donors | # H bond acceptors | # rotatable bonds |
|---|---|---|---|---|---|
| Ex. 1 | 0.94 | 113.11 | 3 | 5 | 6 |
| Ex. 2 | 2.31 | 88.17 | 2 | 4 | 3 |
| Ex. 3 | 1.58 | 92.88 | 2 | 4 | 6 |
| Ex. 4 | 0.54 | 116.67 | 2 | 5 | 6 |
| Ex. 5 | 0.24 | 102.11 | 2 | 5 | 5 |
| Ex. 10 | 0.86 | 102.11 | 2 | 5 | 6 |
| Ex. 22 | 1.25 | 116.67 | 2 | 5 | 6 |
| Ex. 34 | 1.13 | 113.11 | 3 | 5 | 6 |
| Ex. 38 | 1.14 | 108.48 | 2 | 5 | 5 |
| Ex. 55 | 1.35 | 116.67 | 2 | 5 | 6 |
| Ex. 74 | 1.50 | 117.27 | 3 | 5 | 5 |
| Ex. 85 | 0.57 | 113.11 | 3 | 5 | 6 |

The invention claimed is:

1. A compound or a pharmaceutically acceptable salt thereof, selected from

- 2-Cyano-N-((1-((1r,4r)-4-(cyanomethyl)cyclohexyl)-1,6-dihydroimidazo[4,5-d]pyrrolo[2,3-b]pyridin-2-yl)methyl)ethanesulfonamide;
- 2-(1r,4r)-4-(Cyanomethyl)cyclohexyl)-1,6-dihydroimidazo[4,5-d]pyrrolo[2,3-b]pyridin-2-yl)-N-(pyrimidin-4-ylmethyl)acetamide;
- 2-(1r,4r)-4-(Cyanomethyl)cyclohexyl)-1,6-dihydroimidazo[4,5-d]pyrrolo[2,3-b]pyridin-2-yl)-N-(3-hydroxy-2,2-dimethylpropyl)acetamide;
- N-((1r,4r)-4-(Cyanomethyl)cyclohexyl)-2-(1-((1r,4r)-4-(cyanomethyl)cyclohexyl)-1,6-dihydroimidazo[4,5-d]pyrrolo[2,3-b]pyridin-2-yl)acetamide;
- 2-(1r,4r)-4-(Cyanomethyl)cyclohexyl)-1,6-dihydroimidazo[4,5-d]pyrrolo[2,3-b]pyridin-2-yl)-N-(((1S,3R,5R,7S)-3-hydroxyadamantan-1-yl)methyl)acetamide;
- N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide;
- N-(4-Cyanobicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;
- 2-(1r,4r)-4-(Cyanomethyl)cyclohexyl)-1,6-dihydroimidazo[4,5-d]pyrrolo[2,3-b]pyridin-2-yl)-N-((3-hydroxyoxetan-3-yl)methyl)acetamide;
- 2-((1r,4r)-4-(2-(2-(4-Morpholinopiperidin-1-yl)-2-oxoethyl)imidazo[4,5-d]pyrrolo[2,3-b]pyridin-1 (6H)-yl)cyclohexyl)acetonitrile;
- 2-(1-((1 r,4r)-4-(Cyanomethyl)cyclohexyl)-1,6-dihydroimidazo[4,5-d]pyrrolo[2,3-b]pyridin-2-yl)-N-((1r,4r)-4-(hydroxymethyl)cyclohexyl)acetamide;
- 2-(1-((1 r,4r)-4-(Cyanomethyl)cyclohexyl)-1,6-dihydroimidazo[4,5-d]pyrrolo[2,3-b]pyridin-2-yl)-N-(2-hydroxyethyl)acetamide;
- N-((1-((1r,4r)-4-(Cyanomethyl)cyclohexyl)-1,6-dihydroimidazo[4,5-d]pyrrolo[2, 3-b]pyridin-2-yl)methyl)benzimidamide;
- 2-(1-((1 r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide;
- 2-(1-((1 r,4r)-4-(Cyanomethyl)cyclohexyl)-1,6-dihydroimidazo[4,5-d]pyrrolo[2,3-b]pyridin-2-yl)-N-(pyrazin-2-ylmethyl)acetamide;
- N-((1H-imidazol-2-yl)methyl)-2-(1-((1 r,4r)-4-(cyanomethyl)cyclohexyl)-1,6-dihydroimidazo[4,5-d]pyrrolo[2,3-b]pyridin-2-yl)acetamide;
- 2-(1-((1 r,4r)-4-(Cyanomethyl)cyclohexyl)-1,6-dihydroimidazo[4,5-d]pyrrolo[2,3-b]pyridin-2-yl)-N-((1R,3R)-3-hydroxycyclobutyl)acetamide;
- 2-(1-((1 r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide;
- 2-(1-((1r,4r)-4-(Cyanomethyl)cyclohexyl)-1,6-dihydroimidazo[4,5-d]pyrrolo[2,3-b]pyridin-2-yl)-N-((1S,4S)-4-hydroxycyclohexyl)acetamide;
- 2-(1-((1r,4r)-4-(Cyanomethyl)cyclohexyl)-1,6-dihydroimidazo[4,5-d]pyrrolo[2,3-b]pyridin-2-yl)-N-((1s,3r,5R,7S)-3-hydroxyadamantan-1-yl)acetamide;
- N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;
- 2-(1-((1r,4r)-4-(Cyanomethyl)cyclohexyl)-1,6-dihydroimidazo[4,5-d]pyrrolo[2,3-b]pyridin-2-yl)-N-(3-hydroxy-3-methylbutyl)acetamide;
- 2-(1-((1r,4r)-4-(Cyanomethyl)cyclohexyl)-1,6-dihydroimidazo[4,5-d]pyrrolo[2,3-b]pyridin-2-yl)-N-(1-isobutylpiperidin-4-yl)acetamide;
- 2-(1-((1r,4r)-4-(Cyanomethyl)cyclohexyl)-1,6-dihydroimidazo[4,5-d]pyrrolo[2,3-b]pyridin-2-yl)-N-(1H-pyrazol-4-yl)acetamide;
- 2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)benzyl)acetamide;
- 2-((1r,4r)-4-(2-(2-(4-(Hydroxymethyl)piperidin-1-yl)-2-oxoethyl)imidazo[4,5-d] pyrrolo[2,3-b]pyridin-1 (6H)-yl)cyclohexyl)acetonitrile;
- 2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide;
- 2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide;
- 2-((1r,4r)-4-(2-(2-(4-(2-Hydroxypropan-2-yl)piperidin-1-yl)-2-oxoethyl)imidazo[4,5-d]pyrrolo[2,3-b]pyridin-1 (6H)-yl)cyclohexyl)acetonitrile;
- 2-(1-((1r,4r)-4-(Cyanomethyl)cyclohexyl)-1,6-dihydroimidazo[4,5-d]pyrrolo[2,3-b]pyridin-2-yl)-N-(4-(1,1,1,3,3,3-hexafluoro-2-hydroxypropan-2-yl)phenyl)acetamide;
- N-((1-((1r,4r)-4-(Cyanomethyl)cyclohexyl)-1,6-dihydroimidazo[4,5-d]pyrrolo[2,3-b]pyridin-2-yl)methyl)-3-hydroxy-3-methylbutanamide;
- 2-(1-((1r,4r)-4-(Cyanomethyl)cyclohexyl)-1,6-dihydroimidazo[4,5-d]pyrrolo[2,3-b]pyridin-2-yl)-N-(2-methoxyethyl)acetamide;
- 2-(1-((1r,4r)-4-(Cyanomethyl)cyclohexyl)-8-fluoro-1,6-dihydroimidazo[4,5-d]pyrrolo[2,3-b]pyridin-2-yl)-N-(2-hydroxy-2-methylpropyl)acetamide;
- 2-((1r,4r)-4-(2-(1-(Methylsulfonyl)azetidin-3-yl)imidazo[4,5-d]pyrrolo[2,3-b]pyridin-1(6H)-yl)cyclohexyl)acetonitrile;

3-Cyano-N-((1-((1r,4r)-4-(cyanomethyl)cyclohexyl)-1,6-dihydroimidazo[4,5-d]pyrrolo[2,3-b]pyridin-2-yl)methyl)propanamide;

3-(3-(1-((1r,4r)-4-(Cyanomethyl)cyclohexyl)-1,6-dihydroimidazo[4,5-d]pyrrolo[2,3-b]pyridin-2-yl)azetidin-1-yl)-3-oxopropanenitrile;

2-((1r,4r)-4-(2-(1-(2-Hydroxy-2-methylpropyl)piperidin-4-yl)imidazo[4,5-d]pyrrolo[2,3-b]pyridin-1(6H)-yl)cyclohexyl)acetonitrile;

2-(8-chloro-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;

2-(8-bromo-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;

2-(1-((1r,4r)-4-(Cyanomethyl)cyclohexyl)-1,6-dihydroimidazo[4,5-d]pyrrolo[2,3-b]pyridin-2-yl)-N-methylacetamide; and 2-(1-((1r,4r)-4-(Cyanomethyl)cyclohexyl)-1,6-dihydroimidazo[4,5-d]pyrrolo[2,3-b]pyridin-2-yl)-N-(4-cyanophenyl)acetamide.

2. A compound selected from

2-Cyano-N-((1-((1r,4r)-4-(cyanomethyl)cyclohexyl)-1,6-dihydroimidazo[4,5-d]pyrrolo[2,3-b]pyridin-2-yl)methyl)ethanesulfonamide;

2-(1r,4r)-4-(Cyanomethyl)cyclohexyl)-1,6-dihydroimidazo[4,5-d]pyrrolo[2,3-b]pyridin-2-yl)-N-(pyrimidin-4-ylmethyl)acetamide;

2-(1r,4r)-4-(Cyanomethyl)cyclohexyl)-1,6-dihydroimidazo[4,5-d]pyrrolo[2,3-b]pyridin-2-yl)-N-(3-hydroxy-2,2-dimethylpropyl)acetamide;

N-((1r,4r)-4-(Cyanomethyl)cyclohexyl)-2-(1-((1r,4r)-4-(cyanomethyl)cyclohexyl)-1,6-dihydroimidazo[4,5-d]pyrrolo[2,3-b]pyridin-2-yl)acetamide;

2-(1r,4r)-4-(Cyanomethyl)cyclohexyl)-1,6-dihydroimidazo[4,5-d]pyrrolo[2,3-b]pyridin-2-yl)-N-((1S,3R,5R,7S)-3-hydroxyadamantan-1-yl)methyl)acetamide;

N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide;

N-(4-Cyanobicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((3-hydroxyoxetan-3-yl)methyl)acetamide;

2-((1r,4r)-4-(2-(2-(4-Morpholinopiperidin-1-yl)-2-oxoethyl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-((1r,4r)-4-(hydroxymethyl)cyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-(2-hydroxyethyl)acetamide;

N-((1-((1r,4r)-4-(Cyanomethyl)cyclohexyl)-1,6-dihydroimidazo[4,5-d]pyrrolo[2,3-b]pyridin-2-yl)methyl)benzimidamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide;

2-(1-((1r,4r)-4-(Cyanomethyl)cyclohexyl)-1,6-dihydroimidazo[4,5-d]pyrrolo[2,3-b]pyridin-2-yl)-N-(pyrazin-2-ylmethyl)acetamide;

N-((1H-imidazol-2-yl)methyl)-2-(1-((1r,4r)-4-(cyanomethyl)cyclohexyl)-1,6-dihydroimidazo[4,5-d]pyrrolo[2,3-b]pyridin-2-yl)acetamide;

2-(1r,4r)-4-(Cyanomethyl)cyclohexyl)-1,6-dihydroimidazo[4,5-d]pyrrolo[2,3-b]pyridin-2-yl)-N-((1R,3R)-3-hydroxycyclobutyl)acetamide;

2-(1r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1S,4S)-4-hydroxycyclohexyl)acetamide;

2-(1-((1r,4r)-4-(Cyanomethyl)cyclohexyl)-1,6-dihydroimidazo[4,5-d]pyrrolo[2,3-b]pyridin-2-yl)-N-((1 s, 3 r, 5R, 7 S)-3-hydroxyadamantan-1-yl)acetamide;

N-(4-(Cyanomethyl)bicyclo[2.2.1]heptan-1-yl)-2-(1 (cyanomethyl)cyclohexyl)-1,6-dihydroimidazo[4,5-d]pyrrolo[2,3-b]pyridin-2-yl)acetamide;

2-(1-((1 r,4r)-4-(Cyanomethyl)cyclohexyl)-1,6-dihydroimidazo[4,5-d]pyrrolo[2,3-b]pyridin-2-yl)-N-(3-hydroxy-3-methylbutyl)acetamide;

2-(1-((1 r,4r)-4-(Cyanomethyl)cyclohexyl)-1,6-dihydroimidazo[4,5-d]pyrrolo[2,3-b]pyridin-2-yl)-N-(1-isobutylpiperidin-4-yl)acetamide;

2-(1-((1 r,4r)-4-(Cyanomethyl)cyclohexyl)-1,6-dihydroimidazo[4,5-d]pyrrolo[2,3-b]pyridin-2-yl)-N-(1H-pyrazol-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(4-(hydroxymethyl)benzyl)acetamide;

2-((1r,4r)-4-(2-(2-(4-(Hydroxymethyl)piperidin-1-yl)-2-oxoethyl)imidazo[4,5-d]pyrrolo[2,3-b]pyridin-1 (6H)-yl)cyclohexyl)acetonitrile;

2-(1-((1r,4r)-4-(Cyanomethyl)cyclohexyl)-1,6-dihydroimidazo[4,5-d] pyrrolo[2,3-b]pyridin-2-yl)-N-(1H-pyrazol-3-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide;

2-((1r,4r)-4-(2-(2-(4-(2-Hydroxypropan-2-yl)piperidin-1-yl)-2-oxoethyl)imidazo[4,5-d]pyrrolo[2,3-b]pyridin-1 (6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(4-(1,1,1,3,3,3-hexafluoro-2-hydroxypropan-2-yl)phenyl)acetamide;

N-((1-((1r,4r)-4-(Cyanomethyl)cyclohexyl)-1,6-dihydroimidazo[4,5-d]pyrrolo[2,3-b]pyridin-2-yl)methyl)-3-hydroxy-3-methylbutanamide;

2-(1-((1r,4r)-4-(Cyanomethyl)cyclohexyl)-1,6-dihydroimidazo[4,5-d]pyrrolo[2,3-b]pyridin-2-yl)-N-(2-methoxyethyl)acetamide;

2-(1r,4r)-4-(Cyanomethyl)cyclohexyl)-8-fluoro-1,6-dihydroimidazo[4,5-d]pyrrolo[2,3-b]pyridin-2-yl)-N-(2-hydroxy-2-methylpropyl)acetamide;

2-((1r,4r)-4-(2-(1-(Methylsulfonyl)azetidin-3-yl)imidazo[4,5-d]pyrrolo[2,3-b]pyridin-1(6H)-yl)cyclohexyl)acetonitrile;

3-Cyano-N-((1-((1r,4r)-4-(cyanomethyl)cyclohexyl)-1,6-dihydroimidazo[4,5-d]pyrrolo[2,3-b]pyridin-2-yl)methyl)propanamide;

3-(3-(1-((1r,4r)-4-(Cyanomethyl)cyclohexyl)-1,6-dihydroimidazo[4,5-d]pyrrolo[2,3-b]pyridin-2-yl)azetidin-1-yl)-3-oxopropanenitrile;

2-((1r,4r)-4-(2-(1-(2-Hydroxy-2-methylpropyl)piperidin-4-yl)imidazo[4,5-d]pyrrolo[2,3-b]pyridin-1(6H)-yl)cyclohexyl)acetonitrile;

2-(8-chloro-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;

2-(8-bromo-1-((1r,4r)-4-(cyanomethyl)cyclohexyl)-1,6-dihydroimidazo[4,5-d]pyrrolo[2,3-b]pyridin-2-yl)-N-(2-hydroxy-2-methylpropyl)acetamide;

2-(1-((1r,4r)-4-(Cyanomethyl)cyclohexyl)-1,6-dihydroimidazo[4,5-d]pyrrolo[2,3-b]pyridin-2-yl)-N-methylacetamide;

2-(1-((1r,4r)-4-(Cyanomethyl)cyclohexyl)-1,6-dihydroimidazo[4,5-d]pyrrolo[2,3-b]pyridin-2-yl)-N-(4-cyanophenyl)acetamide;

and pharmaceutically acceptable co-crystals thereof.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Gly Gly Glu Glu Glu Glu Tyr Phe Glu Leu Val Lys Lys
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Trp Gly Ala Ile Glu Thr Asp Lys Glu Tyr Tyr Thr Val Lys Asp
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Gly Gly Glu Glu Glu Glu Tyr Phe Glu Leu Val Lys Lys
```

```
<210> SEQ ID NO 4
<211> LENGTH: 7
<212> TYPE: PRT
<213> ORGANISM: Tobacco etch virus

<400> SEQUENCE: 4

Glu Asn Leu Tyr Phe Gln Gly
1               5
```